(12) United States Patent
Bair et al.

(10) Patent No.: US 10,329,275 B2
(45) Date of Patent: Jun. 25, 2019

(54) COMPOUNDS AND COMPOSITIONS FOR THE INHIBITION OF NAMPT

(71) Applicants: Forma TM, LLC, Watertown, MA (US); Genentech, Inc., South San Francisco, CA (US)

(72) Inventors: Kenneth W. Bair, Wellesley, MA (US); Timm R. Baumeister, Watertown, MA (US); Alexandre J. Buckmelter, Acton, MA (US); Karl H. Clodfelter, Watertown, MA (US); Bingsong Han, North Haven, CT (US); Jian Lin, Acton, MA (US); Dominic J. Reynolds, Watertown, MA (US); Chase C. Smith, Rutland, MA (US); Zhongguo Wang, Lexington, MA (US); Xiaozhang Zheng, Lexington, MA (US); Po-Wai Yuen, Beijing (CN)

(73) Assignees: FORMA TM, LLC, Watertown, MA (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/008,378

(22) Filed: Jun. 14, 2018

(65) Prior Publication Data
US 2018/0291000 A1  Oct. 11, 2018

Related U.S. Application Data

(63) Continuation of application No. 13/820,496, filed as application No. PCT/US2011/050320 on Sep. 2, 2011, now abandoned.

(60) Provisional application No. 61/480,423, filed on Apr. 29, 2011, provisional application No. 61/478,995, filed on Apr. 26, 2011, provisional application No. 61/386,037, filed on Sep. 24, 2010, provisional application No. 61/386,044, filed on Sep. 24, 2010, provisional application No. 61/379,812, filed on Sep. 3, 2010, provisional application No. 61/379,819, filed on Sep. 3, 2010.

(51) Int. Cl.
| | |
|---|---|
| C07D 401/12 | (2006.01) |
| C07D 471/04 | (2006.01) |
| C07D 213/54 | (2006.01) |
| C07D 213/75 | (2006.01) |
| C07D 213/81 | (2006.01) |
| C07C 317/42 | (2006.01) |
| C07D 213/74 | (2006.01) |
| C07D 213/84 | (2006.01) |
| A61K 31/437 | (2006.01) |
| A61K 31/44 | (2006.01) |
| A61K 31/4406 | (2006.01) |
| A61K 31/4545 | (2006.01) |
| A61K 31/5377 | (2006.01) |
| A61K 45/06 | (2006.01) |
| C07D 213/40 | (2006.01) |

(52) U.S. Cl.
CPC .......... *C07D 401/12* (2013.01); *A61K 31/437* (2013.01); *A61K 31/44* (2013.01); *A61K 31/4406* (2013.01); *A61K 31/4545* (2013.01); *A61K 31/5377* (2013.01); *A61K 45/06* (2013.01); *C07C 317/42* (2013.01); *C07D 213/40* (2013.01); *C07D 213/54* (2013.01); *C07D 213/74* (2013.01); *C07D 213/75* (2013.01); *C07D 213/81* (2013.01); *C07D 213/84* (2013.01); *C07D 471/04* (2013.01)

(58) Field of Classification Search
CPC .. C07D 401/12; C07D 471/04; C07D 213/54; C07D 213/75; C07D 213/81
See application file for complete search history.

(56) References Cited

U.S. PATENT DOCUMENTS

| | | | |
|---|---|---|---|
| 3,931,203 | A | 1/1976 | Kilbourn et al. |
| 3,994,905 | A | 11/1976 | Kilbourn et al. |
| 4,075,345 | A | 2/1978 | Kilbourn et al. |
| 4,659,724 | A | 4/1987 | Chou |
| 6,949,567 | B2 | 9/2005 | Aschenbrenner et al. |

(Continued)

FOREIGN PATENT DOCUMENTS

| | | |
|---|---|---|
| CN | 102869261 A | 1/2013 |
| DE | 2409686 A1 | 10/1974 |

(Continued)

OTHER PUBLICATIONS

Beauparlant, P. et al., Preclinical development of the nicotinamide phosphoribosyl transferase inhibitor prodrug GMX1777 Anti-Cancer Drugs, 20(5):346-354 (2009).

Bible, K.C. and Kaufmann, S.H., Cytotoxic synergy between flavopiridol (NSC 649890, L86-8275) and various antineoplastic agents: the importance of sequence of administration, Cancer Research, 57(16): 3375-3380 (1997).

(Continued)

*Primary Examiner* — Samira J Jean-Louis
(74) *Attorney, Agent, or Firm* — Choate, Hall & Stewart LLP; Michael A. Shinall; Erica M. D'Amato

(57) ABSTRACT

The present invention relates to compounds and compositions for the inhibition of NAMPT, their synthesis, applications and antidotes. An embodiment of the invention is the provision of a compound of Formula IIIA.

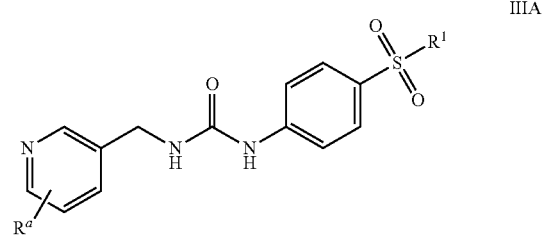

IIIA

10 Claims, No Drawings

(56) References Cited

U.S. PATENT DOCUMENTS

| | | |
|---|---|---|
| 7,365,068 B2 | 4/2008 | Phadke et al. |
| 7,595,326 B2 | 9/2009 | Khan et al. |
| 7,767,706 B2 | 8/2010 | Phadke et al. |
| 8,450,348 B2 | 5/2013 | Murthi et al. |
| 9,169,209 B2 | 10/2015 | Bair et al. |
| 9,458,172 B2 | 10/2016 | Bair et al. |
| 9,555,039 B2 | 1/2017 | Bair et al. |
| 9,676,721 B2 | 6/2017 | Bair et al. |
| 9,822,129 B2 | 11/2017 | Bair et al. |
| 2002/0165236 A1 | 11/2002 | Aschenbrenner et al. |
| 2003/0119876 A1 | 6/2003 | Aschenbrenner et al. |
| 2005/0197371 A1 | 9/2005 | Milanov et al. |
| 2006/0025415 A1 | 2/2006 | Gonzalez et al. |
| 2008/0200523 A1 | 8/2008 | Murthi et al. |
| 2009/0176786 A1 | 7/2009 | Konobe et al. |
| 2013/0273034 A1 | 10/2013 | Bair et al. |
| 2013/0295051 A1 | 11/2013 | Bair et al. |
| 2014/0248240 A1 | 9/2014 | Bair et al. |
| 2014/0275057 A1 | 9/2014 | Bair et al. |
| 2014/0294805 A1 | 10/2014 | Bair et al. |
| 2015/0104384 A1 | 4/2015 | Bair et al. |
| 2015/0175621 A1 | 6/2015 | Bair et al. |
| 2016/0002266 A1 | 1/2016 | Bair et al. |
| 2016/0355514 A1 | 12/2016 | Bair et al. |
| 2017/0137441 A1 | 5/2017 | Bair et al. |
| 2017/0216262 A1 | 8/2017 | Bair et al. |
| 2017/0368039 A1 | 12/2017 | Kenneth et al. |

FOREIGN PATENT DOCUMENTS

| | | |
|---|---|---|
| DE | 2334355 A1 | 1/1975 |
| DE | 10053794 A1 | 5/2002 |
| WO | WO-00/50417 A1 | 8/2000 |
| WO | WO-02/44156 A2 | 6/2002 |
| WO | WO-02/070467 A1 | 9/2002 |
| WO | WO-03/059872 A1 | 7/2003 |
| WO | WO-2008/039999 A1 | 4/2008 |
| WO | WO-2010/023307 A1 | 3/2010 |
| WO | WO-2010/109122 A1 | 9/2010 |
| WO | WO-2010/142735 A1 | 12/2010 |
| WO | WO-2011/109441 A1 | 9/2011 |
| WO | WO-2012031196 A1 | 3/2012 |
| WO | WO-2013127268 A1 | 9/2013 |
| WO | WO-2013130935 A1 | 9/2013 |
| WO | WO-2013130943 A1 | 9/2013 |

OTHER PUBLICATIONS

CAS Registry No. 494839-65-5; STN Entry Date Feb. 26, 2003; 4-(Phenylsulfonyl)-N-(3-pyridinylmethyl).

CAS Registry No. 501911-31-5; STN Entry Date Apr. 7, 2003; 4-(Phenylsulfonyl)-N-(3-pyridinyl)benzamide.

CAS Registry No. 684231-74-1; STN Entry Date May 21, 2004; 4-[(3,4-dihydro-2(1 H)-isoquinolinyl)sulfonyl]-N-[4-(3-pyridinyl)-2-thiazolyl]-benzamide.

Drevs, J. et al., Antiangiogenic potency of FK866/K22.175, a new inhibitor of intracellular NAD bio synthesis, in murine renal cell carcinoma, Anticancer Res., 23(6C): 4853-4858 (2003). 1 Page, Abstract Only.

Hasmann M. and Schemainda, I., FK866, a Highly Specific Non-competitive Inhibitor of Nicotinamide Phosphoribosyltransferase, Represents a Novel Mechanism for Induction of Tumor Cell Apoptosis, Cancer Res., 63(21): 7436-7442 (2003).

International Search Report for PCT/US2011/050320, issued by ISA/EPO, 7 pages (dated Oct. 31, 2011).

Lövborg, H. et al., Structure-activity relationship analysis of cytotoxic cyanoguanidines: selection of CHS 828 as candidate drug, BMC Research Notes, 2(114): 1-7 (2009).

Olesen, U. H. et al., Anticancer agent CHS-828 inhibits cellular synthesis of NAD, Biochem. Biophys. Res. Commun., 367: 799-804 (2008).

Ongkeko, W. et al., Inactivation of Cdc2 increases the level of apoptosis induced by DNA damage, J. Cell Sci., 108(Pt 8): 2897-2904 (1995).

Pogrebniak, A, et al. Chemopotentiating effects of a novel NAD biosynthesis inhibitor, FK866, in combination with antineoplastic agents, Eur J Med Res., 11: 313-321 (2006).

Ravaud, A. et al., Phase I study and guanidine kinetics of CHS-828, a guanidine-containing compound, administered orally as a single dose every 3 weeks in solid tumors: an ECSG/EORTC study, Eur. J. Cancer, 41:702-707 (2005).

Rongvaux, A., et al., Nicotinamide phosphoribosyl transferase/pre-B cell colony-enhancing factor/visfatin is required for lymphocyte development and cellular resistance to genotoxic stress, J. Immunol., 181(7): 4685-4695 (2008).

Sci Finder search report: substances by structure, dated Aug. 15, 2011, 7:12PM with generated Answer set 1.

Written Opinion for PCT/US2011/050320 (4-{[( Pyridin- 3 -Yl -Methyl) Aminocarbonyl] Amino} Benzene—Sulfone Derivatives as NAMPT Inhibitors for Therapy of Diseases Such as Cancer, filed Sep. 2, 2011) issued by ISA/EPO, 12 pages (dated Oct. 31, 2011).

COMPOUNDS AND COMPOSITIONS FOR THE INHIBITION OF NAMPT

PRIORITY CLAIM

This application is a continuation of U.S. application Ser. No. 13/820,496, filed Jul. 2, 2013, which is a U. S. National Application under 35 U.S.C. § 371 of International Patent Application No. PCT/US2011/050320, filed Sep. 2, 2011, which claims priority from U.S. provisional application Ser. Nos. 61/379,812, and 61/379,819 both filed Sep. 3, 2010, Ser. No. 61/386,037, and 61/386,044 both filed Sep. 24, 2010, Ser. No. 61/478,995 filed Apr. 26, 2011 and Ser. No. 61/480,423 filed Apr. 29, 2011, the contents of which are fully incorporated herein by reference.

FIELD OF THE INVENTION

The present invention relates to compounds and composition for inhibition of Nicotinamide phosphoribosyltransferase ("NAMPT"), their synthesis, applications and antidote.

BACKGROUND OF THE INVENTION

Nicotinamide adenine dinucleotide (NAD) plays fundamental roles in both cellular energy metabolism and cellular signaling. In energy metabolism, the chemistry of the pyridine ring allows NAD to readily accept and donate electrons in hydride transfer reactions catalyzed by numerous dehydrogenases.

The preparation of a class of compounds, comprising several subclasses, which act as inhibitors of the formation of nicotinamide adenyl nucleotide, and their use thereof as anti-tumor agents, is already described in the patent applications WO00/50399, WO97/48695, WO97/48696, WO97/48397, WO99/31063, WO99/31060, WO99/31087, WO99/31064, WO00/50399 and WO03/80054.

One of these inhibitors, (E)-N-[4-(1-benzoylpiperidin-4-yl)butyl]-3-(pyridine-3-yl)-acrylamide also known as APO866, FK866, WK175, or WK22.175 and hereinafter referred to as FK866 [International Non-proprietary Name], is especially described in the literature as an anticancer agent. FK866 may be used for treatment of diseases implicating deregulated apoptosis such as cancer. It has been demonstrated in the prior art that FK866 interferes with nicotinamide adenyl dinucleotide (also known and hereinafter referred to as NAD) biosynthesis and induces apoptotic cell death without any DNA damaging effects.

Additionally, FK866 ((E)-N-[4-(1-benzoylpiperidin-4-yl)butyl]-3-(pyridin-3-yl) acrylamide) induces apoptosis in HepG2 cells without having primary effects on cellular energy metabolism. (Hasmann M, Schemainda I. FK866, a Highly Specific Noncompetitive Inhibitor of Nicotinamide Phosphoribosyltransferase, Represents a Novel Mechanism for Induction of Tumor Cell Apoptosis. Cancer Res 2003; 63:7436-7442. [PubMed: 14612543]) Instead of causing immediate cytotoxicity, it inhibits NAMPT and depletes the cells of NAD, suggesting that FK866 could be a promising agent against cancer cells that rely on nicotinamide to synthesize NAD. The crystal structure of the NAMPT-FK866 complex reveals that the compound binds at the nicotinamide-binding site of NAMPT to inhibit its activity. FK866 has been tested in a murine renal cell carcinoma model and shown to display anti-tumor, antimetastatic, and anti-angiogenic activities (Drevs J, et al. Antiangiogenic potency of FK866/K22.175, a new inhibitor of intracellular NAD biosynthesis, in murine renal cell carcinoma. Anticancer Res 2003; 23:4853-4858. [PubMed:14981935]).

In a mouse mammary carcinoma model, FK866 also induces a delay in tumor growth and an enhancement in tumor radiosensitivity accompanied with dose-dependent decreases in NAD levels, pH, and energy status. A chemosensitizing effect of FK866 has also been observed on anti-neoplastic 1-methyl-3-nitro-1-nitrosoguanidinium (MNNG)-induced cell death in THP-1 and K562 leukemia cell lines (Pogrebniak A, et al. Chemopotentiating effects of a novel NAD biosynthesis inhibitor, FK866, in combination with antineoplastic agents. Eur J Med Res 2006; 11:313-321. [PubMed: 17052966]).

The efficacy of GMX1777 was evaluated in xenograft models and the pharmacokinetic profile of GMX1778 and its effect on nicotinamide adenine dinucleotide cellular levels was measured by liquid chromatography/mass spectrometry. (Beauparlant P., et al. Preclinical development of the nicotinamide phosphoribosyl transferase inhibitor prodrug GMX1777. Anticancer Drugs. 2009 June; 20(5):346-54).

GMX1777 is a water-soluble intravenously administered prodrug of GMX1778 that Gemin X in-licensed from LEO Pharma (LEO numbers: EB1627 and CHS828, respectively). These compounds and other substituted cyanoguanidines have the structures of Table 1. None of the compounds of the present invention are cyanoguanidines.

TABLE 1

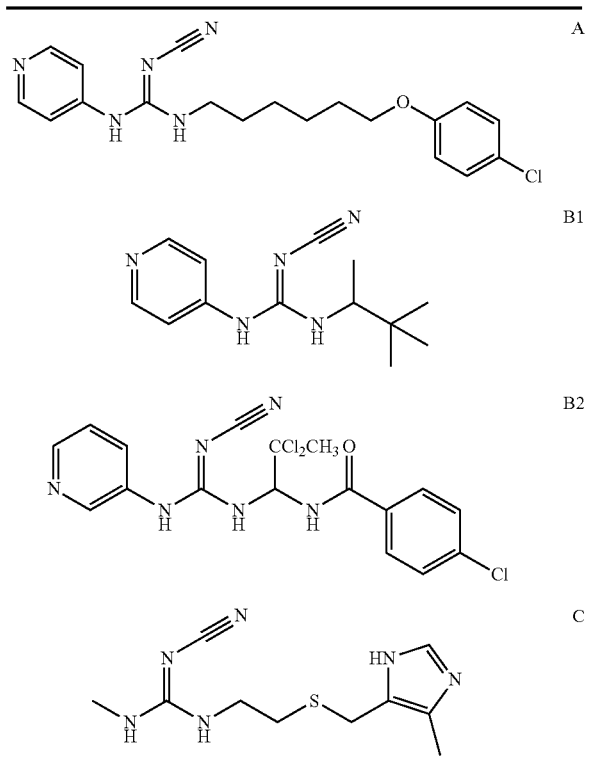

Substituted Cyanoguanidines with Defined Pharmacological Effects:
A Cytotoxic CHS 828;
B Potassium channel openers pinacidil (B1) and 12 g of compound as described in Perez-Medrano et al (B2); and
c Histamine-II receptor antagonist cimetidine. (from Lövborg et al. *BMC Research Notes* 2009 2:114 doi: 10.1186/1756-0500-2-114)

More recently, CHS-828 has been identified as a NAMPT inhibitor (Olesen U H, et al. Anticancer agent CHS-828 inhibits cellular synthesis of NAD. Biochem Biophys Res Commun 2008; 367:799-804. [PubMed: 18201551]). CHS-828 has been shown that this compound potently inhibits cell growth in a broad range of tumor cell lines, although the detailed mechanism for this inhibitory effect of CHS-828 remains undetermined (Ravaud A, et al. Phase I study and guanidine kinetics of CHS-828, a guanidine-containing compound, administered orally as a single dose every 3 weeks in solid tumors: an ECSG/EORTC study. Eur J Cancer 2005; 41:702-707. [PubMed: 15763645]). Both FK866 and CHS-828 are currently in clinical trials for cancer treatments.

There are numerous uses for drugs which inhibit NAMPT.

Lack of NAMPT expression strongly affects development of both T and B lymphocytes. By using mutant forms of this protein and a well-characterized pharmacological inhibitor (FK866), authors demonstrated that the ability of the NAMPT to regulate cell viability during genotoxic stress requires its enzymatic activity. Collectively, these data demonstrate that NAMPT participates in cellular resistance to genotoxic/oxidative stress, and it may confer to cells of the immune system the ability to survive during stressful situations such as inflammation. (Rongvaux, A., et al. *The Journal of Immunology*, 2008, 181: 4685-4695).

NAMPT may also have effects on endothelium (EC) in relation to high glucose levels, oxidative stress and on aging. It is also believed that NAMPT may enable proliferating human EC to resist the oxidative stress of aging and of high glucose, and to productively use excess glucose to support replicative longevity and angiogenic activity.

SUMMARY OF THE INVENTION

One aspect of this invention is the provision of compounds, compositions, kits, and antidotes for the NAMPT pathway in mammals having a compound of the Formula I:

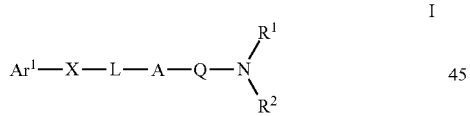

I wherein:

$Ar^1$ is aryl, heteroaryl or heterocycloalkyl, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with aryl, heteroaryl or heterocycloalkyl, still further wherein any of said aryl, heteroaryl and heterocycloalkyl is either unsubstituted or optionally independently substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, —N(R$^3$)—C(O)-alkyl, —N(R$^3$)—C(O)-aryl, —N(R$^3$)—C(O)—O—alkyl, —N(R$^3$)—C(O)—O-aryl, -cycloalkyl, -heterocycloalkyl, -aryl, —C(O)-aryl, —S(O)-aryl, and heteroaryl, with the proviso that no two adjacent ring heteroatoms are both S or both O;

X is a straight or branched $C_1$-$C_6$ alkyl;

L is selected from NHC(O)NH, OC(O)NH, NHC(O)O, OCH$_2$C(O)NH, C(O)NH, NHC(S)NH, OC(S)NH, NHC(S)O, OCH$_2$C(S)NH, or C(S)NH;

A is aryl, heteroaryl, heterocycloalkyl or $C_3$ to $C_8$ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, —N(R$^3$)—C(O)-alkyl, —N(R$^3$)—C(O)-aryl, —N(R$^3$)—C(O)—O-alkyl, —N(R$^3$)—C(O)—O-aryl, -cycloalkyl, -heterocycloalkyl, -aryl, —C(O)-aryl, —S(O)-aryl, and heteroaryl;

Q is C(O), S(O), S(O)$_2$;

R$^3$ is H, alkyl or arylalkyl-;

z is 0, 1 or 2; and either:

(i) (a) R$^1$ is selected from H, a straight or branched $C_1$ to $C_7$ alkyl, straight or branched $C_1$ to $C_7$ alkoxy, straight or branched $C_1$ to $C_4$ hydroxyalkyl, aryl, heteroaryl, heterocycloalkyl, cycloalkyl, arylalkyl-, heteroarylalkyl-, heterocycloalkylalkyl-, cycloalkylalkyl-, hydroxyalkyl-, alkoxyalkyl-, heterospirocycloalkyl and heterospiroheterocycloalkyl, wherein the heteroatoms of said heteroaryl and heterocycloalkyl in the moieties above are independently selected from one or more N, O and S, with the proviso that no two adjacent ring heteroatoms are both S or both O, further wherein R$^1$ can be either unsubstituted or optionally independently (i) either substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-aryl, —S(O$_2$)alkyl, —S(O$_2$)CF$_3$, -cycloalkyl, alkylenedioxy (e.g, methylenedioxy), -heterocycloalkyl, -aryl, and heteroaryl, or (ii) fused with a cycloalkyl, -heterocycloalkyl, -aryl, or heteroaryl; and (b) R$^2$ is selected from H, a straight or branched $C_1$ to $C_7$ alkyl, straight or branched $C_1$ to $C_7$ alkoxy, straight or branched $C_1$ to $C_4$ hydroxyalkyl, aryl, heteroaryl, heterocycloalkyl, cycloalkyl, arylalkyl-, heteroarylalkyl-, heterocycloalkylalkyl-, cycloalkylalkyl-, hydroxyalkyl-, alkoxyalkyl-, heterospirocycloalkyl and heterospiroheterocycloalkyl, wherein the heteroatoms of said heteroaryl and heterocycloalkyl in the moieties above are independently selected from one or more N, O and S, with the proviso that no two adjacent ring heteroatoms are both S or both O, further wherein R$^2$ can be either unsubstituted or optionally independently (i) either substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —OCH$_z$F$_{3-z}$, alkyl, alkenyl, alkynyl, hydroxyalkyl-, (hydroxyalkyl)oxy, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-aryl, —S(O$_2$)alkyl, —S(O$_2$)CF$_3$, -cycloalkyl, alkylenedioxy (e.g, methylenedioxy), -heterocycloalkyl, -aryl, and heteroaryl, or (ii) fused with a cycloalkyl, -heterocycloalkyl, -aryl, or heteroaryl;

or (ii) R$^1$ and R$^2$ are joined together to form, along with the N they are shown attached to in the formula, a C$_3$-C$_8$ heterocycloalkyl, a C$_3$-C$_8$ heterocycloalkenyl, a fused bicyclic heterocycloalkyl, a fused tricyclic heterocycloalkyl, spiroheterocycloalkyl or a heterospiroheterocycloalkyl, wherein each of said heterocycloalkyl, heterocycloalkenyl, spiroheterocycloalkyl and heterospiroheterocycloalkyl can optionally contain one or more heteroatoms in addition to the N atom they are shown attached to in the formula, said heteroatoms being selected from N, S and O, with the proviso that no two adjacent ring heteroatoms are both S or both O, further wherein each of said heterocycloalkyl, fused bicyclic heterocycloalkyl, fused tricyclic heterocycloalkyl, heterocycloalkenyl, spiroheterocycloalkyl and heterospiroheterocycloalkyl can be either unsubstituted or optionally independently substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-aryl, —S(O$_2$)alkyl, —S(O$_2$)CF$_3$, -cycloalkyl, alkylenedioxy (e.g, methylenedioxy), -heterocycloalkyl, -aryl, and heteroaryl;

and pharmaceutically acceptable salts, solvates, esters and isomers thereof, with the proviso that the compound of Formula I is not 1-(pyridin-3-ylmethyl)-3-(4-sulfamoylphenyl)thiourea, 3-[4-(morpholine-4-sulfonyl)phenyl]-1-(pyridine-4-ylmethyl)thiourea or 3-[4-(piperidine-1-sulfonyl)phenyl]-1-(pyridine-4-ylmethyl)thiourea.

Another aspect of this invention is the provision of compounds of Formula I where X, L, Q, Ar$^1$ and A are as defined in Formula I and R$^1$ is selected from H, a straight or branched C$_1$ to C$_7$ alkyl, straight or branched C$_1$ to C$_7$ alkoxy, straight or branched C$_1$ to C$_4$ hydroxyalkyl, aryl, heteroaryl, heterocycloalkyl, cycloalkyl, arylalkyl-, heteroarylalkyl-, heterocycloalkylalkyl-, cycloalkylalkyl-, hydroxyalkyl-, alkoxyalkyl-, spiroheterocycloalkyl and heterospiroheterocycloalkyl, wherein the heteroatoms of said heteroaryl and heterocycloalkyl in the moieties above are independently selected from one or more N, O and S, with the proviso that no two adjacent ring heteroatoms are both S or both O, further wherein R$^1$ can be either unsubstituted or optionally independently (i) either substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-aryl, —S(O$_2$)alkyl, —S(O$_2$)CF$_3$, -cycloalkyl, alkylenedioxy (e.g, methylenedioxy), -heterocycloalkyl, -aryl, and heteroaryl, or (ii) fused with a cycloalkyl, -heterocycloalkyl, -aryl, or heteroaryl; and R$^2$ is selected from H, a straight or branched C$_1$ to C$_7$ alkyl, straight or branched C$_1$ to C$_7$ alkoxy, straight or branched C$_1$ to C$_4$ hydroxyalkyl, aryl, heteroaryl, heterocycloalkyl, cycloalkyl, arylalkyl-, heteroarylalkyl-, heterocycloalkylalkyl-, cycloalkylalkyl-, hydroxyalkyl-, alkoxyalkyl-, spiroheterocycloalkyl and heterospiroheterocycloalkyl, wherein the heteroatoms of said heteroaryl and heterocycloalkyl in the moieties above are independently selected from one or more N, O and S, with the proviso that no two adjacent ring heteroatoms are both S or both O, further wherein R$^2$ can be either unsubstituted or optionally independently (i) either substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-aryl, —S(O$_2$)alkyl, —S(O$_2$)CF$_3$, -cycloalkyl, alkylenedioxy (e.g, methylenedioxy), -heterocycloalkyl, -aryl, and heteroaryl, or (ii) fused with a cycloalkyl, -heterocycloalkyl, -aryl, or heteroaryl;

and pharmaceutically acceptable salts, solvates, esters and isomers thereof, with the proviso that the compound of Formula I is not 1-(pyridin-3-ylmethyl)-3-(4-sulfamoylphenyl)thiourea, 3-[4-(morpholine-4-sulfonyl)phenyl]-1-(pyridine-4-ylmethyl)thiourea or 3-[4-(piperidine-1-sulfonyl)phenyl]-1-(pyrdin-4-ylmethyl)thiourea.

Another aspect of this invention is the provision of compounds of Formula I where X, L, Q, Ar$^1$ and A are as defined in Formula I:

where R$^1$ and R$^2$ are joined together to form, along with the N they are shown attached to in the formula, a C$_3$-C$_8$ heterocycloalkyl, a C$_3$-C$_8$ heterocycloalkenyl, a fused bicyclic heterocycloalkyl, a fused tricyclic heterocycloalkyl, spiroheterocyclaolkyl or a heterospiroheterocycloalkyl, wherein each of said heterocycloalkyl, heterocycloalkenyl, spiroheterocyclaolkyl and heterospiroheterocycloalkyl can optionally contain one or more heteroatoms in addition to the N atom they are shown attached to in the formula, said heteroatoms being selected from N, S and O, with the proviso that no two adjacent ring heteroatoms are both S or both O, further wherein each of said heterocycloalkyl, fused bicyclic heterocycloalkyl, fused tricyclic heterocycloalkyl, heterocycloalkenyl, spiroheterocyclaolkyl and heterospiroheterocycloalkyl can be either unsubstituted or optionally independently substituted with one or more substituents which can be the same or different and are independently selected from the group consisting of deuterium, halo, cyano, isocyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO₂, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R³)—C(O)-alkyl, —N(R³)—C(O)-aryl, —S(O₂)alkyl, —S(O₂)CF₃, -cycloalkyl, alkylenedioxy (e.g, methylenedioxy), -heterocycloalkyl, -aryl, and heteroaryl;

with the proviso that the compound is not 1-(pyridin-3-ylmethyl)-3-(4-sulfamoylphenyl)thiourea, 3-[4-(morpholine-4-sulfonyl)phenyl]-1-(pyridine-4-ylmethyl)thiourea or 3-[4-(piperidine-1-sulfonyl)phenyl]-1-(pyrdin-4-ylmethyl)thiourea.

Another aspect of this invention is the provision of compounds, compositions, kits, and antidotes for the NAMPT pathway in mammals having a compound of the Formula II:

Ar¹—(CHR)$_n$-L-Ar²—X—R¹  II wherein
Ar¹ is aryl, heteroaryl or heterocycloalkyl, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with aryl, heteroaryl or heterocycloalkyl, still further wherein any of said aryl, heteroaryl and heterocycloalkyl is either unsubstituted or optionally independently substituted with one or more substituents which can be the same or different and are independently selected from the group consisting of deuterium, halo, cyano, isocyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, —N(R³)—C(O)-alkyl, —N(R³)—C(O)-aryl, —N(R³)—C(O)—O—alkyl, —N(R³)—C(O)—O-aryl, -cycloalkyl, -heterocycloalkyl, -aryl, —C(O)-aryl, —S(O)-aryl, and heteroaryl, with the proviso that no two adjacent ring heteroatoms are both S or both O;
R is H, a straight or branched C₁-C₆ alkyl, or arylalkyl;
n is 0, 1, 2, 3 or 4;
L is selected from NHC(O)NH, OC(O)NH, NHC(O)O, OCH₂C(O)NH, C(O)NH, NHC(S)NH, OC(S)NH, NHC(S)O, OCH₂C(S)NH, or C(S)NH, with the proviso that when L is C(O)NH, then n is 0;
Ar² is aryl, heteroaryl, heterocycloalkyl or C₃ to C₈ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, isocyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, —N(R³)—C(O)-alkyl, —N(R³)—C(O)-aryl, —N(R³)—C(O)—O-alkyl, —N(R³)—C(O)—O-aryl, -cycloalkyl, -heterocycloalkyl, -aryl, —C(O)-aryl, —S(O)-aryl, and heteroaryl;
X is S, S(O), S(O)₂, O or C(O);
R¹ is cycloalkyl, —CH$_z$F$_{3-z}$, aryl, heterocycloalkyl, heteroaryl, alkyl, -alkenyl, -alkynyl, (aryl)alkyl-, (heteroaryl)alkyl- or (heterocycloalkyl)alkyl-, (i) wherein each of said cycloalkyl, aryl, heterocycloalkyl, heteroaryl and alkyl is either unsubstituted or optionally substituted with 1, 2, 3, 4 or 5 substituents which can be the same or different and are independently selected from the group consisting of deuterium, halo, cyano, amino, aminoalkyl-, (amino)alkoxy-, —CONH₂, —C(O)NH(alkyl), —C(O)N(alkyl)₂, —C(O)NH(aryl), —C(O)N(aryl)₂, —OCH$_z$F$_{3-z}$, alkyl, -alkenyl, -alkynyl, alkoxy-, hydroxy, -alkylhydroxy, aryloxy- or (alkoxyalkyl)amino-, -cycloalkyl, -heterocycloalkyl, -aryl, —S(O)₂-alkyl, —S(O)₂-aryl, —S(O)₂—CF₃, —C(O)N(alkyl)₂, —C(O)alkyl, —NH—C(O)-alkyl, —NH—C(O)-aryl, methylenedioxy, and heteroaryl, (ii) further wherein each of said cycloalkyl, aryl, heterocycloalkyl, and heteroaryl may additionally optionally be fused with independently selected aryl, heteroaryl, heterocycloalkyl or cyloalkyl;
R³ is H, alkyl or arylalkyl-;
z is 0, 1, or 2;
and pharmaceutically acceptable salts, solvates, esters, prodrugs and isomers thereof, with the proviso that the compound of Formula I is not 3-{1-[(4-methoxybenzene)sulfonyl]piperidin-4-yl}-1-(pyridin-3-ylmethyl)urea, or 1-(4-phenoxyphenyl)-3-(pyridin-3-ylmethyl)thiourea.

Another aspect of this invention is the provision of compounds, compositions, kits, and antidotes for the NAMPT pathway in mammals derived from compounds of Formula I and Formula II and having the formula of Formula III:

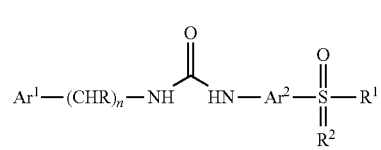

wherein:
Ar¹ is 5 to 12 membered heteroaryl comprising 1, 2, 3 or 4 heteroatom(s) independently selected from N, S or O, wherein said heteroaryl is unsubstituted or substituted by one or more R$^a$ selected from the group consisting of —NH₂, oxo, halo, haloalkyl, —NH(CO)O-alkyl, —C(O)NH₂ and 3,4-dihydroxy-5-methyltetrahydrofurane; and wherein said heteroaryl can comprise one or more N-oxide(s) formed with a N atom member of said heteroaryl, with the proviso that no two adjacent ring heteroatoms are both S or both O;
Ar² is aryl or 5 or 6 membered heteroaryl comprising 1, 2, 3 or 4 heteroatom(s) independently selected from N, S or O;
R is H, a straight or branched C₁-C₆ alkyl, or arylalkyl;
R¹ is —NR³R⁴ wherein R³ is H, alkyl or —S(O)₂alkyl and R⁴ is alkyl, hydroxyalkyl, —S(O)₂alkyl, —(CH₂)$_q$cycloalkyl, —(CH₂)$_q$heterocycloalkyl, aryl, arylalkyl-, —(CH₂)$_q$heteroaryl;
haloalkyl,
cycloalkyl;
aryl;
heterocycloalkyl; or
heteroaryl; wherein:
(i) each of said cycloalkyl, aryl, heterocycloalkyl or heteroaryl is unsubstituted or substituted with 1, 2, 3, 4 or 5 substituents which can be the same or different and are independently selected from the group consisting of:

deuterium, halo, cyano, alkyl, hydroxyl, hydroxyalkyl, hydroxyalkoxy, cyanoalkyl, haloalkyl, alkenyl, alkynyl, alkoxy, alkylalkoxy, haloalkoxy, arylalkenyl-, aryloxy, benzyloxy, oxo, —(CH$_2$)$_q$—NR$^b$R$^c$, —(CH$_2$)$_q$—CONR$^b$R$^c$, —S(O)$_2$-alkyl, —S(O)$_2$-aryl, —S(O)$_2$NH-alkyl, —S(O)$_2$N(alkyl)$_2$, —S(O)$_2$-heterocycloalkyl, —S(O)$_2$—CF$_3$, —C(O)alkyl, —C(O)aryl, —C(O)alkylenylaryl, —C(O)O-alkyl, —NH—C(O)alkyl, —NH—C(O)aryl, methylenedioxy, —(CH$_2$)$_q$cycloalkyl, cycloalkylalkoxy-, aryl, arylalkyl-, —(CH$_2$)$_q$heteroaryl, and —(CH$_2$)$_q$heterocycloalkyl, wherein each of said cycloalkyl, heterocycloalkyl, aryl or heteroaryl may be substituted by one or more halo, nitro, haloalkyl, haloalkoxy, oxo, cyano, alkyl, haloalkyl, or alkoxy and;

(ii) each of said cycloalkyl, heterocycloalkyl, aryl, or heteroaryl may optionally additionally be fused with independently selected aryl, heteroaryl, heterocycloalkyl or cycloalkyl to from a bicyclic or tricyclic group that may be substituted by one or more halo, cyano, alkyl or alkoxy;

R$^2$ is O or absent,

R$^b$ and R$^c$ are independently selected from the group consisting of H, alkyl, hydroxyalkyl, alkoxy, aryl, alkoxyalkyl, —S(O)$_2$alkyl and cycloalkyl or R$^b$ and R$^c$ can form a 5 or 6 membered heterocycloalkyl group together with the nitrogen atom to which they are attached, wherein said heterocycloalkyl group may contain one or more additional heteroatom(s) selected from N, S or 0;

n is 0, or 1;

q is 0, 1 or 2;

and pharmaceutically acceptable salts, solvates, esters and isomers thereof, with the proviso that the compound of Formula III is not 1-(pyridin-3-ylmethyl)-3-(4-sulfamoylphenyl)thiourea, 3-[4-(morpholine-4-sulfonyl)phenyl]-1-(pyridine-4-ylmethyl)thiourea or 3-[4-(piperidine-1-sulfonyl)phenyl]-1-(pyrdin-4-ylmethyl)thiourea.

Another embodiment of the invention is the provision of a compound of Formula III where Ar$^1$ is pyridine, n is 1, Ar$^2$ is phenyl and the Formula becomes Formula IIIA:

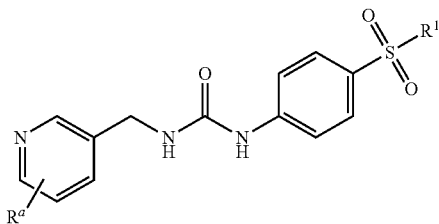

Formula IIIA wherein R$^1$ and R$^a$ are as defined in Formula III with the proviso that the compounds are not N-[4-(phenylsulfonyl)phenyl]-N'-(3-pyridinylmethyl)urea, N,N-diethyl-4-[[[(3-pyridinylmethyl)amino]carbonyl]amino]benzenesulfonamide, or 4-[[[(3-pyridinylmethyl)amino]carbonyl]amino]benzenesulfonamide.

Another aspect of the invention is compounds of Formula IIIA wherein:

R$^a$ is more and can be selected from the group consisting of amino, oxo, halo, halo(C$_1$-C$_6$)alkyl, —NH(CO)O—(C$_1$-C$_6$)alkyl and —C(O)NH$_2$; and wherein said pyridine can comprise a N-oxide formed with its N atom member;

R$^1$ is —NR$^3$R$^4$ wherein R$^3$ is H, C$_1$-C$_6$-alkyl or —S(O)$_2$(C$_1$-C$_6$)alkyl and R$^4$ is (C$_1$-C$_6$)alkyl, hydroxy(C$_1$-C$_6$)alkyl, —S(O)$_2$(C$_1$-C$_6$)alkyl, —(CH$_2$)$_q$cycloalkyl, —(CH$_2$)$_q$heterocycloalkyl, aryl, aryl(C$_1$-C$_6$)alkyl-, —(CH$_2$)$_q$heteroaryl;

halo(C$_1$-C$_6$)alkyl, cycloalkyl;

aryl;

heterocycloalkyl; or heteroaryl wherein:

each of said cycloalkyl, aryl, or heteroaryl is unsubstituted or substituted with 1, 2, 3, 4 or 5 substituents which can be the same or different and are independently selected from the group consisting of:

halo, cyano, (C$_1$-C$_6$)alkyl, hydroxyl, hydroxy(C$_1$-C$_6$)alkyl, hydroxy(C$_1$-C$_6$)alkoxy, halo(C$_1$-C$_6$)alkyl, (C$_1$-C$_6$)alkoxy, (C$_1$-C$_6$)alkyl(C$_1$-C$_6$)alkoxy, halo(C$_1$-C$_6$)alkoxy, aryl(C$_2$-C$_6$)alkenyl-, aryloxy, benzyloxy, oxo, —(CH$_2$)$_q$—NR$^b$R$^c$, —(CH$_2$)$_q$—CONR$^b$R$^c$, —S(O)$_2$—(C$_1$-C$_6$)alkyl, —S(O)$_2$NH—(C$_1$-C$_6$)alkyl, —S(O)$_2$-heterocycloalkyl, —S(O)$_2$—CF$_3$, —C(O)(C$_1$-C$_6$)alkyl, —C(O)aryl, —C(O) (C$_2$-C$_6$)alkylenylaryl, —C(O)O—(C$_1$-C$_6$) alkyl, —(CH$_2$)$_q$cycloalkyl, cycloalkyl(C$_1$-C$_6$) alkoxy-, aryl, aryl(C$_1$-C$_6$)alkyl-, —(CH$_2$)$_q$heteroaryl, and —(CH$_2$)$_q$heterocycloalkyl, wherein each of said cycloalkyl, heterocycloalkyl, aryl or heteroaryl may be substituted by one or more halo, nitro, halo(C$_1$-C$_6$)alkyl, halo(C$_1$-C$_6$)alkoxy, oxo, cyano, (C$_1$-C$_6$)alkyl, halo(C$_1$-C$_6$)alkyl, or (C$_1$-C$_6$) alkoxy;

R$^b$ and R$^c$ are independently selected from the group consisting of H, (C$_1$-C$_6$)alkyl, hydroxy(C$_1$-C$_6$)alkyl, (C$_1$-C$_6$) alkoxy, aryl, (C$_1$-C$_6$)alkoxy(C$_1$-C$_6$)alkyl, —S(O)$_2$(C$_1$-C$_6$) alkyl and (C$_3$-C$_6$)cycloalkyl or R$^b$ and R$^c$ can form a 5 or 6 membered heterocycloalkyl group together with the nitrogen atom to which they are attached, wherein said heterocycloalkyl group may contain one or more additional heteroatom(s) selected from N, S or O q is 0 or 1; and pharmaceutically acceptable salts thereof, with the proviso that the compound of Formula IIIA is not: N-[4-(phenylsulfonyl)phenyl]-N'-(3-pyridinylmethyl)urea, N,N-diethyl-4-[[[(3-pyridinylmethyl)amino]carbonyl] amino]benzenesulfonamide, or 4-[[[(3-pyridinylmethyl) amino]carbonyl]amino]benzenesulfonamide.

Another aspect of this invention is the provision of methods of treating a disease via the inhibition of NAMPT in a subject (e.g., a human) in need thereof by administering to the subject an effective amount of the compound or the pharmaceutical formulation of the present invention.

Still another aspect of this invention is to provide a method for treating, preventing, inhibiting or eliminating a disease or condition in a patient by inhibiting NAMPT in said patient by administering a therapeutically affective amount of at least one compound of this disclosure, wherein said disease or condition is selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spondylitis, gragt-versus-host disease, Alzhemier's disease, cerebrovascular accident, arteriosclerosis, diabetes, glomerulonephritis, metabolic syndrome, non-small cell lung cancer, small cell lung cancer, multiple myeloma, leukemia, lymphomas, squamous cell cancers, kidney cancer, uretral and bladder cancers, cancers of head and neck, cancers of the brain and central nervous system.

Another preferred embodiment is a pharmaceutical formulation comprising a pharmaceutically acceptable compound of the present invention, which provides, upon administration to a human, a decrease in tumor burden and/or metastases. The pharmaceutical formulation can be administered by oral means or other suitable means.

Yet another embodiment is a method of treating ovarian cancer in a subject (e.g., a human) in need thereof by administering to the subject an effective amount of the compound or the pharmaceutical formulation of the present invention.

Yet another embodiment is a method of treating colon cancer in a subject (e.g., a human) in need thereof by administering to the subject an effective amount of the compound or the pharmaceutical formulation of the present invention.

Yet another embodiment is a method of treating breast cancer in a subject (e.g., a human) in need thereof by administering to the subject an effective amount of the pharmaceutical formulation of the present invention. in a subject (e.g., a human) in need thereof by administering to the subject an effective amount of the compound or the pharmaceutical formulation of the present invention.

Yet another embodiment is a method of treating leukemia in a subject (e.g., a human) in need thereof by administering to the subject an effective amount of the compound or the pharmaceutical formulation of the present invention.

Yet another embodiment is a method of treating colon cancer, before or after surgical resection and/or radiation therapy, in a subject (e.g., a human) in need thereof by administering to the subject an effective amount of the compound or the pharmaceutical formulation of the present invention.

Yet another embodiment is a method of treating cancer, before or after surgical resection and/or radiation therapy, in a subject (e.g., a human) in need thereof by administering to the subject an effective amount of the compound or the pharmaceutical formulation of the present invention, including adjunctive therapy to treat nausea, with or without dexamethasone.

Yet another embodiment is a method of treating cancer, before or after surgical resection and or radiation therapy, in a subject (e.g., a human) in need thereof by administering to the subject an effective amount of the compound or the pharmaceutical formulation of the present invention, including adjunctive therapy with one or more additional therapeutic agents, or their pharmaceutically acceptable salts thereof. Non-limiting examples of such additional therapeutic agents include cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil or 5-FU); anti-metabolites (such as methoxtrexate); alkylating agents (such as temozolomide, cyclophosphamide); Farnesyl protein transferase inhibitors (such as, SARASAR™, (4-[2-[4-[(11R)-3,10-dibromo-8-chloro-6,11-dihydro-5H-benzo[5-6]cyclohepta[1,2-b]pyridin-11-yl-]-1-piperidinyl]-2-oxoehtyl]-1-piperidine-carboxamide, or SCH 66336), tipifamib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® (from Astra Zeneca Pharmaceuticals, England), Tarceva® (EGFR kinase inhibitors), antibodies to EGFR (e.g., C225), GLEEVEC® (C-ab1 kinase inhibitor from Novartis Pharmaceuticals, East Hanover, N.J.); interferons such as, for example, Intron® (from Merck & Company), Peg-Intron® (from Merck & Company); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN®. from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade®, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath, 5-fluorouracil and leucovorin, with or without a 5-HT$_3$ receptor inhibitor (e.g., dolansetron, granisetron, ondansetron) with or without dexamethasone.

If formulated as a fixed dose, such combination products employ the compounds of this invention within the dosage range described herein (or as known to those skilled in the art) and the other pharmaceutically active agents or treatments within its dosage range. For example, the CDC2 inhibitor olomucine has been found to act synergistically with known cytotoxic agents in inducing apoptosis (J. Cell Sci., (1995) 108, 2897). The compounds of the invention may also be administered sequentially with known anticancer or cytotoxic agents when a combination formulation is inappropriate. In any combination treatment, the invention is not limited in the sequence of administration; compounds of Formula (I) may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of the invention is a pharmaceutical composition comprising a compound according to the invention and a cell rescuing agent. In a certain embodiment according to the invention, the cell rescuing agent is selected from the group consisting of nicotinamide, nicotinamide mononucleotide (NMN) and nicotinic acid.

Definitions

As used above, and throughout this disclosure, the following terms, unless otherwise indicated, shall be understood to have the following meanings. If a definition is missing, convention definition as known to one skilled in the art controls.

"Patient" includes both human and animals.

"Mammal" means humans and other mammalian animals.

The term "inhibitor" refers to a molecule such as a compound, a drug, an enzyme activator or a hormone that blocks or otherwise interferes with a particular biologic activity.

The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective" amount in any individual case may be determined by one of ordinary skill in the art using routine experimentation. Thus, the expression "effective amount" generally refers to the quantity for which the active substance has therapeutic effects. In the present case the active substance is the inhibitor of the formation of Nicotinamide phosphoribosyltransferase (NAMPT).

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

By "pharmaceutically acceptable" or "pharmacologically acceptable" is meant a material which is not biologically or otherwise substantially undesirable, i.e., the material may be administered to an individual without causing any substantially undesirable biological effects or interacting in a deleterious manner with any of the components of the composition in which it is contained.

"Carrier materials" or what are also referred to as "excipients" include any commonly used excipients in pharmaceutics and should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

As used herein, "alkyl" means a straight chain or branched saturated chain having from 1 to 10 or 1 to 6 ($C_1$-$C_6$) carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, branched or cyclized. As used herein, "lower alkyl" means an alkyl having from 1 to 6 carbon atoms.

As used herein, an "alkenyl group" includes an unbranched or branched hydrocarbon chain having one or more double bonds therein. The double bond of an alkenyl group can be unconjugated or conjugated to another unsaturated group. Illustrative alkenyl groups include, but are not limited to, ($C_2$-$C_8$) or ($C_2$-$C_6$) alkenyl groups, such as ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted.

The term "hydroxyalkyl" denotes an alkyl group as defined above wherein at least one of the hydrogen atoms of the alkyl group is replaced by a hydroxy group. Examples of hydroxyalkyl include, but are not limited to, meththyl, ehtyl propyl, isopropyl, isobutryl, sec-butyl, tert-butyl, pentyl or n-hexyl wherein one or more hydrogen atoms are replaced by OH, as well as those hydroxyalkyl groups specifically illustrated b the examples herein below.

As used herein, "alkynyl group" includes an unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include, but are not limited to, methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred halloalkyl groups are monofluoro-, difluoro- or trifluoro-methyl, -ethyl or -propyl, for example 3,3,3-trifluoropropyl, 2-fluroethyl, 2,2,2-trifluoroethyl, fluoromethyl, trifluoromethyl.

The terms "trifluoromethyl," "sulfonyl," and "carboxyl" include $CF_3$, $SO_2$, and $CO_2H$, respectively.

The term "oxo" means a =O group.

The term alkylhydroxy or hydroxyalkyl means an alkyl group as defined above, wherein at least one of the hydrogen atoms of the alkyl group is replaced by an OH group.

The term "alkoxy" as used herein includes —O-(alkyl), wherein alkyl is defined above.

The term "haloalkoxy" denotes an alkoxy group as defined above wherein at least one of the hydrogen atoms of the alkoxy group is replaced by a halogen atom, preferably fluoro or chloro, most preferably fluoro.

The term "hydroxyalkoxy" means an alkoxy group as defined herein, wherein at least one of the hydrogen atoms of the alkoxy group is replaced by an OH group.

The term "aminoalkyl" as used herein means a group having one or more nitrogen atoms and one or more alkyl groups as defined above on the nitrogen.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Heteroarylalkyl" means a heteroaryl moiety as defined herein linked via an alkyl moiety (defined above) to a parent core. Non-limiting examples of suitable heteroaryls include 2-pyridinylmethyl, quinolinylmethyl and the like.

"Heterocyclylalkyl" means a heterocyclyl moiety as defined herein linked via an alkyl moiety (defined above) to a parent core. Non-limiting examples of suitable heterocyclylalkyls include piperidinylmethyl, piperazinylmethyl and the like.

It should also be noted that any carbon as well as heteroatom with unsatisfied valences in the text, schemes, examples and Tables herein is assumed to have the sufficient number of hydrogen atom(s) to satisfy the valences.

When any variable (e.g., aryl, heterocycle, $R^2$, etc.) occurs more than one time in any constituent or in the Formulas, its definition on each occurrence is independent of its definition at every other occurrence.

The term "N-oxide(s) forms with a N atom member of said heteroaryl" denotes a heterorayl group containing a nitrogen atom that forms a N-oxide. Illustrative and non limiting examples of such N-oxides are:

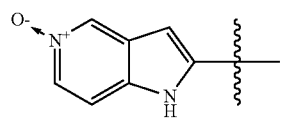

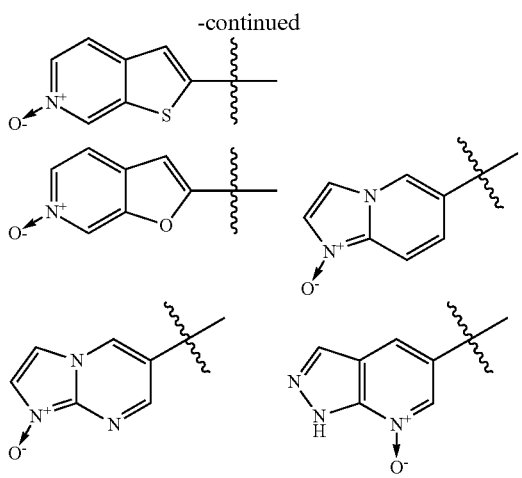

The expression: "wherein said pyridine can comprise a N-oxide formed with its N atom member" denotes the following formula:

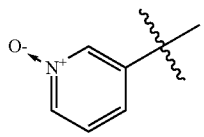

As used herein, the term "composition" is intended to encompass a product comprising the specified ingredients in the specified amounts, as well as any product which results, directly or indirectly, from combination of the specified ingredients in the specified amounts.

The term "deuterium" as used herein means a stable isotope of hydrogen having odd numbers of protons and neutrons.

The term "halo" as used herein means a substituent having at least one halogen selected from fluorine, chlorine, bromine, and iodine.

The term "cyano" as used herein means a substituent having a carbon atom joined to a nitrogen atom by a triple bond.

The term "amino" as used herein means a substituent containing at least one nitrogen atom.

The term "(amino)alkoxy" as used herein means a substituent having at least one amino group and at least one alkoxy group.

The term "aryloxy" as used herein means a substituent of the form Ar—O— where Ar is an aryl group as defined herein.

The term "benzyloxy" denotes a benzyl-O— group.

The term "arylakenyl" denotes an aryl group, as defined herein, attached to the rest of the molecule by an alkenyl group as defined herein.

The term "cycloalkylalkoxy-" denotes a cycloalkyl group as defined herein, attached to the rest of the molecule by an alkoxy group as defined herein.

The term "methylenedioxy" as used herein means a functional group with the structural formula —O—CH$_2$—O— which is connected to the molecule by two chemical bonds via the oxygens.

As used herein, "alkoxyalkyl" means -(alkyl)-O-(alkyl), wherein each "alkyl" is independently an alkyl group defined above.

The term "(alkoxyalkyl)amino" as used herein means a substituent having at least one alkoxyalkyl group as defined above and at least one amino group as defined above.

The term "spirocycloalkyl" as used herein means a spiro group (containing no heteroatom) linked in a spiro manner to a cycloalkyl group. A non-limiting example would be the moiety shown below:

The term "spiroheterocycloalkyl" as used herein means a spiro group (containing no heteroatom) linked in a spiro manner to a heterocycloalkyl group. A non-limiting example would be the moiety shown below:

The term "heterospiroheterocycloalkyl" as used herein means a spiro group (containing a hetero atom such O, N or S) linked in a spiro manner to a heterocycloalkyl group. A non-limiting example would be the moiety shown below:

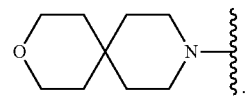

"Aryl" as used herein means a monovalent aromatic hydrocarbon radical of 6-20 or 6-10 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein. Illustrative examples of aryl groups include, but are not limited to, the following moieties:

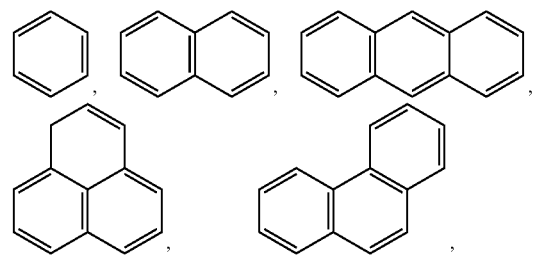

and the like.

Illustrative substituted aryls include:
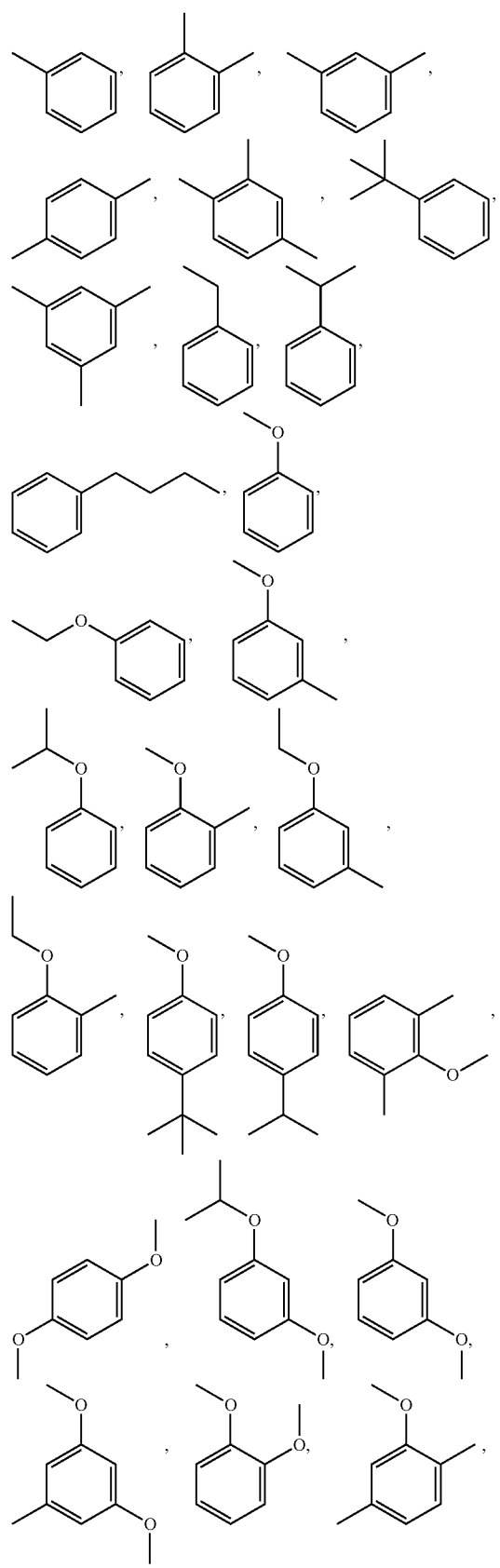
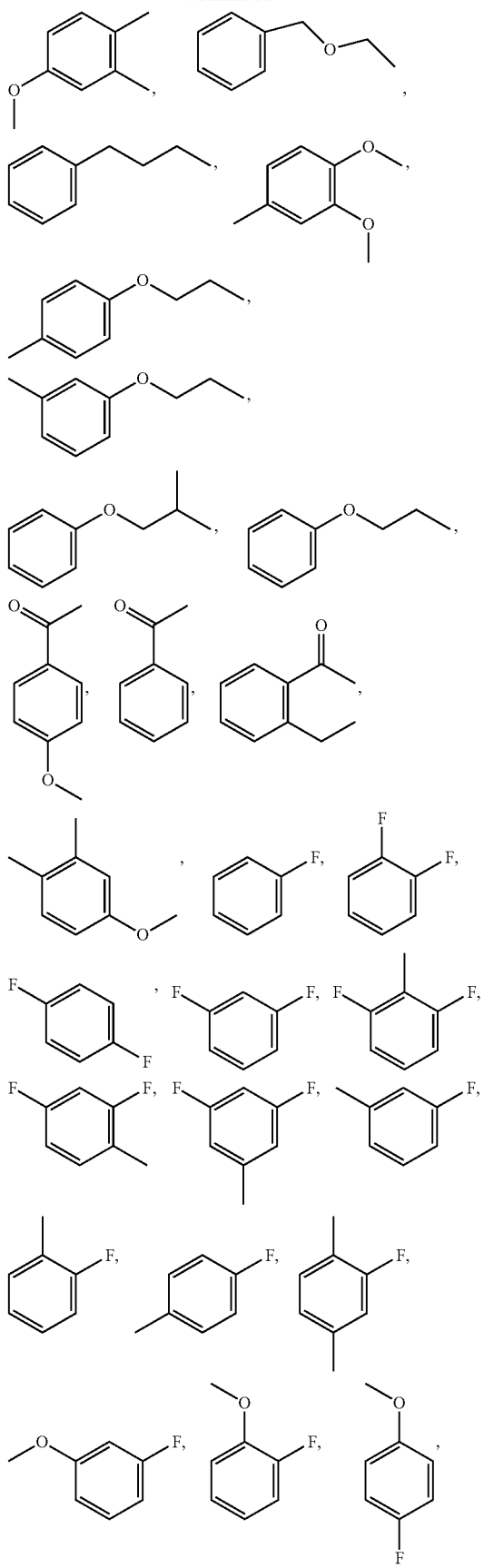

-continued
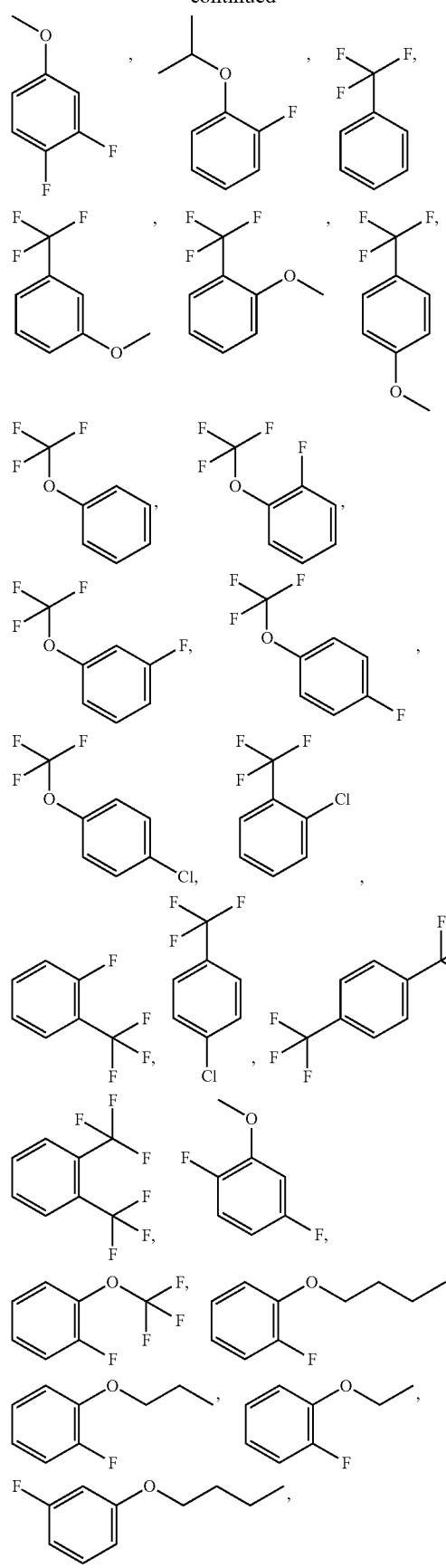
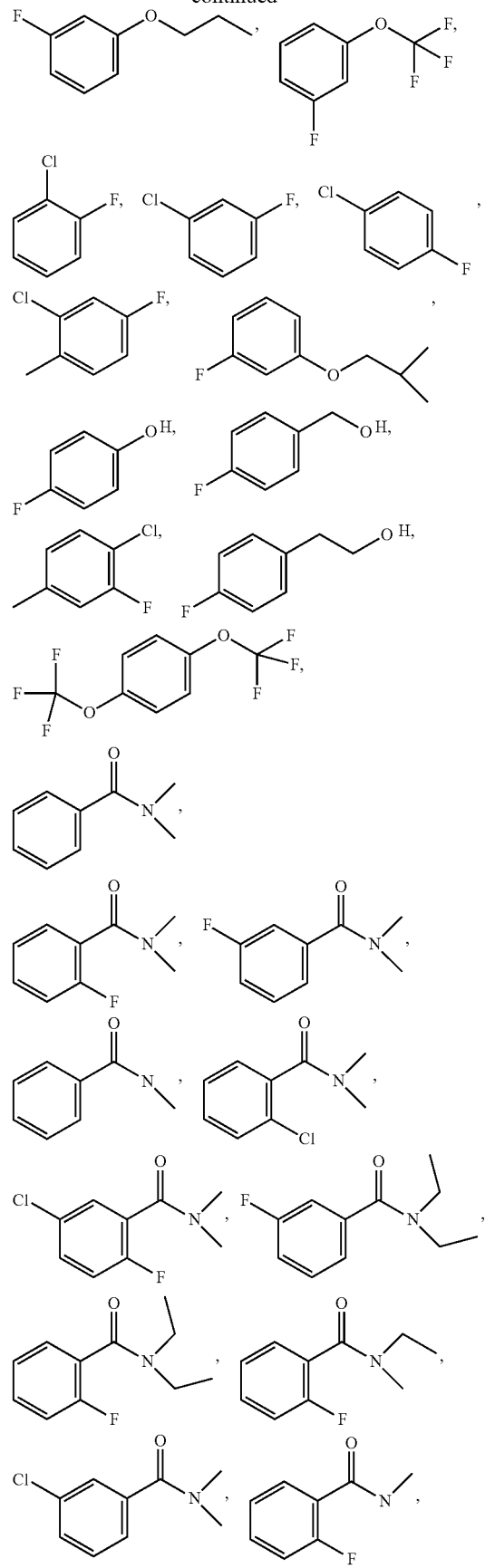

-continued
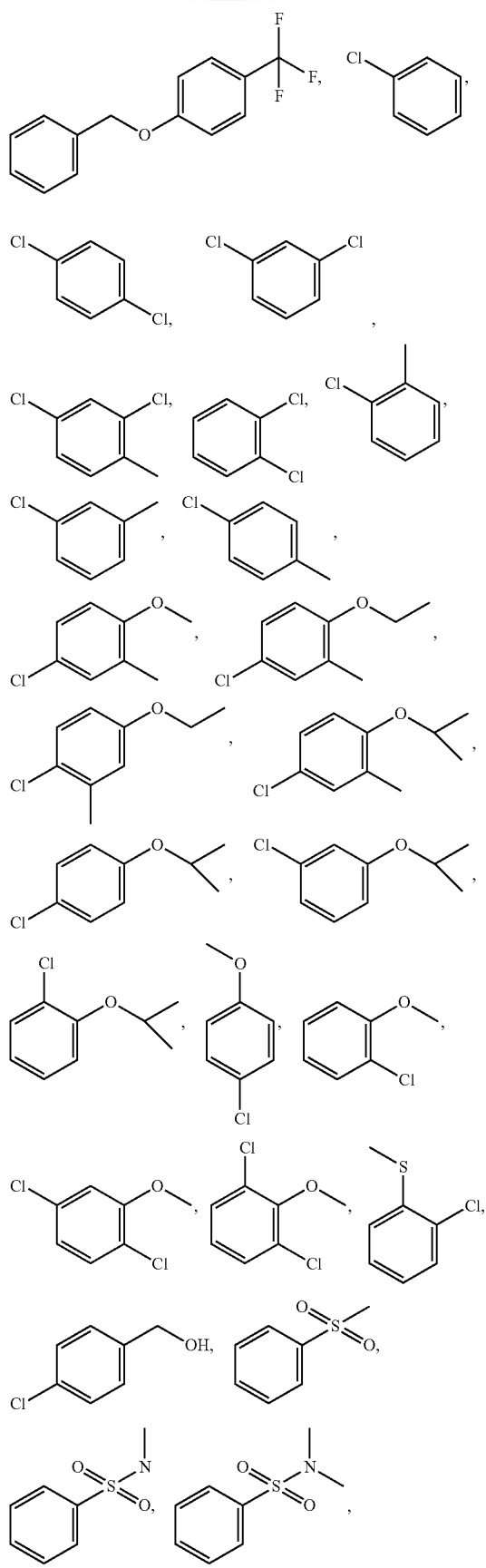
-continued
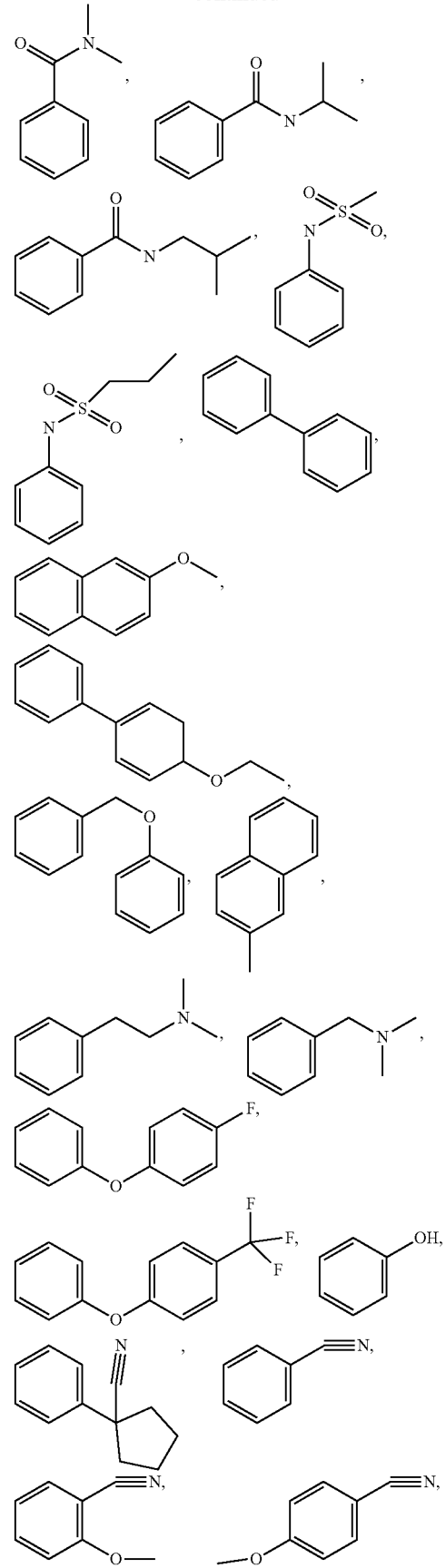

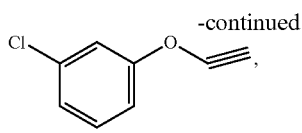

and the like.

As used herein, the term "heteroaryl" refers to a monocyclic, or fused polycyclic, aromatic heterocycle (ring structure having ring atoms selected from carbon atoms as well as nitrogen, oxygen, and sulfur heteroatoms) having from 3 to 24 ring atoms per ring. The term "heteroaryl" as used herein also includes monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein. 5 or 6 membered heteroaryl can be selected from the group consisting of optionally substituted pyridinyl, pyrimidinyl, thiazolyl, imidazolyl, oxazolyl, isoxazolyl, pyrazolyl, pyridinone and benzimidazolyl.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Illustrative examples of heteroaryl and substituted heteroaryl groups include, but are not limited to the following moieties:

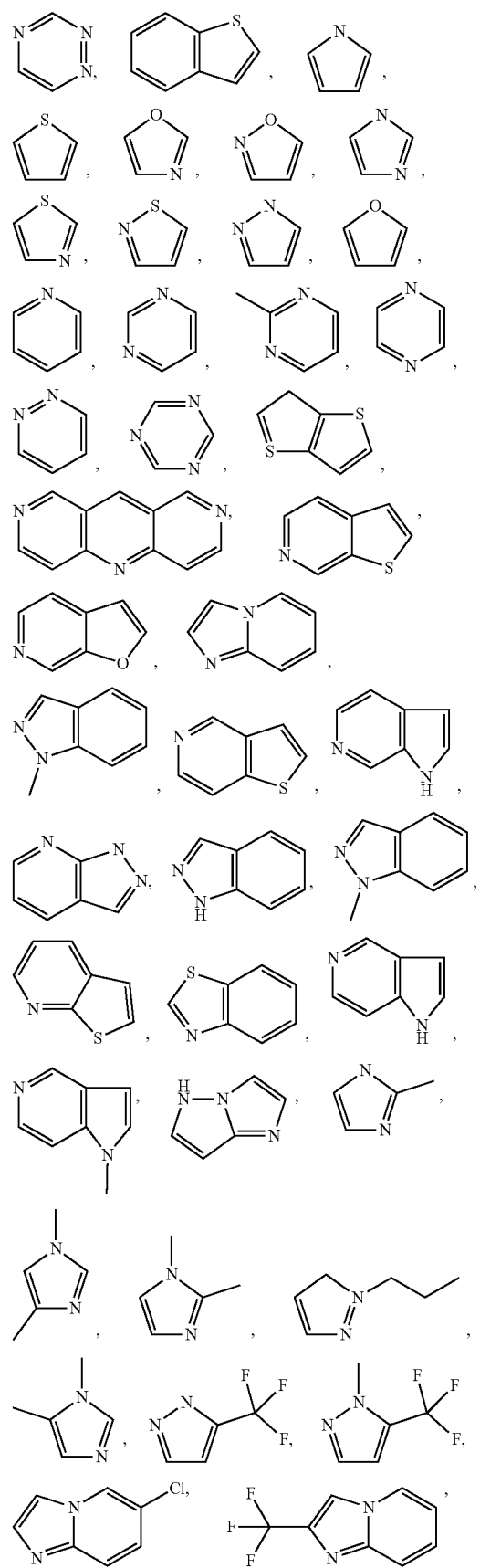

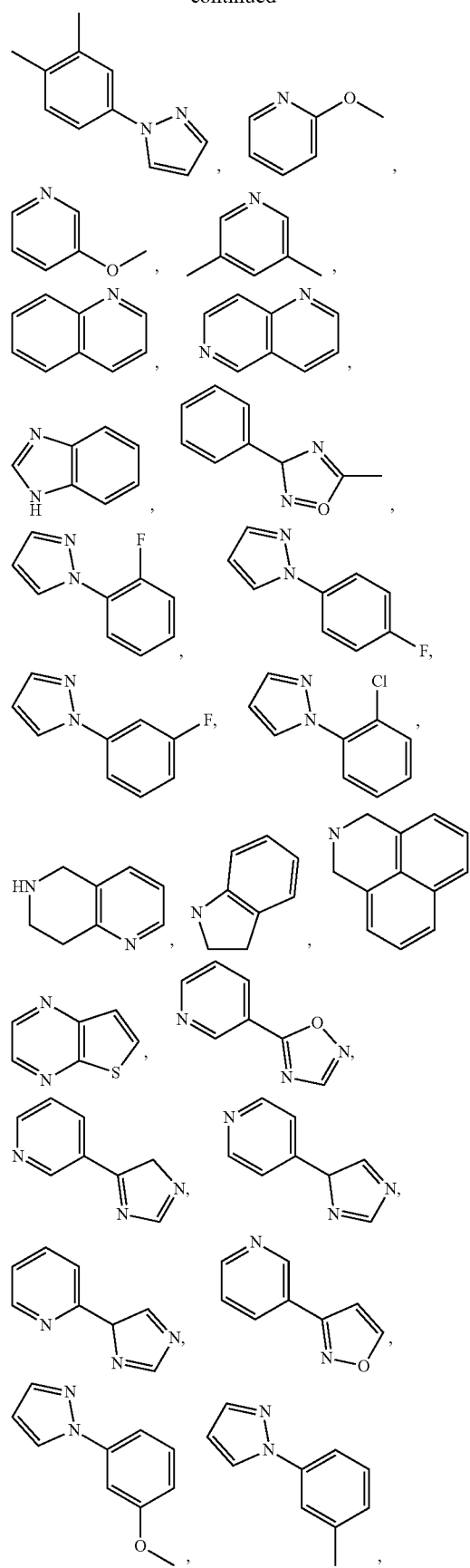
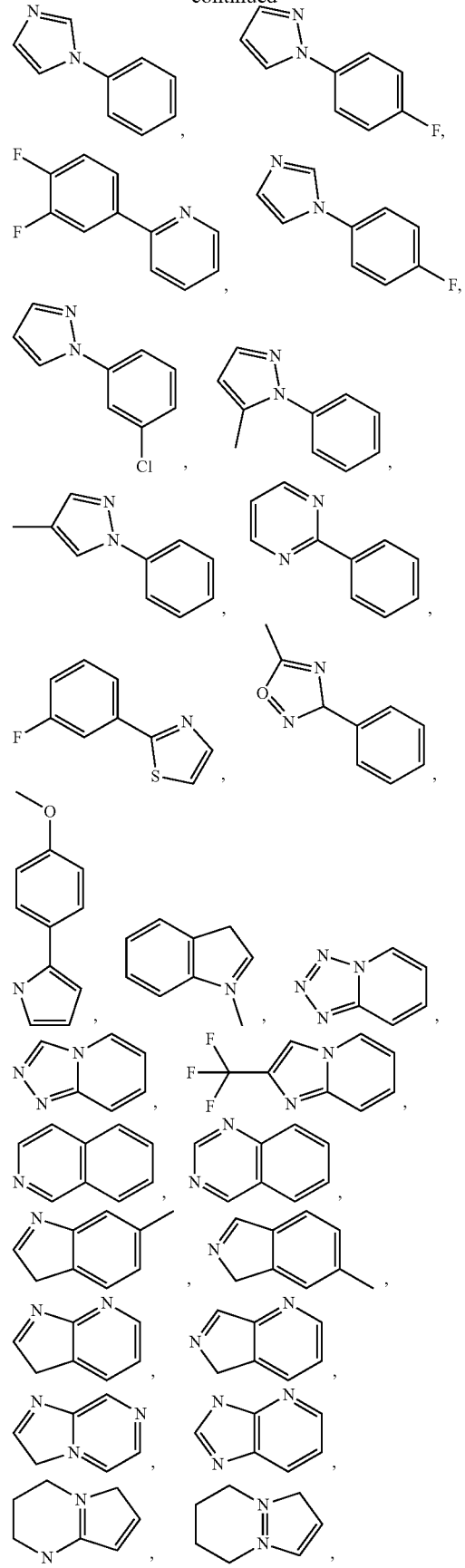

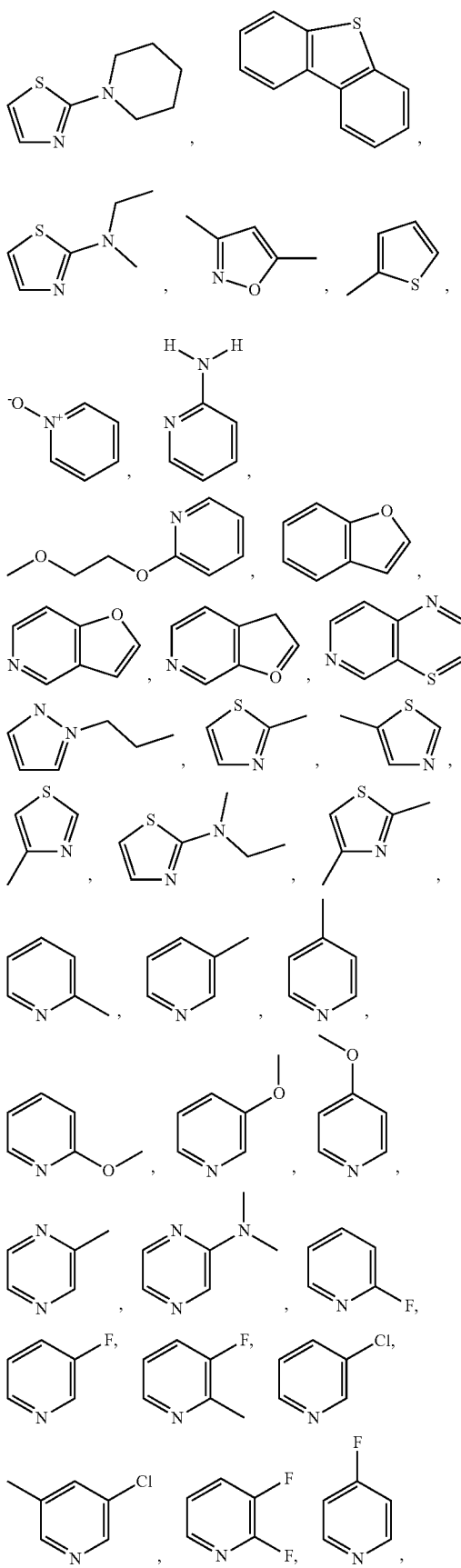

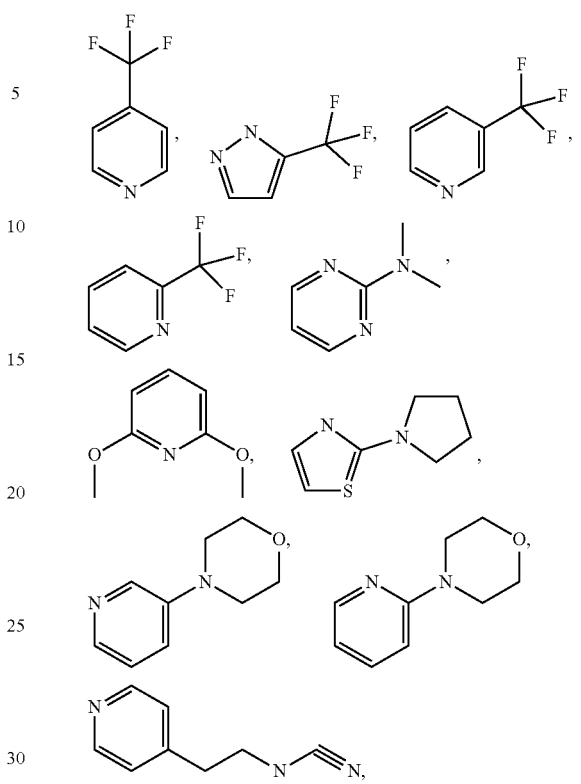

and the like.

The term "bicyclic heteroaryl" means a structure having atoms arranged in two rings fused together with at least two atoms common to each ring, and at least one of the rings being a heteroaryl ring. Non limiting examples of bicyclic heteroaryl comprise 5 to 13 or 5 to 10 membered bicyclic heteroaryl-groups comprising 1, 2, 3 or 4 heteroatoms independently selected from N, S, or O:

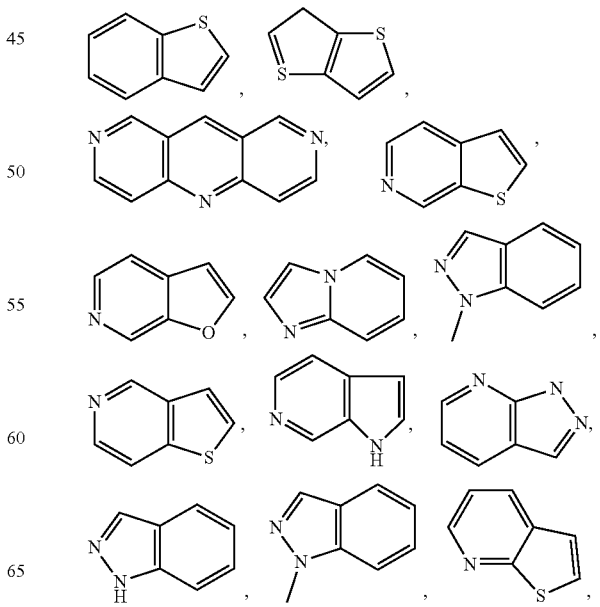

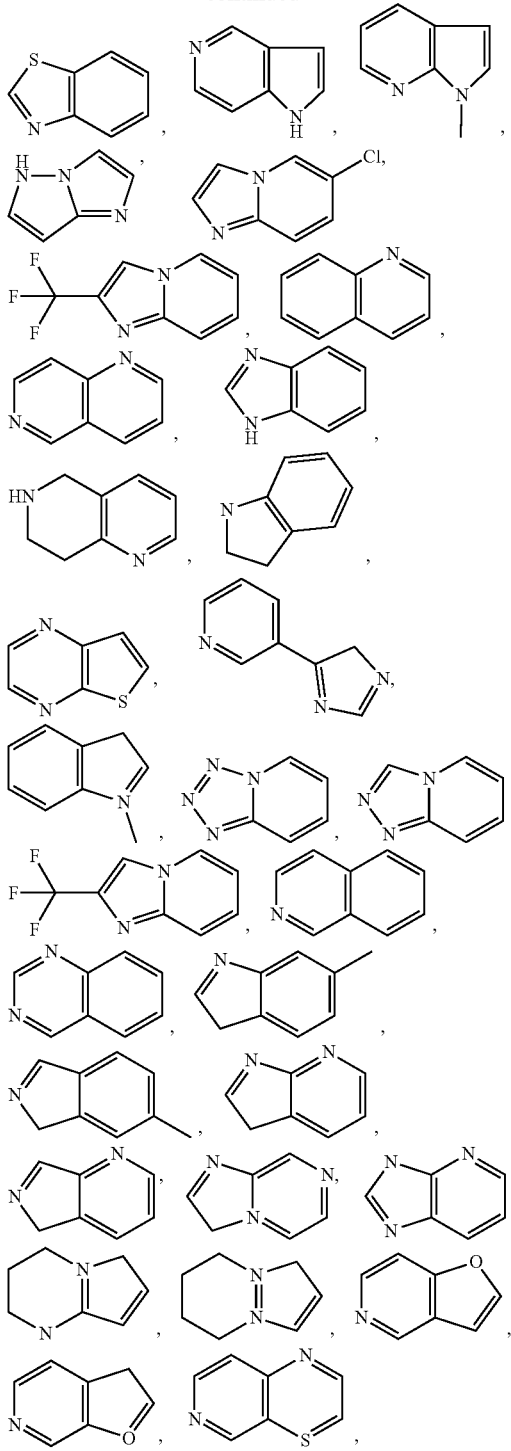

and the like.

Further examples of bicyclic heteroaryls include but are not limited to:

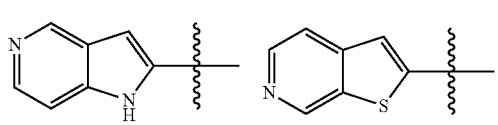

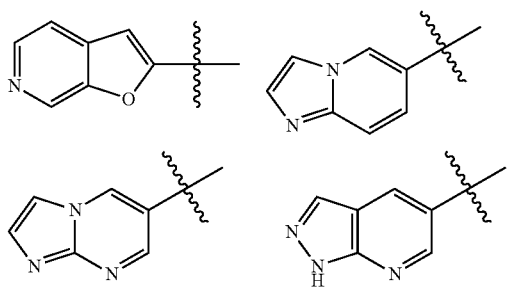

These bicyclic heteroaryl groups can be substituted as defined herein.

As used herein, the term "cycloalkyl" refers to a saturated or partially saturated, monocyclic or fused or spiro polycyclic, carbocycle having from 3 to 24 ($C_3$-$C_{24}$), 3 to 12 ($C_3$-$C_{12}$), 3 to 10 ($C_3$-$C_{10}$) or 3 to 6 ($C_3$-$C_6$) ring atoms per ring. Illustrative examples of cycloalkyl groups include, but are not limited to, the following moieties:

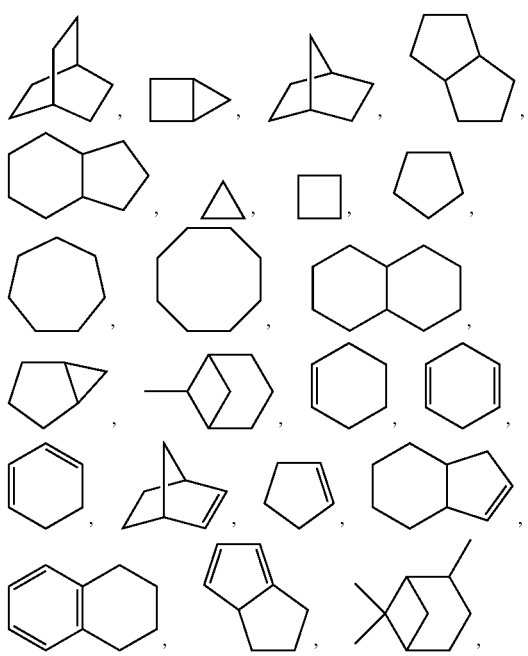

and the like.

As used herein, the term "heterocycloalkyl" refers to a monocyclic, or fused or spiro, polycyclic, ring structure that is saturated or partially saturated and has from 3 to 24 ring atoms per ring selected from C atoms and N, O, and S heteroatoms. Illustrative examples of heterocycloalkyl and substituted heterocycloalkyl groups include, but are not limited to:

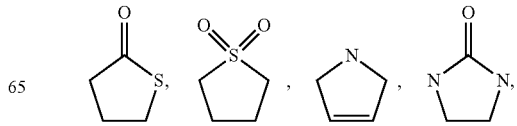

33
-continued
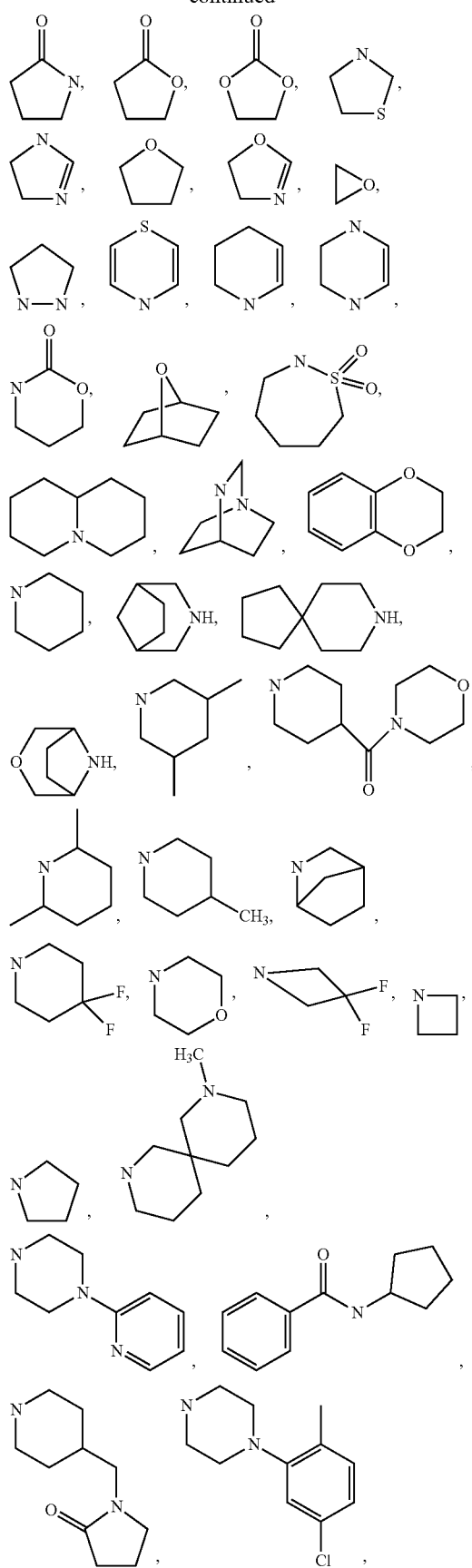
34
-continued
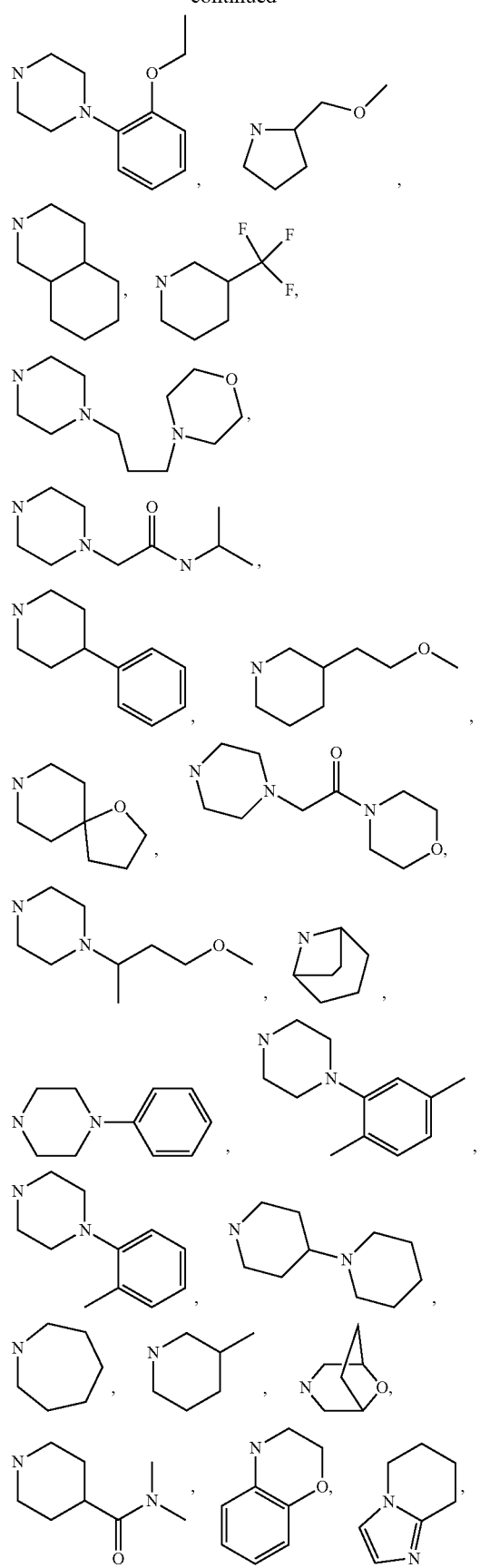

-continued
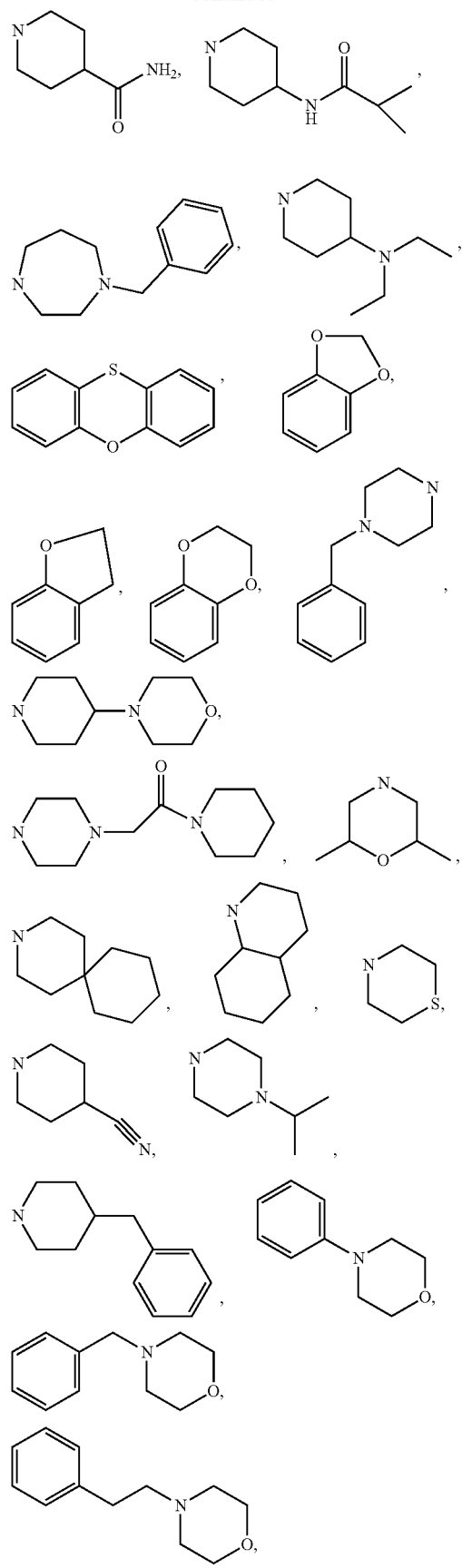
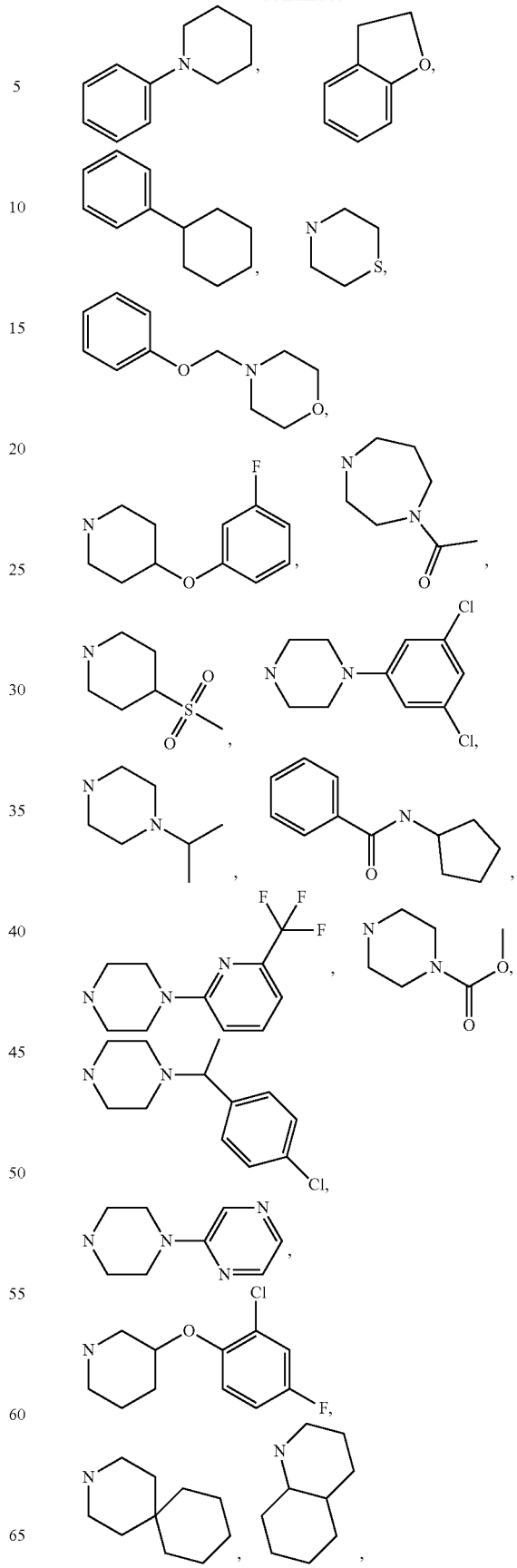

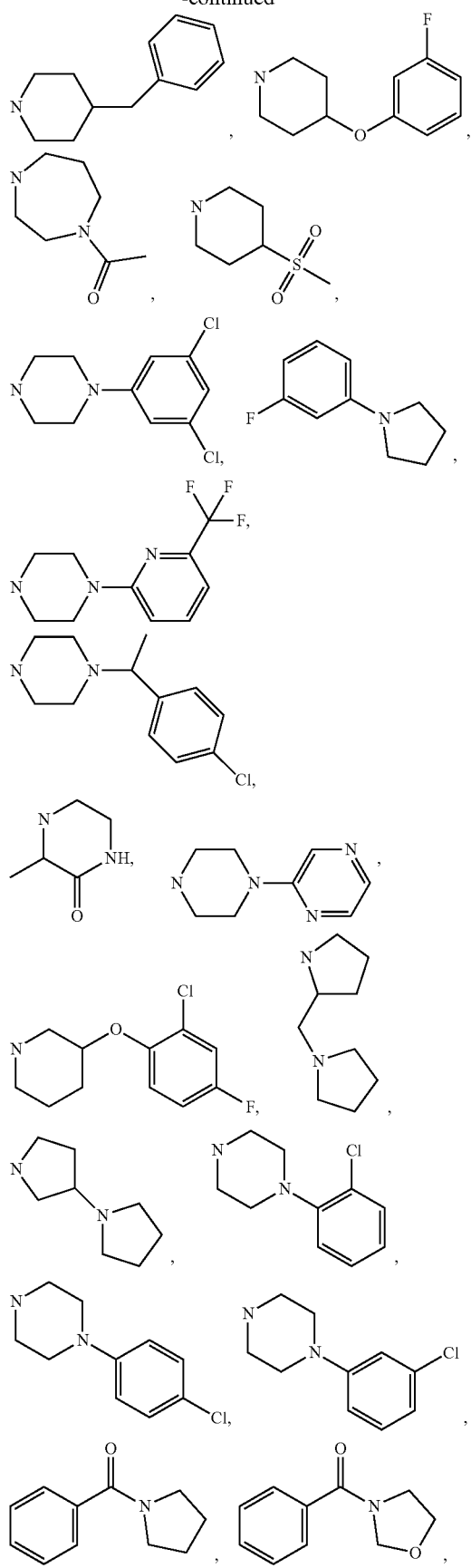
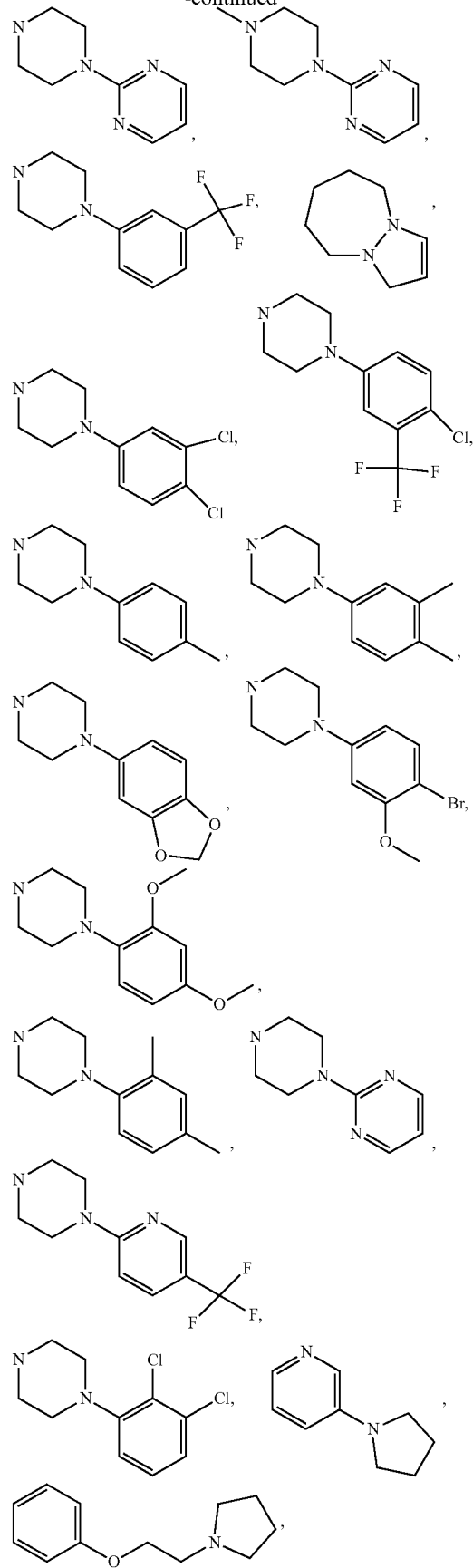

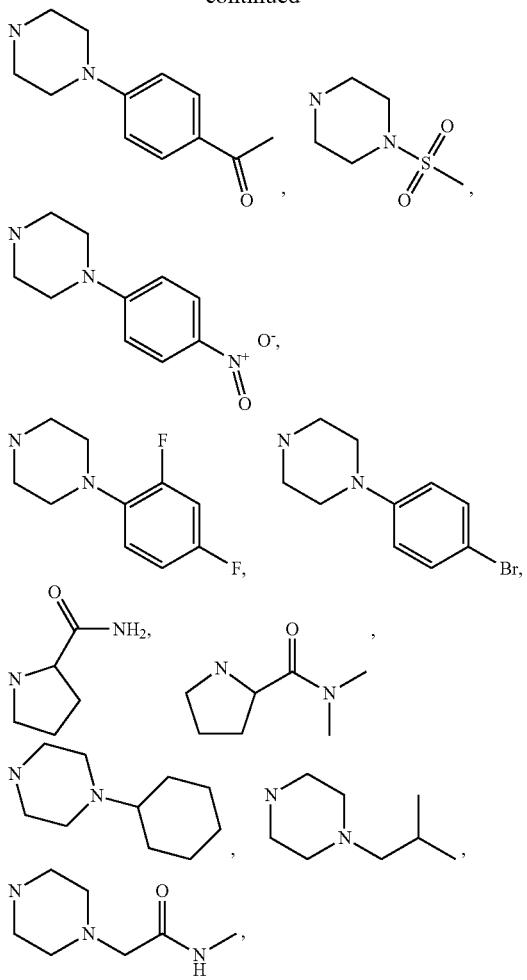

and the like.

Numerical ranges, as used herein, are intended to include sequential whole numbers. For example, a range expressed as "from 0 to 4" would include 0, 1, 2, 3 and 4.

As used herein, the term "substituted" means that the specified group or moiety bears one or more suitable substituents.

As used herein, the term "unsubstituted" means that the specified group bears no substituents.

As used herein, the term "optionally substituted" means that the specified group is unsubstituted or substituted by one or more substituents.

When a multifunctional moiety is shown, the point of attachment to the core is indicated by a line. For e.g. (cycloalkyloxy)alkyl- refers to alkyl being the point of attachment to the core while cycloalkyl is attached to alkyl via the oxy group.

The expression "adjunctive chemotherapeutic agent" generally refers to agents which treat, alleviate, relieve, or ameliorate the side effects of chemotherapeutic agents. Such agents include those which modify blood cell growth and maturation. Examples of adjunctive chemotherapeutic agents include, but are not limited to, filgrastim and erythropoietin. Other such adjunctive chemotherapeutic agents include those which inhibit nausea associated with administration of the chemotherapeutic agents, such as a 5-HT$_3$ receptor inhibitor (e.g., dolansetron, granisetron, or ondansetron), with or without dexamethasone.

The terms "chemotherapeutic agent" and "antineoplastic agent" generally refer to agents, which treat, prevent, cure, heal, alleviate, relieve, alter, remedy, ameliorate, improve, or affect malignancies and their metastasis. Examples of such agents (also known as "antineoplastic agents") include, but are not limited to, prednisone, fluorouracil (e.g., 5-fluorouracil (5-FU)), anastrozole, bicalutamide, carboplatin, cisplatin, chlorambucil, cisplatin, carboplatin, docetaxel, doxorubicin, flutamide, interferon-alpha, letrozole, leuprolide, megestrol, mitomycin, oxaliplatin, paclitaxel, plicamycin (Mithracin™), tamoxifen, thiotepa, topotecan, valrubicin, vinvlastin, vincristine, and any combination of any of the foregoing. Additional such agents are described later.

"Nicotinamide phosphoribosyltransferase" also named NAMPT, NMPRT, NMPRTase or NAmPRTase, (International nomenclature: E.C. 2.4.2.12) is a key enzyme in nicotinamide adenyl dinucleotide (NAD) biosynthesis from the natural precursor nicotinamide.

It must be noted that, as used in the specification and the appended claims, the singular forms "a," "an" and "the" include plural referents unless the context clearly dictates otherwise.

When used as a therapeutic agent the inhibitors of the formation of nicotinamide phosphoribosyltransferase (NAMPT) described herein may be administered with one or more physiologically acceptable excipients. A physiologically acceptable carrier or excipient is a formulation to which the compound can be added to dissolve it or otherwise facilitate its administration.

The dosage forms of the present invention, may contain a mixture of one or more compounds of this invention, and may include additional materials known to those skilled in the art as pharmaceutical excipients. Such pharmaceutical excipients include, for example, the following: Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in dosage forms of the present invention.

The compounds of the invention can form salts which are also within the scope of this invention. Reference to a compound of the Formula herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the Formulas contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

Pharmaceutically acceptable (i.e., non-toxic, physiologically acceptable) salts are preferred, although other salts are also useful. Salts of the compounds of the Formulas may be formed, for example, by reacting a compound of Formulas with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the compounds of the invention are also considered to be part of the invention. Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$) acyl glycerol.

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of the instant Formulas or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the instant Formulas or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of the instant Formulas contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of the instant invention incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C (O)OY$^1$ wherein Y$^1$ is H, ($C_1$-$C_6$)alkyl or benzyl, —C(OY$^2$) Y$^3$ wherein Y$^2$ is ($C_1$-$C_4$) alkyl and Y$^3$ is ($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$) alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS PharmSciTech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of the invention, and salts, solvates, esters and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the various Formulas as well as mixtures thereof, including racemic mixtures, form part of the present invention. In addition, the present invention embraces all geometric and positional isomers. For example, if a compound of the various Formulas incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulas may be atropisomers (e.g., substituted biaryls) and are considered as part of this invention. Enantiomers can also be separated by use of chiral HPLC column.

It is also possible that the compounds of the various Formulas may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the various Formulas incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the various Formulas (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the various Formulas can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

Benefits of the present invention include oral administration of an optimal amount of a nicotinamide phosphoribosyltransferase biosynthesis inhibitor.

Benefits of the present invention include intravenous administration of an optimal amount of a nicotinamide phosphoribosyltransferase biosynthesis inhibitor.

Benefits of the present invention include intraperitoneal administration of an optimal amount of a nicotinamide phosphoribosyltransferase biosynthesis inhibitor.

Benefits of the present invention include intramural administration of an optimal amount of a nicotinamide phosphoribosyltransferase biosynthesis inhibitor.

Benefits of the present invention include intramuscular administration of an optimal amount of a nicotinamide phosphoribosyltransferase biosynthesis inhibitor.

Benefits of the present invention include subcutaneous administration of an optimal amount of a nicotinamide phosphoribosyltransferase biosynthesis inhibitor.

Benefits of the present invention include intra-tumor administration of an optimal amount of a nicotinamide phosphoribosyltransferase biosynthesis inhibitor.

Benefits of the present invention include intrathecal administration of an optimal amount of a nicotinamide phosphoribosyltransferase biosynthesis inhibitor.

Benefits of the present invention include subdural administration of an optimal amount of a nicotinamide phosphoribosyltransferase biosynthesis inhibitor.

Benefits of the present invention include periorbital administration of an optimal amount of a nicotinamide phosphoribosyltransferase biosynthesis inhibitor.

Based on these results, the present invention has important implications for the design of novel treatment strategies for patients with cancer, including leukemias and solid tumors, inflammatory diseases, osteoporosis, atherosclerosis; irritable bowel syndrome and other conditions disclosed herein or that are known to those skilled in the art.

DESCRIPTION OF THE PREFERRED EMBODIMENTS

An aspect of the present invention concerns compounds disclosed herein.

An aspect of the present invention concerns compounds which are or can be inhibitors of the formation of nicotinamide phosphoribosyltransferase.

An aspect of the present invention concerns the use of an inhibitor of the formation of nicotinamide phosphoribosyltransferase for the preparation of a medicament used in the treatment, prevention, inhibition or elimination of tumors.

An aspect of the present invention concerns the use of an inhibitor of the formation of nicotinamide phosphoribosyltransferase for the preparation of a medicament used in the treatment, prevention, inhibition or elimination of cancer.

An aspect of the present invention concerns the use of an inhibitor of the formation of nicotinamide phosphoribosyltransferase for the preparation of a medicament used in the treatment, prevention, inhibition or elimination of cancer, where the cancer is selected from leukemia, lymphoma, ovarian cancer, breast cancer, uterine cancer, colon cancer, cervical cancer, lung cancer, prostate cancer, skin cancer, CNS cancer, bladder cancer, pancreatic cancer and Hodgkin's disease.

The present invention also describes one or more methods of synthesizing the compounds of the present invention.

The invention also describes one or more uses of the compounds of the present invention.

The invention also describes one or more uses of the compounds of the present invention with an adjunctive agent such as use with TNF, GCSF, or other chemotherapeutic agents The invention also describes one or more uses of the pharmaceutical compositions of the present invention.

An aspect of the present invention concerns the use as an inhibitor of the formation of nicotinamide phosphoribosyltransferase for the preparation of a medicament used in the treatment of inflammatory diseases.

An aspect of the present invention concerns the use as an inhibitor of the formation of nicotinamide phosphoribosyltransferase for the preparation of a medicament used in the treatment of inflammatory diseases, such as Irritable Bowel Syndrome or Inflammatory Bowel Disease.

An aspect of the present invention concerns the use as an inhibitor of the formation of nicotinamide phosphoribosyltransferase for the preparation of a medicament used in the treatment of disease of the bone such as osteoporosis.

An aspect of the present invention concerns the use as an inhibitor of the formation of nicotinamide phosphoribosyltransferase for the preparation of a medicament used in the treatment of disease of the cardiovascular system, such as atherosclerosis.

An aspect of the present invention concerns the use as an inhibitor of the formation of nicotinamide phosphoribosyltransferase for the preparation of a medicament used in the treatment of disease or a condition caused by an elevated level of NAMPT.

Such disease or condition is one or more selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system (CNS).

The compounds of the invention can be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease.

More specifically, the compounds can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The compounds of the invention may induce or inhibit apoptosis.

The compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

A further aspect of the invention is a method of inhibiting a NAMPT pathway in an animal, said method comprising administering to said animal a pharmaceutically acceptable amount of a compound of the invention to an animal in need thereof.

A further aspect of the invention is a pharmaceutical formulation comprising a compound of the invention.

Another embodiment of the invention comprises a pharmaceutical formulation of the invention, wherein the pharmaceutical formulation, upon administration to a human, results in a decrease in tumor burden.

Still another embodiment of the invention is a pharmaceutical formulation, further comprising one or more of an antineoplastic agent, a chemotherapeutic agent, or an adjunctive chemotherapeutic agent.

The pharmaceutical formulations of the invention may further comprise a therapeutic effective amount of an adjunctive chemotherapeutic agent.

The adjunctive chemotherapeutic agent may be an agent, which modifies blood cell growth and maturation. Non-limiting examples of adjunctive chemotherapeutic agent are filgrastim, pegfilgrastim and erythropoietin.

The invention is also directed to a method of treating or preventing a disorder associated with excessive rate of growth of cells in a mammal comprising administering to the mammal an effective amount of the pharmaceutical formulation of the invention. Non-limiting examples of disorder include cancer or metastasis from malignant tumors.

Another aspect of the invention is a method of inhibiting tumor cell growth and rate of division in a mammal with cancer, or other disorder associated with abnormally dividing cells comprising administering to the mammal an effective amount of the pharmaceutical formulation of this invention.

Another embodiment of the invention is a method of treating bone pain due to excessive growth of a tumor or metastasis to bone in a mammal in need thereof comprising administering to the mammal an effective amount of the pharmaceutical formulation of this invention.

Still another embodiment of the invention is a method for administering a NAMPT-inhibitor-containing compound to a mammal in need thereof comprising administering to the mammal the pharmaceutical formulation of the invention. In one embodiment, the mammal is a human.

A further embodiment of the invention is a method of preparing a pharmaceutical formulation comprising mixing at least one pharmaceutically acceptable compound of the present invention, and, optionally, one or more pharmaceutically acceptable excipients or additives.

The invention is also directed to methods of synthesizing compounds of the present invention.

Compounds of the Invention

The invention is directed to pharmaceutical compositions comprising one or more compounds as described herein and pharmaceutically acceptable salts, solvates, esters, prodrugs or isomers thereof. The invention further relates to molecules which are useful in inhibiting the enzyme nicotinamide phosphoribosyltransferase (NAMPT) and pharmaceutically acceptable salts, solvates, esters, prodrugs or isomers thereof.

An aspect of the invention is the provision of compounds, compositions, kits, and antidotes for the NAMPT pathway in mammals having a compound of Formula I

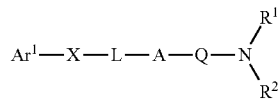

wherein
$Ar^1$ is aryl, heteroaryl or heterocycloalkyl, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with aryl, heteroaryl or heterocycloalkyl, still further wherein any of said aryl, heteroaryl and heterocycloalkyl is either unsubstituted or optionally independently substituted with one or more substituents which can be the same or different and are independently selected from the group consisting of deuterium, halo, cyano, isocyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, alkoxy-, -aryloxy-, (alkoxyalkyl)oxy-, (alkoxyalkyl)amino-, —$N(R^3)$—C(O)-alkyl, —$N(R^3)$—C(O)-aryl, —$N(R^3)$—C(O)—O—alkyl, —$N(R^3)$—C(O)—O-aryl, -cycloalkyl, -heterocycloalkyl, -aryl, —C(O)-aryl, —S(O)-aryl, and heteroaryl, with the proviso that no two adjacent ring heteroatoms are both S or both O;

X is a straight or branched $C_1$-$C_6$ alkyl;
L is selected from NHC(O)NH, OC(O)NH, NHC(O)O, OCH$_2$C(O)NH, C(O)NH, NHC(S)NH, OC(S)NH, NHC(S)O, OCH$_2$C(S)NH, or C(S)NH;
A is aryl, heteroaryl, heterocycloalkyl or $C_3$ to $C_8$ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, isocyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, alkoxy-, -aryloxy-, (alkoxyalkyl)oxy-, (alkoxyalkyl)amino-, —$N(R^3)$—C(O)-alkyl, —$N(R^3)$—C(O)-aryl, —$N(R^3)$—C(O)—O-alkyl, —$N(R^3)$—C(O)—O-aryl, -cycloalkyl, -heterocycloalkyl, -aryl, —C(O)-aryl, —S(O)-aryl, and heteroaryl;
Q is C(O), S(O), S(O)$_2$;
$R^3$ is H, alkyl or arylalkyl-;
z is 0, 1 or 2; and
either:
(i) (a) $R^1$ is selected from H, a straight or branched $C_1$ to $C_7$ alkyl, straight or branched $C_1$ to $C_7$ alkoxy, straight or branched $C_1$ to $C_4$ hydroxyalkyl, aryl, heteroaryl, heterocycloalkyl, cycloalkyl, arylalkyl-, heteroarylalkyl-, heterocycloalkylalkyl-, cycloalkylalkyl-, hydroxyalkyl-, alkoxyalkyl-, heterospirocycloalkyl and heterospiroheterocycloalkyl, wherein the heteroatoms of said heteroaryl and heterocycloalkyl in the moieties above are independently selected from one or more N, O and S, with the proviso that no two adjacent ring heteroatoms are both S or both O, further wherein $R^1$ can be either unsubstituted or optionally independently (i) either substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-aryl, —S(O$_2$)alkyl, —S(O$_2$)CF$_3$, -cycloalkyl, alkylenedioxy (e.g. methylenedioxy), -heterocycloalkyl, -aryl, and heteroaryl, or (ii) fused with a cycloalkyl, -heterocycloalkyl, -aryl, or heteroaryl; and (b) R$^2$ is selected from H, a straight or branched C$_1$ to C$_7$ alkyl, straight or branched C$_1$ to C$_7$ alkoxy, straight or branched C$_1$ to C$_4$ hydroxyalkyl, aryl, heteroaryl, heterocycloalkyl, cycloalkyl, arylalkyl-, heteroarylalkyl-, heterocycloalkylalkyl-, cycloalkylalkyl-, hydroxyalkyl-, alkoxyalkyl-, heterospirocycloalkyl and heterospiroheterocycloalkyl, wherein the heteroatoms of said heteroaryl and heterocycloalkyl in the moieties above are independently selected from one or more N, O and S, with the proviso that no two adjacent ring heteroatoms are both S or both O, further wherein R$^2$ can be either unsubstituted or optionally independently (i) either substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-aryl, —S(O$_2$)alkyl, —S(O$_2$)CF$_3$, -cycloalkyl, alkylenedioxy (e.g. methylenedioxy), -heterocycloalkyl, -aryl, and heteroaryl, or (ii) fused with a cycloalkyl, -heterocycloalkyl, -aryl, or heteroaryl;

or (ii) R$^1$ and R$^2$ are joined together to form, along with the N they are shown attached to in the formula, a C$_3$-C$_8$ heterocycloalkyl, a C$_3$-C$_8$ heterocycloalkenyl, a fused bicyclic heterocycloalkyl, a fused tricyclic heterocycloalkyl, spiroheterocycloalkyl or a heterospiroheterocycloalkyl, wherein each of said heterocycloalkyl, heterocycloalkenyl, spiroheterocycloalkyl and heterospiroheterocycloalkyl can optionally contain one or more heteroatoms in addition to the N atom they are shown attached to in the formula, said heteroatoms being selected from N, S and O, with the proviso that no two adjacent ring heteroatoms are both S or both O, further wherein each of said heterocycloalkyl, fused bicyclic heterocycloalkyl, fused tricyclic heterocycloalkyl, heterocycloalkenyl, spiroheterocycloalkyl and heterospiroheterocycloalkyl can be either unsubstituted or optionally independently substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-alkyl, —S(O$_2$)alkyl, —S(O$_2$)CF$_3$, -cycloalkyl, alkylenedioxy (e.g. methylenedioxy), -heterocycloalkyl, -aryl, and heteroaryl;

and pharmaceutically acceptable salts, solvates, esters and isomers thereof, with the proviso that the compound of Formula I is not 1-(pyridin-3-ylmethyl)-3-(4-sulfamoylphenyl)thiourea, 3-[4-(morpholine-4-sulfonyl)phenyl]-1-(pyridine-4-ylmethyl)thiourea or 3-[4-(piperidine-1-sulfonyl)phenyl]-1-(pyrdin-4-ylmethyl)thiourea.

Another aspect of this invention is the provision of compounds, compositions, kits, and antidotes for the NAMPT pathway in mammals having a compound of the Formula I, where X,L,Q,Ar$^1$ and A are as defined in Formula I and R$^1$ is selected from H, a straight or branched C$_1$ to C$_7$ alkyl, straight or branched C$_1$ to C$_7$ alkoxy, straight or branched C$_1$ to C$_4$ hydroxyalkyl, aryl, heteroaryl, heterocycloalkyl, cycloalkyl, arylalkyl-, heteroarylalkyl-, heterocycloalkylalkyl-, cycloalkylalkyl-, hydroxyalkyl-, alkoxyalkyl-, spirocycloalkyl and heterospiroheterocycloalkyl, wherein the heteroatoms of said heteroaryl and heterocycloalkyl in the moieties above are independently selected from one or more N, O and S, with the proviso that no two adjacent ring heteroatoms are both S or both O, further wherein R$^1$ can be either unsubstituted or optionally independently (i) either substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N(R$^3$)—C(O)-alkyl, —N(R$^3$)—C(O)-aryl, —S(O$_2$)alkyl, —S(O$_2$)CF$_3$, -cycloalkyl, alkylenedioxy (e.g. methylenedioxy), -heterocycloalkyl, -aryl, and heteroaryl, or (ii) fused with a cycloalkyl, -heterocycloalkyl, -aryl, or heteroaryl; and R$^2$ is selected from H, a straight or branched C$_1$ to C$_7$ alkyl, straight or branched C$_1$ to C$_7$ alkoxy, straight or branched C$_1$ to C$_4$ hydroxyalkyl, aryl, heteroaryl, heterocycloalkyl, cycloalkyl, arylalkyl-, heteroarylalkyl-, heterocycloalkylalkyl-, cycloalkylalkyl-, hydroxyalkyl-, alkoxyalkyl-, heterospirocycloalkyl and heterospiroheterocycloalkyl, wherein the heteroatoms of said heteroaryl and heterocycloalkyl in the moieties above are independently selected from one or more N, O and S, with the proviso that no two adjacent ring heteroatoms are both S or both O, further wherein R$^2$ can be either unsubstituted or optionally independently (i) either substituted with one or more substituents which can be the same or different and are independently selected from the group consisting of deuterium, halo, cyano, isocyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —NO$_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N($R^3$)—C(O)-alkyl, —N($R^3$)—C(O)-aryl, —S($O_2$)alkyl, —S($O_2$)$CF_3$, -cycloalkyl, alkylenedioxy (e.g, methylenedioxy), -heterocycloalkyl, -aryl, and heteroaryl, or (ii) fused with a cycloalkyl, -heterocycloalkyl, -aryl, or heteroaryl;

with the proviso that the compound of Formula I is not 1-(pyridin-3-ylmethyl)-3-(4-sulfamoylphenyl)thiourea, 3-[4-(morpholine-4-sulfonyl)phenyl]-1-(pyridine-4-ylmethyl)thiourea or 3-[4-(piperidine-1-sulfonyl)phenyl]-1-(pyrdin-4-ylmethyl)thiourea.

Another aspect of this invention is the provision of compounds, compositions, kits, and antidotes for the NAMPT pathway in mammals having a compound of the Formula I, where X,L,Q, $Ar^1$ and A are as defined in Formula I and $R^1$ and $R^2$ are joined together to form, along with the N they are shown attached to in the formula, a $C_3$-$C_8$ heterocycloalkyl, a $C_3$-$C_8$ heterocycloalkenyl, a fused bicyclic heterocycloalkyl, a fused tricyclic heterocycloalkyl, spiroheterocyclaolkyl or a heterospiroheterocycloalkyl, wherein each of said heterocycloalkyl, heterocycloalkenyl, spiroheterocyclaolkyl and heterospiroheterocycloalkyl can optionally contain one or more heteroatoms in addition to the N atom they are shown attached to in the formula, said heteroatoms being selected from N, S and O, with the proviso that no two adjacent ring heteroatoms are both S or both O, further wherein each of said heterocycloalkyl, fused bicyclic heterocycloalkyl, fused tricyclic heterocycloalkyl, heterocycloalkenyl, spiroheterocyclaolkyl and heterospiroheterocycloalkyl can be either unsubstituted or optionally independently substituted with one or more substituents which can be the same or different and are independently selected from the group consisting of deuterium, halo, cyano, isocyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, alkyl, alkenyl, alkynyl, hydroxyalkyl-, (hydroxyalkyl)oxy, -alkoxy, carboxy, (alkoxyalkyl)-, (heteroaryloxy)alkyl-, —$NO_2$, (alkoxyalkyl)amino-, -alkylamino, dialkylamino, (heterocycloalkyloxo)alkyl-, aryloxy, heterocycloalkyloxy-, aminocarbonyl-, —CHO, —C(O)alkyl, —N($R^3$)—C(O)-alkyl, —N($R^3$)—C(O)-aryl, —S($O_2$)alkyl, —S($O_2$)$CF_3$, -cycloalkyl, alkylenedioxy (e.g, methylenedioxy), -heterocycloalkyl, -aryl, and heteroaryl;

$R^3$ is H, alkyl or arylalkyl with the proviso that the compound is not 1-(pyridin-3-ylmethyl)-3-(4-sulfamoylphenyl)thiourea, 3-[4-(morpholine-4-sulfonyl)phenyl]-1-(pyridine-4-ylmethyl)thiourea or 3-[4-(piperidine-1-sulfonyl)phenyl]-1-(pyrdin-4-ylmethyl)thiourea.

In one embodiment, the invention relates to compounds of Formula I and pharmaceutically acceptable salts, solvates, ester or isomers thereof.

In the compounds of Formula I, the various moieties and substituents are independently selected.

The following embodiments are directed to Formula I as applicable. Further, the moieties aryl, heteroaryl, heterocycloalkyl, cycloalkyl, spiroheterocycloalkyl and heterospiroheterocycloalkyl as well as their representative moieties in these embodiments can be independently unsubstituted or optionally substituted or optionally fused as described earlier. Any one or more of the embodiments relating to Formula I below can be combined with one or more other embodiments of Formula I.

An embodiment of the invention is the provision of a compound of Formula I, where the various moieties are independently selected, $Ar^1$ is aryl, and z, X, L, A, Q, $R^1$, $R^2$ and $R^3$ are as defined.

An embodiment of the invention is the provision of a compound of Formula I, where the various moieties are independently selected, $Ar^1$ is heteroaryl, and z, X, L, A, Q, $R^1$, $R^2$ and $R^3$ are as defined.

An embodiment of the invention is the provision of a compound of Formula I, where the various moieties are independently selected, $Ar^1$ is heterocycloalkyl, and z, X, L, A, Q, $R^1$, $R^2$ and $R^3$ are as defined.

An embodiment of the invention is the provision of a compound of Formula I, where the various moieties are independently selected, $Ar^1$ is aryl fused with an aryl, heteroaryl or heterocycloalkyl, and z, X, L, A, Q, $R^1$, $R^2$ and $R^3$ are as defined.

An embodiment of the invention is the provision of a compound of Formula I, where the various moieties are independently selected, $Ar^1$ is heteroaryl fused with an aryl, heteroaryl or heterocycloalkyl, and z, X, L, A, Q, $R^1$, $R^2$ and $R^3$ are as defined.

An embodiment of the invention is the provision of a compound of Formula I, where the various moieties are independently selected, $Ar^1$ is heterocycloalkyl fused with an aryl, heteroaryl or heterocycloalkyl, and z, X, L, A, Q, $R^1$, $R^2$ and $R^3$ are as defined.

An embodiment of the invention is the provision of a compound of Formula I, where the various moieties are independently selected, $Ar^1$ is aryl substituted as shown under Formula I, IA or IB, and z, X, L, A, Q, $R^1$, $R^2$ and $R^3$ are as defined.

An embodiment of the invention is the provision of a compound of Formula I, where the various moieties are independently selected, $Ar^1$ is heteroaryl substituted as shown under Formula I, IA or IB, and z, X, L, A, Q, $R^1$, $R^2$ and $R^3$ are as defined.

An embodiment of the invention is the provision of a compound of Formula I, where the various moieties are independently selected, $Ar^1$ is heterocycloalkyl substituted as shown under Formula I, IA or IB, and z, X, L, A, Q, $R^1$, $R^2$ and $R^3$ are as defined.

An embodiment of the invention is the provision of a compound of Formula I, where the various moieties are independently selected, X is a straight chain alkyl, and $Ar^1$, z, L, A, Q, $R^1$, $R^2$ and $R^3$ are as defined.

An embodiment of the invention is the provision of a compound of Formula I, where the various moieties are independently selected, X is a branched chain alkyl, and $Ar^1$, z, L, A, Q, $R^1$, $R^2$ and $R^3$ are as defined.

An embodiment of the invention is the provision of a compound of Formula I, where the various moieties are independently selected, L is —N(H)—C(O)—N(H)—, and $Ar^1$, z, X, A, Q, $R^1$, $R^2$ and $R^3$ are as defined.

An embodiment of the invention is the provision of a compound of Formula I, where the various moieties are independently selected, Q is —S($O_2$)—, and $Ar^1$, z, X, A, $R^1$, $R^2$ and $R^3$ are as defined.

An embodiment of the invention is the provision of a compound of Formula I, where the various moieties are independently selected, $R^3$ is H, and $Ar^1$, z, X, A, Q, $R^1$, and $R^2$ are as defined.

An embodiment of the invention is the provision of a compound of Formula I, where the various moieties are independently selected, $R^3$ is alkyl, and $Ar^1$, z, X, A, Q, $R^1$, and $R^2$ are as defined.

An embodiment of the invention is the provision of a compound of Formula I, where the various moieties are independently selected, $R^3$ is arylalkyl, and $Ar^1$, z, X, A, Q, $R^1$, and $R^2$ are as defined.

An embodiment of the invention is the provision of a compound of Formula I, where the various moieties are independently selected, z is 0, and $Ar^1$, X, A, Q, $R^1$, $R^2$ and $R^3$ are as defined.

An embodiment of the invention is the provision of a compound of Formula I, where the various moieties are independently selected, z is 1, and $Ar^1$, X, A, Q, $R^1$, $R^2$ and $R^3$ are as defined.

An embodiment of the invention is the provision of a compound of Formula I, where the various moieties are independently selected, z is 2, and $Ar^1$, X, A, Q, $R^1$, $R^2$ and $R^3$ are as defined.

An embodiment of the invention is the provision of a compound of Formula I, where the various moieties are independently selected, $R^1$ is H, and $Ar^1$, z, X, A, Q, $R^2$ and $R^3$ are as defined.

An embodiment of the invention is the provision of a compound of Formula I, where the various moieties are independently selected, $R^2$ is H, and $Ar^1$, z, X, A, Q, $R^2$ and $R^3$ are as defined.

An embodiment of the invention is the provision of a compound of Formula I, where the various moieties are independently selected, $R^1$ and $R^2$ are H, and $Ar^1$, z, X, A, Q, and $R^3$ are as defined.

An embodiment of the invention is the provision of a compound of Formula I, where the various moieties are independently selected, $R^1$ is H, $R^2$ is alkyl, and $Ar^1$, z, X, A, Q, and $R^3$ are as defined.

An embodiment of the invention is the provision of a compound of Formula I, where the various moieties are independently selected, $R^1$ is H, $R^2$ is aryl, and $Ar^1$, z, X, A, Q, and $R^3$ are as defined.

An embodiment of the invention is the provision of a compound of Formula I, where the various moieties are independently selected, $R^1$ is H, $R^2$ is heteroaryl, and $Ar^1$, z, X, A, Q, and $R^3$ are as defined.

An embodiment of the invention is the provision of a compound of Formula I, where the various moieties are independently selected, $R^1$ is H, $R^2$ is heterocycloalkyl, and $Ar^1$, z, X, A, Q, and $R^3$ are as defined.

An embodiment of the invention is the provision of a compound of Formula I, where the various moieties are independently selected, $R^1$ is H, $R^2$ is cycloalkyl, and $Ar^1$, z, X, A, Q, and $R^3$ are as defined.

An embodiment of the invention is the provision of a compound of Formula I, where the various moieties are independently selected, $R^1$ is H, $R^2$ is alkoxy, and $Ar^1$, z, X, A, Q, and $R^3$ are as defined.

An embodiment of the invention is the provision of a compound of Formula I, where the various moieties are independently selected, $R^1$ is H, $R^2$ is hydroxyalkyl, and $Ar^1$, z, X, A, Q, and $R^3$ are as defined.

An embodiment of the invention is the provision of a compound of Formula I, where the various moieties are independently selected, $R^1$ is H, $R^2$ is aryloxy, and $Ar^1$, z, X, A, Q, and $R^3$ are as defined.

An embodiment of the invention is the provision of a compound of Formula I, where the various moieties are independently selected, $R^1$ is H, $R^2$ is arylalkyl, and $Ar^1$, z, X, A, Q, and $R^3$ are as defined.

An embodiment of the invention is the provision of a compound of Formula I, where the various moieties are independently selected, $R^1$ is H, $R^2$ is heteroarylalkyl, and $Ar^1$, z, X, A, Q, and $R^3$ are as defined.

An embodiment of the invention is the provision of a compound of Formula I, where the various moieties are independently selected, $R^1$ is H, $R^2$ is cycloalkylalkyl-, and $Ar^1$, z, X, A, Q, and $R^3$ are as defined.

An embodiment of the invention is the provision of a compound of Formula I, where the various moieties are independently selected, $R^1$ is H, $R^2$ is heterocycloalkylalkyl, and $Ar^1$, z, X, A, Q, and $R^3$ are as defined.

An embodiment of the invention is the provision of a compound of Formula I, where the various moieties are independently selected, $R^1$ is H, $R^2$ is alkoxyalkyl, and $Ar^1$, z, X, A, Q, and $R^3$ are as defined.

An embodiment of the invention is the provision of a compound of Formula I, where the various moieties are independently selected, $R^1$ is H, $R^2$ is spiroheterocycloalkyl, and $Ar^1$, z, X, A, Q, and $R^3$ are as defined.

An embodiment of the invention is the provision of a compound of Formula I, where the various moieties are independently selected, $R^1$ is H, $R^2$ is spiroheterocycloalkylalkyl, and $Ar^1$, z, X, A, Q, and $R^3$ are as defined.

An embodiment of the invention is the provision of a compound of Formula I, where the various moieties are independently selected, $R^1$ is H, $R^2$ is alkyl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is aryl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is heteroaryl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is heterocycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is cycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is aryloxy with the aryl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is arylalkyl with the aryl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is heteroarylalkyl with the heteroaryl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is cycloalkylalkyl- with the cycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is heterocycloalkylalkyl with the heterocycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is spiroheterocycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is spiroheterocycloalkylalkyl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is alkyl, and $Ar^1$, z, X, A, Q, and $R^3$ are as defined.

An embodiment of the invention is the provision of a compound of Formula I, where the various moieties are independently selected, $R^1$ is alkyl, $R^2$ is aryl, and $Ar^1$, z, X, A, Q, and $R^3$ are as defined.

An embodiment of the invention is the provision of a compound of Formula I, where the various moieties are independently selected, $R^1$ is alkyl, $R^2$ is heteroaryl, and $Ar^1$, z, X, A, Q, and $R^3$ are as defined.

An embodiment of the invention is the provision of a compound of Formula I, where the various moieties are independently selected, $R^1$ is alkyl, $R^2$ is heterocycloalkyl, and $Ar^1$, z, X, A, Q, and $R^3$ are as defined.

An embodiment of the invention is the provision of a compound of Formula I, where the various moieties are independently selected, $R^1$ is alkyl, $R^2$ is cycloalkyl, and $Ar^1$, z, X, A, Q, and $R^3$ are as defined.

An embodiment of the invention is the provision of a compound of Formula I, where the various moieties are independently selected, $R^1$ is alkyl, $R^2$ is aryloxy, and $Ar^1$, z, X, A, Q, and $R^3$ are as defined.

An embodiment of the invention is the provision of a compound of Formula I, where the various moieties are independently selected, $R^1$ is alkyl, $R^2$ is arylalkyl, and $Ar^1$, z, X, A, Q, and $R^3$ are as defined.

An embodiment of the invention is the provision of a compound of Formula I, where the various moieties are independently selected, $R^1$ is alkyl, $R^2$ is heteroarylalkyl, and $Ar^1$, z, X, A, Q, and $R^3$ are as defined.

An embodiment of the invention is the provision of a compound of Formula I, where the various moieties are independently selected, $R^1$ is alkyl, $R^2$ is cycloalkylalkyl-, and $Ar^1$, z, X, A, Q, and $R^3$ are as defined.

An embodiment of the invention is the provision of a compound of Formula I, where the various moieties are independently selected, $R^1$ is alkyl, $R^2$ is heterocycloalkylalkyl, and $Ar^1$, z, X, A, Q, and $R^3$ are as defined.

An embodiment of the invention is the provision of a compound of Formula I, where the various moieties are independently selected, $R^1$ is alkyl, $R^2$ is spiroheterocycloalkyl, and $Ar^1$, z, X, A, Q, and $R^3$ are as defined.

An embodiment of the invention is the provision of a compound of Formula I, where the various moieties are independently selected, $R^1$ is alkyl, $R^2$ is spiroheterocycloalkylalkyl, and $Ar^1$, z, X, A, Q, and $R^3$ are as defined.

An embodiment of the invention is the provision of a compound of Formula I, where the various moieties are independently selected, $R^1$ is alkyl, $R^2$ is alkyl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is aryl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is heteroaryl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is heterocycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is cycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is aryloxy with the aryl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is arylalkyl with the aryl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is heteroarylalkyl with the heteroaryl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is cycloalkylalkyl- with the cycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is heterocycloalkylalkyl with the heterocycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is spiroheterocycloalkyl substituted or fused as described earlier, and $Ar^1$, z, X, A, Q, and $R^3$ are as defined.

An embodiment of the invention is the provision of a compound of Formula I, where the various moieties are independently selected, $R^1$ is alkyl, $R^2$ is spiroheterocycloalkylalkyl substituted or fused as described earlier, and $Ar^1$, z, X, A, Q, and $R^3$ are as defined.

An embodiment of the invention is the provision of a compound of Formula I, where the various moieties are independently selected, $R^1$ is H, $R^2$ is bicycloheptanyl (unsubstituted, substituted or fused as described earlier), and $Ar^1$, z, X, A, Q, and $R^3$ are as defined.

An embodiment of the invention is the provision of a compound of Formula I, where the various moieties are independently selected, $R^1$ is H, $R^2$ is cyclopropyl (unsubstituted, substituted or fused as described earlier), and $Ar^1$, z, X, A, Q, and $R^3$ are as defined.

An embodiment of the invention is the provision of a compound of Formula I, where the various moieties are independently selected, $R^1$ is H, $R^2$ is cyclobutyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is cyclopentyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is cyclopentylmethyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is benzyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is furanyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is furanylmethyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is phenyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is naphthalenyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is biphenylmethyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is biphenyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is tolyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is pyridinyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is unsubstituted, pyridinylmethyl (substituted or fused as described earlier), and Ar¹, z, X, A, Q, and R³ are as defined.

An embodiment of the invention is the provision of a compound of Formula I, where the various moieties are independently selected, R¹ is H, R² is phenylethyl (unsubstituted, substituted or fused as described earlier), and Ar¹, z, X, A, Q, and R³ are as defined.

An embodiment of the invention is the provision of a compound of Formula I, where the various moieties are independently selected, R¹ is benzyl (unsubstituted, substituted or fused as described earlier), R² is benzyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is quinolinyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is oxazolyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is indazolyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is dihydrobenzodioxepinyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is pyrazolyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is terrahydronaphthalenyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is isoquinolinyl (unsubstituted, substituted or fused as described earlier), and Ar¹, z, X, A, Q, and R³ are as defined.

An embodiment of the invention is the provision of a compound of Formula I, where the various moieties are independently selected, R¹ is H, R² is oxolanyl (unsubstituted, substituted or fused as described earlier), and Ar¹, z, X, A, Q, and R³ are as defined.

An embodiment of the invention is the provision of a compound of Formula I, where the various moieties are independently selected, R¹ and R² are joined together to form, along with the N, a heterocycloalkyl (unsubstituted or substituted as described earlier), and Ar¹, z, X, A, Q, and R³ are as defined.

An embodiment of the invention is the provision of a compound of Formula I, where the various moieties are independently selected, R¹ and R² are joined together to form, along with the N, a heterocycloalkenyl (unsubstituted or substituted as described earlier), and Ar¹, z, X, A, Q, and R³ are as defined.

An embodiment of the invention is the provision of a compound of Formula I, where the various moieties are independently selected, R¹ and R² are joined together to form, along with the N, a fused bicyclic heterocycloalkyl (unsubstituted or substituted as described earlier), and Ar¹, z, X, A, Q, and R³ are as defined.

An embodiment of the invention is the provision of a compound of Formula I, where the various moieties are independently selected, R¹ and R² are joined together to form, along with the N, a fused tricyclic heterocycloalkyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a spiroheterocycloalkyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a heterospiroheterocycloalkyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a piperidinyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a piperazinyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a morpholinyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, an azapenyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, an azetidinyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a oxaazabicyclooctanyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, an azabicycloheptanyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a dihydrobenzoxazinyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a dihydroindolyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a thiomorpholinyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, an azatricyclotridecapentaenyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, an azaspirodecanyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a terrahydronaphthyridinyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, an azabicyclooctanyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a diazepanyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a decahydroquinolyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a diazaspiroundecanyl (unsubstituted or substituted as described earlier), and $Ar^1$, z, X, A, Q, and $R^3$ are as defined.

An embodiment of the invention is the provision of a compound of Formula I, where the various moieties are independently selected, $R^1$ and $R^2$ are joined together to form, along with the N, a terahydroisoquinolinyl (unsubstituted or substituted as described earlier), and $Ar^1$, z, X, A, Q, and $R^3$ are as defined.

An embodiment of the invention is the provision of a compound of Formula I, where the various moieties are independently selected, $Ar^1$, z, X, A, Q, and $R^3$ are as defined, and $R^1$ and $R^2$ are the same or different, wherein said $R^1$ and $R^2$ independently are unsubstituted or substituted with one or more substituents which can be the same or different and are independently selected from the group consisting of —C(O)NH$_2$, alkyl, —C(O)NH(alkyl), —C(O)N(alkyl)$_2$, halo, morpholinyl, alkoxyalkyl-, alkenyl, alkyl, CF$_3$, OH, CN, phenyl, isocyano, —N(H)C(O)CH$_3$, phenylethyl-, —C(O)CH$_3$, phenoxy, —S(O$_2$)CH$_3$, —S(O$_2$)CF$_3$, pyrazinyl, —OCHF$_2$, OCF$_3$, OCH$_2$F, —CH=CH$_2$, methylenedioxy, ethylenedioxy, benzyloxy, piperidinyl, —C(O)O—CH$_3$, phenoxy, oxopiperazinyl, oxopyrrolidinylmethyl-, NH2, NH(alkyl), —N(alkyl)$_2$, morpholinyloxoethyl-, oxopyrrolidinylmethyl-, azapanyl, nitrophenyl-, cyclopropyl, hydroxymethyl-, (hydroxyalkyl)oxy-, isopropyl, ethyl, methyl and phenylpropenyl-.

An embodiment of the invention is the provision of a compound of Formula I, where the various moieties are independently selected, Ar$^1$, z, X, A, Q, and R$^3$ are as defined, and R$^1$ and R$^2$ are joined together to form, along with the N, a C$_3$-C$_8$ heterocycloalkyl, a C$_3$-C$_8$ heterocycloalkenyl, a fused bicyclic heterocycloalkyl, a fused tricyclic heterocycloalkyl, spiroheterocycloalkyl or a heterospiroheterocycloalkyl, wherein each of said C$_3$-C$_8$ heterocycloalkyl, a C$_3$-C$_8$ heterocycloalkenyl, a fused bicyclic heterocycloalkyl, a fused tricyclic heterocycloalkyl, spiroheterocycloalkyl or a heterospiroheterocycloalkyl independently is unsubstituted or bears one or more substituents which can be the same or different and are independently selected from the group consisting of —C(O)NH$_2$, alkyl, —C(O)NH(alkyl), —C(O)N(alkyl)$_2$, halo, morpholinyl, alkoxyalkyl-, alkenyl, alkyl, CF$_3$, OH, CN, phenyl, isocyano, —N(H)C(O)CH$_3$, phenylethyl-, —C(O)CH$_3$, phenoxy, —S(O$_2$)CH$_3$, —S(O$_2$)CF$_3$, pyrazinyl, —OCHF$_2$, OCF$_3$, OCH$_2$F, —CH=CH$_2$, methylenedioxy, ethylenedioxy, benzyloxy, piperidinyl, —C(O)O—CH$_3$, phenoxy, oxopiperazinyl, oxopyrrolidinylmethyl-, NH2, NH(alkyl), —N(alkyl)$_2$, morpholinyloxoethyl-, oxopyrrolidinylmethyl-, azapanyl, nitrophenyl-, cyclopropyl, hydroxymethyl-, (hydroxyalkyl)oxy-, isopropyl, ethyl, methyl and phenylpropenyl-.

An embodiment of the invention is the provision of a compound of Formula I where NR$^1$R$^2$ is acyclic, where the various moieties are independently selected, Ar$^1$ is aryl, R$^1$ is H, R$^2$ is aryl, and z, X, L, A, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, R$^2$ is heteroaryl, and z, X, L, A, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, R$^2$ is heterocycloalkyl, and z, X, L, A, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, R$^2$ is spiroheterocycloalkyl, and z, X, L, A, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, R$^2$ is heterospiroheterocycloalkyl, and z, X, L, A, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is aryl, and z, X, L, A, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is heteroaryl, and z, X, L, A, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is heterocycloalkyl, and z, X, L, A, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is spiroheterocycloalkyl, and z, X, L, A, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is heterospiroheterocycloalkyl, and z, X, L, A, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, R$^2$ is aryl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, A is phenyl, R$^2$ is heteroaryl, and z, X, L, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, A is phenyl, R$^2$ is heterocycloalkyl, and z, X, L, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, A is phenyl, R$^2$ is spiroheterocycloalkyl, and z, X, L, Q, and R$^3$ are as defined.

An embodiment of the invention is the provision of a compound of Formula I where NR$^1$R$^2$ is acyclic, where the various moieties are independently selected, Ar$^1$ is aryl, R$^1$ is H, A is phenyl, R$^2$ is heterospiroheterocycloalkyl, and z, X, L, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is aryl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is heteroaryl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is heterocycloalkyl, and z, X, L, A, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is spiroheterocycloalkyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is heteroaryl, R$^1$ is H, R$^2$ is heterospiroheterocycloalkyl, A is phenyl, and z, X, L, Q, and R$^3$ are as defined.

An embodiment of the invention is the provision of a compound of Formula I where NR$^1$R$^2$ is acyclic, where the various moieties are independently selected, $Ar^1$ is phenyl, $R^1$ is H, $R^2$ is aryl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is phenyl, $R^1$ is H, A is phenyl, $R^2$ is heteroaryl, and z, X, L, Q, and $R^3$ are as defined.

An embodiment of the invention is the provision of a compound of Formula I where $NR^1R^2$ is acyclic, where the various moieties are independently selected, $Ar^1$ is phenyl, $R^1$ is H, A is phenyl, $R^2$ is heterocycloalkyl, and z, X, L, Q, and $R^3$ are as defined.

An embodiment of the invention is the provision of a compound of Formula I where $NR^1R^2$ is acyclic, where the various moieties are independently selected, $Ar^1$ is phenyl, $R^1$ is H, A is phenyl, $R^2$ is spiroheterocycloalkyl, and z, X, L, Q, and $R^3$ are as defined.

An embodiment of the invention is the provision of a compound of Formula I where $NR^1R^2$ is acyclic, where the various moieties are independently selected, $Ar^1$ is phenyl, $R^1$ is H, A is phenyl, $R^2$ is heterospiroheterocycloalkyl, and z, X, L, Q, and $R^3$ are as defined.

An embodiment of the invention is the provision of a compound of Formula I where $NR^1R^2$ is acyclic, where the various moieties are independently selected, $Ar^1$ is heteroaryl, $R^1$ is H, $R^2$ is aryl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is heteroaryl, $R^1$ is H, $R^2$ is heteroaryl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is heteroaryl, $R^1$ is H, $R^2$ is heterocycloalkyl, and z, X, L, A, Q, and $R^3$ are as defined.

An embodiment of the invention is the provision of a compound of Formula I where $NR^1R^2$ is acyclic, where the various moieties are independently selected, $Ar^1$ is heteroaryl, $R^1$ is H, $R^2$ is spiroheterocycloalkyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is heteroaryl, $R^1$ is H, $R^2$ is heterospiroheterocycloalkyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is pyridyl, $R^1$ is H, $R^2$ is aryl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is pyridyl, $R^1$ is H, $R^2$ is heteroaryl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is pyridyl, $R^1$ is H, $R^2$ is heterocycloalkyl, and z, X, L, A, Q, and $R^3$ are as defined.

An embodiment of the invention is the provision of a compound of Formula I where $NR^1R^2$ is acyclic, where the various moieties are independently selected, $Ar^1$ is pyridyl, $R^1$ is H, $R^2$ is spiroheterocycloalkyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is pyridyl, $R^1$ is H, $R^2$ is heterospiroheterocycloalkyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is aryl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is heteroaryl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is heterocycloalkyl, and z, X, L, A, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is spiroheterocycloalkyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is heterospiroheterocycloalkyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is pyrrolyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is pyrrolyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is pyridinylmethyl, and z, X, L, A, Q, and $R^3$ are as defined.

An embodiment of the invention is the provision of a compound of Formula I where $NR^1R^2$ is acyclic, where the various moieties are independently selected, $Ar^1$ is pyridinyl, $R^1$ is H, $R^2$ is pyrrolyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is piperidinyl, $R^1$ is H, $R^2$ is pyrrolyl, A is phenyl, and z, X, L, Q, and $R^3$ are as defined.

An embodiment of the invention is the provision of a compound of Formula I where $NR^1R^2$ is acyclic, where the various moieties are independently selected, $Ar^1$ is pyridinyl, $R^1$ is H, $R^2$ is pyridinylmethyl, and z, X, L, A, Q, and $R^3$ are as defined.

An embodiment of the invention is the provision of a compound of Formula I where $NR^1R^2$ is acyclic, where the various moieties are independently selected, Ar$^1$ is pyridinyl, R$^1$ is H, R$^2$ is alkyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is hydroxyalkyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is phenylalkyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is cycloalkyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is oxolanyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is quinolinyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is oxazolyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is spiroheterocycloakyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is heterospiroheterocycloakyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is tetrahydronaphthalenyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is dihydrobenzodioxepinyl, A is phenyl, and z, X, L, Q, and R$^3$ are as defined.

An embodiment of the invention is the provision of a compound of Formula I where NR$^1$R$^2$ is acyclic, where the various moieties are independently selected, Ar$^1$ is pyridinyl, R$^1$ is H, R$^2$ is alkoxyalkyl, A is phenyl, and z, X, L, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is piperidinyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is morpholinyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is piperazinyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is azapenyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is azetidinyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is oxaazabicyclooctanyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is azabicycloheptanyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is dihydrobenzoxazinyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is dihydroindolyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is thiomorpholinyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is azatricyclotridecapentaenyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is azaspirodecanyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is azaspiroundecanyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is tetrahydronaphthyridinyl, and z, X, L, A, Q, and R$^3$ are as defined.

An embodiment of the invention is the provision of a compound of Formula I where NR$^1$R$^2$ is cyclic, where the various moieties are independently selected, Ar$^1$ is aryl, NR$^1$R$^2$ is azabicyclooctanyl, and z, X, L, A, Q, and R$^3$ are as defined.

An embodiment of the invention is the provision of a compound of Formula I where $NR^1R^2$ is cyclic, where the various moieties are independently selected, $Ar^1$ is aryl, $NR^1R^2$ is diazepanyl, and z, X, L, A, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is decahydroquinolinyl, and z, X, L, A, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is diazaspiroundecanyl, and z, X, L, A, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is tetrahydroisoquinolinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is piperidinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is morpholinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is piperazinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azapenyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azetidinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is oxaazabicyclooctanyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azabicycloheptanyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is dihydrobenzoxazinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is dihydroindolyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is thiomorpholinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azatricyclotridecapentaenyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azaspirodecanyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azaspiroundecanyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is tetrahydronaphthyridinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azabicyclooctanyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is diazepanyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is decahydroquinolinyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is diazaspiroundecanyl, and z, X, L, A, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is tetrahydroisoquinolinyl, and z, X, L, A, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is piperidinyl, A is phenyl, and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is morpholinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is piperazinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is azapenyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is azetidinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is oxaazabicyclooctanyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is azabicycloheptanyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is dihydrobenzoxazinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is dihydroindolyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is thiomorpholinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is azatricyclotridecapentaenyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is azaspirodecanyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is azaspiroundecanyl, A is phenyl and z, X, L, Q, and $R^3$ are as defined.

An embodiment of the invention is the provision of a compound of Formula I where $NR^1R^2$ is cyclic), where the various moieties are independently selected, $Ar^1$ is aryl, $NR^1R^2$ is tetrahydronaphthyridinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is azabicyclooctanyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is diazepanyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is decahydroquinolinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is diazaspiroundecanyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is aryl, $NR^1R^2$ is tetrahydroisoquinolinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is piperidinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is morpholinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is piperazinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azapenyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azetidinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is oxaazabicyclooctanyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is azabicycloheptanyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is dihydrobenzoxazinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is dihydroindolyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, $NR^1R^2$ is thiomorpholinyl, A is phenyl and z, X, L, Q, and $R^3$ are as defined.

An embodiment of the invention is the provision of a compound of Formula I where $NR^1R^2$ is cyclic, where the various moieties are independently selected, $Ar^1$ is heteroaryl, NR¹R² is azatricyclotridecapentaenyl, A is phenyl and z, X, L, Q, and R³ are as defined.

An embodiment of the invention is the provision of a compound of Formula I where NR¹R² is cyclic, where the various moieties are independently selected, Ar¹ is heteroaryl, NR¹R² is azaspirodecanyl, A is phenyl and z, X, L, Q, and R³ are as defined.

An embodiment of the invention is the provision of a compound of Formula I where NR¹R² is cyclic, where the various moieties are independently selected, Ar¹ is heteroaryl, NR¹R² is azaspiroundecanyl, A is phenyl and z, X, L, Q, and R³ are as defined.

An embodiment of the invention is the provision of a compound of Formula I where NR¹R² is cyclic, where the various moieties are independently selected, Ar¹ is heteroaryl, NR¹R² is tetrahydronaphthyridinyl, A is phenyl and z, X, L, Q, and R³ are as defined.

An embodiment of the invention is the provision of a compound of Formula I where NR¹R² is cyclic, where the various moieties are independently selected, Ar¹ is heteroaryl, NR¹R² is azabicyclooctanyl, A is phenyl and z, X, L, Q, and R³ are as defined.

An embodiment of the invention is the provision of a compound of Formula I where NR¹R² is cyclic, where the various moieties are independently selected, Ar¹ is heteroaryl, NR¹R² is diazepanyl, A is phenyl and z, X, L, Q, and R³ are as defined.

An embodiment of the invention is the provision of a compound of Formula I where NR¹R² is cyclic, where the various moieties are independently selected, Ar¹ is heteroaryl, NR¹R² is decahydroquinolinyl, A is phenyl and z, X, L, Q, and R³ are as defined.

An embodiment of the invention is the provision of a compound of Formula I where NR¹R² is cyclic, where the various moieties are independently selected, Ar¹ is heteroaryl, NR¹R² is diazaspiroundecanyl, A is phenyl and z, X, L, Q, and R³ are as defined.

An embodiment of the invention is the provision of a compound of Formula I where NR¹R² is cyclic, where the various moieties are independently selected, Ar¹ is heteroaryl, NR¹R² is tetrahydroisoquinolinyl, A is phenyl and z, X, L, Q, and R³ are as defined.

Another embodiment of this invention is the provision of compounds, compositions, kits, and antidotes for the NAMPT pathway in mammals having a compound of the Formula II:

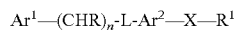

wherein

Ar¹ is aryl, heteroaryl or heterocycloalkyl, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with aryl, heteroaryl or heterocycloalkyl, still further wherein any of said aryl, heteroaryl and heterocycloalkyl is either unsubstituted or optionally independently substituted with one or more substituents which can be the same or different and are independently selected from the group consisting of deuterium, halo, cyano, isocyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, —N(R³)—C(O)-alkyl, —N(R³)—C(O)-aryl, —N(R³)—C(O)—O-alkyl, —N(R³)—C(O)—O-aryl, -cycloalkyl, -heterocycloalkyl, -aryl, —C(O)-aryl, —S(O)-aryl, and heteroaryl, with the proviso that no two adjacent ring heteroatoms are both S or both O;

R is H, a straight or branched C₁-C₆ alkyl, or arylalkyl;

n is 0, 1, 2, 3 or 4;

L is selected from NHC(O)NH, OC(O)NH, NHC(O)O, OCH₂C(O)NH, C(O)NH, NHC(S)NH, OC(S)NH, NHC(S)O, OCH₂C(S)NH, or C(S)NH, with the proviso that when L is C(O)NH, then n is 0;

Ar² is aryl, heteroaryl, heterocycloalkyl or C₃ to C₈ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, isocyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, —N(R³)—C(O)-alkyl, —N(R³)—C(O)-aryl, —N(R³)—C(O)—O-alkyl, —N(R³)—C(O)—O-aryl, -cycloalkyl, -heterocycloalkyl, -aryl, —C(O)-aryl, —S(O)-aryl, and heteroaryl;

X is S, S(O), S(O)₂, O or C(O);

R¹ is cycloalkyl, —CH$_z$F$_{3-z}$, aryl, heterocycloalkyl, heteroaryl, alkyl, -alkenyl, -alkynyl, (aryl)alkyl-, (heteroaryl)alkyl- or (heterocycloalkyl)alkyl-, (i) wherein each of said cycloalkyl, aryl, heterocycloalkyl, heteroaryl and alkyl is either unsubstituted or optionally substituted with 1, 2, 3, 4 or 5 substituents which can be the same or different and are independently selected from the group consisting of deuterium, halo, cyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, alkyl, -alkenyl, -alkynyl, alkoxy-, hydroxy, -alkylhydroxy, aryloxy- or (alkoxyalkyl)amino-, -cycloalkyl, -heterocycloalkyl, -aryl, —S(O)₂-alkyl, —S(O)₂-aryl, —S(O)₂—CF₃, —C(O)N(alkyl)₂, —C(O)alkyl, —NH—C(O)-alkyl, —NH—C(O)-aryl, methylenedioxy, and heteroaryl, (ii) further wherein each of said cycloalkyl, aryl, heterocycloalkyl, and heteroaryl may additionally optionally be fused with independently selected aryl, heteroaryl, heterocycloalkyl or cyloalkyl;

R³ is H, alkyl or arylalkyl-;

z is 0, 1, or 2;

and pharmaceutically acceptable salts, solvates, esters, prodrugs and isomers thereof, with the proviso that the compound of Formula I is not 3-{1-[(4-methoxybenzene)sulfonyl]piperidin-4-yl}-1-(pyridin-3-ylmethyl)urea, or 1-(4-phenoxyphenyl)-3-(pyridin-3-ylmethyl)thiourea.

In the compounds of Formula II, the various moieties are independently selected.

The following embodiments are directed to Formula II as applicable. Further, the moieties aryl, heteroaryl, heterocycloalkyl, cycloalkyl, spiroheterocycloalkyl and heterospiroheterocycloalkyl as well as their representative moieties in these embodiments can be independently unsubstituted or optionally substituted or optionally fused as described earlier. Any one or more of the embodiments relating to Formula II below can be combined with one or more other embodiments of Formula II.

An embodiment of the invention is the provision of a compound of Formula II, where the various moieties are independently selected, Ar¹ is aryl, and z, X, L, n, Ar², R¹ and R³ are as defined.

An embodiment of the invention is the provision of a compound of Formula II, where the various moieties are independently selected, $Ar^1$ is heteroaryl, and z, X, L, n, $Ar^2$, $R^1$ and $R^3$ are as defined.

An embodiment of the invention is the provision of a compound of Formula II, where the various moieties are independently selected, $Ar^1$ is heterocycloalkyl, and z, X, L, n, $Ar^2$, $R^1$ and $R^3$ are as defined.

An embodiment of the invention is the provision of a compound of Formula II, where the various moieties are independently selected, $Ar^1$ is aryl fused with an aryl, heteroaryl or heterocycloalkyl, and z, X, L, n, $Ar^2$, $R^1$ and $R^3$ are as defined.

An embodiment of the invention is the provision of a compound of Formula II, where the various moieties are independently selected, $Ar^1$ is heteroaryl fused with an aryl, heteroaryl or heterocycloalkyl, and z, X, L, n, $Ar^2$, $R^1$ and $R^3$ are as defined.

An embodiment of the invention is the provision of a compound of Formula II, where the various moieties are independently selected, $Ar^1$ is heterocycloalkyl fused with an aryl, heteroaryl or heterocycloalkyl, and z, X, L, n, $Ar^2$, $R^1$ and $R^3$ are as defined.

An embodiment of the invention is the provision of a compound of Formula II, where the various moieties are independently selected, $Ar^1$ is aryl substituted as shown under Formula II, and z, X, L, n, $Ar^2$, $R^1$ and $R^3$ are as defined.

An embodiment of the invention is the provision of a compound of Formula II, where the various moieties are independently selected, $Ar^1$ is heteroaryl substituted as shown under Formula II, and z, X, L, n, $Ar^2$, $R^1$ and $R^3$ are as defined.

An embodiment of the invention is the provision of a compound of Formula II, where the various moieties are independently selected, $Ar^1$ is heterocycloalkyl substituted as shown under Formula II, and z, X, L, n, $Ar^2$, $R^1$ and $R^3$ are as defined.

An embodiment of the invention is the provision of a compound of Formula II, where the various moieties are independently selected, $Ar^1$ is aryl, R is H, and z, X, L, n, $Ar^2$, $R^1$ and $R^3$ are as defined.

An embodiment of the invention is the provision of a compound of Formula II, where the various moieties are independently selected, $Ar^1$ is aryl, R is a straight chain alkyl, and z, X, L, n, $Ar^2$, $R^1$ and $R^3$ are as defined.

An embodiment of the invention is the provision of a compound of Formula II, where the various moieties are independently selected, $Ar^1$ is aryl, R is a branched chain alkyl, and z, X, L, n, $Ar^2$, $R^1$ and $R^3$ are as defined.

An embodiment of the invention is the provision of a compound of Formula II, where the various moieties are independently selected, $Ar^1$ is aryl, R is H, n is 1, and z, X, L, $Ar^2$, $R^1$ and $R^3$ are as defined.

An embodiment of the invention is the provision of a compound of Formula II, where the various moieties are independently selected, $Ar^1$ is aryl, R is a straight chain alkyl, n is 1, and z, X, L, $Ar^2$, $R^1$ and $R^3$ are as defined.

An embodiment of the invention is the provision of a compound of Formula II, where the various moieties are independently selected, $Ar^1$ is aryl, R is a branched chain alkyl, n is 1, and z, X, L, $Ar^2$, $R^1$ and $R^3$ are as defined.

An embodiment of the invention is the provision of a compound of Formula II, where the various moieties are independently selected, $Ar^1$ is aryl, R is H, n is 1, L is —N(H)—C(O)—N(H)—, and z, X, $Ar^2$, $R^1$ and $R^3$ are as defined.

An embodiment of the invention is the provision of a compound of Formula II, where the various moieties are independently selected, $Ar^1$ is aryl, R is a straight chain alkyl, n is 1, L is —N(H)—C(O)—N(H)—, and z, X, $Ar^2$, $R^1$ and $R^3$ are as defined.

An embodiment of the invention is the provision of a compound of Formula II, where the various moieties are independently selected, $Ar^1$ is aryl, R is a branched chain alkyl, n is 1, L is —N(H)—C(O)—N(H)—, and z, X, $Ar^2$, $R^1$ and $R^3$ are as defined.

An embodiment of the invention is the provision of a compound of Formula II, where the various moieties are independently selected, $Ar^1$ is aryl, R is H, n is 1, L is —N(H)—C(O)—N(H)—, X is —S($O_2$)—, and z, $Ar^2$, $R^1$ and $R^3$ are as defined.

An embodiment of the invention is the provision of a compound of Formula II, where the various moieties are independently selected, $Ar^1$ is aryl, R is a straight chain alkyl, n is 1, L is —N(H)—C(O)—N(H)—, X is —S($O_2$)—, and z, $Ar^2$, $R^1$ and $R^3$ are as defined.

An embodiment of the invention is the provision of a compound of Formula II, where the various moieties are independently selected, $Ar^1$ is aryl, R is a branched chain alkyl, n is 1, L is —N(H)—C(O)—N(H)—, X is —S($O_2$)—, and z, $Ar^2$, $R^1$ and $R^3$ are as defined.

An embodiment of the invention is the provision of a compound of Formula II, where the various moieties are independently selected, $Ar^1$ is aryl, R is H, n is 1, L is —N(H)—C(O)—N(H)—, X is —S(O)—, and z, $Ar^2$, $R^1$ and $R^3$ are as defined.

An embodiment of the invention is the provision of a compound of Formula II, where the various moieties are independently selected, $Ar^1$ is aryl, R is a straight chain alkyl, n is 1, L is —N(H)—C(O)—N(H)—, X is —S(O)—, and z, $Ar^2$, $R^1$ and $R^3$ are as defined.

An embodiment of the invention is the provision of a compound of Formula II, where the various moieties are independently selected, $Ar^1$ is aryl, R is a branched chain alkyl, n is 1, L is —N(H)—C(O)—N(H)—, X is —S(O)—, and z, $Ar^2$, $R^1$ and $R^3$ are as defined.

An embodiment of the invention is the provision of a compound of Formula II, where the various moieties are independently selected, $Ar^1$ is aryl, R is H, n is 1, L is —N(H)—C(O)—N(H)—, X is —C(O)—, and z, $Ar^2$, $R^1$ and $R^3$ are as defined.

An embodiment of the invention is the provision of a compound of Formula II, where the various moieties are independently selected, $Ar^1$ is aryl, R is a straight chain alkyl, n is 1, L is —N(H)—C(O)—N(H)—, X is —C(O)—, and z, $Ar^2$, $R^1$ and $R^3$ are as defined.

An embodiment of the invention is the provision of a compound of Formula II, where the various moieties are independently selected, $Ar^1$ is aryl, R is a branched chain alkyl, n is 1, L is —N(H)—C(O)—N(H)—, X is —C(O)—, and z, $Ar^2$, $R^1$ and $R^3$ are as defined.

An embodiment of the invention is the provision of a compound of Formula II, where the various moieties are independently selected, $Ar^1$ is aryl, R is H, n is 1, L is —N(H)—C(O)—N(H)—, X is —O—, and z, $Ar^2$, $R^1$ and $R^3$ are as defined.

An embodiment of the invention is the provision of a compound of Formula II, where the various moieties are independently selected, $Ar^1$ is aryl, R is a straight chain alkyl, n is 1, L is —N(H)—C(O)—N(H)—, X is —O—, and z, $Ar^2$, $R^1$ and $R^3$ are as defined.

An embodiment of the invention is the provision of a compound of Formula II, where the various moieties are independently selected, Ar$^1$ is aryl, R is a branched chain alkyl, n is 1, L is —N(H)—C(O)—N(H)—, X is —O—, and z, Ar$^2$, R$^1$ and R$^3$ are as defined.

An embodiment of the invention is the provision of a compound of Formula II, where the various moieties are independently selected, Ar$^1$ is heteroaryl, R is H, and z, X, L, n, Ar$^2$, R$^1$ and R$^3$ are as defined.

An embodiment of the invention is the provision of a compound of Formula II, where the various moieties are independently selected, Ar$^1$ is heteroaryl, R is a straight chain alkyl, and z, X, L, n, Ar$^2$, R$^1$ and R$^3$ are as defined.

An embodiment of the invention is the provision of a compound of Formula II, where the various moieties are independently selected, Ar$^1$ is heteroaryl, R is a branched chain alkyl, and z, X, L, n, Ar$^2$, R$^1$ and R$^3$ are as defined.

An embodiment of the invention is the provision of a compound of Formula II, where the various moieties are independently selected, Ar$^1$ is heteroaryl, R is H, n is 1, and z, X, L, Ar$^2$, R$^1$ and R$^3$ are as defined.

An embodiment of the invention is the provision of a compound of Formula II, where the various moieties are independently selected, Ar$^1$ is heteroaryl, R is a straight chain alkyl, n is 1, and z, X, L, Ar$^2$, R$^1$ and R$^3$ are as defined.

An embodiment of the invention is the provision of a compound of Formula II, where the various moieties are independently selected, Ar$^1$ is heteroaryl, R is a branched chain alkyl, n is 1, and z, X, L, Ar$^2$, R$^1$ and R$^3$ are as defined.

An embodiment of the invention is the provision of a compound of Formula II, where the various moieties are independently selected, Ar$^1$ is heteroaryl, R is H, n is 1, L is —N(H)—C(O)—N(H)—, X is —S(O$_2$)—, and z, Ar$^2$, R$^1$ and R$^3$ are as defined.

An embodiment of the invention is the provision of a compound of Formula II, where the various moieties are independently selected, Ar$^1$ is heteroaryl, R is a straight chain alkyl, n is 1, L is —N(H)—C(O)—N(H)—, X is —S(O$_2$)—, and z, Ar$^2$, R$^1$ and R$^3$ are as defined.

An embodiment of the invention is the provision of a compound of Formula II, where the various moieties are independently selected, Ar$^1$ is heteroaryl, R is a branched chain alkyl, n is 1, L is —N(H)—C(O)—N(H)—, X is —S(O$_2$)—, and z, Ar$^2$, R$^1$ and R$^3$ are as defined.

An embodiment of the invention is the provision of a compound of Formula II, where the various moieties are independently selected, Ar$^1$ is heteroaryl, R is H, n is 1, L is —N(H)—C(O)—N(H)—, X is —S(O)—, and z, Ar$^2$, R$^1$ and R$^3$ are as defined.

An embodiment of the invention is the provision of a compound of Formula II, where the various moieties are independently selected, Ar$^1$ is heteroaryl, R is a straight chain alkyl, n is 1, L is —N(H)—C(O)—N(H)—, X is —S(O)—, and z, Ar$^2$, R$^1$ and R$^3$ are as defined.

An embodiment of the invention is the provision of a compound of Formula II, where the various moieties are independently selected, Ar$^1$ is heteroaryl, R is a branched chain alkyl, n is 1, L is —N(H)—C(O)—N(H)—, X is —S(O)—, and z, Ar$^2$, R$^1$ and R$^3$ are as defined.

An embodiment of the invention is the provision of a compound of Formula II, where the various moieties are independently selected, Ar$^1$ is heteroaryl, R is H, n is 1, L is —N(H)—C(O)—N(H)—, X is —C(O)—, and z, Ar$^2$, R$^1$ and R$^3$ are as defined.

An embodiment of the invention is the provision of a compound of Formula II, where the various moieties are independently selected, Ar$^1$ is heteroaryl, R is a straight chain alkyl, n is 1, L is —N(H)—C(O)—N(H)—, X is —C(O)—, and z, Ar$^2$, R$^1$ and R$^3$ are as defined.

An embodiment of the invention is the provision of a compound of Formula II, where the various moieties are independently selected, Ar$^1$ is heteroaryl, R is a branched chain alkyl, n is 1, L is —N(H)—C(O)—N(H)—, X is —C(O)—, and z, Ar$^2$, R$^1$ and R$^3$ are as defined.

An embodiment of the invention is the provision of a compound of Formula II, where the various moieties are independently selected, Ar$^1$ is heteroaryl, R is H, n is 1, L is —N(H)—C(O)—N(H)—, X is —O—, and z, Ar$^2$, R$^1$ and R$^3$ are as defined.

An embodiment of the invention is the provision of a compound of Formula II, where the various moieties are independently selected, Ar$^1$ is heteroaryl, R is a straight chain alkyl, n is 1, L is —N(H)—C(O)—N(H)—, X is —O—, and z, Ar$^2$, R$^1$ and R$^3$ are as defined.

An embodiment of the invention is the provision of a compound of Formula II, where the various moieties are independently selected, Ar$^1$ is heteroaryl, R is a branched chain alkyl, n is 1, L is —N(H)—C(O)—N(H)—, X is —O—, and z, Ar$^2$, R$^1$ and R$^3$ are as defined.

An embodiment of the invention is the provision of a compound of Formula II, where the various moieties are independently selected, Ar$^1$ is heteroaryl, R is H, Ar$^2$ is aryl, and z, X, L, n, R$^1$ and R$^3$ are as defined.

An embodiment of the invention is the provision of a compound of Formula II, where the various moieties are independently selected, Ar$^1$ is heteroaryl, R is a straight chain alkyl, Ar$^2$ is aryl, and z, X, L, n, R$^1$ and R$^3$ are as defined.

An embodiment of the invention is the provision of a compound of Formula II, where the various moieties are independently selected, Ar$^1$ is heteroaryl, R is a branched chain alkyl, Ar$^2$ is aryl, and z, X, L, n, R$^1$ and R$^3$ are as defined.

An embodiment of the invention is the provision of a compound of Formula II, where the various moieties are independently selected, Ar$^1$ is heteroaryl, R is H, n is 1, Ar$^2$ is aryl, and z, X, L, R$^1$ and R$^3$ are as defined.

An embodiment of the invention is the provision of a compound of Formula II, where the various moieties are independently selected, Ar$^1$ is heteroaryl, R is a straight chain alkyl, Ar$^2$ is aryl, n is 1, and z, X, L, R$^1$ and R$^3$ are as defined.

An embodiment of the invention is the provision of a compound of Formula II, where the various moieties are independently selected, Ar$^1$ is heteroaryl, R is a branched chain alkyl, Ar$^2$ is aryl, n is 1, and z, X, L, R$^1$ and R$^3$ are as defined.

An embodiment of the invention is the provision of a compound of Formula II, where the various moieties are independently selected, Ar$^1$ is heteroaryl, R is H, n is 1, L is —N(H)—C(O)—N(H)—, X is —S(O$_2$)—, Ar$^2$ is aryl, and z, R$^1$ and R$^3$ are as defined.

An embodiment of the invention is the provision of a compound of Formula II, where the various moieties are independently selected, Ar$^1$ is heteroaryl, R is a straight chain alkyl, n is 1, L is —N(H)—C(O)—N(H)—, X is —S(O$_2$)—, Ar$^2$ is aryl, and z, R$^1$ and R$^3$ are as defined.

An embodiment of the invention is the provision of a compound of Formula II, where the various moieties are independently selected, Ar$^1$ is heteroaryl, R is a branched chain alkyl, n is 1, L is —N(H)—C(O)—N(H)—, X is —S(O$_2$)—, Ar$^2$ is aryl, and z, R$^1$ and R$^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —S(O)—, $Ar^2$ is aryl, and z, $R^1$ and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —S(O)—, $Ar^2$ is aryl, and z, $R^1$ and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —S(O)—, $Ar^2$ is aryl, and z, $R^1$ and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —C(O)—, $Ar^2$ is aryl, and z, $R^1$ and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —C(O)—, $Ar^2$ is aryl, and z, $R^1$ and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —C(O)—, $Ar^2$ is aryl, and z, $R^1$ and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —O—, $Ar^2$ is aryl, and z, $R^1$ and $R^3$ are as defined. An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —O—, $Ar^2$ is aryl, and z, $R^1$ and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —O—, $Ar^2$ is aryl, and z, $R^1$ and $R^3$ are as defined.

An embodiment of the invention is the provision of a compound of Formula II, where the various moieties are independently selected, $Ar^1$ is heteroaryl, R is H, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a straight chain alkyl, $Ar^2$ is aryl, $R^1$ is cycloalkyl, and z, X, L, n, and $R^3$ are as defined.

An embodiment of the invention is the provision of a compound, of Formula II where the various moieties are independently selected, $Ar^1$ is heteroaryl, R is a branched chain alkyl, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is H, n is 1, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a straight chain alkyl, $Ar^2$ is aryl, n is 1, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a branched chain alkyl, $Ar^2$ is aryl, n is 1, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —S($O_2$)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —S($O_2$)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —S($O_2$)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —S(O)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —S(O)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —S(O)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —C(O)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —C(O)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —C(O)—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —O—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —O—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —O—, $Ar^2$ is aryl, $R^1$ is cycloalkyl, and z, X, L, n, and $R^3$ are as defined.

An embodiment of the invention is the provision of a compound of Formula II, where the various moieties are independently selected, $Ar^1$ is heteroaryl, R is H, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a straight chain alkyl, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a branched chain alkyl, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is H, n is 1, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a straight chain alkyl, $Ar^2$ is aryl, n is 1, $R^1$ is aryl, and z, X, L, n, and $R^3$ are as defined.

An embodiment of the invention is the provision of a compound of Formula II, where the various moieties are independently selected, $Ar^1$ is heteroaryl, R is a branched chain alkyl, $Ar^2$ is aryl, n is 1, $R^1$ is aryl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —$S(O_2)$—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —$S(O_2)$—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —$S(O_2)$—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —S(O)—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —S(O)—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —S(O)—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —C(O)—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —C(O)—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —C(O)—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —O—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —O—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —O—, $Ar^2$ is aryl, $R^1$ is aryl, and z, X, L, n, and $R^3$ are as defined.

An embodiment of the invention is the provision of a compound of Formula II, where the various moieties are independently selected, $Ar^1$ is heteroaryl, R is H, $Ar^2$ is heteroaryl, $R^1$ is aryl, and z, X, L, n, and $R^3$ are as defined.

An embodiment of the invention is the provision of a compound, of Formula II where the various moieties are independently selected, $Ar^1$ is heteroaryl, R is a straight chain alkyl, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a branched chain alkyl, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is H, n is 1, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a straight chain alkyl, $Ar^2$ is aryl, n is 1, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a branched chain alkyl, $Ar^2$ is aryl, n is 1, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —$S(O_2)$—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —S(O$_2$)—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —S(O$_2$)—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —S(O)—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —S(O)—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —S(O)—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —C(O)—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —C(O)—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —C(O)—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —O—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —O—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —O—, $Ar^2$ is aryl, $R^1$ is heteroaryl, and z, X, L, n, and $R^3$ are as defined.

An embodiment of the invention is the provision of a compound of Formula II, where the various moieties are independently selected, $Ar^1$ is heteroaryl, R is H, $Ar^2$ is heteroaryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is a straight chain alkyl, $Ar^2$ is aryl, $R^1$ is $CF_3$, and z, X, L, n, and $R^3$ are as defined.

An embodiment of the invention is the provision of a compound of Formula II where the various moieties are independently selected, $Ar^1$ is heteroaryl, R is a branched chain alkyl, $Ar^2$ is aryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is H, n is 1, $Ar^2$ is aryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is a straight chain alkyl, $Ar^2$ is aryl, n is 1, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is a branched chain alkyl, $Ar^2$ is aryl, n is 1, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —S(O$_2$)—, $Ar^2$ is aryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —S(O$_2$)—, $Ar^2$ is aryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —S(O$_2$)—, $Ar^2$ is aryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —S(O)—, $Ar^2$ is aryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is a straight chain alkyl, n is 1, L is —N(H)—C(O)—N(H)—, X is —S(O)—, $Ar^2$ is aryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is a branched chain alkyl, n is 1, L is —N(H)—C(O)—N(H)—, X is —S(O)—, $Ar^2$ is aryl, $R^1$ is $CF_3$, and z, X, L, n, and $R^3$ are as defined.

An embodiment of the invention is the provision of a compound of Formula II, where the various moieties are independently selected, $Ar^1$ is heteroaryl, R is H, n is 1, L is —N(H)—C(O)—N(H)—, X is —C(O)—, $Ar^2$ is aryl, $R^1$ is $CF_3$, and z, X, L, n, and $R^3$ are as defined.

An embodiment of the invention is the provision of a compound, where the various moieties are independently selected, $Ar^1$ is heteroaryl, R is a straight chain alkyl, n is 1, L is —N(H)—C(O)—N(H)—, X is —C(O)—, Ar² is aryl, R¹ is CF₃, and z, X, L, n, and R³ are as defined.

An embodiment of the invention is the provision of a compound of Formula II, where the various moieties are independently selected, Ar¹ is heteroaryl, R is a branched chain alkyl, n is 1, L is —N(H)—C(O)—N(H)—, X is —C(O)—, Ar² is aryl, R¹ is CF₃, and z, X, L, n, and R³ are as defined.

An embodiment of the invention is the provision of a compound of Formula II, where the various moieties are independently selected, Ar¹ is heteroaryl, R is H, n is 1, L is —N(H)—C(O)—N(H)—, X is —O—, Ar² is aryl, R¹ is CF₃, and z, X, L, n, and R³ are as defined.

An embodiment of the invention is the provision of a compound of Formula II, where the various moieties are independently selected, Ar¹ is heteroaryl, R is a straight chain alkyl, n is 1, L is —N(H)—C(O)—N(H)—, X is —O—, Ar² is aryl, R¹ is CF₃, and z, X, L, n, and R³ are as defined.

An embodiment of the invention is the provision of a compound of Formula II, where the various moieties are independently selected, Ar¹ is heteroaryl, R is a branched chain alkyl, n is 1, L is —N(H)—C(O)—N(H)—, X is —O—, Ar² is aryl, R¹ is CF₃, and z, X, L, n, and R³ are as defined.

An embodiment of the invention is the provision of a compound of Formula II, where the various moieties are independently selected, Ar¹ is selected from the group consisting of pyridinyl, imidazopyridinyl, pyrazolyl, quinolinyl and thienopyridinyl. Each of these moieties may be unsubstituted or optionally independently substituted with one or more groups which can be the same or different and are independently selected from the group consisting of —NH₂, —N(alkyl)₂, (alkoxyalkyl)oxy-, and pyrazolyl.

An embodiment of the invention is the provision of a compound of Formula II, where the various moieties are independently selected, R¹ is selected from the group consisting of cyclopentyl, CF₃, phenyl, naphthalenyl, pyrimidinyl, oxazolyl, 8-oxatricyclotridecahexaenyl and thienyl. Each of these moieties may be unsubstituted or optionally independently substituted with one or more groups which can be the same or different and are independently selected from the group consisting of —C(O)NH₂, —S(O₂)CH₃, F, Cl, Br, methylenedioxy, CF₃, OCF₃, alkyl, alkoxy, pyrazolyl, C(O)CH₃ and phenoxy.

An especially preferred moiety for Ar¹—(CHR)ₙ-L- in Formula II is the moiety:

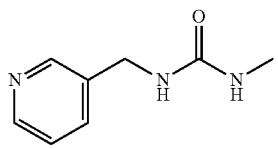

Another aspect of this invention is the provision of compounds, compositions, kits, and antidotes for the NAMPT pathway in mammals derived from compounds of Formula I and Formula II and having the Formula III:

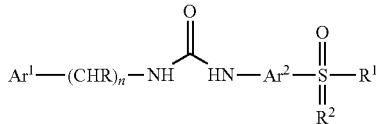

wherein,

Ar¹ is 5 to 12 membered heteroaryl comprising 1, 2, 3 or 4 heteroatom(s) independently selected from N, S or O, wherein said heteroaryl is unsubstituted or substituted by one or more Rᵃ selected from the group consisting of —NH₂, oxo, halo, haloalkyl, —NH(CO)O-alkyl, —C(O)NH₂ and 3,4-dihydroxy-5-methyltetrahydrofurane; and wherein said heteroaryl can comprise one or more N-oxide(s) formed with a N atom member of said heteroaryl, with the proviso that no two adjacent ring heteroatoms are both S or both O;

Ar² is aryl or 5 or 6 membered heteroaryl comprising 1, 2, 3 or 4 heteroatom(s) independently selected from N, S or O;

R is H, a straight or branched C₁-C₆ alkyl, or arylalkyl;

R¹ is —NR³R⁴ wherein R³ is H, alkyl or —S(O)₂alkyl and R⁴ is alkyl, hydroxyalkyl, —S(O)₂alkyl, —(CH₂)_qcycloalkyl, —(CH₂)_qheterocycloalkyl, aryl, arylalkyl-, —(CH₂)_qheteroaryl; haloalkyl, cycloalkyl; aryl; heterocycloalkyl; or heteroaryl; wherein:

each of said cycloalkyl, aryl, or heteroaryl is unsubstituted or substituted with 1, 2, 3, 4 or 5 substituents which can be the same or different and are independently selected from the group consisting of:

deuterium, halo, cyano, alkyl, hydroxyl, hydroxyalkyl, hydroxyalkoxy, cyanoalkyl, haloalkyl, alkenyl, alkynyl, alkoxy, alkylalkoxy, haloalkoxy, arylalkenyl-, aryloxy, benzyloxy, oxo, —(CH₂)_q—NR^bR^c, —(CH₂)_q—CONR^bR^c, —S(O)₂-alkyl, —S(O)₂-aryl, —S(O)₂NH-alkyl, —S(O)₂N(alkyl)₂, —S(O)₂-heterocycloalkyl, —S(O)₂—CF₃, —C(O)alkyl, —C(O)aryl, —C(O)alkylenylaryl, —C(O)O-alkyl, —NH—C(O)alkyl, —NH—C(O)aryl, methylenedioxy, —(CH₂)_qcycloalkyl, cycloalkylalkoxy-, aryl, arylalkyl-, —(CH₂)_qheteroaryl, and —(CH₂)_qheterocycloalkyl, wherein each of said cycloalkyl, heterocycloalkyl, aryl or heteroaryl may be substituted by one or more halo, nitro, haloalkyl, haloalkoxy, oxo, cyano, alkyl, haloalkyl, or alkoxy and;

each of said cycloalkyl, heterocycloalkyl, aryl, or heteroaryl may optionally additionally be fused with independently selected aryl, heteroaryl, heterocycloalkyl or cycloalkyl to from a bicyclic or tricyclic group that may be substituted by one or more halo, cyano, alkyl or alkoxy;

R² is O or absent,

R^b and R^c are independently selected from the group consisting of H, alkyl, hydroxyalkyl, alkoxy, aryl, alkoxyalkyl, —S(O)₂alkyl and cycloalkyl or R^b and R^c can form a 5 or 6 membered heterocycloalkyl group together with the nitrogen atom to which they are attached, wherein said heterocycloalkyl group may contain one or more additional heteroatom(s) selected from N, S or O;

n is 0, or 1;

q is 0, 1 or 2;

and pharmaceutically acceptable salts, solvates, esters and isomers thereof, with the proviso that the compound of Formula I is not 1-(pyridin-3-ylmethyl)-3-(4-sulfamoylphenyl)thiourea, 3-[4-(morpholine-4-sulfonyl)phenyl]-1-(pyridine-4-ylmethyl)thiourea or 3-[4-(piperidine-1-sulfonyl)phenyl]-1-(pyrdin-4-ylmethyl)thiourea.

In an embodiment, this invention discloses compounds of Formula III and pharmaceutically acceptable salts, solvates, ester or isomers thereof.

In the compounds of Formula III, the various moieties are independently selected.

The following embodiments are directed to Formula III as applicable. Further, the moieties aryl, heteroaryl, heterocycloalkyl, cycloalkyl, spiroheterocycloalkyl and heterospiroheterocycloalkyl as well as their representative moieties in these embodiments can be independently unsubstituted or optionally substituted or optionally fused as described earlier. Any one or more of the embodiments related to Formula III below can be combined with one or more other embodiments of Formula III.

An embodiment of the invention is the provision of a compound of Formula III, where the various moieties are independently selected and $Ar^2$ is aryl.

An embodiment of the invention is the provision of a compound of Formula III, where the various moieties are independently selected and $Ar^2$ is phenyl.

An embodiment of the invention is the provision of a compound of Formula III, where the various moieties are independently selected and $Ar^2$ has the following formula:

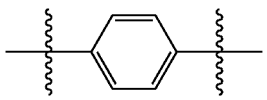 [SMILES: *c1ccc(*)cc1]

An embodiment of the invention is the provision of a compound of Formula III, where the various moieties are independently selected and $Ar^1$ is pyridine.

An embodiment of the invention is the provision of a compound of Formula III, where the various moieties are independently selected and $Ar^1$ has the following formula:

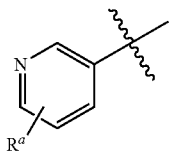

where $R^a$ is selected from the group consisting of —$NH_2$, oxo, halo, haloalkyl, —NH(CO)O-alkyl, —C(O)$NH_2$ and 3,4-dihydroxy-5-methyltetrahydrofurane.

An embodiment of the invention is the provision of a compound of Formula III, where the various moieties are independently selected and $Ar^1$ has the formula of:

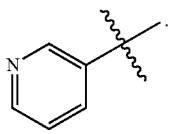

An embodiment of the invention is the provision of a compound of Formula III, where the various moieties are independently selected and n is 1.

An embodiment of the invention is the provision of a compound of Formula III, where the various moieties are independently selected, $Ar^1$ is pyridine and n is 1.

An embodiment of the invention is the provision of a compound of Formula III, where the various moieties are independently selected, $Ar^1$ is pyridine, n is 1 and $Ar^2$ is aryl.

An embodiment of the invention is the provision of a compound of Formula III, where the various moieties are independently selected, $Ar^1$ is pyridine, n is 1 and $Ar^2$ is phenyl.

An embodiment of the invention is the provision of a compound of Formula III, where the various moieties are independently selected, $Ar^1$ is pyridine and $Ar^2$ is phenyl.

An embodiment of the invention is the provision of a compound of Formula III, where the various moieties are independently selected and $Ar^2$ has the following formula:

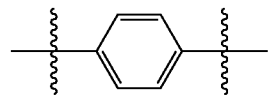

and $Ar^1$ is pyridine.

An embodiment of the invention is the provision of a compound of Formula III, where the various moieties are independently selected and R is H.

An embodiment of the invention is the provision of a compound of Formula III, where the various moieties are independently selected, $Ar^1$ is pyridine and R is H.

An embodiment of the invention is the provision of a compound of Formula III, where the various moieties are independently selected, n is 1 and R is H.

An embodiment of the invention is the provision of a compound of Formula III, where the various moieties are independently selected, $Ar^2$ is phenyl and R is H.

An embodiment of the invention is the provision of a compound of Formula III, where the various moieties are independently selected, n is 1, $Ar^2$ is phenyl and R is H.

An embodiment of the invention is the provision of a compound of Formula III, where the various moieties are independently selected, $Ar^1$ is pyridine, n is 1, $Ar^2$ is phenyl and R is H.

An embodiment of the invention is the provision of a compound of Formula III, where the various moieties are independently selected and $R^1$ is —$NR^3R^4$ wherein $R^3$ is H, alkyl or —$S(O)_2$alkyl and $R^4$ is alkyl, hydroxyalkyl, —$S(O)_2$ alkyl, —$(CH_2)_q$cycloalkyl, —$(CH_2)_q$heterocycloalkyl, aryl, arylalkyl-, —$(CH_2)_q$heteroaryl.

An embodiment of the invention is the provision of a compound of Formula III, where the various moieties are independently selected and $R^1$ is —$NR^3R^4$ wherein $R^3$ is H and $R^4$ is aryl.

An embodiment of the invention is the provision of a compound of Formula III, where the various moieties are independently selected, $Ar^1$ is pyridine and $R^1$ is —$NR^3R^4$ wherein $R^3$ is H and $R^4$ is aryl.

An embodiment of the invention is the provision of a compound of Formula III, where the various moieties are independently selected, $Ar^2$ is phenyl and $R^1$ is —$NR^3R^4$ wherein $R^3$ is H and $R^4$ is aryl.

An embodiment of the invention is the provision of a compound of Formula III, where the various moieties are independently selected, $Ar^1$ is pyridine, $Ar^2$ is phenyl and $R^1$ is —$NR^3R^4$ wherein $R^3$ is H and $R^4$ is aryl.

An embodiment of the invention is the provision of a compound of Formula III, where the various moieties are independently selected, $Ar^1$ is pyridine, n is 1, and $R^1$ is —$NR^3R^4$ wherein $R^3$ is H and $R^4$ is aryl.

An embodiment of the invention is the provision of a compound of Formula III, where the various moieties are independently selected, $Ar^1$ is pyridine, n is 1, $Ar^2$ is phenyl and $R^1$ is —$NR^3R^4$ wherein $R^3$ is H and $R^4$ is aryl.

An embodiment of the invention is the provision of a compound of Formula III, where the various moieties are independently selected and $R^1$ is haloalkyl.

An embodiment of the invention is the provision of a compound of Formula IIII, where the various moieties are independently selected, $Ar^1$ is pyridine and $R^1$ is haloalkyl.

An embodiment of the invention is the provision of a compound of Formula III, where the various moieties are independently selected, $Ar^2$ is phenyl and $R^1$ is haloalkyl.

An embodiment of the invention is the provision of a compound of Formula III, where the various moieties are independently selected, $Ar^1$ is pyridine, $Ar^2$ is phenyl and $R^1$ is haloalkyl.

An embodiment of the invention is the provision of a compound of Formula III, where the various moieties are independently selected, $Ar^2$ is phenyl and $R^1$ is haloalkyl.

An embodiment of the invention is the provision of a compound, where the various moieties are independently selected, $Ar^1$ is pyridine, $Ar^2$ is phenyl and $R^1$ is haloalkyl.

An embodiment of the invention is the provision of a compound of Formula III, where the various moieties are independently selected, $Ar^1$ is pyridine, n is 1, and $R^1$ is haloalkyl.

An embodiment of the invention is the provision of a compound of Formula III, where the various moieties are independently selected, $Ar^1$ is pyridine, n is 1, $Ar^2$ is phenyl and $R^1$ is haloalkyl.

An embodiment of the invention is the provision of a compound of Formula III, where the various moieties are independently selected and $R^1$ is unsubstituted or substituted $C_3$-$C_{12}$-cycloalkyl.

An embodiment of the invention is the provision of a compound of Formula III, where the various moieties are independently selected, $Ar^1$ is pyridine and $R^1$ is unsubstituted or substituted $C_3$-$C_{12}$-cycloalkyl.

An embodiment of the invention is the provision of a compound of Formula III, where the various moieties are independently selected, $Ar^2$ is phenyl and $R^1$ is unsubstituted or substituted $C_3$-$C_{12}$-cycloalkyl.

An embodiment of the invention is the provision of a compound of Formula III, where the various moieties are independently selected, $Ar^1$ is pyridine, $Ar^2$ is phenyl and $R^1$ is unsubstituted or substituted $C_3$-$C_{12}$-cycloalkyl.

An embodiment of the invention is the provision of a compound of Formula III, where the various moieties are independently selected, $Ar^1$ is pyridine, n is 1, and $R^1$ is unsubstituted or substituted $C_3$-$C_{12}$-cycloalkyl.

An embodiment of the invention is the provision of a compound of Formula III, where the various moieties are independently selected, $Ar^1$ is pyridine, n is 1, $Ar^2$ is phenyl and $R^1$ is unsubstituted or substituted $C_3$-$C_{12}$-cycloalkyl.

An embodiment of the invention is the provision of a compound of Formula III, where the various moieties are independently selected and $R^1$ is unsubstituted or substituted $C_3$-$C_{12}$-cycloalkyl, wherein the cycloalkyl is selected from the group consisting of cyclopropyl, cyclopentane, cycloheptyl, azaspiro[4.5]decane, bicyclo[2.2.1]heptan, bicyclo[3.1.1]heptan, adamantane, and (1S,2S,3S,5R)-2,6,6-trimethylbicyclo[3.1.1]heptan.

An embodiment of the invention is the provision of a compound of Formula III, where the various moieties are independently selected, $Ar^1$ is pyridine and $R^1$ is unsubstituted or substituted $C_3$-$C_{12}$-cycloalkyl, wherein the cycloalkyl is selected from the group consisting of cyclopropyl, cyclopentane, cycloheptyl, azaspiro[4.5]decane, bicyclo[2.2.1]heptan, bicyclo[3.1.1]heptan, adamantane, and (1S,2S,3S,5R)-2,6,6-trimethylbicyclo[3.1.1]heptan.

An embodiment of the invention is the provision of a compound of Formula III, where the various moieties are independently selected, $Ar^2$ is phenyl and $R^1$ is unsubstituted or substituted $C_3$-$C_{12}$-cycloalkyl, wherein the cycloalkyl is selected from the group consisting of cyclopropyl, cyclopentane, cycloheptyl, azaspiro[4.5]decane, bicyclo[2.2.1]heptan, bicyclo[3.1.1]heptan, adamantane, and (1S,2S,3S,5R)-2,6,6-trimethylbicyclo[3.1.1]heptan.

An embodiment of the invention is the provision of a compound of Formula III, where the various moieties are independently selected, $Ar^1$ is pyridine, $Ar^2$ is phenyl and $R^1$ is unsubstituted or substituted $C_3$-$C_{12}$-cycloalkyl, wherein the cycloalkyl is selected from the group consisting of cyclopropyl, cyclopentane, cycloheptyl, azaspiro[4.5]decane, bicyclo[2.2.1]heptan, bicyclo[3.1.1]heptan, adamantane, and (1S,2S,3S,5R)-2,6,6-trimethylbicyclo[3.1.1]heptan.

An embodiment of the invention is the provision of a compound of Formula III, where the various moieties are independently selected, $Ar^1$ is pyridine, n is 1, and $R^1$ is unsubstituted or substituted $C_3$-$C_{12}$-cycloalkyl, wherein the cycloalkyl is selected from the group consisting of cyclopropyl, cyclopentane, cycloheptyl, azaspiro[4.5]decane, bicyclo[2.2.1]heptan, bicyclo[3.1.1]heptan, adamantane, and (1S,2S,3S,5R)-2,6,6-trimethylbicyclo[3.1.1]heptan.

An embodiment of the invention is the provision of a compound of Formula III, where the various moieties are independently selected, $Ar^1$ is pyridine, n is 1, $Ar^2$ is phenyl and $R^1$ is unsubstituted or substituted $C_3$-$C_{12}$-cycloalkyl, wherein the cycloalkyl is selected from the group consisting of cyclopropyl, cyclopentane, cycloheptyl, azaspiro[4.5]decane, bicyclo[2.2.1]heptan, bicyclo[3.1.1]heptan, adamantane, and (1S,2S,3S,5R)-2,6,6-trimethylbicyclo[3.1.1]heptan.

An embodiment of the invention is the provision of a compound of Formula III, where the various moieties are independently selected and $R^1$ is unsubstituted or substituted $C_6$-$C_{10}$-aryl.

An embodiment of the invention is the provision of a compound of Formula III, where the various moieties are independently selected, $Ar^1$ is pyridine and $R^1$ is unsubstituted or substituted $C_6$-$C_{10}$-aryl.

An embodiment of the invention is the provision of a compound of Formula III, where the various moieties are independently selected, $Ar^2$ is phenyl and $R^1$ is unsubstituted or substituted $C_6$-$C_{10}$-aryl.

An embodiment of the invention is the provision of a compound of Formula III, where the various moieties are independently selected, $Ar^1$ is pyridine, $Ar^2$ is phenyl and $R^1$ is unsubstituted or substituted $C_6$-$C_{10}$-aryl.

An embodiment of the invention is the provision of a compound of Formula III, where the various moieties are independently selected, $Ar^1$ is pyridine, n is 1, and $R^1$ is unsubstituted or substituted $C_6$-$C_{10}$-aryl.

An embodiment of the invention is the provision of a compound of Formula III, where the various moieties are independently selected, $Ar^1$ is pyridine, n is 1, $Ar^2$ is phenyl and $R^1$ is unsubstituted or substituted $C_6$-$C_{10}$-aryl.

An embodiment of the invention is the provision of a compound of Formula III, where the various moieties are independently selected and $R^1$ is unsubstituted or substituted $C_6$-$C_{10}$-aryl, wherein the aryl is selected from the group consisting of phenyl, naphatalene, tetrahydronaphthalene, and 1H-inden-5-yl.

An embodiment of the invention is the provision of a compound of Formula III, where the various moieties are independently selected, $Ar^1$ is pyridine and $R^1$ is unsubstituted or substituted $C_6$-$C_{10}$-aryl, wherein the aryl is selected from the group consisting of phenyl, naphatalene, tetrahydronaphthalene, and 1H-inden-5-yl.

An embodiment of the invention is the provision of a compound of Formula III, where the various moieties are independently selected, $Ar^2$ is phenyl and $R^1$ is unsubstituted or substituted $C_6$-$C_{10}$-aryl, wherein the aryl is selected from the group consisting of phenyl, naphatalene, tetrahydronaphthalene, and 1H-inden-5-yl.

An embodiment of the invention is the provision of a compound of Formula III, where the various moieties are independently selected, $Ar^1$ is pyridine, $Ar^2$ is phenyl and $R^1$ is unsubstituted or substituted $C_6$-$C_{10}$-aryl, wherein the aryl is selected from the group consisting of phenyl, naphatalene, tetrahydronaphthalene, and 1H-inden-5-yl.

An embodiment of the invention is the provision of a compound, where the various moieties are independently selected, $Ar^1$ is pyridine, n is 1, and $R^1$ is unsubstituted or substituted $C_6$-$C_{10}$-aryl, wherein the aryl is selected from the group consisting of phenyl, naphatalene, tetrahydronaphthalene, and 1H-inden-5-yl.

An embodiment of the invention is the provision of a compound of Formula III, where the various moieties are independently selected, $Ar^1$ is pyridine, n is 1, $Ar^2$ is phenyl and $R^1$ is unsubstituted or substituted $C_6$-$C_{10}$-aryl, wherein the aryl is selected from the group consisting of phenyl, naphatalene, tetrahydronaphthalene, and 1H-inden-5-yl.

An embodiment of the invention is the provision of a compound of Formula III, where the various moieties are independently selected and $R^1$ is unsubstituted or substituted heterocycloalkyl.

An embodiment of the invention is the provision of a compound of Formula III, where the various moieties are independently selected, $Ar^1$ is pyridine and $R^1$ is unsubstituted or substituted heterocycloalkyl.

An embodiment of the invention is the provision of a compound of Formula III, where the various moieties are independently selected, $Ar^2$ is phenyl and $R^1$ is unsubstituted or substituted heterocycloalkyl.

An embodiment of the invention is the provision of a compound of Formula III, where the various moieties are independently selected, $Ar^1$ is pyridine, $Ar^2$ is phenyl and $R^1$ is unsubstituted or substituted heterocycloalkyl.

An embodiment of the invention is the provision of a compound of Formula III, where the various moieties are independently selected, $Ar^2$ is aryl and $R^1$ is unsubstituted or substituted heterocycloalkyl.

An embodiment of the invention is the provision of a compound of Formula III, where the various moieties are independently selected, $Ar^1$ is pyridine, n is 1, and $R^1$ is unsubstituted or substituted heterocycloalkyl.

An embodiment of the invention is the provision of a compound of Formula III, where the various moieties are independently selected, $Ar^1$ is pyridine, n is 1, $Ar^2$ is phenyl and $R^1$ is unsubstituted or substituted heterocycloalkyl.

An embodiment of the invention is the provision of a compound of Formula III, where the various moieties are independently selected and $R^1$ is unsubstituted or substituted 5 to 12 membered heterocycloalkyl comprising 1, 2 or 3 heteroatoms selected from N, O and S.

An embodiment of the invention is the provision of a compound of Formula III, where the various moieties are independently selected, $Ar^1$ is pyridine and $R^1$ is unsubstituted or substituted 5 to 12 membered heterocycloalkyl comprising 1, 2 or 3 heteroatoms selected from N, O and S.

An embodiment of the invention is the provision of a compound, where the various moieties are independently selected, $Ar^2$ is phenyl and $R^1$ is unsubstituted or substituted 5 to 12 membered heterocycloalkyl comprising 1, 2 or 3 heteroatoms selected from N, O and S.

An embodiment of the invention is the provision of a compound of Formula III, where the various moieties are independently selected, $Ar^1$ is pyridine, $Ar^2$ is phenyl and $R^1$ is unsubstituted or substituted 5 to 12 membered heterocycloalkyl comprising 1, 2 or 3 heteroatoms selected from N, O and S.

An embodiment of the invention is the provision of a compound of Formula III, where the various moieties are independently selected, $Ar^1$ is pyridine, n is 1, and $R^1$ is unsubstituted or substituted 5 to 12 membered heterocycloalkyl comprising 1, 2 or 3 heteroatoms selected from N, O and S.

An embodiment of the invention is the provision of a compound of Formula III, where the various moieties are independently selected, $Ar^1$ is pyridine, n is 1, $Ar^2$ is phenyl and $R^1$ is unsubstituted or substituted 5 to 12 membered heterocycloalkyl comprising 1, 2 or 3 heteroatoms selected from N, O and S.

An embodiment of the invention is the provision of a compound of Formula III, where the various moieties are independently selected and $R^1$ is unsubstituted or substituted 5 to 12 membered heterocycloalkyl comprising 1, 2 or 3 heteroatoms selected from N, O and S, wherein the heterocycloalkyl is selected from the group consisting of azetidine, piperidine, pyrrolidine, piperazine, thiophorpholine, 2,8-diazaspiro[5.5]undecane, 8-oxa-3-azabicyclo[3.2.1]octane, 1,4-diazepane, 2-oxa-8-azaspiro[4.5]decane, and decahydroquinoline.

An embodiment of the invention is the provision of a compound of Formula III, where the various moieties are independently selected, $Ar^1$ is pyridine and $R^1$ is unsubstituted or substituted 5 to 12 membered heterocycloalkyl comprising 1, 2 or 3 heteroatoms selected from N, O and S, wherein the heterocycloalkyl is selected from the group consisting of azetidine, piperidine, pyrrolidine, piperazine, thiophorpholine, 2,8-diazaspiro[5.5]undecane, 8-oxa-3-azabicyclo[3.2.1]octane, 1,4-diazepane, 2-oxa-8-azaspiro[4.5]decane, and decahydroquinoline.

An embodiment of the invention is the provision of a compound of Formula III, where the various moieties are independently selected, $Ar^2$ is phenyl and $R^1$ is unsubstituted or substituted 5 to 12 membered heterocycloalkyl comprising 1, 2 or 3 heteroatoms selected from N, O and S, wherein the heterocycloalkyl is selected from the group consisting of azetidine, piperidine, pyrrolidine, piperazine, thiophorpholine, 2,8-diazaspiro[5.5]undecane, 8-oxa-3-azabicyclo[3.2.1]octane, 1,4-diazepane, 2-oxa-8-azaspiro[4.5]decane, and decahydroquinoline.

An embodiment of the invention is the provision of a compound of Formula III, where the various moieties are independently selected, $Ar^1$ is pyridine, $Ar^2$ is phenyl and $R^1$ is unsubstituted or substituted 5 to 12 membered heterocycloalkyl comprising 1, 2 or 3 heteroatoms selected from N, O and S, wherein the heterocycloalkyl is selected from the group consisting of azetidine, piperidine, pyrrolidine, piperazine, thiophorpholine, 2,8-diazaspiro[5.5]undecane, 8-oxa-3-azabicyclo[3.2.1]octane, 1,4-diazepane, 2-oxa-8-azaspiro[4.5]decane, and decahydroquinoline.

An embodiment of the invention is the provision of a compound of Formula III, where the various moieties are independently selected, $Ar^1$ is pyridine, n is 1, and $R^1$ is unsubstituted or substituted 5 to 12 membered heterocycloalkyl comprising 1, 2 or 3 heteroatoms selected from N, O and S, wherein the heterocycloalkyl is selected from the group consisting of azetidine, piperidine, pyrrolidine, piperazine, thiophorpholine, 2,8-diazaspiro[5.5]undecane, 8-oxa-3-azabicyclo[3.2.1]octane, 1,4-diazepane, 2-oxa-8-azaspiro[4.5]decane, and decahydroquinoline.

An embodiment of the invention is the provision of a compound of Formula III, where the various moieties are independently selected, $Ar^1$ is pyridine, n is 1, $Ar^2$ is phenyl and $R^1$ is unsubstituted or substituted 5 to 12 membered heterocycloalkyl comprising 1, 2 or 3 heteroatoms selected from N, O and S, wherein the heterocycloalkyl is selected from the group consisting of azetidine, piperidine, pyrrolidine, piperazine, thiophorpholine, 2,8-diazaspiro[5.5]undecane, 8-oxa-3-azabicyclo[3.2.1]octane, 1,4-diazepane, 2-oxa-8-azaspiro[4.5]decane, and decahydroquinoline.

An embodiment of the invention is the provision of a compound of Formula III, where the various moieties are independently selected and $R^1$ is unsubstituted or substituted heteroaryl.

An embodiment of the invention is the provision of a compound of Formula III, where the various moieties are independently selected, $Ar^1$ is pyridine and $R^1$ is unsubstituted or substituted heteroaryl.

An embodiment of the invention is the provision of a compound of Formula III, where the various moieties are independently selected, $Ar^2$ is phenyl and $R^1$ is unsubstituted or substituted heteroaryl.

An embodiment of the invention is the provision of a compound of Formula III, where the various moieties are independently selected, $Ar^1$ is pyridine, $Ar^2$ is phenyl and $R^1$ is unsubstituted or substituted heteroaryl.

An embodiment of the invention is the provision of a compound of Formula III, where the various moieties are independently selected, $Ar^2$ is aryl and $R^1$ is unsubstituted or substituted heteroaryl.

An embodiment of the invention is the provision of a compound of Formula III, where the various moieties are independently selected, $Ar^1$ is pyridine, n is 1, and $R^1$ is unsubstituted or substituted heteroaryl.

An embodiment of the invention is the provision of a compound of Formula III, where the various moieties are independently selected, $Ar^1$ is pyridine, n is 1, $Ar^2$ is phenyl and $R^1$ is unsubstituted or substituted heteroaryl.

An embodiment of the invention is the provision of a compound of Formula III, where the various moieties are independently selected and $R^1$ is unsubstituted or substituted 5 to 12 heteroaryl comprising 1, 2 or 3 heteroatoms selected from N, O and S.

An embodiment of the invention is the provision of a compound of Formula III, where the various moieties are independently selected, $Ar^1$ is pyridine and $R^1$ is unsubstituted or substituted 5 to 12 heteroaryl comprising 1, 2 or 3 heteroatoms selected from N, O and S.

An embodiment of the invention is the provision of a compound, where the various moieties are independently selected, $Ar^2$ is phenyl and $R^1$ is unsubstituted or substituted 5 to 12 heteroaryl comprising 1, 2 or 3 heteroatoms selected from N, O and S.

An embodiment of the invention is the provision of a compound of Formula III, where the various moieties are independently selected, $Ar^1$ is pyridine, $Ar^2$ is phenyl and $R^1$ is unsubstituted or substituted 5 to 12 heteroaryl comprising 1, 2 or 3 heteroatoms selected from N, O and S.

An embodiment of the invention is the provision of a compound of Formula III, where the various moieties are independently selected, $Ar^1$ is pyridine, n is 1, and $R^1$ is unsubstituted or substituted 5 to 12 heteroaryl comprising 1, 2 or 3 heteroatoms selected from N, O and S.

An embodiment of the invention is the provision of a compound of Formula III, where the various moieties are independently selected, $Ar^1$ is pyridine, n is 1, $Ar^2$ is phenyl and $R^1$ is unsubstituted or substituted 5 to 12 heteroaryl comprising 1, 2 or 3 heteroatoms selected from N, O and S.

An embodiment of the invention is the provision of a compound of Formula III, where the various moieties are independently selected and $R^1$ is unsubstituted or substituted 5 to 12 heteroaryl comprising 1, 2 or 3 heteroatoms selected from N, O and S, wherein the heteroaryl is selected from the group consisting of 1,3,4-oxadiazol, (1R)-3-oxo-3H-spiro[2-benzofuran-1,3'-pyrrolidine, 3,4-dihydro-2H-1,4-benzoxazine, oxo-2,3-dihydro-1H-indol, 3,4-dihydro-2H-1,5-benzodioxepin, 1,2,3,4-tetrahydroisoquinoline, indole, indazole, thiophene, pyrazol, pyridine, pyrimidine, 1,2-oxazole, 8-oxatricyclo[7.4.0.0$^{2,7}$]trideca-1(9),2(7),3,5,10,12-hexaene, 5-oxo-5,6,7,8-tetrahydronaphthalen-1-yl, phenoxathiine, 3-azaspiro[5.5]undecane, azatricyclo[7.3.1.0$^{5,13}$]trideca-1(13),5,7,9,11-pentaene, (4aR,8aS)-decahydroisoquinoline, and 5,6,7,8-tetrahydro-1,6-naphthyridine.

An embodiment of the invention is the provision of a compound of Formula III, where the various moieties are independently selected, $Ar^1$ is pyridine and $R^1$ is unsubstituted or substituted 5 to 12 heteroaryl comprising 1, 2 or 3 heteroatoms selected from N, O and S, wherein the heteroaryl is selected from the group consisting of 1,3,4-oxadiazol, (1R)-3-oxo-3H-spiro[2-benzofuran-1,3'-pyrrolidine, 3,4-dihydro-2H-1,4-benzoxazine, oxo-2,3-dihydro-1H-indol, 3,4-dihydro-2H-1,5-benzodioxepin, 1,2,3,4-tetrahydroisoquinoline, indole, indazole, thiophene, pyrazol, pyridine, pyrimidine, 1,2-oxazole, 8-oxatricyclo[7.4.0.0$^{2,7}$]trideca-1(9),2(7),3,5,10,12-hexaene, 5-oxo-5,6,7,8-tetrahydronaphthalen-1-yl, phenoxathiine, 3-azaspiro[5.5]undecane, azatricyclo[7.3.1.0$^{5,13}$]trideca-1(13),5,7,9,11-pentaene, (4aR,8aS)-decahydroisoquinoline, and 5,6,7,8-tetrahydro-1,6-naphthyridine.

An embodiment of the invention is the provision of a compound of Formula III, where the various moieties are independently selected, $Ar^2$ is phenyl and $R^1$ is unsubstituted or substituted 5 to 12 heteroaryl comprising 1, 2 or 3 heteroatoms selected from N, O and S, wherein the heteroaryl is selected from the group consisting of 1,3,4-oxadiazol, (1R)-3-oxo-3H-spiro[2-benzofuran-1,3'-pyrrolidine, 3,4-dihydro-2H-1,4-benzoxazine, oxo-2,3-dihydro-1H-indol, 3,4-dihydro-2H-1,5-benzodioxepin, 1,2,3,4-tetrahydroisoquinoline, indole, indazole, thiophene, pyrazol, pyridine, pyrimidine, 1,2-oxazole, 8-oxatricyclo[7.4.0.0$^{2,7}$]trideca-1(9),2(7),3,5,10,12-hexaene, 5-oxo-5,6,7,8-tetrahydronaphthalen-1-yl, phenoxathiine, 3-azaspiro[5.5]undecane, azatricyclo[7.3.1.0$^{5,13}$]trideca-1(13),5,7,9,11-pentaene, (4aR,8aS)-decahydroisoquinoline, and 5,6,7,8-tetrahydro-1,6-naphthyridine.

An embodiment of the invention is the provision of a compound of Formula III, where the various moieties are independently selected, $Ar^1$ is pyridine, $Ar^2$ is phenyl and $R^1$ is unsubstituted or substituted 5 to 12 heteroaryl comprising 1, 2 or 3 heteroatoms selected from N, O and S, wherein the heteroaryl is selected from the group consisting of 1,3,4-oxadiazol, (1R)-3-oxo-3H-spiro[2-benzofuran-1,3'-pyrrolidine, 3,4-dihydro-2H-1,4-benzoxazine, oxo-2,3-dihydro-1H-indol, 3,4-dihydro-2H-1,5-benzodioxepin, 1,2,3,4-tetrahydroisoquinoline, indole, indazole, thiophene, pyrazol, pyridine, pyrimidine, 1,2-oxazole, 8-oxatricyclo[7.4.0.0$^{2,7}$]trideca-1(9),2(7),3,5,10,12-hexaene, 5-oxo-5,6,7,8-tetrahydronaphthalen-1-yl, phenoxathiine, 3-azaspiro[5.5]undecane, azatricyclo[7.3.1.0$^{5,13}$]trideca-1(13),5,7,9,11-pentaene, (4aR,8aS)-decahydroisoquinoline, and 5,6,7,8-tetrahydro-1,6-naphthyridine.

An embodiment of the invention is the provision of a compound of Formula III, where the various moieties are independently selected, $Ar^1$ is pyridine, n is 1, and $R^1$ is unsubstituted or substituted unsubstituted or substituted 5 to 12 heteroaryl comprising 1, 2 or 3 heteroatoms selected from N, O and S, wherein the heteroaryl is selected from the group consisting of 1,3,4-oxadiazol, (1R)-3-oxo-3H-spiro[2-benzofuran-1,3'-pyrrolidine, 3,4-dihydro-2H-1,4-benzoxazine, oxo-2,3-dihydro-1H-indol, 3,4-dihydro-2H-1,5-benzodioxepin, 1,2,3,4-tetrahydroisoquinoline, indole, indazole, thiophene, pyrazol, pyridine, pyrimidine, 1,2-oxazole, 8-oxatricyclo[7.4.0.0$^{2,7}$]trideca-1(9),2(7),3,5,10,12-hexaene, 5-oxo-5,6,7,8-tetrahydronaphthalen-1-yl, phenoxathiine, 3-azaspiro[5.5]undecane, azatricyclo[7.3.1.0$^{5,13}$]trideca-1(13),5,7,9,11-pentaene, (4aR,8aS)-decahydroisoquinoline, and 5,6,7,8-tetrahydro-1,6-naphthyridine.

An embodiment of the invention is the provision of a compound of Formula III, where the various moieties are independently selected, $Ar^1$ is pyridine, n is 1, $Ar^2$ is phenyl and $R^1$ is unsubstituted or substituted unsubstituted or substituted 5 to 12 heteroaryl comprising 1, 2 or 3 heteroatoms selected from N, O and S, wherein the heteroaryl is selected from the group consisting of 1,3,4-oxadiazol, (1R)-3-oxo-3H-spiro[2-benzofuran-1,3'-pyrrolidine, 3,4-dihydro-2H-1,4-benzoxazine, oxo-2,3-dihydro-1H-indol, 3,4-dihydro-2H-1,5-benzodioxepin, 1,2,3,4-tetrahydroisoquinoline, indole, indazole, thiophene, pyrazol, pyridine, pyrimidine, 1,2-oxazole, 8-oxatricyclo[7.4.0.0$^{2,7}$]trideca-1(9),2(7),3,5,10,12-hexaene, 5-oxo-5,6,7,8-tetrahydronaphthalen-1-yl, phenoxathiine, 3-azaspiro[5.5]undecane, azatricyclo[7.3.1.0$^{5,13}$]trideca-1(13),5,7,9,11-pentaene, (4aR,8aS)-decahydroisoquinoline, and 5,6,7,8-tetrahydro-1,6-naphthyridine.

Another embodiment of the invention is the provision of a compound of Formula III where $Ar^1$ is pyridine, n is 1, $Ar^2$ is phenyl and the Formula becomes Formula III A:

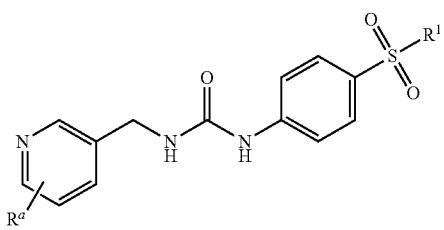

Formula IIIA wherein $R^1$ and $R^a$ are as defined in Formula III with the proviso that the compounds are not N-[4-(phenylsulfonyl)phenyl]-N'-(3-pyridinylmethyl)urea, N,N-diethyl-4-[[[(3-pyridinylmethyl)amino]carbonyl]amino]benzenesulfonamide, or 4-[[[(3-pyridinylmethyl)amino]carbonyl]amino]benzenesulfonamide.

Another embodiment of the invention is compounds of Formula III where $Ar^2$ is phenyl and Ar1 has the structure of

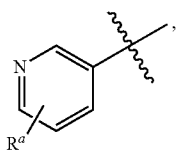

and the formula becomes Formula IIIB

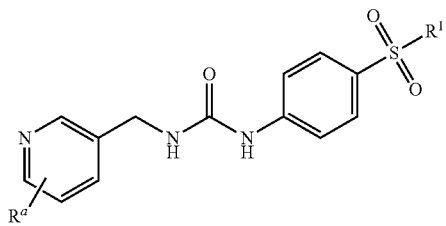

Formula IIIB wherein:

$R^a$ is one of more and can be selected from the group consisting of amino, oxo, halo, halo($C_1$-$C_6$)alkyl, —NH(CO)O—($C_1$-$C_6$)alkyl and —C(O)NH$_2$; and wherein said pyridine can comprise a N-oxide formed with its N atom member;

$R^1$ is —NR$^3$R$^4$ wherein $R^3$ is H, $C_1$-$C_6$-alkyl or —S(O)$_2$($C_1$-$C_6$)alkyl and $R^4$ is ($C_1$-$C_6$)alkyl, hydroxy($C_1$-$C_6$)alkyl, —S(O)$_2$($C_1$-$C_6$)alkyl, —(CH$_2$)$_q$cycloalkyl, —(CH$_2$)$_q$heterocycloalkyl, aryl, aryl($C_1$-$C_6$)alkyl-, —(CH$_2$)$_q$heteroaryl; halo($C_1$-$C_6$)alkyl, cycloalkyl;

aryl;

heterocycloalkyl; or heteroaryl wherein:

each of said cycloalkyl, aryl, or heteroaryl is unsubstituted or substituted with 1, 2, 3, 4 or 5 substituents which can be the same or different and are independently selected from the group consisting of:

halo, cyano, ($C_1$-$C_6$)alkyl, hydroxyl, hydroxy($C_1$-$C_6$)alkyl, hydroxy($C_1$-$C_6$)alkoxy, halo($C_1$-$C_6$)alkyl, ($C_1$-$C_6$)alkoxy, ($C_1$-$C_6$)alkyl($C_1$-$C_6$)alkoxy, halo($C_1$-$C_6$)alkoxy, aryl($C_2$-$C_6$)alkenyl-, aryloxy, benzyloxy, oxo, —(CH$_2$)$_q$—NR$^b$R$^c$, —(CH$_2$)$_q$—CONR$^b$R$^c$, —S(O)$_2$—($C_1$-$C_6$)alkyl, —S(O)$_2$NH—($C_1$-$C_6$)alkyl, —S(O)$_2$-heterocycloalkyl, —S(O)$_2$—CF$_3$, —C(O)($C_1$-$C_6$)alkyl, —C(O)aryl, —C(O) ($C_2$-$C_6$)alkylenylaryl, —C(O)O—($C_1$-$C_6$)alkyl, —(CH$_2$)$_q$cycloalkyl, cycloalkyl($C_1$-$C_6$)alkoxy-, aryl, aryl($C_1$-$C_6$)alkyl-, —(CH$_2$)$_q$heteroaryl, and —(CH$_2$)$_q$heterocycloalkyl, wherein each of said cycloalkyl, heterocycloalkyl, aryl or heteroaryl may be substituted by one or more halo, nitro, halo($C_1$-$C_6$)alkyl, halo($C_1$-$C_6$)alkoxy, oxo, cyano, ($C_1$-$C_6$)alkyl, halo($C_1$-$C_6$)alkyl, or ($C_1$-$C_6$)alkoxy;

$R^b$ and $R^c$ are independently selected from the group consisting of H, ($C_1$-$C_6$)alkyl, hydroxy($C_1$-$C_6$)alkyl, ($C_1$-$C_6$)alkoxy, aryl, ($C_1$-$C_6$)alkoxy($C_1$-$C_6$)alkyl, —S(O)$_2$($C_1$-$C_6$)alkyl and ($C_3$-$C_6$)cycloalkyl or $R^b$ and $R^c$ can form a 5 or 6 membered heterocycloalkyl group together with the nitrogen atom to which they are attached, wherein said heterocycloalkyl group may contain one or more additional heteroatom(s) selected from N, S or O q is 0 or 1; and pharmaceutically acceptable salts thereof, with the proviso that the compounds of Formula Ia are not:

N-[4-(phenylsulfonyl)phenyl]-N'-(3-pyridinylmethyl)urea,

N,N-diethyl-4-[[[(3-pyridinylmethyl)amino]carbonyl]amino]benzenesulfonamide, or 4-[[[(3-pyridinylmethyl)amino]carbonyl]amino]benzenesulfonamide.

An embodiment of the invention is compounds of Formula IIIB, wherein $R^1$ is —$NR^3R^4$ wherein $R^3$ is H, alkyl or —$S(O)_2$alkyl and $R^4$ is alkyl, hydroxyalkyl, —$S(O)_2$alkyl, —$(CH_2)_q$cycloalkyl, —$(CH_2)_q$heterocycloalkyl, aryl, arylalkyl-, —$(CH_2)_q$heteroaryl.

Another embodiment of the invention is compounds of Formula IIIB, where $R^1$ is $NR^3R^4$ wherein $R^3$ is H and $R^4$ is aryl.

Another embodiment of the invention is compounds of Formula IIIB wherein $R^1$ is haloalkyl.

Another embodiment of the invention is compounds of Formula IIIB wherein $R^1$ is unsubstituted or substituted $C_3$-$C_{12}$-cycloalkyl.

Still another embodiment of the invention is compounds of Formula IIIB, wherein $R^1$ is unsubstituted or substituted $C_3$-$C_{12}$-cycloalkyl and the cycloalkyl is selected from the group consisting of cyclopropyl, cyclopentane, cycloheptyl, azaspiro[4.5]decane, bicyclo[2.2.1]heptan, bicyclo[3.1.1]heptan, adamantane, and (1S,2S,3S,5R)-2,6,6-trimethylbicyclo[3.1.1]heptan.

Yet another embodiment of the invention is compounds of Formula IIIB wherein $R^1$ is unsubstituted or substituted $C_6$-$C_{10}$-aryl.

A further embodiment of the invention is compounds of Formula III B wherein $R^1$ is unsubstituted or substituted $C_6$-$C_{10}$-aryl and the aryl is selected from the group consisting of phenyl, naphatalene, tetrahydronaphthalene, and 1H-inden-5-yl.

Another embodiment of the invention is compounds of Formula IIIB, wherein $R^1$ is unsubstituted or substituted heterocycloalkyl.

One embodiment of the invention is compounds of Formula III B, wherein $R^1$ is unsubstituted or substituted 5 to 12 membered heterocycloalkyl comprising 1, 2 or 3 heteroatoms selected from N, O and S.

One embodiment of the invention is compounds of Formula IIIB, wherein $R^1$ is unsubstituted or substituted 5 to 12 membered heterocycloalkyl comprising 1, 2 or 3 heteroatoms selected from N, O and S, and the heterocycloalkyl is selected from the group consisting of azetidine, piperidine, pyrrolidine, piperazine, thiophorpholine, 2,8-diazaspiro[5.5]undecane, 8-oxa-3-azabicyclo[3.2.1]octane, 1,4-diazepane, 2-oxa-8-azaspiro[4.5]decane, and decahydroquinoline.

Another embodiment of the invention is compounds of Formula IIIB, wherein $R^1$ is unsubstituted or substituted heteroaryl.

Another embodiment of the invention is compounds of Formula IIIB, wherein $R^1$ is unsubstituted or substituted 5 to 12 heteroaryl comprising 1, 2 or 3 heteroatoms selected from N, O and S.

Still another embodiment of the invention is compounds of Formula IIIB, wherein $R^1$ is unsubstituted or substituted 5 to 12 heteroaryl comprising 1, 2 or 3 heteroatoms selected from N, O and S, and the heteroaryl is selected from the group consisting of 1,3,4-oxadiazol, (1R)-3-oxo-3H-spiro[2-benzofuran-1,3'-pyrrolidine, 3,4-dihydro-2H-1,4-benzoxazine, oxo-2,3-dihydro-1H-indol, 3,4-dihydro-2H-1,5-benzodioxepin, 1,2,3,4-tetrahydroisoquinoline, indole, indazole, thiophene, pyrazol, pyridine, pyrimidine, 1,2-oxazole, 8-oxatricyclo[7.4.0.0$^{2,7}$]trideca-1(9),2(7),3,5,10,12-hexaene, 5-oxo-5,6,7,8-tetrahydronaphthalen-1-yl, phenoxathiine, 3-azaspiro[5.5]undecane, azatricyclo[7.3.1.0$^{5,13}$]trideca-1(13),5,7,9,11-pentaene, (4aR,8aS)-decahydroisoquinoline, and 5,6,7,8-tetrahydro-1,6-naphthyridine Illustrative compounds of the invention are:

| Structure | Chemical Name |
|---|---|
| 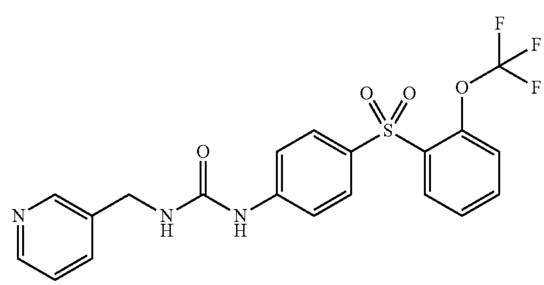 [SMILES: O=C(NCc1cccnc1)Nc1ccc(S(=O)(=O)c2ccccc2OC(F)(F)F)cc1] | 1-(pyridin-3-ylmethyl)-3-(4-{[2-(trifluoromethoxy)benzene]sulfonyl}phenyl)urea |
| 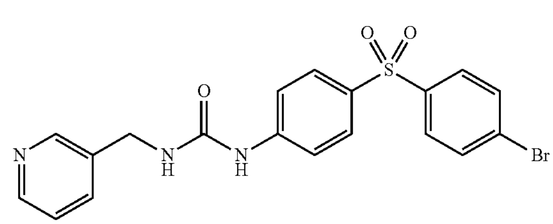 [SMILES: O=C(NCc1cccnc1)Nc1ccc(S(=O)(=O)c2ccc(Br)cc2)cc1] | 3-{4-[(4-bromobenzene)sulfonyl]phenyl}-1-(pyridin-3-ylmethyl)urea |

-continued

| Structure | Chemical Name |
|---|---|
| 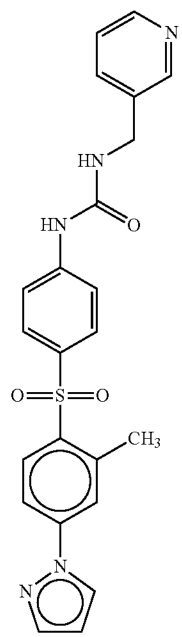 | 3-(4-{[2-methyl-4-(1H-pyrazol-1-yl)benzene]sulfonyl}phenyl)-1-(pyridin-3-ylmethyl)urea |
| 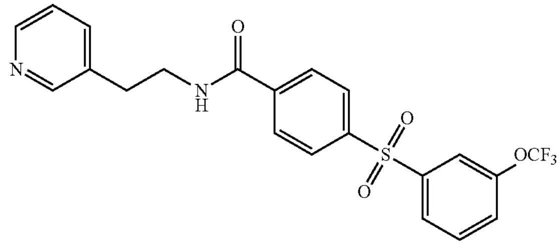 [SMILES: O=C(NCCc1cccnc1)c1ccc(S(=O)(=O)c2cccc(OC(F)(F)F)c2)cc1] | N-[2-(pyridin-3-yl)ethyl]-4-{[3-(trifluoromethoxy)benzene]sulfonyl}benzamide |
| 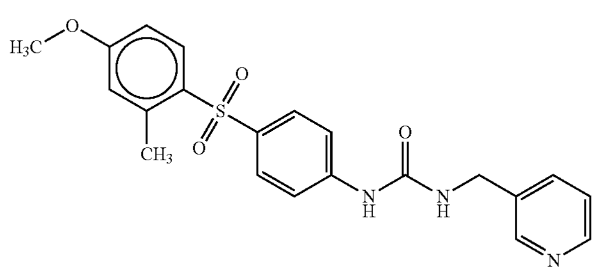 | 3-{4-[(4-methoxy-2-methylbenzene)sulfonyl]phenyl}-1-(pyridin-3-ylmethyl)urea |
| 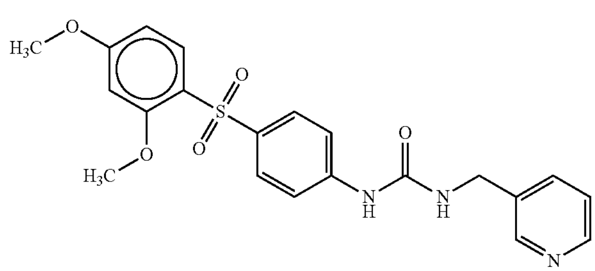 | 3-{4-[(2,4-dimethoxybenzene)sulfonyl]phenyl}-1-(pyridin-3-ylmethyl)urea |

-continued

| Structure | Chemical Name |
|---|---|
| 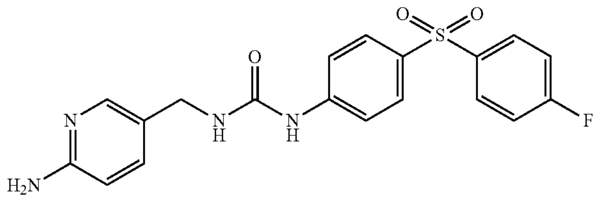 [SMILES: Nc1ccc(CNC(=O)Nc2ccc(S(=O)(=O)c3ccc(F)cc3)cc2)cn1] | 1-[(6-aminopyridin-3-yl)methyl]-3-{4-[(4-fluorobenzene)sulfonyl]phenyl}urea |
| 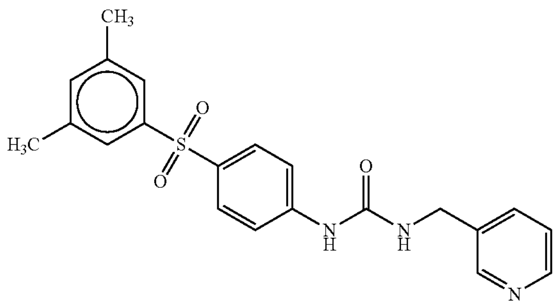 | 3-{4-[(3,5-dimethylbenzene)sulfonyl]phenyl}-1-(pyridin-3-ylmethyl)urea |
| 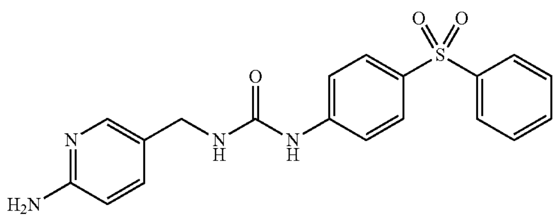 [SMILES: Nc1ccc(CNC(=O)Nc2ccc(S(=O)(=O)c3ccccc3)cc2)cn1] | 1-[(6-aminopyridin-3-yl)methyl]-3-[4-(benzenesulfonyl)phenyl]urea |
| 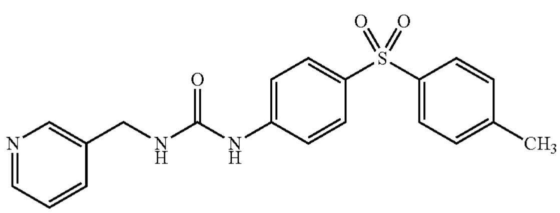 [SMILES: Cc1ccc(S(=O)(=O)c2ccc(NC(=O)NCc3cccnc3)cc2)cc1] | 3-{4-[(4-methylbenzene)sulfonyl]phenyl}-1-(pyridin-3-ylmethyl)urea |
| 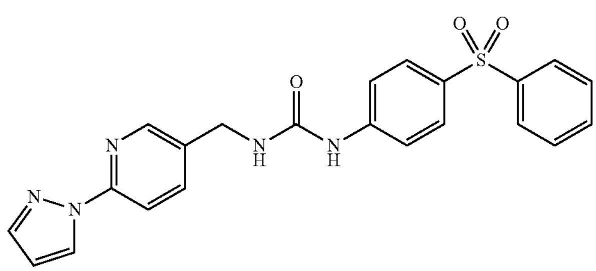 [SMILES: O=C(NCc1ccc(-n2cccn2)nc1)Nc1ccc(S(=O)(=O)c2ccccc2)cc1] | 3-[4-(benzenesulfonyl)phenyl]-1-{[6-(1H-pyrazol-1-yl)pyridin-3-yl]methyl}urea |
| 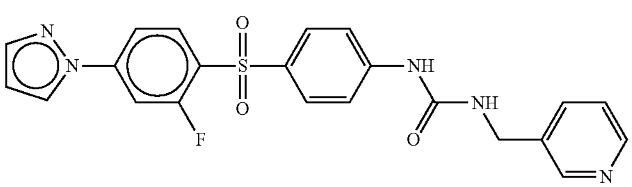 | 3-(4-{[2-fluoro-4-(1H-pyrazol-1-yl)benzene]sulfonyl}phenyl)-1-(pyridin-3-ylmethyl)urea |
| 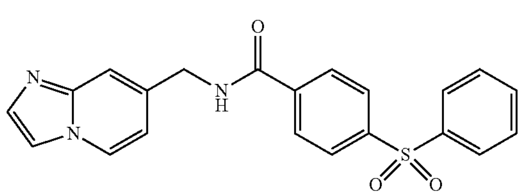 [SMILES: O=C(NCc1ccn2ccnc2c1)c1ccc(S(=O)(=O)c2ccccc2)cc1] | 4-(benzenesulfonyl)-N-{imidazo[1,2-a]pyridin-7-ylmethyl}benzamide |

| Structure | Chemical Name |
|---|---|
| 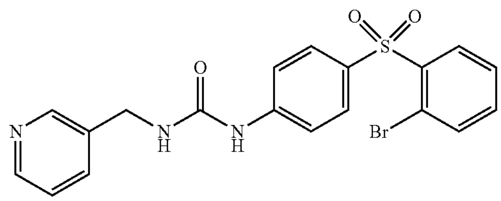 [SMILES: O=C(NCc1cccnc1)Nc1ccc(S(=O)(=O)c2ccccc2Br)cc1] | 3-{4-[(2-bromobenzene)sulfonyl]phenyl}-1-(pyridin-3-ylmethyl)urea |
| 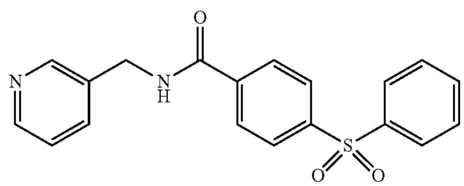 [SMILES: O=C(NCc1cccnc1)c1ccc(S(=O)(=O)c2ccccc2)cc1] | 4-(benzenesulfonyl)-N-(pyridin-3-ylmethyl)benzamide |
| 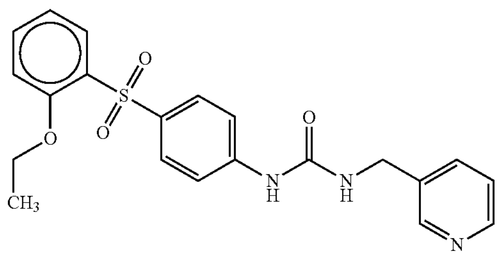 | 3-{4-[(2-ethoxybenzene)sulfonyl]phenyl}-1-(pyridin-3-ylmethyl)urea |
| 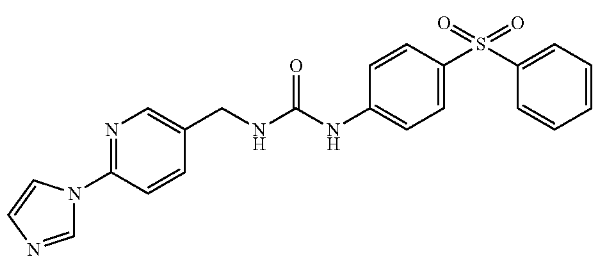 [SMILES: O=C(NCc1ccc(-n2ccnc2)nc1)Nc1ccc(S(=O)(=O)c2ccccc2)cc1] | 3-[4-(benzenesulfonyl)phenyl]-1-{[6-(1H-imidazol-1-yl)pyridin-3-yl]methyl}urea |
| 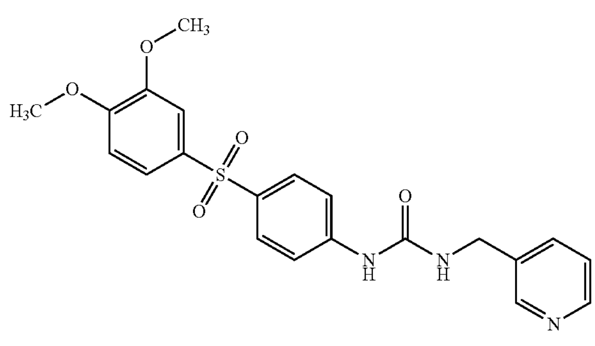 [SMILES: COc1ccc(S(=O)(=O)c2ccc(NC(=O)NCc3cccnc3)cc2)cc1OC] | 3-{4-[(3,4-dimethoxybenzene)sulfonyl]phenyl}-1-(pyridin-3-ylmethyl)urea |
| 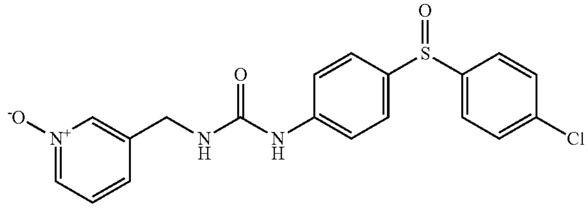 [SMILES: O=C(NCc1ccc[n+]([O-])c1)Nc1ccc(S(=O)c2ccc(Cl)cc2)cc1] | 3-{[({4-[(4-chlorobenzene)sulfinyl]phenyl}carbamoyl)amino]methyl}pyridin-1-ium-1-olate |

| Structure | Chemical Name |
|---|---|
| 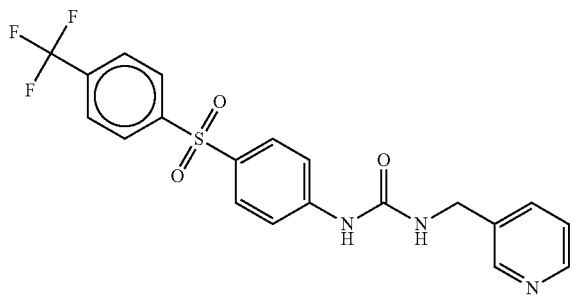 | 1-(pyridin-3-ylmethyl)-3-(4-{[4-(trifluoromethyl)benzene]sulfonyl}phenyl)urea |
| 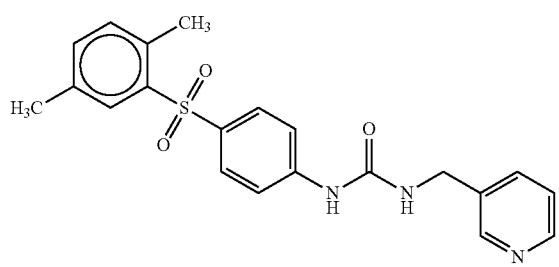 | 3-{4-[(2,5-dimethylbenzene)sulfonyl]phenyl}-1-(pyridin-3-ylmethyl)urea |
| 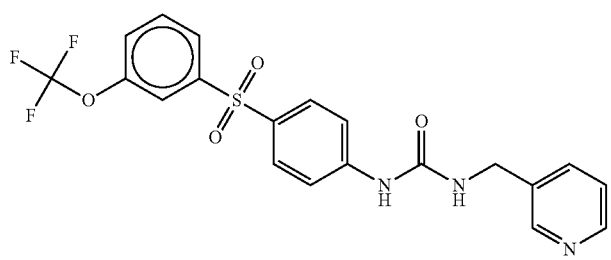 | 1-(pyridin-3-ylmethyl)-3-(4-{[3-(trifluoromethoxy)benzene]sulfonyl}phenyl)urea |
| 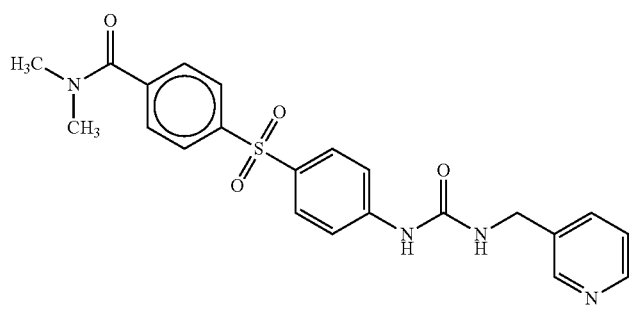 | N,N-dimethyl-4-[(4-{[(pyridin-3-ylmethyl)carbamoyl]amino}benzene)sulfonyl]benzamide |

| Structure | Chemical Name |
|---|---|
| 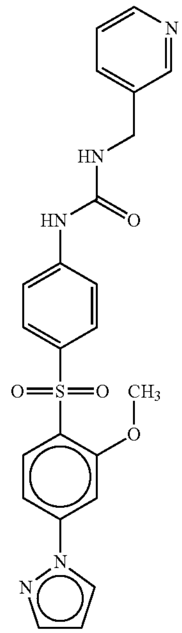 | 3-(4-{[2-methoxy-4-(1H-pyrazol-1-yl)benzene]sulfonyl}phenyl)-1-(pyridin-3-ylmethyl)urea |
| 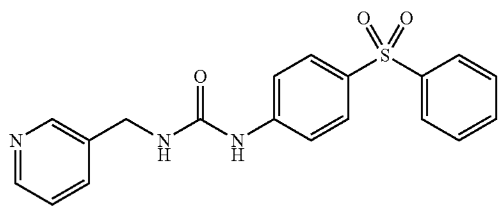 [SMILES: O=C(NCc1cccnc1)Nc1ccc(S(=O)(=O)c2ccccc2)cc1] | 3-[4-(benzenesulfonyl)phenyl]-1-(pyridin-3-ylmethyl)urea |
| 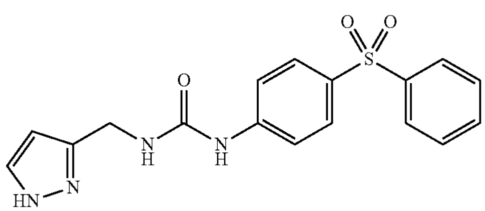 [SMILES: O=C(NCc1cc[nH]n1)Nc1ccc(S(=O)(=O)c2ccccc2)cc1] | 1-[4-(benzenesulfonyl)phenyl]-3-(1H-pyrazol-3-ylmethyl)urea |
| 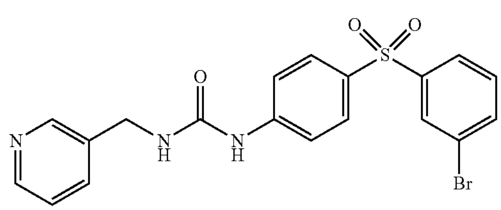 [SMILES: O=C(NCc1cccnc1)Nc1ccc(S(=O)(=O)c2cccc(Br)c2)cc1] | 3-{4-[(3-bromobenzene)sulfonyl]phenyl}-1-(pyridin-3-ylmethyl)urea |
| 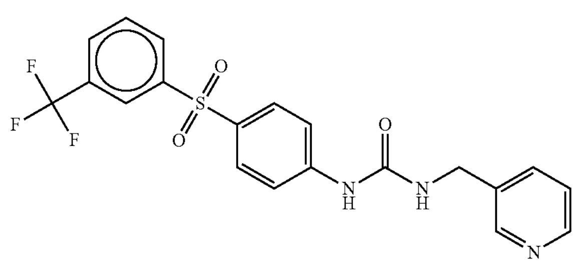 | 1-(pyridin-3-ylmethyl)-3-(4-{[3-(trifluoromethyl)benzene]sulfonyl}phenyl)urea |

-continued

| Structure | Chemical Name |
|---|---|
| 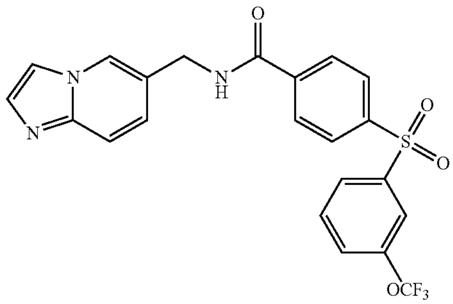 [SMILES: O=C(NCc1ccc2nccn2c1)c1ccc(S(=O)(=O)c2cccc(OC(F)(F)F)c2)cc1] | N-{imidazo[1,2-a]pyridin-6-ylmethyl}-4-{[3-(trifluoromethoxy)benzene]sulfonyl}benzamide |
| 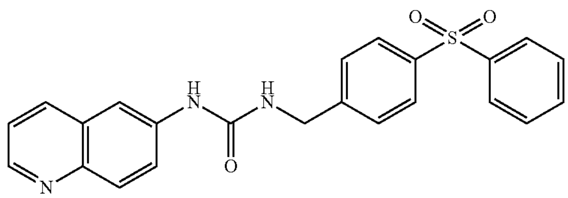 [SMILES: O=C(NCc1ccc(S(=O)(=O)c2ccccc2)cc1)Nc1ccc2ncccc2c1] | 1-{[4-(benzenesulfonyl)phenyl]methyl}-3-(quinolin-6-yl)urea |
| 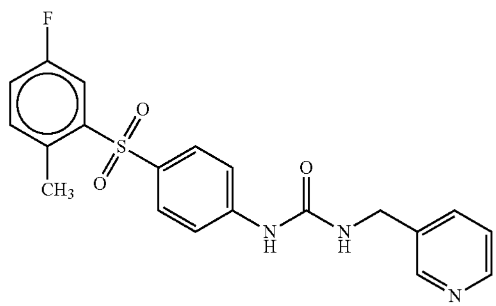 | 3-{4-[(5-fluoro-2-methylbenzene)sulfonyl]phenyl}-1-(pyridin-3-ylmethyl)urea |
| 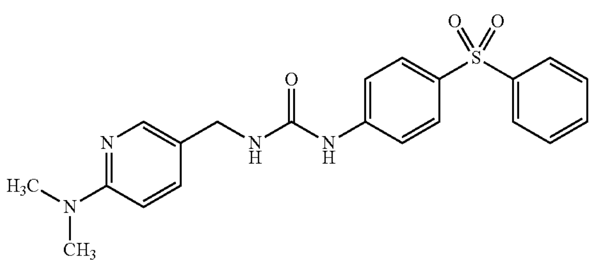 [SMILES: CN(C)c1ccc(CNC(=O)Nc2ccc(S(=O)(=O)c3ccccc3)cc2)cn1] | 3-[4-(benzenesulfonyl)phenyl]-1-{[6-(dimethylamino)pyridin-3-yl]methyl}urea |
| 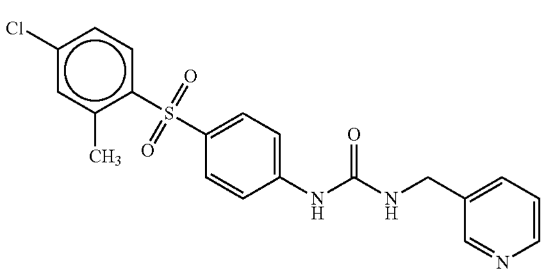 | 3-{4-[(4-chloro-2-methylbenzene)sulfonyl]phenyl}-1-(pyridin-3-ylmethyl)urea |
| 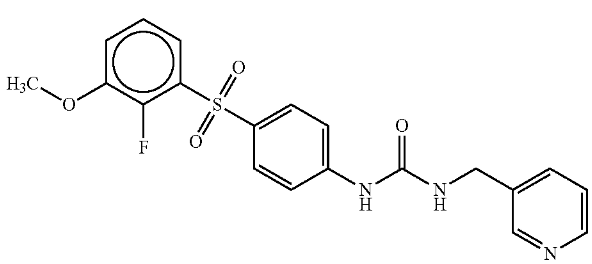 | 3-{4-[(2-fluoro-3-methoxybenzene)sulfonyl]phenyl}-1-(pyridin-3-ylmethyl)urea |

| Structure | Chemical Name |
|---|---|
| 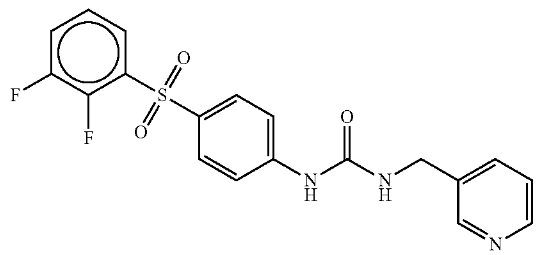 | 3-{4-[(2,3-difluorobenzene)sulfonyl]phenyl}-1-(pyridin-3-ylmethyl)urea |
| 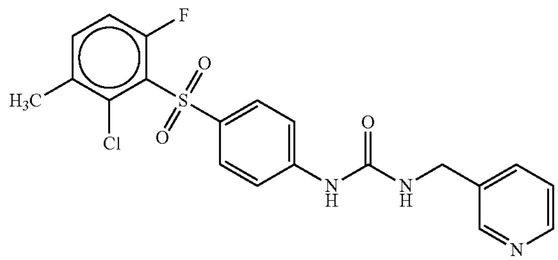 | 3-{4-[(2-chloro-6-fluoro-3-methylbenzene)sulfonyl]phenyl}-1-(pyridin-3-ylmethyl)urea |
| 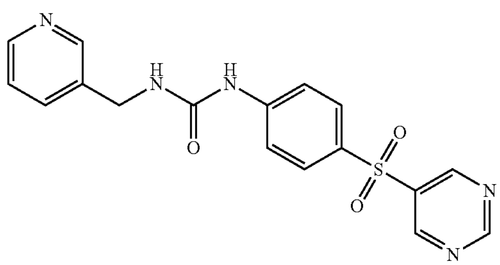 [SMILES: O=C(NCc1cccnc1)Nc1ccc(S(=O)(=O)c2cncnc2)cc1] | 3-(pyridin-3-ylmethyl)-1-[4-(pyrimidine-5-sulfonyl)phenyl]urea |
| 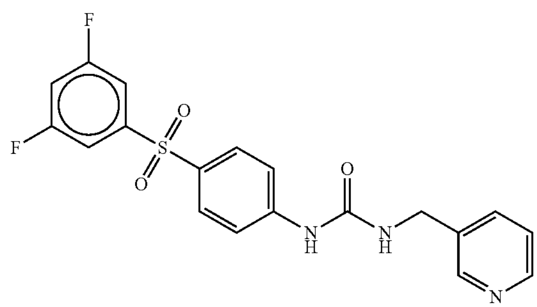 | 3-{4-[(3,5-difluorobenzene)sulfonyl]phenyl}-1-(pyridin-3-ylmethyl)urea |
| 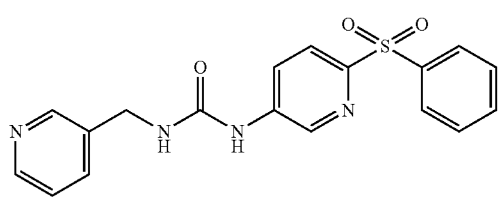 [SMILES: O=C(NCc1cccnc1)Nc1ccc(S(=O)(=O)c2ccccc2)nc1] | 1-[6-(benzenesulfonyl)pyridin-3-yl]-3-(pyridin-3-ylmethyl)urea |
| 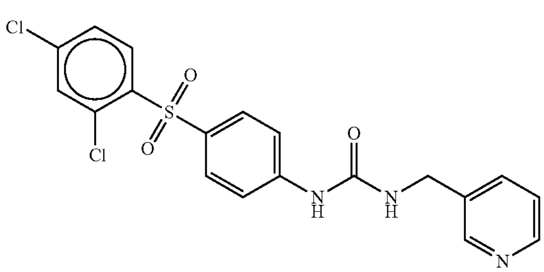 | 3-{4-[(2,4-dichlorobenzene)sulfonyl]phenyl}-1-(pyridin-3-ylmethyl)urea |

| Structure | Chemical Name |
|---|---|
| 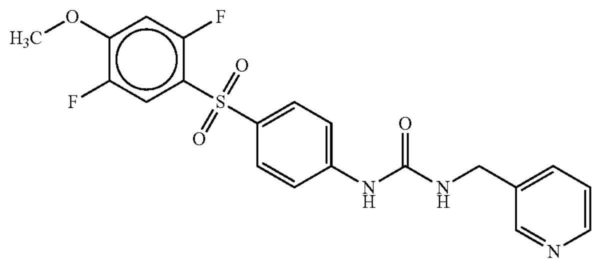 | 3-{4-[(2,5-difluoro-4-methoxybenzene)sulfonyl]phenyl}-1-(pyridin-3-ylmethyl)urea |
| 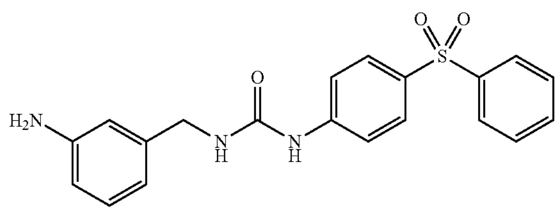 [SMILES: Nc1cccc(CNC(=O)Nc2ccc(S(=O)(=O)c3ccccc3)cc2)c1] | 1-[(3-aminophenyl)methyl]-3-[4-(benzenesulfonyl)phenyl]urea |
| 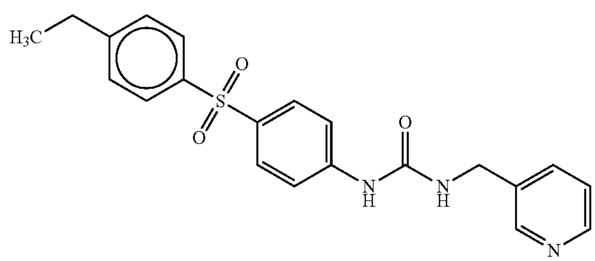 | 3-{4-[(4-ethylbenzene)sulfonyl]phenyl}-1-(pyridin-3-ylmethyl)urea |
| 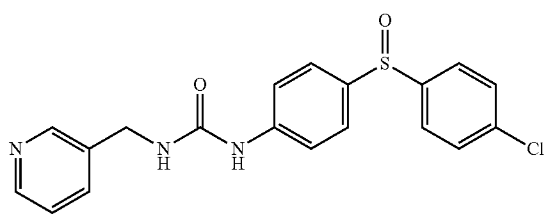 [SMILES: O=C(NCc1cccnc1)Nc1ccc(S(=O)c2ccc(Cl)cc2)cc1] | 3-{4-[(4-chlorobenzene)sulfinyl]phenyl}-1-(pyridin-3-ylmethyl)urea |
| 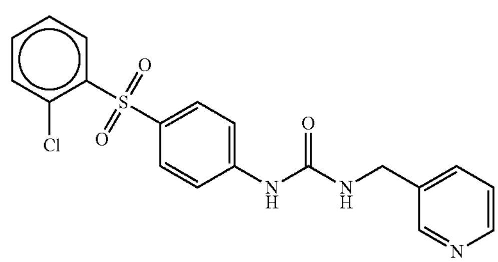 | 3-{4-[(2-chlorobenzene)sulfonyl]phenyl}-1-(pyridin-3-ylmethyl)urea |
| 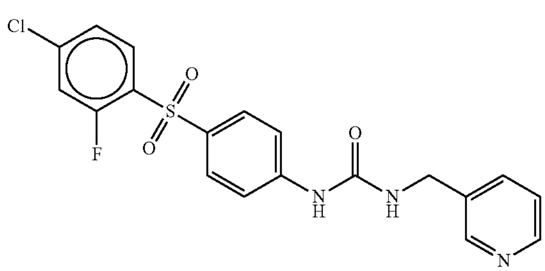 | 3-{4-[(4-chloro-2-fluorobenzene)sulfonyl]phenyl}-1-(pyridin-3-ylmethyl)urea |

-continued

| Structure | Chemical Name |
|---|---|
| 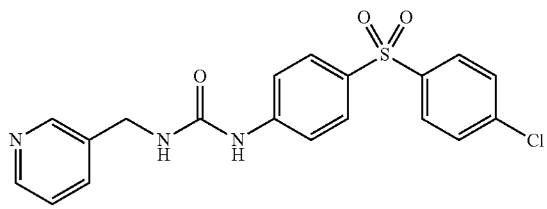 [SMILES: O=C(NCc1cccnc1)Nc1ccc(S(=O)(=O)c2ccc(Cl)cc2)cc1] | 3-{4-[(4-chlorobenzene)sulfonyl]phenyl}-1-(pyridin-3-ylmethyl)urea |
| 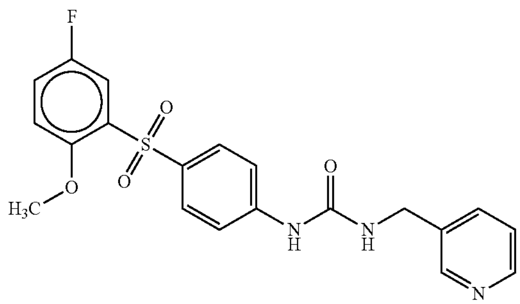 | 3-{4-[(5-fluoro-2-methoxybenzene)sulfonyl]phenyl}-1-(pyridin-3-ylmethyl)urea |
| 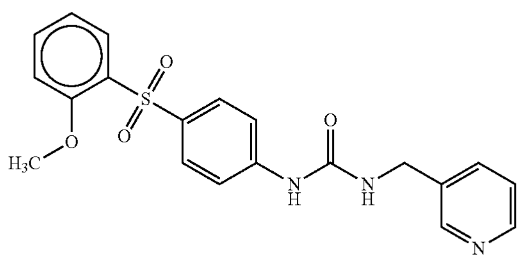 | 3-{4-[(2-methoxybenzene)sulfonyl]phenyl}-1-(pyridin-3-ylmethyl)urea |
| 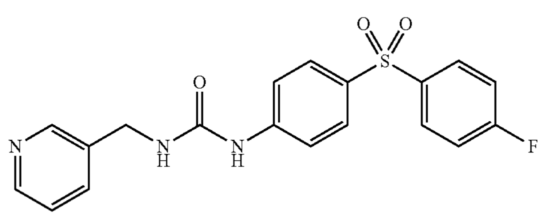 [SMILES: O=C(NCc1cccnc1)Nc1ccc(S(=O)(=O)c2ccc(F)cc2)cc1] | 3-{4-[(4-fluorobenzene)sulfonyl]phenyl}-1-(pyridin-3-ylmethyl)urea |
| 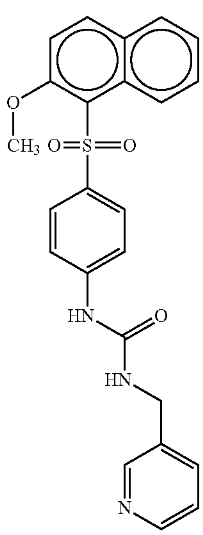 | 3-[4-(2-methoxynaphthalene-1-sulfonyl)phenyl]-1-(pyridin-3-ylmethyl)urea |

-continued

| Structure | Chemical Name |
|---|---|
| 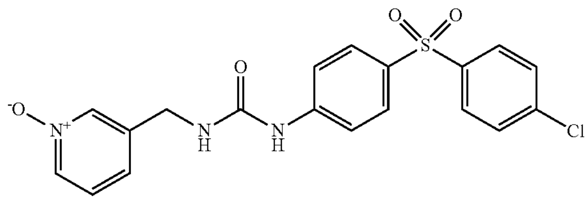 [SMILES: O=C(NCc1ccc[n+]([O-])c1)Nc1ccc(S(=O)(=O)c2ccc(Cl)cc2)cc1] | 3-{[({4-[(4-chlorobenzene)sulfonyl]phenyl}carbamoyl)amino]methyl}pyridin-1-ium-1-olate |
| 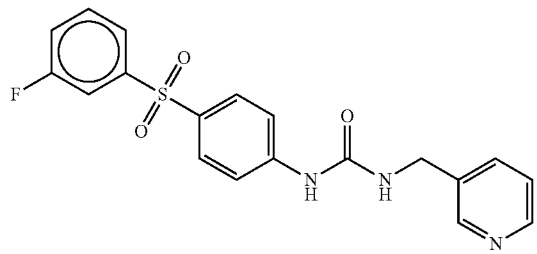 | 3-{4-[(3-fluorobenzene)sulfonyl]phenyl}-1-(pyridin-3-ylmethyl)urea |
| 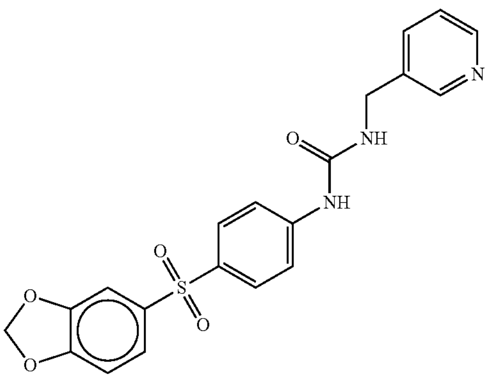 | 1-[4-(2H-1,3-benzodioxole-5-sulfonyl)phenyl]-3-(pyridin-3-ylmethyl)urea |
| 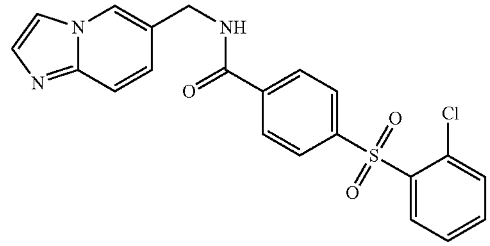 [SMILES: O=C(NCc1ccc2nccn2c1)c1ccc(S(=O)(=O)c2ccccc2Cl)cc1] | 4-[(2-chlorobenzene)sulfonyl]-N-{imidazo[1,2-a]pyridin-6-ylmethyl}benzamide |
| 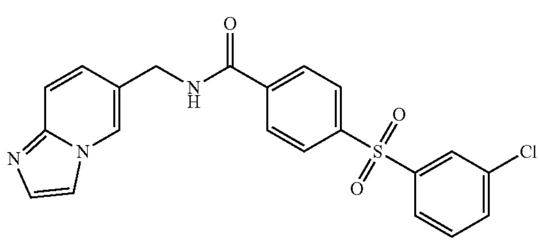 [SMILES: O=C(NCc1ccc2nccn2c1)c1ccc(S(=O)(=O)c2cccc(Cl)c2)cc1] | 4-[(3-chlorobenzene)sulfonyl]-N-{imidazo[1,2-a]pyridin-6-ylmethyl}benzamide |
| 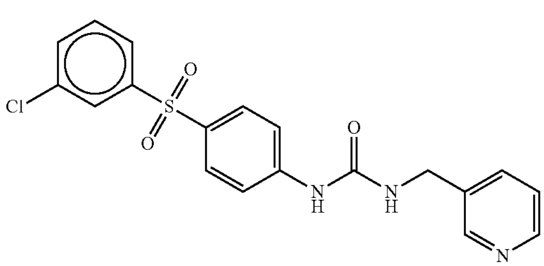 | 3-{4-[(3-chlorobenzene)sulfonyl]phenyl}-1-(pyridin-3-ylmethyl)urea |

| Structure | Chemical Name |
|---|---|
| 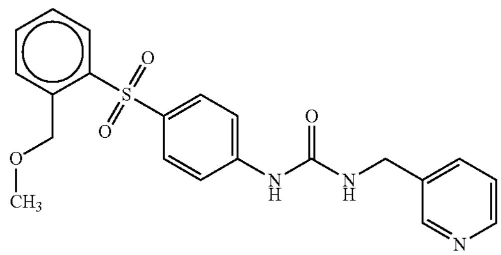 | 3-(4-{[2-(methoxymethyl)benzene]sulfonyl}phenyl)-1-(pyridin-3-ylmethyl)urea |
| 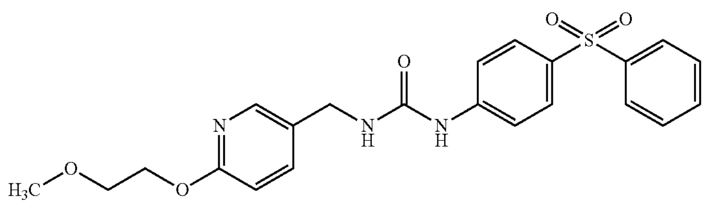 [SMILES: COCCOc1ccc(CNC(=O)Nc2ccc(S(=O)(=O)c3ccccc3)cc2)cn1] | 3-[4-(benzenesulfonyl)phenyl]-1-{[6-(2-methoxyethoxy)pyridin-3-yl]methyl}urea |
| 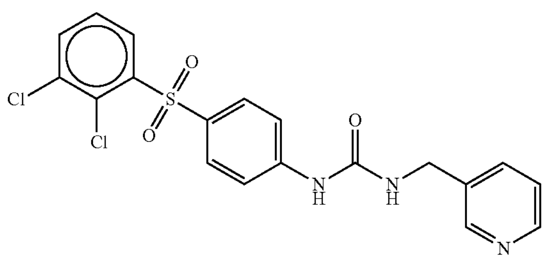 | 3-{4-[(2,3-dichlorobenzene)sulfonyl]phenyl}-1-(pyridin-3-ylmethyl)urea |
| 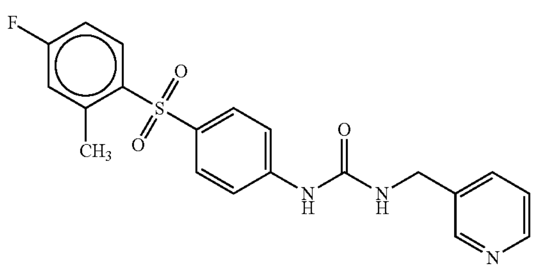 | 3-{4-[(4-fluoro-2-methylbenzene)sulfonyl]phenyl}-1-(pyridin-3-ylmethyl)urea |
| 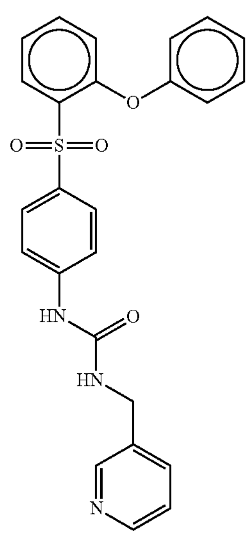 | 1-{4-[(2-phenoxybenzene)sulfonyl]phenyl}-3-(pyridin-3-ylmethyl)urea |

| Structure | Chemical Name |
|---|---|
| 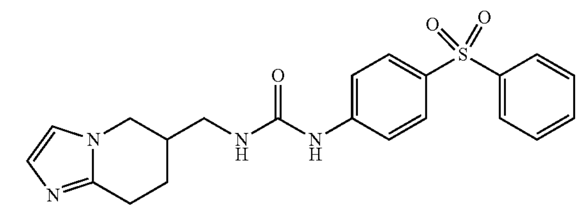 [SMILES: O=C(NCC1CCc2nccn2C1)Nc1ccc(S(=O)(=O)c2ccccc2)cc1] | 1-[4-(benzenesulfonyl)phenyl]-3-{5H,6H,7H,8H-imidazo[1,2-a]pyridin-6-ylmethyl}urea |
| 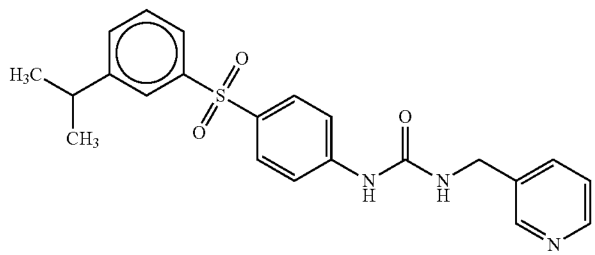 | 3-(4-{[3-(propan-2-yl)benzene]sulfonyl}phenyl)-1-(pyridin-3-ylmethyl)urea |
| 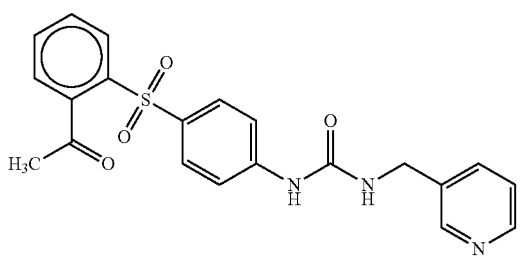 | 3-{4-[(2-acetylbenzene)sulfonyl]phenyl}-1-(pyridin-3-ylmethyl)urea |
| 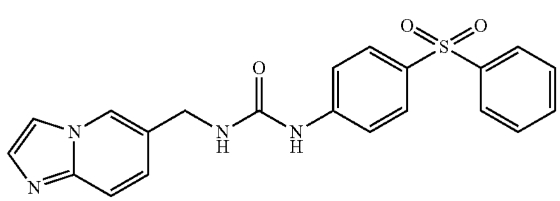 [SMILES: O=C(NCc1ccc2nccn2c1)Nc1ccc(S(=O)(=O)c2ccccc2)cc1] | 1-[4-(benzenesulfonyl)phenyl]-3-{imidazo[1,2-a]pyridin-6-ylmethyl}urea |
| 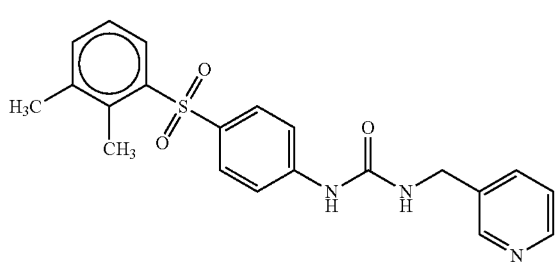 | 3-{4-[(2,3-dimethylbenzene)sulfonyl]phenyl}-1-(pyridin-3-ylmethyl)urea |
| 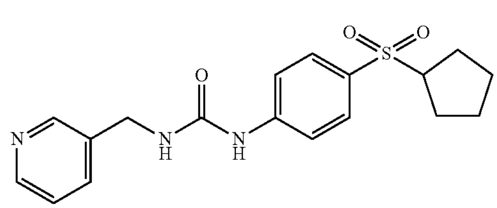 [SMILES: O=C(NCc1cccnc1)Nc1ccc(S(=O)(=O)C2CCCC2)cc1] | 1-[4-(cyclopentanesulfonyl)phenyl]-3-(pyridin-3-ylmethyl)urea |

| Structure | Chemical Name |
|---|---|
| 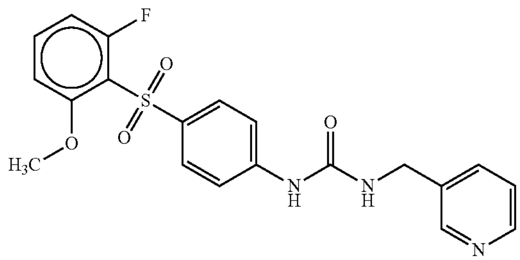 | 3-{4-[(2-fluoro-6-methoxybenzene)sulfonyl]phenyl}-1-(pyridin-3-ylmethyl)urea |
| 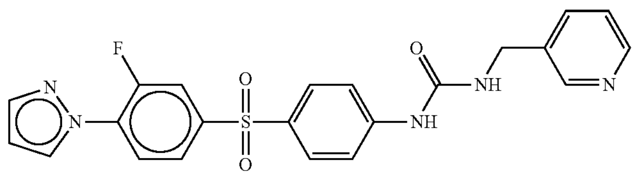 | 3-(4-{[3-fluoro-4-(1H-pyrazol-1-yl)benzene]sulfonyl}phenyl)-1-(pyridin-3-ylmethyl)urea |
| 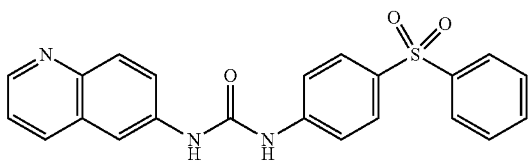 [SMILES: O=C(Nc1ccc(S(=O)(=O)c2ccccc2)cc1)Nc1ccc2ncccc2c1] | 3-[4-(benzenesulfonyl)phenyl]-1-(quinolin-6-yl)urea |
| 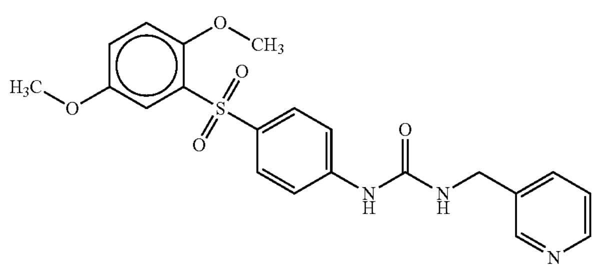 | 3-{4-[(2,5-dimethoxybenzene)sulfonyl]phenyl}-1-(pyridin-3-ylmethyl)urea |
| 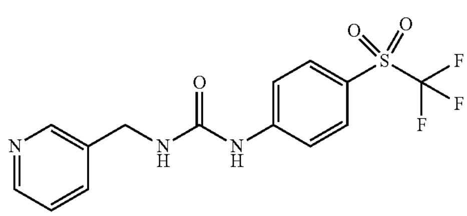 [SMILES: O=C(NCc1cccnc1)Nc1ccc(S(=O)(=O)C(F)(F)F)cc1] | 1-(pyridin-3-ylmethyl)-3-[4-(trifluoromethane)sulfonylphenyl]urea |
| 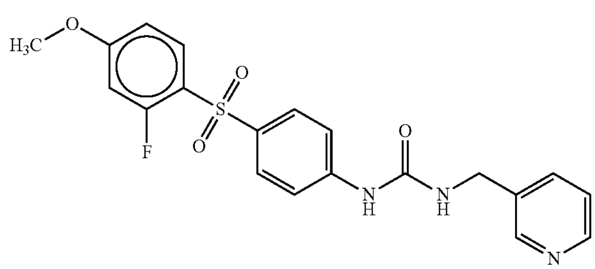 | 3-{4-[(2-fluoro-4-methoxybenzene)sulfonyl]phenyl}-1-(pyridin-3-ylmethyl)urea |
| 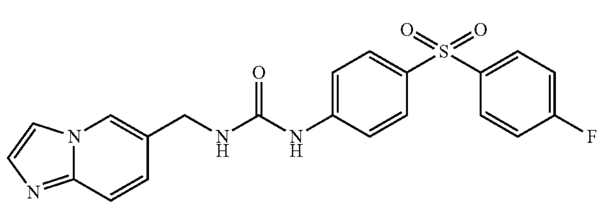 [SMILES: O=C(NCc1ccc2nccn2c1)Nc1ccc(S(=O)(=O)c2ccc(F)cc2)cc1] | 1-{4-[(4-fluorobenzene)sulfonyl]phenyl}-3-{imidazo[1,2-a]pyridin-6-ylmethyl}urea |

-continued

| Structure | Chemical Name |
|---|---|
| 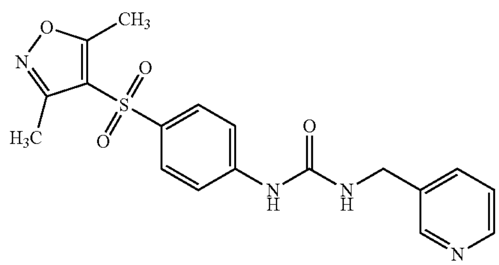 [SMILES: Cc1noc(C)c1S(=O)(=O)c1ccc(NC(=O)NCc2cccnc2)cc1] | 3-[4-(3,5-dimethyl-1,2-oxazole-4-sulfonyl)phenyl]-1-(pyridin-3-ylmethyl)urea |
| 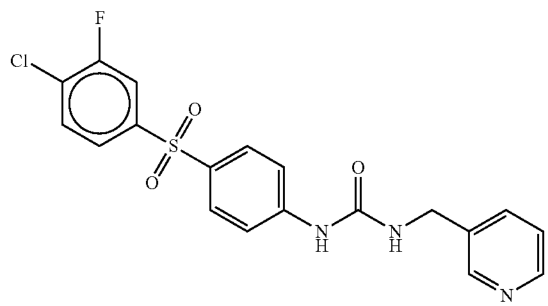 | 3-{4-[(4-chloro-3-fluorobenzene)sulfonyl]phenyl}-1-(pyridin-3-ylmethyl)urea |
| 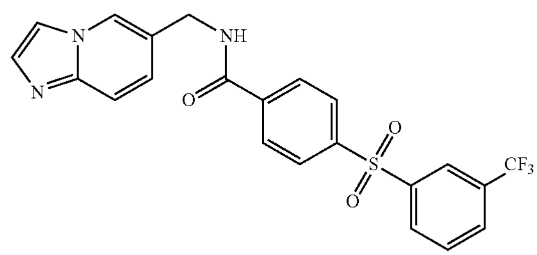 [SMILES: O=C(NCc1ccc2nccn2c1)c1ccc(S(=O)(=O)c2cccc(C(F)(F)F)c2)cc1] | N-{imidazo[1,2-a]pyridin-6-ylmethyl}-4-{[3-(trifluoromethyl)benzene]sulfonyl}benzamide |
| 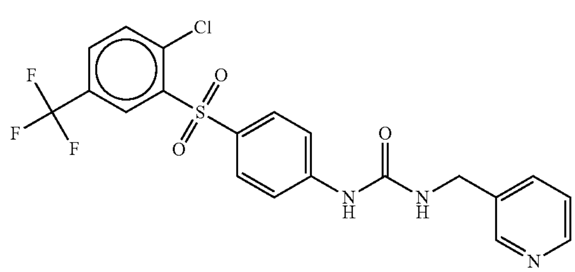 | 3-(4-{[2-chloro-5-(trifluoromethyl)benzene]sulfonyl}phenyl)-1-(pyridin-3-ylmethyl)urea |
| 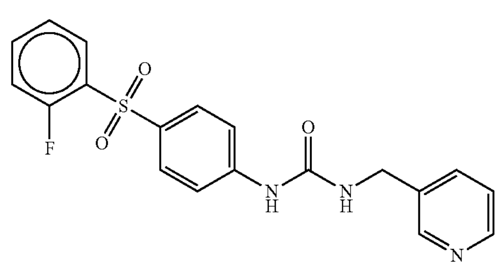 | 3-{4-[(2-fluorobenzene)sulfonyl]phenyl}-1-(pyridin-3-ylmethyl)urea |

| Structure | Chemical Name |
|---|---|
| 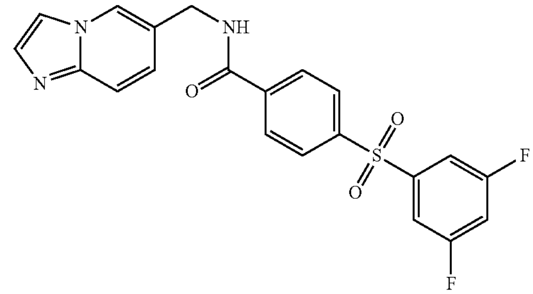 [SMILES: O=C(NCc1ccc2nccn2c1)c1ccc(S(=O)(=O)c2cc(F)cc(F)c2)cc1] | 4-[(3,5-difluorobenzene)sulfonyl]-N-{imidazo[1,2-a]pyridin-6-ylmethyl}benzamide |
| 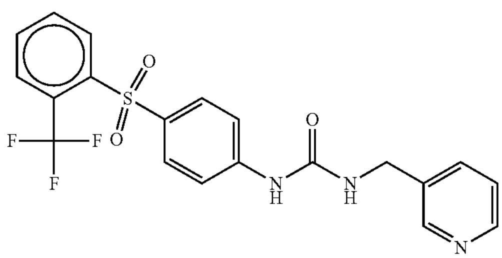 | 1-(pyridin-3-ylmethyl)-3-(4-{[2-(trifluoromethyl)benzene]sulfonyl}phenyl)urea |
| 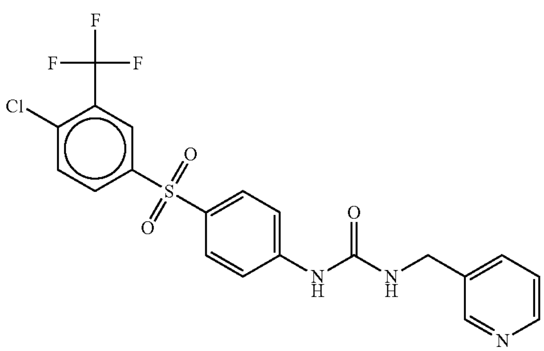 | 3-(4-{[4-chloro-3-(trifluoromethyl)benzene]sulfonyl}phenyl)-1-(pyridin-3-ylmethyl)urea |
| 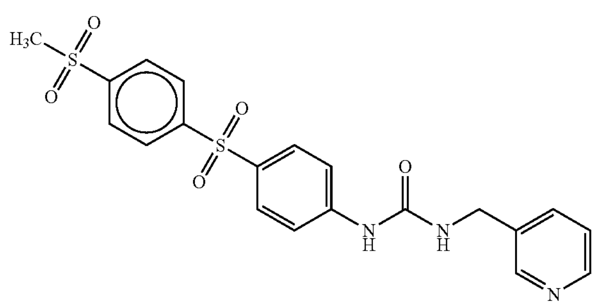 | 3-{4-[(4-methanesulfonylbenzene)sulfonyl]phenyl}-1-(pyridin-3-ylmethyl)urea |
| 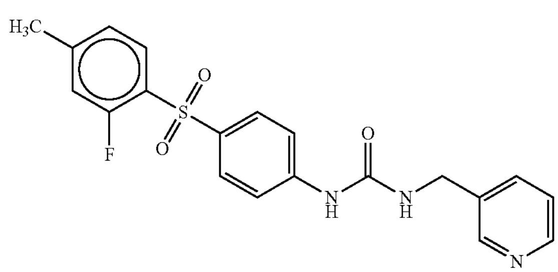 | 3-{4-[(2-fluoro-4-methylbenzene)sulfonyl]phenyl}-1-(pyridin-3-ylmethyl)urea |

-continued

| Structure | Chemical Name |
|---|---|
| 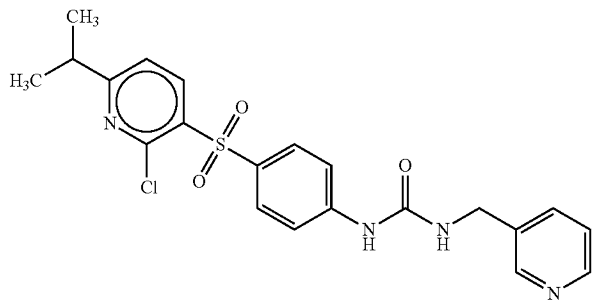 | 3-{4-[2-chloro-6-(propan-2-yl)pyridine-3-sulfonyl]phenyl}-1-(pyridin-3-ylmethyl)urea |
| 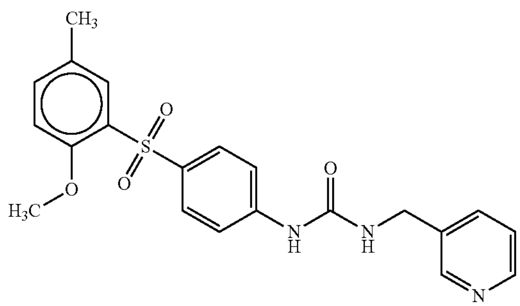 | 3-{4-[(2-methoxy-5-methylbenzene)sulfonyl]phenyl}-1-(pyridin-3-ylmethyl)urea |
| 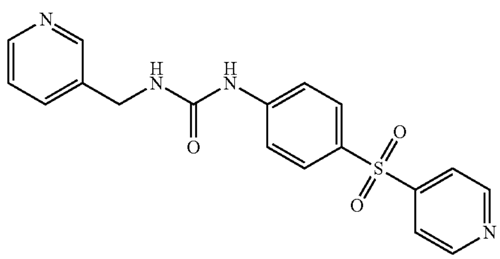 [SMILES: O=C(NCc1cccnc1)Nc1ccc(S(=O)(=O)c2ccncc2)cc1] | 3-(pyridin-3-ylmethyl)-1-[4-(pyridine-4-sulfonyl)phenyl]urea |
| 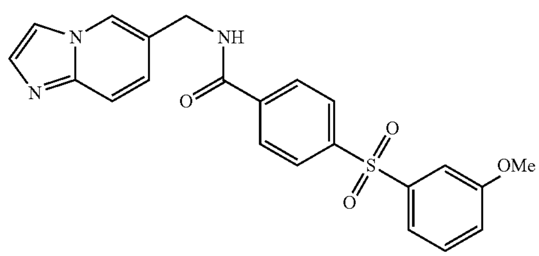 [SMILES: COc1cccc(S(=O)(=O)c2ccc(C(=O)NCc3ccc4nccn4c3)cc2)c1] | N-{imidazo[1,2-a]pyridin-6-ylmethyl}-4-[(3-methoxybenzene)sulfonyl]benzamide |
| 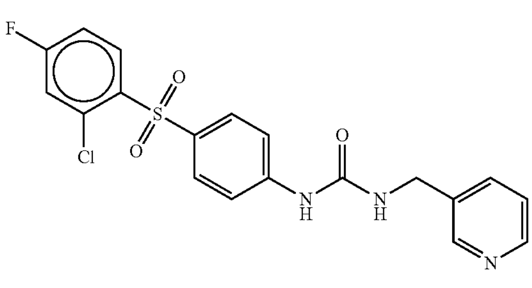 | 3-{4-[(2-chloro-4-fluorobenzene)sulfonyl]phenyl}-1-(pyridin-3-ylmethyl)urea |

-continued

| Structure | Chemical Name |
|---|---|
| 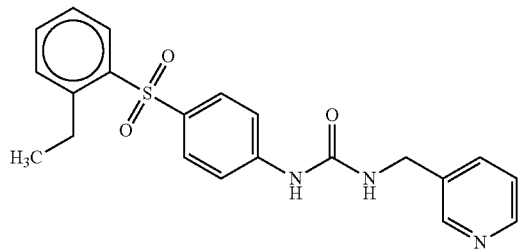 | 3-{4-[(2-ethylbenzene)sulfonyl]phenyl}-1-(pyridin-3-ylmethyl)urea |
| 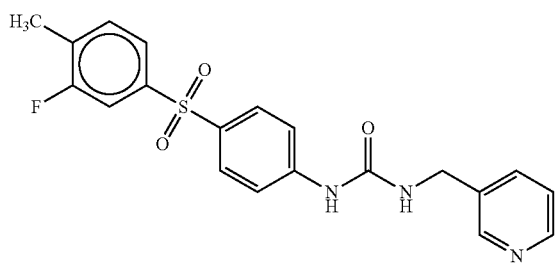 | 3-{4-[(3-fluoro-4-methylbenzene)sulfonyl]phenyl}-1-(pyridin-3-ylmethyl)urea |
| 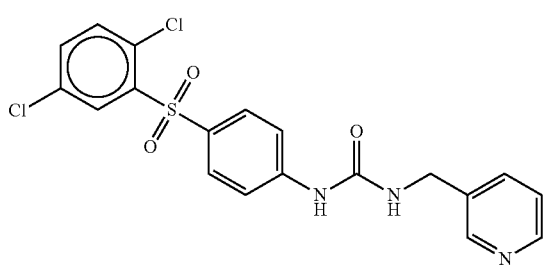 | 3-{4-[(2,5-dichlorobenzene)sulfonyl]phenyl}-1-(pyridin-3-ylmethyl)urea |
| 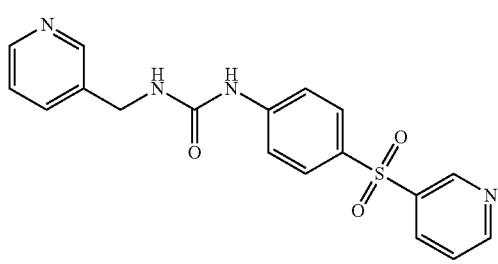 [SMILES: O=C(NCc1cccnc1)Nc1ccc(S(=O)(=O)c2cccnc2)cc1] | 3-(pyridin-3-ylmethyl)-1-[4-(pyridine-3-sulfonyl)phenyl]urea |
| 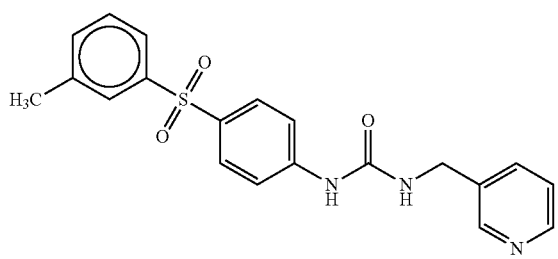 | 3-{4-[(3-methylbenzene)sulfonyl]phenyl}-1-(pyridin-3-ylmethyl)urea |
| 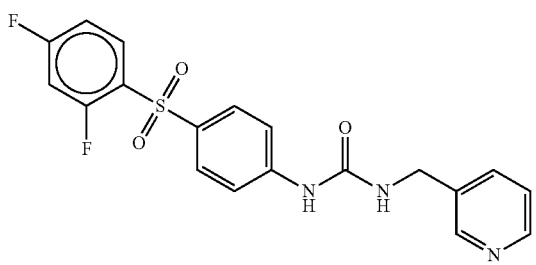 | 3-{4-[(2,4-difluorobenzene)sulfonyl]phenyl}-1-(pyridin-3-ylmethyl)urea |

-continued

| Structure | Chemical Name |
|---|---|
| 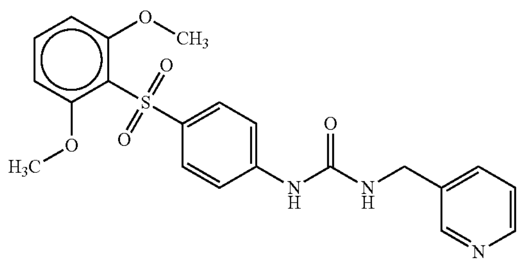 | 3-{4-[(2,6-dimethoxybenzene)sulfonyl]phenyl}-1-(pyridin-3-ylmethyl)urea |
| | 1-(4-{8-oxatricyclo[7.4.0.0²,⁷]trideca-1(9),2(7),3,5,10,12-hexaene-6-sulfonyl}phenyl)-3-(pyridin-3-ylmethyl)urea |
| 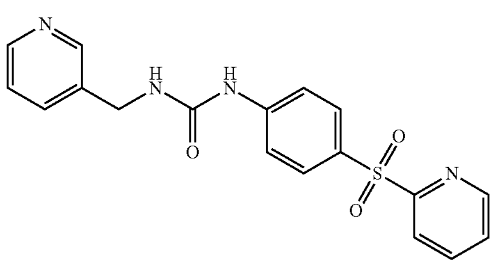 [SMILES: O=C(NCc1cccnc1)Nc1ccc(S(=O)(=O)c2ccccn2)cc1] | 3-(pyridin-3-ylmethyl)-1-[4-(pyridine-2-sulfonyl)phenyl]urea |
| 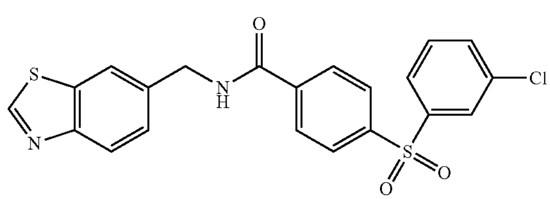 [SMILES: O=C(NCc1ccc2ncsc2c1)c1ccc(S(=O)(=O)c2cccc(Cl)c2)cc1] | N-(1,3-benzothiazol-6-ylmethyl)-4-[(3-chlorobenzene)sulfonyl]benzamide |
| 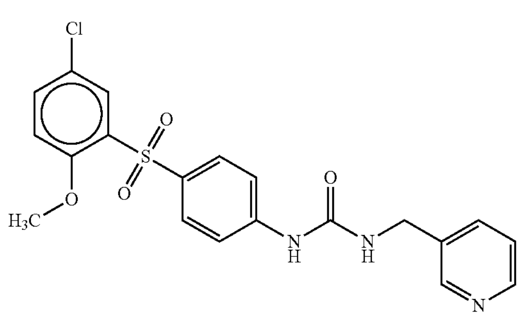 | 3-{4-[(5-chloro-2-methoxybenzene)sulfonyl]phenyl}-1-(pyridin-3-ylmethyl)urea |

-continued

| Structure | Chemical Name |
|---|---|
| 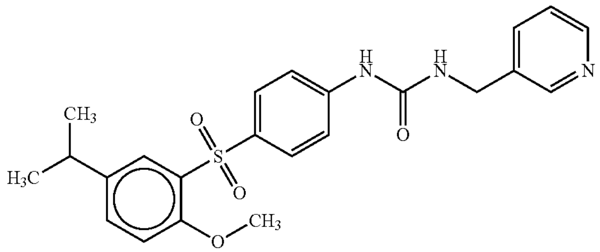 | 3-(4-{[2-methoxy-5-(propan-2-yl)benzene]sulfonyl}phenyl)-1-(pyridin-3-ylmethyl)urea |
| 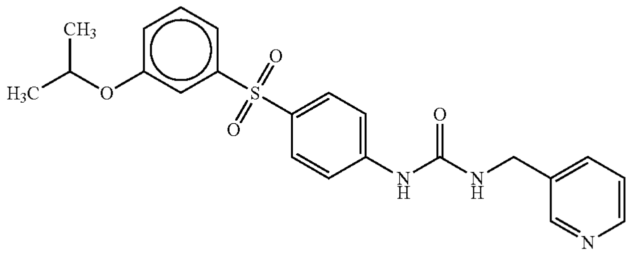 | 3-(4-{[3-(propan-2-yloxy)benzene]sulfonyl}phenyl)-1-(pyridin-3-ylmethyl)urea |
| 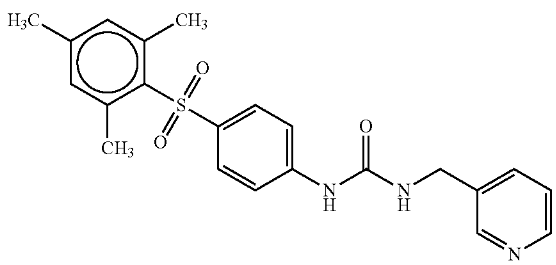 | 1-(pyridin-3-ylmethyl)-3-{4-[(2,4,6-trimethylbenzene)sulfonyl]phenyl}urea |
| 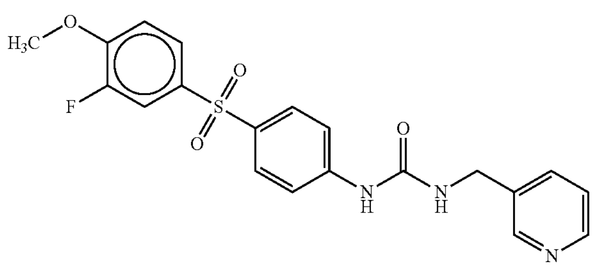 | 3-{4-[(3-fluoro-4-methoxybenzene)sulfonyl]phenyl}-1-(pyridin-3-ylmethyl)urea |
| 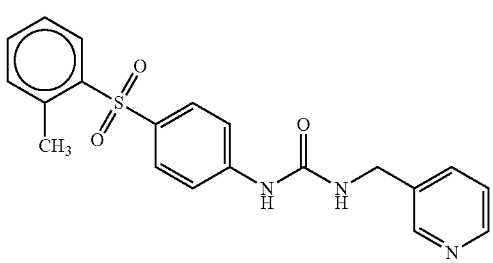 | 3-{4-[(2-methylbenzene)sulfonyl]phenyl}-1-(pyridin-3-ylmethyl)urea |
| 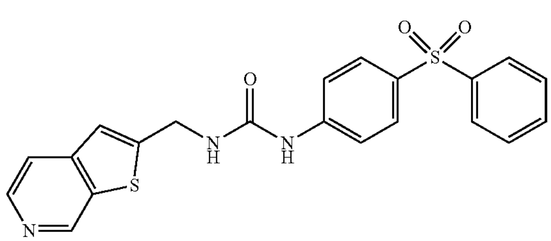 [SMILES: O=C(NCc1cc2ccncc2s1)Nc1ccc(S(=O)(=O)c2ccccc2)cc1] | 1-[4-(benzenesulfonyl)phenyl]-3-{thieno[2,3-c]pyridin-2-ylmethyl}urea |

-continued

| Structure | Chemical Name |
|---|---|
| 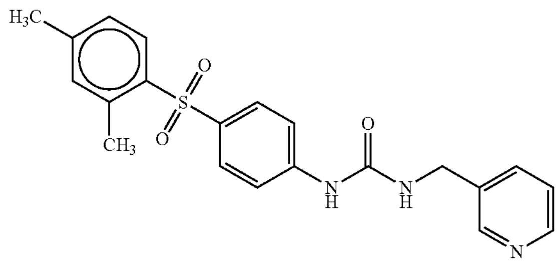 | 3-{4-[(2,4-dimethylbenzene)sulfonyl]phenyl}-1-(pyridin-3-ylmethyl)urea |
| 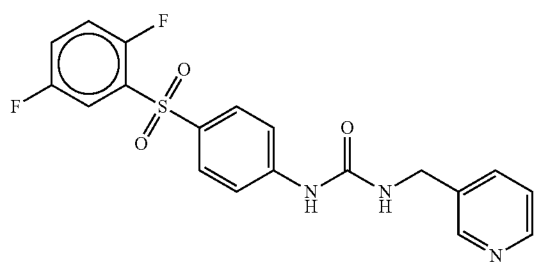 | 3-{4-[(2,5-difluorobenzene)sulfonyl]phenyl}-1-(pyridin-3-ylmethyl)urea |
| 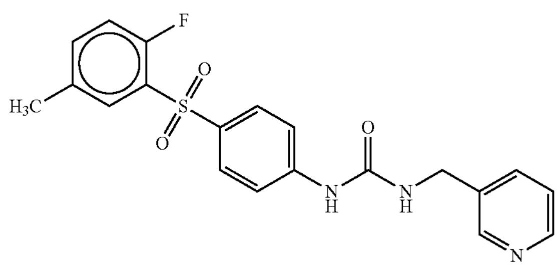 | 3-{4-[(2-fluoro-5-methylbenzene)sulfonyl]phenyl}-1-(pyridin-3-ylmethyl)urea |
| 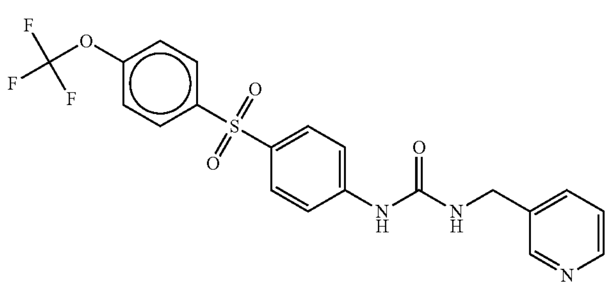 | 1-(pyridin-3-ylmethyl)-3-(4-{[4-(trifluoromethoxy)benzene]sulfonyl}phenyl)urea |
| 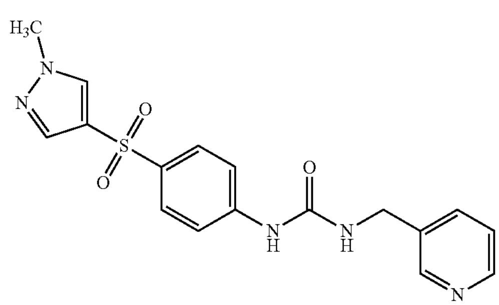 [SMILES: Cn1cc(S(=O)(=O)c2ccc(NC(=O)NCc3cccnc3)cc2)cn1] | 3-[4-(1-methyl-1H-pyrazole-4-sulfonyl)phenyl]-1-(pyridin-3-ylmethyl)urea |

-continued

| Structure | Chemical Name |
|---|---|
| 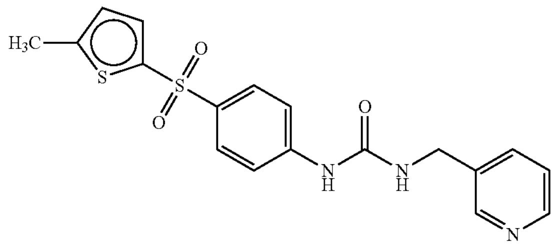 | 3-[4-(5-methylthiophene-2-sulfonyl)phenyl]-1-(pyridin-3-ylmethyl)urea |
| 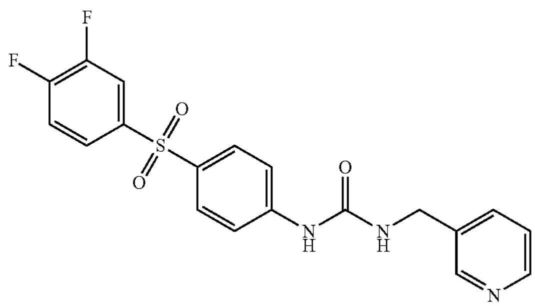 [SMILES: O=C(NCc1cccnc1)Nc1ccc(S(=O)(=O)c2ccc(F)c(F)c2)cc1] | 3-{4-[(3,4-difluorobenzene)sulfonyl]phenyl}-1-(pyridin-3-ylmethyl)urea |
| 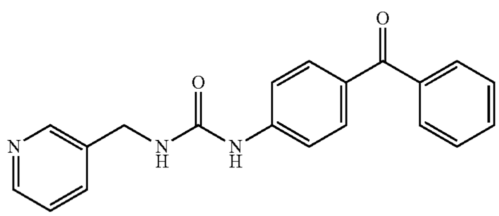 [SMILES: O=C(NCc1cccnc1)Nc1ccc(C(=O)c2ccccc2)cc1] | 1-(4-benzoylphenyl)-3-(pyridin-3-ylmethyl)urea |
| 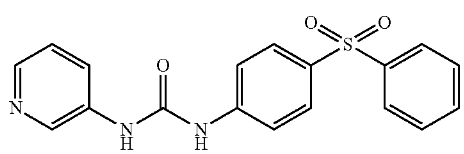 [SMILES: O=C(Nc1ccc(S(=O)(=O)c2ccccc2)cc1)Nc1cccnc1] | 3-[4-(benzenesulfonyl)phenyl]-1-(pyridin-3-yl)urea |
| 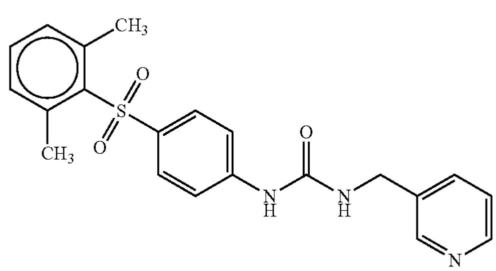 | 3-{4-[(2,6-dimethylbenzene)sulfonyl]phenyl}-1-(pyridin-3-ylmethyl)urea |
| 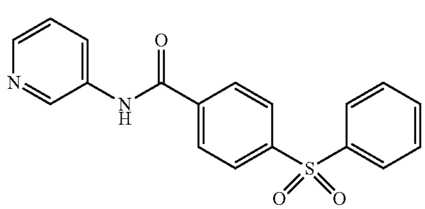 [SMILES: O=C(Nc1cccnc1)c1ccc(S(=O)(=O)c2ccccc2)cc1] | 4-(benzenesulfonyl)-N-(pyridin-3-yl)benzamide |
| 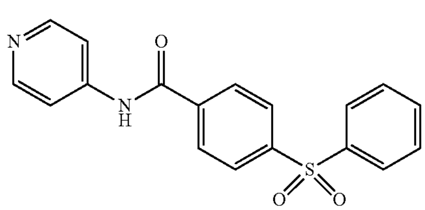 [SMILES: O=C(Nc1ccncc1)c1ccc(S(=O)(=O)c2ccccc2)cc1] | 4-(benzenesulfonyl)-N-(pyridin-4-yl)benzamide |

-continued

| Structure | Chemical Name |
|---|---|
| 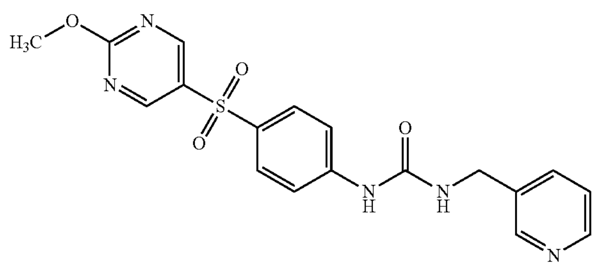 [SMILES: COc1ncc(S(=O)(=O)c2ccc(NC(=O)NCc3cccnc3)cc2)cn1] | 3-[4-(2-methoxypyrimidine-5-sulfonyl)phenyl]-1-(pyridin-3-ylmethyl)urea |
| 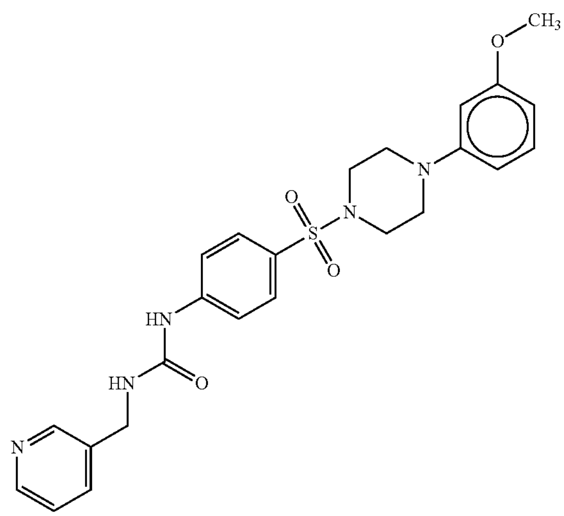 | 3-{4-[4-(3-methoxyphenyl)piperazine-1-sulfonyl]phenyl}-1-(pyridin-3-ylmethyl)urea |
| 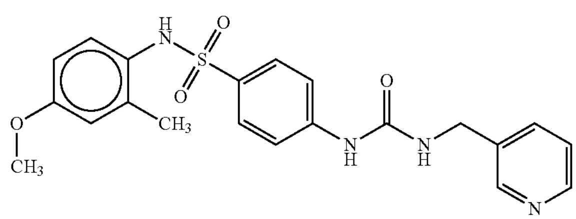 | 3-{4-[(4-methoxy-2-methylphenyl)sulfamoyl]phenyl}-1-(pyridin-3-ylmethyl)urea |
| 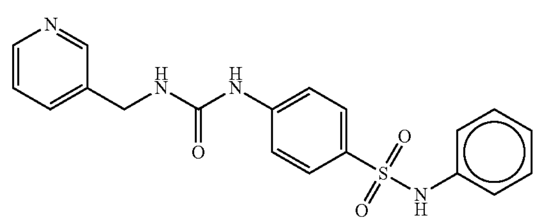 | 1-[4-(phenylsulfamoyl)phenyl]-3-(pyridin-3-ylmethyl)urea |
| 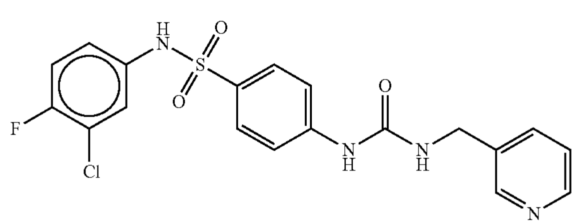 | 3-{4-[(3-chloro-4-fluorophenyl)sulfamoyl]phenyl}-1-(pyridin-3-ylmethyl)urea |

| Structure | Chemical Name |
|---|---|
| 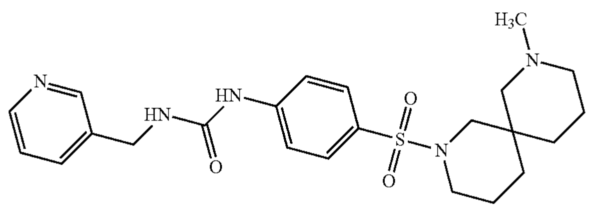 [SMILES: CN1CCCC2(CCCN(S(=O)(=O)c3ccc(NC(=O)NCc4cccnc4)cc3)C2)C1] | 3-(4-{8-methyl-2,8-diazaspiro[5.5]undecane-2-sulfonyl}phenyl)-1-(pyridin-3-ylmethyl)urea |
| 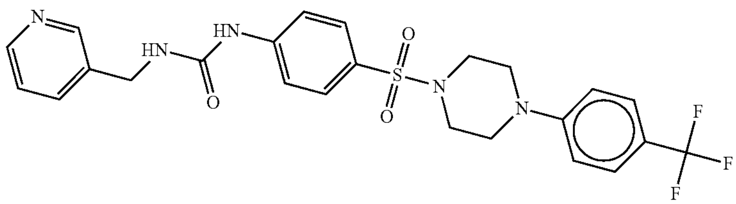 | 1-(pyridin-3-ylmethyl)-3-(4-{4-[4-(trifluoromethyl)phenyl]piperazine-1-sulfonyl}phenyl)urea |
| 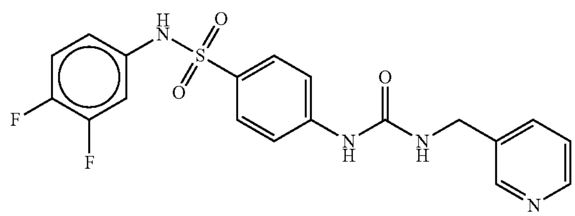 | 3-{4-[(3,4-difluorophenyl)sulfamoyl]phenyl}-1-(pyridin-3-ylmethyl)urea |
| 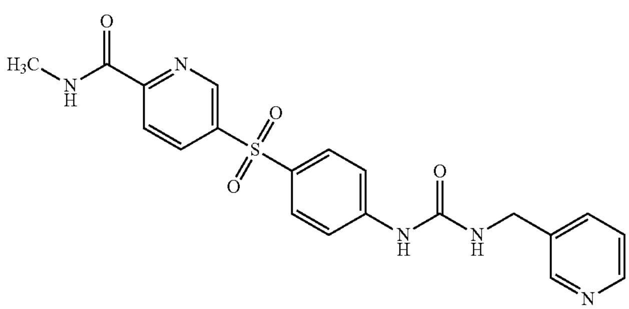 [SMILES: CNC(=O)c1ccc(S(=O)(=O)c2ccc(NC(=O)NCc3cccnc3)cc2)cn1] | N-methyl-5-[(4-{[(pyridin-3-ylmethyl)carbamoyl]amino}benzene)sulfonyl]pyridine-2-carboxamide |
| 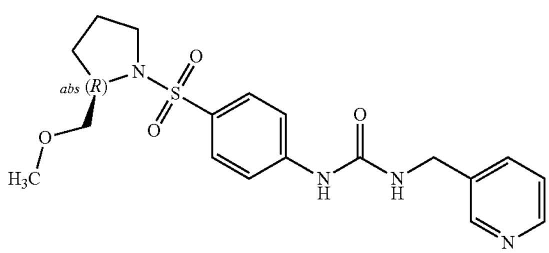 | 3-{4-[(2R)-2-(methoxymethyl)pyrrolidine-1-sulfonyl]phenyl}-1-(pyridin-3-ylmethyl)urea |
| 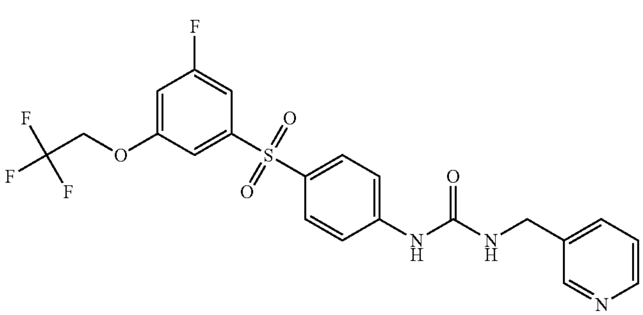 [SMILES: O=C(NCc1cccnc1)Nc1ccc(S(=O)(=O)c2cc(F)cc(OCC(F)(F)F)c2)cc1] | 3-(4-{[3-fluoro-5-(2,2,2-trifluoroethoxy)benzene]sulfonyl}phenyl)-1-(pyridin-3-ylmethyl)urea |

-continued

| Structure | Chemical Name |
|---|---|
| 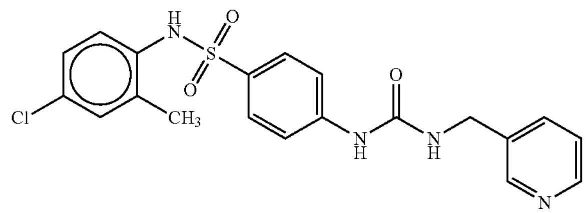 | 3-{4-[(4-chloro-2-methylphenyl)sulfamoyl]phenyl}-1-(pyridin-3-ylmethyl)urea |
| 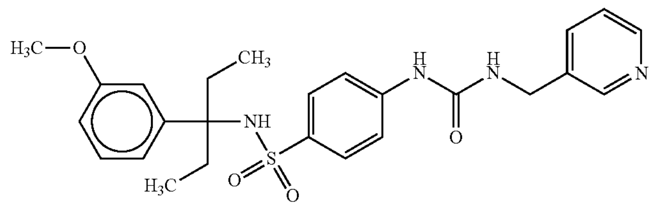 | 3-(4-{[3-(3-methoxyphenyl)pentan-3-yl]sulfamoyl}phenyl)-1-(pyridin-3-ylmethyl)urea |
| 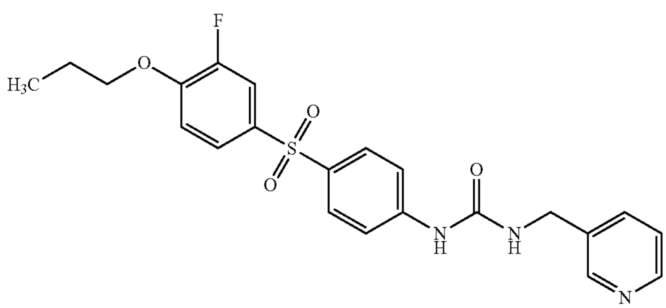 | 3-{4-[(3-fluoro-4-propoxybenzene)sulfonyl]phenyl}-1-(pyridin-3-ylmethyl)urea |
| 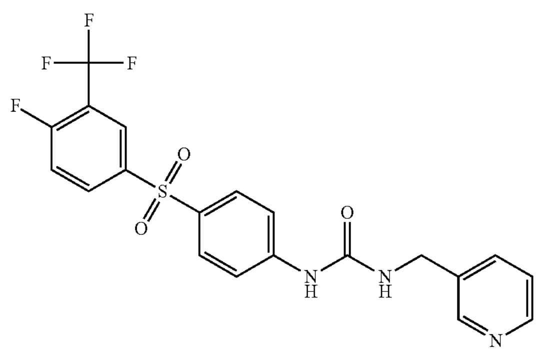 [SMILES: O=C(NCc1cccnc1)Nc1ccc(S(=O)(=O)c2ccc(F)c(C(F)(F)F)c2)cc1] | 3-(4-{[4-fluoro-3-(trifluoromethyl)benzene]sulfonyl}phenyl)-1-(pyridin-3-ylmethyl)urea |
| 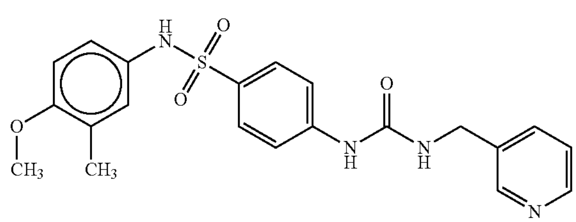 | 3-{4-[(4-methoxy-3-methylphenyl)sulfamoyl]phenyl}-1-(pyridin-3-ylmethyl)urea |
| 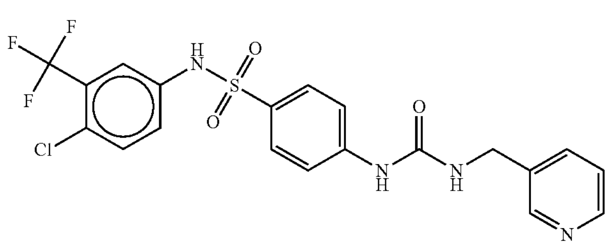 | 3-(4-{[4-chloro-3-(trifluoromethyl)phenyl]sulfamoyl}phenyl)-1-(pyridin-3-ylmethyl)urea |

-continued

| Structure | Chemical Name |
|---|---|
| 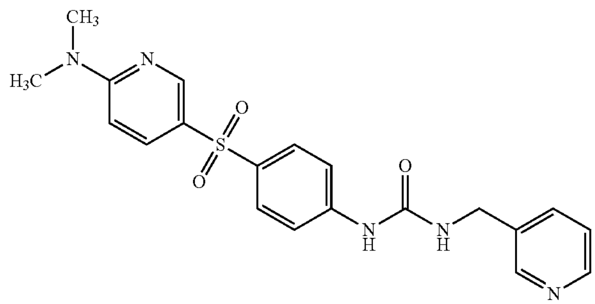 [SMILES: CN(C)c1ccc(S(=O)(=O)c2ccc(NC(=O)NCc3cccnc3)cc2)cn1] | 3-{4-[6-(dimethylamino)pyridine-3-sulfonyl]phenyl}-1-(pyridin-3-ylmethyl)urea |
| 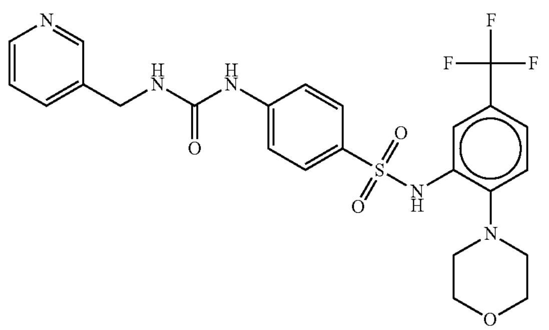 | 3-(4-{[2-(morpholin-4-yl)-5-(trifluoromethyl)phenyl]sulfamoyl}phenyl)-1-(pyridin-3-ylmethyl)urea |
| 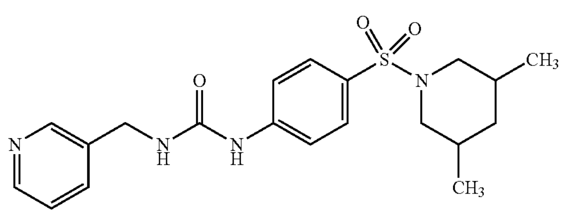 [SMILES: CC1CC(C)CN(S(=O)(=O)c2ccc(NC(=O)NCc3cccnc3)cc2)C1] | 1-[4-(3,5-dimethylpiperidine-1-sulfonyl)phenyl]-3-(pyridin-3-ylmethyl)urea |
| 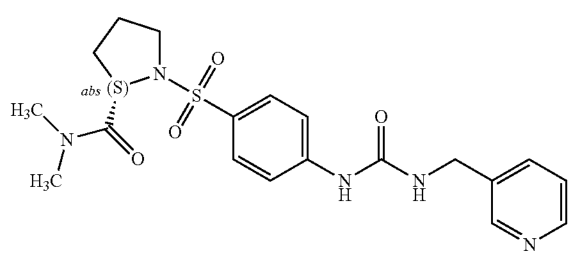 | (2S)-N,N-dimethyl-1-[(4-{[(pyridin-3-ylmethyl)carbamoyl]amino}benzene)sulfonyl]pyrrolidine-2-carboxamide |
| 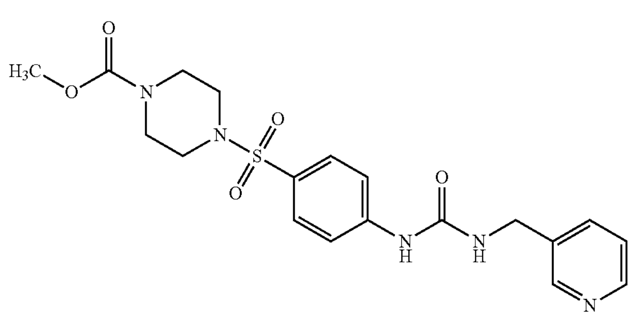 [SMILES: COC(=O)N1CCN(S(=O)(=O)c2ccc(NC(=O)NCc3cccnc3)cc2)CC1] | methyl 4-[(4-{[(pyridin-3-ylmethyl)carbamoyl]amino}benzene)sulfonyl]piperazine-1-carboxylate |

-continued

| Structure | Chemical Name |
|---|---|
| 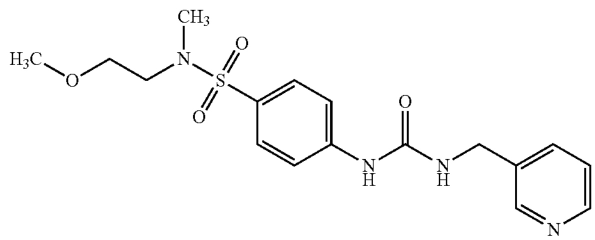 [SMILES: COCCN(C)S(=O)(=O)c1ccc(NC(=O)NCc2cccnc2)cc1] | 3-{4-[(2-methoxyethyl)(methyl)sulfamoyl]phenyl}-1-(pyridin-3-ylmethyl)urea |
| 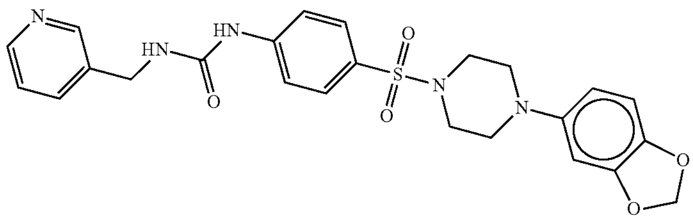 | 1-{4-[4-(2H-1,3-benzodioxol-5-yl)piperazine-1-sulfonyl]phenyl}-3-(pyridin-3-ylmethyl)urea |
| 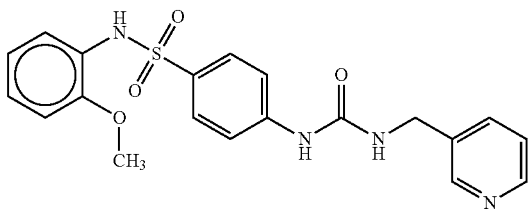 | 3-{4-[(2-methoxyphenyl)sulfamoyl]phenyl}-1-(pyridin-3-ylmethyl)urea |
| 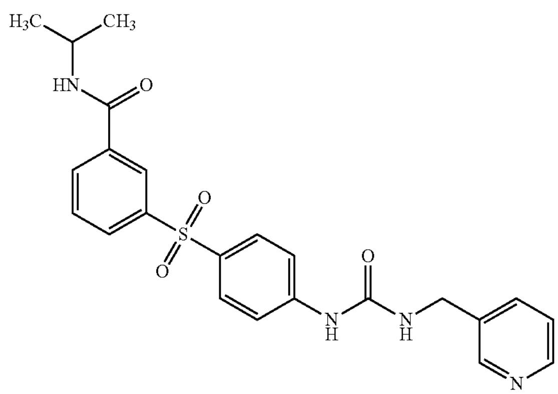 [SMILES: CC(C)NC(=O)c1cccc(S(=O)(=O)c2ccc(NC(=O)NCc3cccnc3)cc2)c1] | N-(propan-2-yl)-3-[(4-{[(pyridin-3-ylmethyl)carbamoyl]amino}benzene)sulfonyl]benzamide |
| 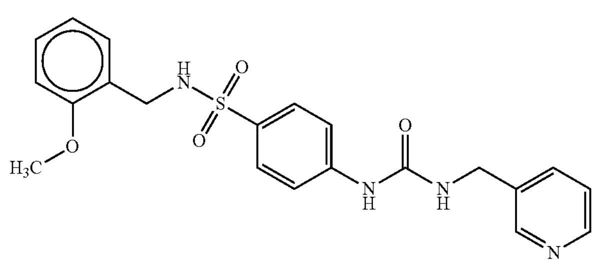 | 3-(4-{[(2-methoxyphenyl)methyl]sulfamoyl}phenyl)-1-(pyridin-3-ylmethyl)urea |
| 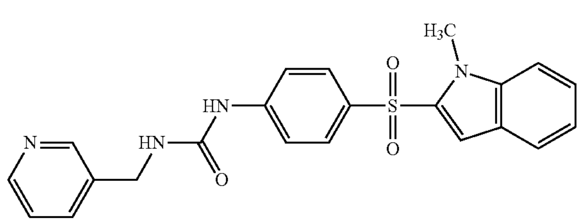 [SMILES: Cn1c(S(=O)(=O)c2ccc(NC(=O)NCc3cccnc3)cc2)cc2ccccc21] | 3-[4-(1-methyl-1H-indole-2-sulfonyl)phenyl]-1-(pyridin-3-ylmethyl)urea |

-continued

| Structure | Chemical Name |
|---|---|
| 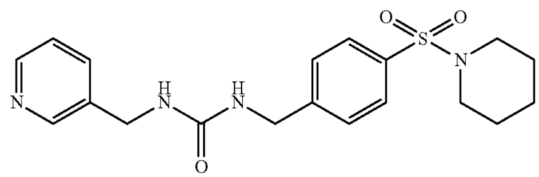 [SMILES: O=C(NCc1ccc(S(=O)(=O)N2CCCCC2)cc1)NCc1cccnc1] | 3-{[4-(piperidine-1-sulfonyl)phenyl]methyl}-1-(pyridin-3-ylmethyl)urea |
| 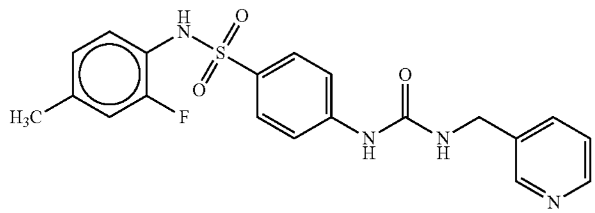 | 3-{4-[(2-fluoro-4-methylphenyl)sulfamoyl]phenyl}-1-(pyridin-3-ylmethyl)urea |
| 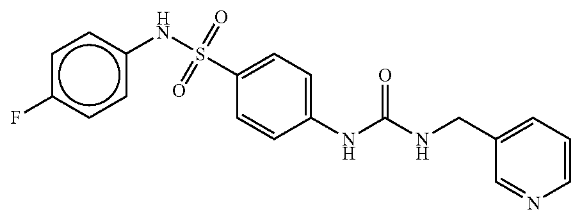 | 3-{4-[(4-fluorophenyl)sulfamoyl]phenyl}-1-(pyridin-3-ylmethyl)urea |
| 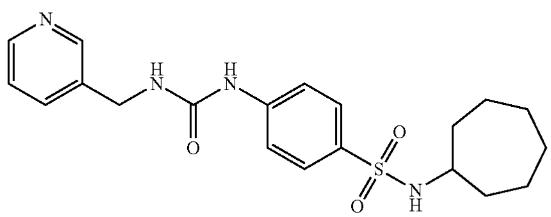 [SMILES: O=C(NCc1cccnc1)Nc1ccc(S(=O)(=O)NC2CCCCCC2)cc1] | 1-[4-(cycloheptylsulfamoyl)phenyl]-3-(pyridin-3-ylmethyl)urea |
| 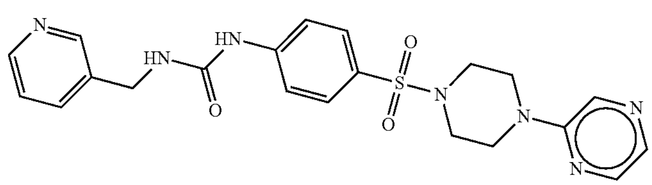 | 1-{4-[4-(pyrazin-2-yl)piperazine-1-sulfonyl]phenyl}-3-(pyridin-3-ylmethyl)urea |
| 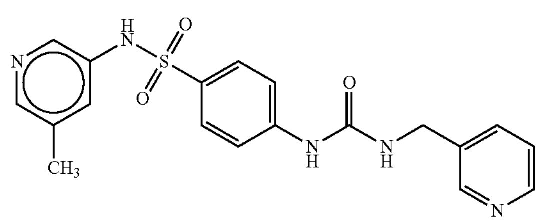 | 3-{4-[(5-methylpyridin-3-yl)sulfamoyl]phenyl}-1-(pyridin-3-ylmethyl)urea |
| 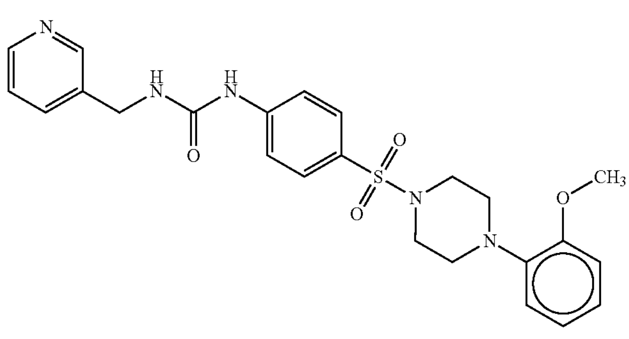 | 3-{4-[4-(2-methoxyphenyl)piperazine-1-sulfonyl]phenyl}-1-(pyridin-3-ylmethyl)urea |

-continued

| Structure | Chemical Name |
|---|---|
| 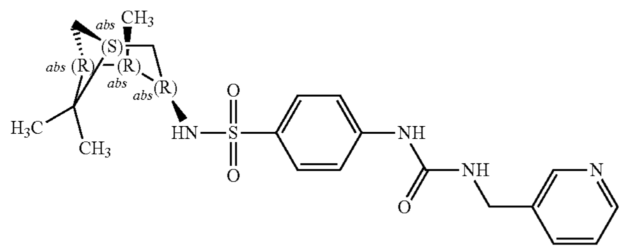 | 1-(pyridin-3-ylmethyl)-3-(4-{[(1R,2R,3R,5S)-2,6,6-trimethylbicyclo[3.1.1]heptan-3-yl]sulfamoyl}phenyl)urea |
| 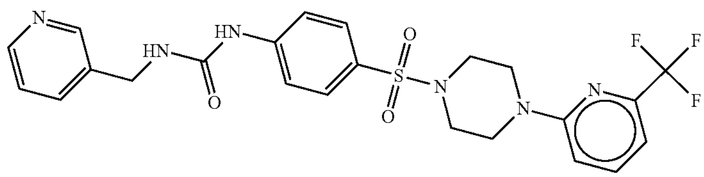 | 1-(pyridin-3-ylmethyl)-3-(4-{4-[6-(trifluoromethyl)pyridin-2-yl]piperazine-1-sulfonyl}phenyl)urea |
| 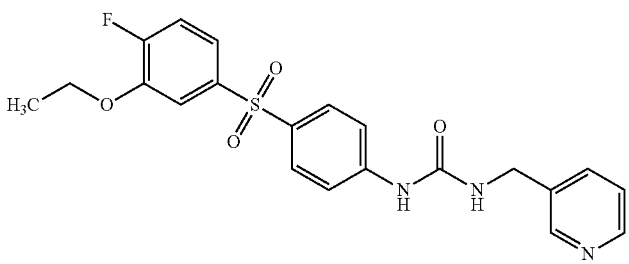 [SMILES: CCOc1cc(S(=O)(=O)c2ccc(NC(=O)NCc3cccnc3)cc2)ccc1F] | 3-{4-[(3-ethoxy-4-fluorobenzene)sulfonyl]phenyl}-1-(pyridin-3-ylmethyl)urea |
| 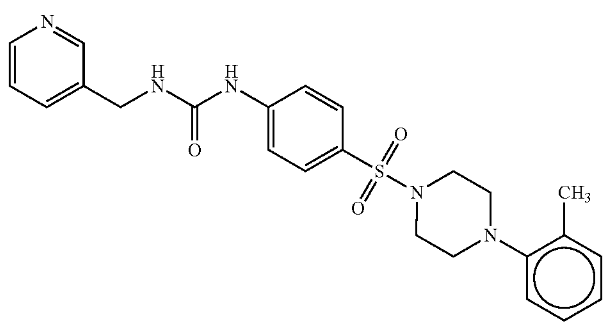 | 3-{4-[4-(2-methylphenyl)piperazine-1-sulfonyl]phenyl}-1-(pyridin-3-ylmethyl)urea |
| 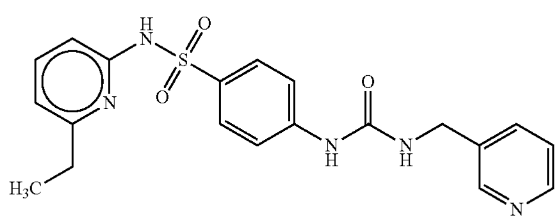 | 3-{4-[(6-ethylpyridin-2-yl)sulfamoyl]phenyl}-1-(pyridin-3-ylmethyl)urea |
| 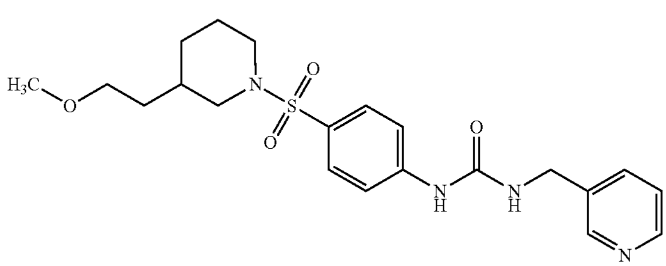 [SMILES: COCCC1CCCN(S(=O)(=O)c2ccc(NC(=O)NCc3cccnc3)cc2)C1] | 3-{4-[3-(2-methoxyethyl)piperidine-1-sulfonyl]phenyl}-1-(pyridin-3-ylmethyl)urea |

| Structure | Chemical Name |
|---|---|
| 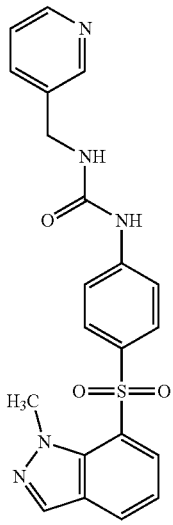 [SMILES: Cn1ncc2cccc(S(=O)(=O)c3ccc(NC(=O)NCc4cccnc4)cc3)c21] | 3-[4-(1-methyl-1H-indazole-7-sulfonyl)phenyl]-1-(pyridin-3-ylmethyl)urea |
| 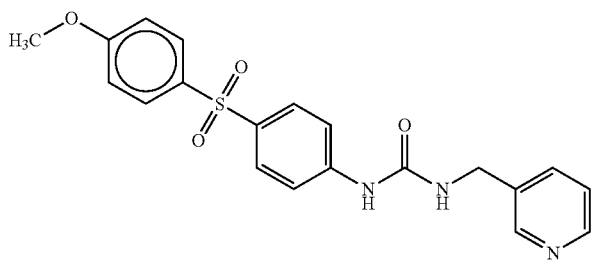 | 3-{4-[(4-methoxybenzene)sulfonyl]phenyl}-1-(pyridin-3-ylmethyl)urea |
| 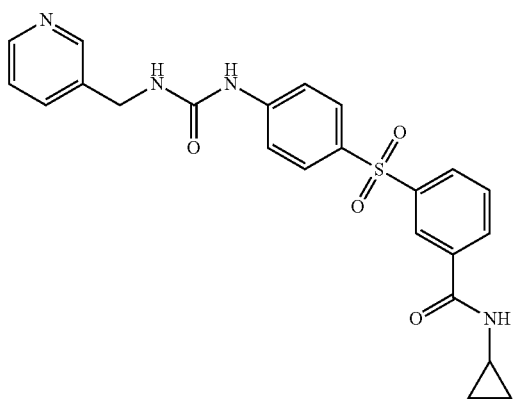 [SMILES: O=C(NCc1cccnc1)Nc1ccc(S(=O)(=O)c2cccc(C(=O)NC3CC3)c2)cc1] | N-cyclopropyl-3-[(4-{[(pyridin-3-ylmethyl)carbamoyl]amino}benzene)sulfonyl]benzamide |
| 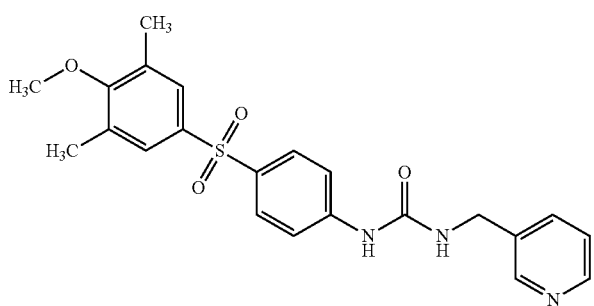 [SMILES: COc1c(C)cc(S(=O)(=O)c2ccc(NC(=O)NCc3cccnc3)cc2)cc1C] | 3-{4-[(4-methoxy-3,5-dimethylbenzene)sulfonyl]phenyl}-1-(pyridin-3-ylmethyl)urea |

-continued

| Structure | Chemical Name |
|---|---|
| 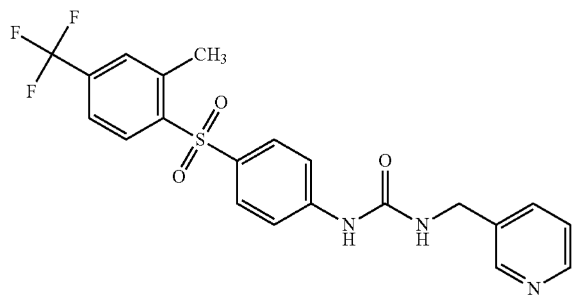 [SMILES: Cc1cc(C(F)(F)F)ccc1S(=O)(=O)c1ccc(NC(=O)NCc2cccnc2)cc1] | 3-(4-{[2-methyl-4-(trifluoromethyl)benzene]sulfonyl}phenyl)-1-(pyridin-3-ylmethyl)urea |
| 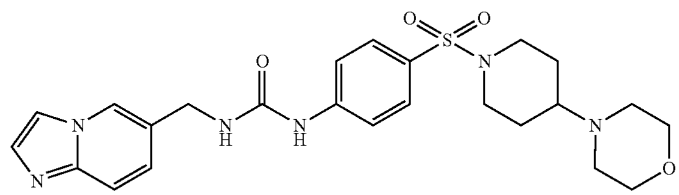 [SMILES: O=C(NCc1ccc2nccn2c1)Nc1ccc(S(=O)(=O)N2CCC(N3CCOCC3)CC2)cc1] | 3-{imidazo[1,2-a]pyridin-6-ylmethyl}-1-{4-[4-(morpholin-4-yl)piperidine-1-sulfonyl]phenyl}urea |
| 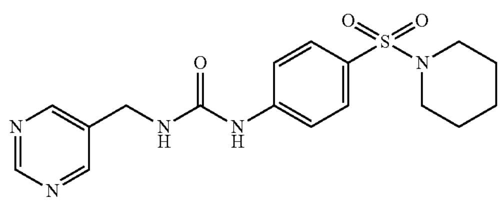 [SMILES: O=C(NCc1cncnc1)Nc1ccc(S(=O)(=O)N2CCCCC2)cc1] | 3-[4-(piperidine-1-sulfonyl)phenyl]-1-(pyrimidin-5-ylmethyl)urea |
| 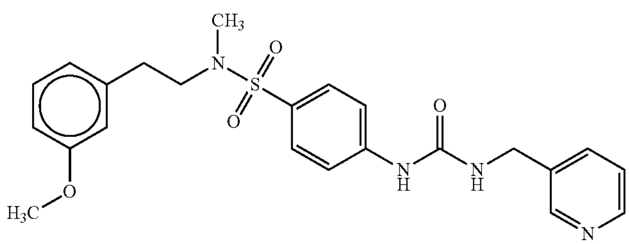 | 3-(4-{[2-(3-methoxyphenyl)ethyl](methyl)sulfamoyl}phenyl)-1-(pyridin-3-ylmethyl)urea |
| 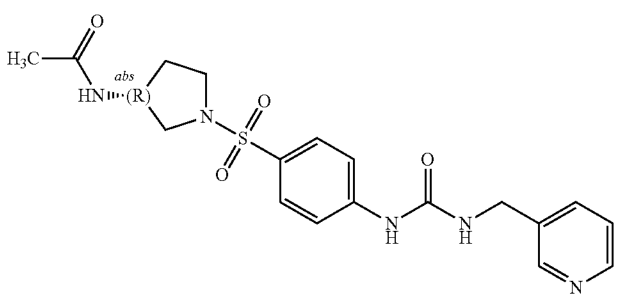 | N-[(3R)-1-[(4-{[(pyridin-3-ylmethyl)carbamoyl]amino}benzene)sulfonyl]pyrrolidin-3-yl]acetamide |
| 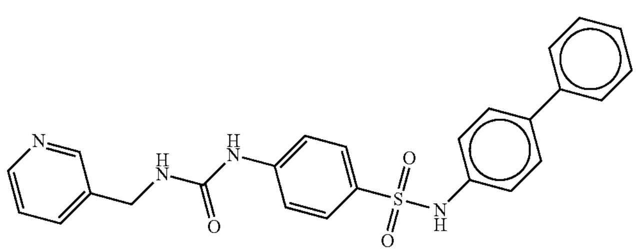 | 1-{4-[(4-phenylphenyl)sulfamoyl]phenyl}-3-(pyridin-3-ylmethyl)urea |

| Structure | Chemical Name |
|---|---|
| 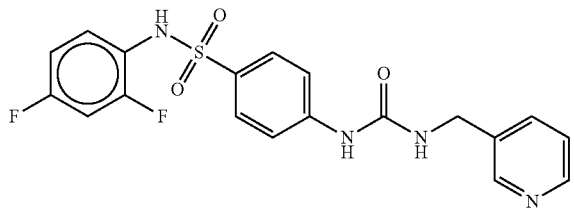 | 3-{4-[(2,4-difluorophenyl)sulfamoyl]phenyl}-1-(pyridin-3-ylmethyl)urea |
| 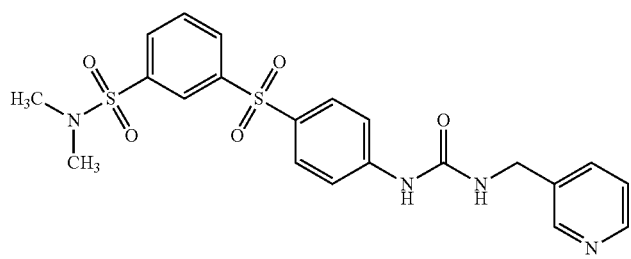 [SMILES: CN(C)S(=O)(=O)c1cccc(S(=O)(=O)c2ccc(NC(=O)NCc3cccnc3)cc2)c1] | 3-(4-{[3-(dimethylsulfamoyl)benzene]sulfonyl}phenyl)-1-(pyridin-3-ylmethyl)urea |
| 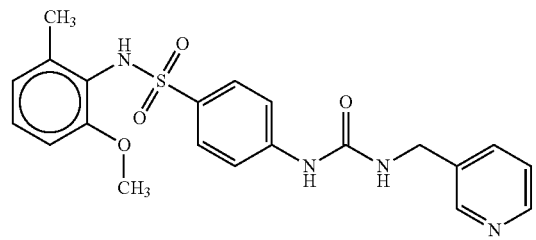 | 3-{4-[(2-methoxy-6-methylphenyl)sulfamoyl]phenyl}-1-(pyridin-3-ylmethyl)urea |
| 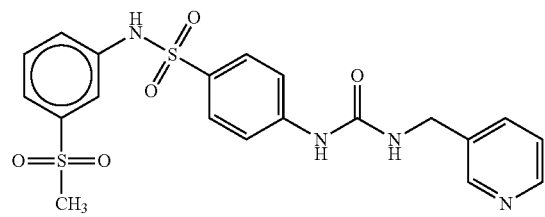 | 3-{4-[(3-methanesulfonylphenyl)sulfamoyl]phenyl}-1-(pyridin-3-ylmethyl)urea |
| 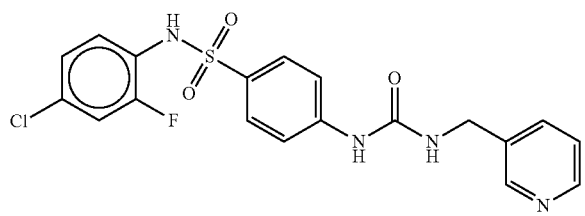 | 3-{4-[(4-chloro-2-fluorophenyl)sulfamoyl]phenyl}-1-(pyridin-3-ylmethyl)urea |
| 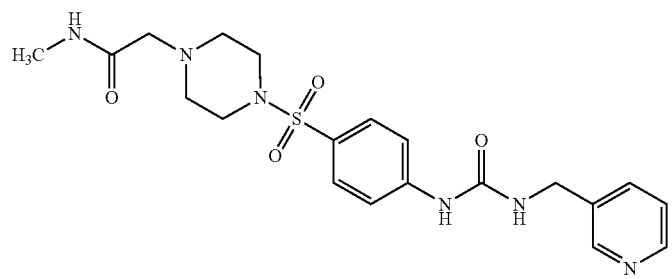 [SMILES: CNC(=O)CN1CCN(S(=O)(=O)c2ccc(NC(=O)NCc3cccnc3)cc2)CC1] | N-methyl-2-{4-[(4-{[(pyridin-3-ylmethyl)carbamoyl]amino}benzene)sulfonyl]piperazin-1-yl}acetamide |

-continued

| Structure | Chemical Name |
|---|---|
| 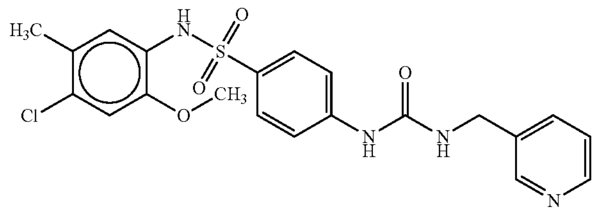 | 3-{4-[(4-chloro-2-methoxy-5-methylphenyl)sulfamoyl]phenyl}-1-(pyridin-3-ylmethyl)urea |
| 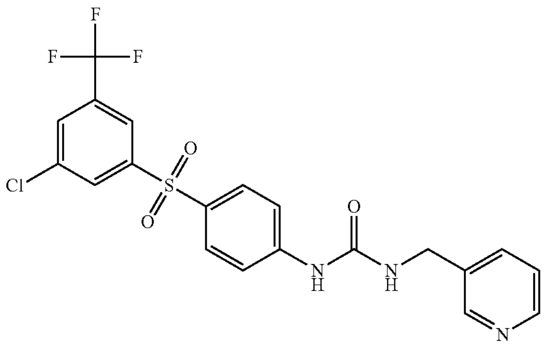 [SMILES: O=C(NCc1cccnc1)Nc1ccc(S(=O)(=O)c2cc(Cl)cc(C(F)(F)F)c2)cc1] | 3-(4-{[3-chloro-5-(trifluoromethyl)benzene]sulfonyl}phenyl)-1-(pyridin-3-ylmethyl)urea |
| 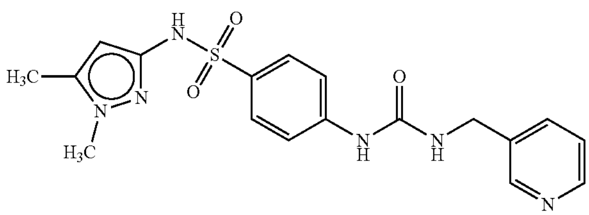 | 3-{4-[(1,5-dimethyl-1H-pyrazol-3-yl)sulfamoyl]phenyl}-1-(pyridin-3-ylmethyl)urea |
| 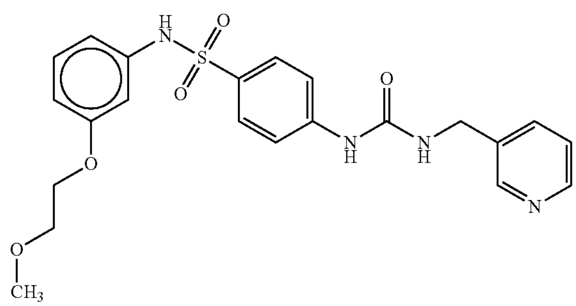 | 3-(4-{[3-(2-methoxyethoxy)phenyl]sulfamoyl}phenyl)-1-(pyridin-3-ylmethyl)urea |
| 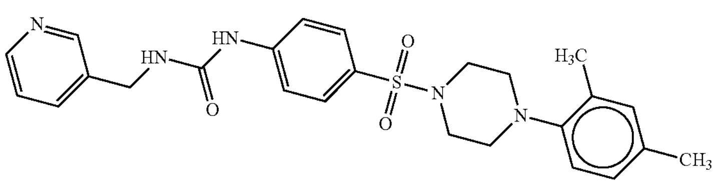 | 3-{4-[4-(2,4-dimethylphenyl)piperazine-1-sulfonyl]phenyl}-1-(pyridin-3-ylmethyl)urea |
| 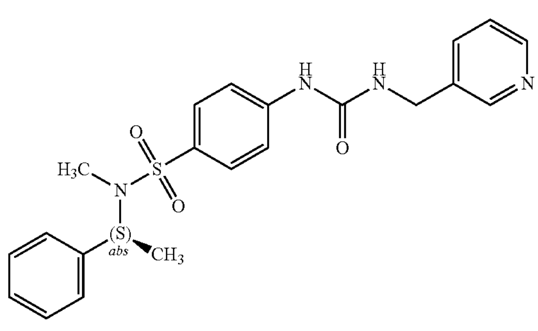 | 3-(4-{methyl[(1S)-1-phenylethyl]sulfamoyl}phenyl)-1-(pyridin-3-ylmethyl)urea |

| Structure | Chemical Name |
|---|---|
| 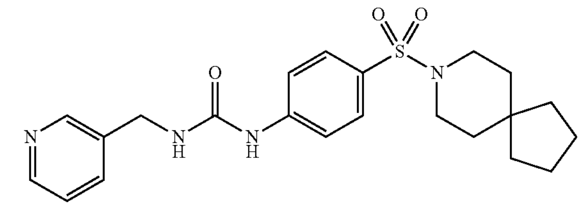 [SMILES: O=C(NCc1cccnc1)Nc1ccc(S(=O)(=O)N2CCC3(CCCC3)CC2)cc1] | 1-(4-{8-azaspiro[4.5]decane-8-sulfonyl}phenyl)-3-(pyridin-3-ylmethyl)urea |
| 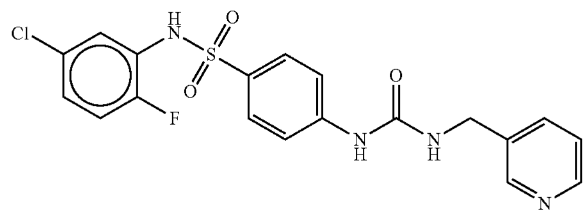 | 3-{4-[(5-chloro-2-fluorophenyl)sulfamoyl]phenyl}-1-(pyridin-3-ylmethyl)urea |
| 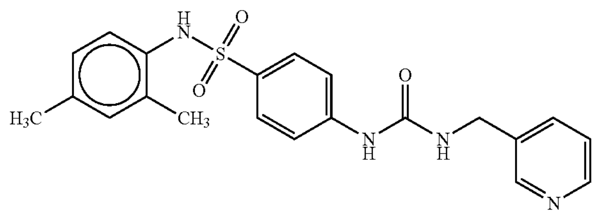 | 3-{4-[(2,4-dimethylphenyl)sulfamoyl]phenyl}-1-(pyridin-3-ylmethyl)urea |
| 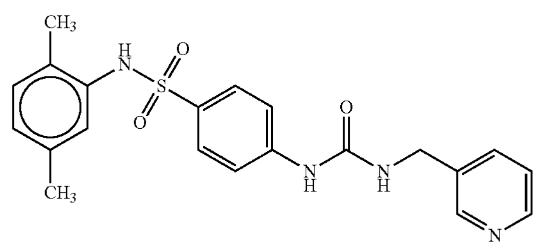 | 3-{4-[(2,5-dimethylphenyl)sulfamoyl]phenyl}-1-(pyridin-3-ylmethyl)urea |
| 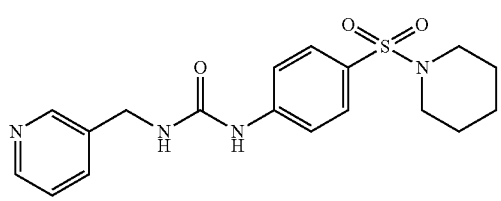 [SMILES: O=C(NCc1cccnc1)Nc1ccc(S(=O)(=O)N2CCCCC2)cc1] | 1-[4-(piperidine-1-sulfonyl)phenyl]-3-(pyridin-3-ylmethyl)urea |
| 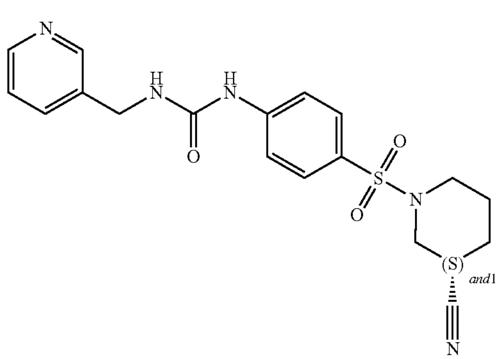 | 1-{4-[(3S)-3-cyanopiperidine-1-sulfonyl]phenyl}-3-(pyridin-3-ylmethyl)urea |

| Structure | Chemical Name |
|---|---|
| 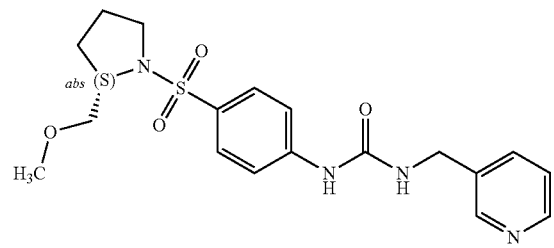 | 3-{4-[(2S)-2-(methoxymethyl)pyrrolidine-1-sulfonyl]phenyl}-1-(pyridin-3-ylmethyl)urea |
| 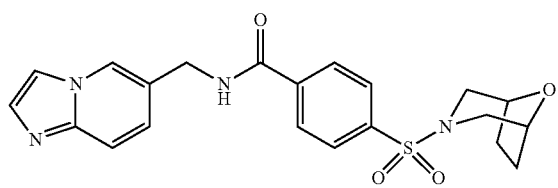 [SMILES: O=C(NCc1ccc2nccn2c1)c1ccc(S(=O)(=O)N2CC3CCC(C2)O3)cc1] | N-{imidazo[1,2-a]pyridin-6-ylmethyl}-4-{8-oxa-3-azabicyclo[3.2.1]octane-3-sulfonyl}benzamide |
| 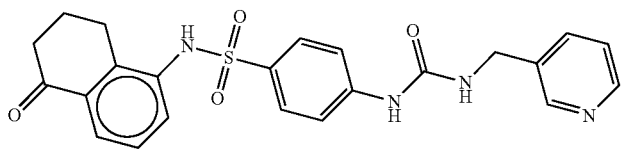 | 1-{4-[(5-oxo-5,6,7,8-tetrahydronaphthalen-1-yl)sulfamoyl]phenyl}-3-(pyridin-3-ylmethyl)urea |
| 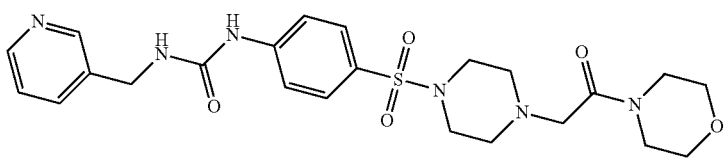 [SMILES: O=C(NCc1cccnc1)Nc1ccc(S(=O)(=O)N2CCN(CC(=O)N3CCOCC3)CC2)cc1] | 1-(4-{4-[2-(morpholin-4-yl)-2-oxoethyl]piperazine-1-sulfonyl}phenyl)-3-(pyridin-3-ylmethyl)urea |
| 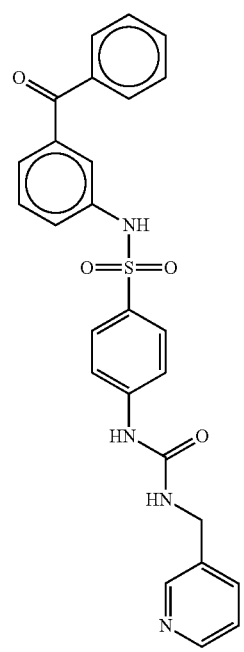 | 1-{4-[(3-benzoylphenyl)sulfamoyl]phenyl}-3-(pyridin-3-ylmethyl)urea |

-continued

| Structure | Chemical Name |
|---|---|
| 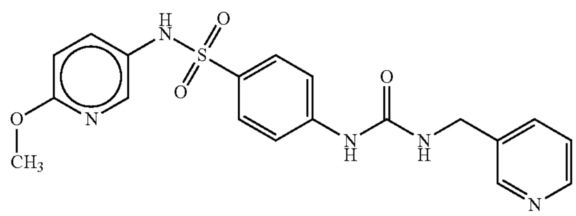 | 3-{4-[(6-methoxypyridin-3-yl)sulfamoyl]phenyl}-1-(pyridin-3-ylmethyl)urea |
| 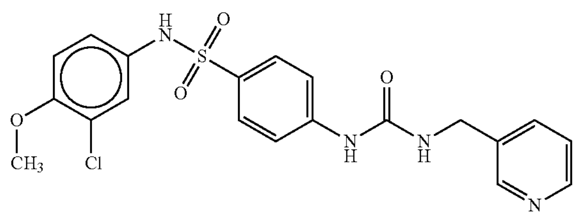 | 3-{4-[(3-chloro-4-methoxyphenyl)sulfamoyl]phenyl}-1-(pyridin-3-ylmethyl)urea |
| 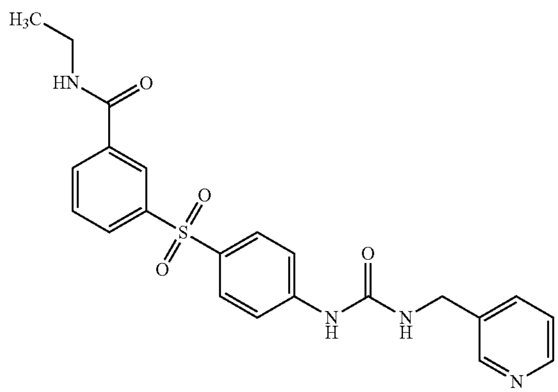 [SMILES: CCNC(=O)c1cccc(S(=O)(=O)c2ccc(NC(=O)NCc3cccnc3)cc2)c1] | N-ethyl-3-[(4-{[(pyridin-3-ylmethyl)carbamoyl]amino}benzene)sulfonyl]benzamide |
| 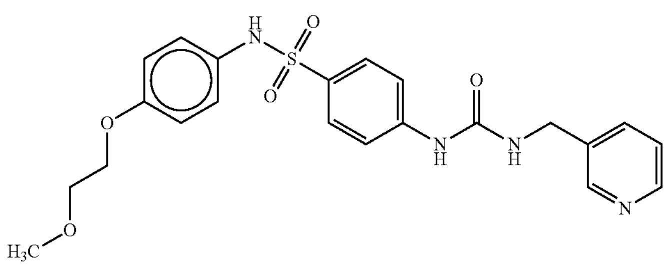 | 3-(4-{[4-(2-methoxyethoxy)phenyl]sulfamoyl}phenyl)-1-(pyridin-3-ylmethyl)urea |
| 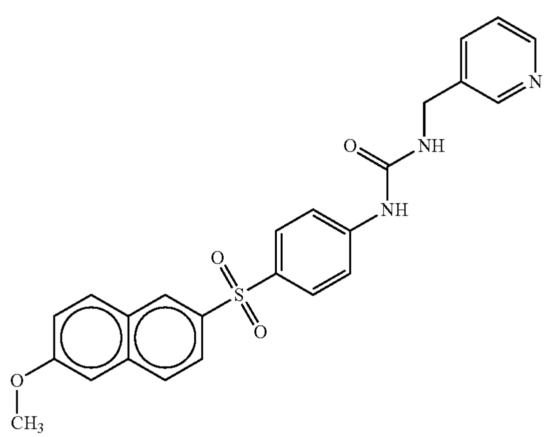 | 3-[4-(6-methoxynaphthalene-2-sulfonyl)phenyl]-1-(pyridin-3-ylmethyl)urea |

-continued

| Structure | Chemical Name |
|---|---|
| 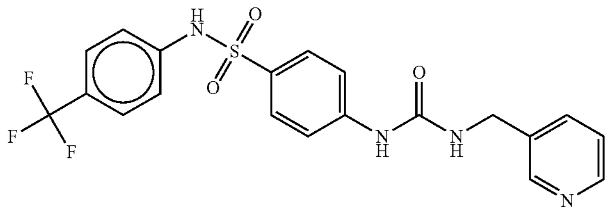 | 1-(pyridin-3-ylmethyl)-3-(4-{[4-(trifluoromethyl)phenyl]sulfamoyl}phenyl)urea |
| 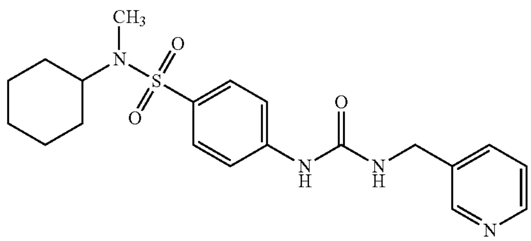 [SMILES: CN(C1CCCCC1)S(=O)(=O)c1ccc(NC(=O)NCc2cccnc2)cc1] | 3-{4-[cyclohexyl(methyl)sulfamoyl]phenyl}-1-(pyridin-3-ylmethyl)urea |
| 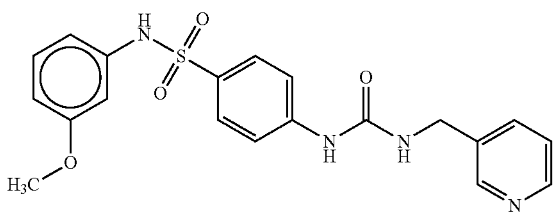 | 3-{4-[(3-methoxyphenyl)sulfamoyl]phenyl}-1-(pyridin-3-ylmethyl)urea |
| 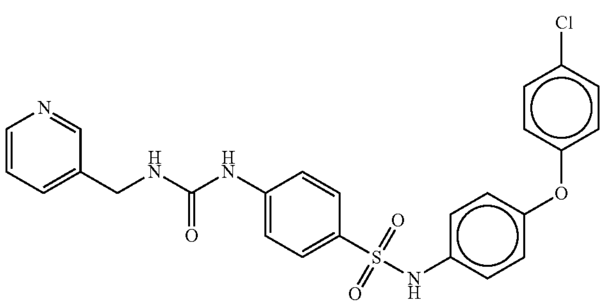 | 3-(4-{[4-(4-chlorophenoxy)phenyl]sulfamoyl}phenyl)-1-(pyridin-3-ylmethyl)urea |
| 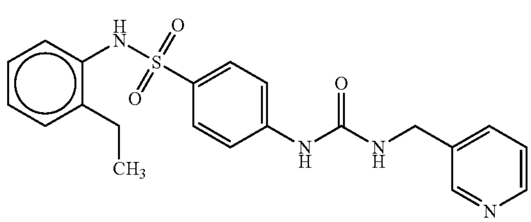 | 3-{4-[(2-ethylphenyl)sulfamoyl]phenyl}-1-(pyridin-3-ylmethyl)urea |
| 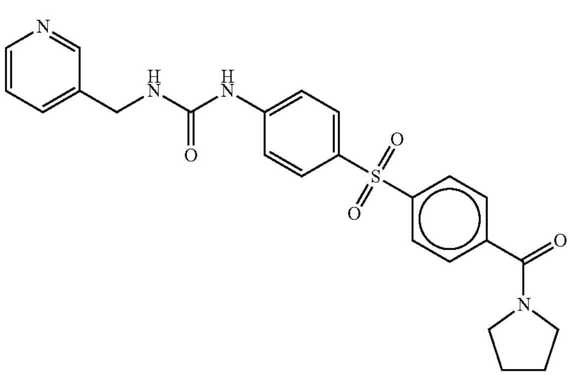 | 3-(pyridin-3-ylmethyl)-1-[4-({4-[(pyrrolidin-1-yl)carbonyl]benzene}sulfonyl)phenyl]urea |

-continued

| Structure | Chemical Name |
|---|---|
| 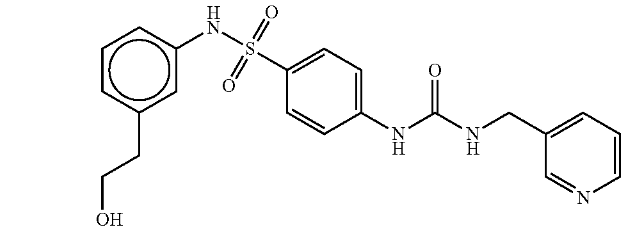 | 3-(4-{[3-(2-hydroxyethyl)phenyl]sulfamoyl}phenyl)-1-(pyridin-3-ylmethyl)urea |
| 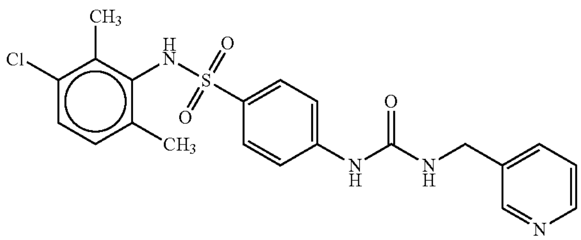 | 3-{4-[(3-chloro-2,6-dimethylphenyl)sulfamoyl]phenyl}-1-(pyridin-3-ylmethyl)urea |
| 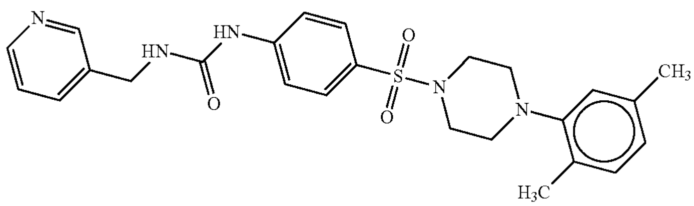 | 3-{4-[4-(2,5-dimethylphenyl)piperazine-1-sulfonyl]phenyl}-1-(pyridin-3-ylmethyl)urea |
| 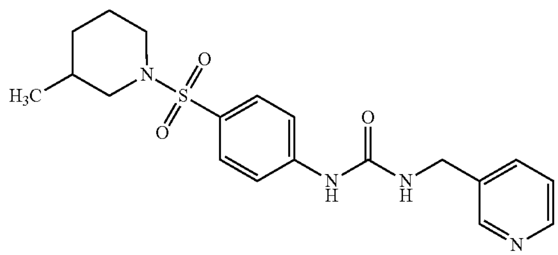 [SMILES: CC1CCCN(S(=O)(=O)c2ccc(NC(=O)NCc3cccnc3)cc2)C1] | 3-[4-(3-methylpiperidine-1-sulfonyl)phenyl]-1-(pyridin-3-ylmethyl)urea |
| 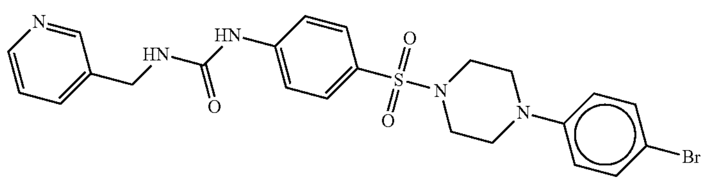 | 3-{4-[4-(4-bromophenyl)piperazine-1-sulfonyl]phenyl}-1-(pyridin-3-ylmethyl)urea |
| 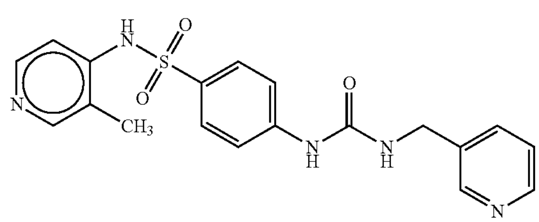 | 3-{4-[(3-methylpyridin-4-yl)sulfamoyl]phenyl}-1-(pyridin-3-ylmethyl)urea |
| 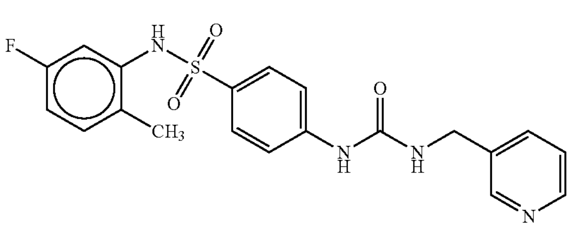 | 3-{4-[(5-fluoro-2-methylphenyl)sulfamoyl]phenyl}-1-(pyridin-3-ylmethyl)urea |

-continued

| Structure | Chemical Name |
|---|---|
| 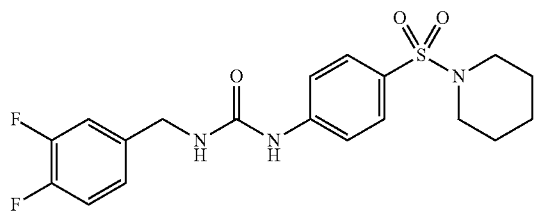 [SMILES: O=C(NCc1ccc(F)c(F)c1)Nc1ccc(S(=O)(=O)N2CCCCC2)cc1] | 1-[(3,4-difluorophenyl)methyl]-3-[4-(piperidine-1-sulfonyl)phenyl]urea |
| 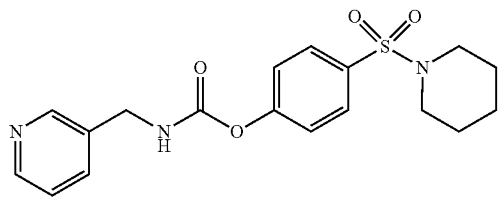 [SMILES: O=C(NCc1cccnc1)Oc1ccc(S(=O)(=O)N2CCCCC2)cc1] | 4-(piperidine-1-sulfonyl)phenyl N-(pyridin-3-ylmethyl)carbamate |
| 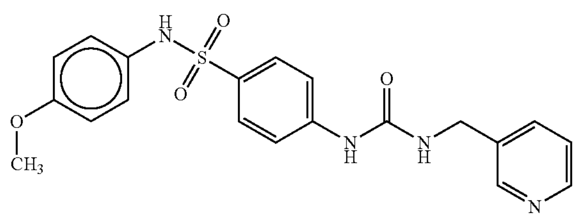 | 3-{4-[(4-methoxyphenyl)sulfamoyl]phenyl}-1-(pyridin-3-ylmethyl)urea |
| 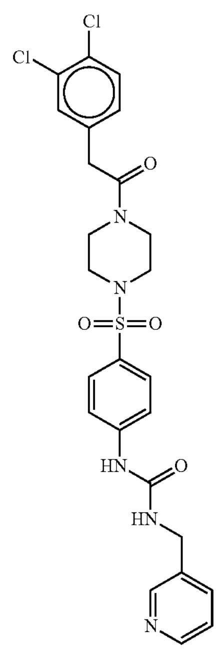 | 3-(4-{4-[2-(3,4-dichlorophenyl)acetyl]piperazine-1-sulfonyl}phenyl)-1-(pyridin-3-ylmethyl)urea |
| 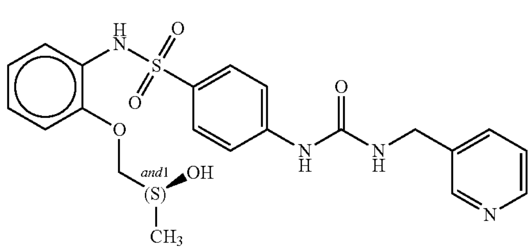 | 3-[4-({2-[(2S)-2-hydroxypropoxy]phenyl}sulfamoyl)phenyl]-1-(pyridin-3-ylmethyl)urea |

| Structure | Chemical Name |
|---|---|
| 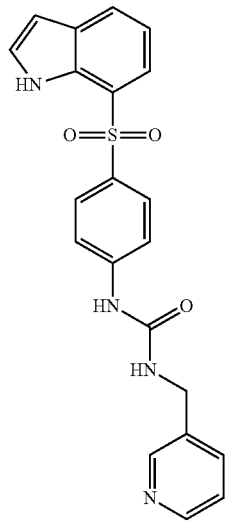 [SMILES: O=C(NCc1cccnc1)Nc1ccc(S(=O)(=O)c2cccc3cc[nH]c23)cc1] | 1-[4-(1H-indole-7-sulfonyl)phenyl]-3-(pyridin-3-ylmethyl)urea |
| 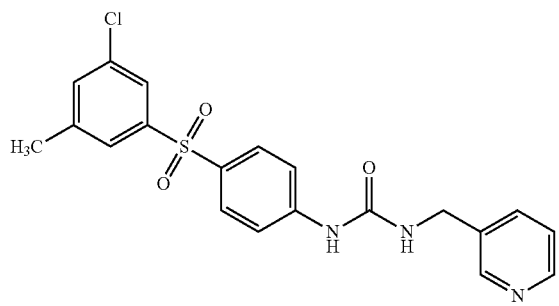 [SMILES: Cc1cc(Cl)cc(S(=O)(=O)c2ccc(NC(=O)NCc3cccnc3)cc2)c1] | 3-{4-[(3-chloro-5-methylbenzene)sulfonyl]phenyl}-1-(pyridin-3-ylmethyl)urea |
| 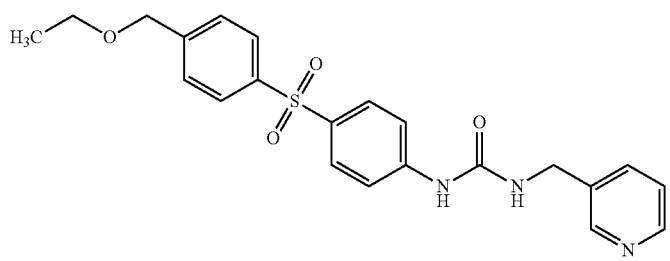 [SMILES: CCOCc1ccc(S(=O)(=O)c2ccc(NC(=O)NCc3cccnc3)cc2)cc1] | 3-(4-{[4-(ethoxymethyl)benzene]sulfonyl}phenyl)-1-(pyridin-3-ylmethyl)urea |
| 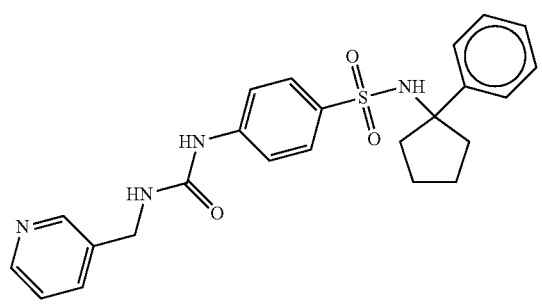 | 1-{4-[(1-phenylcyclopentyl)sulfamoyl]phenyl}-3-(pyridin-3-ylmethyl)urea |

-continued

| Structure | Chemical Name |
|---|---|
| 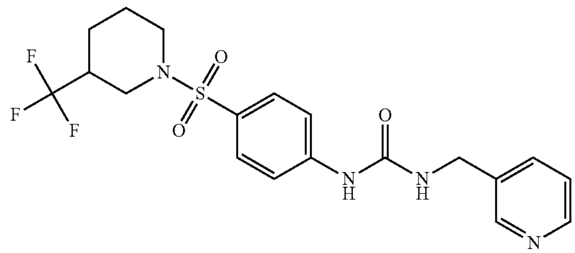 [SMILES: O=C(NCc1cccnc1)Nc1ccc(S(=O)(=O)N2CCCC(C(F)(F)F)C2)cc1] | 1-(pyridin-3-ylmethyl)-3-{4-[3-(trifluoromethyl)piperidine-1-sulfonyl]phenyl}urea |
| 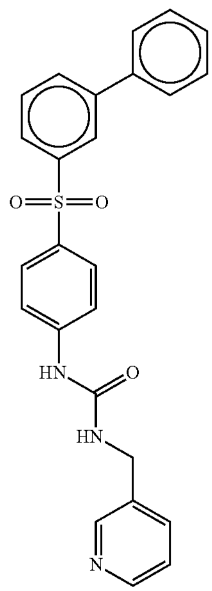 | 1-{4-[(3-phenylbenzene)sulfonyl]phenyl}-3-(pyridin-3-ylmethyl)urea |
| 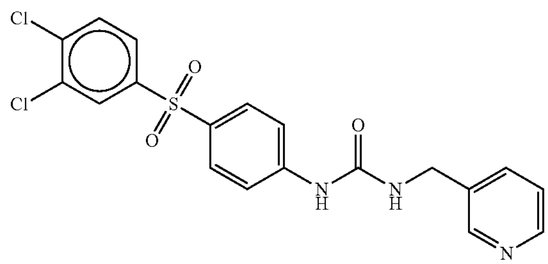 | 3-{4-[(3,4-dichlorobenzene)sulfonyl]phenyl}-1-(pyridin-3-ylmethyl)urea |
| 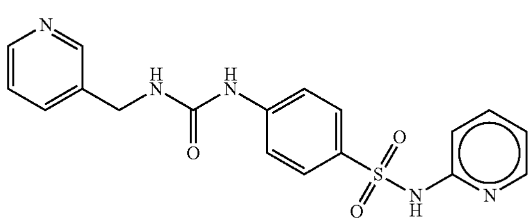 | 1-{4-[(pyridin-2-yl)sulfamoyl]phenyl}-3-(pyridin-3-ylmethyl)urea |
| 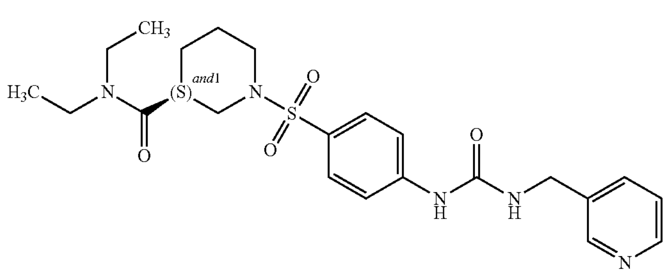 | (3S)-N,N-diethyl-[(4-{[(pyridin-3-ylmethyl)carbamoyl]amino}benzene)sulfonyl]piperidine-3-carboxamide |

-continued

| Structure | Chemical Name |
|---|---|
| 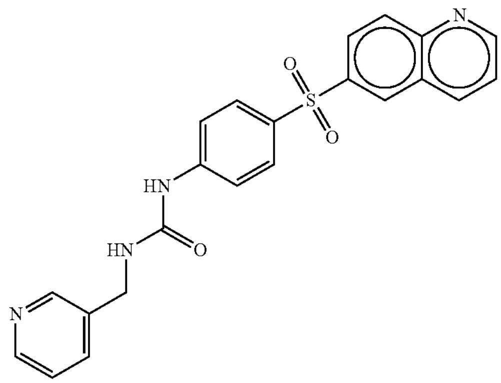 | 3-(pyridin-3-ylmethyl)-1-[4-(quinoline-6-sulfonyl)phenyl]urea |
| 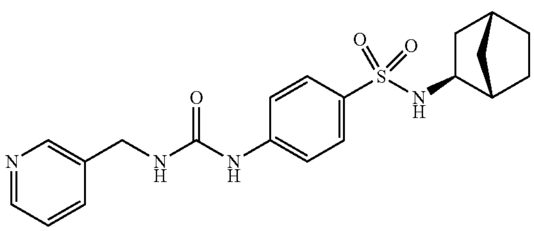 [SMILES: O=C(NCc1cccnc1)Nc1ccc(S(=O)(=O)N[C@H]2C[C@@H]3CC[C@H]2C3)cc1] | 1-(4-{[(1S,2S,4R)-bicyclo[2.2.1]heptan-2-yl]sulfamoyl}phenyl)-3-(pyridin-3-ylmethyl)urea |
| 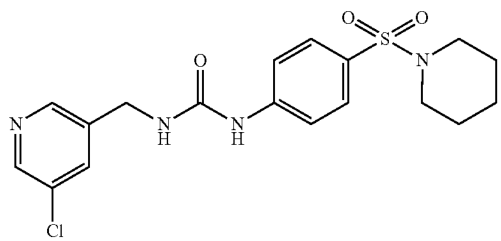 | 3-[(5-chloropyridin-3-yl)methyl]-1-[4-(piperidine-1-sulfonyl)phenyl]urea |
| 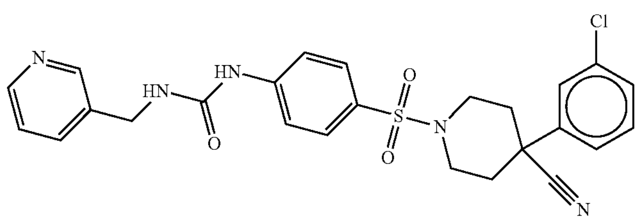 | 3-{4-[4-(3-chlorophenyl)-4-cyanopiperidine-1-sulfonyl]phenyl}-1-(pyridin-3-ylmethyl)urea |
| 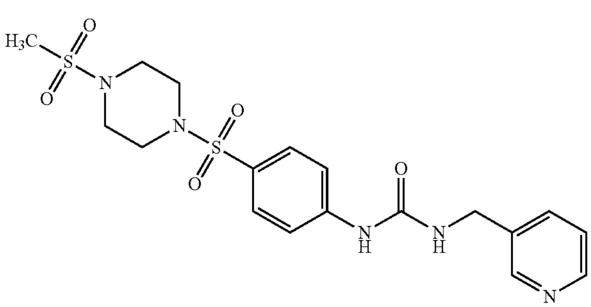 | 3-[4-(4-methanesulfonylpiperazine-1-sulfonyl)phenyl]-1-(pyridin-3-ylmethyl)urea |
| 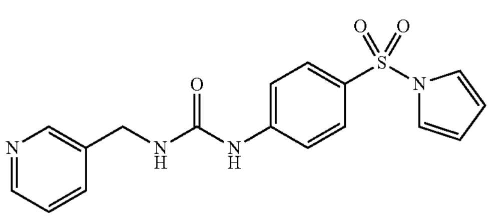 [SMILES: O=C(NCc1cccnc1)Nc1ccc(S(=O)(=O)n2cccc2)cc1] | 1-(pyridin-3-ylmethyl)-3-[4-(1H-pyrrole-1-sulfonyl)phenyl]urea |

| Structure | Chemical Name |
|---|---|
| 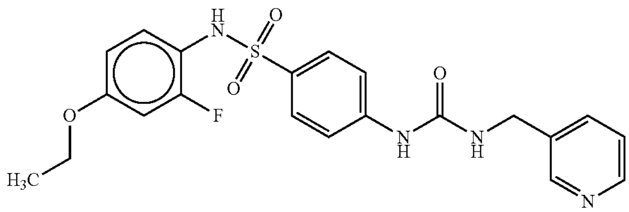 | 3-{4-[(4-ethoxy-2-fluorophenyl)sulfamoyl]phenyl}-1-(pyridin-3-ylmethyl)urea |
| 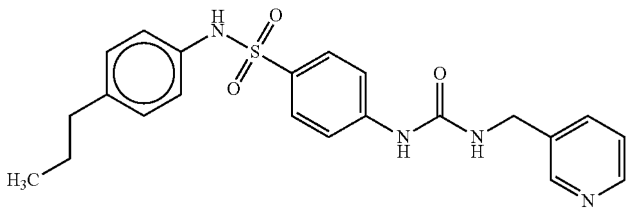 | 3-{4-[(4-propylphenyl)sulfamoyl]phenyl}-1-(pyridin-3-ylmethyl)urea |
| 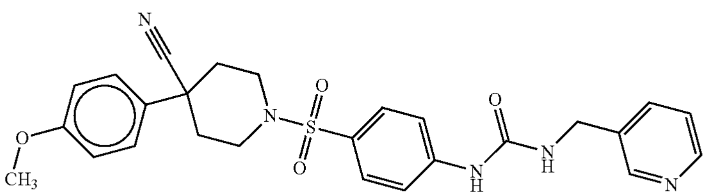 | 3-{4-[4-cyano-4-(4-methoxyphenyl)piperidine-1-sulfonyl]phenyl}-1-(pyridin-3-ylmethyl)urea |
| 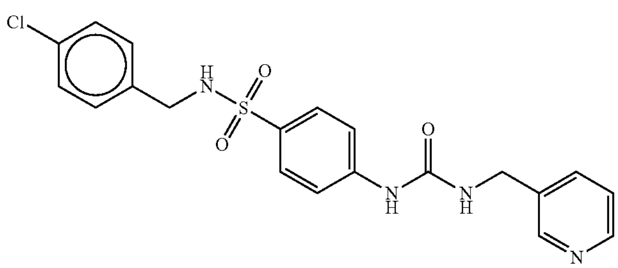 | 3-(4-{[(4-chlorophenyl)methyl]sulfamoyl}phenyl)-1-(pyridin-3-ylmethyl)urea |
| 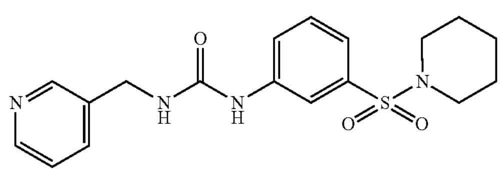 [SMILES: O=C(NCc1cccnc1)Nc1cccc(S(=O)(=O)N2CCCCC2)c1] | 1-[3-(piperidine-1-sulfonyl)phenyl]-3-(pyridin-3-ylmethyl)urea |
| 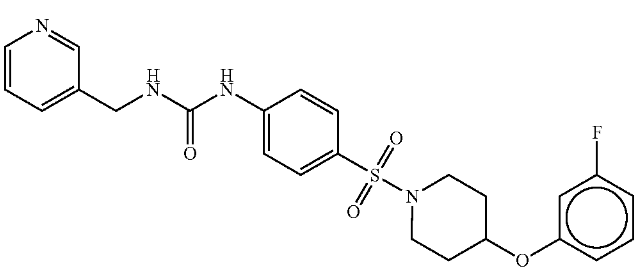 | 3-{4-[4-(3-fluorophenoxy)piperidine-1-sulfonyl]phenyl}-1-(pyridin-3-ylmethyl)urea |
| 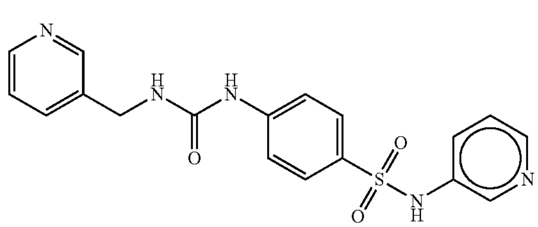 | 1-{4-[(pyridin-3-yl)sulfamoyl]phenyl}-3-(pyridin-3-ylmethyl)urea |

| Structure | Chemical Name |
|---|---|
| 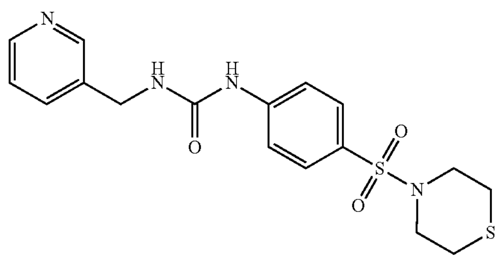 [SMILES: O=C(NCc1cccnc1)Nc1ccc(S(=O)(=O)N2CCSCC2)cc1] | 3-(pyridin-3-ylmethyl)-1-[4-(thiomorpholine-4-sulfonyl)phenyl]urea |
| 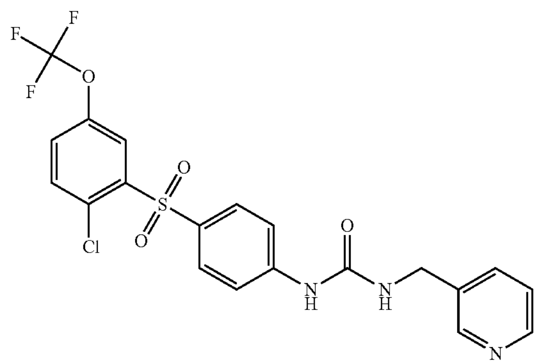 [SMILES: O=C(NCc1cccnc1)Nc1ccc(S(=O)(=O)c2cc(OC(F)(F)F)ccc2Cl)cc1] | 3-(4-{[2-chloro-5-(trifluoromethoxy)benzene]sulfonyl}phenyl)-1-(pyridin-3-ylmethyl)urea |
| 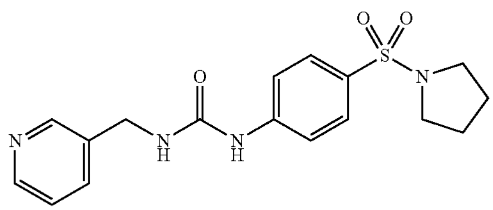 [SMILES: O=C(NCc1cccnc1)Nc1ccc(S(=O)(=O)N2CCCC2)cc1] | 3-(pyridin-3-ylmethyl)-1-[4-(pyrrolidine-1-sulfonyl)phenyl]urea |
| 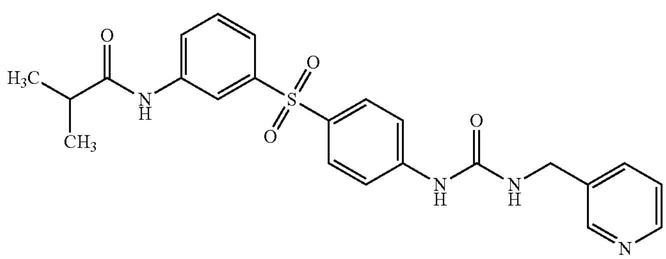 [SMILES: CC(C)C(=O)Nc1cccc(S(=O)(=O)c2ccc(NC(=O)NCc3cccnc3)cc2)c1] | 2-methyl-N-{3-[(4-{[(pyridin-3-ylmethyl)carbamoyl]amino}benzene)sulfonyl]phenyl}propanamide |
| 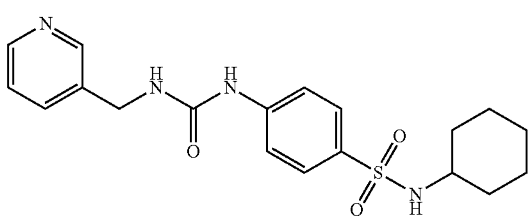 [SMILES: O=C(NCc1cccnc1)Nc1ccc(S(=O)(=O)NC2CCCCC2)cc1] | 1-[4-(cyclohexylsulfamoyl)phenyl]-3-(pyridin-3-ylmethyl)urea |
| 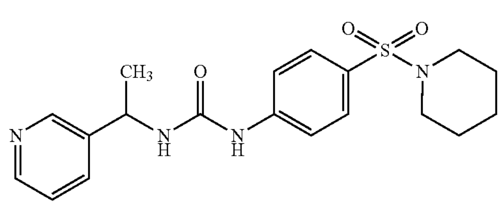 [SMILES: CC(NC(=O)Nc1ccc(S(=O)(=O)N2CCCCC2)cc1)c1cccnc1] | 3-[4-(piperidine-1-sulfonyl)phenyl]-1-[1-(pyridin-3-yl)ethyl]urea |

-continued

| Structure | Chemical Name |
|---|---|
| 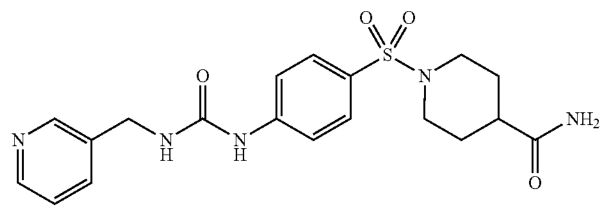 [SMILES: NC(=O)C1CCN(S(=O)(=O)c2ccc(NC(=O)NCc3cccnc3)cc2)CC1] | 1-[(4-{[(pyridin-3-ylmethyl)carbamoyl]amino}benzene)sulfonyl]piperidine-4-carboxamide |
| 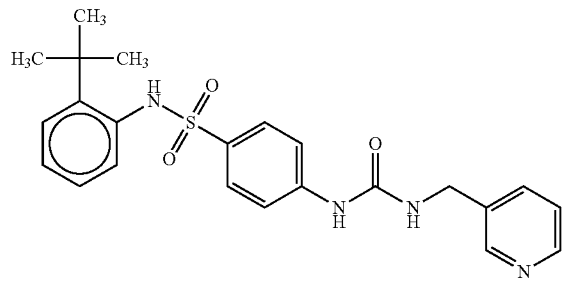 | 3-{4-[(2-tert-butylphenyl)sulfamoyl]phenyl}-1-(pyridin-3-ylmethyl)urea |
| 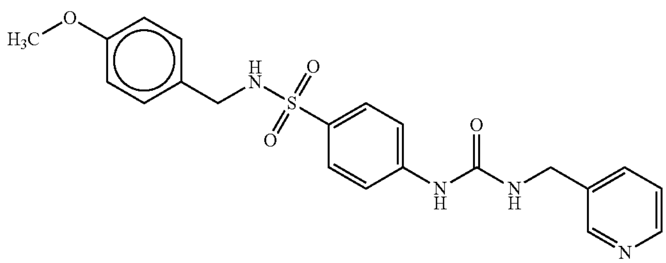 | 3-(4-{[(4-methoxyphenyl)methyl]sulfamoyl}phenyl)-1-(pyridin-3-ylmethyl)urea |
| 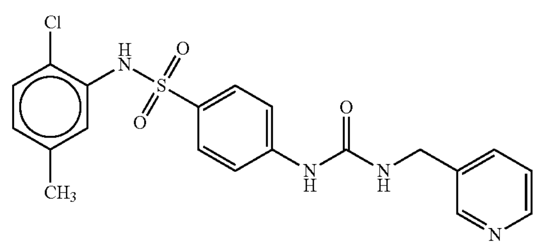 | 3-{4-[(2-chloro-5-methylphenyl)sulfamoyl]phenyl}-1-(pyridin-3-ylmethyl)urea |
| 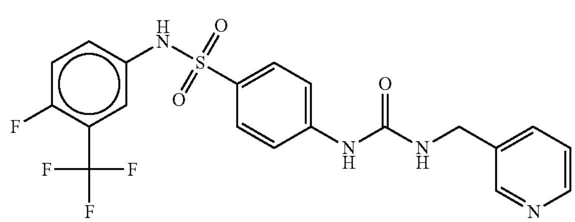 | 3-(4-{[4-fluoro-3-(trifluoromethyl)phenyl]sulfamoyl}phenyl)-1-(pyridin-3-ylmethyl)urea |
| 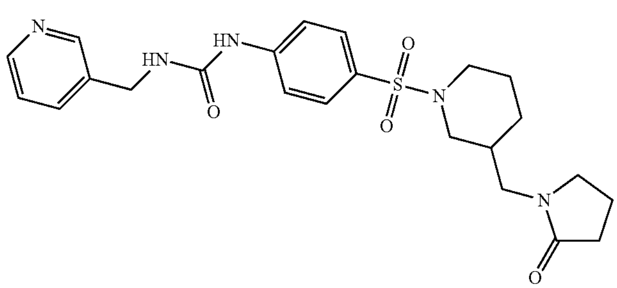 [SMILES: O=C(NCc1cccnc1)Nc1ccc(S(=O)(=O)N2CCCC(CN3CCCC3=O)C2)cc1] | 1-(4-{3-[(2-oxopyrrolidin-1-yl)methyl]piperidine-1-sulfonyl}phenyl)-3-(pyridin-3-ylmethyl)urea |

| Structure | Chemical Name |
|---|---|
| 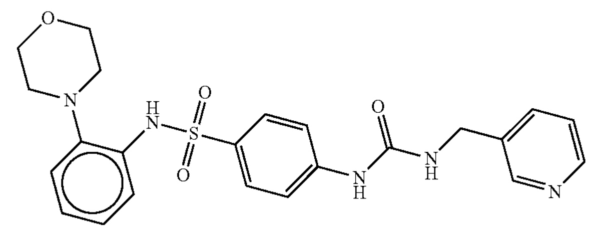 | 1-(4-{[2-(morpholin-4-yl)phenyl]sulfamoyl}phenyl)-3-(pyridin-3-ylmethyl)urea |
| 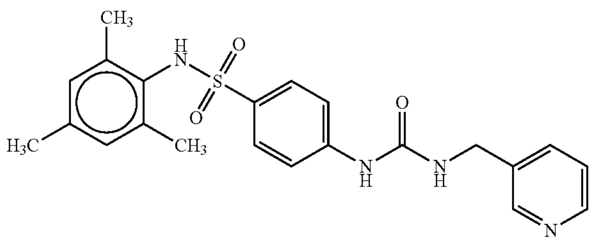 | 1-(pyridin-3-ylmethyl)-3-{4-[(2,4,6-trimethylphenyl)sulfamoyl]phenyl}urea |
| 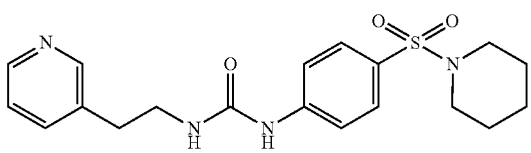 [SMILES: O=C(NCCc1cccnc1)Nc1ccc(S(=O)(=O)N2CCCCC2)cc1] | 3-[4-(piperidine-1-sulfonyl)phenyl]-1-[2-(pyridin-3-yl)ethyl]urea |
| 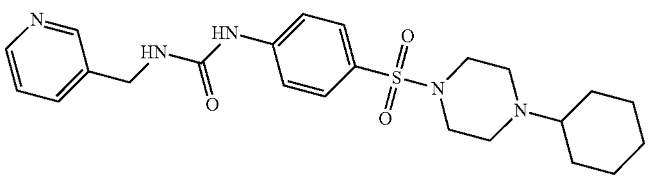 [SMILES: O=C(NCc1cccnc1)Nc1ccc(S(=O)(=O)N2CCN(C3CCCCC3)CC2)cc1] | 1-[4-(4-cyclohexylpiperazine-1-sulfonyl)phenyl]-3-(pyridin-3-ylmethyl)urea |
| 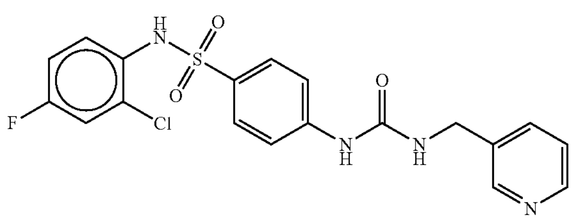 | 3-{4-[(2-chloro-4-fluorophenyl)sulfamoyl]phenyl}-1-(pyridin-3-ylmethyl)urea |
| 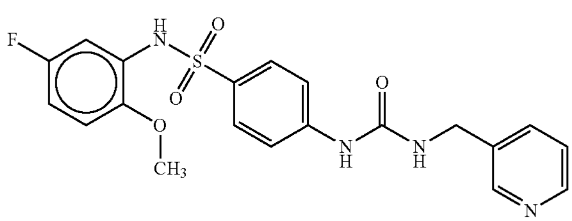 | 3-{4-[(5-fluoro-2-methoxyphenyl)sulfamoyl]phenyl}-1-(pyridin-3-ylmethyl)urea |
| 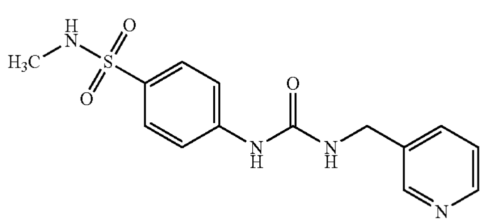 [SMILES: CNS(=O)(=O)c1ccc(NC(=O)NCc2cccnc2)cc1] | 3-[4-(methylsulfamoyl)phenyl]-1-(pyridin-3-ylmethyl)urea |

| Structure | Chemical Name |
|---|---|
| 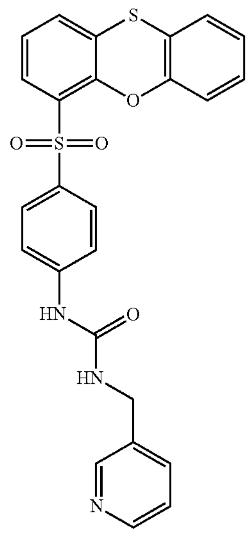 [SMILES: O=C(NCc1cccnc1)Nc1ccc(S(=O)(=O)c2cccc3c2Oc2ccccc2S3)cc1] | 1-[4-(phenoxathiine-4-sulfonyl)phenyl]-3-(pyridin-3-ylmethyl)urea |
| 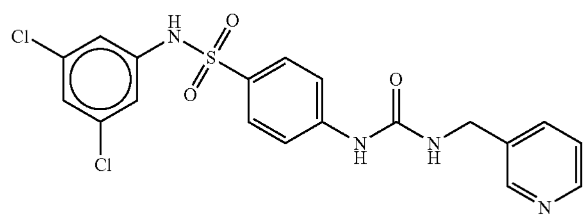 | 3-{4-[(3,5-dichlorophenyl)sulfamoyl]phenyl}-1-(pyridin-3-ylmethyl)urea |
| 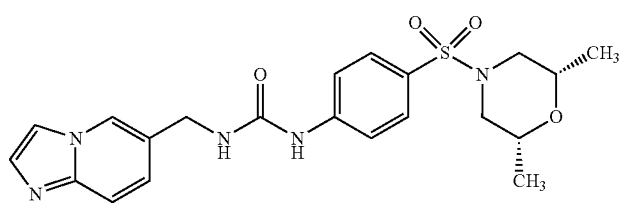 [SMILES: C[C@@H]1CN(S(=O)(=O)c2ccc(NC(=O)NCc3ccc4nccn4c3)cc2)C[C@H](C)O1] | 1-{4-[(2R,6S)-2,6-dimethylmorpholine-4-sulfonyl]phenyl}-3-{imidazo[1,2-a]pyridin-6-ylmethyl}urea |
| 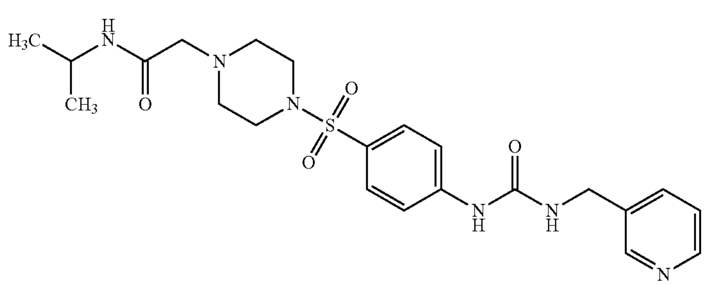 [SMILES: CC(C)NC(=O)CN1CCN(S(=O)(=O)c2ccc(NC(=O)NCc3cccnc3)cc2)CC1] | N-(propan-2-yl)-2-{4-[(4-{[(pyridin-3-ylmethyl)carbamoyl]amino}benzene)sulfonyl]piperazin-1-yl}acetamide |
| 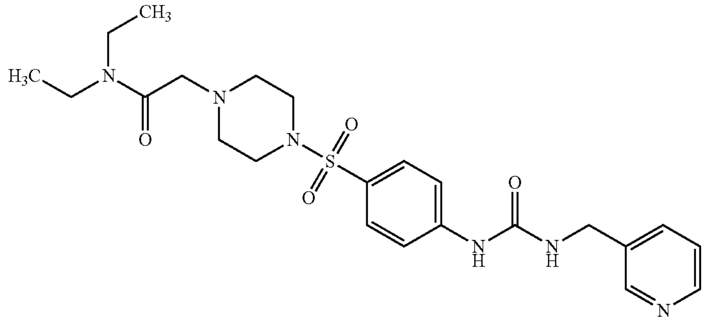 [SMILES: CCN(CC)C(=O)CN1CCN(S(=O)(=O)c2ccc(NC(=O)NCc3cccnc3)cc2)CC1] | N,N-diethyl-2-{4-[(4-{[(pyridin-3-ylmethyl)carbamoyl]amino}benzene)sulfonyl]piperazin-1-yl}acetamide |

-continued

| Structure | Chemical Name |
|---|---|
| 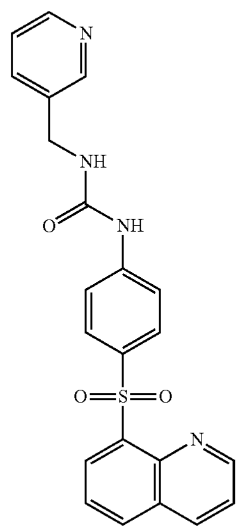 [SMILES: O=C(NCc1cccnc1)Nc1ccc(S(=O)(=O)c2cccc3cccnc23)cc1] | 3-(pyridin-3-ylmethyl)-1-[4-(quinoline-8-sulfonyl)phenyl]urea |
| 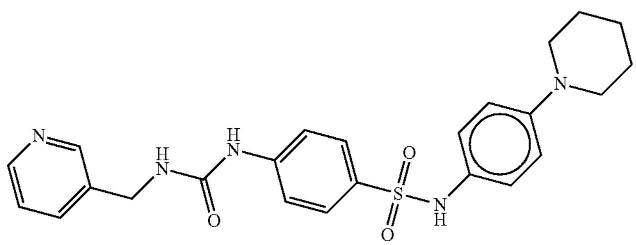 | 1-(4-{[4-(piperidin-1-yl)phenyl]sulfamoyl}phenyl)-3-(pyridin-3-ylmethyl)urea |
| 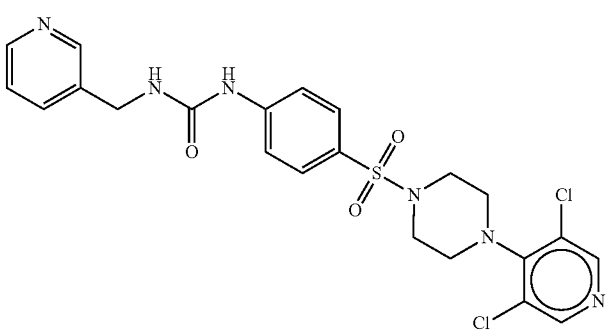 | 3-{4-[4-(3,5-dichloropyridin-4-yl)piperazine-1-sulfonyl]phenyl}-1-(pyridin-3-ylmethyl)urea |
| 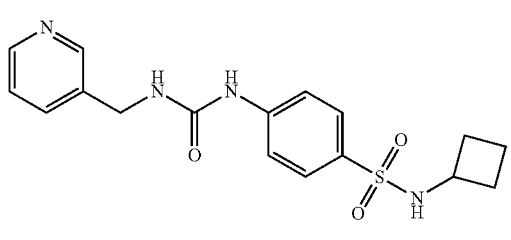 [SMILES: O=C(NCc1cccnc1)Nc1ccc(S(=O)(=O)NC2CCC2)cc1] | 1-[4-(cyclobutylsulfamoyl)phenyl]-3-(pyridin-3-ylmethyl)urea |
| 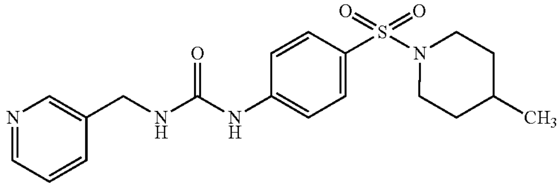 [SMILES: CC1CCN(S(=O)(=O)c2ccc(NC(=O)NCc3cccnc3)cc2)CC1] | 3-[4-(4-methylpiperidine-1-sulfonyl)phenyl]-1-(pyridin-3-ylmethyl)urea |

-continued

| Structure | Chemical Name |
|---|---|
| 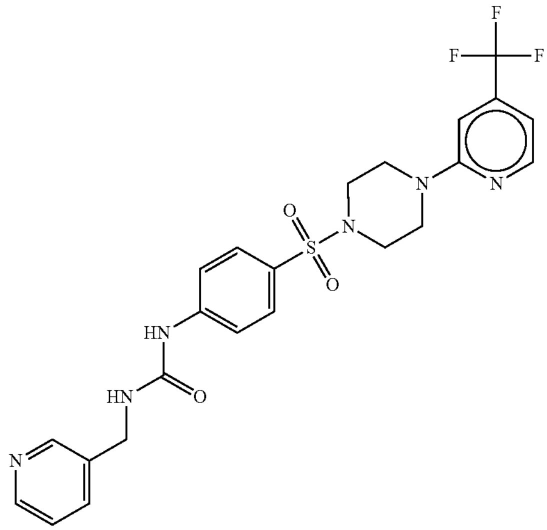 | 1-(pyridin-3-ylmethyl)-3-(4-{4-[4-(trifluoromethyl)pyridin-2-yl]piperazine-1-sulfonyl}phenyl)urea |
| 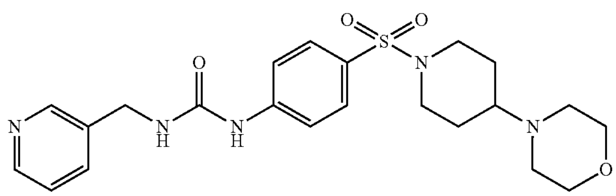 [SMILES: O=C(NCc1cccnc1)Nc1ccc(S(=O)(=O)N2CCC(N3CCOCC3)CC2)cc1] | 1-{4-[4-(morpholin-4-yl)piperidine-1-sulfonyl]phenyl}-3-(pyridin-3-ylmethyl)urea |
| 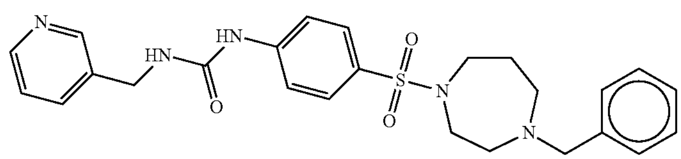 | 1-[4-(4-benzyl-1,4-diazepane-1-sulfonyl)phenyl]-3-(pyridin-3-ylmethyl)urea |
| 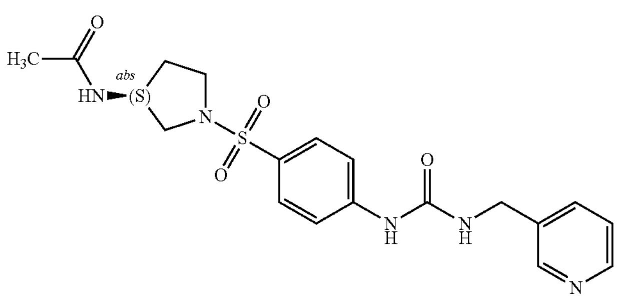 | N-[(3S)-1-[(4-{[(pyridin-3-ylmethyl)carbamoyl]amino}benzene)sulfonyl]pyrrolidin-3-yl]acetamide |
| 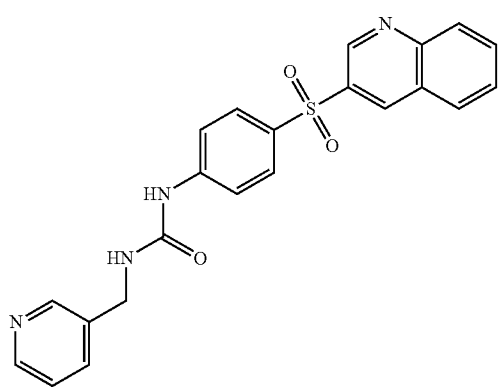 [SMILES: O=C(NCc1cccnc1)Nc1ccc(S(=O)(=O)c2cnc3ccccc3c2)cc1] | 3-(pyridin-3-ylmethyl)-1-[4-(quinoline-3-sulfonyl)phenyl]urea |

-continued

| Structure | Chemical Name |
|---|---|
| 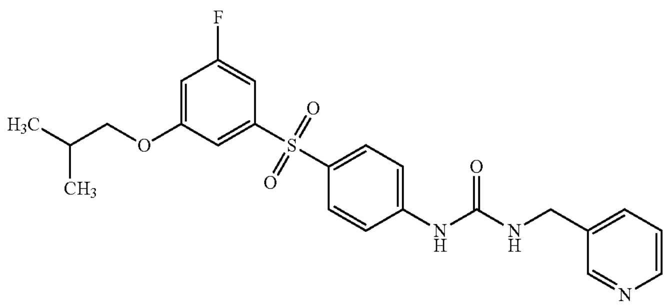 [SMILES: CC(C)COc1cc(F)cc(S(=O)(=O)c2ccc(NC(=O)NCc3cccnc3)cc2)c1] | 3-(4-{[3-fluoro-5-(2-methylpropoxy)benzene]sulfonyl}phenyl)-1-(pyridin-3-ylmethyl)urea |
| 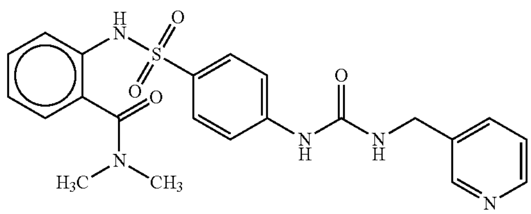 | N,N-dimethyl-2-[(4-{[(pyridin-3-ylmethyl)carbamoyl]amino}benzene)sulfonamido]benzamide |
| 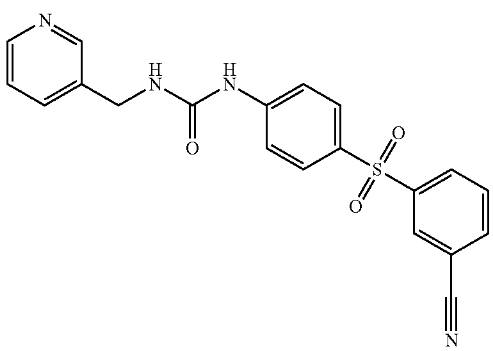 [SMILES: N#Cc1cccc(S(=O)(=O)c2ccc(NC(=O)NCc3cccnc3)cc2)c1] | 1-{4-[(3-cyanobenzene)sulfonyl]phenyl}-3-(pyridin-3-ylmethyl)urea |
| 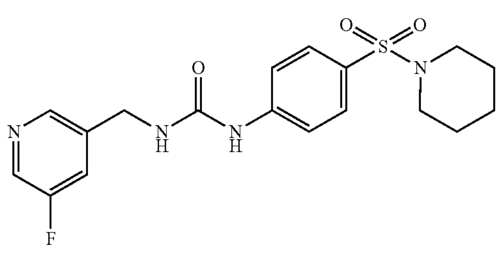 [SMILES: O=C(NCc1cncc(F)c1)Nc1ccc(S(=O)(=O)N2CCCCC2)cc1] | 3-[(5-fluoropyridin-3-yl)methyl]-1-[4-(piperidine-1-sulfonyl)phenyl]urea |
| 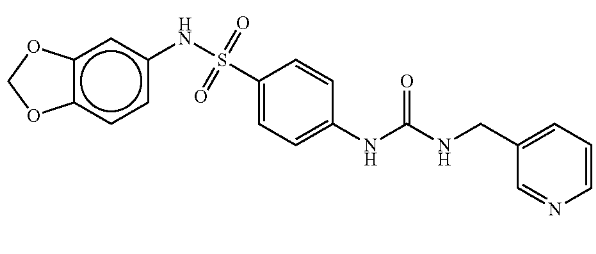 | 1-{4-[(2H-1,3-benzodioxol-5-yl)sulfamoyl]phenyl}-3-(pyridin-3-ylmethyl)urea |

| Structure | Chemical Name |
|---|---|
| 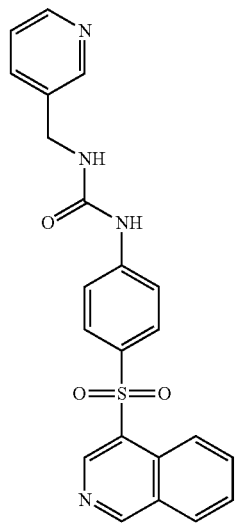 [SMILES: O=C(NCc1cccnc1)Nc1ccc(S(=O)(=O)c2cncc3ccccc23)cc1] | 1-[4-(isoquinoline-4-sulfonyl)phenyl]-3-(pyridin-3-ylmethyl)urea |
| 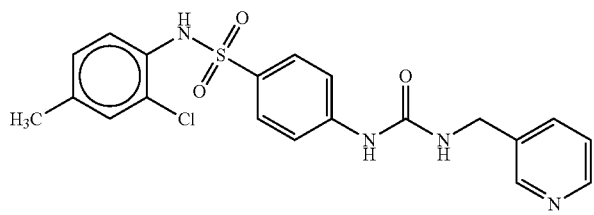 | 3-{4-[(2-chloro-4-methylphenyl)sulfamoyl]phenyl}-1-(pyridin-3-ylmethyl)urea |
| 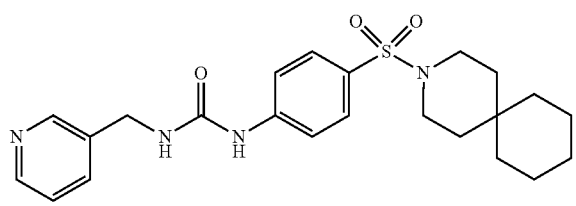 [SMILES: O=C(NCc1cccnc1)Nc1ccc(S(=O)(=O)N2CCC3(CCCCC3)CC2)cc1] | 1-(4-{3-azaspiro[5.5]undecane-3-sulfonyl}phenyl)-3-(pyridin-3-ylmethyl)urea |
| 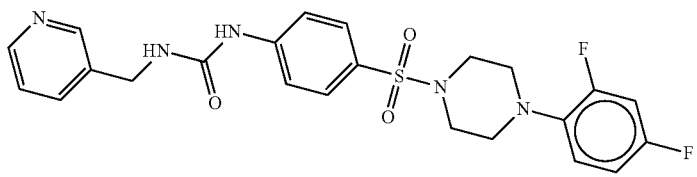 | 3-{4-[4-(2,4-difluorophenyl)piperazine-1-sulfonyl]phenyl}-1-(pyridin-3-ylmethyl)urea |
| 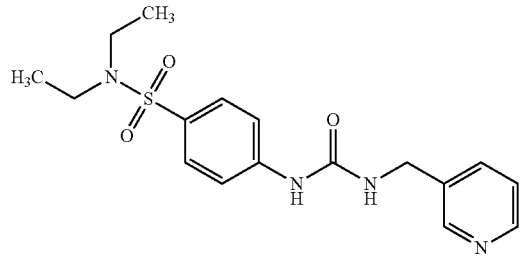 [SMILES: CCN(CC)S(=O)(=O)c1ccc(NC(=O)NCc2cccnc2)cc1] | 3-[4-(diethylsulfamoyl)phenyl]-1-(pyridin-3-ylmethyl)urea |

-continued

| Structure | Chemical Name |
|---|---|
| 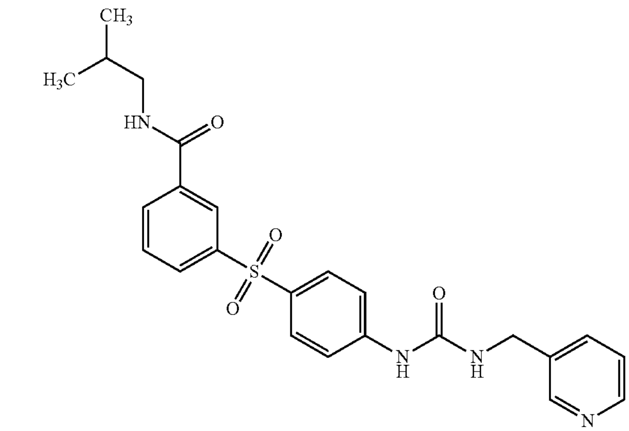 [SMILES: CC(C)CNC(=O)c1cccc(S(=O)(=O)c2ccc(NC(=O)NCc3cccnc3)cc2)c1] | N-(2-methylpropyl)-3-[(4-{[(pyridin-3-ylmethyl)carbamoyl]amino}benzene)sulfonyl]benzamide |
| 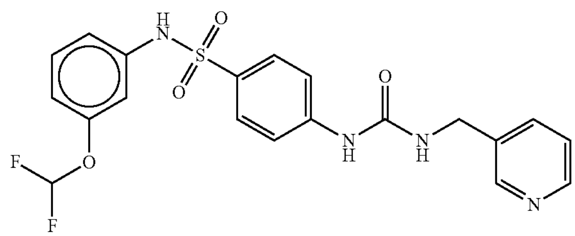 | 3-(4-{[3-(difluoromethoxy)phenyl]sulfamoyl}phenyl)-1-(pyridin-3-ylmethyl)urea |
| 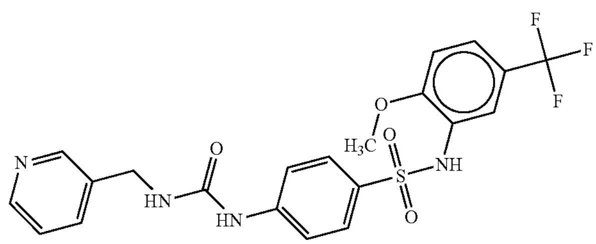 | 3-(4-{[2-methoxy-5-(trifluoromethyl)phenyl]sulfamoyl}phenyl)-1-(pyridin-3-ylmethyl)urea |
| 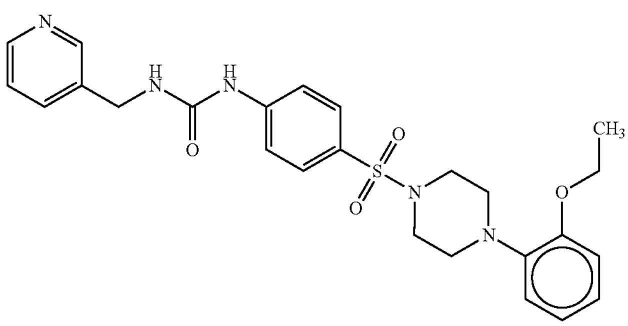 | 3-{4-[4-(2-ethoxyphenyl)piperazine-1-sulfonyl]phenyl}-1-(pyridin-3-ylmethyl)urea |
| 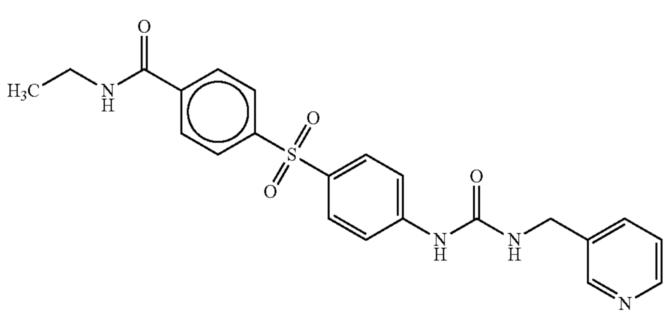 | N-ethyl-4-[(4-{[(pyridin-3-ylmethyl)carbamoyl]amino}benzene)sulfonyl]benzamide |

-continued

| Structure | Chemical Name |
|---|---|
| 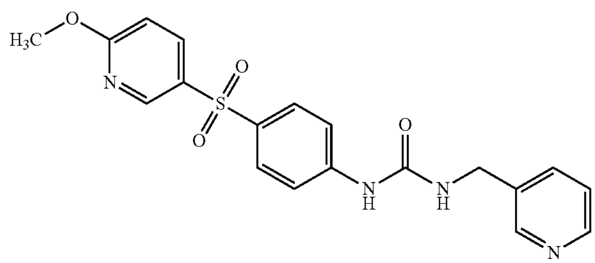 [SMILES: COc1ccc(S(=O)(=O)c2ccc(NC(=O)NCc3cccnc3)cc2)cn1] | 3-[4-(6-methoxypyridine-3-sulfonyl)phenyl]-1-(pyridin-3-ylmethyl)urea |
| 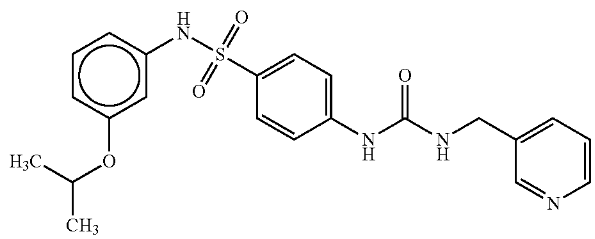 | 3-(4-{[3-(propan-2-yloxy)phenyl]sulfamoyl}phenyl)-1-(pyridin-3-ylmethyl)urea |
| 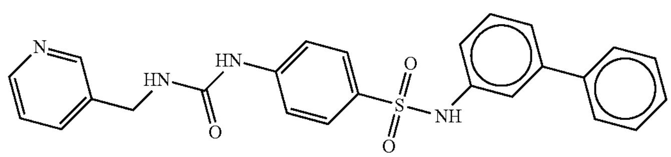 | 1-{4-[(3-phenylphenyl)sulfamoyl]phenyl}-3-(pyridin-3-ylmethyl)urea |
| 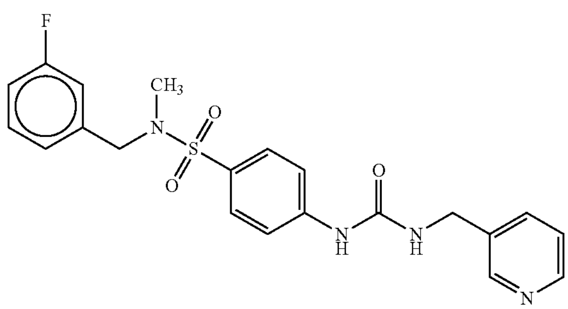 | 3-(4-{[(3-fluorophenyl)methyl](methyl)sulfamoyl}phenyl)-1-(pyridin-3-ylmethyl)urea |
| 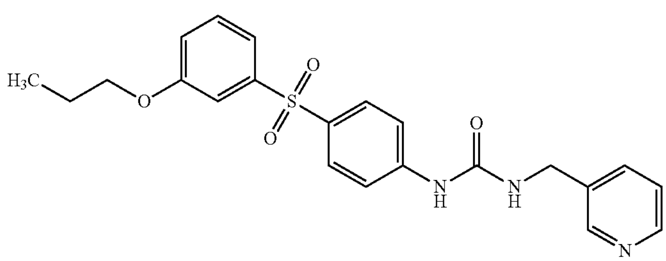 [SMILES: CCCOc1cccc(S(=O)(=O)c2ccc(NC(=O)NCc3cccnc3)cc2)c1] | 3-{4-[(3-propoxybenzene)sulfonyl]phenyl}-1-(pyridin-3-ylmethyl)urea |
| 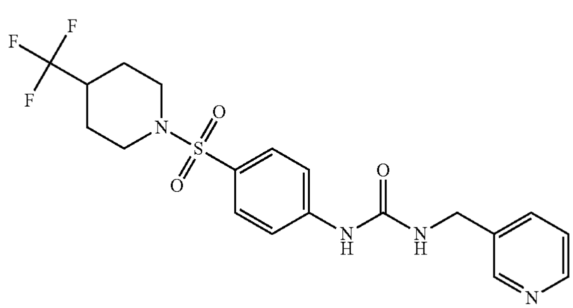 [SMILES: O=C(NCc1cccnc1)Nc1ccc(S(=O)(=O)N2CCC(C(F)(F)F)CC2)cc1] | 1-(pyridin-3-ylmethyl)-3-{4-[4-(trifluoromethyl)piperidine-1-sulfonyl]phenyl}urea |

-continued

| Structure | Chemical Name |
|---|---|
| 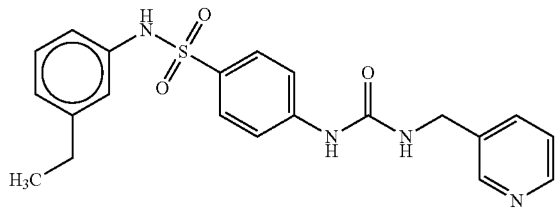 | 3-{4-[(3-ethylphenyl)sulfamoyl]phenyl}-1-(pyridin-3-ylmethyl)urea |
| 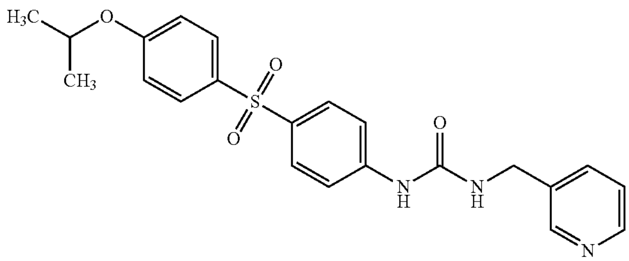 [SMILES: CC(C)Oc1ccc(S(=O)(=O)c2ccc(NC(=O)NCc3cccnc3)cc2)cc1] | 3-(4-{[4-(propan-2-yloxy)benzene]sulfonyl}phenyl)-1-(pyridin-3-ylmethyl)urea |
| 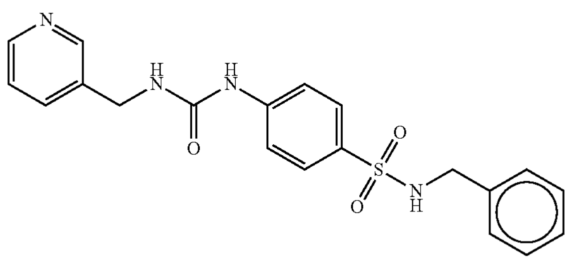 | 1-[4-(benzylsulfamoyl)phenyl]-3-(pyridin-3-ylmethyl)urea |
| 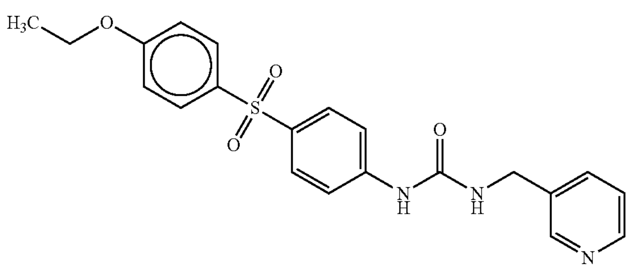 | 3-{4-[(4-ethoxybenzene)sulfonyl]phenyl}-1-(pyridin-3-ylmethyl)urea |
| 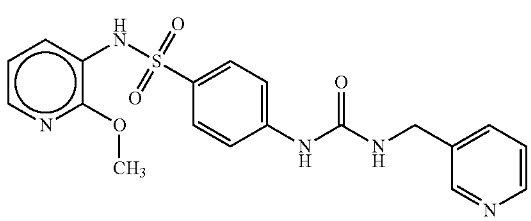 | 3-{4-[(2-methoxypyridin-3-yl)sulfamoyl]phenyl}-1-(pyridin-3-ylmethyl)urea |
| 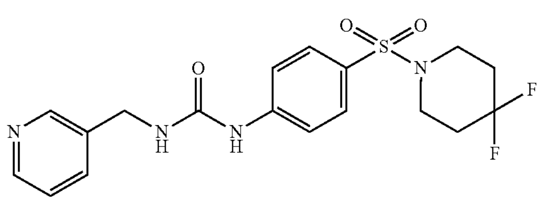 [SMILES: O=C(NCc1cccnc1)Nc1ccc(S(=O)(=O)N2CCC(F)(F)CC2)cc1] | 1-[4-(4,4-difluoropiperidine-1-sulfonyl)phenyl]-3-(pyridin-3-ylmethyl)urea |

-continued
| Structure | Chemical Name |
|---|---|
| 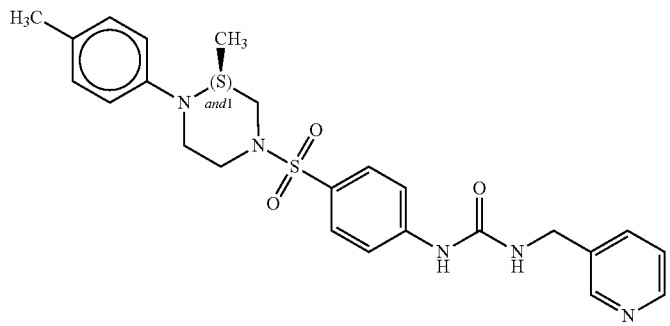 | 3-{4-[(3S)-3-methyl-4-(4-methylphenyl)piperazine-1-sulfonyl]phenyl}-1-(pyridin-3-ylmethyl)urea |
| 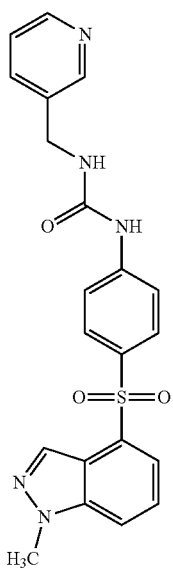 [SMILES: Cn1ncc2c(S(=O)(=O)c3ccc(NC(=O)NCc4cccnc4)cc3)cccc21] | 3-[4-(1-methyl-1H-indazole-4-sulfonyl)phenyl]-1-(pyridin-3-ylmethyl)urea |
| 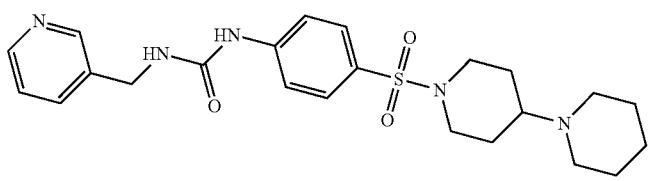 [SMILES: O=C(NCc1cccnc1)Nc1ccc(S(=O)(=O)N2CCC(N3CCCCC3)CC2)cc1] | 1-{4-[4-(piperidin-1-yl)piperidine-1-sulfonyl]phenyl}-3-(pyridin-3-ylmethyl)urea |
| 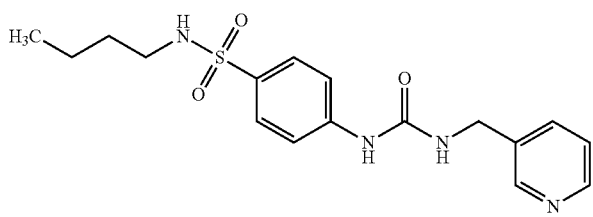 [SMILES: CCCCNS(=O)(=O)c1ccc(NC(=O)NCc2cccnc2)cc1] | 3-[4-(butylsulfamoyl)phenyl]-1-(pyridin-3-ylmethyl)urea |
| 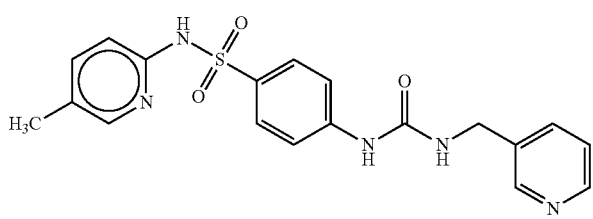 | 3-{4-[(5-methylpyridin-2-yl)sulfamoyl]phenyl}-1-(pyridin-3-ylmethyl)urea |

| Structure | Chemical Name |
|---|---|
| 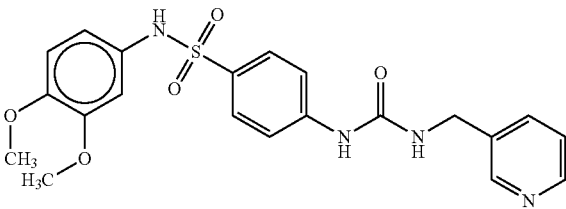 | 3-{4-[(3,4-dimethoxyphenyl)sulfamoyl]phenyl}-1-(pyridin-3-ylmethyl)urea |
| 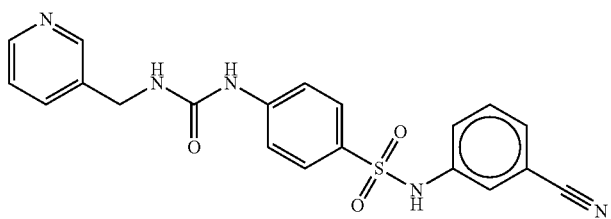 | 1-{4-[(3-cyanophenyl)sulfamoyl]phenyl}-3-(pyridin-3-ylmethyl)urea |
| 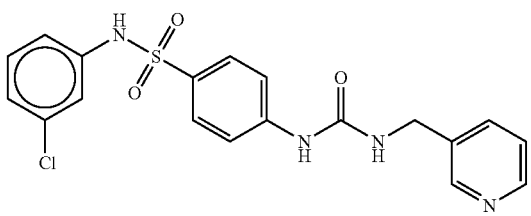 | 3-{4-[(3-chlorophenyl)sulfamoyl]phenyl}-1-(pyridin-3-ylmethyl)urea |
| 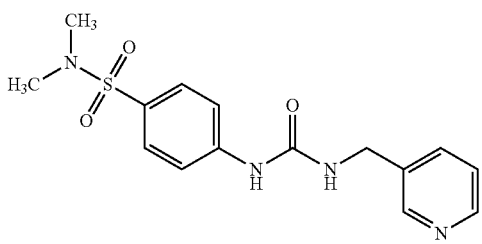 [SMILES: CN(C)S(=O)(=O)c1ccc(NC(=O)NCc2cccnc2)cc1] | 3-[4-(dimethylsulfamoyl)phenyl]-1-(pyridin-3-ylmethyl)urea |
| 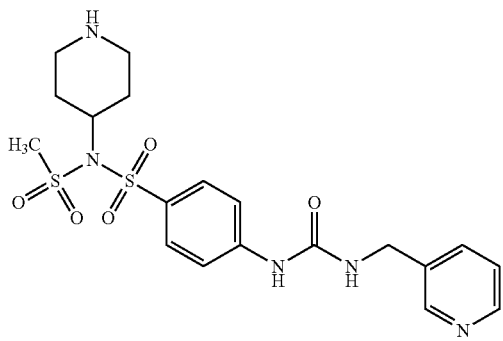 [SMILES: CS(=O)(=O)N(C1CCNCC1)S(=O)(=O)c1ccc(NC(=O)NCc2cccnc2)cc1] | 3-{4-[methanesulfonyl(piperidin-4-yl)sulfamoyl]phenyl}-1-(pyridin-3-ylmethyl)urea |

| Structure | Chemical Name |
|---|---|
| 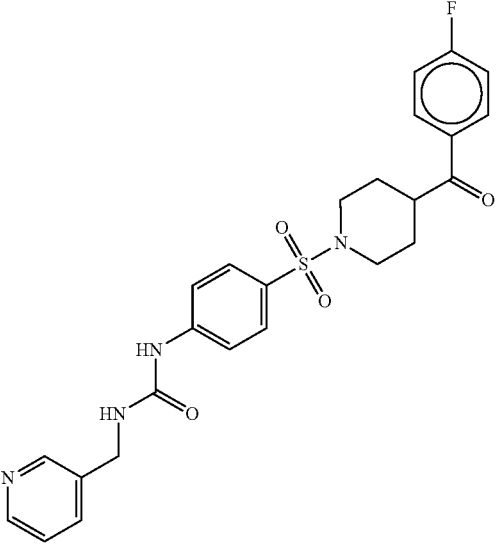 | 3-(4-{4-[(4-fluorophenyl)carbonyl]piperidine-1-sulfonyl}phenyl)-1-(pyridin-3-ylmethyl)urea |
| 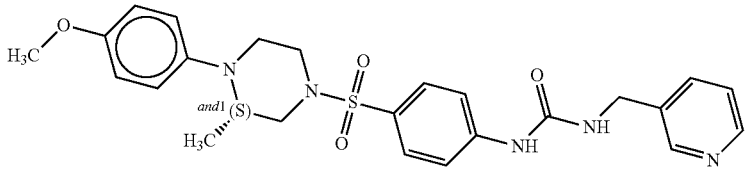 | 3-{4-[(3S)-4-(4-methoxyphenyl)-3-methylpiperazine-1-sulfonyl]phenyl}-1-(pyridin-3-ylmethyl)urea |
| 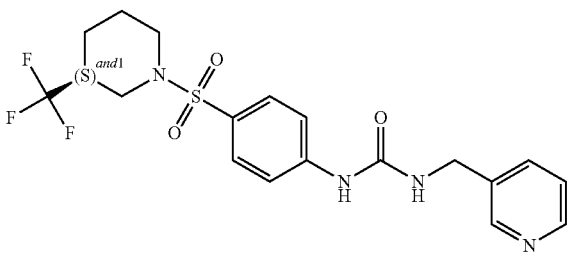 | 1-(pyridin-3-ylmethyl)-3-{4-[(3S)-3-(trifluoromethyl)piperidine-1-sulfonyl]phenyl}urea |
| 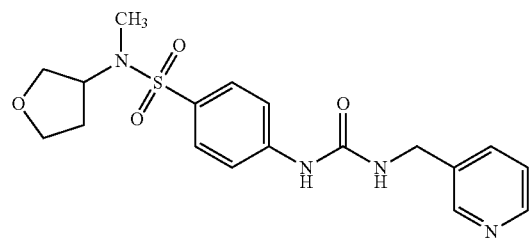 [SMILES: CN(C1CCOC1)S(=O)(=O)c1ccc(NC(=O)NCc2cccnc2)cc1] | 3-{4-[methyl(oxolan-3-yl)sulfamoyl]phenyl}-1-(pyridin-3-ylmethyl)urea |

-continued

| Structure | Chemical Name |
|---|---|
| 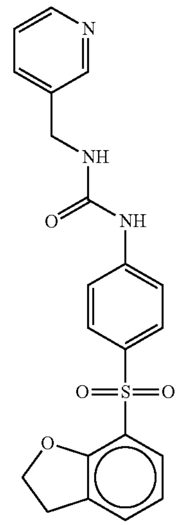 | 1-[4-(2,3-dihydro-1-benzofuran-7-sulfonyl)phenyl]-3-(pyridin-3-ylmethyl)urea |
| 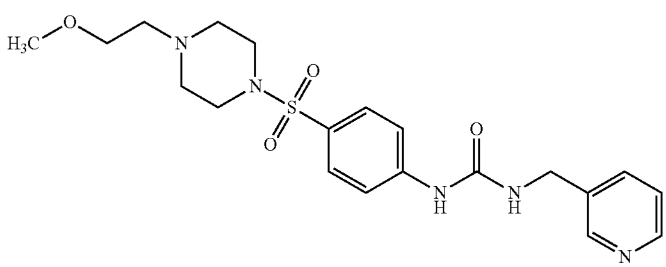 [SMILES: COCCN1CCN(S(=O)(=O)c2ccc(NC(=O)NCc3cccnc3)cc2)CC1] | 3-{4-[4-(2-methoxyethyl)piperazine-1-sulfonyl]phenyl}-1-(pyridin-3-ylmethyl)urea |
| 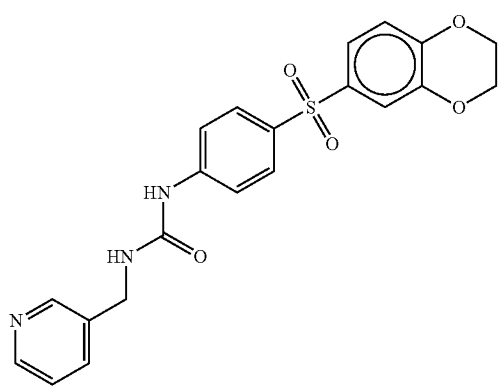 | 1-[4-(2,3-dihydro-1,4-benzodioxine-6-sulfonyl)phenyl]-3-(pyridin-3-ylmethyl)urea |
| 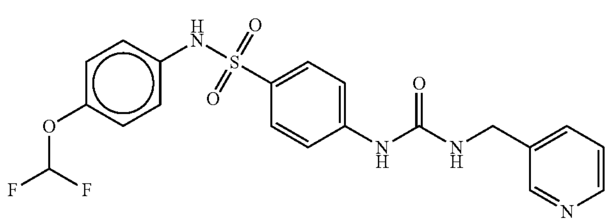 | 3-(4-{[4-(difluoromethoxy)phenyl]sulfamoyl}phenyl)-1-(pyridin-3-ylmethyl)urea |
| 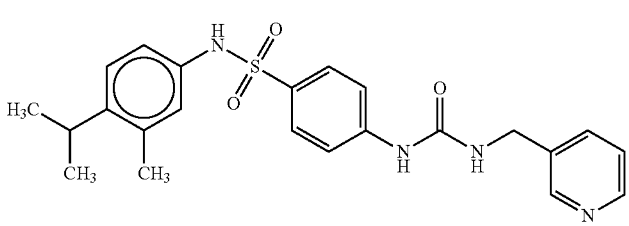 | 3-(4-{[3-methyl-4-(propan-2-yl)phenyl]sulfamoyl}phenyl)-1-(pyridin-3-ylmethyl)urea |

-continued

| Structure | Chemical Name |
|---|---|
| 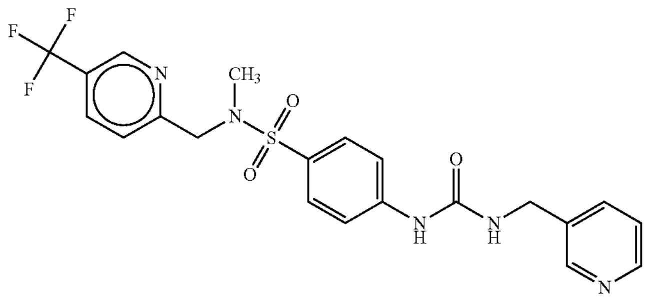 | 3-{4-[methyl({[5-(trifluoromethyl)pyridin-2-yl]methyl})sulfamoyl]phenyl}-1-(pyridin-3-ylmethyl)urea |
| 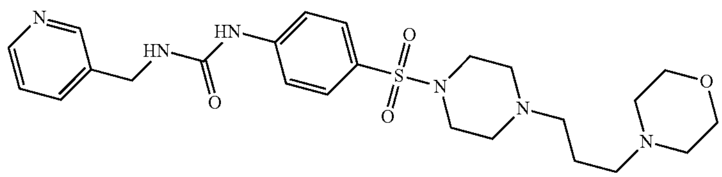 [SMILES: O=C(NCc1cccnc1)Nc1ccc(S(=O)(=O)N2CCN(CCCN3CCOCC3)CC2)cc1] | 1-(4-{4-[3-(morpholin-4-yl)propyl]piperazine-1-sulfonyl}phenyl)-3-(pyridin-3-ylmethyl)urea |
| 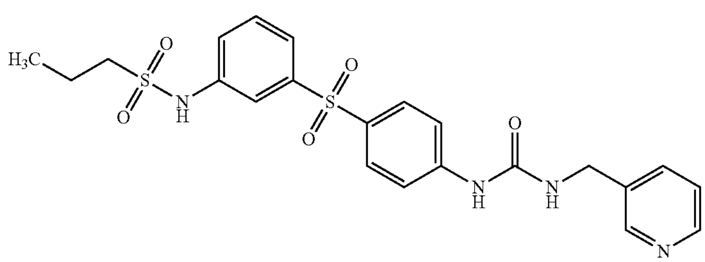 [SMILES: CCCS(=O)(=O)Nc1cccc(S(=O)(=O)c2ccc(NC(=O)NCc3cccnc3)cc2)c1] | 3-(4-{[3-(propane-1-sulfonamido)benzene]sulfonyl}phenyl)-1-(pyridin-3-ylmethyl)urea |
| 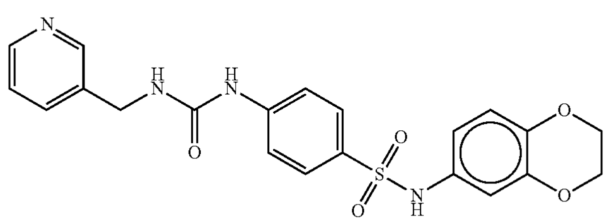 | 1-{4-[(2,3-dihydro-1,4-benzodioxin-6-yl)sulfamoyl]phenyl}-3-(pyridin-3-ylmethyl)urea |
| 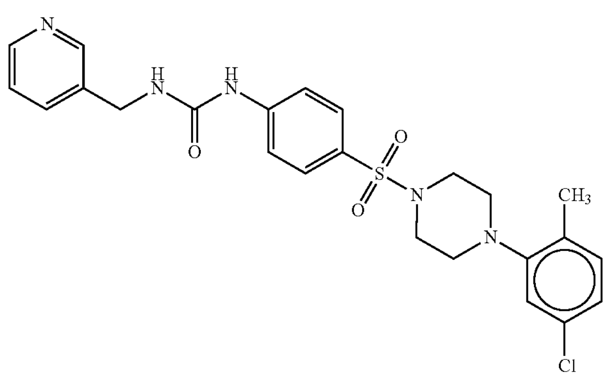 | 3-{4-[4-(5-chloro-2-methylphenyl)piperazine-1-sulfonyl]phenyl}-1-(pyridin-3-ylmethyl)urea |
| 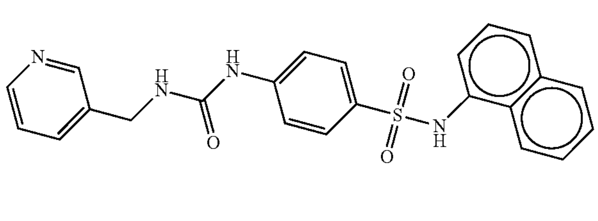 | 1-{4-[(naphthalen-1-yl)sulfamoyl]phenyl}-3-(pyridin-3-ylmethyl)urea |

| Structure | Chemical Name |
|---|---|
| 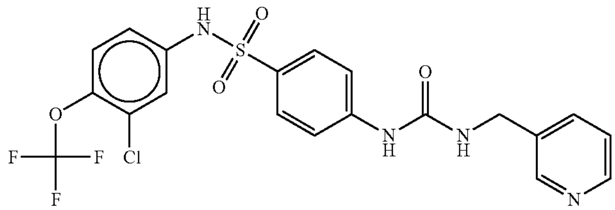 | 3-(4-{[3-chloro-4-(trifluoromethoxy)phenyl]sulfamoyl}phenyl)-1-(pyridin-3-ylmethyl)urea |
| 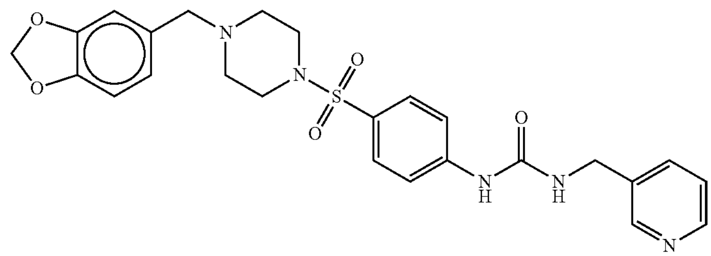 | 1-{4-[4-(2H-1,3-benzodioxol-5-ylmethyl)piperazine-1-sulfonyl]phenyl}-3-(pyridin-3-ylmethyl)urea |
| 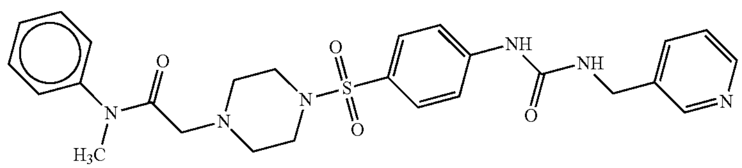 | N-methyl-N-phenyl-2-{4-[(4-{[(pyridin-3-ylmethyl)carbamoyl]amino}benzene)sulfonyl]piperazin-1-yl}acetamide |
| 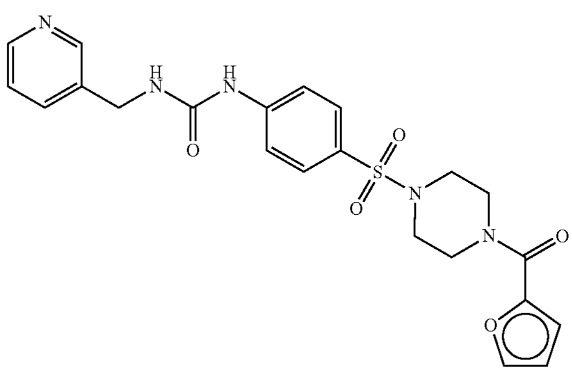 | 1-(4-{4-[(furan-2-yl)carbonyl]piperazine-1-sulfonyl}phenyl)-3-(pyridin-3-ylmethyl)urea |
| 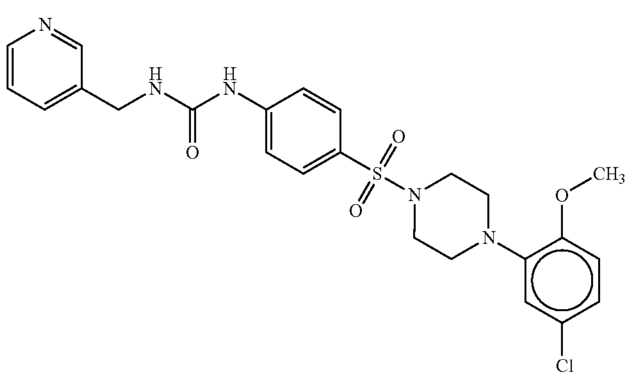 | 3-{4-[4-(5-chloro-2-methoxyphenyl)piperazine-1-sulfonyl]phenyl}-1-(pyridin-3-ylmethyl)urea |

| Structure | Chemical Name |
|---|---|
| 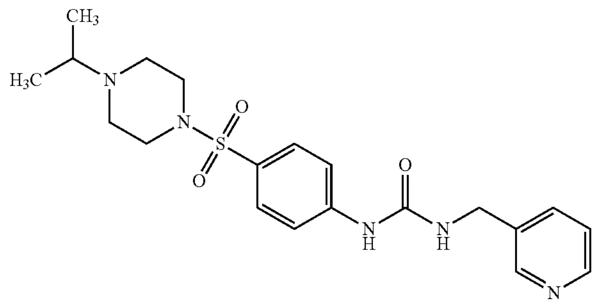 [SMILES: CC(C)N1CCN(S(=O)(=O)c2ccc(NC(=O)NCc3cccnc3)cc2)CC1] | 3-{4-[4-(propan-2-yl)piperazine-1-sulfonyl]phenyl}-1-(pyridin-3-ylmethyl)urea |
| 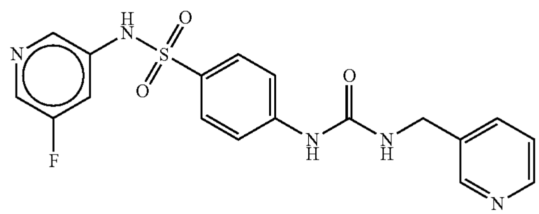 | 3-{4-[(5-fluoropyridin-3-yl)sulfamoyl]phenyl}-1-(pyridin-3-ylmethyl)urea |
| 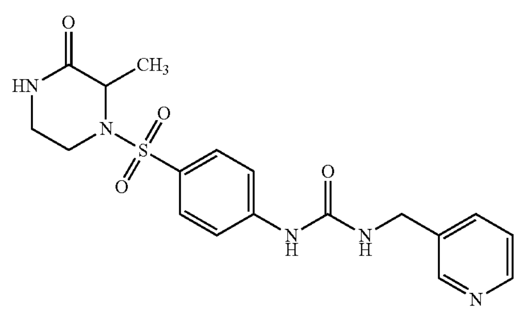 [SMILES: CC1C(=O)NCCN1S(=O)(=O)c1ccc(NC(=O)NCc2cccnc2)cc1] | 3-[4-(2-methyl-3-oxopiperazine-1-sulfonyl)phenyl]-1-(pyridin-3-ylmethyl)urea |
| 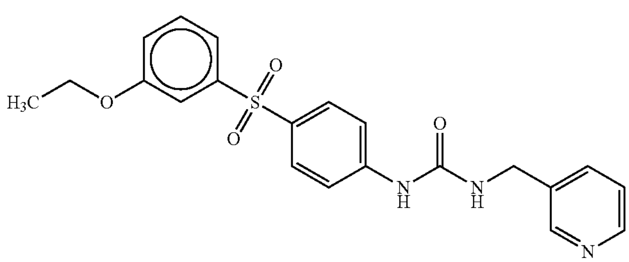 | 3-{4-[(3-ethoxybenzene)sulfonyl]phenyl}-1-(pyridin-3-ylmethyl)urea |
| 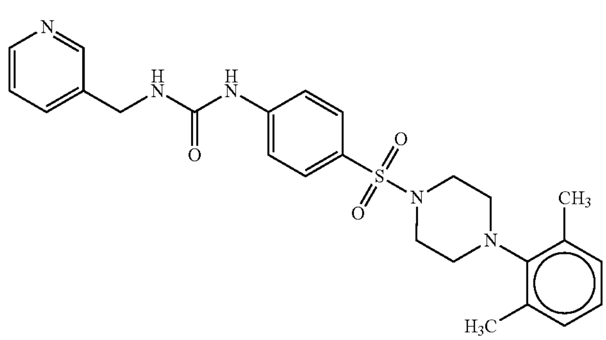 | 3-{4-[4-(2,6-dimethylphenyl)piperazine-1-sulfonyl]phenyl}-1-(pyridin-3-ylmethyl)urea |

| Structure | Chemical Name |
|---|---|
| 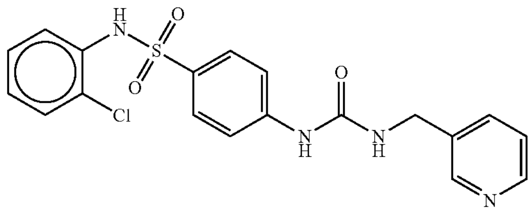 | 3-{4-[(2-chlorophenyl)sulfamoyl]phenyl}-1-(pyridin-3-ylmethyl)urea |
| 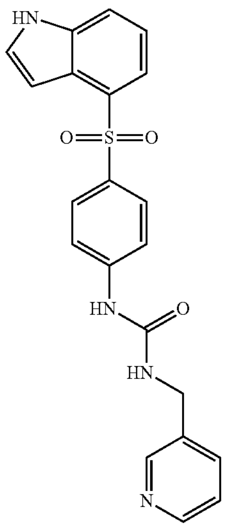 [SMILES: O=C(NCc1cccnc1)Nc1ccc(S(=O)(=O)c2cccc3[nH]ccc23)cc1] | 1-[4-(1H-indole-4-sulfonyl)phenyl]-3-(pyridin-3-ylmethyl)urea |
| 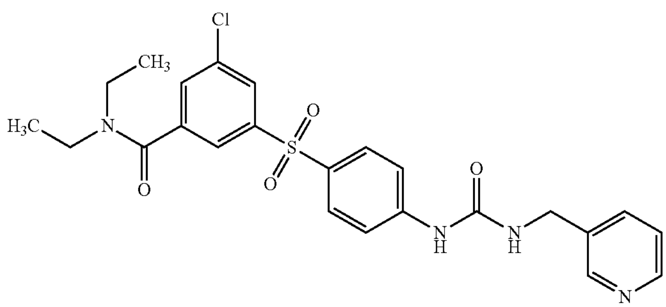 [SMILES: CCN(CC)C(=O)c1cc(Cl)cc(S(=O)(=O)c2ccc(NC(=O)NCc3cccnc3)cc2)c1] | 3-chloro-N,N-diethyl-5-[(4-{[(pyridin-3-ylmethyl)carbamoyl]amino}benzene)sulfonyl]benzamide |
| 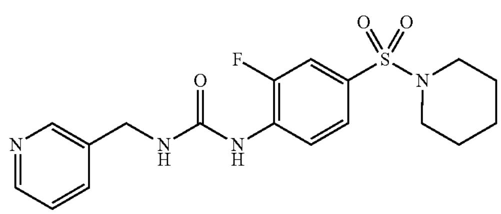 [SMILES: O=C(NCc1cccnc1)Nc1ccc(S(=O)(=O)N2CCCCC2)cc1F] | 3-[2-fluoro-4-(piperidine-1-sulfonyl)phenyl]-1-(pyridin-3-ylmethyl)urea |
| 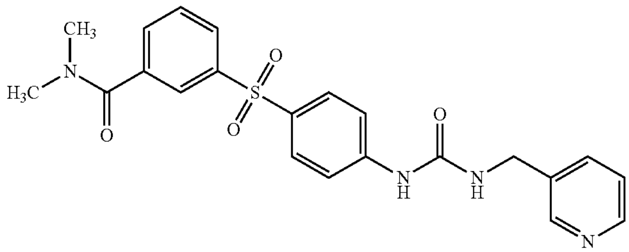 [SMILES: CN(C)C(=O)c1cccc(S(=O)(=O)c2ccc(NC(=O)NCc3cccnc3)cc2)c1] | N,N-dimethyl-3-[(4-{[(pyridin-3-ylmethyl)carbamoyl]amino}benzene)sulfonyl]benzamide |

| Structure | Chemical Name |
|---|---|
| | 1-(pyridin-3-ylmethyl)-3-[4-({[3-(trifluoromethyl)phenyl]methyl}sulfamoyl)phenyl]urea |
| 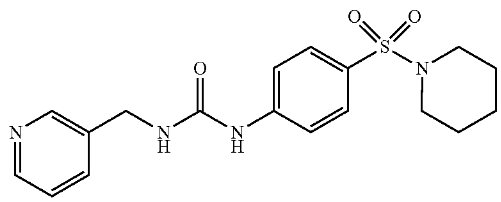 [SMILES: O=C(NCc1cccnc1)Nc1ccc(S(=O)(=O)N2CCCCC2)cc1] | pyridin-3-ylmethyl N-[4-(piperidine-1-sulfonyl)phenyl]carbamate |
| 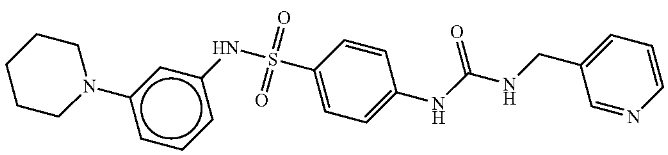 | 1-(4-{[3-(piperidin-1-yl)phenyl]sulfamoyl}phenyl)-3-(pyridin-3-ylmethyl)urea |
| 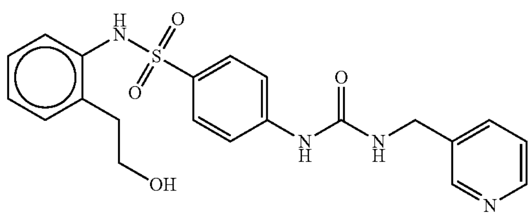 | 3-(4-{[2-(2-hydroxyethyl)phenyl]sulfamoyl}phenyl)-1-(pyridin-3-ylmethyl)urea |
| 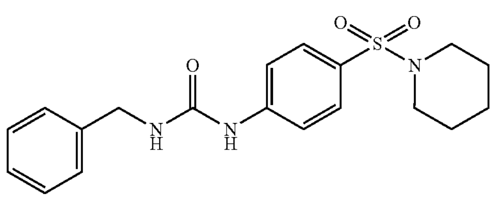 [SMILES: O=C(NCc1ccccc1)Nc1ccc(S(=O)(=O)N2CCCCC2)cc1] | 3-benzyl-1-[4-(piperidine-1-sulfonyl)phenyl]urea |
| 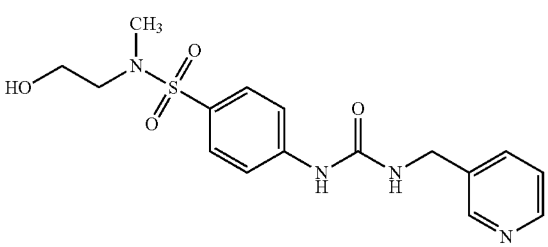 [SMILES: CN(CCO)S(=O)(=O)c1ccc(NC(=O)NCc2cccnc2)cc1] | 3-{4-[(2-hydroxyethyl)(methyl)sulfamoyl]phenyl}-1-(pyridin-3-ylmethyl)urea |
| | 1-(pyridin-3-ylmethyl)-3-(4-{[4-(trifluoromethane)sulfonylphenyl]sulfamoyl}phenyl)urea |

| Structure | Chemical Name |
|---|---|
| 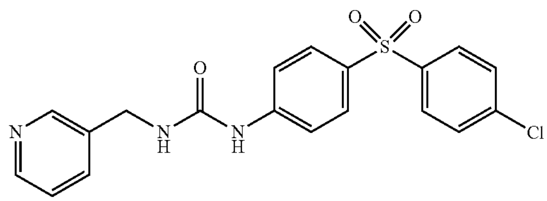 [SMILES: O=C(NCc1cccnc1)Nc1ccc(S(=O)(=O)c2ccc(Cl)cc2)cc1] | 3-{4-[(4-chlorobenzene)sulfonyl]phenyl}-1-(pyridin-3-ylmethyl)urea |
| 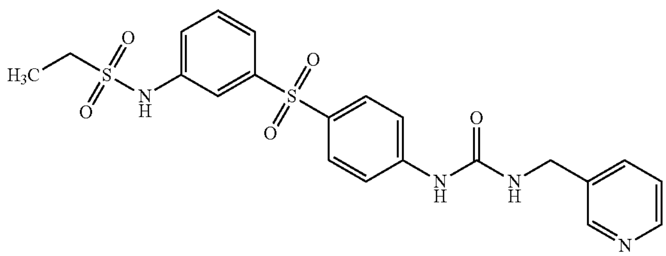 [SMILES: CCS(=O)(=O)Nc1cccc(S(=O)(=O)c2ccc(NC(=O)NCc3cccnc3)cc2)c1] | 3-{4-[(3-ethanesulfonamidobenzene)sulfonyl]phenyl}-1-(pyridin-3-ylmethyl)urea |
| 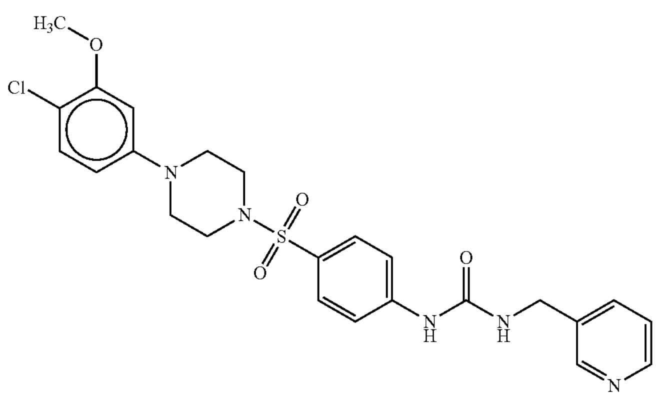 | 3-{4-[4-(4-chloro-3-methoxyphenyl)piperazine-1-sulfonyl]phenyl}-1-(pyridin-3-ylmethyl)urea |
| 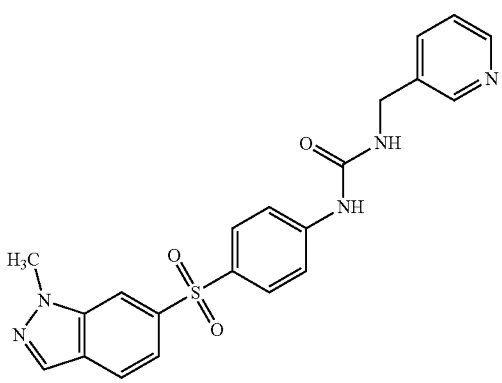 [SMILES: Cn1ncc2ccc(S(=O)(=O)c3ccc(NC(=O)NCc4cccnc4)cc3)cc21] | 3-[4-(1-methyl-1H-indazole-6-sulfonyl)phenyl]-1-(pyridin-3-ylmethyl)urea |
| 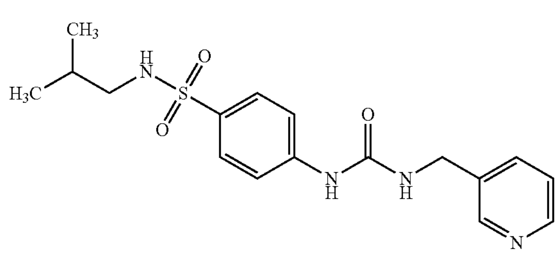 [SMILES: CC(C)CNS(=O)(=O)c1ccc(NC(=O)NCc2cccnc2)cc1] | 3-{4-[(2-methylpropyl)sulfamoyl]phenyl}-1-(pyridin-3-ylmethyl)urea |

-continued

| Structure | Chemical Name |
|---|---|
| 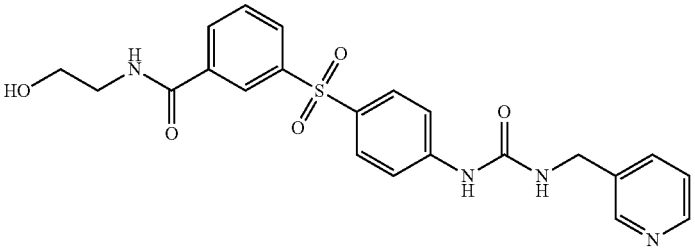 [SMILES: O=C(NCc1cccnc1)Nc1ccc(S(=O)(=O)c2cccc(C(=O)NCCO)c2)cc1] | N-(2-hydroxyethyl)-3-[(4-{[(pyridin-3-ylmethyl)carbamoyl]amino}benzene)sulfonyl]benzamide |
| 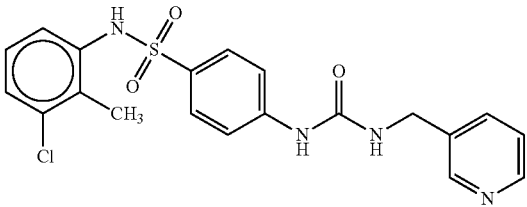 | 3-{4-[(3-chloro-2-methylphenyl)sulfamoyl]phenyl}-1-(pyridin-3-ylmethyl)urea |
| 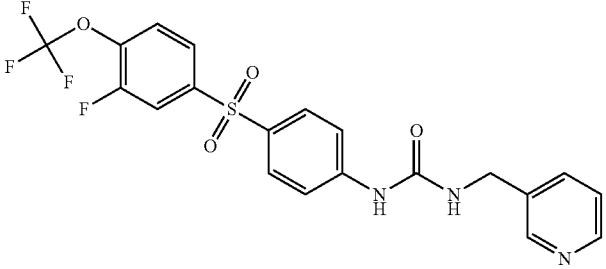 [SMILES: O=C(NCc1cccnc1)Nc1ccc(S(=O)(=O)c2ccc(OC(F)(F)F)c(F)c2)cc1] | 3-(4-{[3-fluoro-4-(trifluoromethoxy)benzene]sulfonyl}phenyl)-1-(pyridin-3-ylmethyl)urea |
| 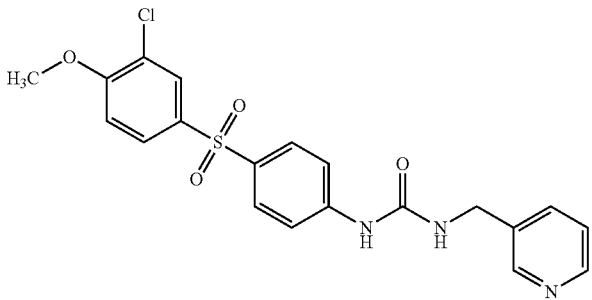 [SMILES: COc1ccc(S(=O)(=O)c2ccc(NC(=O)NCc3cccnc3)cc2)cc1Cl] | 3-{4-[(3-chloro-4-methoxybenzene)sulfonyl]phenyl}-1-(pyridin-3-ylmethyl)urea |
| 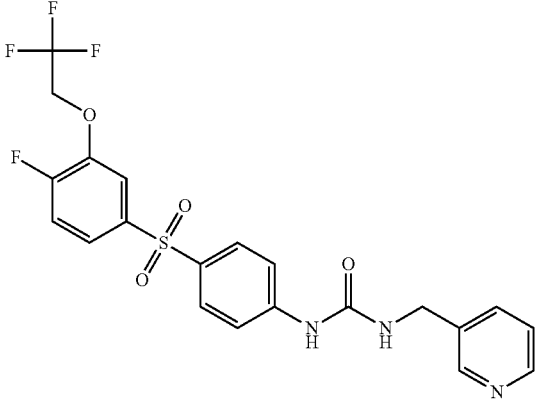 [SMILES: O=C(NCc1cccnc1)Nc1ccc(S(=O)(=O)c2ccc(F)c(OCC(F)(F)F)c2)cc1] | 3-(4-{[4-fluoro-3-(2,2,2-trifluoroethoxy)benzene]sulfonyl}phenyl)-1-(pyridin-3-ylmethyl)urea |

-continued

| Structure | Chemical Name |
|---|---|
| 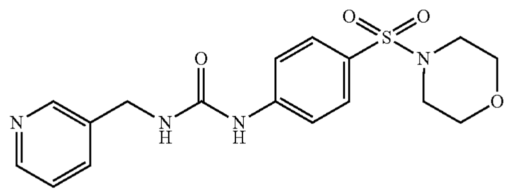 [SMILES: O=C(NCc1cccnc1)Nc1ccc(S(=O)(=O)N2CCOCC2)cc1] | 1-[4-(morpholine-4-sulfonyl)phenyl]-3-(pyridin-3-ylmethyl)urea |
| 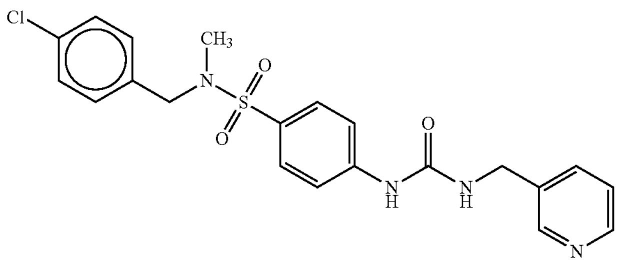 | 3-(4-{[(4-chlorophenyl)methyl](methyl)sulfamoyl}phenyl)-1-(pyridin-3-ylmethyl)urea |
| 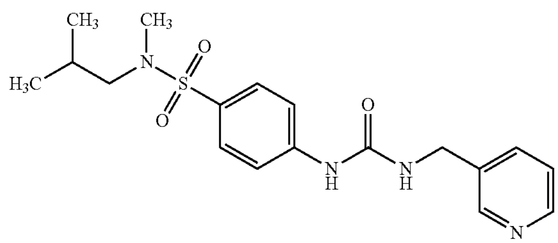 [SMILES: CC(C)CN(C)S(=O)(=O)c1ccc(NC(=O)NCc2cccnc2)cc1] | 3-{4-[methyl(2-methylpropyl)sulfamoyl]phenyl}-1-(pyridin-3-ylmethyl)urea |
| 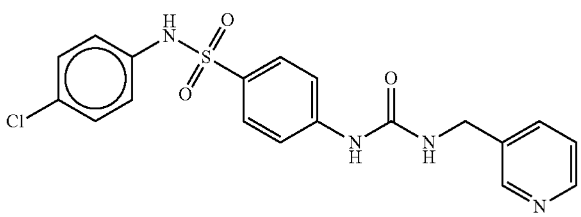 | 3-{4-[(4-chlorophenyl)sulfamoyl]phenyl}-1-(pyridin-3-ylmethyl)urea |
| 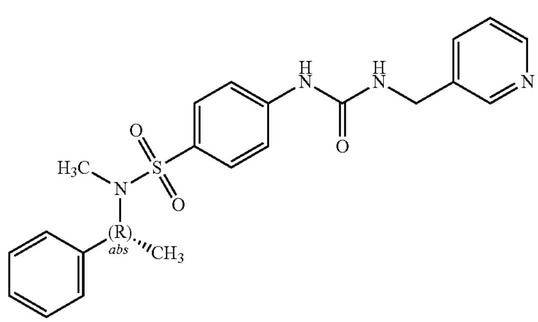 | 3-(4-{methyl[(1R)-1-phenylethyl]sulfamoyl}phenyl)-1-(pyridin-3-ylmethyl)urea |
| 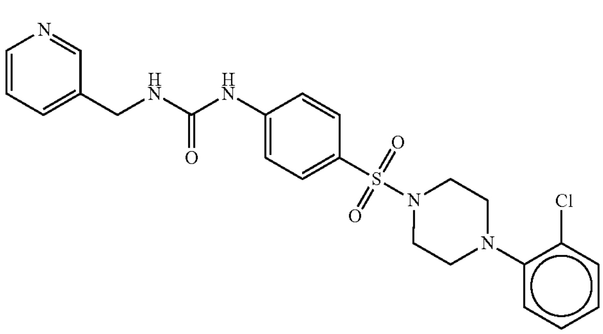 | 3-{4-[4-(2-chlorophenyl)piperazine-1-sulfonyl]phenyl}-1-(pyridin-3-ylmethyl)urea |

-continued

| Structure | Chemical Name |
|---|---|
| 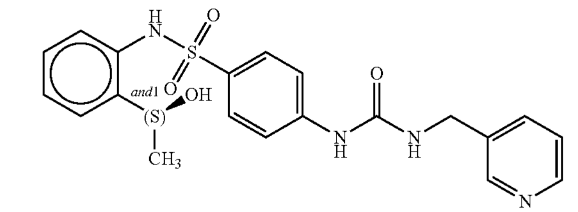 | 3-[4-({2-[(1S)-1-hydroxyethyl]phenyl}sulfamoyl)phenyl]-1-(pyridin-3-ylmethyl)urea |
| 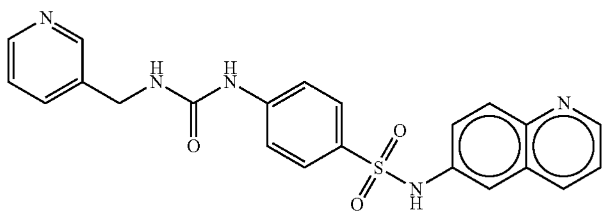 | 3-(pyridin-3-ylmethyl)-1-{4-[(quinolin-6-yl)sulfamoyl]phenyl}urea |
| 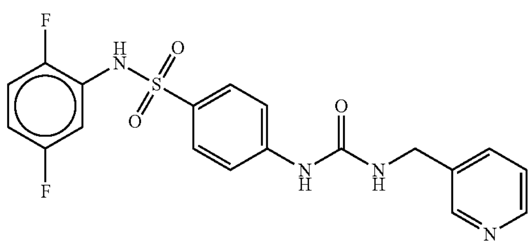 | 3-{4-[(2,5-difluorophenyl)sulfamoyl]phenyl}-1-(pyridin-3-ylmethyl)urea |
| 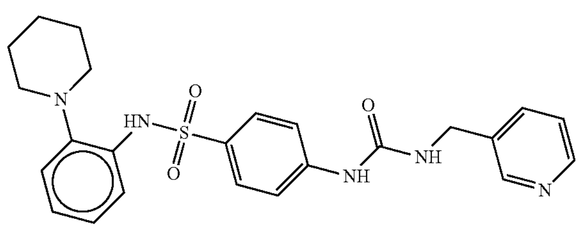 | 1-(4-{[2-(piperidin-1-yl)phenyl]sulfamoyl}phenyl)-3-(pyridin-3-ylmethyl)urea |
| 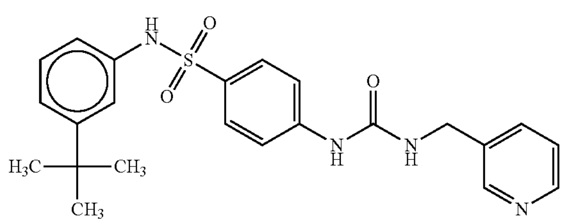 | 3-{4-[(3-tert-butylphenyl)sulfamoyl]phenyl}-1-(pyridin-3-ylmethyl)urea |
| 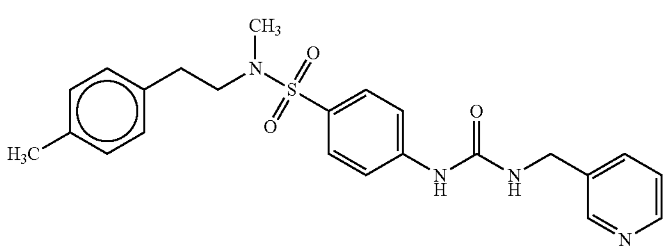 | 3-(4-{methyl[2-(4-methylphenyl)ethyl]sulfamoyl}phenyl)-1-(pyridin-3-ylmethyl)urea |

-continued

| Structure | Chemical Name |
|---|---|
| 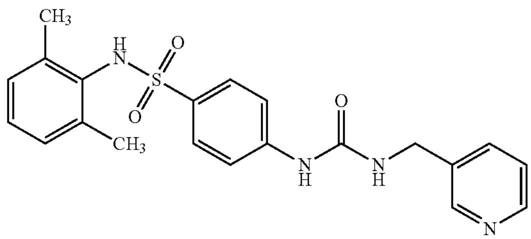 [SMILES: Cc1cccc(C)c1NS(=O)(=O)c1ccc(NC(=O)NCc2cccnc2)cc1] | 3-{4-[(2,6-dimethylphenyl)sulfamoyl]phenyl}-1-(pyridin-3-ylmethyl)urea |
| 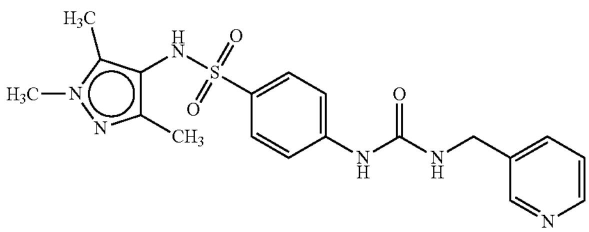 | 1-(pyridin-3-ylmethyl)-3-{4-[(1,3,5-trimethyl-1H-pyrazol-4-yl)sulfamoyl]phenyl}urea |
| | 1-(4-{3-azatricyclo[7.3.1.0⁵,¹³]trideca-1(13),5,7,9,11-pentaene-3-sulfonyl}phenyl)-3-(pyridin-3-ylmethyl)urea |
| 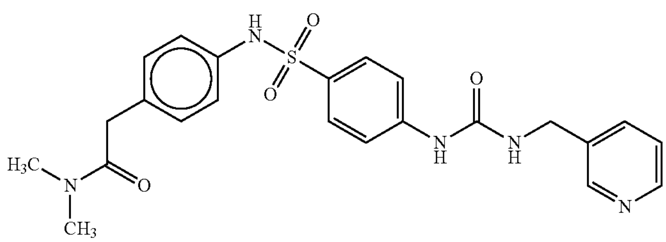 | N,N-dimethyl-2-{4-[(4-{[(pyridin-3-ylmethyl)carbamoyl]amino}benzene)sulfonamido]phenyl}acetamide |
| 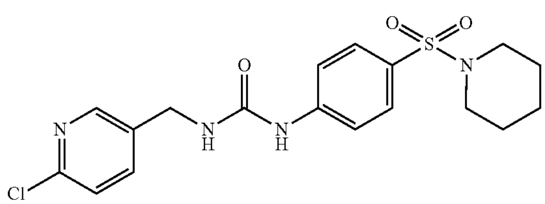 [SMILES: O=C(NCc1ccc(Cl)nc1)Nc1ccc(S(=O)(=O)N2CCCCC2)cc1] | 3-[(6-chloropyridin-3-yl)methyl]-1-[4-(piperidine-1-sulfonyl)phenyl]urea |
| 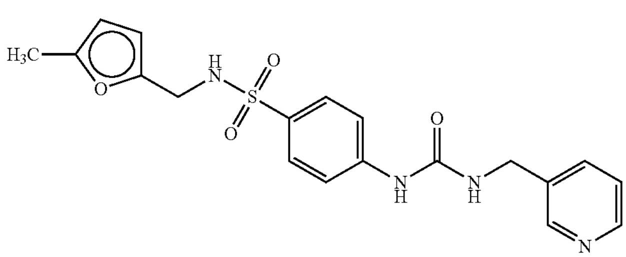 | 3-(4-{[(5-methylfuran-2-yl)methyl]sulfamoyl}phenyl)-1-(pyridin-3-ylmethyl)urea |
| 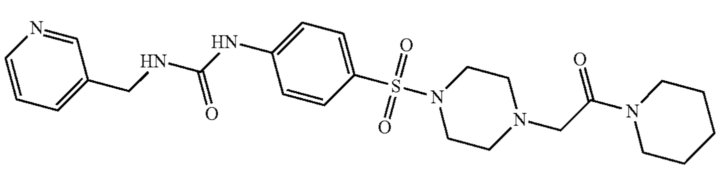 [SMILES: O=C(NCc1cccnc1)Nc1ccc(S(=O)(=O)N2CCN(CC(=O)N3CCCCC3)CC2)cc1] | 1-(4-{4-[2-oxo-2-(piperidin-1-yl)ethyl]piperazine-1-sulfonyl}phenyl)-3-(pyridin-3-ylmethyl)urea |

| Structure | Chemical Name |
| --- | --- |
| 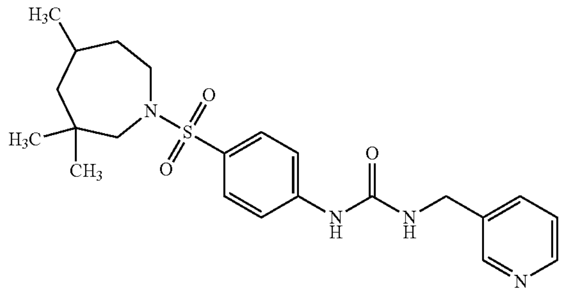 [SMILES: CC1CCN(S(=O)(=O)c2ccc(NC(=O)NCc3cccnc3)cc2)CC(C)(C)C1] | 1-(pyridin-3-ylmethyl)-3-[4-(3,3,5-trimethylazepane-1-sulfonyl)phenyl]urea |
| 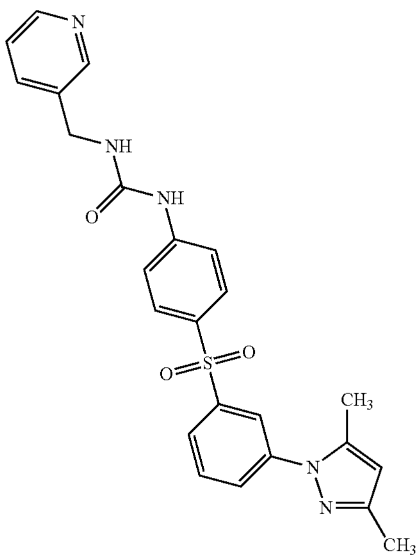 [SMILES: Cc1cc(C)n(-c2cccc(S(=O)(=O)c3ccc(NC(=O)NCc4cccnc4)cc3)c2)n1] | 3-(4-{[3-(3,5-dimethyl-1H-pyrazol-1-yl)benzene]sulfonyl}phenyl)-1-(pyridin-3-ylmethyl)urea |
| 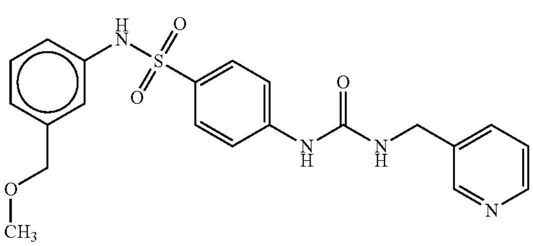 | 3-(4-{[3-(methoxymethyl)phenyl]sulfamoyl}phenyl)-1-(pyridin-3-ylmethyl)urea |
| 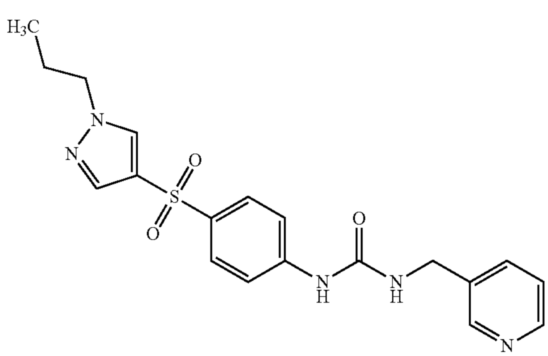 [SMILES: CCCn1cc(S(=O)(=O)c2ccc(NC(=O)NCc3cccnc3)cc2)cn1] | 3-[4-(1-propyl-1H-pyrazole-4-sulfonyl)phenyl]-1-(pyridin-3-ylmethyl)urea |

-continued

| Structure | Chemical Name |
|---|---|
| 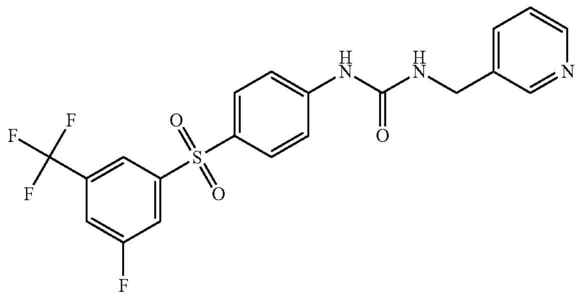 [SMILES: O=C(NCc1cccnc1)Nc1ccc(S(=O)(=O)c2cc(F)cc(C(F)(F)F)c2)cc1] | 3-(4-{[3-fluoro-5-(trifluoromethyl)benzene]sulfonyl}phenyl)-1-(pyridin-3-ylmethyl)urea |
| 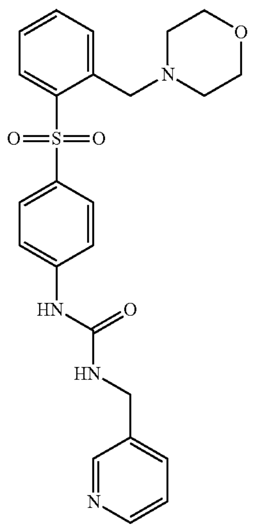 [SMILES: O=C(NCc1cccnc1)Nc1ccc(S(=O)(=O)c2ccccc2CN2CCOCC2)cc1] | 1-(4-{[2-(morpholin-4-ylmethyl)benzene]sulfonyl}phenyl)-3-(pyridin-3-ylmethyl)urea |
| 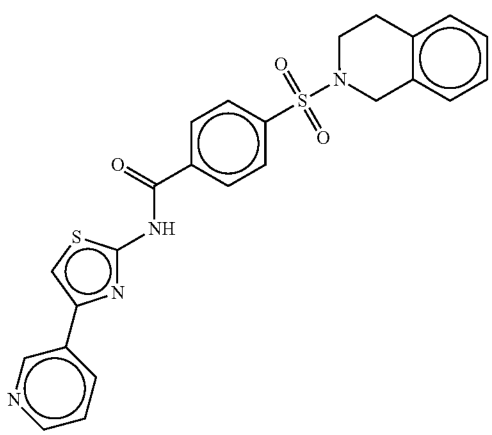 | N-[4-(pyridin-3-yl)-1,3-thiazol-2-yl]-4-(1,2,3,4-tetrahydroisoquinoline-2-sulfonyl)benzamide |
| 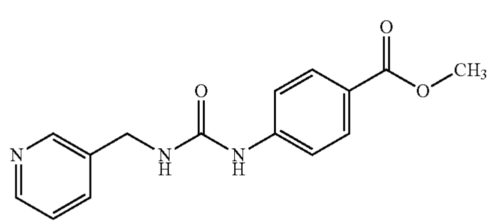 [SMILES: COC(=O)c1ccc(NC(=O)NCc2cccnc2)cc1] | methyl 4-{[(pyridin-3-ylmethyl)carbamoyl]amino}benzoate |

| Structure | Chemical Name |
|---|---|
| 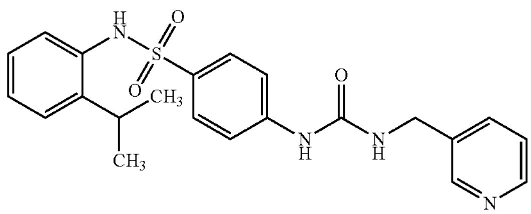 [SMILES: CC(C)c1ccccc1NS(=O)(=O)c1ccc(NC(=O)NCc2cccnc2)cc1] | 3-(4-{[2-(propan-2-yl)phenyl]sulfamoyl}phenyl)-1-(pyridin-3-ylmethyl)urea |
| 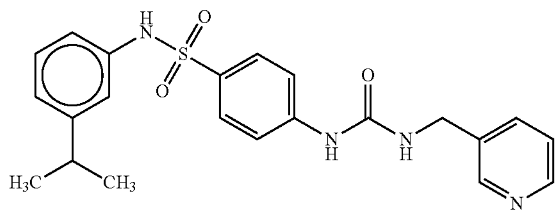 | 3-(4-{[3-(propan-2-yl)phenyl]sulfamoyl}phenyl)-1-(pyridin-3-ylmethyl)urea |
| 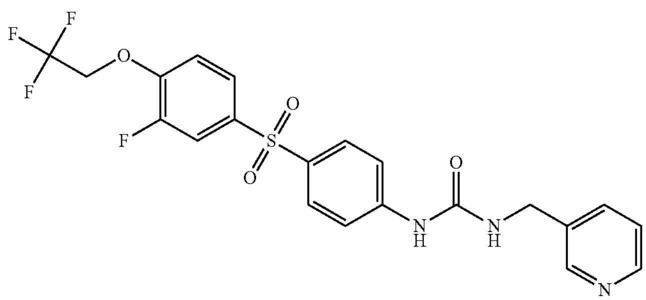 [SMILES: O=C(NCc1cccnc1)Nc1ccc(S(=O)(=O)c2ccc(OCC(F)(F)F)c(F)c2)cc1] | 3-(4-{[3-fluoro-4-(2,2,2-trifluoroethoxy)benzene]sulfonyl}phenyl)-1-(pyridin-3-ylmethyl)urea |
| 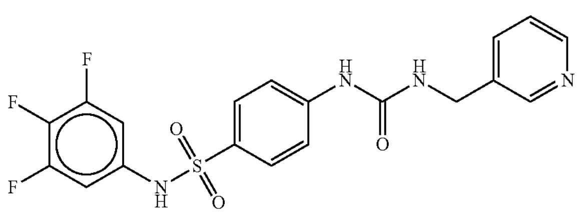 | 1-(pyridin-3-ylmethyl)-3-{4-[(3,4,5-trifluorophenyl)sulfamoyl]phenyl}urea |
| 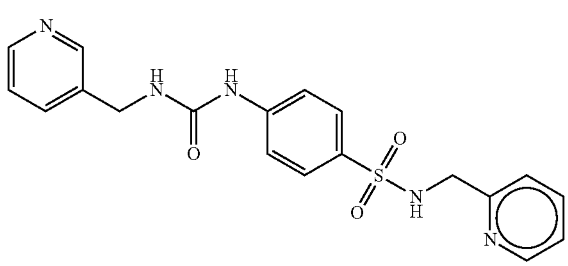 | 1-{4-[(pyridin-2-ylmethyl)sulfamoyl]phenyl}-3-(pyridin-3-ylmethyl)urea |
| 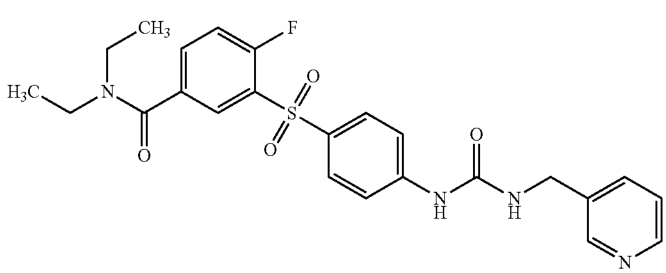 [SMILES: CCN(CC)C(=O)c1ccc(F)c(S(=O)(=O)c2ccc(NC(=O)NCc3cccnc3)cc2)c1] | N,N-diethyl-4-fluoro-3-[(4-{[(pyridin-3-ylmethyl)carbamoyl]amino}benzene)sulfonyl]benzamide |

-continued

| Structure | Chemical Name |
|---|---|
| 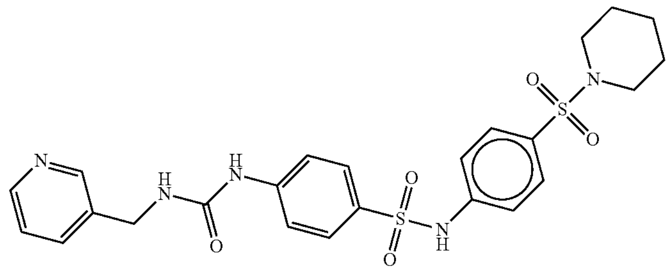 | 1-(4-{[4-(piperidine-1-sulfonyl)phenyl]sulfamoyl}phenyl)-3-(pyridin-3-ylmethyl)urea |
| 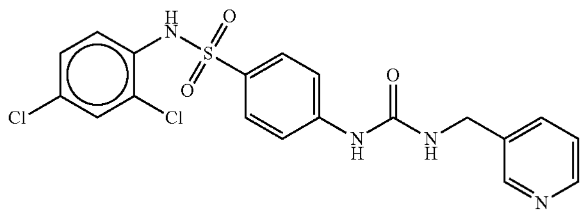 | 3-{4-[(2,4-dichlorophenyl)sulfamoyl]phenyl}-1-(pyridin-3-ylmethyl)urea |
| 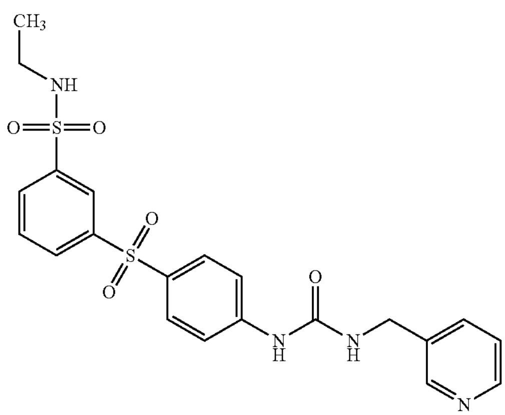 [SMILES: CCNS(=O)(=O)c1cccc(S(=O)(=O)c2ccc(NC(=O)NCc3cccnc3)cc2)c1] | 3-(4-{[3-(ethylsulfamoyl)benzene]sulfonyl}phenyl)-1-(pyridin-3-ylmethyl)urea |
| 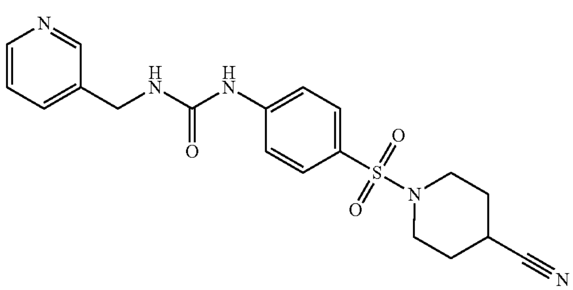 [SMILES: N#CC1CCN(S(=O)(=O)c2ccc(NC(=O)NCc3cccnc3)cc2)CC1] | 1-[4-(4-cyanopiperidine-1-sulfonyl)phenyl]-3-(pyridin-3-ylmethyl)urea |
| 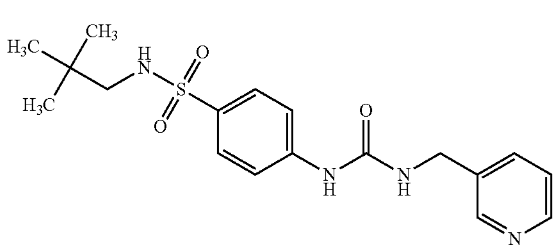 [SMILES: CC(C)(C)CNS(=O)(=O)c1ccc(NC(=O)NCc2cccnc2)cc1] | 3-{4-[(2,2-dimethylpropyl)sulfamoyl]phenyl}-1-(pyridin-3-ylmethyl)urea |

| Structure | Chemical Name |
|---|---|
| 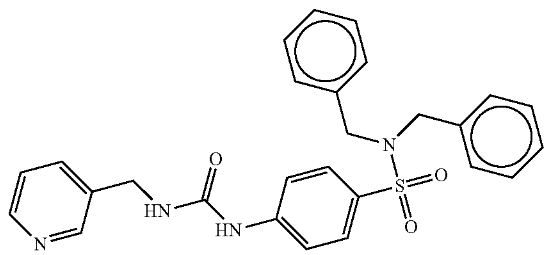 | 1-[4-(dibenzylsulfamoyl)phenyl]-3-(pyridin-3-ylmethyl)urea |
| 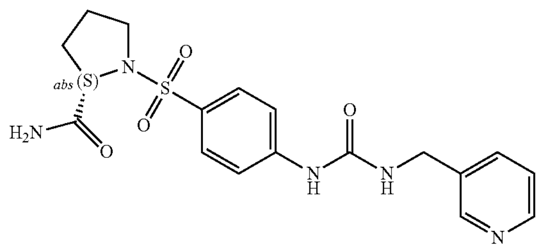 | (2S)-1-[(4-{[(pyridin-3-ylmethyl)carbamoyl]amino}benzene)sulfonyl]pyrrolidine-2-carboxamide |
| 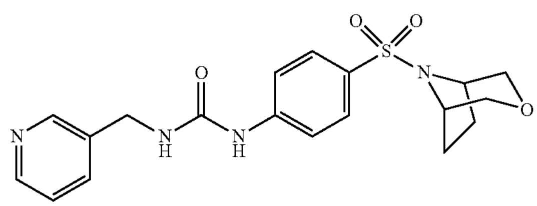 [SMILES: O=C(NCc1cccnc1)Nc1ccc(S(=O)(=O)N2C3CCC2COC3)cc1] | 1-(4-{3-oxa-8-azabicyclo[3.2.1]octane-8-sulfonyl}phenyl)-3-(pyridin-3-ylmethyl)urea |
| 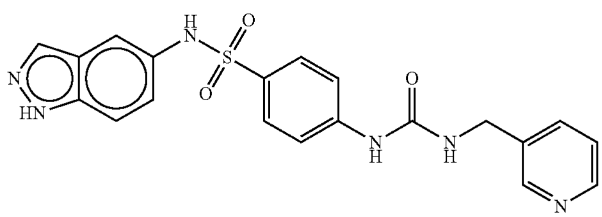 | 1-{4-[(1H-indazol-5-yl)sulfamoyl]phenyl}-3-(pyridin-3-ylmethyl)urea |
| 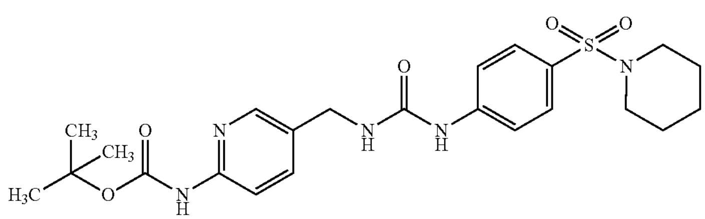 [SMILES: CC(C)(C)OC(=O)Nc1ccc(CNC(=O)Nc2ccc(S(=O)(=O)N3CCCCC3)cc2)cn1] | tert-butyl N-{5-[({[4-(piperidine-1-sulfonyl)phenyl]carbamoyl}amino)methyl]pyridin-2-yl}carbamate |
| 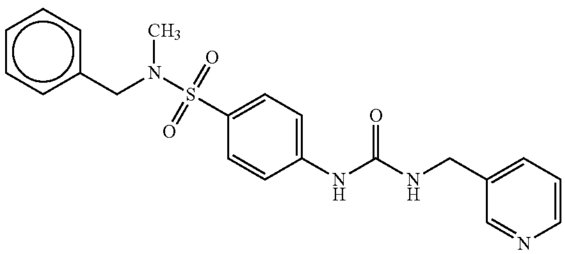 | 3-{4-[benzyl(methyl)sulfamoyl]phenyl}-1-(pyridin-3-ylmethyl)urea |

| Structure | Chemical Name |
|---|---|
| 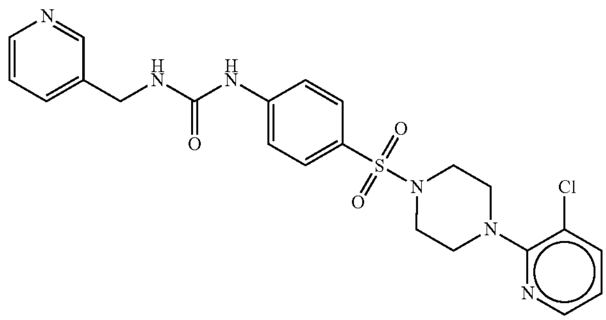 | 3-{4-[4-(3-chloropyridin-2-yl)piperazine-1-sulfonyl]phenyl}-1-(pyridin-3-ylmethyl)urea |
| 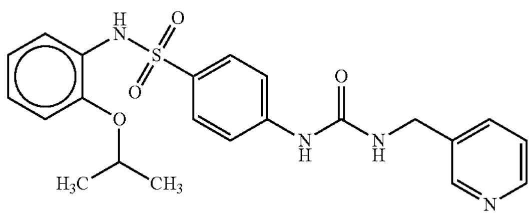 | 3-(4-{[2-(propan-2-yloxy)phenyl]sulfamoyl}phenyl)-1-(pyridin-3-ylmethyl)urea |
| 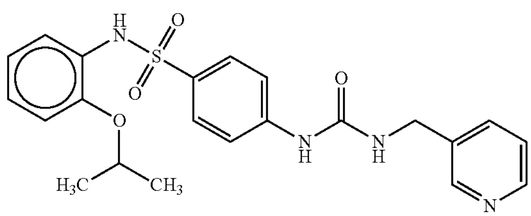 | 3{4-[(3-methanesulfonamidobenzene)sulfonyl]phenyl}-1-(pyridin-3-ylmethyl)urea |
| 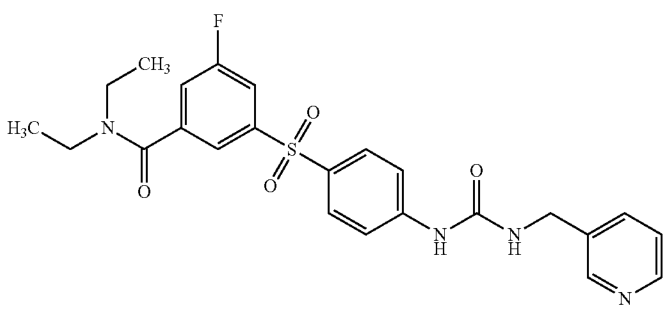 | N,N-diethyl-3-fluoro-5-[(4-{[(pyridin-3-ylmethyl)carbamoyl]amino}benzene)sulfonyl]benzamide |
| 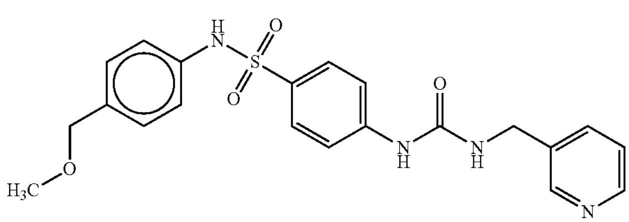 | 3-(4-{[4-(methoxymethyl)phenyl]sulfamoyl}phenyl)-1-(pyridin-3-ylmethyl)urea |
| 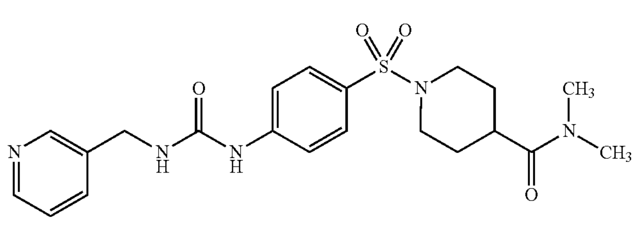 [SMILES: CN(C)C(=O)C1CCN(S(=O)(=O)c2ccc(NC(=O)NCc3cccnc3)cc2)CC1] | N,N-dimethyl-1-[(4-{[(pyridin-3-ylmethyl)carbamoyl]amino}benzene)sulfonyl]piperidine-4-carboxamide |

-continued
| Structure | Chemical Name |
|---|---|
| 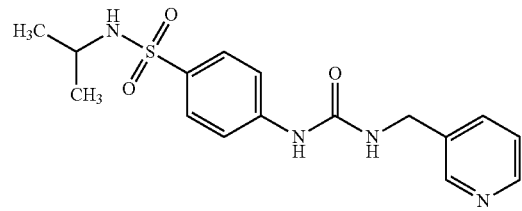 [SMILES: CC(C)NS(=O)(=O)c1ccc(NC(=O)NCc2cccnc2)cc1] | 3-{4-[(propan-2-yl)sulfamoyl]phenyl}-1-(pyridin-3-ylmethyl)urea |
| 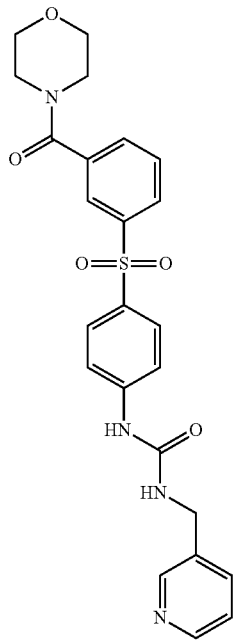 [SMILES: O=C(NCc1cccnc1)Nc1ccc(S(=O)(=O)c2cccc(C(=O)N3CCOCC3)c2)cc1] | 1-[4-({3-[(morpholin-4-yl)carbonyl]benzene}sulfonyl)phenyl]-3-(pyridin-3-ylmethyl)urea |
| 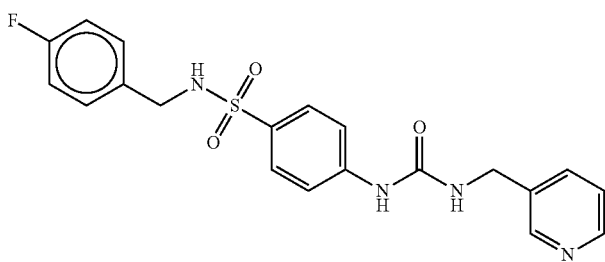 | 3-(4-{[(4-fluorophenyl)methyl]sulfamoyl}phenyl)-1-(pyridin-3-ylmethyl)urea |
| 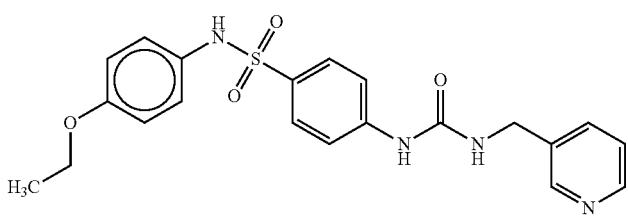 | 3-{4-[(4-ethoxyphenyl)sulfamoyl]phenyl}-1-(pyridin-3-ylmethyl)urea |
| 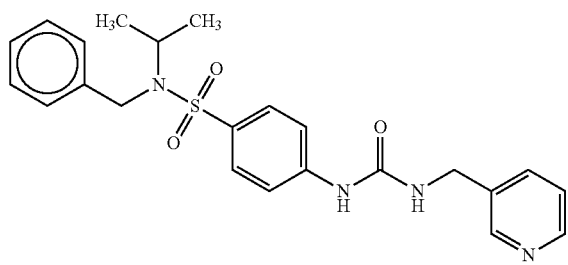 | 3-{4-[benzyl(propan-2-yl)sulfamoyl]phenyl}-1-(pyridin-3-ylmethyl)urea |

| Structure | Chemical Name |
|---|---|
| 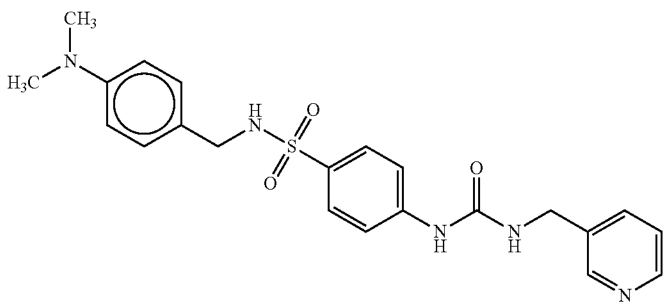 | 3-[4-({[4-(dimethylamino)phenyl]methyl}sulfamoyl)phenyl]-1-(pyridin-3-ylmethyl)urea |
| 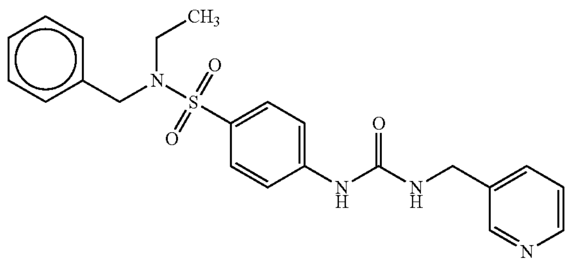 | 3-{4-[benzyl(ethyl)sulfamoyl]phenyl}-1-(pyridin-3-ylmethyl)urea |
| 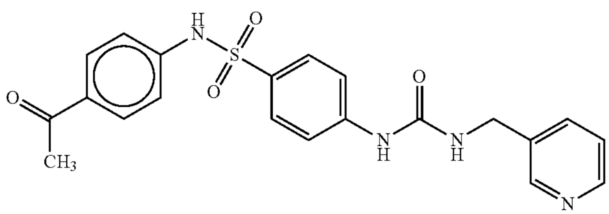 | 3-{4-[(4-acetylphenyl)sulfamoyl]phenyl}-1-(pyridin-3-ylmethyl)urea |
| 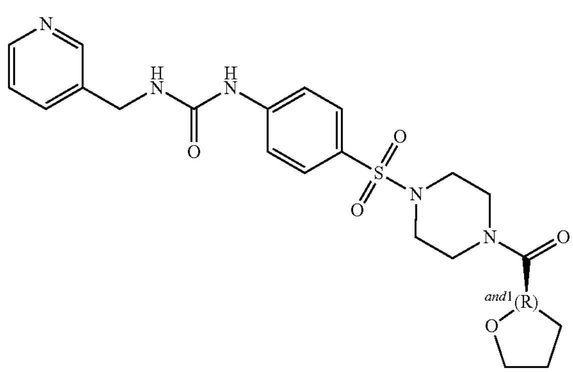 | 1-[4-(4-{[(2R)-oxolan-2-yl]carbonyl}piperazine-1-sulfonyl)phenyl]-3-(pyridin-3-ylmethyl)urea |
| 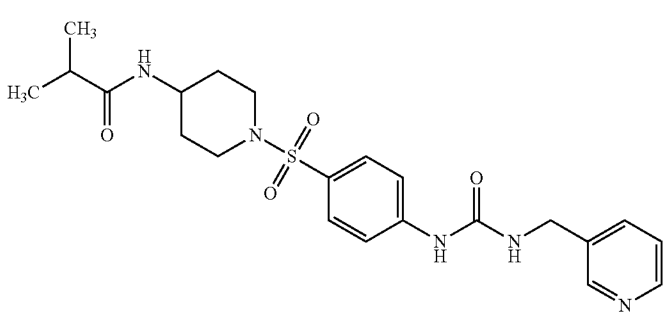 [SMILES: CC(C)C(=O)NC1CCN(S(=O)(=O)c2ccc(NC(=O)NCc3cccnc3)cc2)CC1] | 2-methyl-N-{1-[(4-{[(pyridin-3-ylmethyl)carbamoyl]amino}benzene)sulfonyl]piperidin-4-yl}propanamide |

-continued

| Structure | Chemical Name |
|---|---|
| 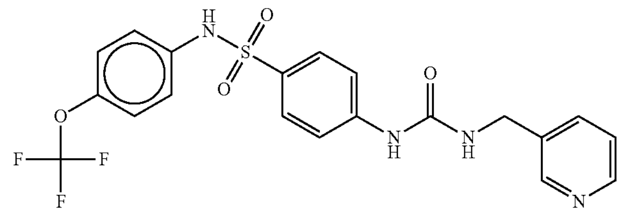 | 1-(pyridin-3-ylmethyl)-3-(4-{[4-(trifluoromethoxy)phenyl]sulfamoyl}phenyl)urea |
| 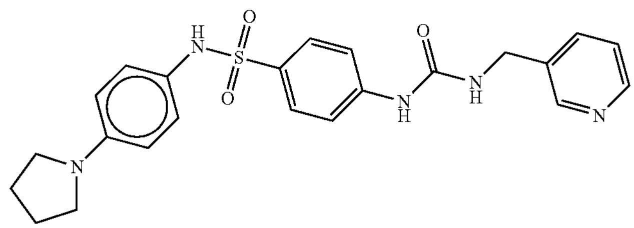 | 3-(pyridin-3-ylmethyl)-1-(4-{[4-(pyrrolidin-1-yl)phenyl]sulfamoyl}phenyl)urea |
| | 3-(4-{[(3-chlorophenyl)methyl]sulfamoyl}phenyl)-1-(pyridin-3-ylmethyl)urea |
| 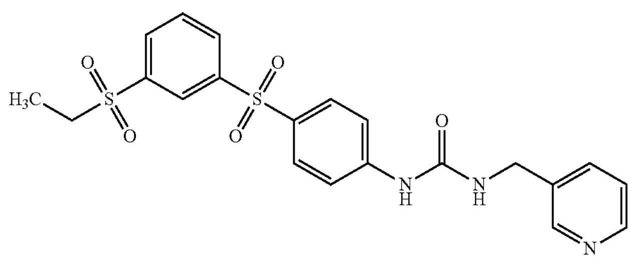 [SMILES: CCS(=O)(=O)c1cccc(S(=O)(=O)c2ccc(NC(=O)NCc3cccnc3)cc2)c1] | 3-(4-{[3-(ethanesulfonyl)benzene]sulfonyl}phenyl)-1-(pyridin-3-ylmethyl)urea |
| 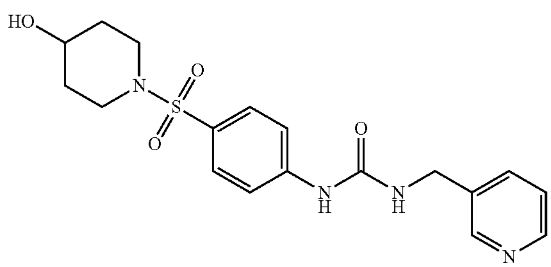 [SMILES: O=C(NCc1cccnc1)Nc1ccc(S(=O)(=O)N2CCC(O)CC2)cc1] | 3-[4-(4-hydroxypiperidine-1-sulfonyl)phenyl]-1-(pyridin-3-ylmethyl)urea |
| 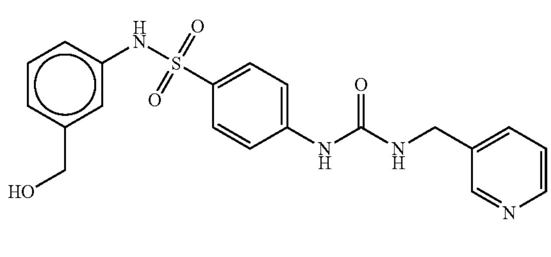 | 3-(4-{[3-(hydroxymethyl)phenyl]sulfamoyl}phenyl)-1-(pyridin-3-ylmethyl)urea |

| Structure | Chemical Name |
|---|---|
| 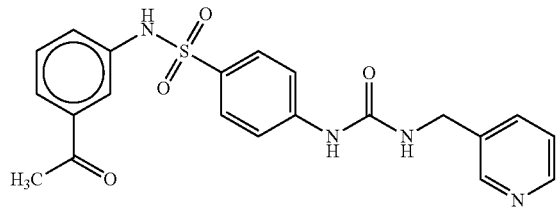 | 3-{4-[(3-acetylphenyl)sulfamoyl]phenyl}-1-(pyridin-3-ylmethyl)urea |
| 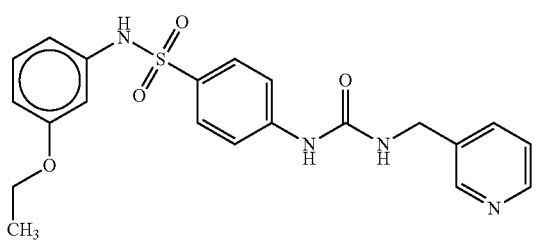 | 3-{4-[(3-ethoxyphenyl)sulfamoyl]phenyl}-1-(pyridin-3-ylmethyl)urea |
| 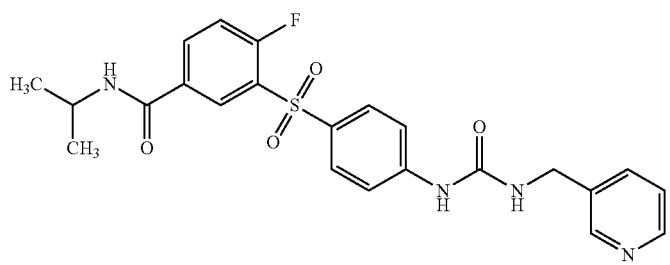 [SMILES: CC(C)NC(=O)c1ccc(F)c(S(=O)(=O)c2ccc(NC(=O)NCc3cccnc3)cc2)c1] | 4-fluoro-N-(propan-2-yl)-3-[(4-{[(pyridin-3-ylmethyl)carbamoyl]amino}benzene)sulfonyl]benzamide |
| 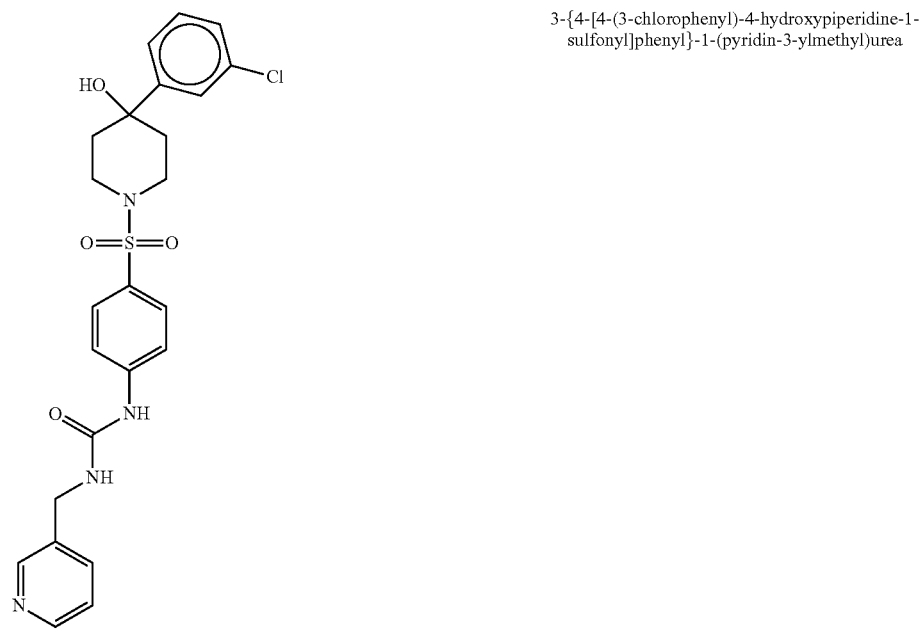 | 3-{4-[4-(3-chlorophenyl)-4-hydroxypiperidine-1-sulfonyl]phenyl}-1-(pyridin-3-ylmethyl)urea |

-continued

| Structure | Chemical Name |
|---|---|
| 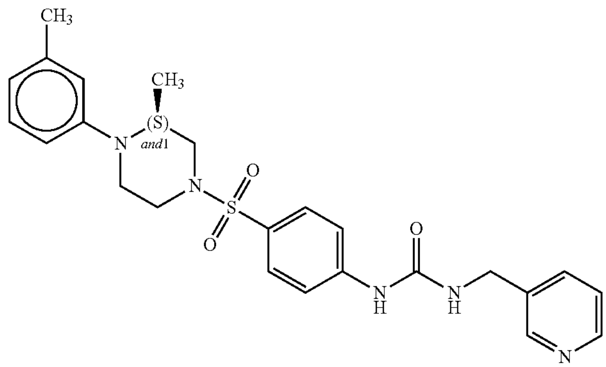 | 3-{4-[(3S)-3-methyl-4-(3-methylphenyl)piperazine-1-sulfonyl]phenyl}-1-(pyridin-3-ylmethyl)urea |
| 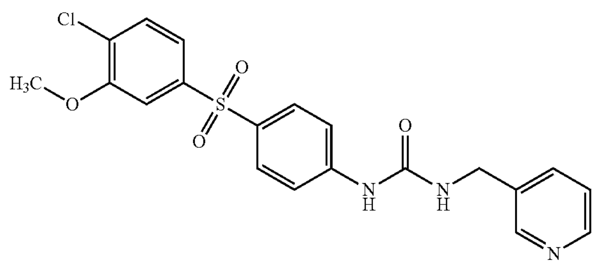 | 3-{4-[(4-chloro-3-methoxybenzene)sulfonyl]phenyl}-1-(pyridin-3-ylmethyl)urea |
| 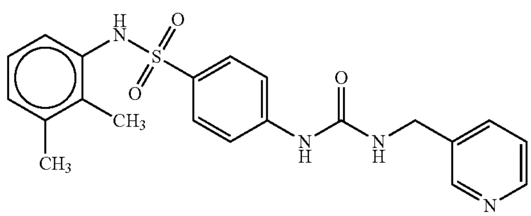 | 3-{4-[(2,3-dimethylphenyl)sulfamoyl]phenyl}-1-(pyridin-3-ylmethyl)urea |
| 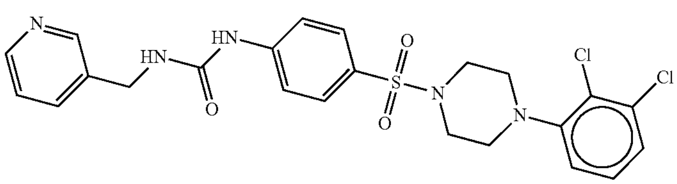 | 3-{4-[4-(2,3-dichlorophenyl)piperazine-1-sulfonyl]phenyl}-1-(pyridin-3-ylmethyl)urea |
| 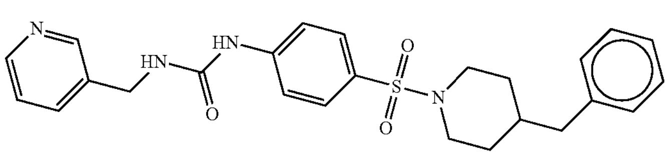 | 1-[4-(4-benzylpiperidine-1-sulfonyl)phenyl]-3-(pyridin-3-ylmethyl)urea |
| 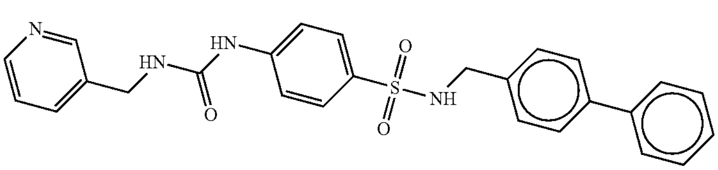 | 1-(4-{[(4-phenylphenyl)methyl]sulfamoyl}phenyl)-3-(pyridin-3-ylmethyl)urea |
| 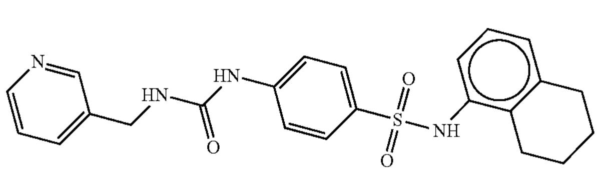 | 3-(pyridin-3-ylmethyl)-1-{4-[(5,6,7,8-tetrahydronaphthalen-1-yl)sulfamoyl]phenyl}urea |

-continued

| Structure | Chemical Name |
|---|---|
| 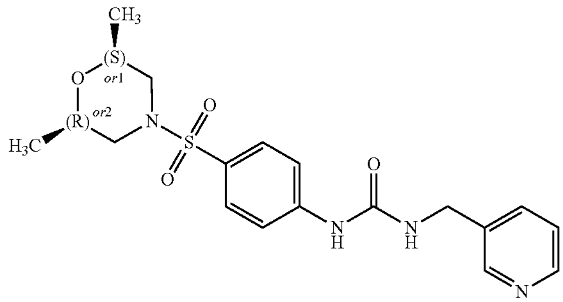 | rel-3-{4-[(2R,6S)-2,6-dimethylmorpholine-4-sulfonyl]phenyl}-1-(pyridin-3-ylmethyl)urea |
| 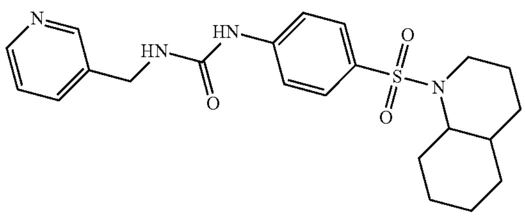 [SMILES: O=C(NCc1cccnc1)Nc1ccc(S(=O)(=O)N2CCCC3CCCCC32)cc1] | 1-[4-(decahydroquinoline-1-sulfonyl)phenyl]-3-(pyridin-3-ylmethyl)urea |
| 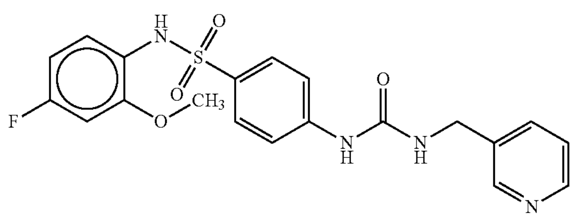 | 3-{4-[(4-fluoro-2-methoxyphenyl)sulfamoyl]phenyl}-1-(pyridin-3-ylmethyl)urea |
| 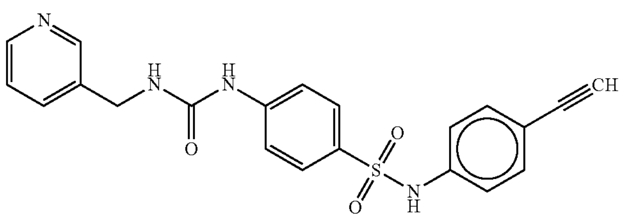 | 1-{4-[(4-ethynylphenyl)sulfamoyl]phenyl}-3-(pyridin-3-ylmethyl)urea |
| 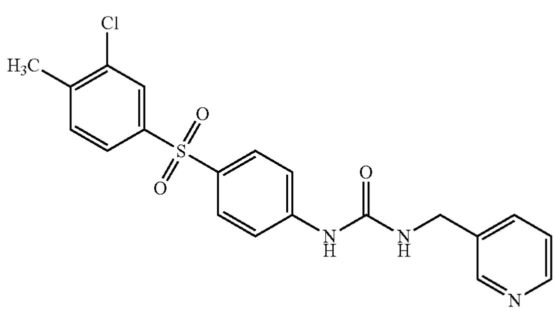 [SMILES: Cc1ccc(S(=O)(=O)c2ccc(NC(=O)NCc3cccnc3)cc2)cc1Cl] | 3-{4-[(3-chloro-4-methylbenzene)sulfonyl]phenyl}-1-(pyridin-3-ylmethyl)urea |
| 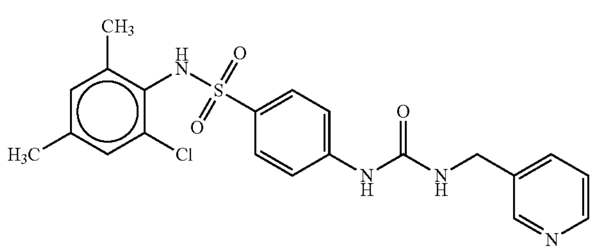 | 3-{4-[(2-chloro-4,6-dimethylphenyl)sulfamoyl]phenyl}-1-(pyridin-3-ylmethyl)urea |

| Structure | Chemical Name |
|---|---|
| 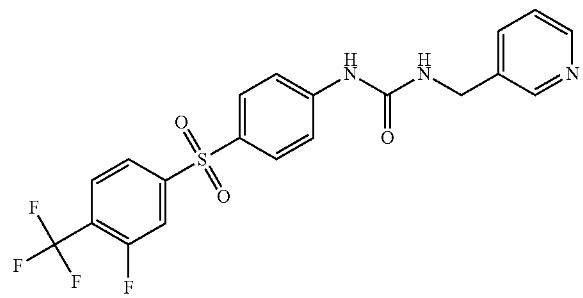 [SMILES: O=C(NCc1cccnc1)Nc1ccc(S(=O)(=O)c2ccc(C(F)(F)F)c(F)c2)cc1] | 3-(4-{[3-fluoro-4-(trifluoromethyl)benzene]sulfonyl}phenyl)-1-(pyridin-3-ylmethyl)urea |
| 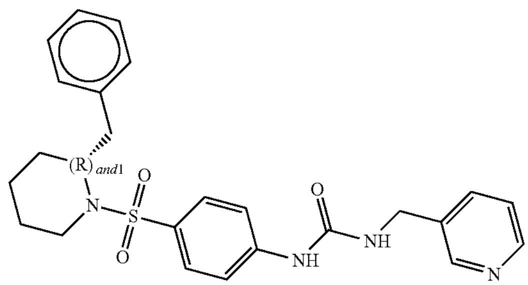 | 1-{4-[(2R)-2-benzylpiperidine-1-sulfonyl]phenyl}-3-(pyridin-3-ylmethyl)urea |
| 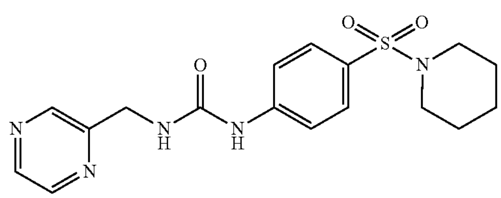 [SMILES: O=C(NCc1cnccn1)Nc1ccc(S(=O)(=O)N2CCCCC2)cc1] | 3-[4-(piperidine-1-sulfonyl)phenyl]-1-(pyrazin-2-ylmethyl)urea |
| 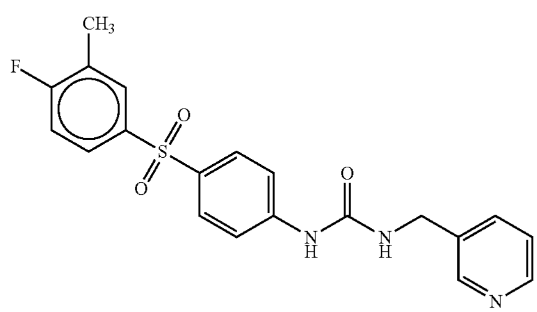 | 3-{4-[(4-fluoro-3-methylbenzene)sulfonyl]phenyl}-1-(pyridin-3-ylmethyl)urea |
| 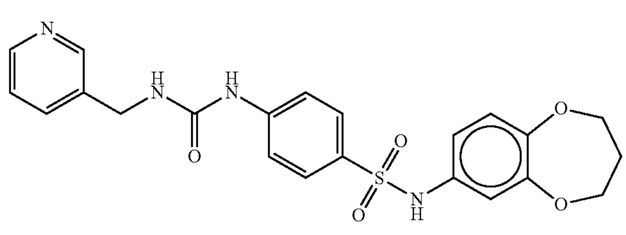 | 1-{4-[(3,4-dihydro-2H-1,5-benzodioxepin-7-yl)sulfamoyl]phenyl}-3-(pyridin-3-ylmethyl)urea |

| Structure | Chemical Name |
|---|---|
| 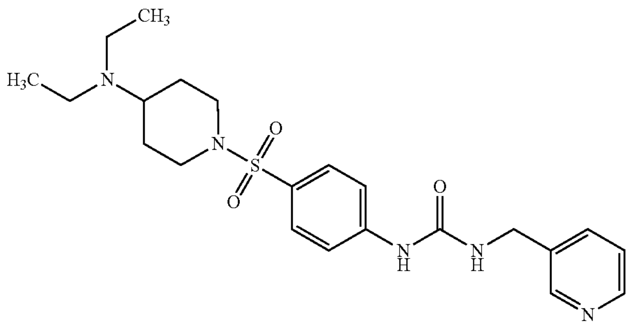 [SMILES: CCN(CC)C1CCN(S(=O)(=O)c2ccc(NC(=O)NCc3cccnc3)cc2)CC1] | 3-{4-[4-(diethylamino)piperidine-1-sulfonyl]phenyl}-1-(pyridin-3-ylmethyl)urea |
| 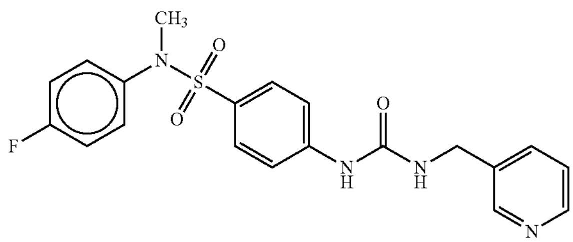 | 3-{4-[(4-fluorophenyl)(methyl)sulfamoyl]phenyl}-1-(pyridin-3-ylmethyl)urea |
| 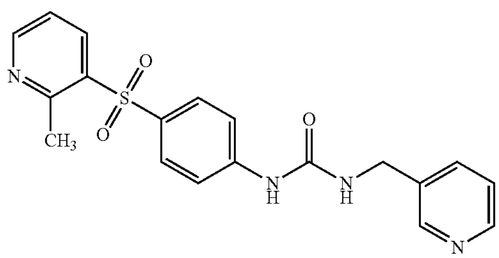 [SMILES: Cc1ncccc1S(=O)(=O)c1ccc(NC(=O)NCc2cccnc2)cc1] | 3-[4-(2-methylpyridine-3-sulfonyl)phenyl]-1-(pyridin-3-ylmethyl)urea |
| 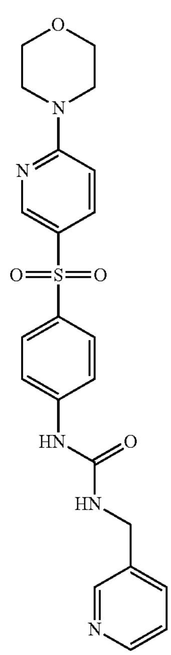 [SMILES: O=C(NCc1cccnc1)Nc1ccc(S(=O)(=O)c2ccc(N3CCOCC3)nc2)cc1] | 1-{4-[6-(morpholin-4-yl)pyridine-3-sulfonyl]phenyl}-3-(pyridin-3-ylmethyl)urea |

| Structure | Chemical Name |
|---|---|
| 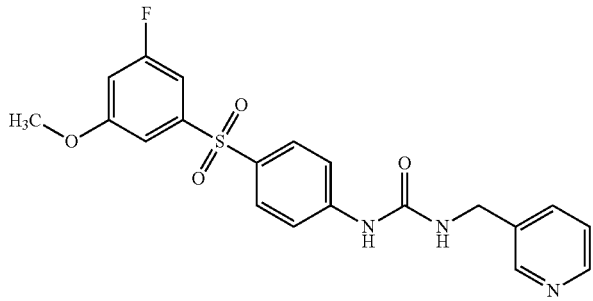 [SMILES: COc1cc(F)cc(S(=O)(=O)c2ccc(NC(=O)NCc3cccnc3)cc2)c1] | 3-{4-[(3-fluoro-5-methoxybenzene)sulfonyl]phenyl}-1-(pyridin-3-ylmethyl)urea |
| 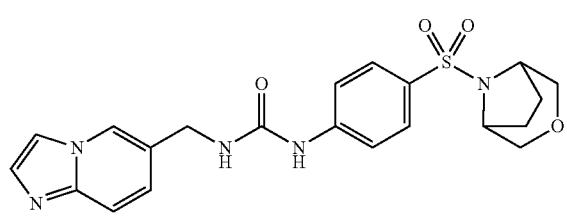 [SMILES: O=C(NCc1ccc2nccn2c1)Nc1ccc(S(=O)(=O)N2C3CCC2COC3)cc1] | 3-{imidazo[1,2-a]pyridin-6-ylmethyl}-1-(4-{3-oxa-8-azabicyclo[3.2.1]octane-8-sulfonyl}phenyl)urea |
| 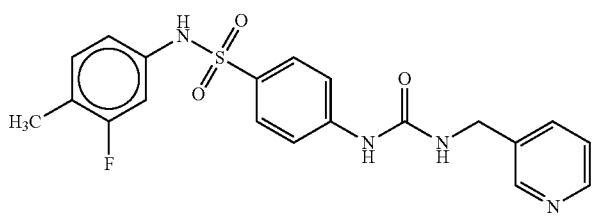 | 3-{4-[(3-fluoro-4-methylphenyl)sulfamoyl]phenyl}-1-(pyridin-3-ylmethyl)urea |
| 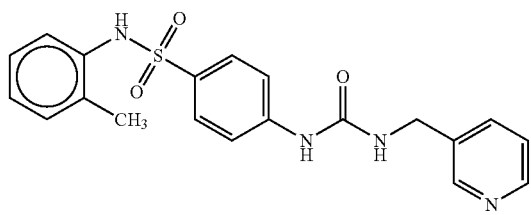 | 3-{4-[(2-methylphenyl)sulfamoyl]phenyl}-1-(pyridin-3-ylmethyl)urea |
| 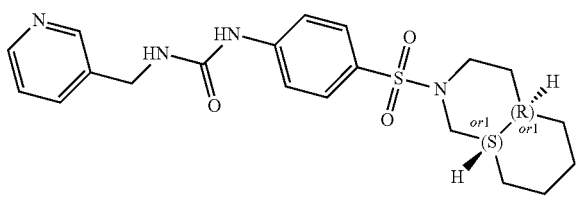 | rel-3-{4-[(4aR,8aS)-decahydroisoquinoline-2-sulfonyl]phenyl}-1-(pyridin-3-ylmethyl)urea |
| 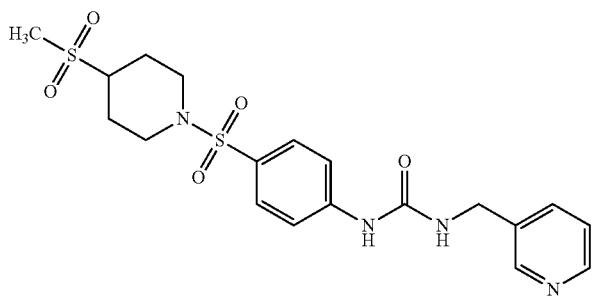 [SMILES: CS(=O)(=O)C1CCN(S(=O)(=O)c2ccc(NC(=O)NCc3cccnc3)cc2)CC1] | 3-[4-(4-methanesulfonylpiperidine-1-sulfonyl)phenyl]-1-(pyridin-3-ylmethyl)urea |

-continued

| Structure | Chemical Name |
|---|---|
| 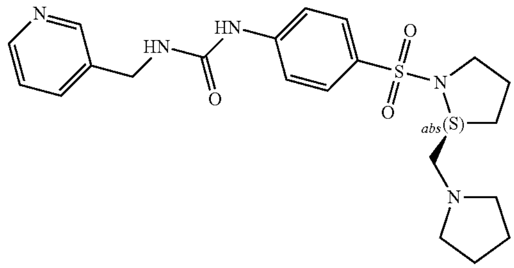 | 3-(pyridin-3-ylmethyl)-1-{4-[(2S)-2-(pyrrolidin-1-ylmethyl)pyrrolidine-1-sulfonyl]phenyl}urea |
| 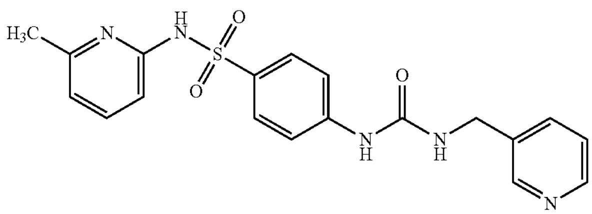 [SMILES: Cc1cccc(NS(=O)(=O)c2ccc(NC(=O)NCc3cccnc3)cc2)n1] | 3-{4-[(6-methylpyridin-2-yl)sulfamoyl]phenyl}-1-(pyridin-3-ylmethyl)urea |
| 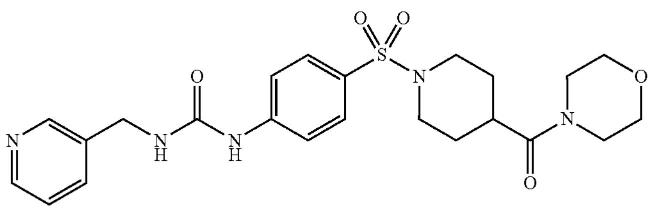 [SMILES: O=C(NCc1cccnc1)Nc1ccc(S(=O)(=O)N2CCC(C(=O)N3CCOCC3)CC2)cc1] | 3-(4-{4-[(morpholin-4-yl)carbonyl]piperidine-1-sulfonyl}phenyl)-1-(pyridin-3-ylmethyl)urea |
| 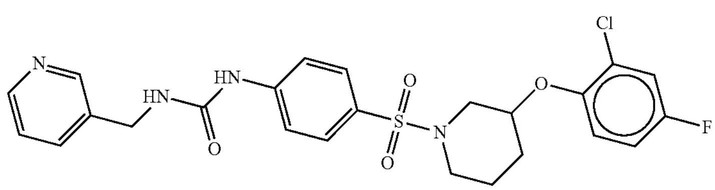 | 3-{4-[3-(2-chloro-4-fluorophenoxy)piperidine-1-sulfonyl]phenyl}-1-(pyridin-3-ylmethyl)urea |
| 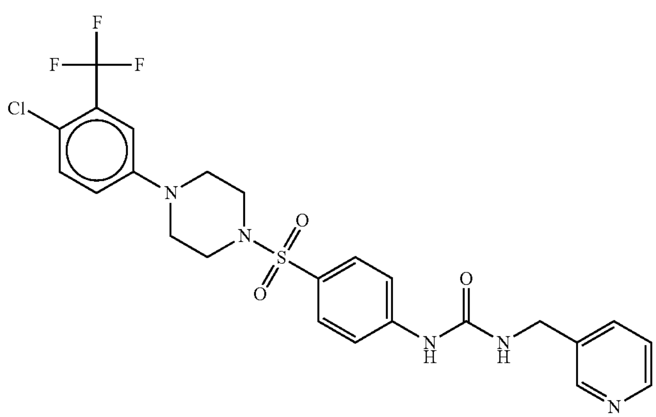 | 3-(4-{4-[4-chloro-3-(trifluoromethyl)phenyl]piperazine-1-sulfonyl}phenyl)-1-(pyridin-3-ylmethyl)urea |
| 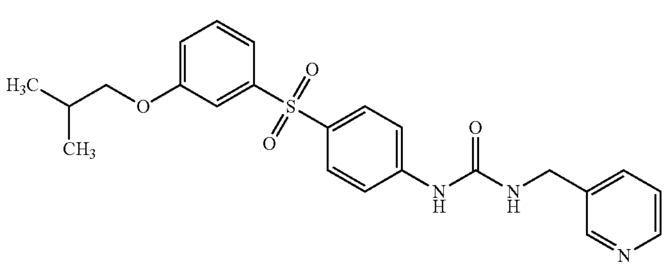 [SMILES: CC(C)COc1cccc(S(=O)(=O)c2ccc(NC(=O)NCc3cccnc3)cc2)c1] | 3-(4-{[3-(2-methylpropoxy)benzene]sulfonyl}phenyl)-1-(pyridin-3-ylmethyl)urea |

-continued

| Structure | Chemical Name |
|---|---|
| 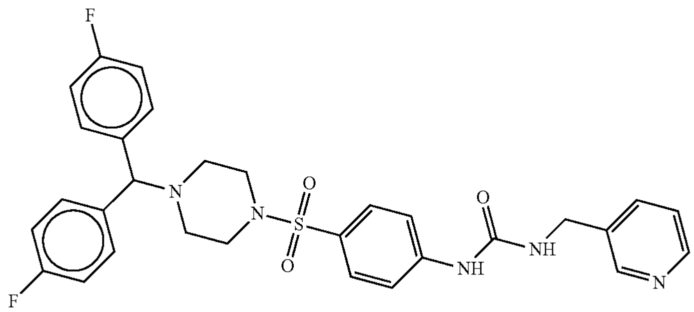 | 3-(4-{4-[bis(4-fluorophenyl)methyl]piperazine-1-sulfonyl}phenyl)-1-(pyridin-3-ylmethyl)urea |
| 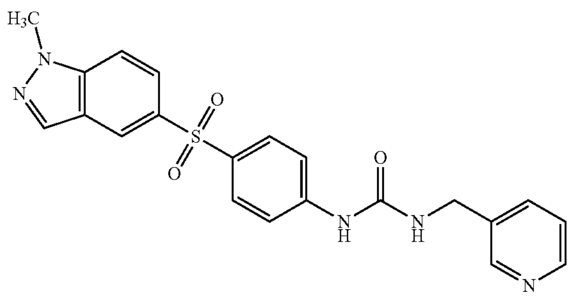 [SMILES: Cn1ncc2cc(S(=O)(=O)c3ccc(NC(=O)NCc4cccnc4)cc3)ccc21] | 3-[4-(1-methyl-1H-indazole-5-sulfonyl)phenyl]-1-(pyridin-3-ylmethyl)urea |
| 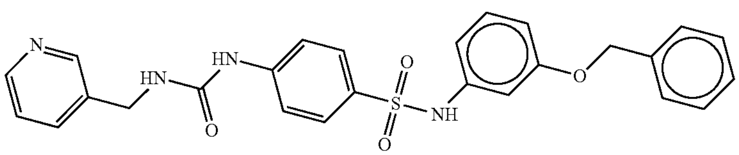 | 1-(4-{[3-(benzyloxy)phenyl]sulfamoyl}phenyl)-3-(pyridin-3-ylmethyl)urea |
| 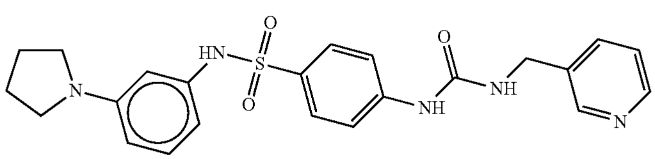 | 3-(pyridin-3-ylmethyl)-1-(4-{[3-(pyrrolidin-1-yl)phenyl]sulfamoyl}phenyl)urea |
| 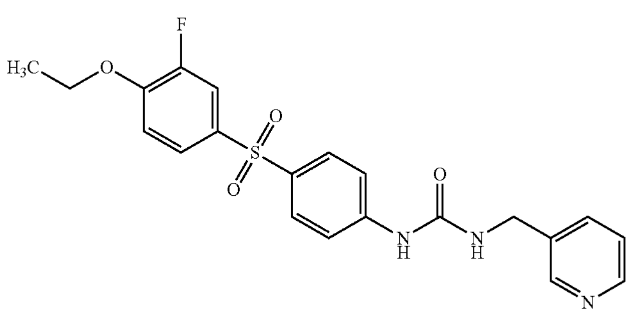 [SMILES: CCOc1ccc(S(=O)(=O)c2ccc(NC(=O)NCc3cccnc3)cc2)cc1F] | 3-{4-[(4-ethoxy-3-fluorobenzene)sulfonyl]phenyl}-1-(pyridin-3-ylmethyl)urea |
| 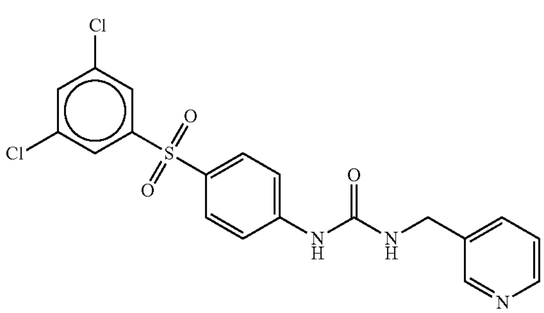 | 3-{4-[(3,5-dichlorobenzene)sulfonyl]phenyl}-1-(pyridin-3-ylmethyl)urea |

-continued

| Structure | Chemical Name |
|---|---|
| 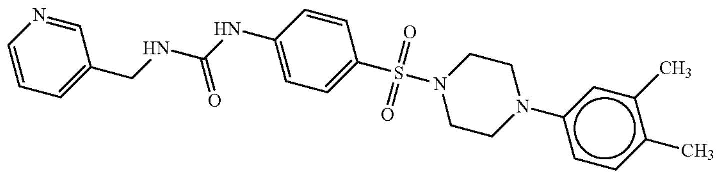 | 4-{4-[3,4-dimethylphenyl)piperazine-1-sulfonyl]phenyl}-1-(pyridin-3-ylmethyl)urea |
| 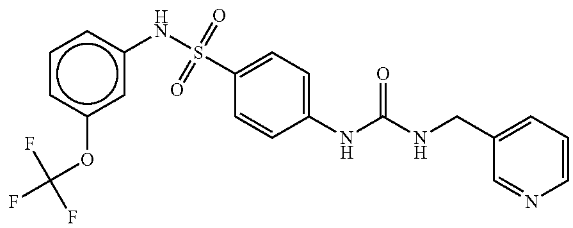 | 1-(pyridin-3-ylmethyl)-3-(4-{[3-(trifluoromethoxy)phenyl]sulfamoyl}phenyl)urea |
| 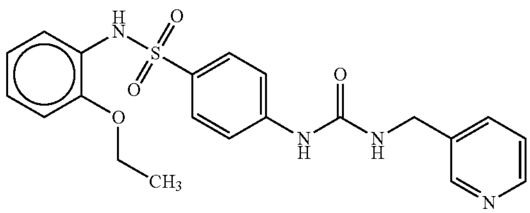 | 3-{4-[(2-ethoxyphenyl)sulfamoyl]phenyl}-1-(pyridin-3-ylmethyl)urea |
| 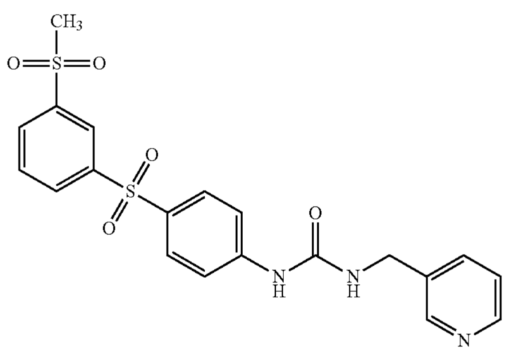 [SMILES: CS(=O)(=O)c1cccc(S(=O)(=O)c2ccc(NC(=O)NCc3cccnc3)cc2)c1] | 3-{4-[(3-methanesulfonylbenzene)sulfonyl]phenyl}-1-(pyridin-3-ylmethyl)urea |
| 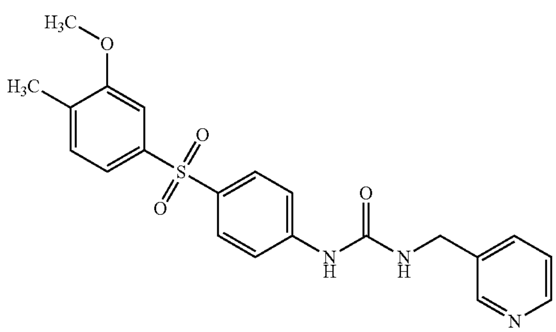 [SMILES: COc1cc(S(=O)(=O)c2ccc(NC(=O)NCc3cccnc3)cc2)ccc1C] | 3-{4-[(3-methoxy-4-methylbenzene)sulfonyl]phenyl}-1-(pyridin-3-ylmethyl)urea |
| 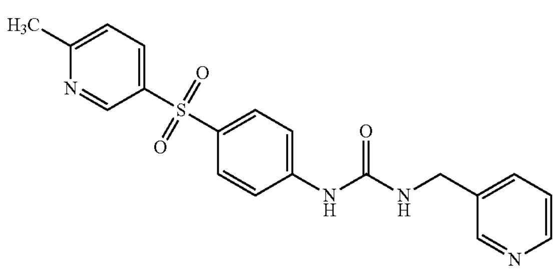 [SMILES: Cc1ccc(S(=O)(=O)c2ccc(NC(=O)NCc3cccnc3)cc2)cn1] | 3-[4-(6-methylpyridine-3-sulfonyl)phenyl]-1-(pyridin-3-ylmethyl)urea |

| Structure | Chemical Name |
|---|---|
| 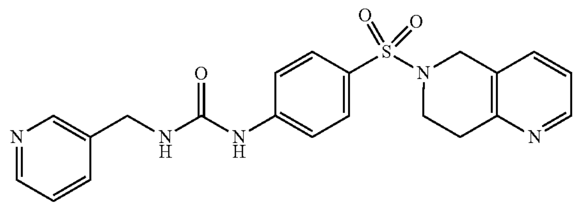 [SMILES: O=C(NCc1cccnc1)Nc1ccc(S(=O)(=O)N2CCc3ncccc3C2)cc1] | 3-(pyridin-3-ylmethyl)-1-[4-(5,6,7,8-tetrahydro-1,6-naphthyridine-6-sulfonyl)phenyl]urea |
| 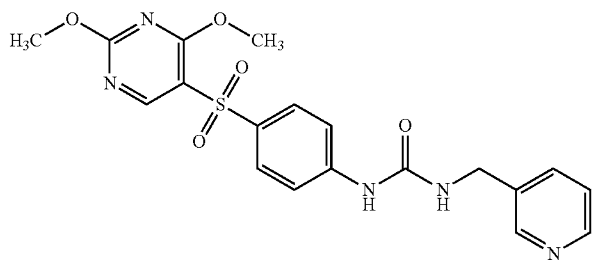 [SMILES: COc1ncc(S(=O)(=O)c2ccc(NC(=O)NCc3cccnc3)cc2)c(OC)n1] | 3-[4-(2,4-dimethoxypyrimidine-5-sulfonyl)phenyl]-1-(pyridin-3-ylmethyl)urea |
| 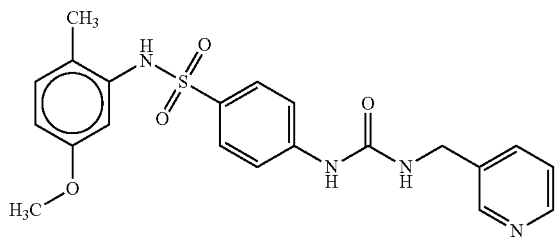 | 3-{4-[(5-methoxy-2-methylphenyl)sulfamoyl]phenyl}-1-(pyridin-3-ylmethyl)urea |
| 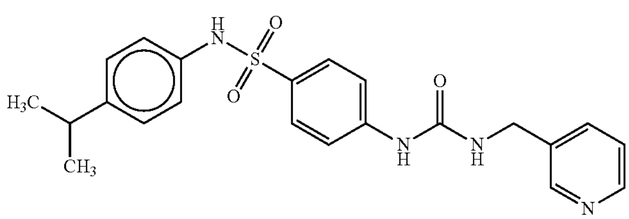 | 3-(4-{[4-(propan-2-yl)phenyl]sulfamoyl}phenyl)-1-(pyridin-3-ylmethyl)urea |
| 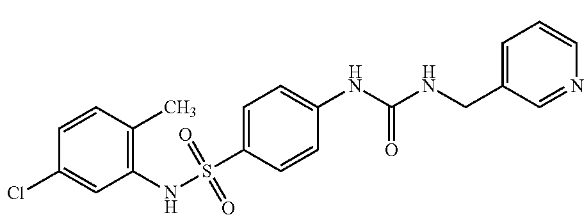 [SMILES: Cc1ccc(Cl)cc1NS(=O)(=O)c1ccc(NC(=O)NCc2cccnc2)cc1] | 3-{4-[(5-chloro-2-methylphenyl)sulfamoyl]phenyl}-1-(pyridin-3-ylmethyl)urea |
| 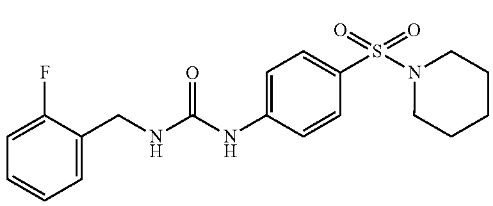 [SMILES: O=C(NCc1ccccc1F)Nc1ccc(S(=O)(=O)N2CCCCC2)cc1] | 3-[(2-fluorophenyl)methyl]-1-[4-(piperidine-1-sulfonyl)phenyl]urea |

-continued

| Structure | Chemical Name |
|---|---|
| 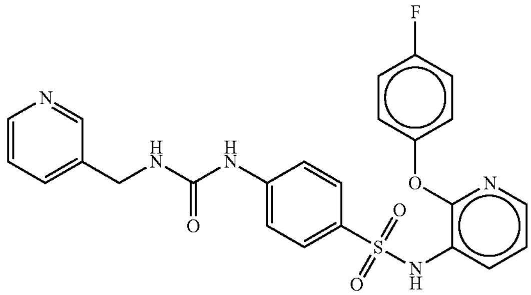 | 3-(4-{[2-(4-fluorophenoxy)pyridin-3-yl]sulfamoyl}phenyl)-1-(pyridin-3-ylmethyl)urea |
| 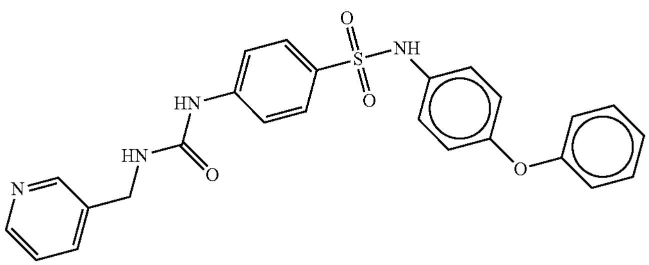 | 1-{4-[(4-phenoxyphenyl)sulfamoyl]phenyl}-3-(pyridin-3-ylmethyl)urea |
| 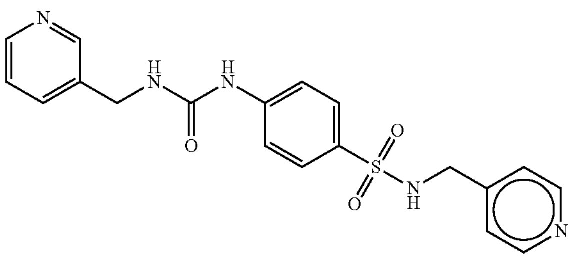 | 3-(pyridin-3-ylmethyl)-1-{4-[(pyridin-4-ylmethyl)sulfamoyl]phenyl}urea |
| 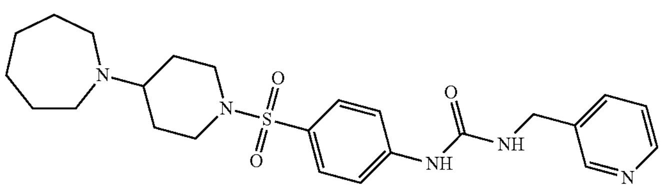 [SMILES: O=C(NCc1cccnc1)Nc1ccc(S(=O)(=O)N2CCC(N3CCCCCC3)CC2)cc1] | 1-{4-[4-(azepan-1-yl)piperidine-1-sulfonyl]phenyl}-3-(pyridin-3-ylmethyl)urea |
| 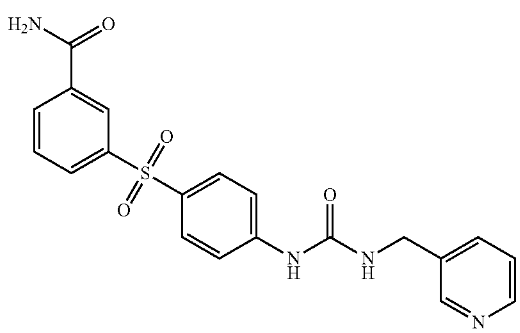 [SMILES: NC(=O)c1cccc(S(=O)(=O)c2ccc(NC(=O)NCc3cccnc3)cc2)c1] | 3-[(4-{[(pyridin-3-ylmethyl)carbamoyl]amino}benzene)sulfonyl]benzamide |

| Structure | Chemical Name |
|---|---|
| 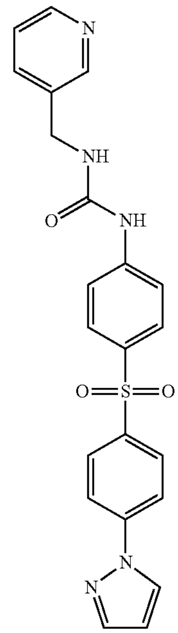 [SMILES: O=C(NCc1cccnc1)Nc1ccc(S(=O)(=O)c2ccc(-n3cccn3)cc2)cc1] | 1-(4-{[4-(1H-pyrazol-1-yl)benzene]sulfonyl}phenyl)-3-(pyridin-3-ylmethyl)urea |
| 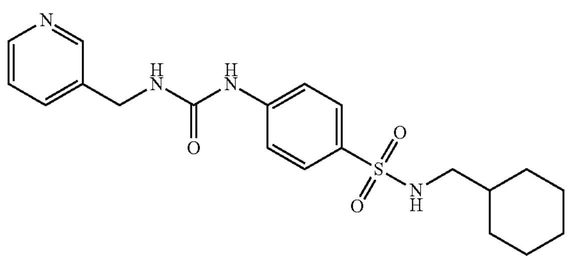 [SMILES: O=C(NCc1cccnc1)Nc1ccc(S(=O)(=O)NCC2CCCCC2)cc1] | 1-{4-[(cyclohexylmethyl)sulfamoyl]phenyl}-3-(pyridin-3-ylmethyl)urea |
| 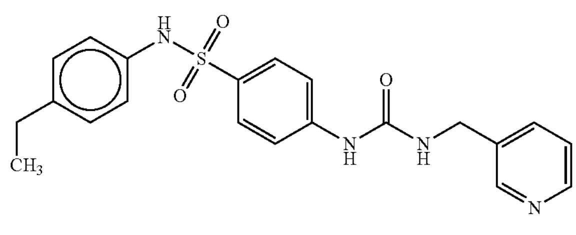 | 3-{4-[(4-ethylphenyl)sulfamoyl]phenyl}-1-(pyridin-3-ylmethyl)urea |
| 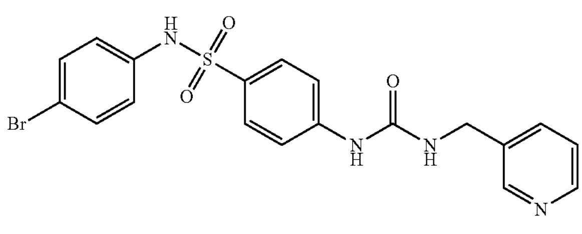 [SMILES: O=C(NCc1cccnc1)Nc1ccc(S(=O)(=O)Nc2ccc(Br)cc2)cc1] | 3-{4-[(4-bromophenyl)sulfamoyl]phenyl}-1-(pyridin-3-ylmethyl)urea |
| 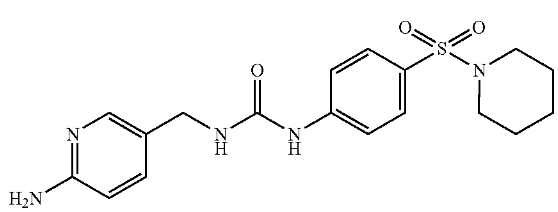 [SMILES: Nc1ccc(CNC(=O)Nc2ccc(S(=O)(=O)N3CCCCC3)cc2)cn1] | 3-[(6-aminopyridin-3-yl)methyl]-1-[4-(piperidine-1-sulfonyl)phenyl]urea |

-continued

| Structure | Chemical Name |
|---|---|
| 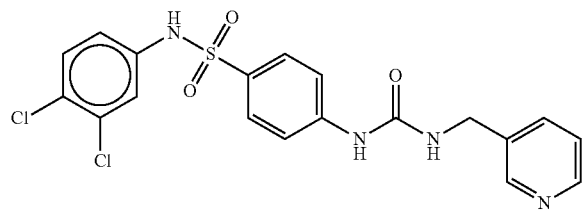 | 3-{4-[(3,4-dichlorophenyl)sulfamoyl]phenyl}-1-(pyridin-3-ylmethyl)urea |
| 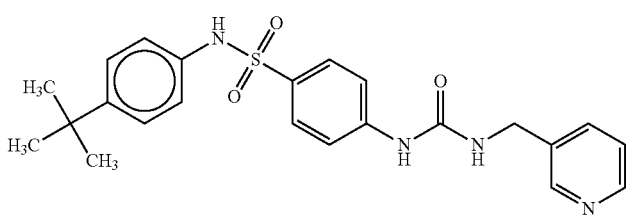 | 3-{4-[(4-tert-butylphenyl)sulfamoyl]phenyl}-1-(pyridin-3-ylmethyl)urea |
| 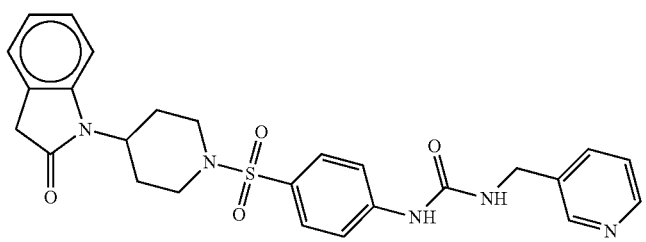 | 1-{4-[4-(2-oxo-2,3-dihydro-1H-indol-1-yl)piperidine-1-sulfonyl]phenyl}-3-(pyridin-3-ylmethyl)urea |
| 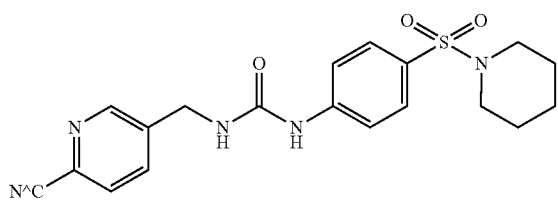 | 1-[(6-isocyanopyridin-3-yl)methyl]-3-[4-(piperidine-1-sulfonyl)phenyl]urea |
| 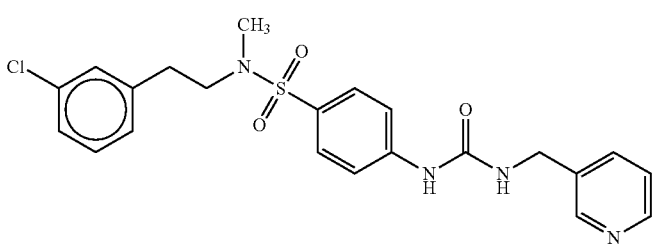 | 3-(4-{[2-(3-chlorophenyl)ethyl](methyl)sulfamoyl}phenyl)-1-(pyridin-3-ylmethyl)urea |
| 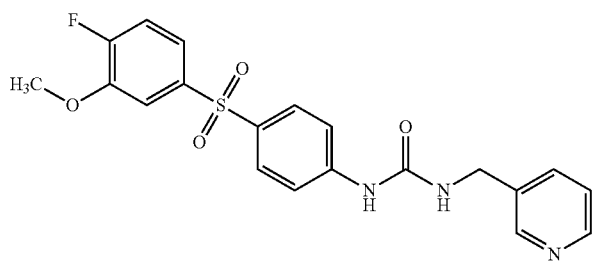 [SMILES: COc1cc(S(=O)(=O)c2ccc(NC(=O)NCc3cccnc3)cc2)ccc1F] | 3-{4-[(4-fluoro-3-methoxybenzene)sulfonyl]phenyl}-1-(pyridin-3-ylmethyl)urea |

-continued

| Structure | Chemical Name |
|---|---|
| 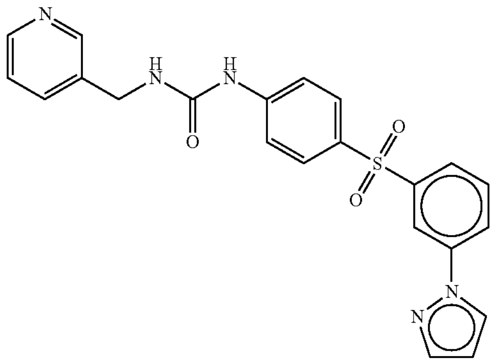 | 1-(4-{[3-(1H-pyrazol-1-yl)benzene]sulfonyl}phenyl)-3-(pyridin-3-ylmethyl)urea |
| 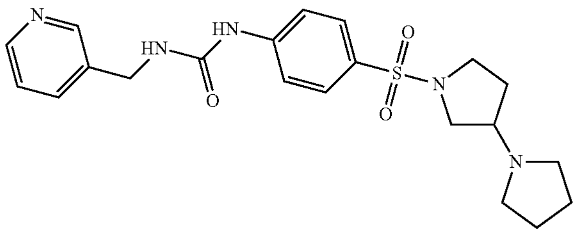 [SMILES: O=C(NCc1cccnc1)Nc1ccc(S(=O)(=O)N2CCC(N3CCCC3)C2)cc1] | 3-(pyridin-3-ylmethyl)-1-{4-[3-(pyrrolidin-1-yl)pyrrolidine-1-sulfonyl]phenyl}urea |
| 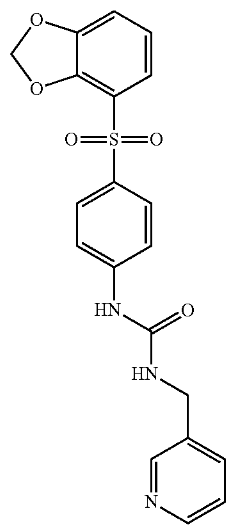 [SMILES: O=C(NCc1cccnc1)Nc1ccc(S(=O)(=O)c2cccc3c2OCO3)cc1] | 1-[4-(2H-1,3-benzodioxole-4-sulfonyl)phenyl]-3-(pyridin-3-ylmethyl)urea |
| 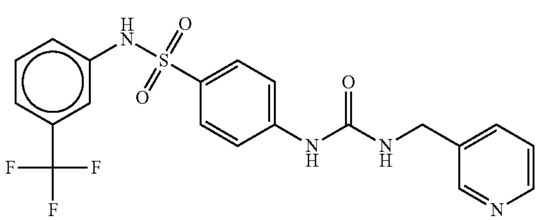 | 1-(pyridin-3-ylmethyl)-3-(4-{[3-(trifluoromethyl)phenyl]sulfamoyl}phenyl)urea |
| 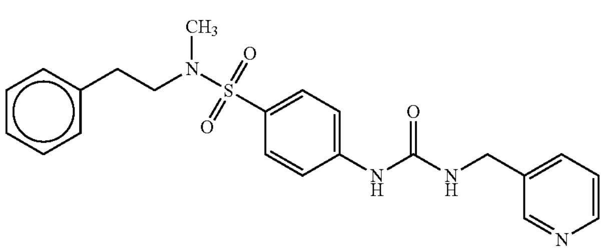 | 3-{4-[methyl(2-phenylethyl)sulfamoyl]phenyl}-1-(pyridin-3-ylmethyl)urea |

| Structure | Chemical Name |
|---|---|
| 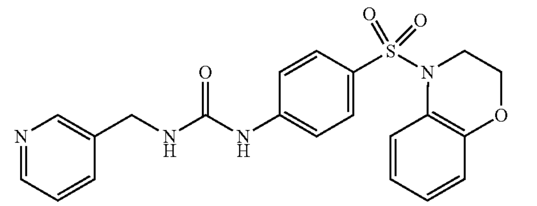 [SMILES: O=C(NCc1cccnc1)Nc1ccc(S(=O)(=O)N2CCOc3ccccc32)cc1] | 1-[4-(3,4-dihydro-2H-1,4-benzoxazine-4-sulfonyl)phenyl]-3-(pyridin-3-ylmethyl)urea |
| 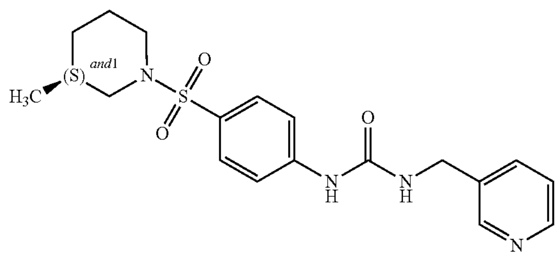 | 3-{4-[(3S)-3-methylpiperidine-1-sulfonyl]phenyl}-1-(pyridin-3-ylmethyl)urea |
| 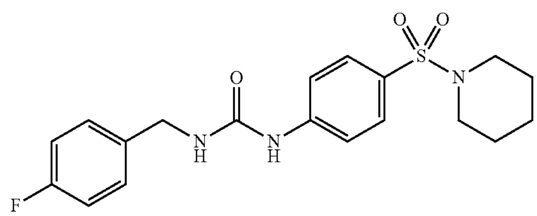 [SMILES: O=C(NCc1ccc(F)cc1)Nc1ccc(S(=O)(=O)N2CCCCC2)cc1] | 1-[(4-fluorophenyl)methyl]-3-[4-(piperidine-1-sulfonyl)phenyl]urea |
| 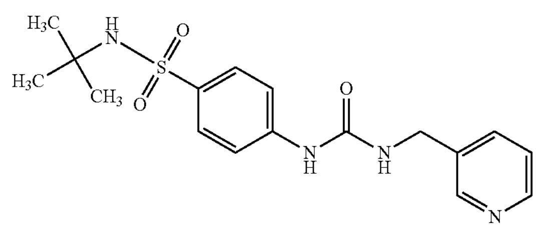 [SMILES: CC(C)(C)NS(=O)(=O)c1ccc(NC(=O)NCc2cccnc2)cc1] | 3-[4-(tert-butylsulfamoyl)phenyl]-1-(pyridin-3-ylmethyl)urea |
| 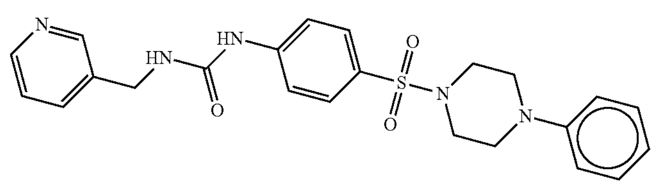 | 1-[4-(4-phenylpiperazine-1-sulfonyl)phenyl]-3-(pyridin-3-ylmethyl)urea |
| 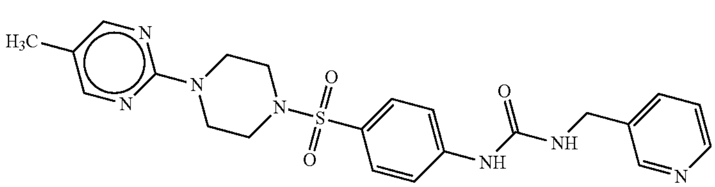 | 3-{4-[4-(5-methylpyrimidin-2-yl)piperazine-1-sulfonyl]phenyl}-1-(pyridin-3-ylmethyl)urea |
| 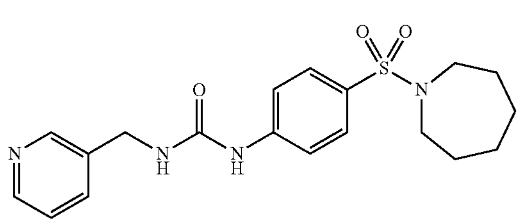 [SMILES: O=C(NCc1cccnc1)Nc1ccc(S(=O)(=O)N2CCCCCC2)cc1] | 3-[4-(azepane-1-sulfonyl)phenyl]-1-(pyridin-3-ylmethyl)urea |

-continued

| Structure | Chemical Name |
|---|---|
| 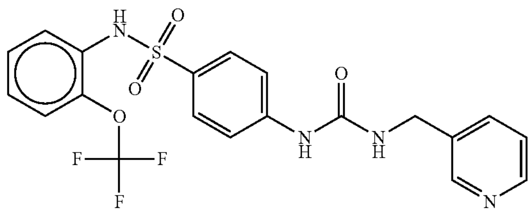 | 1-(pyridin-3-ylmethyl)-3-(4-{[2-(trifluoromethoxy)phenyl]sulfamoyl}phenyl)urea |
| 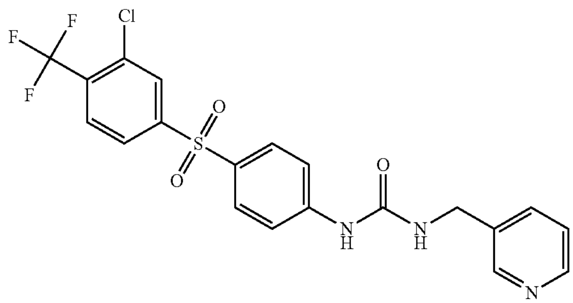 [SMILES: O=C(NCc1cccnc1)Nc1ccc(S(=O)(=O)c2ccc(C(F)(F)F)c(Cl)c2)cc1] | 3-(4-{[3-chloro-4-(trifluoromethyl)benzene]sulfonyl}phenyl)-1-(pyridin-3-ylmethyl)urea |
| 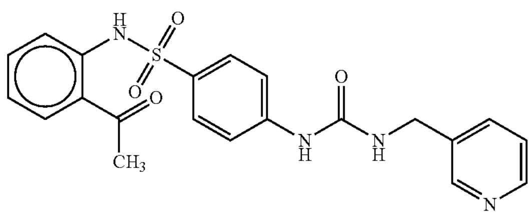 | 3-{4-[(2-acetylphenyl)sulfamoyl]phenyl}-1-(pyridin-3-ylmethyl)urea |
| 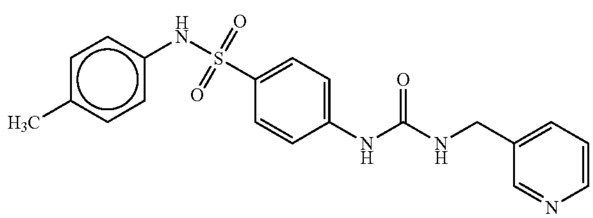 | 3-{4-[(4-methylphenyl)sulfamoyl]phenyl}-1-(pyridin-3-ylmethyl)urea |
| 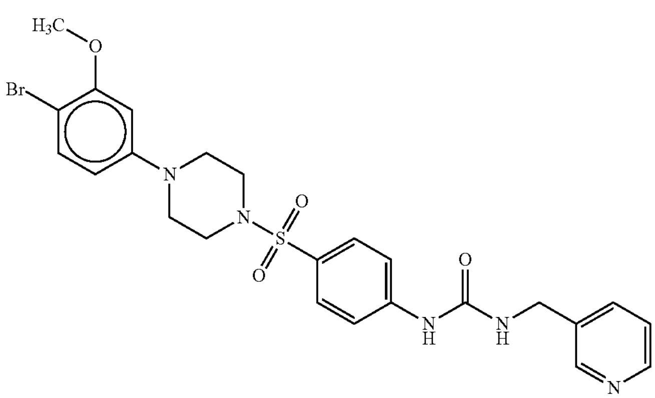 | 3-{4-[4-(4-bromo-3-methoxyphenyl)piperazine-1-sulfonyl]phenyl}-1-(pyridin-3-ylmethyl)urea |
| 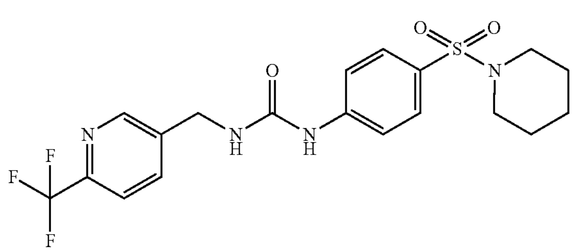 [SMILES: O=C(NCc1ccc(C(F)(F)F)nc1)Nc1ccc(S(=O)(=O)N2CCCCC2)cc1] | 3-[4-(piperidine-1-sulfonyl)phenyl]-1-{[6-(trifluoromethyl)pyridin-3-yl]methyl}urea |

| Structure | Chemical Name |
|---|---|
| 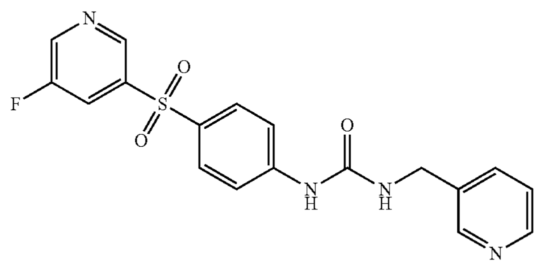 [SMILES: O=C(NCc1cccnc1)Nc1ccc(S(=O)(=O)c2cncc(F)c2)cc1] | 3-[4-(5-fluoropyridine-3-sulfonyl)phenyl]-1-(pyridin-3-ylmethyl)urea |
| 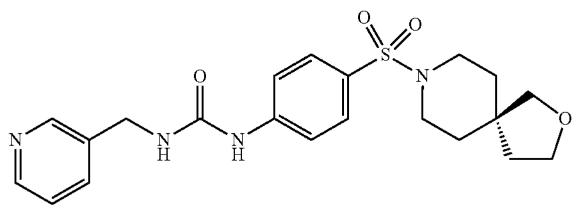 | 1-(4-{2-oxa-8-azaspiro[4.5]decane-8-sulfonyl}phenyl)-3-(pyridin-3-ylmethyl)urea |
| 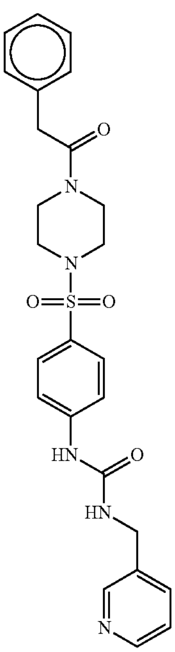 | 1-{4-[4-(2-phenylacetyl)piperazine-1-sulfonyl]phenyl}-3-(pyridin-3-ylmethyl)urea |
| 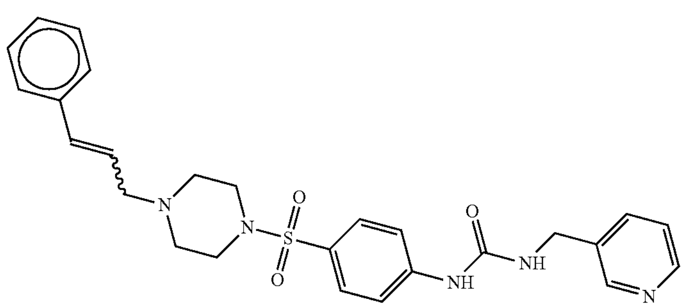 | 1-{4-[4-(3-phenylprop-2-en-1-yl)piperazine-1-sulfonyl]phenyl}-3-(pyridin-3-ylmethyl)urea |

| Structure | Chemical Name |
|---|---|
| 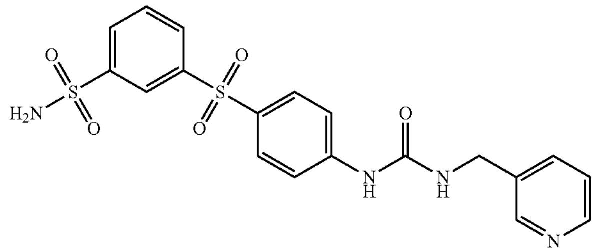 [SMILES: NS(=O)(=O)c1cccc(S(=O)(=O)c2ccc(NC(=O)NCc3cccnc3)cc2)c1] | 1-(pyridin-3-ylmethyl)-3-{4-[(3-sulfamoylbenzene)sulfonyl]phenyl}urea |
| 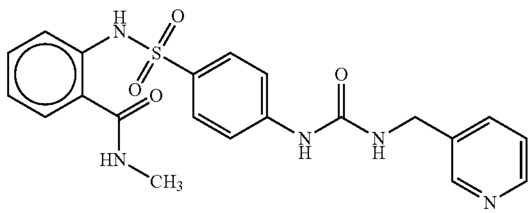 | N-methyl-2-[(4-{[(pyridin-3-ylmethyl)carbamoyl]amino}benzene)sulfonamido]benzamide |
| 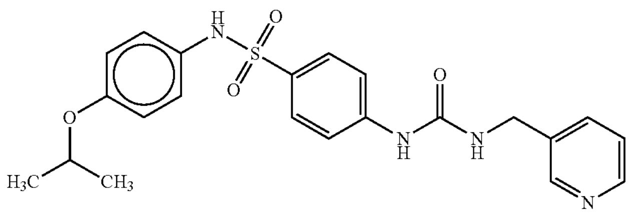 | 3-(4-{[4-(propan-2-yloxy)phenyl]sulfamoyl}phenyl)-1-(pyridin-3-ylmethyl)urea |
| 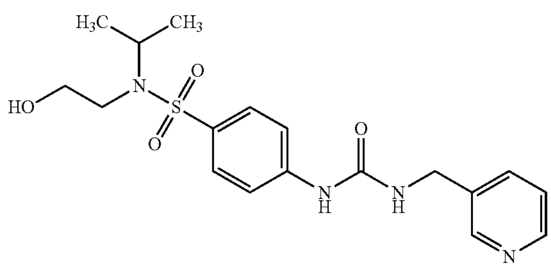 [SMILES: CC(C)N(CCO)S(=O)(=O)c1ccc(NC(=O)NCc2cccnc2)cc1] | 3-{4-[(2-hydroxyethyl)(propan-2-yl)sulfamoyl]phenyl}-1-(pyridin-3-ylmethyl)urea |
| 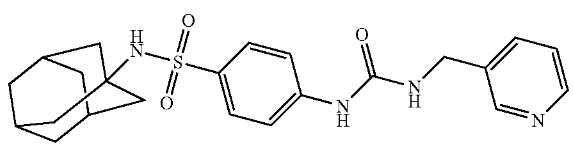 [SMILES: O=C(NCc1cccnc1)Nc1ccc(S(=O)(=O)NC23CC4CC(CC(C4)C2)C3)cc1] | 1-{4-[(adamantan-1-yl)sulfamoyl]phenyl}-3-(pyridin-3-ylmethyl)urea |
| 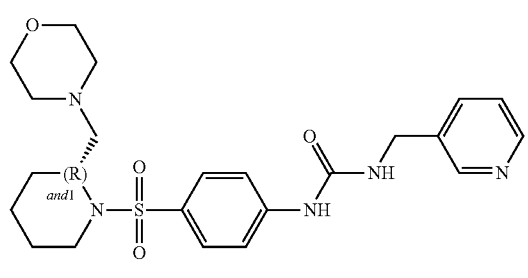 | 1-{4-[(2R)-2-(morpholin-4-ylmethyl)piperidine-1-sulfonyl]phenyl}-3-(pyridin-3-ylmethyl)urea |
| 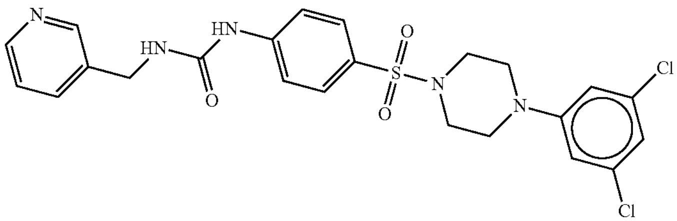 | 3-{4-[4-(3,5-dichlorophenyl)piperazine-1-sulfonyl]phenyl}-1-(pyridin-3-ylmethyl)urea |

-continued

| Structure | Chemical Name |
|---|---|
| 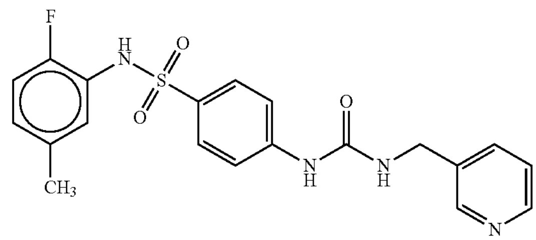 | 3-{4-[(2-fluoro-5-methylphenyl)sulfamoyl]phenyl}-1-(pyridin-3-ylmethyl)urea |
| 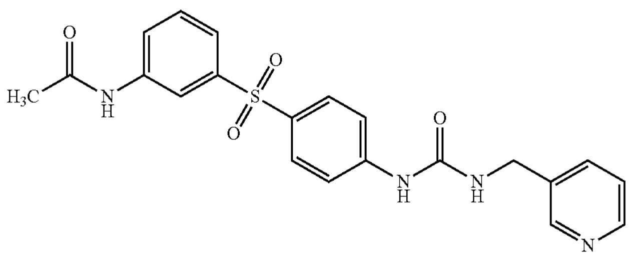 [SMILES: CC(=O)Nc1cccc(S(=O)(=O)c2ccc(NC(=O)NCc3cccnc3)cc2)c1] | N-{3-[(4-{[(pyridin-3-ylmethyl)carbamoyl]amino}benzene)sulfonyl]phenyl}acetamide |
| 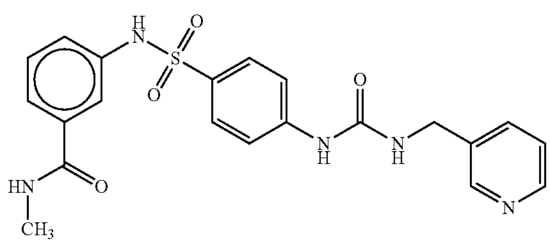 | N-methyl-3-[(4-{[(pyridin-3-ylmethyl)carbamoyl]amino}benzene)sulfonamido]benzamide |
| 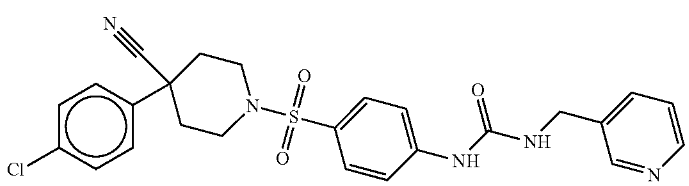 | 3-{4-[4-(4-chlorophenyl)-4-cyanopiperidine-1-sulfonyl]phenyl}-1-(pyridin-3-ylmethyl)urea |
| 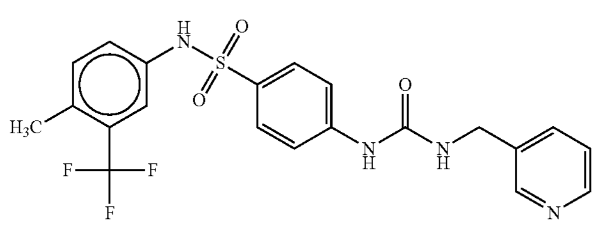 | 3-(4-{[4-methyl-3-(trifluoromethyl)phenyl]sulfamoyl}phenyl)-1-(pyridin-3-ylmethyl)urea |
| 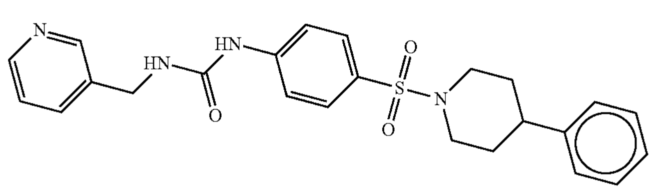 | 1-[4-(4-phenylpiperidine-1-sulfonyl)phenyl]-3-(pyridin-3-ylmethyl)urea |

-continued

| Structure | Chemical Name |
|---|---|
| 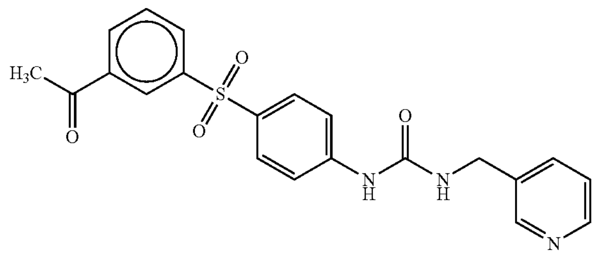 | 3-{4-[(3-acetylbenzene)sulfonyl]phenyl}-1-(pyridin-3-ylmethyl)urea |
| 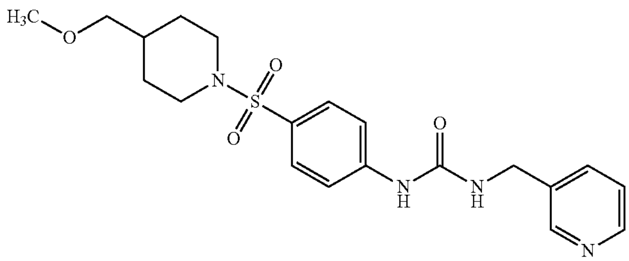 [SMILES: COCC1CCN(S(=O)(=O)c2ccc(NC(=O)NCc3cccnc3)cc2)CC1] | 3-{4-[4-(methoxymethyl)piperidine-1-sulfonyl]phenyl}-1-(pyridin-3-ylmethyl)urea |
| 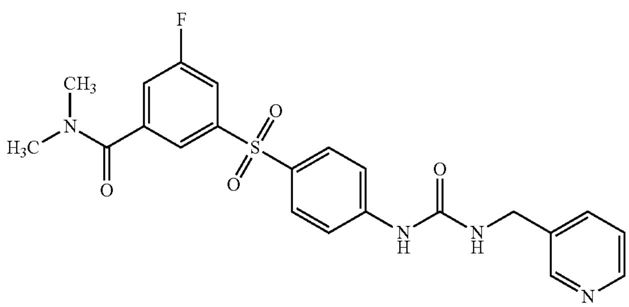 [SMILES: CN(C)C(=O)c1cc(F)cc(S(=O)(=O)c2ccc(NC(=O)NCc3cccnc3)cc2)c1] | 3-fluoro-N,N-dimethyl-5-[(4-{[(pyridin-3-ylmethyl)carbamoyl]amino}benzene)sulfonyl]benzamide |
| 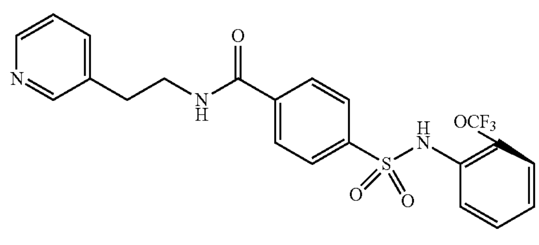 | N-[2-(pyridin-3-yl)ethyl]-4-{[3-(trifluoromethoxy)phenyl]sulfamoyl}benzamide |
| 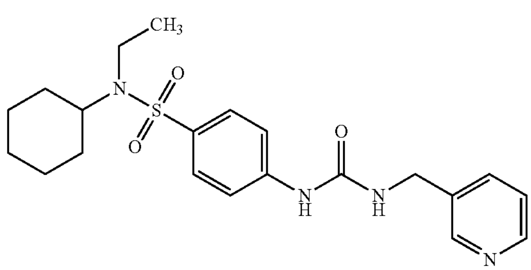 [SMILES: CCN(C1CCCCC1)S(=O)(=O)c1ccc(NC(=O)NCc2cccnc2)cc1] | 3-{4-[cyclohexyl(ethyl)sulfamoyl]phenyl}-1-(pyridin-3-ylmethyl)urea |
| 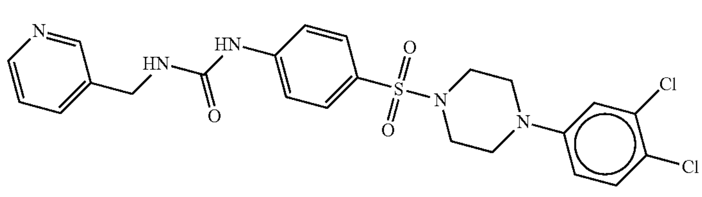 | 3-{4-[4-(3,4-dichlorophenyl)piperazine-1-sulfonyl]phenyl}-1-(pyridin-3-ylmethyl)urea |

| Structure | Chemical Name |
|---|---|
| 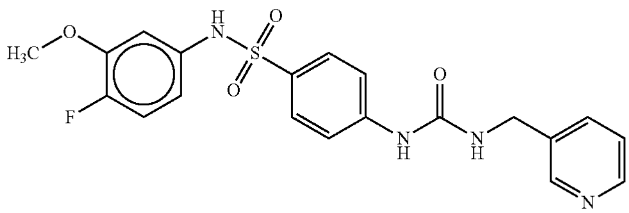 | 3-{4-[(4-fluoro-3-methoxyphenyl)sulfamoyl]phenyl}-1-(pyridin-3-ylmethyl)urea |
| 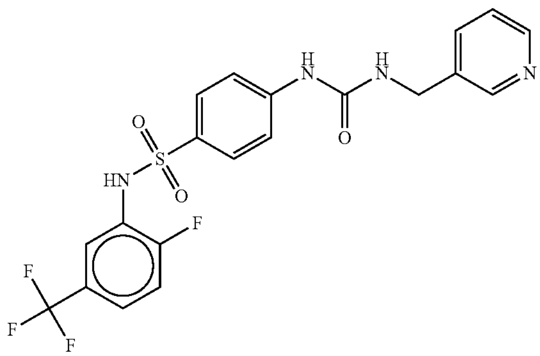 | 3-(4-{[2-fluoro-5-(trifluoromethyl)phenyl]sulfamoyl}phenyl)-1-(pyridin-3-ylmethyl)urea |
| 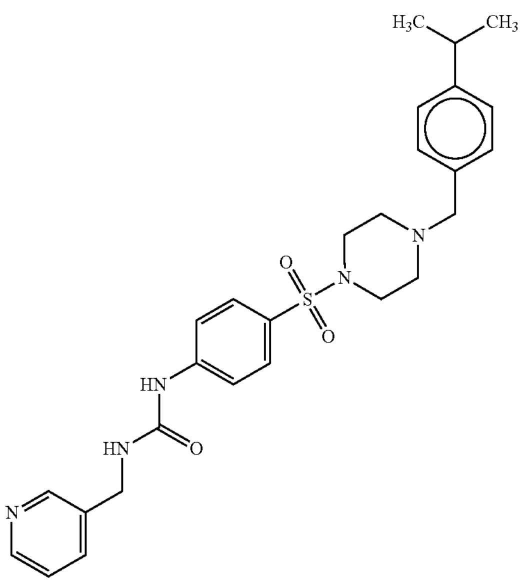 | 3-[4-(4-{[4-(propan-2-yl)phenyl]methyl}piperazine-1-sulfonyl)phenyl]-1-(pyridin-3-ylmethyl)urea |
| 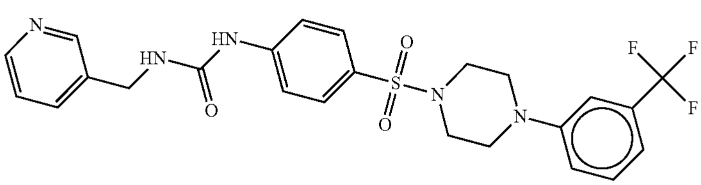 | 1-(pyridin-3-ylmethyl)-3-(4-{4-[3-(trifluoromethyl)phenyl]piperazine-1-sulfonyl}phenyl)urea |
| 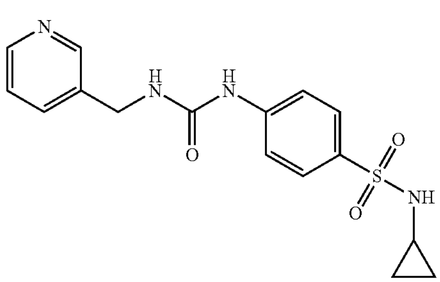 [SMILES: O=C(NCc1cccnc1)Nc1ccc(S(=O)(=O)NC2CC2)cc1] | 1-[4-(cyclopropylsulfamoyl)phenyl]-3-(pyridin-3-ylmethyl)urea |

| Structure | Chemical Name |
|---|---|
| 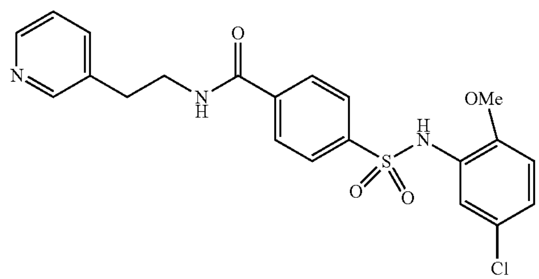 [SMILES: COc1ccc(Cl)cc1NS(=O)(=O)c1ccc(C(=O)NCCc2cccnc2)cc1] | 4-[(5-chloro-2-methoxyphenyl)sulfamoyl]-N-[2-(pyridin-3-yl)ethyl]benzamide |
| 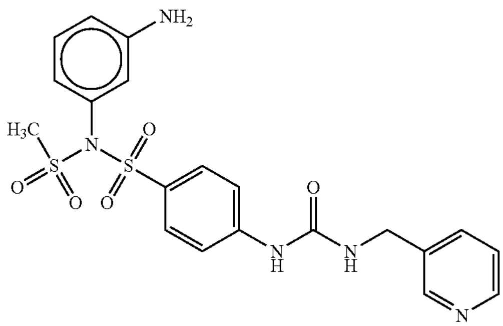 | 3-{4-[(3-aminophenyl)(methanesulfonyl)sulfamoyl]phenyl}-1-(pyridin-3-ylmethyl)urea |
| 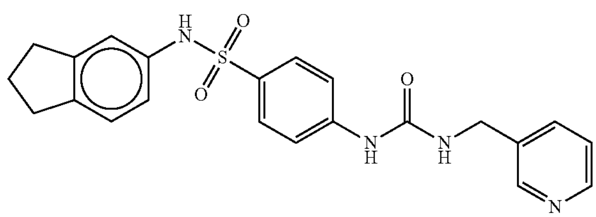 | 1-{4-[(2,3-dihydro-1H-inden-5-yl)sulfamoyl]phenyl}-3-(pyridin-3-ylmethyl)urea |
| 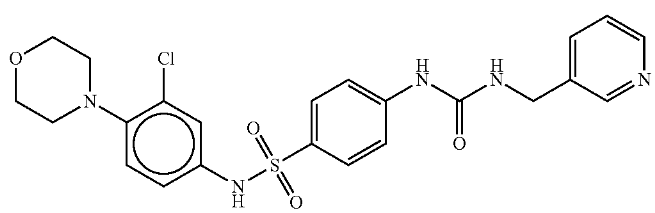 | 3-(4-{[3-chloro-4-(morpholin-4-yl)phenyl]sulfamoyl}phenyl)-1-(pyridin-3-ylmethyl)urea |
| 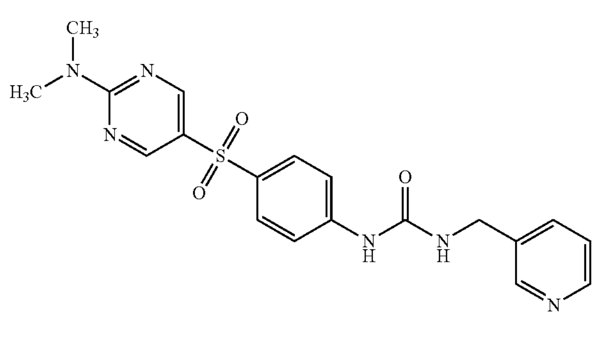 [SMILES: CN(C)c1ncc(S(=O)(=O)c2ccc(NC(=O)NCc3cccnc3)cc2)cn1] | 3-{4-[2-(dimethylamino)pyrimidine-5-sulfonyl]phenyl}-1-(pyridin-3-ylmethyl)urea |

-continued

| Structure | Chemical Name |
|---|---|
| 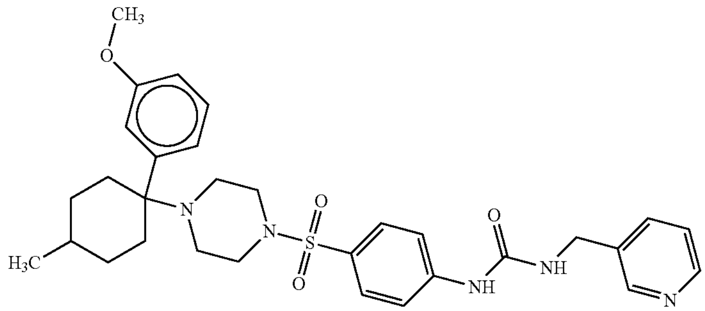 | 3-(4-{4-[1-(3-methoxyphenyl)-4-methylcyclohexyl]piperazine-1-sulfonyl}phenyl)-1-(pyridin-3-ylmethyl)urea |
| 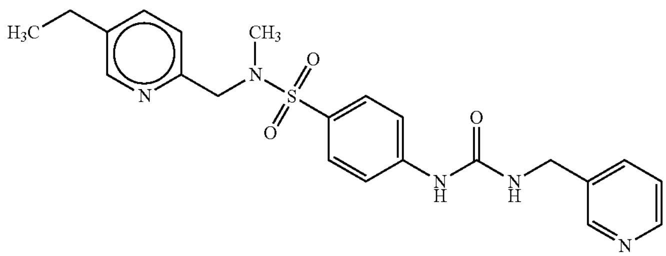 | 3-(4-{[(5-ethylpyridin-2-yl)methyl](methyl)sulfamoyl}phenyl)-1-(pyridin-3-ylmethyl)urea |
| 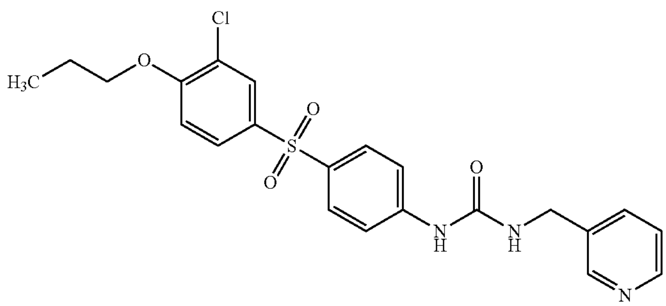 [SMILES: CCCOc1ccc(S(=O)(=O)c2ccc(NC(=O)NCc3cccnc3)cc2)cc1Cl] | 3-{4-[(3-chloro-4-propoxybenzene)sulfonyl]phenyl}-1-(pyridin-3-ylmethyl)urea |
| 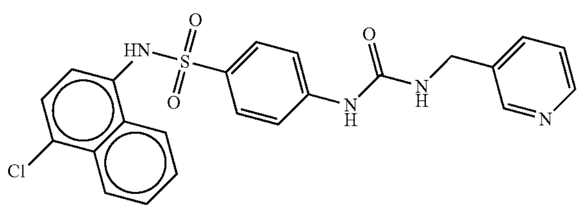 | 3-{4-[(4-chloronaphthalen-1-yl)sulfamoyl]phenyl}-1-(pyridin-3-ylmethyl)urea |
| 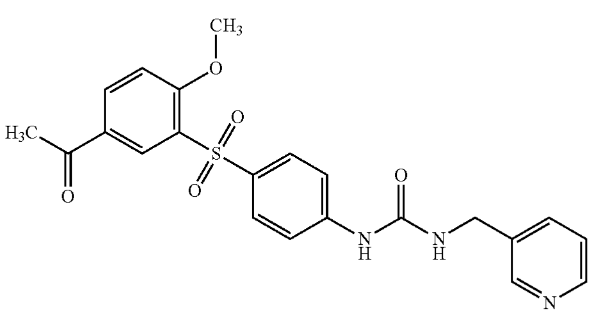 [SMILES: COc1ccc(C(C)=O)cc1S(=O)(=O)c1ccc(NC(=O)NCc2cccnc2)cc1] | 3-{4-[(5-acetyl-2-methoxybenzene)sulfonyl]phenyl}-1-(pyridin-3-ylmethyl)urea |
| 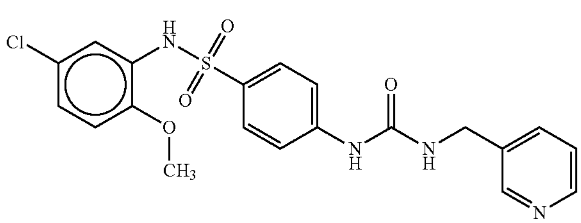 | 3-{4-[(5-chloro-2-methoxyphenyl)sulfamoyl]phenyl}-1-(pyridin-3-ylmethyl)urea |

-continued

| Structure | Chemical Name |
|---|---|
| 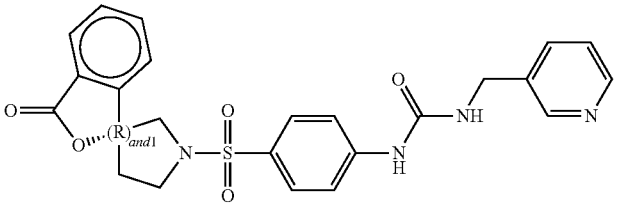 | 1-{4-[(1R)-3-oxo-3H-spiro[2-benzofuran-1,3'-pyrrolidine]-1'-ylsulfonyl]phenyl}-3-(pyridin-3-ylmethyl)urea |
| 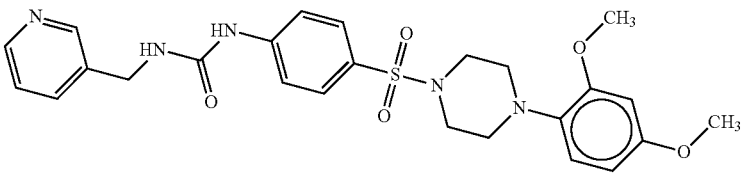 | 3-{4-[4-(2,4-dimethoxyphenyl)piperazine-1-sulfonyl]phenyl}-1-(pyridin-3-ylmethyl)urea |
| 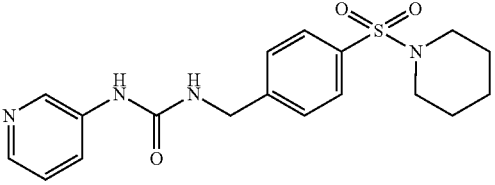 [SMILES: O=C(NCc1ccc(S(=O)(=O)N2CCCCC2)cc1)Nc1cccnc1] | 3-{[4-(piperidine-1-sulfonyl)phenyl]methyl}-1-(pyridin-3-yl)urea |
| 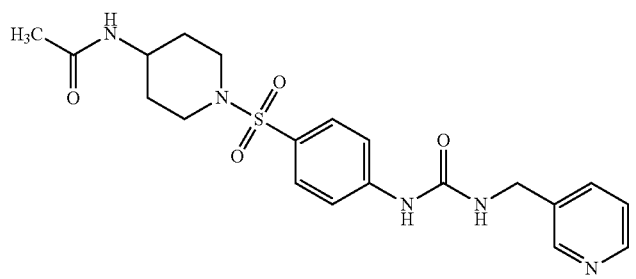 [SMILES: CC(=O)NC1CCN(S(=O)(=O)c2ccc(NC(=O)NCc3cccnc3)cc2)CC1] | N-{1-[(4-{[(pyridin-3-ylmethyl)carbamoyl]amino}benzene)sulfonyl]piperidin-4-yl}acetamide |
| 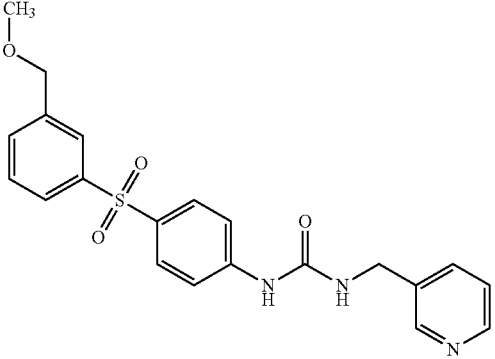 [SMILES: COCc1cccc(S(=O)(=O)c2ccc(NC(=O)NCc3cccnc3)cc2)c1] | 3-(4-{[3-(methoxymethyl)benzene]sulfonyl}phenyl)-1-(pyridin-3-ylmethyl)urea |
| 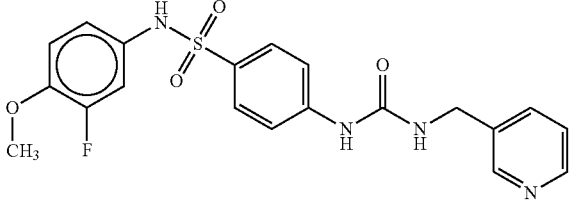 | 3-{4-[(3-fluoro-4-methoxyphenyl)sulfamoyl]phenyl}-1-(pyridin-3-ylmethyl)urea |

-continued

| Structure | Chemical Name |
|---|---|
| 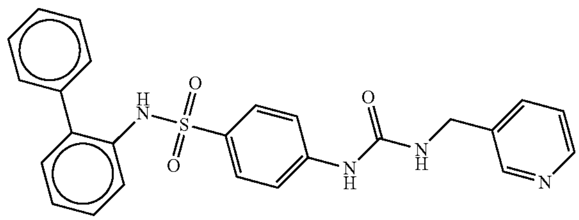 | 1-{4-[(2-phenylphenyl)sulfamoyl]phenyl}-3-(pyridin-3-ylmethyl)urea |
| 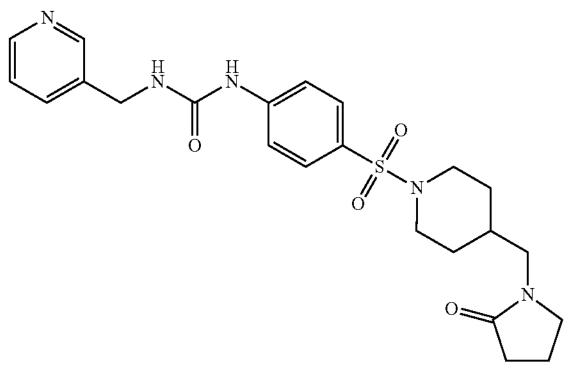 [SMILES: O=C(NCc1cccnc1)Nc1ccc(S(=O)(=O)N2CCC(CN3CCCC3=O)CC2)cc1] | 1-(4-{4-[(2-oxopyrrolidin-1-yl)methyl]piperidine-1-sulfonyl}phenyl)-3-(pyridin-3-ylmethyl)urea |
| 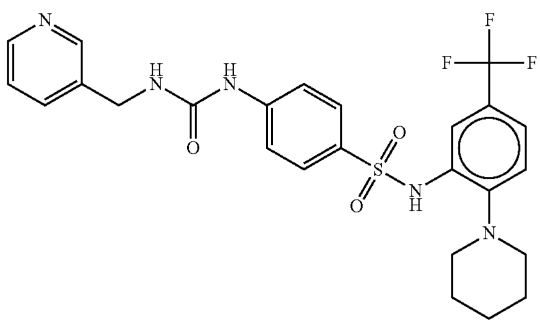 | 3-(4-{[2-(piperidin-1-yl)-5-(trifluoromethyl)phenyl]sulfamoyl}phenyl)-1-(pyridin-3-ylmethyl)urea |
| 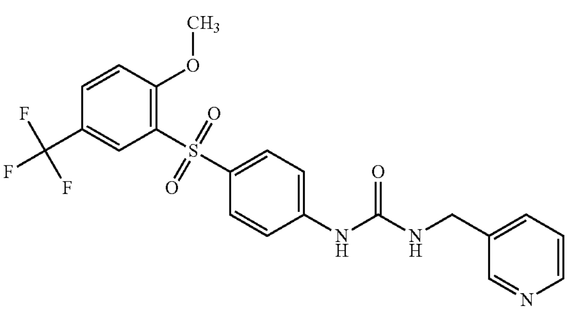 [SMILES: COc1ccc(C(F)(F)F)cc1S(=O)(=O)c1ccc(NC(=O)NCc2cccnc2)cc1] | 3-(4-{[2-methoxy-5-(trifluoromethyl)benzene]sulfonyl}phenyl)-1-(pyridin-3-ylmethyl)urea |
| 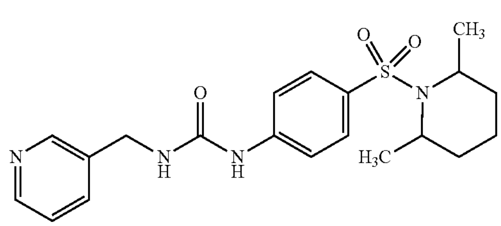 [SMILES: CC1CCCC(C)N1S(=O)(=O)c1ccc(NC(=O)NCc2cccnc2)cc1] | 1-[4-(2,6-dimethylpiperidine-1-sulfonyl)phenyl]-3-(pyridin-3-ylmethyl)urea |

-continued

| Structure | Chemical Name |
|---|---|
| 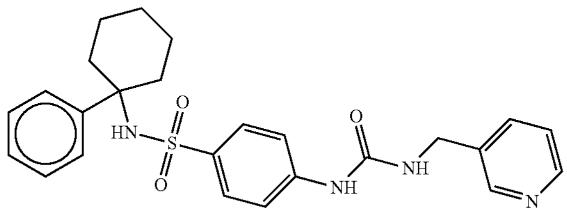 | 1-{4-[(1-phenylcyclohexyl)sulfamoyl]phenyl}-3-(pyridin-3-ylmethyl)urea |
| 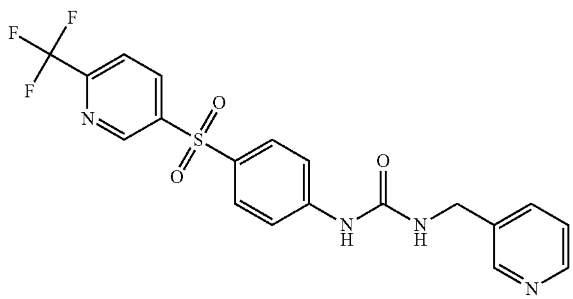 [SMILES: O=C(NCc1cccnc1)Nc1ccc(S(=O)(=O)c2ccc(C(F)(F)F)nc2)cc1] | 1-(pyridin-3-ylmethyl)-3-{4-[6-(trifluoromethyl)pyridine-3-sulfonyl]phenyl}urea |
| 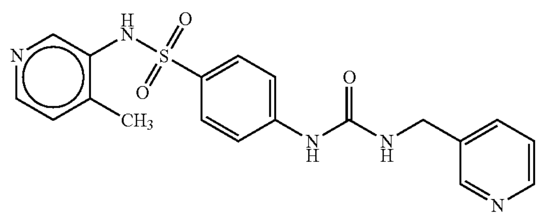 | 3-{4-[(4-methylpyridin-3-yl)sulfamoyl]phenyl}-1-(pyridin-3-ylmethyl)urea |
| 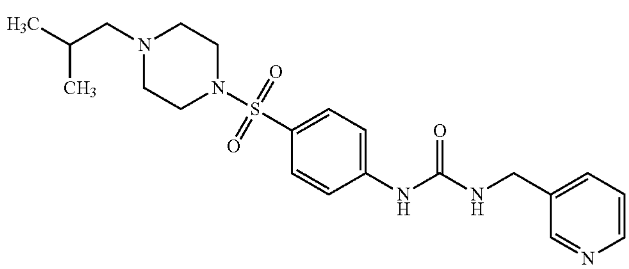 [SMILES: CC(C)CN1CCN(S(=O)(=O)c2ccc(NC(=O)NCc3cccnc3)cc2)CC1] | 3-{4-[4-(2-methylpropyl)piperazine-1-sulfonyl]phenyl}-1-(pyridin-3-ylmethyl)urea |
| 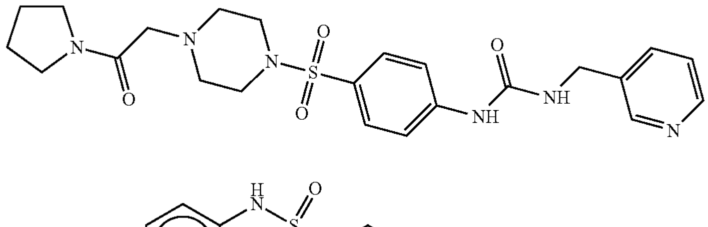 | 1-(4-{4-[2-oxo-2-(pyrrolidin-1-yl)ethyl]piperazine-1-sulfonyl}phenyl)-3-(pyridin-3-ylmethyl)urea |
| 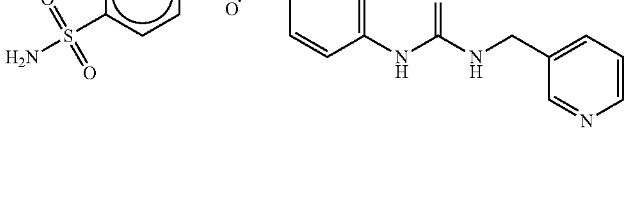 | 1-(pyridin-3-ylmethyl)-3-{4-[(4-sulfamoylphenyl)sulfamoyl]phenyl}urea |

-continued

| Structure | Chemical Name |
|---|---|
| 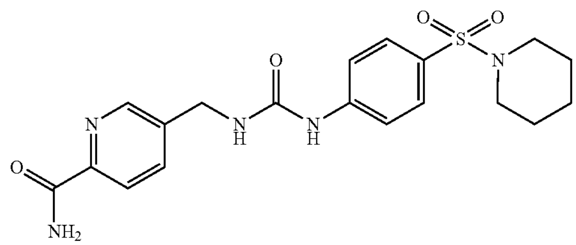 [SMILES: NC(=O)c1ccc(CNC(=O)Nc2ccc(S(=O)(=O)N3CCCCC3)cc2)cn1] | 5-[({[4-(piperidine-1-sulfonyl)phenyl]carbamoyl}amino)methyl]pyridine-2-carboxamide |
| 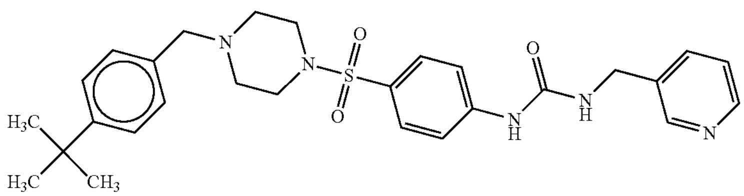 | 3-(4-{4-[(4-tert-butylphenyl)methyl]piperazine-1-sulfonyl}phenyl)-1-(pyridin-3-ylmethyl)urea |
| 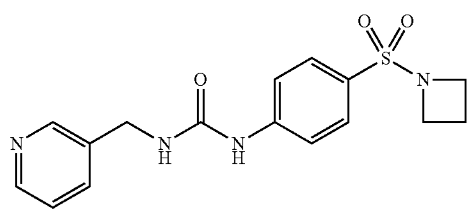 [SMILES: O=C(NCc1cccnc1)Nc1ccc(S(=O)(=O)N2CCC2)cc1] | 3-[4-(azetidine-1-sulfonyl)phenyl]-1-(pyridin-3-ylmethyl)urea |
| 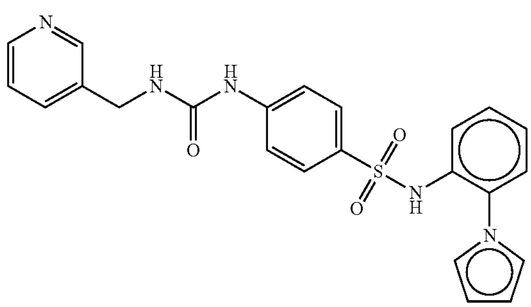 | 3-(pyridin-3-ylmethyl)-1-(4-{[2-(1H-pyrrol-1-yl)phenyl]sulfamoyl}phenyl)urea |
| 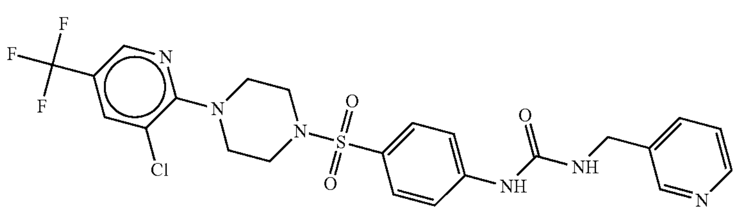 | 3-(4-{4-[3-chloro-5-(trifluoromethyl)pyridin-2-yl]piperazine-1-sulfonyl}phenyl)-1-(pyridin-3-ylmethyl)urea |
| 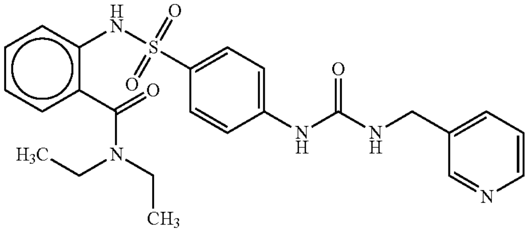 | N,N-diethyl-2-[(4-{[(pyridin-3-ylmethyl)carbamoyl]amino}benzene)sulfonamido]benzamide |

-continued

| Structure | Chemical Name |
|---|---|
| 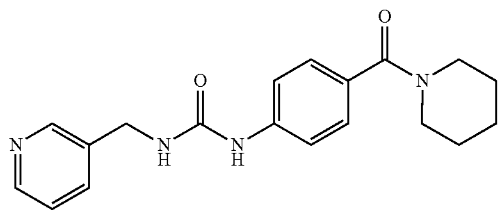 [SMILES: O=C(NCc1cccnc1)Nc1ccc(C(=O)N2CCCCC2)cc1] | 1-{4-[(piperidin-1-yl)carbonyl]phenyl}-3-(pyridin-3-ylmethyl)urea |
| 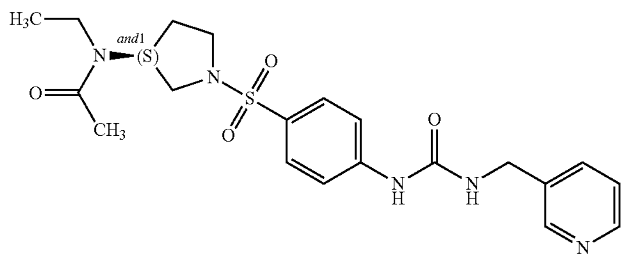 | N-ethyl-N-[(3S)-1-[(4-{[(pyridin-3-ylmethyl)carbamoyl]amino}benzene)sulfonyl]pyrrolidin-3-yl]acetamide |
| 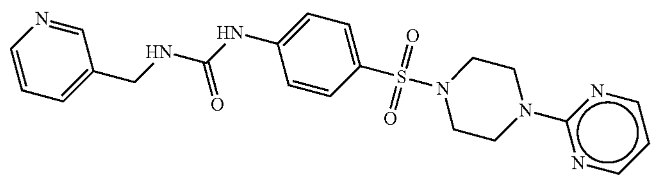 | 3-(pyridin-3-ylmethyl)-1-{4-[4-(pyrimidin-2-yl)piperazine-1-sulfonyl]phenyl}urea |
| 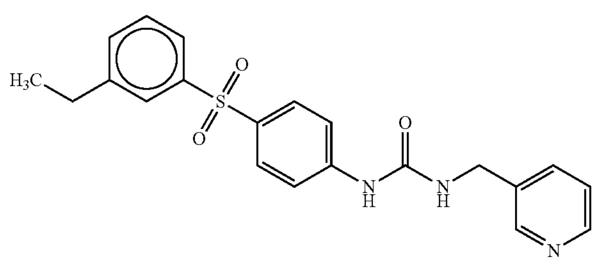 | 3-{4-[(3-ethylbenzene)sulfonyl]phenyl}-1-(pyridin-3-ylmethyl)urea |
| 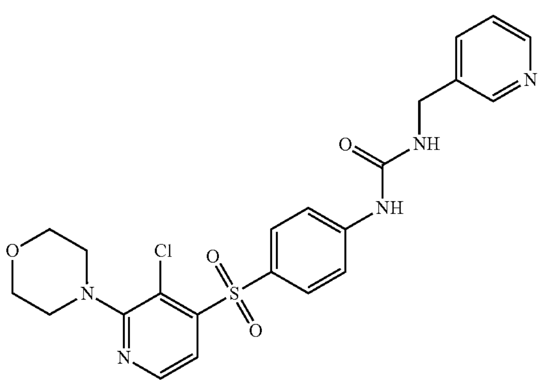 [SMILES: O=C(NCc1cccnc1)Nc1ccc(S(=O)(=O)c2ccnc(N3CCOCC3)c2Cl)cc1] | 3-{4-[3-chloro-2-(morpholin-4-yl)pyridine-4-sulfonyl]phenyl}-1-(pyridin-3-ylmethyl)urea |
| 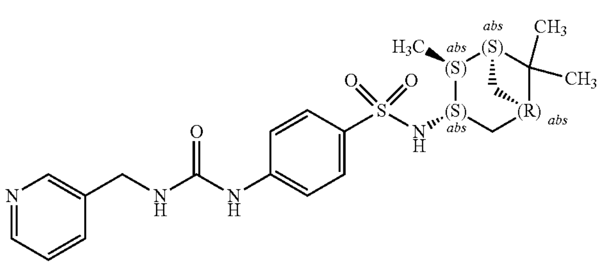 | 3-(pyridin-3-ylmethyl)-1-(4-{[(1S,2S,3S,5R)-2,6,6-trimethylbicyclo[3.1.1]heptan-3-yl]sulfamoyl}phenyl)urea |

-continued

| Structure | Chemical Name |
|---|---|
| 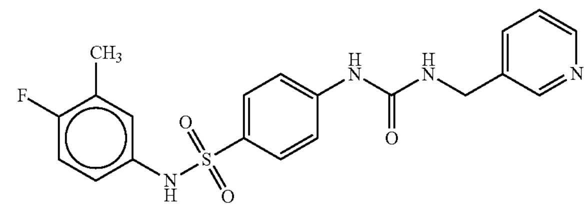 | 3-{4-[(4-fluoro-3-methylphenyl)sulfamoyl]phenyl}-1-(pyridin-3-ylmethyl)urea |
| 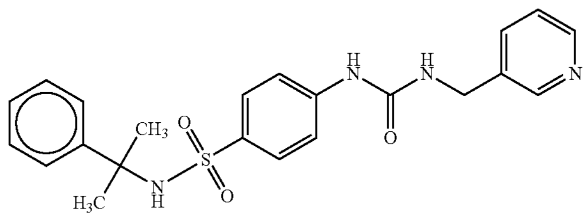 | 3-{4-[(2-phenylpropan-2-yl)sulfamoyl]phenyl}-1-(pyridin-3-ylmethyl)urea |
| 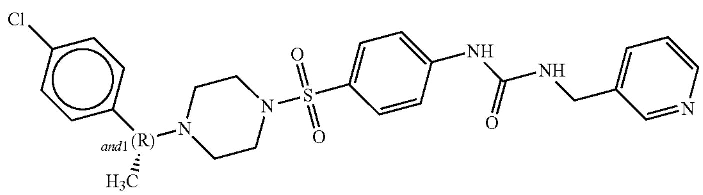 | 3-(4-{4-[(1R)-1-(4-chlorophenyl)ethyl]piperazine-1-sulfonyl}phenyl)-1-(pyridin-3-ylmethyl)urea |
| 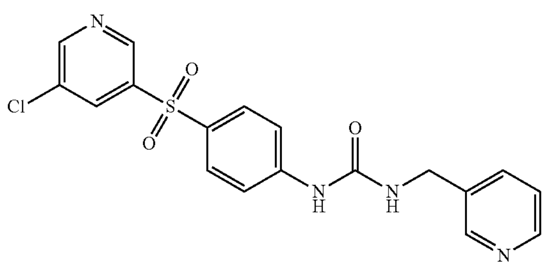 [SMILES: O=C(NCc1cccnc1)Nc1ccc(S(=O)(=O)c2cncc(Cl)c2)cc1] | 3-[4-(5-chloropyridine-3-sulfonyl)phenyl]-1-(pyridin-3-ylmethyl)urea |
| 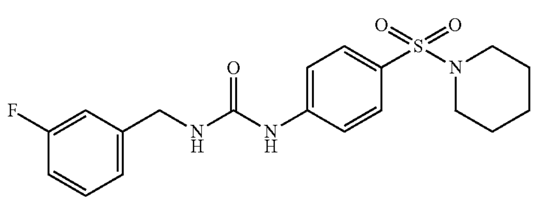 [SMILES: O=C(NCc1cccc(F)c1)Nc1ccc(S(=O)(=O)N2CCCCC2)cc1] | 3-[(3-fluorophenyl)methyl]-1-[4-(piperidine-1-sulfonyl)phenyl]urea |
| 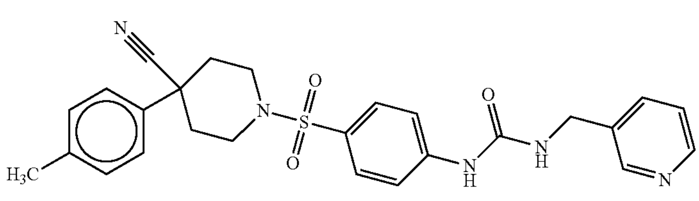 | 3-{4-[4-cyano-4-(4-methylphenyl)piperidine-1-sulfonyl]phenyl}-1-(pyridin-3-ylmethyl)urea |
| 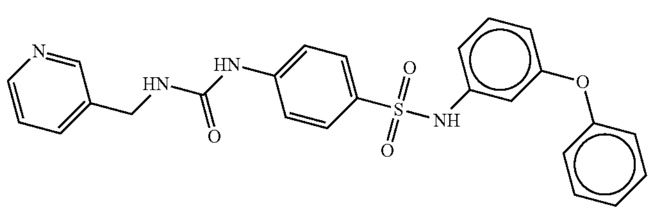 | 1-{4-[(3-phenoxyphenyl)sulfamoyl]phenyl}-3-(pyridin-3-ylmethyl)urea |

| Structure | Chemical Name |
|---|---|
| 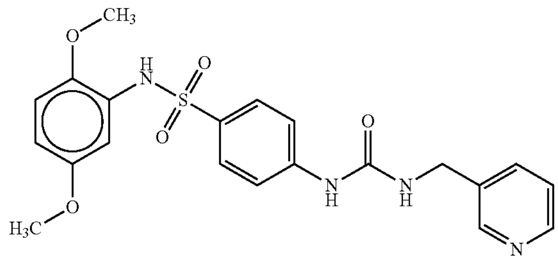 | 3-{4-[(2,5-dimethoxyphenyl)sulfamoyl]phenyl}-1-(pyridin-3-ylmethyl)urea |
| 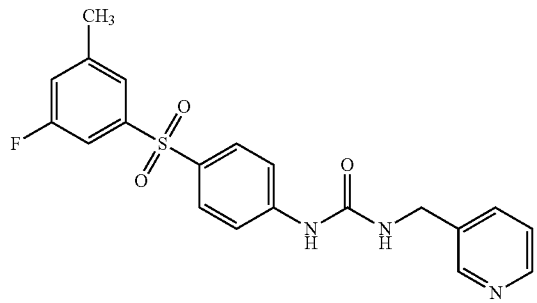 [SMILES: Cc1cc(F)cc(S(=O)(=O)c2ccc(NC(=O)NCc3cccnc3)cc2)c1] | 3-{4-[(3-fluoro-5-methylbenzene)sulfonyl]phenyl}-1-(pyridin-3-ylmethyl)urea |
| 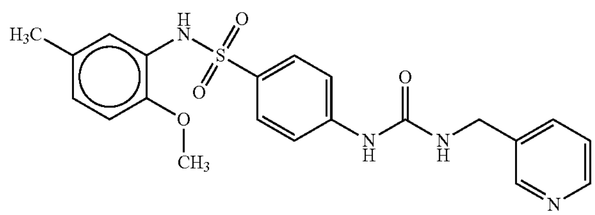 | 3-{4-[(2-methoxy-5-methylphenyl)sulfamoyl]phenyl}-1-(pyridin-3-ylmethyl)urea |
| 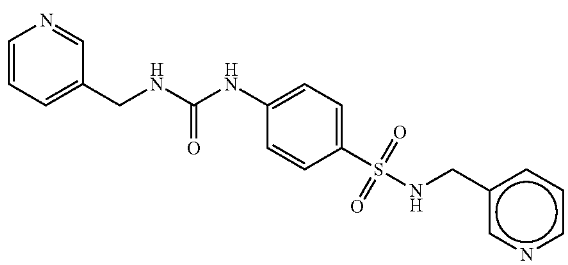 | 3-(pyridin-3-ylmethyl)-1-{4-[(pyridin-3-ylmethyl)sulfamoyl]phenyl}urea |
| 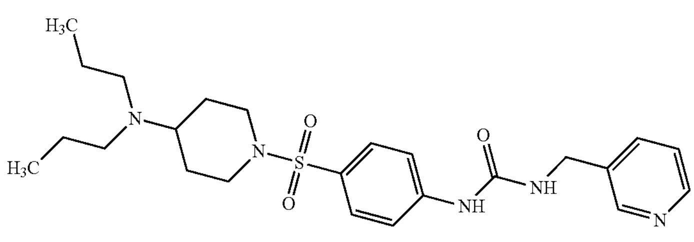 [SMILES: CCCN(CCC)C1CCN(S(=O)(=O)c2ccc(NC(=O)NCc3cccnc3)cc2)CC1] | 3-{4-[4-(dipropylamino)piperidine-1-sulfonyl]phenyl}-1-(pyridin-3-ylmethyl)urea |
| 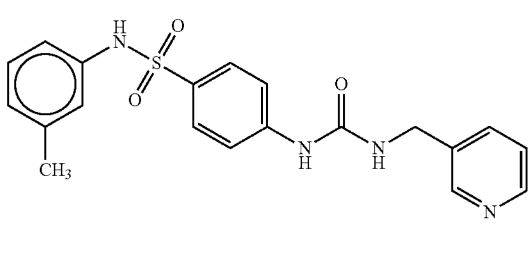 | 3-{4-[(3-methylphenyl)sulfamoyl]phenyl}-1-(pyridin-3-ylmethyl)urea |

-continued

| Structure | Chemical Name |
|---|---|
| 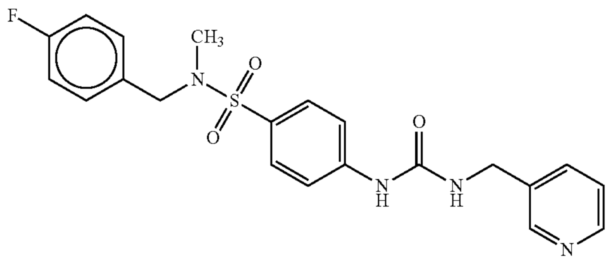 | 3-(4-{[(4-fluorophenyl)methyl](methyl)sulfamoyl}phenyl)-1-(pyridin-3-ylmethyl)urea |
| 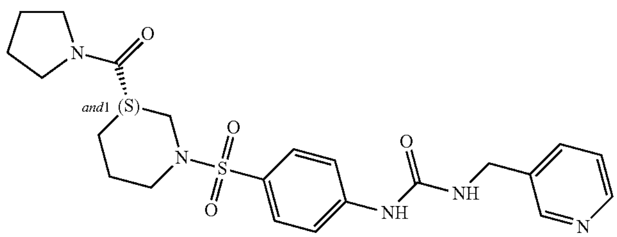 | 3-(pyridin-3-ylmethyl)-1-{4-[(3S)-3-[(pyrrolidin-1-yl)carbonyl]piperidine-1-sulfonyl]phenyl}urea |
| 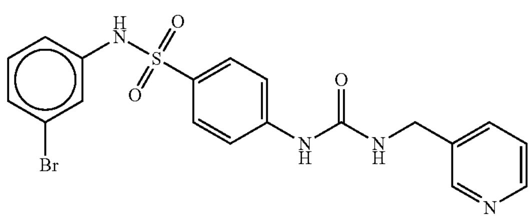 | 3-{4-[(3-bromophenyl)sulfamoyl]phenyl}-1-(pyridin-3-ylmethyl)urea |
| 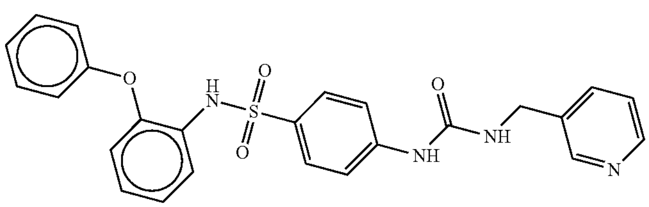 | 1-{4-[(2-phenoxyphenyl)sulfamoyl]phenyl}-3-(pyridin-3-ylmethyl)urea |
| 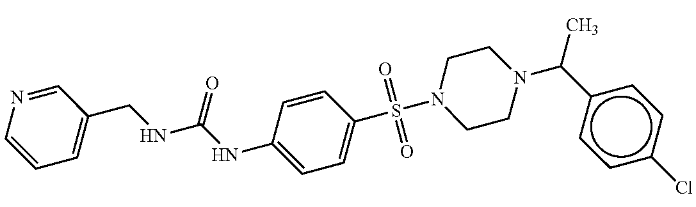 | 3-(4-{4-[1-(4-chlorophenyl)ethyl]piperazine-1-sulfonyl}phenyl)-1-(pyridin-3-ylmethyl)urea |
| 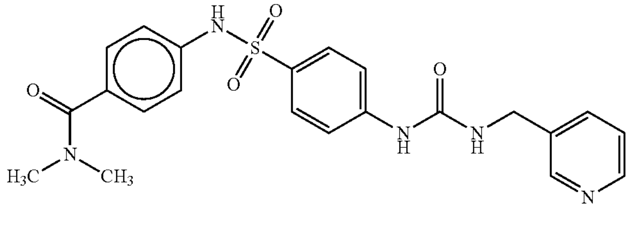 | N,N-dimethyl-4-[(4-{[(pyridin-3-ylmethyl)carbamoyl]amino}benzene)sulfonamido]benzamide |

-continued

| Structure | Chemical Name |
|---|---|
| 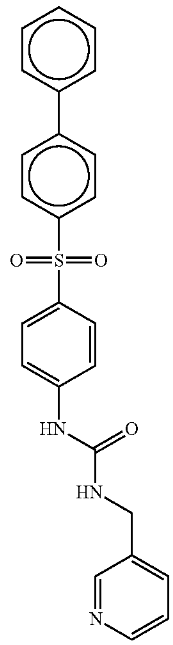 | 1-{4-[(4-phenylbenzene)sulfonyl]phenyl}-3-(pyridin-3-ylmethyl)urea |
| 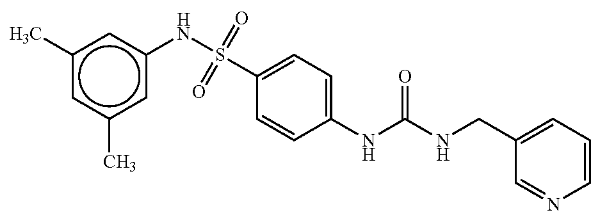 | 3-{4-[(3,5-dimethylphenyl)sulfamoyl]phenyl}-1-(pyridin-3-ylmethyl)urea |
| 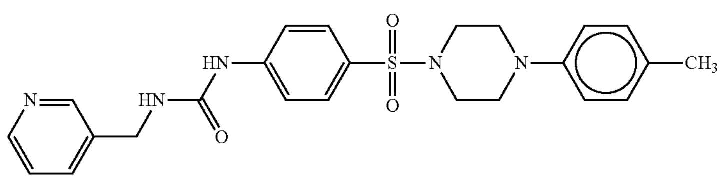 | 3-{4-[4-(4-methylphenyl)piperazine-1-sulfonyl]phenyl}-1-(pyridin-3-ylmethyl)urea |
| 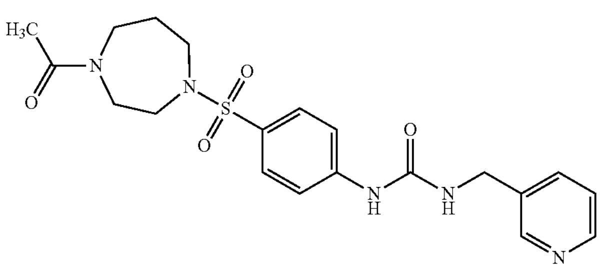 [SMILES: CC(=O)N1CCCN(S(=O)(=O)c2ccc(NC(=O)NCc3cccnc3)cc2)CC1] | 3-[4-(4-acetyl-1,4-diazepane-1-sulfonyl)phenyl]-1-(pyridin-3-ylmethyl)urea |
| 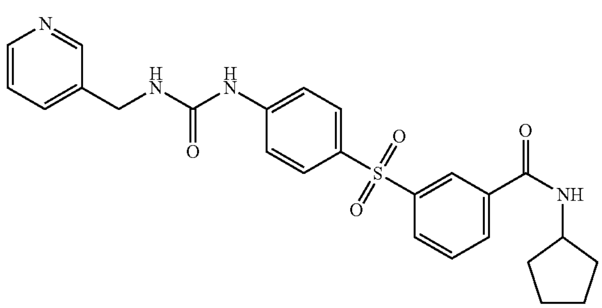 [SMILES: O=C(NCc1cccnc1)Nc1ccc(S(=O)(=O)c2cccc(C(=O)NC3CCCC3)c2)cc1] | N-cyclopentyl-3-[(4-{[(pyridin-3-ylmethyl)carbamoyl]amino}benzene)sulfonyl]benzamide |

| Structure | Chemical Name |
| --- | --- |
| 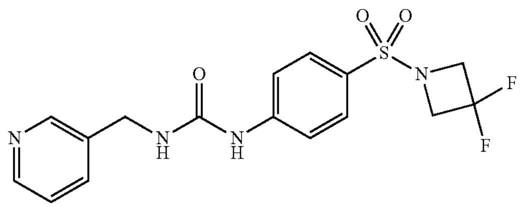 [SMILES: O=C(NCc1cccnc1)Nc1ccc(S(=O)(=O)N2CC(F)(F)C2)cc1] | 3-[4-(3,3-difluoroazetidine-1-sulfonyl)phenyl]-1-(pyridin-3-ylmethyl)urea |
| 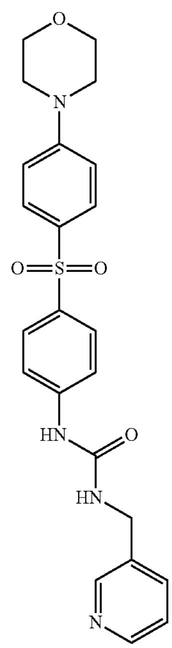 | 1-(4-{[4-(morpholin-4-yl)benzene]sulfonyl}phenyl)-3-(pyridin-3-ylmethyl)urea |
| 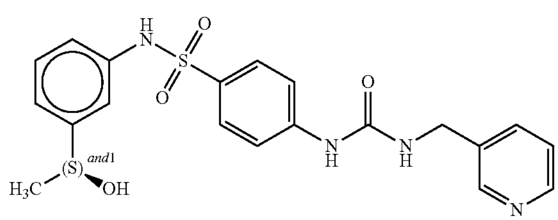 | 3-[4-({3-[(1S)-1-hydroxyethyl]phenyl}sulfamoyl)phenyl]-1-(pyridin-3-ylmethyl)urea |
| 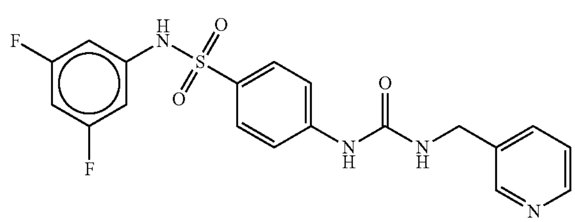 | 3-{4-[(3,5-difluorophenyl)sulfamoyl]phenyl}-1-(pyridin-3-ylmethyl)urea |
| 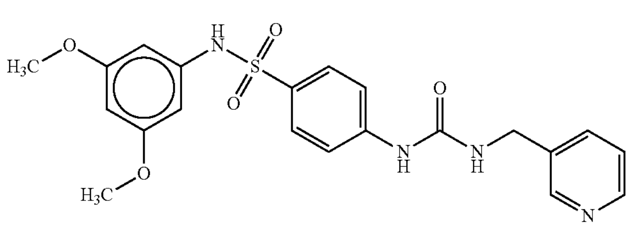 | 3-{4-[(3,5-dimethoxyphenyl)sulfamoyl]phenyl}-1-(pyridin-3-ylmethyl)urea |

-continued

| Structure | Chemical Name |
|---|---|
| 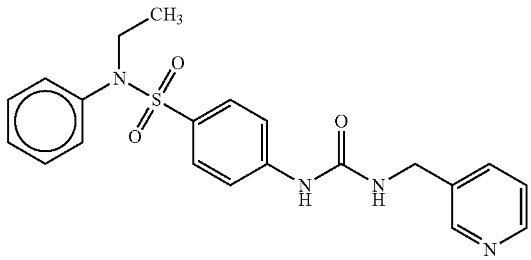 | 3-{4-[ethyl(phenyl)sulfamoyl]phenyl}-1-(pyridin-3-ylmethyl)urea |
| 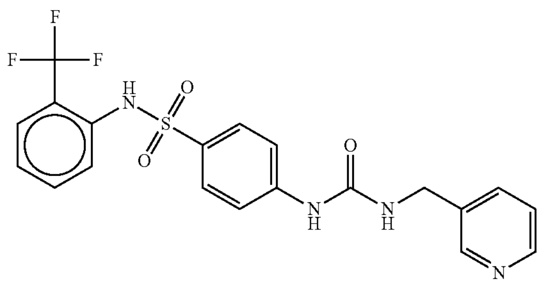 | 1-(pyridin-3-ylmethyl)-3-(4-{[2-(trifluoromethyl)phenyl]sulfamoyl}phenyl)urea |
| 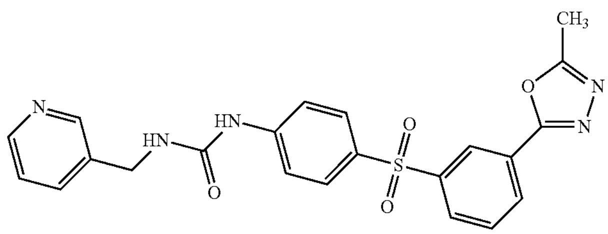 [SMILES: Cc1nnc(-c2cccc(S(=O)(=O)c3ccc(NC(=O)NCc4cccnc4)cc3)c2)o1] | 3-(4-{[3-(5-methyl-1,3,4-oxadiazol-2-yl)benzene]sulfonyl}phenyl)-1-(pyridin-3-ylmethyl)urea |
| 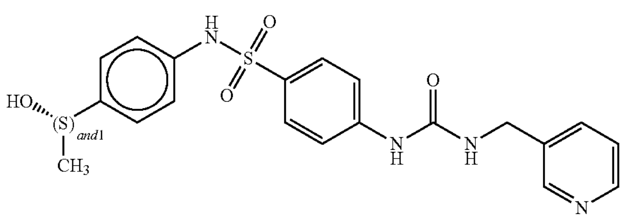 | 3-[4-({4-[(1S)-1-hydroxyethyl]phenyl}sulfamoyl)phenyl]-1-(pyridin-3-ylmethyl)urea |
| 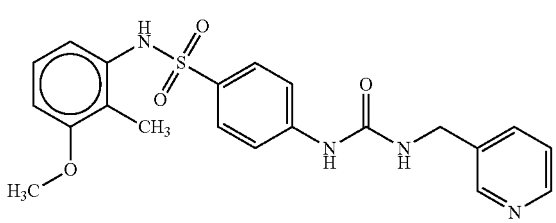 | 3-{4-[(3-methoxy-2-methylphenyl)sulfamoyl]phenyl}-1-(pyridin-3-ylmethyl)urea |
| 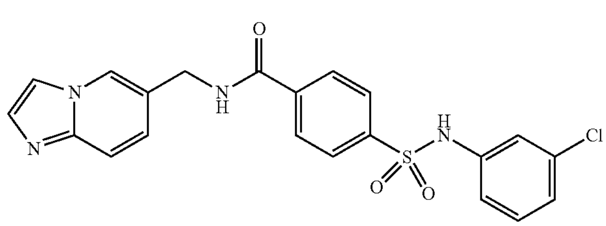 [SMILES: O=C(NCc1ccc2nccn2c1)c1ccc(S(=O)(=O)Nc2cccc(Cl)c2)cc1] | 4-[(3-chlorophenyl)sulfamoyl]-N-{imidazo[1,2-a]pyridin-6-ylmethyl}benzamide |

-continued

| Structure | Chemical Name |
|---|---|
| 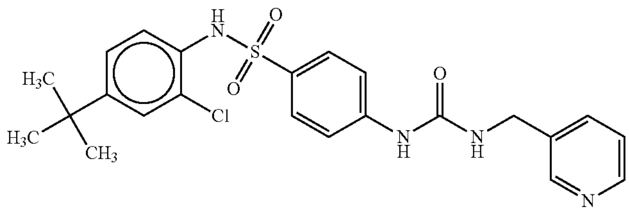 | 3-{4-[(4-tert-butyl-2-chlorophenyl)sulfamoyl]phenyl}-1-(pyridin-3-ylmethyl)urea |
| | 1-(4-{8-azabicyclo[3.2.1]octane-8-sulfonyl}phenyl)-3-(pyridin-3-ylmethyl)urea |
| 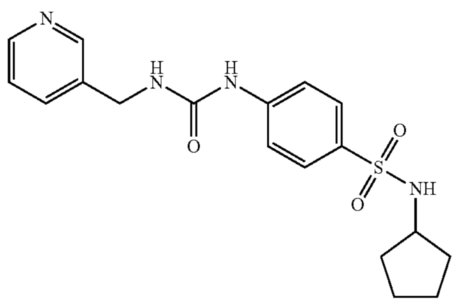 [SMILES: O=C(NCc1cccnc1)Nc1ccc(S(=O)(=O)NC2CCCC2)cc1] | 1-[4-(cyclopentylsulfamoyl)phenyl]-3-(pyridin-3-ylmethyl)urea |
| 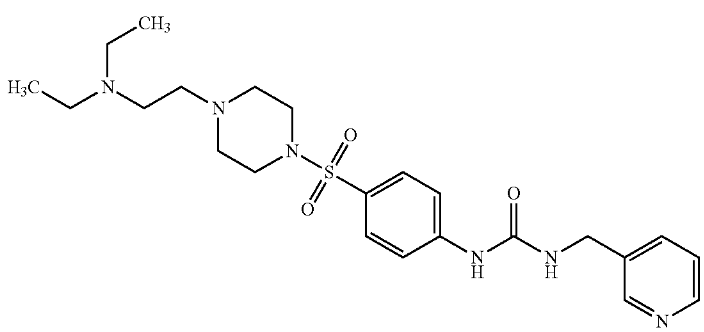 [SMILES: CCN(CC)CCN1CCN(S(=O)(=O)c2ccc(NC(=O)NCc3cccnc3)cc2)CC1] | 3-(4-{4-[2-(diethylamino)ethyl]piperazine-1-sulfonyl}phenyl)-1-(pyridin-3-ylmethyl)urea |
| 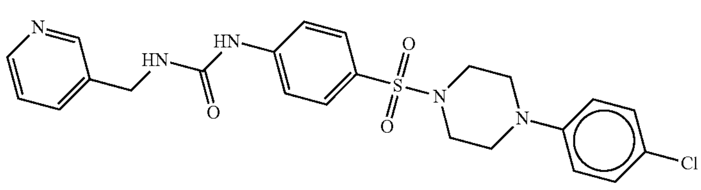 | 3-{4-[4-(4-chlorophenyl)piperazine-1-sulfonyl]phenyl}-1-(pyridin-3-ylmethyl)urea |
| 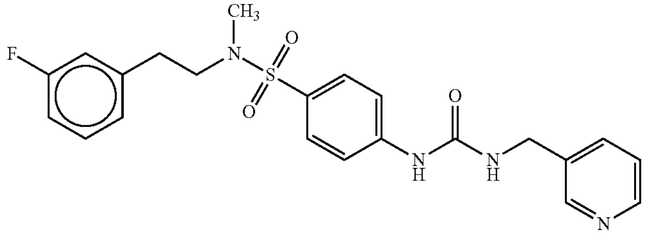 | 3-(4-{[2-(3-fluorophenyl)ethyl](methyl)sulfamoyl}phenyl)-1-(pyridin-3-ylmethyl)urea |

| Structure | Chemical Name |
|---|---|
| 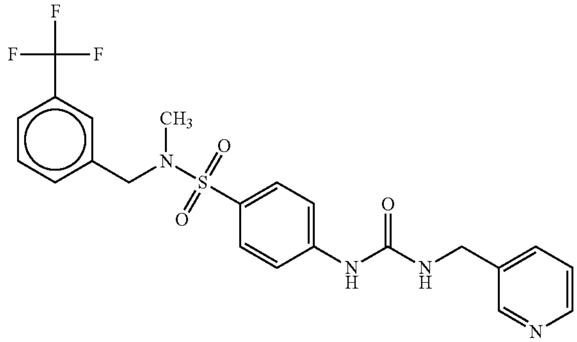 | 3-{4-[methyl({[3-(trifluoromethyl)phenyl]methyl})sulfamoyl]phenyl}-1-(pyridin-3-ylmethyl)urea |
| 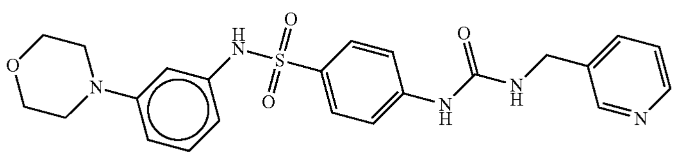 | 1-(4-{[3-(morpholin-4-yl)phenyl]sulfamoyl}phenyl)-3-(pyridin-3-ylmethyl)urea |
| 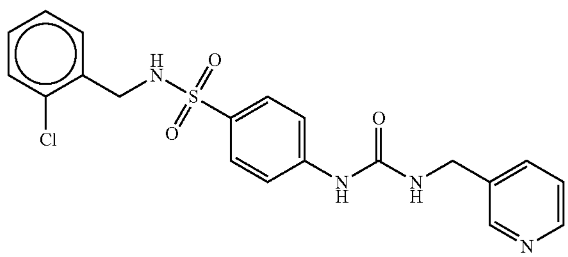 | 3-(4-{[(2-chlorophenyl)methyl]sulfamoyl}phenyl)-1-(pyridin-3-ylmethyl)urea |
| 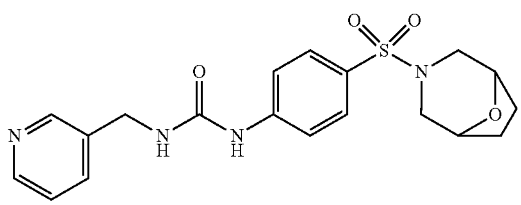 [SMILES: O=C(NCc1cccnc1)Nc1ccc(S(=O)(=O)N2CC3CCC(C2)O3)cc1] | 1-(4-{8-oxa-3-azabicyclo[3.2.1]octane-3-sulfonyl}phenyl)-3-(pyridin-3-ylmethyl)urea |
| 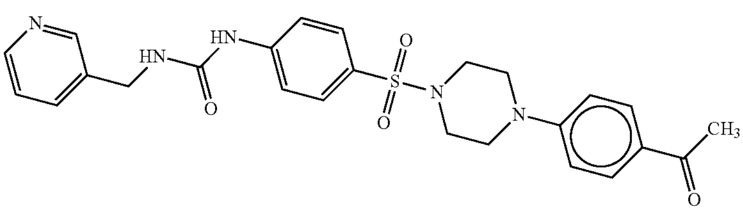 | 3-{4-[4-(4-acetylphenyl)piperazine-1-sulfonyl]phenyl}-1-(pyridin-3-ylmethyl)urea |
| 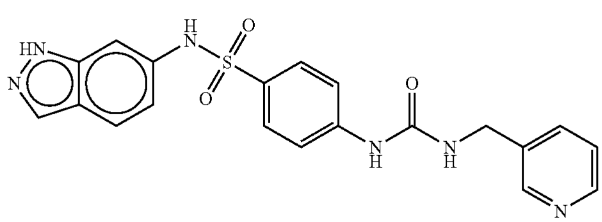 | 1-{4-[(1H-indazol-6-yl)sulfamoyl]phenyl}-3-(pyridin-3-ylmethyl)urea |
| 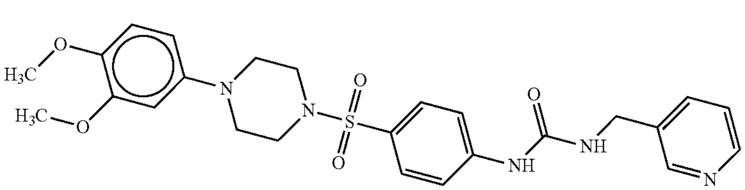 | 3-{4-[4-(3,4-dimethoxyphenyl)piperazine-1-sulfonyl]phenyl}-1-(pyridin-3-ylmethyl)urea |

-continued

| Structure | Chemical Name |
|---|---|
| 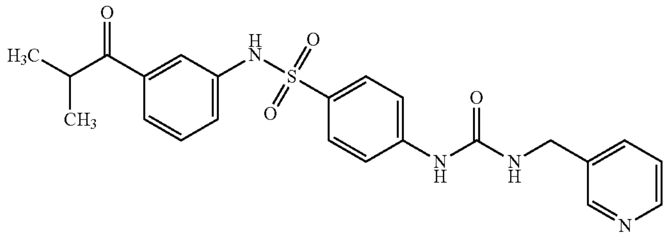 [SMILES: CC(C)C(=O)c1cccc(NS(=O)(=O)c2ccc(NC(=O)NCc3cccnc3)cc2)c1] | N,N-dimethyl-3-[(4-{[(pyridin-3-ylmethyl)carbamoyl]amino}benzene)sulfonamido]benzamide |
| 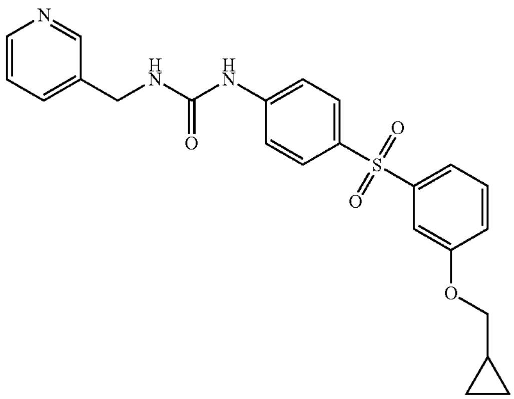 [SMILES: O=C(NCc1cccnc1)Nc1ccc(S(=O)(=O)c2cccc(OCC3CC3)c2)cc1] | 1-(4-{[3-(cyclopropylmethoxy)benzene]sulfonyl}phenyl)-3-(pyridin-3-ylmethyl)urea |
| 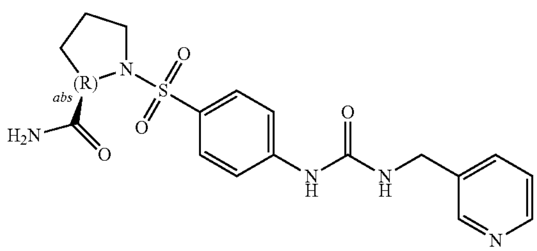 | (2R)-1-[(4-{[(pyridin-3-ylmethyl)carbamoyl]amino}benzene)sulfonyl]pyrrolidine-2-carboxamide |
| 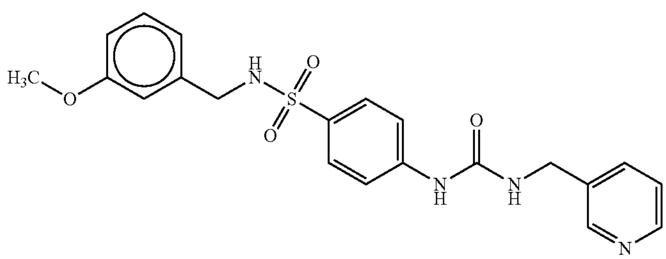 | 3-(4{[(3-methoxyphenyl)methyl]sulfamoyl}phenyl)-1-(pyridin-3-ylmethyl)urea |
| 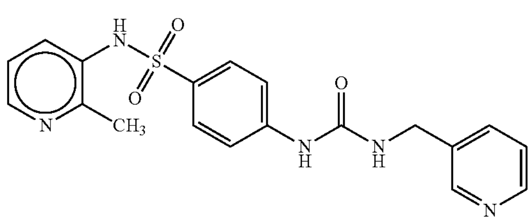 | 3-{4-[(2-methylpyridin-3-yl)sulfamoyl]phenyl}-1-(pyridin-3-ylmethyl)urea |
| 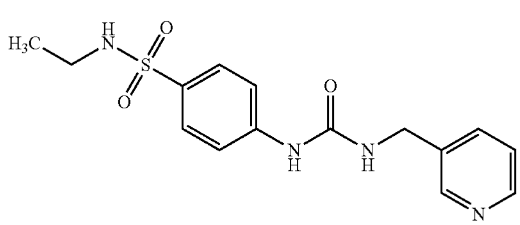 [SMILES: CCNS(=O)(=O)c1ccc(NC(=O)NCc2cccnc2)cc1] | 3-[4-(ethylsulfamoyl)phenyl]-1-(pyridin-3-ylmethyl)urea |

-continued

| Structure | Chemical Name |
|---|---|
| 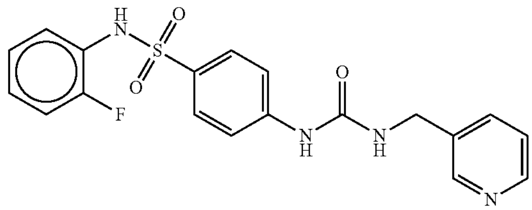 | 3-{4-[(2-fluorophenyl)sulfamoyl]phenyl}-1-(pyridin-3-ylmethyl)urea |
| 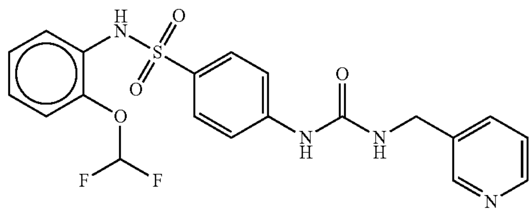 | 3-(4-{[2-(difluoromethoxy)phenyl]sulfamoyl}phenyl)-1-(pyridin-3-ylmethyl)urea |
| 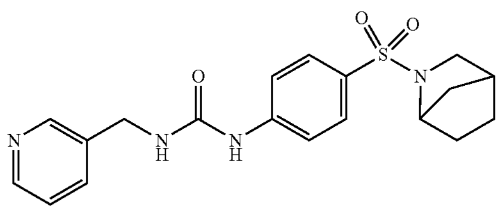 [SMILES: O=C(NCc1cccnc1)Nc1ccc(S(=O)(=O)N2CC3CCC2C3)cc1] | 1-(4-{2-azabicyclo[2.2.1]heptane-2-sulfonyl}phenyl)-3-(pyridin-3-ylmethyl)urea |
| 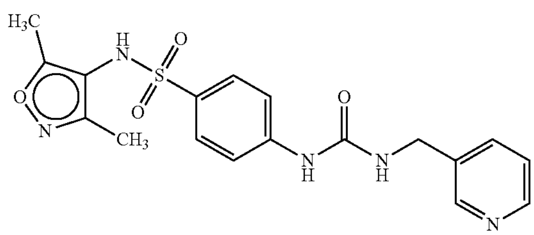 | 3-{4-[(3,5-dimethyl-1,2-oxazol-4-yl)sulfamoyl]phenyl}-1-(pyridin-3-ylmethyl)urea |
| 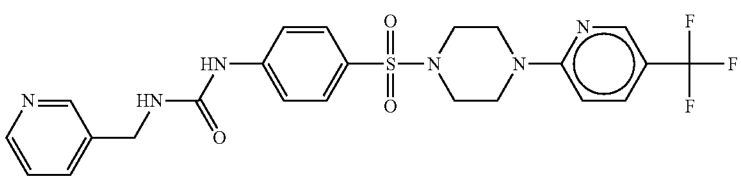 | 1-(pyridin-3-ylmethyl)-3-(4-{4-[5-(trifluoromethyl)pyridin-2-yl]piperazine-1-sulfonyl}phenyl)urea |
| 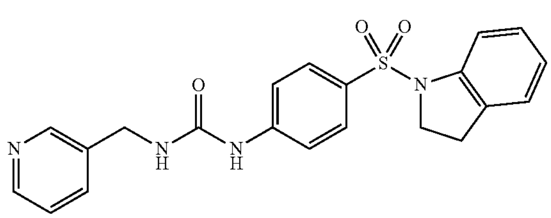 [SMILES: O=C(NCc1cccnc1)Nc1ccc(S(=O)(=O)N2CCc3ccccc32)cc1] | 3-[4-(2,3-dihydro-1H-indole-1-sulfonyl)phenyl]-1-(pyridin-3-ylmethyl)urea |
| 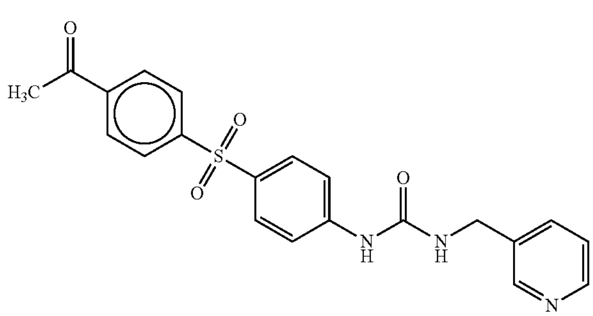 | 3-{4-[(4-acetylbenzene)sulfonyl]phenyl}-1-(pyridin-3-ylmethyl)urea |

-continued

| Structure | Chemical Name |
|---|---|
| 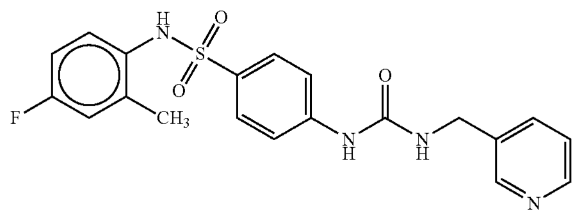 | 3-{4-[(4-fluoro-2-methylphenyl)sulfamoyl]phenyl}-1-(pyridin-3-ylmethyl)urea |
| 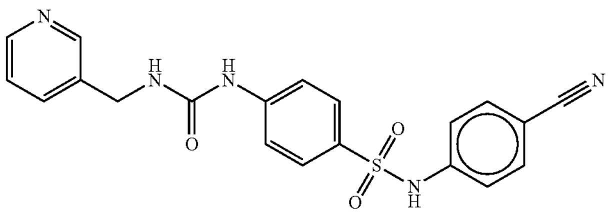 | 1-{4-[(4-cyanophenyl)sulfamoyl]phenyl}-3-(pyridin-3-ylmethyl)urea |
| 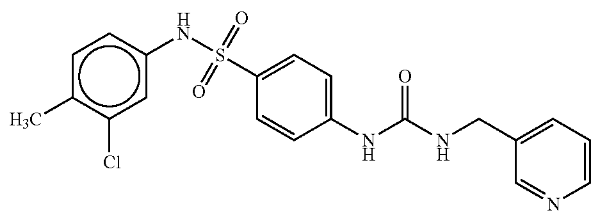 | 3-{4-[(3-chloro-4-methylphenyl)sulfamoyl]phenyl}-1-(pyridin-3-ylmethyl)urea |
| 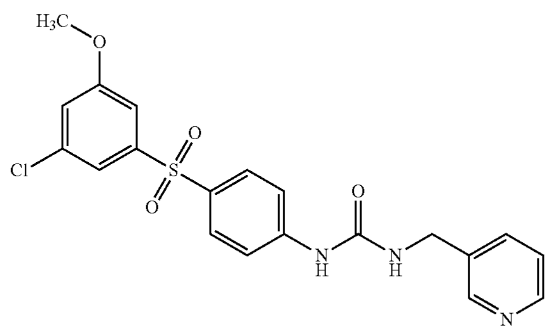 [SMILES: COc1cc(Cl)cc(S(=O)(=O)c2ccc(NC(=O)NCc3cccnc3)cc2)c1] | 3-{4-[(3-chloro-5-methoxybenzene)sulfonyl]phenyl}-1-(pyridin-3-ylmethyl)urea |
| 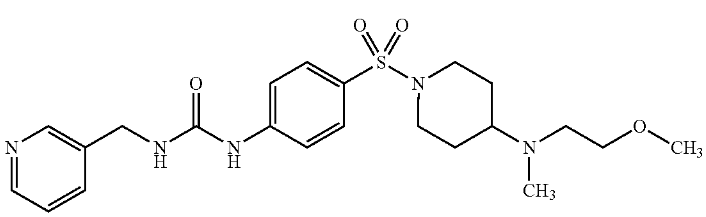 [SMILES: COCCN(C)C1CCN(S(=O)(=O)c2ccc(NC(=O)NCc3cccnc3)cc2)CC1] | 1-(4-(4-((2-methoxyethyl)(methyl)amino)piperidin-1-ylsulfonyl)phenyl)-3-(pyridin-3-ylmethyl)urea |
| 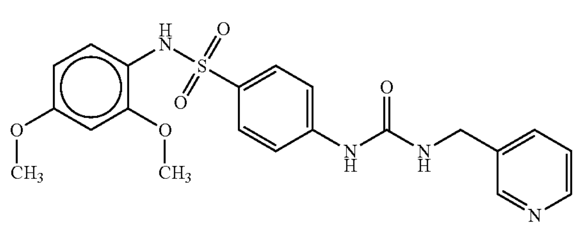 | 3-{4-[(2,4-dimethoxyphenyl)sulfamoyl]phenyl}-1-(pyridin-3-ylmethyl)urea |

| Structure | Chemical Name |
|---|---|
| 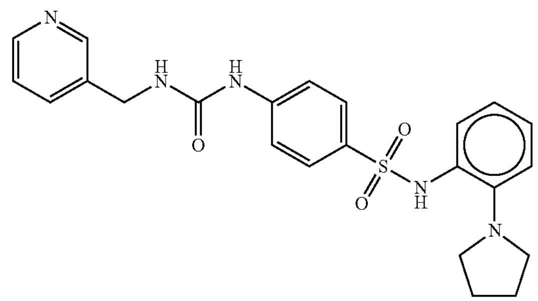 | 3-(pyridin-3-ylmethyl)-1-(4-{[2-(pyrrolidin-1-yl)phenyl]sulfamoyl}phenyl)urea |
| 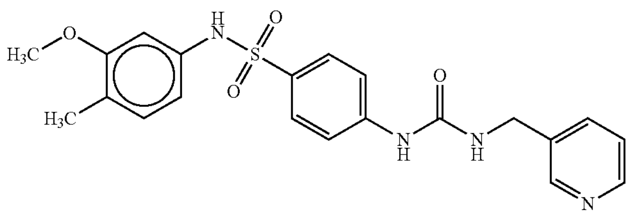 | 3-{4-[(3-methoxy-4-methylphenyl)sulfamoyl]phenyl}-1-(pyridin-3-ylmethyl)urea |
| 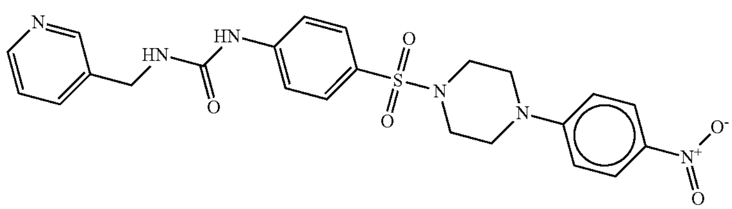 | 3-{4-[4-(4-nitrophenyl)piperazine-1-sulfonyl]phenyl}-1-(pyridin-3-ylmethyl)urea |
| 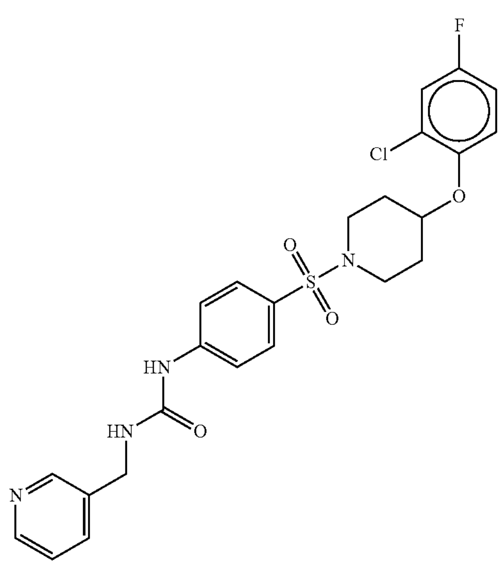 | 3-{4-[4-(2-chloro-4-fluorophenoxy)piperidine-1-sulfonyl]phenyl}-1-(pyridin-3-ylmethyl)urea |
| 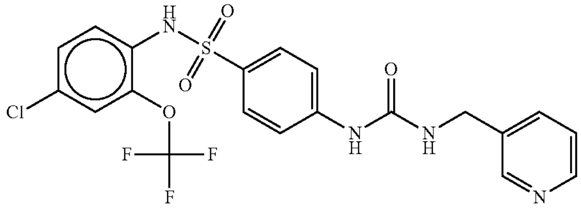 | 3-(4-{[4-chloro-2-(trifluoromethoxy)phenyl]sulfamoyl}phenyl)-1-(pyridin-3-ylmethyl)urea |

-continued

| Structure | Chemical Name |
|---|---|
| 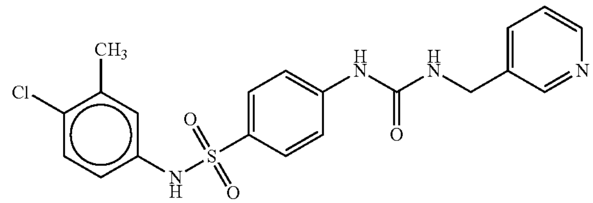 | 3-{4-[(4-chloro-3-methylphenyl)sulfamoyl]phenyl}-1-(pyridin-3-ylmethyl)urea |
| 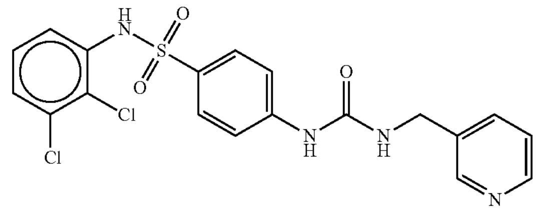 | 3-{4-[(2,3-dichlorophenyl)sulfamoyl]phenyl}-1-(pyridin-3-ylmethyl)urea |
| 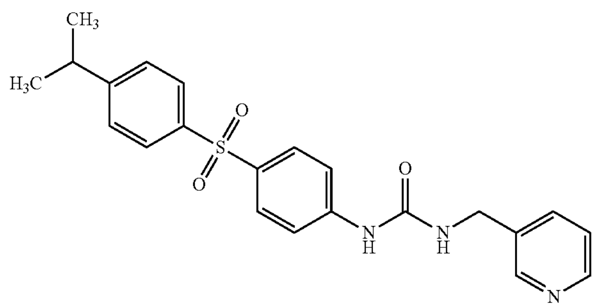 [SMILES: CC(C)c1ccc(S(=O)(=O)c2ccc(NC(=O)NCc3cccnc3)cc2)cc1] | 3-(4-{[4-(propan-2-yl)benzene]sulfonyl}phenyl)-1-(pyridin-3-ylmethyl)urea |
| 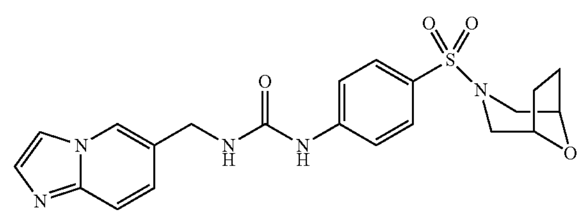 [SMILES: O=C(NCc1ccc2nccn2c1)Nc1ccc(S(=O)(=O)N2CC3CCC(C2)O3)cc1] | 3-{imidazo[1,2-a]pyridin-6-ylmethyl}-1-(4-{8-oxa-3-azabicyclo[3.2.1]octane-3-sulfonyl}phenyl)urea |
| 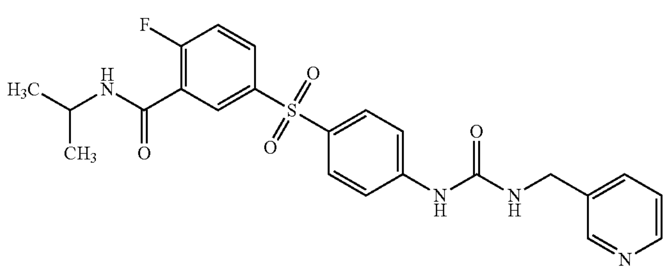 [SMILES: CC(C)NC(=O)c1cc(S(=O)(=O)c2ccc(NC(=O)NCc3cccnc3)cc2)ccc1F] | 2-fluoro-N-(propan-2-yl)-5-[(4-{[(pyridin-3-ylmethyl)carbamoyl]amino}benzene)sulfonyl]benzamide |
| 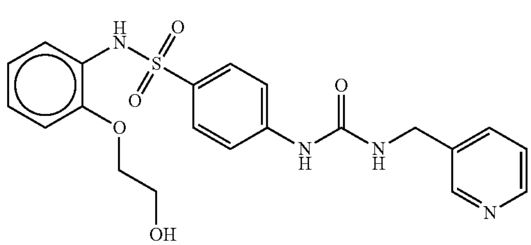 | 3-(4-{[2-(2-hydroxyethoxy)phenyl]sulfamoyl}phenyl)-1-(pyridin-3-ylmethyl)urea |

| Structure | Chemical Name |
|---|---|
| 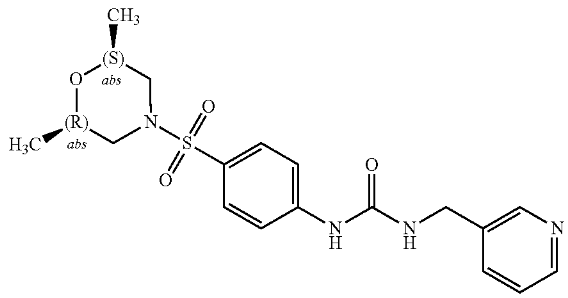 | 3-{4-[(2R,6S)-2,6-dimethylmorpholine-4-sulfonyl]phenyl}-1-(pyridin-3-ylmethyl)urea |
| 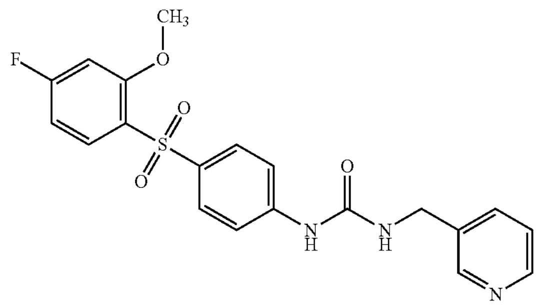 [SMILES: COc1cc(F)ccc1S(=O)(=O)c1ccc(NC(=O)NCc2cccnc2)cc1] | 3-{4-[(4-fluoro-2-methoxybenzene)sulfonyl]phenyl}-1-(pyridin-3-ylmethyl)urea |
| 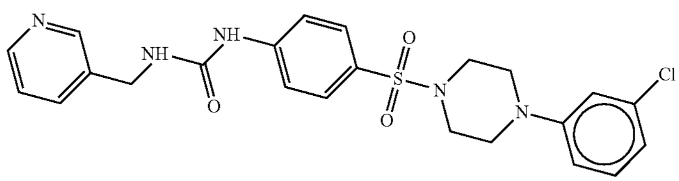 | 3-{4-[4-(3-chlorophenyl)piperazine-1-sulfonyl]phenyl}-1-(pyridin-3-ylmethyl)urea |
| 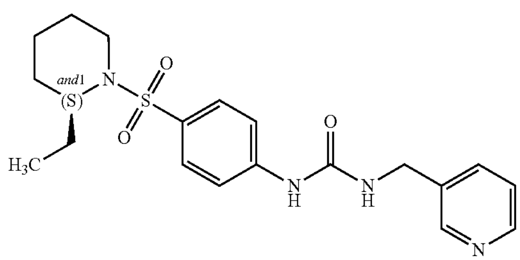 | 3-{4-[(2S)-2-ethylpiperidine-1-sulfonyl]phenyl}-1-(pyridin-3-ylmethyl)urea |
| 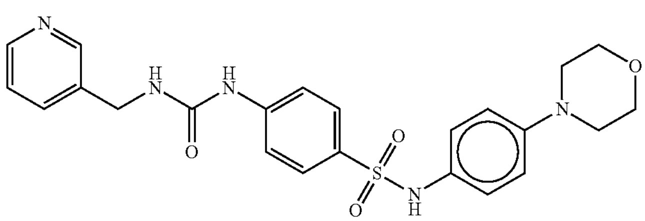 | 1-(4-{[4-(morpholin-4-yl)phenyl]sulfamoyl}phenyl)-3-(pyridin-3-ylmethyl)urea |
| 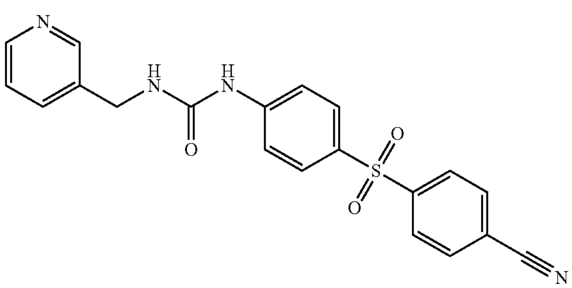 [SMILES: N#Cc1ccc(S(=O)(=O)c2ccc(NC(=O)NCc3cccnc3)cc2)cc1] | 1-{4-[(4-cyanobenzene)sulfonyl]phenyl}-3-(pyridin-3-ylmethyl)urea |

-continued

| Structure | Chemical Name |
|---|---|
| 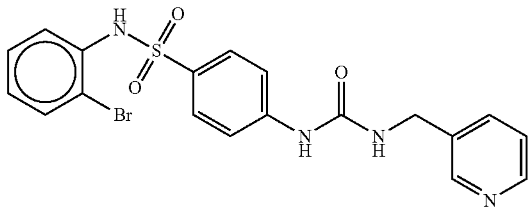 | 3-{4-[(2-bromophenyl)sulfamoyl]phenyl}-1-(pyridin-3-ylmethyl)urea |
| 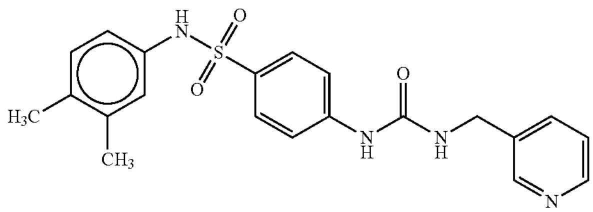 | 3-{4-[(3,4-dimethylphenyl)sulfamoyl]phenyl}-1-(pyridin-3-ylmethyl)urea |
| 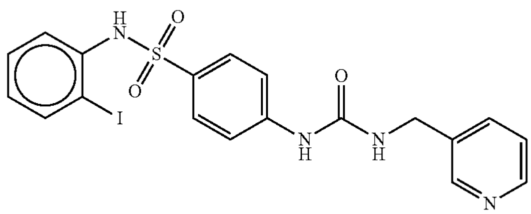 | 3-{4-[(2-iodophenyl)sulfamoyl]phenyl}-1-(pyridin-3-ylmethyl)urea |
| 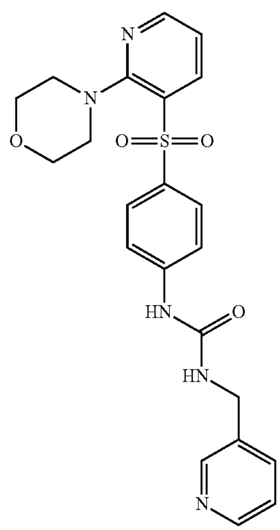 [SMILES: O=C(NCc1cccnc1)Nc1ccc(S(=O)(=O)c2cccnc2N2CCOCC2)cc1] | 1-{4-[2-(morpholin-4-yl)pyridine-3-sulfonyl]phenyl}-3-(pyridin-3-ylmethyl)urea |
| 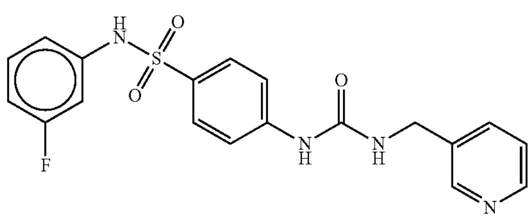 | 3-{4-[(3-fluorophenyl)sulfamoyl]phenyl}-1-(pyridin-3-ylmethyl)urea |
| 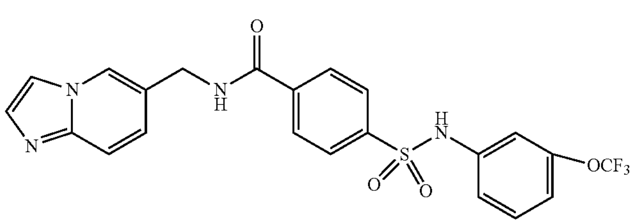 [SMILES: O=C(NCc1ccc2nccn2c1)c1ccc(S(=O)(=O)Nc2cccc(OC(F)(F)F)c2)cc1] | N-{imidazo[1,2-a]pyridin-6-ylmethyl}-4-{[3-(trifluoromethoxy)phenyl]sulfamoyl}benzamide |

| Structure | Chemical Name |
|---|---|
| 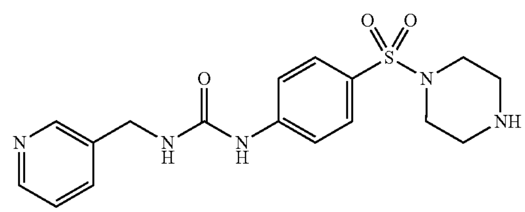 [SMILES: O=C(NCc1cccnc1)Nc1ccc(S(=O)(=O)N2CCNCC2)cc1] | 1-[4-(piperazine-1-sulfonyl)phenyl]-3-(pyridin-3-ylmethyl)urea |
| 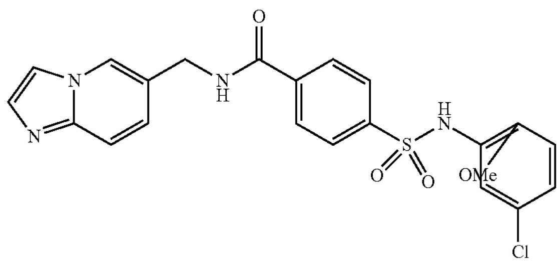 [SMILES: COc1ccc(Cl)cc1NS(=O)(=O)c1ccc(C(=O)NCc2ccc3nccn3c2)cc1] | 4-[(5-chloro-2-methoxyphenyl)sulfamoyl]-N-{imidazo[1,2-a]pyridin-6-ylmethyl}benzamide |

The following compounds are not compounds of the invention but are NAMPT inhibitors:

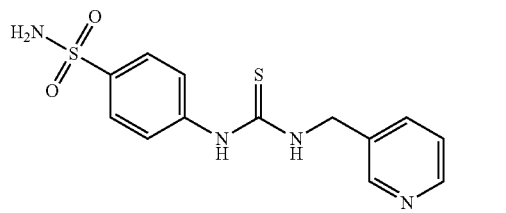

1-(pyridin-3-ylmethyl)-3-(4-sulfamoylphenyl)thiourea

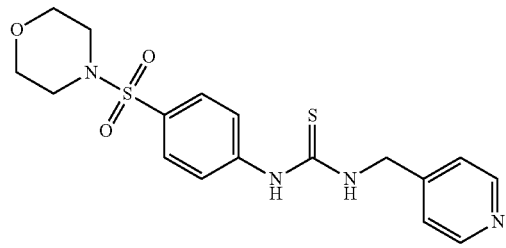

3-[4-(morpholine-4-sulfonyl)phenyl]-1-(pyridin-4-ylmethyl)thiourea

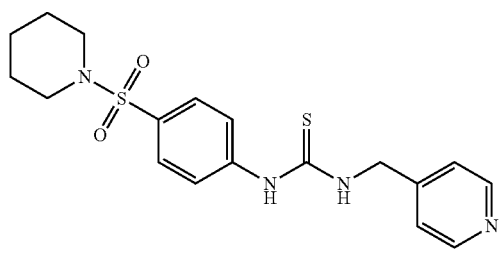

3-[4-(piperidine-1-sulfonyl)phenyl]-1-(pyridin-4-ylmethyl)thiourea

The disclosures in this application of all articles and references, including patents and patent applications are incorporated herein by reference.

EXAMPLES

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis. Unless otherwise specified, all reagents and solvents are of standard commercial grade and are used without further purification.

The following are illustrative, but non-limiting, examples of certain embodiments of the present invention.

Definitions Used in the Following Schemes and Elsewhere Herein are $CDCl_3$ deuterated chloroform
δ chemical shift (ppm)
DCM dichloromethane or methylene chloride
DIEA N, N-diisopropylethylamine
DMA N, N-dimethylacetamide
DMAP N, N-dimethylpyridin-4-amine
DMF dimethylformamide
DMSO dimethylsulfoxide
DMSO-$d_6$ deuterated dimethylsulfoxide
EDCI N1-((ethylimino)methylene)-N3,N3-dimethylpropane-1,3-diamine hydrochloride
EtOAc ethyl acetate
EtOH ethanol
GF/F glass microfiber filter
$^1$H NMR proton nuclear magnetic resonance HOAc acetic acid
HATU 2-(3H-[1,2,3]triazolo[4,5-b]pyridin-3-yl)-1,1,3,3-tetramethylisouronium hexafluorophosphate
HOBT 1H-benzo[d][1,2,3]triazol-1-ol hydrate
HPLC high pressure liquid chromatography
MHz megahertz
KOAc potassium acetate
i-PrOH isopropanol
LC-MS liquid chromatography/mass spectrometry
(M+1) mass+1
m-CPBA m-chloroperbenzoic acid
MeOH methanol
$N_2$ nitrogen
$NaHCO_3$ sodium bicarbonate
$MgSO_4$ magnesium sulfate
SRB Sulforhodamine B colorimetric assay
TEA triethylamine
THF tetrahydrofuran
TLC thin layer chromatography Preparation of Compounds The compounds of the present invention can be prepared through numerous routes well-known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below.

Compounds of the present invention urea-sulfonamide (IV) can be synthesized by following the steps outlined in Scheme 1.

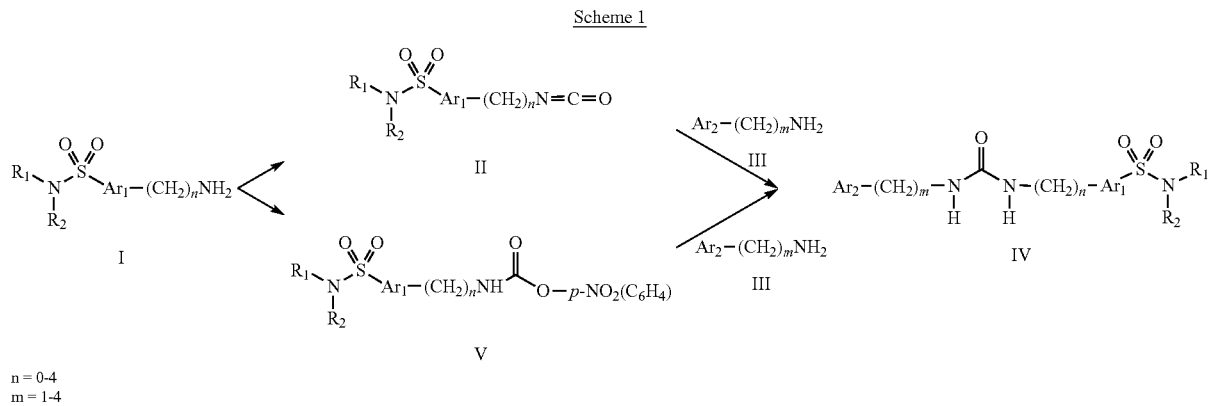

n = 0-4
m = 1-4

Intermediate II can be obtained by treating I with phosgene, thiophosgene, carbonyldiimidazole, or other such activating group in an inert solvent such as dichloromethane, benzene, or toluene at temperatures ranging from −78° C. to 200° C. Intermediate V can be obtained by treating I with 4-nitrophenyl carbonochloridate in an inert solvent such as dichloromethane, benzene, or toluene at temperatures ranging from −78° C. to 200° C. The compound of present invention IV can be obtained by treating compound III with either II or V in an organic solvent at temperatures ranging from −78° C. to 200° C.

Compounds of the present invention urea-sulfone (IV) can be synthesized by following the steps outlined in Scheme 2.

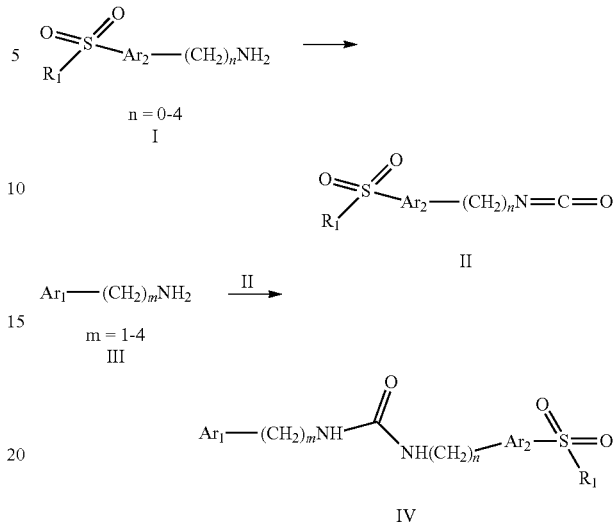

Intermediate II can be obtained by treating I with phosgene, thiophosgene, carbonyldiimidazole (or similar reagent) in an inert solvent such as dichloromethane, benzene, or toluene at temperatures ranging from −78° C. to 200° C. The compound of present invention IV can be obtained by treating intermediate II with III in an organic solvent at temperatures ranging from −78° C. to 200° C.

The compound of present invention urea-sulfone IV can also be synthesized by following the steps outlined in Scheme 2A.

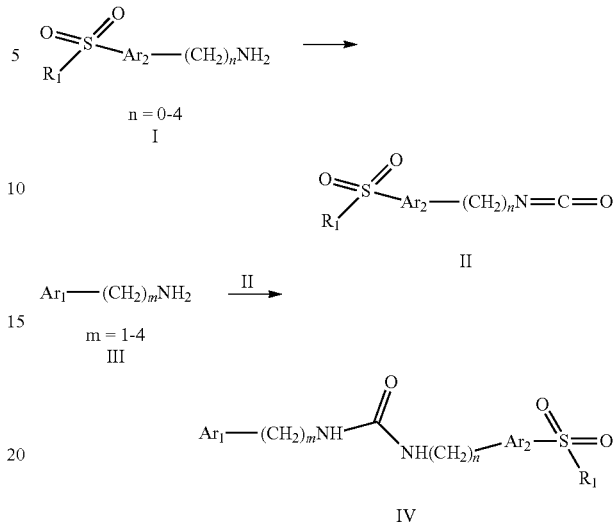

-continued

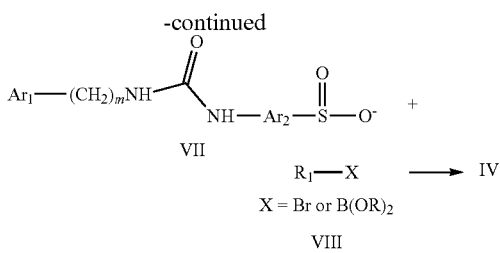

Intermediate VI can be obtained by treating III with V in an inert solvent such as dichloromethane and benzene at temperatures ranging from −78° C. to 200° C. Treatment of VI with agents such as NaBH$_4$, NaI, or Na$_2$S$_2$O$_3$ in a solvent such as water or THF at temperatures ranging from −78° C. to 200° C. gives intermediate VII. Compound IV can be obtained by treating VII and VIII with a suitable transition metal catalyst such as, but not limited to, Pd(PPh$_3$)$_4$, palladium(II) acetate, or Cu(OAc)$_2$ in the presence of a base (eg: K$_2$CO$_3$, Cs$_2$CO$_3$, NR$_1$R$_2$R$_3$, NaOR, KOR) in an inert solvent such as N, N-dialkylformamide, N, N-dialkylacetamide, or dichloromethane at temperatures ranging from −78° C. to 200° C.

Those having skill in the art will recognize that the starting materials may be varied and additional steps may be employed to produce the compounds encompassed by the present inventions (as demonstrated by the following examples). Unless otherwise specified, all reagents and solvents are of standard commercial grade and are used without further purification.

The disclosures in this application of all articles and references, including patents, are incorporated herein by reference.

Preparation of Representative Urea-Sulfonamide and Urea Sofone Analogues

These examples illustrate the preparation of representative substituted urea-sulfonamide and urea-sulfone analogues.

Example 1

1-((5-fluoropyridin-3-yl)methyl)-3-(4-(piperidin-1-ylsulfonyl)phenyl)urea

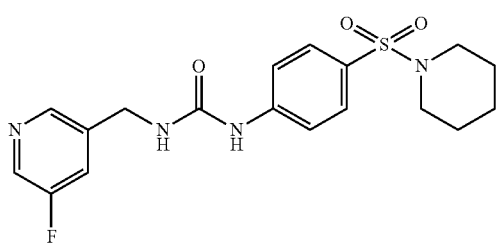 [SMILES: O=C(NCc1cncc(F)c1)Nc1ccc(S(=O)(=O)N2CCCCC2)cc1]

Triphosgene (41 mg, 0.137 mmol) was dissolved in DCM (5 mL) and cooled to −10° C. under N$_2$ atmosphere. To this cooled solution was added dropwise a mixture of 4-(piperidin-1-ylsulfonyl) aniline (100 mg, 0.416 mmol) and TEA (127 mg, 1.25 mmol) in DCM (5 mL). The mixture was stirred at −10° C. for 5 minutes and allowed to warm up to room temperature for 1 hour. A solution of 5-fluoropyridin-3-yl)methanamine (55 mg, 0.50 mmol) and TEA (127 mg, 1.25 mmol) in DCM (5 mL) was then added. The reaction mixture was stirred at room temperature for 16 hours. The mixture was diluted with DCM (25 mL), washed with brine (2×15 mL), dried over MgSO$_4$, filtered and concentrated under reduced pressure. The crude was purified by Biotage using 5% MeOH/DCM to afford the desired product as a white amorphous powder.

$^1$H NMR (300 MHz, CDCl$_3$): δ 9.23 (s, 1H), 8.36-8.48 (m, 2H), 7.50-7.68 (m, 5H), 6.95 (t, 1H), 4.36 (d, 2H), 2.75-2.90 (m, 4H), 1.48-1.75 (m, 4H), 1.38-1.42 (m, 2H)

LC-MS: 393.04 (M+1).

Example 2

N-(naphthalen-1-yl)-4-(3-(pyridin-3-ylmethyl)ureido)benzenesulfonamide

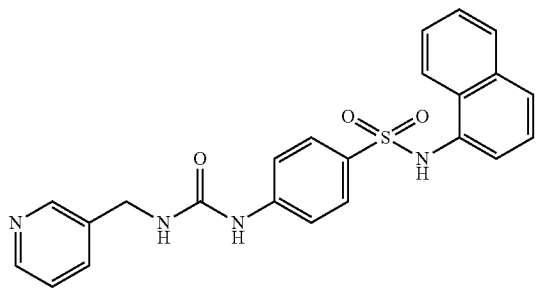 [SMILES: O=C(NCc1cccnc1)Nc1ccc(S(=O)(=O)Nc2cccc3ccccc23)cc1]

A: N-(naphthalen-1-yl)-4-nitrobenzenesulfonamide

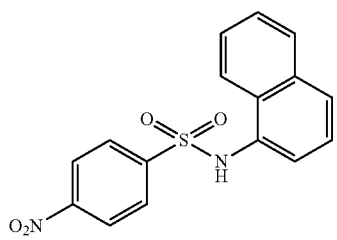

To a cooled solution of naphthalen-1-amine (2000 mg, 13.97 mmol) in pyridine (45.0 mL) was added DMAP (171 mg, 1.4 mmol) and a solution of 4-nitrobenzene-1-sulfonyl chloride (3410 mg, 15.4 mmol) in pyridine (15.0 mL) at 0° C. The mixture was stirred at 0° C. for 15 min and heated to 80° C. for 16 h. After being cooled to room temperature, the mixture was acidified with 2M HCl, extracted with EtOAc (3×50 mL), washed several times with brine, dried over MgSO$_4$ and concentrated in vacuo. The crude was purified by Combiflash using (5% EtOAc/hexanes) to afford the title compound.

$^1$H NMR (300 MHz, CD$_3$OD): δ 7.21-7.38 (m, 6H), 7.68-7.85 (m, 4H), 8.15-8.20 (m, 2H).

LC-MS: 329.14 (M+1).

B: 4-amino-N-(naphthalen-1-yl)benzenesulfonamide

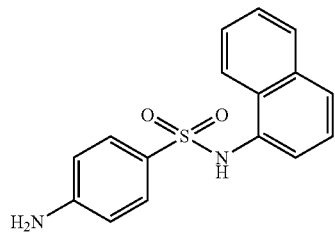 [SMILES: O=[N+]([O-])c1ccc(S(=O)(=O)Nc2cccc3ccccc23)cc1]

A mixture of N-(naphthalen-1-yl)-4-nitrobenzenesulfonamide (3.9 g, 12 mmol) and tin (II) chloride dihydrate (13.5 g, 60 mmol) was refluxed in EtOAc (120 mL) for 2.5 h. After being cooled to room temperature, the mixture was treated with 2N NaOH (100 mL) and stirred for 1 h, then filtered through celite and washed with EtOAc. The combined filtrates were concentrated in vacuo. The crude was purified by Combiflash using (40% EtOAc/hexanes) to afford the title compound.

$^1$H NMR (300 MHz, CD$_3$OD): δ 6.45-6.51 (m, 2H), 7.12-7.18 (m, 1H), 7.25-7.38 (m, 5H), 7.65 (d, 1H), 7.72-7.76 (m, 1H), 7.91-7.98 (m, 1H).

LC-MS: 299.04 (M+1).

C: N-(naphthalen-1-yl)-4-(3-(pyridin-3-ylmethyl)ureido)benzenesulfonamide

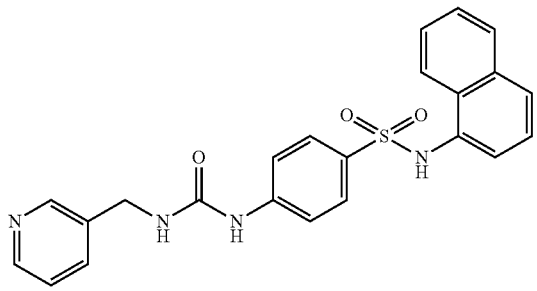 [SMILES: O=C(NCc1cccnc1)Nc1ccc(S(=O)(=O)Nc2cccc3ccccc23)cc1]

A mixture of 4-amino-N-(naphthalen-1-yl)benzenesulfonamide (1000 mg, 3.35 mmol) and 4-nitrophenyl carbonochloridate (676 mg, 3.35 mmol) in DCM (35 mL) was stirred and cooled to 0° C. under N$_2$ atmosphere, followed by addition of pyridine (1060 mg, 13.41 mmol). After being stirred for 10 minutes, pyridin-3-methanamine (1087 mg, 10.5 mmol) was added and the reaction mixture was stirred for 40 minutes at room temperature. The mixture was then diluted with DCM-MeOH (100 mL, 1:1), washed with water (5×40 mL), dried over MgSO$_4$, and concentrated under vacuum. The residue was purified by flash chromatography using 10% MeOH/DCM to afford the title compound.

$^1$H NMR (300 MHz, DMSO-d$_6$): δ 4.21 (d, 2H), 6.82-6.88 (m, 1H), 7.10-7.16 (m, 1H), 7.32-7.55 (m, 8H), 7.58-7.68 (m, 2H), 7.85-7.89 (m, 1H), 8.05-8.10 (m, 1H), 8.40-8.46 (m, 1H), 8.52 (s, 1H), 9.08 (s, 1H), 10.08 (s, 1H).

LC-MS: 433.25 (M+1).

Example 3

1-(4-(4,4-difluoropiperidin-1-ylsulfonyl)phenyl)-3-(pyridin-3-ylmethyl)urea

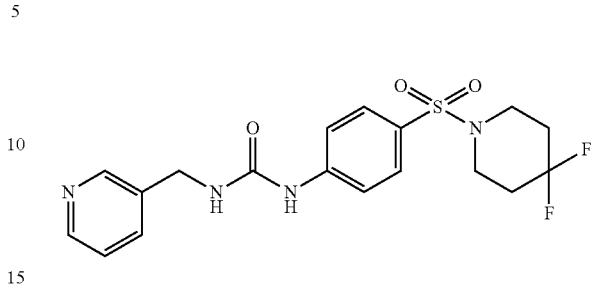

A: 4-(3-(pyridin-3-ylmethyl)ureido)benzene-1-sulfonyl chloride

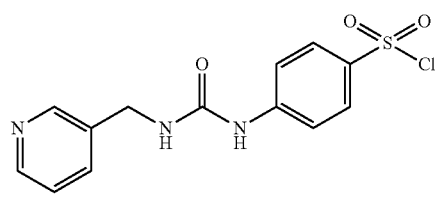 [SMILES: O=C(NCc1cccnc1)Nc1ccc(S(=O)(=O)Cl)cc1]

To an ice-cooled solution of 4-isocyanatobenzene-1-sulfonyl chloride (6 g, 27.6 mmol) in THF (250 mL) was added pyridin-3-ylmethanamine (2.79 mL, 27.6 mmol). The mixture was allowed to slowly warm to room temperature over 16 hours. The resulting precipitates were filtered off. The filtrate was concentrated to half volume and then treated with 200 mL of anhydrous ether. The resulting precipitates were filtered again, and the mother liquor was treated with 200 mL of anhydrous ether. The combined precipitates were collected as the title compound and used for next step without further purification.

$^1$H NMR (300 MHz, CDCl$_3$): δ 4.54 (s, 2H), 7.21 (br s, 1H), 7.33 (d, 2H), 7.47 (d, 2H), 8.08 (dd, 1H), 8.55 (dt, 1H), 8.50 (m, 2H), 9.24 (s, 1H).

B: 1-(4-(4,4-difluoropiperidin-1-ylsulfonyl)phenyl)-3-(pyridin-3-ylmethyl)urea

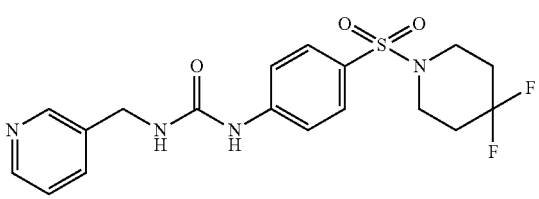 [SMILES: O=C(NCc1cccnc1)Nc1ccc(S(=O)(=O)N2CCC(F)(F)CC2)cc1]

To an ice-cooled solution of 4,4-difluoropiperidine hydrochloride (2 g, 12.69 mmol) and triethylamine (4.72 mL, 33.8 mmol) in anhydrous dichloromethane (100 mL) was added 4-(3-(pyridin-3-ylmethyl)ureido)benzene-1-sulfonyl chloride (4.24 g, 8.46 mmol) in one portion. The mixture was stirred at 0° C. for 5 minutes and at room temperature for 16 hours. The mixture was diluted with methylene chloride and washed successively with saturated aqueous sodium bicarbonate, water, and saturated aqueous sodium chloride. The organic extract was dried over MgSO$_4$, filtered and concentrated under vacuum. The crude was purified by Biotage using 10% MeOH/DCM to give the title compound.

$^1$H NMR (300 MHz, DMSO-d$_6$): δ 2.05 (m, 4H), 3.02 (t, 4H), 4.33 (d, 2H), 6.93 (t, 1H), 7.36 (dd, 1H), 7.64 (m, 4H), 7.71 (m, 1H), 8.46 (d, 1H), 8.53 (s, 1H), 9.24 (s, 1H);

LC-MS: 410.40 (M+1)

Anal. Calcd. for C$_{18}$H$_{20}$F$_2$N$_4$O$_3$S: C, 52.67; H, 4.91; N, 13.65; F, 9.26; S, 7.81.

Found: C, 52.44; H, 4.85; N, 13.49; F, 9.26; S, 7.53.

Example 4

1-(4-(4-morphohnopiperidin-1-ylsulfonyl)phenyl)-3-(pyridin-3-ylmethyl)urea

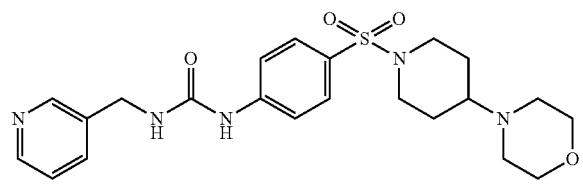

A: 4-(1-(4-nitrophenylsulfonyl)piperidin-4-yl)morpholine

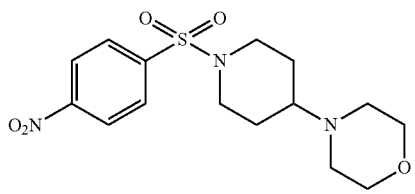 [SMILES: O=[N+]([O-])c1ccc(S(=O)(=O)N2CCC(N3CCOCC3)CC2)cc1]

To an ice-cooled solution of 4-nitrobenzene-1-sulfonyl chloride (4 g, 18.05 mmol) in DCM (50 mL) was added a solution of 4-piperidin-4-yl)morpholine (3.69 g, 21.66 mmol) and TEA (3.77 mL, 27.1 mmol) in DCM (920 mL). The mixture was stirred at 0° C. for 15 minutes and at room temperature for 16 hours. The mixture was diluted with DCM, washed with 1M NaOH, brine, dried over Na$_2$SO$_4$ and concentrated in vacuo. The residue was treated with ether and the resulting precipitates were collected to give the title compound.

$^1$H NMR (300 MHz, CDCl$_3$): δ 8.32-8.39 (m, 2H), 7.89-7.97 (m, 2H), 3.84 (d, 2H), 3.60-3.71 (m, 4H), 2.15-2.50 (m, 6H), 2.09-2.19 (m, 1H), 1.85-1.92 (m, 2H), 1.50-1.70 (m, 2H)

LC-MS: 356.06 (M+1).

B: 4-(4-morpholinopiperidin-1-ylsulfonyl)aniline

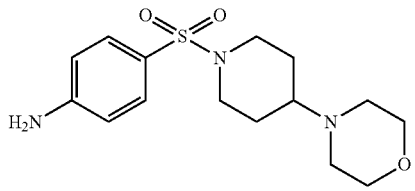

A mixture of 4-(1-(4-nitrophenylsulfonyl)piperidin-4-yl)morpholine (6.2 g, 17.44 mmol) and Raney Ni (1.02 g) in HOAc (50 mL) was hydrogenated for 16 h at 50 psi. The reaction mixture was filtered and the filtrate was concentrated. The residue was suspended in water (50 mL) and neutralized with saturated aqueous NaHCO$_3$. The precipitate was collected and dried under reduced pressure to afford the title compound.

$^1$H NMR (300 MHz, DMSO-d$_6$): δ 7.21 (d, 2H), 6.61 (d, 2H), 6.03 (br s, 2H) 3.45-3.65 (m, 6H), 2.30-2.41 (m, 4H), 1.95-2.17 (m, 3H), 1.69-1.79 (m, 2H), 1.30-1.45 (m, 2H)

LC-MS: 326.07 (M+1)

C: 1-(4-(4-morpholinopiperidin-1-ylsulfonyl)phenyl)-3-(pyridin-3-ylmethyl)urea

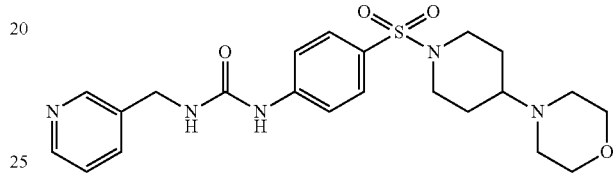

The title compound was prepared following Example 1, substituting pyridin-3-ylmethanamine and 4-(4-morpholinopiperidin-1-ylsulfonyl)aniline for (5-fluoropyridin-3-yl)methanamine and 4-(piperidin-1-ylsulfonyl)aniline, respectively.

$^1$H NMR (300 MHz, DMSO-d$_6$): δ 9.17 (s, 1H), 8.51 (d, 1H), 8.44 (dd, 1H), 7.68 (dd, 1H), 7.52-7.69 (m, 4H), 7.30-7.38 (m, 1H), 6.89 (t, 1H), 4.32 (d, 2H), 3.45-3.59 (m, 6H), 2.30-2.41 (m, 4H), 2.00-2.17 (m, 3H), 1.69-1.79 (m, 2H), 1.30-1.44 (m, 2H)

LC-MS: 460.21 (M+1).

Example 5

1-[(6-cyanopyridin-3-yl)methyl]-3-[4-(piperidine-1-sulfonyl)phenyl]urea

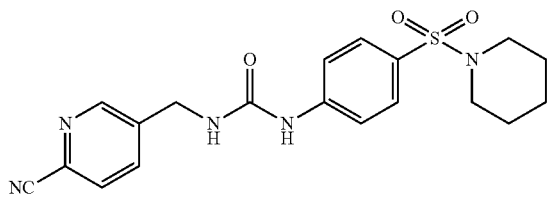 [SMILES: N#Cc1ccc(CNC(=O)Nc2ccc(S(=O)(=O)N3CCCCC3)cc2)cn1]

Triphosgene (41 mg, 0.137 mmol) was dissolved in DCM (5 mL) and cooled to −10° C. under N$_2$ atmosphere. To this cooled solution was added dropwise a mixture of 4-(piperidin-1-ylsulfonyl) aniline (100 mg, 0.416 mmol) and TEA (127 mg, 1.25 mmol) in DCM (5 mL). The mixture was stirred at −10° C. for 5 minutes and allowed to warm up to room temperature for 1 hour. A solution of 5-(aminomethyl)picolinonitrile HCl (85 mg, 0.50 mmol) and TEA (2.52 mmol) in DCM (5 mL) was then added. The reaction mixture was stirred at room temperature for 16 hours. The mixture was diluted with DCM (25 mL), washed with brine (2×15 mL), dried over MgSO$_4$, filtered and concentrated under reduced pressure. The crude was purified by Biotage using 5% MeOH/DCM to afford the desired product as a white amorphous powder (54 mg, 32.5% yield).

$^1$H NMR (300 MHz, DMSO-d$_6$): δ 8.63 (s, 1H), 7.79 (m, 2H), 7.60 (m, 2H), 7.48-7.54 (m, 3H), 6.10 (m, 1H), 4.50 (d, 2H), 2.93 (m, 4H), 1.61 (m, 4H), 1.41 (m, 2H)

LC-MS: 400.01 (M+1).

Example 6

5-((3-(4-(piperidin-1-yl)phenyl)ureido)methyl)picolinamide

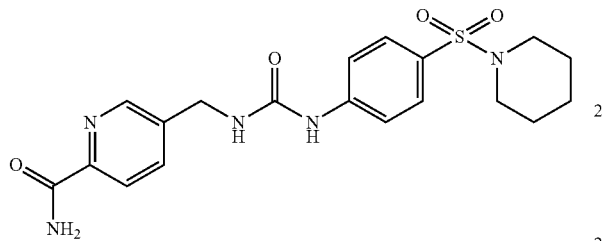

To a solution of 1-((6-cyanopyridin-3-yl)methyl)-3-(4-(piperidin-1-ylsulfonyl)phenyl) urea (Example 5, 49 mg, 0.123 mmol) and potassium carbonate (33.9 mg, 0.245 mmol) in DMSO (5 mL) was added hydrogen peroxide (0.038 ml, 0.368 mmol). The mixture was stirred at room temperature for 16 hours, then was diluted with EtOAc and washed successively with 1M NaOH and brine. The extracts were dried over Na$_2$SO$_4$, filtered, concentrated in vacuo, and purified by Biotage using 10% MeOH/DCM to afford the title compound.

$^1$H NMR (300 MHz, DMSO-d$_6$): δ 9.00 (s, 1H), 8.42 (m, 2H), 7.62 (dd, 1H), 7.52-7.57 (m, 3H), 7.30-7.34 (m, 1H), 6.34 (t, 1H), 3.36-3.39 (m, 2H), 2.74-2.82 (m, 4H), 1.51 (m, 4H) 1.32 (m, 2H)

LC-MS: 418.14 (M+1).

Example 7 tert-butyl N-{5-[({[4-(piperidine-1-sulfonyl)phenyl]carbamoyl}amino)methyl]pyridin-2-yl}carbamate

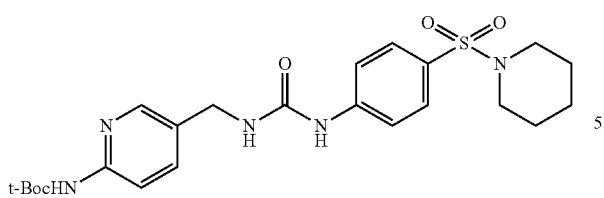

Triphosgene (122 mg, 0.412 mmol) was dissolved in DCM (5 mL) and cooled to −10° C. under N$_2$ atmosphere. To this cooled solution was added dropwise a mixture of 4-(piperidin-1-ylsulfonyl) aniline (300 mg, 1.248 mmol) and TEA (2.52 mmol) in DCM (10 mL). The mixture was stirred at −10° C. for 5 minutes and allowed to warm up to room temperature for 1 hour. A solution tert-butyl 5-(aminomethyl)pyridin-2-ylcarbamate (293 mg, 1.311 mmol) and TEA (2.52 mmol) in DCM (5 mL) was then added. The reaction mixture was stirred at room temperature for 16 hours. The mixture was diluted with DCM (25 mL), washed with brine (2×15 mL), dried over MgSO$_4$, filtered and concentrated under reduced pressure. The crude was purified by Biotage using 5% MeOH/DCM to afford the desired product as a white amorphous powder (200 mg, 32.7% yield).

$^1$H NMR (300 MHz, DMSO-d$_6$): δ 8.19 (s, 1H), 7.81 (m, 1H), 7.74 (s, 1H), 7.62 (m, 4H), 4.36 (s, 2H), 2.93 (t, 4H), 1.62 (m, 4H), 1.52 (s, 9H), 1.42 (m, 2H)

LC-MS: 489.99 (M+1).

Example 8

1-((6-aminopyridin-3-yl)methyl-3-(4-(piperidine-1-ylsulfonyl) urea

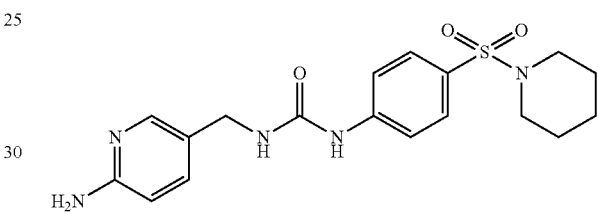

A solution of tert-butyl 5-((3-(4-(piperidin-1-ylsulfonyl)phenyl)ureido)methyl)-pyridin-2-yl carbamate (Example 7, 87 mg, 0.178 mmol) in 20 ml of 1:1 TFA/DCM was stirred at room temperature for 16 hours. After removal of the solvent, the residue was purified by Biotage using 10% MeOH (2 M NH$_3$)/DCM to afford the title compound.

$^1$H NMR (300 MHz, DMSO-d$_6$): δ 8.00 (s, 1H), 7.81 (m, 1H), 7.7.40-7.50 (m, 4H), 7.20-7.35 (dd, 1H), 6.38 (d, 1H). 5.77 (t, 1H), 4.18 (d, 2H), 2.85 (m, 4H), 1.53 (m, 4H), 1.32 (m, 2H)

LC-MS: 390.02 (M+1).

Example 9

4-(N-(5-chloro-2-methoxyphenyl)sulfamoyl)-N-(imidazo[1,2-a]pyridin-6-ylmethyl)benzamide

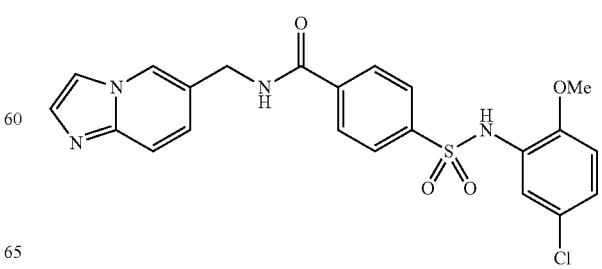

349

A. N-(5-chloro-2-methoxyphenyl)-4-cyanobenzenesulfonamide

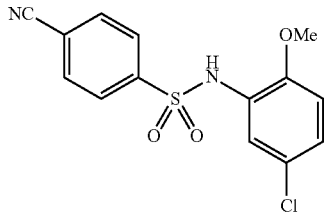 [SMILES: COc1ccc(Cl)cc1NS(=O)(=O)c1ccc(C#N)cc1]

To a solution of 5-chloro-2-methoxyaniline (821 mg, 5.21 mmol, 1.05 eq) and DMAP (61 mg, 0.496 mmol, 0.1 eq) in pyridine (15 mL) cooled to 0° C. was added dropwise a solution of 4-cyanobenzene-1-sulfonyl chloride (1.0 g, 4.96 mmol, 1.0 eq) in pyridine (5 mL). The reaction was heated at 80° C. overnight then all volatiles were removed in vacuo. The resulting residue was dissolved in dichloromethane (20 mL), washed sequentially with 1N hydrochloric acid (20 mL), water (20 mL) and saturated sodium chloride (20 mL) then dried over anhydrous sodium sulfate, filtered and concentrated under vacuum. The resulting residue was triturated twice with hexanes (10 mL) and once with diethyl ether (10 mL) and then dried under vacuum to afford N-(5-chloro-2-methoxyphenyl)-4-cyanobenzenesulfonamide (1.19 g, 74%) as a pale purple solid a portion of which was used without further purification in the subsequent step.

B. 4-(N-(5-chloro-2-methoxyphenyl)sulfamoyl)benzoic acid

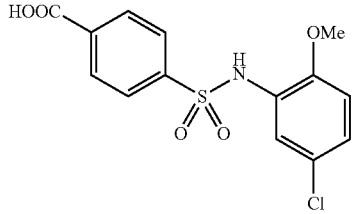 [SMILES: COc1ccc(Cl)cc1NS(=O)(=O)c1ccc(C(=O)O)cc1]

N-(5-chloro-2-methoxyphenyl)-4-cyanobenzenesulfonamide (0.387 mmol, 125 mg) was dissolved in 2-propanol (8.0 mL) and 1.8 M aqueous potassium hydroxide (6.5 mL, 11.6 mmol). The reaction was heated at 75° C. for 18 hours then cooled to ambient temperature and the 2-propanol removed on a rotary evaporator. The aqueous phase was extracted with ethyl acetate (5 mL) then the pH was adjusted to pH 2-3 with 2N hydrochloric acid and the aqueous phase was extracted thrice with ethyl acetate (10 mL). The combined organic phase was dried over anhydrous sodium sulfate, filtered and concentrated in vacuo to afford 4-(N-(5-chloro-2-methoxyphenyl)sulfamoyl)benzoic acid as a white solid (123 mg, 93%) which was used without further purification in the subsequent step.

350

C. 4-(N-(5-chloro-2-methoxyphenyl)sulfamoyl)-N-(imidazo[1,2-a]pyridin-6-ylmethyl)benzamide

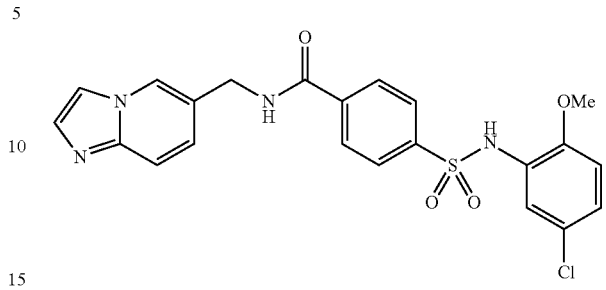

To a solution of 4-(N-(5-chloro-2-methoxyphenyl)sulfamoyl)benzoic acid (116 mg, 0.340 mmol, 1 eq) in dry DMF (3 mL) was added imidazo[1,2-a]pyridin-7-ylmethanamine (50 mg, 0.340 mmol, 1 eq), followed by benzotriazol-1-yl-oxytripyrrolidinophosphonium hexafluorophosphate (PyBOP, 194 mg, 0.374 mmol, 1.1 eq) and diisopropylethylamine (71 µL, 0.408 mmol, 1.2 eq). The resultant yellow solution stirred at ambient temperature for 4.5 hrs the all volatiles were removed under vacuum. The crude material was purified by flash column chromatography (eluting with 2-8% methanol/dichloromethane) to afford the title compound as a colorless oil which upon repeated trituration with Et$_2$O gave a white solid (91 mg, 57%).

LCMS MH$^+$=471.1

$^1$H NMR (DMSO): δH 9.95 (s, 1H), 9.24 (t, 1H), 8.49 (s, 1H), 8.00 (2, 2H), 7.94 (s, 1H), 7.82 (d, 2H), 7.53 (m, 2H), 7.19 (m, 3H), 6.94 (d, 1H), 4.47 (d, 2H) and 3.48 (s, 3H).

Example 10

1-(4-(phenylsulfonyl)phenyl)-3-(pyridin-3-ylmethyl)urea

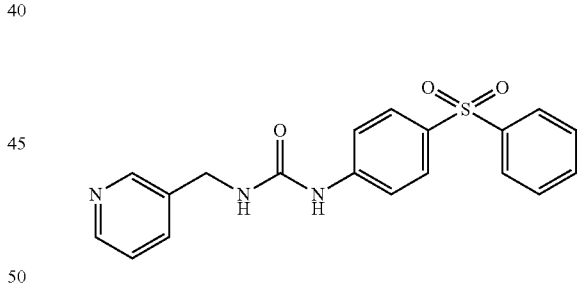

A solution of triphosgene (84 mg, 0.283 mmol) in DCM (5.0 mL) was cooled to −10° C. under N$_2$ atmosphere and was treated dropwise with a solution of 4-(phenylsulfonyl)aniline (200 mg, 0.857 mmol) and TEA (260 mg, 2.57 mmol) in DCM (5.0 mL). The mixture was stirred at −10° C. for 5 minutes, then at ambient temperature for 1 hour, whereupon this mixture was added to a solution of pyridin-3-ylmethanamine (97 mg, 0.90 mmol) and TEA (260 mg, 2.57 mmol) in DCM (5.0 mL). The mixture was stirred for 16 hours at ambient temperature, and then was diluted with DCM (25 mL), washed with brine (2×15 mL), and dried over MgSO$_4$. After filtration, the filtrate was concentrated under vacuum and purified by Biotage using 5% MeOH/DCM to afford the title compound.

$^1$H NMR (300 MHz, DMSO-d$_6$): δ 4.29 (d, 2H), 6.90 (t, 1H), 7.26-7.35 (m, 1H), 7.54-7.70 (m, 6H), 7.65-7.80 (m,

2H), 7.81-7.90 (m, 2H), 8.40-8.45 (m, 1H), 8.49-8.55 (m, 1H), 9.21 (s, 1H). LC-MS: 368.15 (M+H).

Example 11

1-(pyridin-3-ylmethyl)-3-(4-(2-(trifluoromethoxy)phenylsulfonyl)phenyl)urea

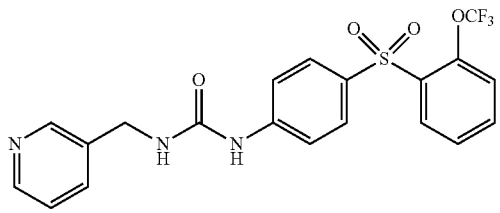 [SMILES: O=C(NCc1cccnc1)Nc1ccc(S(=O)(=O)c2ccccc2OC(F)(F)F)cc1]

A: 4-(3-(pyridin-3-ylmethyl)ureido)benzene-1-sulfonyl chloride:

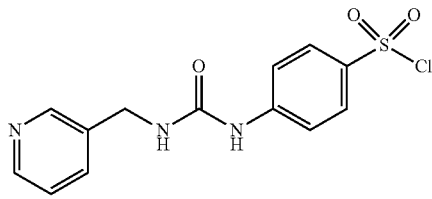 [SMILES: O=C(NCc1cccnc1)Nc1ccc(S(=O)(=O)Cl)cc1]

4-Isocyanatobenzene-1-sulfonyl chloride (6 g, 27.6 mmol) was taken up in THF (250 mL) and cooled to 0° C., whereupon pyridin-3-ylmethanamine (2.79 mL, 27.6 mmol) was added and the resulting mixture was allowed to warm slowly to ambient temperature over 16 hours. The mixture was filtered and the filtrate was concentrated to half its original volume and was treated with 200 mL of anhydrous Et$_2$O. The precipitates were again filtered off and the filtrate was treated with 200 mL of anhydrous Et$_2$O. The resulting precipitates were collected by vacuum filtration and used in the next step without further purification.

$^1$H NMR (300 MHz, CDCl$_3$): δ 4.54 (s, 2H), 7.21 (br s, 1H), 7.33 (d, 2H), 7.47 (d, 2H), 8.08 (dd, 1H), 8.55 (dt, 1H), 8.50 (m, 2H), 9.24 (s, 1H).

B: Ammonium 4-(3-(pyridin-3-ylmethyl)ureido)benzenesulfinate

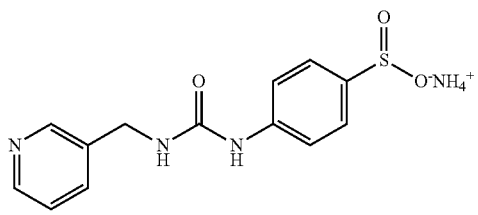

4-(3-(Pyridin-3-ylmethyl)ureido)benzene-1-sulfonyl chloride (3.99 g, 12.25 mmol) was added to a solution of sodium sulfite (6.18 g, 49.0 mmol) and sodium bicarbonate (6.17 g, 73.5 mmol) in water (175 mL), and the resulting mixture was stirred at 80° C. for 3 hours. The mixture was then concentrated to dryness under reduced pressure, and the resulting solids were triturated with hot DMF (100 mL) and the solids filtered off. The solvent was then removed under reduced pressure, and the resulting residue was triturated with hot DCM (100 mL) and the off-white crystalline solids were collected by vacuum filtration. The solids were purified by SCX ion-exchange column (eluting with 5:1 CH$_3$CN/NH$_4$OH) to afford the title compound.

$^1$H NMR (300 MHz, CDCl$_3$): δ 4.28 (d, 2H), 7.35 (m, 6H), 7.70 (dt, 1H), 8.42 (dd, 1H), 8.51 (d, 1H), 9.23 (br s, 1H). LC-MS: 292.01 (M+1)

C: 1-(pyridin-3-ylmethyl)-3-(4-(2-(trifluoromethoxy)phenylsulfonyl)phenyl)urea

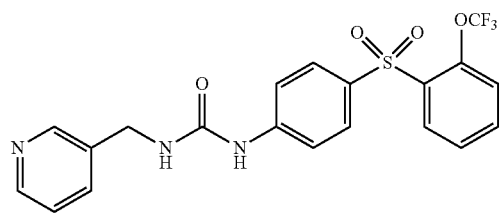 [SMILES: O=C(NCc1cccnc1)Nc1ccc(S(=O)(=O)c2ccccc2OC(F)(F)F)cc1]

A mixture of ammonium 4-(3-(pyridin-3-ylmethyl)ureido)benzenesulfinate (30.8 mg, 0.1 mmol), 2-(trifluoromethyl)phenylboronic acid (25.7 mg, 0.125 mmol), copper(II) acetate (22.7 mg, 0.125 mmol), and TEA (0.063 mL, 0.45 mmol) in DMSO (1.5 mL) was heated at 60° C. for 16 hours. The mixture was cooled to ambient temperature and was partitioned between EtOAc and brine. The organic layer was separated, dried (MgSO$_4$), concentrated, and purified by PTLC (100% EtOAc) to afford the title compound.

$^1$H NMR (300 MHz, DMSO-d$_6$): δ 9.26 (s, 1H), 8.50 (d, 1H), 8.44-8.42 (m, 1H), 8.17-8.14 (m, 1H), 7.84-7.78 (m, 1H), 7.75-7.59 (m, 6H), 7.52-7.49 (m, 1H), 7.35-7.31 (m, 1H), 6.93 (t, 1H), 4.30 (d, 2H). LC-MS: 452.09 (M+1)

Example 12

1-(3-aminobenzyl)-3-(4-(phenylsulfonyl)phenyl)urea

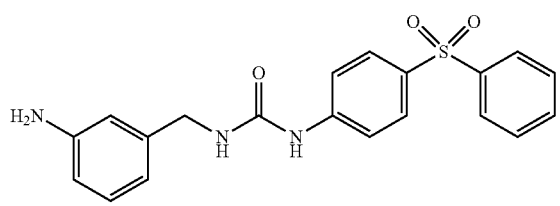 [SMILES: Nc1cccc(CNC(=O)Nc2ccc(S(=O)(=O)c3ccccc3)cc2)c1]

A: tert-butyl 3-((3-(4-(phenylsulfonyl)phenyl)ureido)methyl)phenylcarbamate

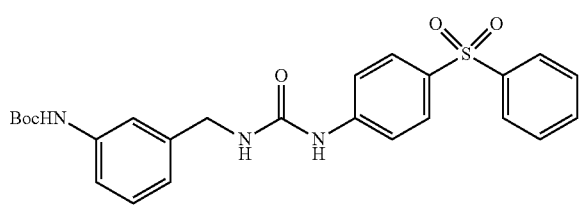 [SMILES: CC(C)(C)OC(=O)Nc1cccc(CNC(=O)Nc2ccc(S(=O)(=O)c3ccccc3)cc2)c1]

The title compound was prepared according to Example 1, substituting tert-butyl 3-(aminomethyl)phenylcarbamate for pyridin-3-ylmethanamine.

$^1$H NMR (300 MHz, CDCl$_3$): δ 7.82-7.89 (m, 2H), 7.70-7.76 (m, 2H), 7.42-7.58 (m, 4H), 7.38 (d, 2H), 7.29 (s, 1H), 7.10-7.16 (m, 2H), 6.62-6.89 (m, 1H), 6.65 (s, 1H), 5.52 (t, 1H), 4.22 (d, 2H), 1.47 (s, 9H) LC-MS: 482.08 (M+H).

B: 4-(3-(pyridin-3-ylmethyl)ureido)benzene-1-sulfonyl chloride

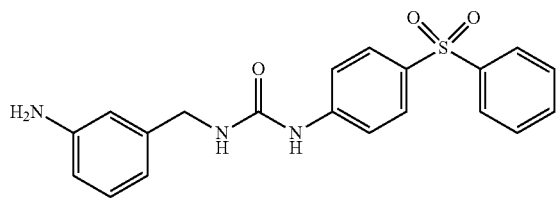 [SMILES: Nc1cccc(CNC(=O)Nc2ccc(S(=O)(=O)c3ccccc3)cc2)c1]

A solution of tert-butyl 3-((3-(4-(phenylsulfonyl)phenyl)ureido)methyl)phenyl-carbamate (390 mg, 0.810 mmol) and TFA (5 mL, 64.9 mmol) in DCM (10 mL) was stirred at ambient temperature for 16 hours. The mixture was concentrated and partitioned between DCM and saturated NaHCO$_3$. The organic layer was washed with brine (2×15 mL), dried over Na$_2$SO$_4$, filtered, and concentrated. The residue was purified by Biotage using 10% MeOH/DCM to offer the title compound.

$^1$H NMR (300 MHz, DMSO-d$_6$): δ 9.21 (s, 1H), 8.49-8.55 (m, 2H), 8.40-8.45 (m, 2H), 7.81-7.90 (m, 5H), 6.90 (t, 1H), 6.69 (t, 1H), 6.40-6.50 (m, 3H), 5.41 (br, s, 2H), 4.14 (d, 2H) LC-MS: 382.28 (M+H).

Example 13

1-(4-(4-chlorophenylthio)phenyl)-3-(pyridin-3-ylmethyl)urea

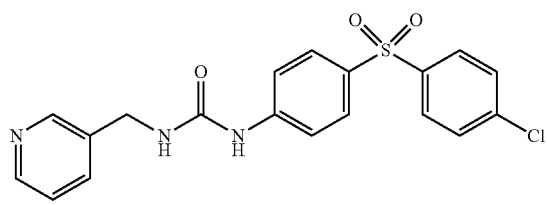 [SMILES: O=C(NCc1cccnc1)Nc1ccc(S(=O)(=O)c2ccc(Cl)cc2)cc1]

A: 4-(4-chlorophenylthio)aniline

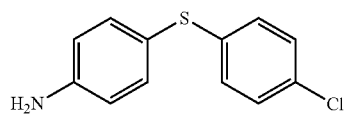 [SMILES: Nc1ccc(Sc2ccc(Cl)cc2)cc1]

A solution of (4-chlorophenyl)(4-nitrophenyl)sulfane (1.71 g, 6.44 mmol) in 2:1 MeOH/EtOAc (75 mL) was treated with platinum(IV) oxide (100 mg) and the resulting mixture was placed under an atmosphere of hydrogen (45 psi) for 16 hours. The mixture was filtered through GF/F paper, rinsed with MeOH, and concentrated under reduced pressure to afford the title compound as a yellow solid.

$^1$H NMR (300 MHz, CDCl$_3$): δ 7.32-7.27 (m, 2H), 7.19-7.14 (m, 2H), 7.05-7.01 (m, 2H), 6.70-6.65 (m, 2H), 3.83 (s, 2H).

B: 1-(4-(4-chlorophenylthio)phenyl)-3-(pyridin-3-ylmethyl)urea

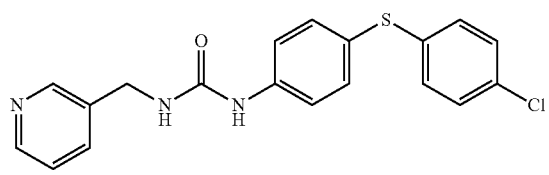 [SMILES: O=C(NCc1cccnc1)Nc1ccc(Sc2ccc(Cl)cc2)cc1]

The title compound was prepared according to Example 1, substituting 4-(4-chlorophenylthio)aniline for 4-(phenylsulfonyl)aniline.

$^1$H NMR (DMSO-d$_6$): δ 8.90 (s, 1H), 8.51 (d, 1H), 8.45-8.43 (m, 1H), 7.71-7.67 (m, 1H), 7.51-7.46 (m, 2H), 7.37-7.31 (m, 5H), 7.11-7.06 (m, 2H), 6.81 (t, 1H), 4.30 (d, 2H).

C. 1-(4-(4-chlorophenylthio)phenyl)-3-(pyridin-3-ylmethyl)urea

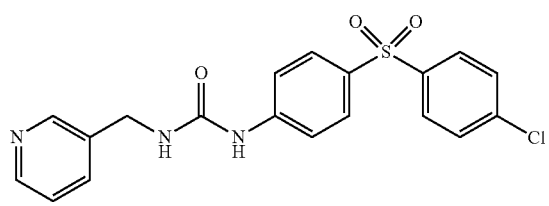 [SMILES: O=C(NCc1cccnc1)Nc1ccc(S(=O)(=O)c2ccc(Cl)cc2)cc1]

A solution of 1-(4-(4-chlorophenylthio)phenyl)-3-(pyridin-3-ylmethyl)urea (50 mg, 0.135 mmol) in 10:1 DCM:MeOH (3.3 mL) was treated with m-CPBA (2.0 equiv), and the solution was stirred for 16 hours at ambient temperature. The mixture was then diluted with saturated NaHCO$_3$ and DCM and the layers separated. The organic layer was dried over MgSO$_4$ and purified by PTLC (6% MeOH/DCM) to afford the title compound.

$^1$H NMR (300 MHz, DMSO-d$_6$): δ 9.24 (s, 1H), 8.49 (s, 1H), 8.43-8.42 (m, 1H), 7.88 (d, 2H), 7.79 (d, 2H), 7.68-7.58 (m, 5H), 7.35-7.31 (m, 1H), 6.92 (t, 1H), 4.30 (d, 2H). LC-MS: 402.00 (M+1)

Example 14

1-((6-(dimethylamino)pyridin-3-yl)methyl)-3-(4-(phenylsulfonyl)phenyl)urea

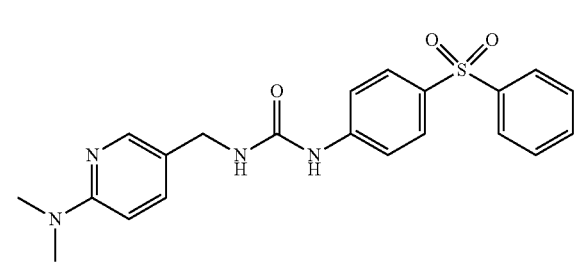 [SMILES: CN(C)c1ccc(CNC(=O)Nc2ccc(S(=O)(=O)c3ccccc3)cc2)cn1]

A: 6-(dimethylamino)nicotinonitrile

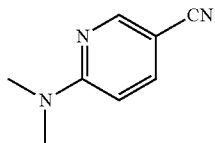

In a sealed tube, 6-chloronicotinonitrile (510 mg, 3.68 mmol) was taken up in DMF (4 mL) and dimethylamine (4.0 mL of a 2.0M THF solution) and DIEA (3.0 mL, 17.18 mmol) were added. The mixture was heated to 140° C. for 17 hours, and was then diluted with EtOAc and washed with brine (3×) and dried (MgSO$_4$). After filtration and concentration, the residue was purified by Biotage SP1 (100% MeOH/DCM/NH$_3$) to afford the title compound as a pale yellow solid.

$^1$H NMR (300 MHz, CDCl$_3$): δ 8.40 (d, 1H), 7.60-7.56 (m, 1H), 6.49-6.46 (m, 1H), 3.15 (s, 6H).

B: 5-(aminomethyl)-N,N-dimethylpyridin-2-amine

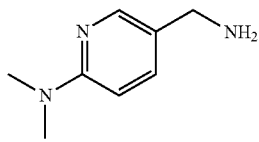

A solution of 6-(dimethylamino)nicotinonitrile (506 mg, 3.44 mmol) in 2:1 2N NH$_3$ (75 mL) was treated with Raney Nickel and placed under a 40 psi atmosphere of hydrogen for 16 hours. The mixture was then carefully filtered through Celite (caution: to minimize danger of fire, do not allow solids to become dry), the filtrate concentrated to dryness, and purified by Biotage SP1 (DCM/MeOH/NH$_3$). The concentrated fractions were then triturated with Et$_2$O to afford the title compound as a white solid.

$^1$H NMR (300 MHz, DMSO-d$_6$): δ 7.97-7.94 (m, 1H), 7.48-7.37 (m, 1H), 6.57 (d, 1H), 3.95 (d, 2H), 3.55 (br s, 2H), 2.96 (s, 6H).

C: 1-((6-(dimethylamino)pyridin-3-yl)methyl)-3-(4-(phenylsulfonyl)phenyl)urea

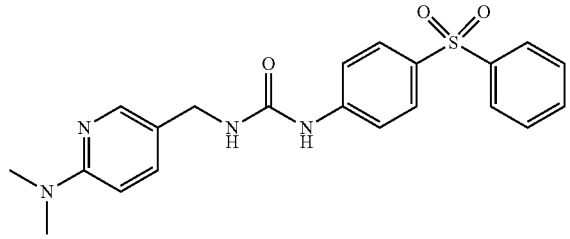 [SMILES: CN(C)c1ccc(CNC(=O)Nc2ccc(S(=O)(=O)c3ccccc3)cc2)cn1]

The title compound was prepared according to Example 1, substituting 5-(aminomethyl)-N,N-dimethylpyridin-2-amine for pyridin-3-ylmethanamine.

$^1$H NMR (300 MHz, DMSO-d6): δ 9.05 (s, 1H), 7.99 (d, 1H), 7.90-7.86 (m, 2H), 7.77 (d, 2H), 7.65-7.55 (m, 5H), 7.44-7.41 (m, 1H), 6.66 (t, 1H), 6.57 (d, 1H), 4.10 (d, 2H), 2.96 (s, 6H). LC-MS: 411.06 (M+1)

Example 15

1-(4-(4-bromophenylsulfonyl)phenyl)-3-(pyridin-3-ylmethyl)urea

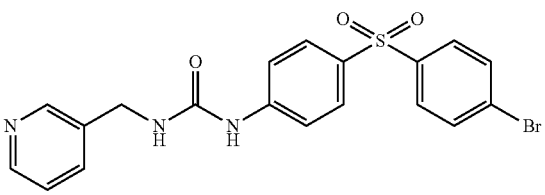 [SMILES: O=C(NCc1cccnc1)Nc1ccc(S(=O)(=O)c2ccc(Br)cc2)cc1]

A: (4-bromophenyl)(4-nitrophenyl)sulfane

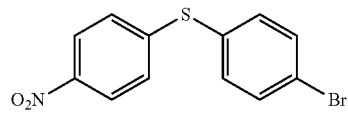 [SMILES: O=[N+]([O-])c1ccc(Sc2ccc(Br)cc2)cc1]

A solution of 4-bromobenzenethiol (4.97 g, 26.3 mmol) in DMF (50 mL) was cooled to 0° C. and treated with K$_2$CO$_3$ (4.3 g, 31.1 mmol). After addition was complete, the solution was warmed to ambient temperature over 15 minutes and then 1-fluoro-4-nitrobenzene (2.62 mL, 24.70 mmol) was added. The mixture was heated to 80° C. for 16 hours, and was then poured onto ice and diluted with EtOAc. The layers were separated and the organic layer was washed successively with saturated NaHCO$_3$ and brine (2×). The organics were dried over MgSO$_4$, filtered, and concentrated to afford the title compound as a yellow solid.

$^1$H NMR (300 MHz, DMSO-d$_6$): δ 8.18-8.13 (m, 2H), 7.87-7.84 (m, 2H), 7.53-7.41 (m, 2H), 7.31-7.27 (m, 2H).

B: 4-bromo-2-(4-nitrophenylsulfonyl)benzene

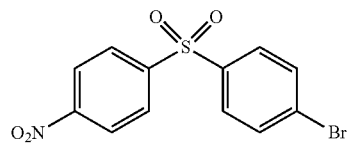

A solution of (4-bromophenyl)(4-nitrophenyl)sulfane (3.942 g, 12.71 mmol) in CHCl$_3$ (40 ml) was cooled in an ice bath and treated with m-CPBA (2.2 equiv) portionwise. The mixture was allowed to warm slowly to ambient temperature over 16 hours, then the mixture was filtered through GF/F paper and the filtrate washed with 1N NaOH and brine. The organics were dried over MgSO$_4$, filtered, and concentrated to the crude solid. The solid can be triturated (if desired) with DCM and collected by vacuum filtration to afford the title compound.

$^1$H NMR (300 MHz, DMSO-d$_6$): δ 8.42-8.36 (m, 4H), 8.18-8.13 (m, 2H), 7.87-7.84 (m, 2H).

C: 4-(2-bromophenylsulfonyl)aniline

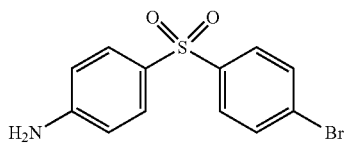 [SMILES: Nc1ccc(S(=O)(=O)c2ccc(Br)cc2)cc1]

A mixture of 1-bromo-4-(4-nitrophenylsulfonyl)benzene (1.57 g, 4.59 mmol) and tin(II) chloride dihydrate (4.35 g, 22.94 mmol) was heated in EtOH (40 mL) for 2 hours at 70° C. The volatiles were removed under reduced pressure, and the residue was taken up in EtOAc (100 mL) and 2N NaOH (40 mL). The mixture was stirred vigorously for 1 hour, then filtered through Celite. The organic layer was separated, dried over MgSO$_4$, and purified by Biotage SP1 to afford the title compound.

$^1$H NMR (300 MHz, DMSO-d$_6$): δ d 7.78-7.71 (m, 4H), 7.52 (d, 2H), 6.59 (d, 2H), 6.22 (s, 2H).

D: 1-(4-(4-bromophenylsulfonyl)phenyl)-3-(pyridin-3-ylmethyl)urea

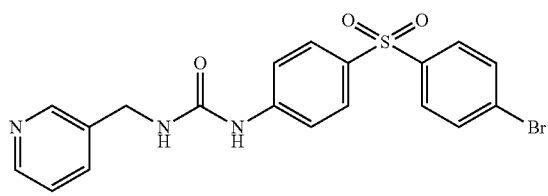 [SMILES: O=C(NCc1cccnc1)Nc1ccc(S(=O)(=O)c2ccc(Br)cc2)cc1]

The title compound was prepared according to Example 1, substituting 4-(4-bromophenylsulfonyl)aniline for 4-(phenylsulfonyl)aniline $^1$H NMR (300 MHz, DMSO-d$_6$): δ 9.26 (s, 1H), 8.50 (d, 1H), 8.44-8.42 (m, 1H), 7.83-7.70 (m, 6H), 7.69-7.65 (m, 1H), 7.62-7.58 (m, 2H), 7.35-7.31 (m, 1H), 6.93 (t, 1H), 4.30 (d, 2H). LC-MS: 447.95 (M+1).

Example 16

1-[(6-aminopyridin-3-yl)methyl]-3-[4-(benzenesulfonyl)phenyl]urea

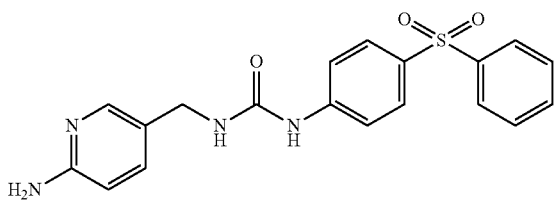 [SMILES: Nc1ccc(CNC(=O)Nc2ccc(S(=O)(=O)c3ccccc3)cc2)cn1]

A: tert-butyl 5-((3-(4-(phenylsulfonyl)phenyl)ureido)methyl)pyridin-2-ylcarbamate

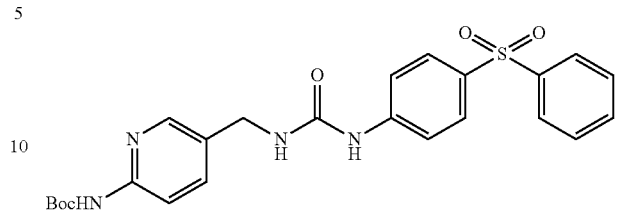

A solution of 4-phenylsulfonylaniline (1.5 g, 6.43 mmol) in EtOAc (10 mL) was added dropwise over 30 minutes to a solution of phosgene (6 ml, 20% in Toluene) in toluene (5 mL), and was then heated to reflux for 5 hours. The volatiles were removed under reduced pressure, and DCM (50 mL), tert-butyl 5-(aminomethyl) pyidin-2-yl carbamate (1.507 g, 6.75 mol), and DIEA (4 mL) were added to the residue. The mixture was stirred at ambient temperature for 16 hours, then was diluted with DCM and washed with saturated sodium bicarbonate. The organics were dried over MgSO$_4$, concentrated, and purified by Biotage SP1 to afford the title compound.

$^1$H NMR (300 MHz, DMSO-d$_6$): δ 9.69 (s, 1H), 9.15 (s, 1H), 8.14 (s, 1H), 7.87 (dd, 2H), 7.78 (m, 2H), 7.70-7.73 (m, 1H), 7.57-7.66 (m, 6H), 6.81 (t, 1H), 4.21 (d, 2H), 1.44 (s, 9H).

B: 1-[(6-aminopyridin-3-yl)methyl]-3-[4-(benzenesulfonyl)phenyl]urea

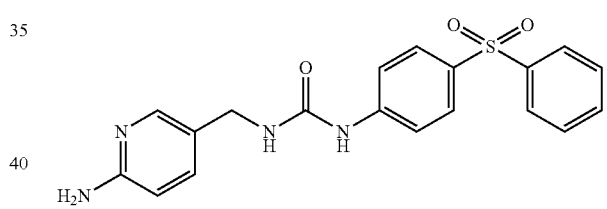

The title compound was prepared according to Example 3B, substituting tert-butyl 5-((3-(4-(phenylsulfonyl)phenyl)ureido)methyl)pyridin-2-ylcarbamate for tert-butyl 3-((3-(4-(phenylsulfonyl)phenyl)ureido)methyl)phenyl-carbamate.

$^1$H NMR (300 MHz, CDCl$_3$): δ 9.03 (s, 1H), 7.86-7.89 (m, 2H), 7.78-7.81 (m, 3H), 7.58-7.77 (m, 5H), 7.27-7.31 (dd, 1H), 6.63 (t, 1H), 6.37 (d, 1H), 5.81 (s, 2H), 4.06 (d, 2H) LC-MS: 383.13 (M+1).

Example 17

1-(4-(phenylsulfonyl)phenyl)-3-(pyridin-3-ylmethyl)urea

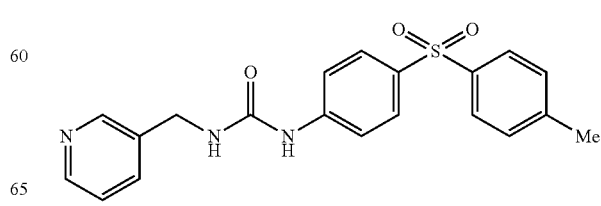

A mixture of (9,9-dimethyl-9H-xanthene-4,5-diyl)bis(diphenylphosphine) (37.8 mg, 0.065 mmol), Cs$_2$CO$_3$ (319 mg, 0.980 mmol), tri(dibenzylideneacetone)dipalladium(0) (29.9 mg, 0.033 mmol), sodium 4-methylbenzenesulfinate (140 mg, 0.784 mmol), 1-(4-bromophenyl)-3-(pyridine-3-ylmethyl)urea (200 mg, 0.653 mg), and tertrabutylammonium iodide (290 mg, 0.784 mmol) in toluene (10 mL) was heated at 100° C. for 16 hours. The mixture was cooled to ambient temperature and DCM was added. The organic layer was washed successively with water and brine, dried over MgSO$_4$, concentrated, and purified by Biotage SP1 to afford the title compound.

$^1$H NMR (300 MHz, CDCl$_3$): δ 8.47 (s, 1H), 8.44 (d, 1H), 8.32 (s, 1H), 7.69-7.74 (m, 4H), 7.63 (d, 1H), 7.47-7.51 (dd, 2H), 7.26-7.46 (m, 3H), 6.12 (s, 1H), 4.38 (d, 2H), 2.37 (s, 3H) LC-MS: 382.15 (M+1).

Example 18

N-(imidazo[1,2-a]pyridin-6-ylmethyl)-4-(phenylsulfonyl)benzamide

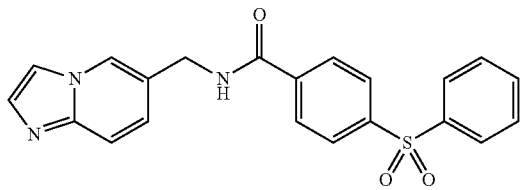 [SMILES: O=C(NCc1ccc2nccn2c1)c1ccc(S(=O)(=O)c2ccccc2)cc1]

A. 4-sulfonylbenzonitrile

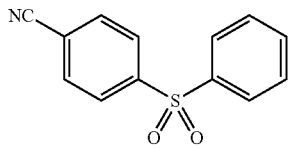 [SMILES: N#Cc1ccc(S(=O)(=O)c2ccccc2)cc1]

4-fluorobenzonitrile (46.5 mmol, 5.63 g) and sodium benzenesulfinate (51.1 mmol, 8.39 g) were dissolved in DMSO (35.8 mL). The reaction was heated at 130° C. for 48 hours then cooled to ambient temperature and poured onto ice. The precipitated solids were collected by suction filtration, washed with water and then dried under vacuum to afford 4-sulfonylbenzonitrile (11.2 g) a portion of which was used in the subsequent step without further purification.

B. 4-phenylsulfonylbenzoic acid

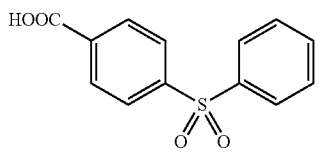 [SMILES: O=C(O)c1ccc(S(=O)(=O)c2ccccc2)cc1]

4-sulfonylbenzonitrile (4.11 mmol, 1.0 g) was dissolved in 2-propanol (88 mL) and 1.0 M aqueous potassium hydroxide (140 mL). The reaction was heated at 75° C. for 18 hours then cooled to ambient temperature and the 2-propanol removed on a rotary evaporator. The aqueous phase was extracted with ethyl acetate (70 mL) then the pH was adjusted to pH 2-3 with 6N hydrochloric acid and the aqueous phase was extracted thrice with ethyl acetate (100 mL). The combined organic phase was dried over anhydrous magnesium sulfate, filtered and concentrated in vacuo to afford 4-phenylsulfonylbenzoic acid as a white solid (1.01 g) a portion of which was used without further purification in the subsequent step.

C. N-(imidazo[1,2-a]pyridin-6-ylmethyl)-4-(phenylsulfonyl)benzamide

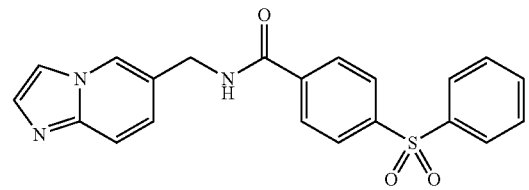 [SMILES: O=C(NCc1ccc2nccn2c1)c1ccc(S(=O)(=O)c2ccccc2)cc1]

Oxalyl chloride (66.7 μL, 0.763 mmol) was added dropwise to a solution of 4-phenylsulfonylbenzoic acid (100 mg, 0.381 mmol) in dichloromethane (3.81 mL) at 0° C. The reaction stirred for 2 hours then all volatiles were removed under vacuum. The crude 4-phenylsulfonylbenzoyl chloride was re-dissolved in dichloromethane (3.8 mL) then imidazo[1,2-a]pyridin-7-ylmethanamine hydrochloride (77 mg, 0.419 mmol) and triethylamine (117 μL, 0.839 mmol) were added successively. The reaction stirred for 1 hour at ambient temperature then saturated sodium bicarbonate (3.8 mL) was added. The organic phase was separated, washed with saturated sodium chloride (3 mL), dried over anhydrous magnesium sulfate and concentrated in vacuum. The resulting residue was purified by flash column chromatography (eluting with 5% methanol/dichlormethane) to afford the title compound as a white solid (73 mg, 49%).

LCMS MH$^+$=391.9

$^1$H NMR (MeOD): δH 8.29 (s, 1H), 8.00 (s, 4H), 7.93 (d, 2H), 7.65-7.48 (m, 6H), 7.27 (dd, 1H) and 4.50 (s, 2H).

ASSAYS

Assay Example 1

Biochemical Inhibition Assay
NAMPT Protein Purification

Recombinant His-tagged NAMPT was produced in *E. coli* cells, purified over a Ni column, and further purified over a size-exclusion column by XTAL Biostructures.

The NAMPT Enzymatic Reaction

The NAMPT enzymatic reactions were carried out in Buffer A (50 mM Hepes pH 7.5, 50 mM NaCl, 5 mM MgCl$_2$, and 1 mM THP) in 96-well V-bottom plates. The compound titrations were performed in a separate dilution plate by serially diluting the compounds in DMSO to make a 100× stock. Buffer A (89 μL) containing 33 nM of NAMPT protein was added to 1 ΞL of 100× compound plate containing controls (e.g. DMSO or blank). The compound and enzyme mix was incubated for 15 minutes at room temperature, then 10 μL of 10× substrate and co-factors in Buffer A were added to the test well to make a final concentration of 1 μM NAM, 100 μM 5-Phospho-D-ribose 1-diphosphate (PRPP), and 2.5 mM Adenosine 5'-triphosphate (ATP). The reaction was allowed to proceed for 30 minutes at room temperature, then was quenched with the addition of 11 μL of a solution of formic acid and L-Cystathionine to make a final concentration of 1% formic acid and 10 μM L-Cystathionine. Background and signal strength was determined by addition (or non-addition) of a serial dilution of NMN to a pre-quenched enzyme and cofactor mix.

Quantification of NMN

A mass spectrometry-based assay was used to measure the NAMPT reaction product (NMN) and the internal control (L-Cystathionine). NMN and L-Cystathionine were detected using the services of Biocius Lifesciences with the Rapid-Fire system. In short, the NMN and L-Cystathionine are bound to a graphitic carbon cartridge in 0.1% formic acid, eluted in 30% acetonitrile buffer, and injected into a Sciex 4000 mass spectrometer. The components of the sample were ionized with electrospray ionization and the positive ions were detected. The Q1 (parent ion) and Q3 (fragment ion) masses of NMN were 334.2 and 123.2, respectively. The Q1 and Q3 for L-Cystathionine were 223.1 and 134.1, respectively. The fragments are quantified and the analyzed by the following method.

% Inhibitions are Determined Using this Method.

First the NMN signal is normalized to the L-Cystathionine signal by dividing the NMN signal by the L-Cystathionine signal for each well. The signal from the background wells are averaged and subtracted from the test plates. The compound treated cells re then assayed for % inhibition by using this formula.

$$\% \mathit{Inh} = 100 - 100 * x/y$$

wherein x denotes the average signal of the compound treated wells and y denotes the average signal of the DMSO treated wells.

IC50s are Determined Using Excel and this Formula.

$$IC50 = 10^{\wedge}(LOG\ 10(X) + (((50 - \%\ \mathit{Inh}\text{at Cmpd Concentration 1})/(XX - YY) * (LOG\ 10(X) - LOG\ 10(Y))))$$

wherein X denotes the compound concentration 1, Y denotes the compound concentration 2, XX denotes the % inhibition at compound concentration 1 (X), and YY denotes the % inhibition at compound concentration 2 (Y).

The NAMPT-inhibitor compounds of this invention have IC50 values that are under 10 μM, preferably under 1 μM, more preferably under 0.1 μM, and most preferably under 0.01 μM. Results for representative compounds are provided in Table 3 below.

Assay Example 2

In-Vitro Cell Proliferation Assay

A2780 cells were seeded in 96-well plates at 1×10³ cells/well in 180 μL of culture medium (10% FBS, 1% Pen/Strep Amphotecricin B, RPMI-1640) with and without the addition of either β-nicotinamide mononucleotide (NMN) or nicotinamide (NAM). After overnight incubation at 37° C. and 5% $CO_2$, the compound titrations were performed in a separate dilution plate by serially diluting the compounds in DMSO to make a 1000× stock. The compounds were then further diluted to 10× final concentration in culture media, whereupon 20 μL of each dilution was added to the plated cells with controls (e.g. DMSO and blank) to make a final volume of 200 μL. The final DMSO concentration in each well was 0.1%. The plates were then incubated for 72 hours at 37° C. in a 5% $CO_2$ incubator. The number of viable cells was then assessed using sulforhodamine B (SRB) assay. Cells were fixed at 4° C. for 1 hour with the addition of 50 μL 30% trichloroacetic acid (TCA) to make a final concentration of 6% TCA. The plates were washed four times with $H_2O$ and allowed to dry for at least 1 hour, whereupon 100 μL of a 4% SRB in 1% acetic acid solution was added to each well and incubated at room temperature for at least 30 minutes. The plates were then washed three times with 1% acetic acid, dried, and treated with 100 μL of 10 mM Tris-Base solution. The plates were then read in a microplate reader at an absorbance of 570 nm. Background was generated on a separate plate with media only.

Method for Determining % Inhibition

First, the signals from the background plate are averaged, then the background was subtracted from the test plates. The compound-treated cells were then assayed for % inhibition by using the following formula:

$$\% \mathit{Inh} = 100 - 100 * x/y$$

wherein x denotes the average signal of the compound-treated cells and y denotes the average signal of the DMSO-treated cells.

Formula for Determining $IC_{50}$ Values:

$$IC50 = 10^{\wedge}(LOG\ 10(X) + (((50 - \%\ \mathit{Inh}\text{at Cmpd Concentration 1})/(XX - YY) * (LOG\ 10(X) - LOG\ 10(Y))))$$

wherein X denotes the compound concentration 1, Y denotes the compound concentration 2, XX denotes the % inhibition at compound concentration 1 (X), and YY denotes the % inhibition at compound concentration 2 (Y).

Specificity of Cytotoxicity.

Inhibition of NAMPT could be reversed by the addition of NAM or NMN. The specificity of the compounds were determined via cell viability assay in the presence of the compound and either NAM or NMN. Percent inhibitions were determined using the method given above.

The NAMPT-inhibitor compounds of this invention have IC50 values that are preferably under 1 μM, more preferably under 0.1 μM, and most preferably under 0.01 μM. Most preferable compounds of this invention are compounds that have both the enzymatic IC50-value and the A2780 IC50-value under under 10 μM, preferably under 1 μM, more preferably under 0.1 μM, and most preferably under 0.01 μM.

Results for representative compounds is provided in Table 3 below.

TABLE 3

| Compound | Biochem IC50 uM | A2780 IC50 uM |
|---|---|---|
| (3S)-N,N-diethyl-1-[(4-{[(pyridin-3-ylmethyl)carbamoyl]amino}benzene)sulfonyl]piperidine-3-carboxamide | 0.006 | 0.025 |
| 1-(4-{[(1S,2S,4R)-bicyclo[2.2.1]heptan-2-yl]sulfamoyl}phenyl)-3-(pyridin-3-ylmethyl)urea | 0.007 | 0.046 |
| 1-(4-{[2-(morpholin-4-yl)phenyl]sulfamoyl}phenyl)-3-(pyridin-3-ylmethyl)urea | 0.005 | 0.011 |

TABLE 3-continued

| Compound | Biochem IC50 uM | A2780 IC50 uM |
| --- | --- | --- |
| 1-(4-{[2-(piperidin-1-yl)phenyl]sulfamoyl}phenyl)-3-(pyridin-3-ylmethyl)urea | 0.004 | 0.018 |
| 1-(4-{[3-(morpholin-4-yl)phenyl]sulfamoyl}phenyl)-3-(pyridin-3-ylmethyl)urea | 0.006 | 0.103 |
| 1-(4-{[4-(morpholin-4-yl)phenyl]sulfamoyl}phenyl)-3-(pyridin-3-ylmethyl)urea | 0.005 | 0.173 |
| 1-(4-{[4-(piperidin-1-yl)phenyl]sulfamoyl}phenyl)-3-(pyridin-3-ylmethyl)urea | 0.004 | 0.054 |
| 1-(4-{2-azabicyclo[2.2.1]heptane-2-sulfonyl}phenyl)-3-(pyridin-3-ylmethyl)urea | 0.01 | 0.236 |
| 1-(4-{2-oxa-8-azaspiro[4.5]decane-8-sulfonyl}phenyl)-3-(pyridin-3-ylmethyl)urea | 0.005 | 0.089 |
| 1-(4-{3-[(2-oxopyrrolidin-1-yl)methyl]piperidine-1-sulfonyl}phenyl)-3-(pyridin-3-ylmethyl)urea | 0.003 | 0.143 |
| 1-(4-{3-azaspiro[5.5]undecane-3-sulfonyl}phenyl)-3-(pyridin-3-ylmethyl)urea | 0.011 | 0.145 |
| 1-(4-{3-azatricyclo[7.3.1.0$^{5,13}$]trideca-1(13),5,7,9,11-pentaene-3-sulfonyl}phenyl)-3-(pyridin-3-ylmethyl)urea | 0.002 | 0.026 |
| 1-(4-{3-oxa-8-azabicyclo[3.2.1]octane-8-sulfonyl}phenyl)-3-(pyridin-3-ylmethyl)urea | 0.012 | 0.287 |
| 1-(4-{4-[(2-oxopyrrolidin-1-yl)methyl]piperidine-1-sulfonyl}phenyl)-3-(pyridin-3-ylmethyl)urea | 0.002 | 0.078 |
| 1-(4-{4-[(furan-2-yl)carbonyl]piperazine-1-sulfonyl}phenyl)-3-(pyridin-3-ylmethyl)urea | 0.004 | 0.168 |
| 1-(4-{4-[2-(morpholin-4-yl)-2-oxoethyl]piperazine-1-sulfonyl}phenyl)-3-(pyridin-3-ylmethyl)urea | 0.004 | 0.135 |
| 1-(4-{4-[2-oxo-2-(piperidin-1-yl)ethyl]piperazine-1-sulfonyl}phenyl)-3-(pyridin-3-ylmethyl)urea | 0.009 | 0.021 |
| 1-(4-{4-[2-oxo-2-(pyrrolidin-1-yl)ethyl]piperazine-1-sulfonyl}phenyl)-3-(pyridin-3-ylmethyl)urea | 0.004 | 0.099 |
| 1-(4-{4-[3-(morpholin-4-yl)propyl]piperazine-1-sulfonyl}phenyl)-3-(pyridin-3-ylmethyl)urea | 0.003 | 0.024 |
| 1-(4-{8-azabicyclo[3.2.1]octane-8-sulfonyl}phenyl)-3-(pyridin-3-ylmethyl)urea | 0.004 | 0.064 |
| 1-(4-{8-azaspiro[4.5]decane-8-sulfonyl}phenyl)-3-(pyridin-3-ylmethyl)urea | 0.004 | 0.343 |
| 1-(4-{8-oxa-3-azabicyclo[3.2.1]octane-3-sulfonyl}phenyl)-3-(pyridin-3-ylmethyl)urea | 0.007 | 0.029 |
| 1-(pyridin-3-ylmethyl)-3-(4-{[(1R,2R,3R,5S)-2,6,6-trimethylbicyclo[3.1.1]heptan-3-yl]sulfamoyl}phenyl)urea | 0.08 | 0.091 |
| 1-(pyridin-3-ylmethyl)-3-(4-{[2-(trifluoromethoxy)phenyl]sulfamoyl}phenyl)urea | 0.0012 | 0.007 |
| 1-(pyridin-3-ylmethyl)-3-(4-{[3-(trifluoromethyl)phenyl]sulfamoyl}phenyl)urea | 0.006 | |
| 1-(pyridin-3-ylmethyl)-3-[4-(1H-pyrrole-1-sulfonyl)phenyl]urea | 0.019 | 1.788 |
| 1-(pyridin-3-ylmethyl)-3-{4-[(3S)-3-(trifluoromethyl)piperidine-1-sulfonyl]phenyl}urea | 0.003 | 0.029 |
| 1-(pyridin-3-ylmethyl)-3-{4-[3-(trifluoromethyl)piperidine-1-sulfonyl]phenyl}urea | 0.003 | 0.026 |
| 1-[(3,4-difluorophenyl)methyl]-3-[4-(piperidine-1-sulfonyl)phenyl]urea | 0.092 | 29 |
| 1-[(4-{[(pyridin-3-ylmethyl)carbamoyl]amino}benzene)sulfonyl]piperidine-4-carboxamide | 0.01 | 1.481 |
| 1-[(4-fluorophenyl)methyl]-3-[4-(piperidine-1-sulfonyl)phenyl]urea | 0.245 | 25 |
| 1-[(6-isocyanopyridin-3-yl)methyl]-3-[4-(piperidine-1-sulfonyl)phenyl]urea | 1.734 | >30 |
| 1-[3-(piperidine-1-sulfonyl)phenyl]-3-(pyridin-3-ylmethyl)urea | >30 | >30 |
| 1-[4-(2,6-dimethylpiperidine-1-sulfonyl)phenyl]-3-(pyridin-3-ylmethyl)urea | 0.011 | 0.164 |
| 1-[4-(3,4-dihydro-2H-1,4-benzoxazine-4-sulfonyl)phenyl]-3-(pyridin-3-ylmethyl)urea | 0.01 | 0.459 |
| 1-[4-(3,5-dimethylpiperidine-1-sulfonyl)phenyl]-3-(pyridin-3-ylmethyl)urea | 0.006 | 0.014 |
| 1-[4-(4,4-difluoropiperidine-1-sulfonyl)phenyl]-3-(pyridin-3-ylmethyl)urea | 0.025 | 0.299 |
| 1-[4-(4-{[(2R)-oxolan-2-yl]carbonyl}piperazine-1-sulfonyl)phenyl]-3-(pyridin-3-ylmethyl)urea | 0.008 | 0.030 |
| 1-[4-(4-benzyl-1,4-diazepane-1-sulfonyl)phenyl]-3-(pyridin-3-ylmethyl)urea | 0.005 | 0.137 |
| 1-[4-(4-phenylpiperazine-1-sulfonyl)phenyl]-3-(pyridin-3-ylmethyl)urea | 0.005 | |
| 1-[4-(4-phenylpiperidine-1-sulfonyl)phenyl]-3-(pyridin-3-ylmethyl)urea | 0.003 | |
| 1-[4-(cycloheptylsulfamoyl)phenyl]-3-(pyridin-3-ylmethyl)urea | 0.003 | 0.080 |
| 1-[4-(cyclohexylsulfamoyl)phenyl]-3-(pyridin-3-ylmethyl)urea | 0.001 | 0.204 |
| 1-[4-(decahydroquinoline-1-sulfonyl)phenyl]-3-(pyridin-3-ylmethyl)urea | 0.011 | 0.014 |
| 1-[4-(dibenzylsulfamoyl)phenyl]-3-(pyridin-3-ylmethyl)urea | 0.0008 | 0.0003 |
| 1-[4-(morpholine-4-sulfonyl)phenyl]-3-(pyridin-3-ylmethyl)urea | 0.023 | 1.35 |
| 1-[4-(piperidine-1-sulfonyl)phenyl]-3-(pyridin-3-ylmethyl)urea | 0.011 | 0.167 |
| 1-{4-[(1-phenylcyclopentyl)sulfamoyl]phenyl}-3-(pyridin-3-ylmethyl)urea | 0.029 | 0.180 |
| 1-{4-[(1R)-3-oxo-3H-spiro[2-benzofuran-1,3'-pyrrolidine]-1'-ylsulfonyl]phenyl}-3-(pyridin-3-ylmethyl)urea | 0.005 | 0.041 |

TABLE 3-continued

| Compound | Biochem IC50 uM | A2780 IC50 uM |
|---|---|---|
| 1-{4-[(2-phenylphenyl)sulfamoyl]phenyl}-3-(pyridin-3-ylmethyl)urea | 0.003 | 0.047 |
| 1-{4-[(2R)-2-(morpholin-4-ylmethyl)piperidine-1-sulfonyl]phenyl}-3-(pyridin-3-ylmethyl)urea | 0.051 | 0.081 |
| 1-{4-[(2R)-2-benzylpiperidine-1-sulfonyl]phenyl}-3-(pyridin-3-ylmethyl)urea | 0.004 | 0.024 |
| 1-{4-[(2R,6S)-2,6-dimethylmorpholine-4-sulfonyl]phenyl}-3-{imidazo[1,2-a]pyridin-6-ylmethyl}urea | 0.008 | 0.025 |
| 1-{4-[(cyclohexylmethyl)sulfamoyl]phenyl}-3-(pyridin-3-ylmethyl)urea | 0.004 | 0.181 |
| 1-{4-[(naphthalen-1-yl)sulfamoyl]phenyl}-3-(pyridin-3-ylmethyl)urea | 0.001 | 0.019 |
| 1-{4-[4-(2-oxo-2,3-dihydro-1H-indol-1-yl)piperidine-1-sulfonyl]phenyl}-3-(pyridin-3-ylmethyl)urea | 0.003 | 0.058 |
| 1-{4-[4-(azepan-1-yl)piperidine-1-sulfonyl]phenyl}-3-(pyridin-3-ylmethyl)urea | 0.005 | 0.006 |
| 1-{4-[4-(morpholin-4-yl)piperidine-1-sulfonyl]phenyl}-3-(pyridin-3-ylmethyl)urea | 0.009 | 0.013 |
| 1-{4-[4-(piperidin-1-yl)piperidine-1-sulfonyl]phenyl}-3-(pyridin-3-ylmethyl)urea | 0.007 | 0.013 |
| 2-methyl-N-{1-[(4-{[(pyridin-3-ylmethyl)carbamoyl]amino}benzene)sulfonyl]piperidin-4-yl}propanamide | 0.005 | 0.123 |
| 3-(4-{[(2-chlorophenyl)methyl]sulfamoyl}phenyl)-1-(pyridin-3-ylmethyl)urea | 0.003 | 0.201 |
| 3-(4-{[(2-methoxyphenyl)methyl]sulfamoyl}phenyl)-1-(pyridin-3-ylmethyl)urea | 0.008 | 0.097 |
| 3-(4-{[(3-fluorophenyl)methyl](methyl)sulfamoyl}phenyl)-1-(pyridin-3-ylmethyl)urea | 0.002 | 0.156 |
| 3-(4-{[(4-chlorophenyl)methyl](methyl)sulfamoyl}phenyl)-1-(pyridin-3-ylmethyl)urea | 0.002 | 0.484 |
| 3-(4-{[(4-fluorophenyl)methyl](methyl)sulfamoyl}phenyl)-1-(pyridin-3-ylmethyl)urea | 0.003 | |
| 3-(4-{[(4-methoxyphenyl)methyl]sulfamoyl}phenyl)-1-(pyridin-3-ylmethyl)urea | 0.016 | 0.507 |
| 3-(4-{[(5-ethylpyridin-2-yl)methyl](methyl)sulfamoyl}phenyl)-1-(pyridin-3-ylmethyl)urea | 0.005 | 0.134 |
| 3-(4-{[2-(4-fluorophenoxy)pyridin-3-yl]sulfamoyl}phenyl)-1-(pyridin-3-ylmethyl)urea | 0.011 | 0.149 |
| 3-(4-{[2-(difluoromethoxy)phenyl]sulfamoyl}phenyl)-1-(pyridin-3-ylmethyl)urea | 0.0006 | 0.031 |
| 3-(4-{[2-(morpholin-4-yl)-5-(trifluoromethyl)phenyl]sulfamoyl}phenyl)-1-(pyridin-3-ylmethyl)urea | 0.008 | 0.007 |
| 3-(4-{[2-(piperidin-1-yl)-5-(trifluoromethyl)phenyl]sulfamoyl}phenyl)-1-(pyridin-3-ylmethyl)urea | 0.005 | 0.022 |
| 3-(4-{[2-(propan-2-yloxy)phenyl]sulfamoyl}phenyl)-1-(pyridin-3-ylmethyl)urea | 0.002 | 0.015 |
| 3-(4-{[2-methoxy-5-(trifluoromethyl)phenyl]sulfamoyl}phenyl)-1-(pyridin-3-ylmethyl)urea | 0.0001 | 0.002 |
| 3-(4-{[3-chloro-4-(morpholin-4-yl)phenyl]sulfamoyl}phenyl)-1-(pyridin-3-ylmethyl)urea | 0.001 | 0.024 |
| 3-(4-{[3-methyl-4-(propan-2-yl)phenyl]sulfamoyl}phenyl)-1-(pyridin-3-ylmethyl)urea | 0.002 | 0.108 |
| 3-(4-{[4-chloro-2-(trifluoromethoxy)phenyl]sulfamoyl}phenyl)-1-(pyridin-3-ylmethyl)urea | 0.006 | 0.113 |
| 3-(4-{[4-methyl-3-(trifluoromethyl)phenyl]sulfamoyl}phenyl)-1-(pyridin-3-ylmethyl)urea | 0.002 | 0.179 |
| 3-(4-{4-[(4-fluorophenyl)carbonyl]piperidine-1-sulfonyl}phenyl)-1-(pyridin-3-ylmethyl)urea | 0.010 | 0.206 |
| 3-(4-{4-[(morpholin-4-yl)carbonyl]piperidine-1-sulfonyl}phenyl)-1-(pyridin-3-ylmethyl)urea | 0.008 | 0.04 |
| 3-(4-{4-[1-(3-methoxyphenyl)-4-methylcyclohexyl]piperazine-1-sulfonyl}phenyl)-1-(pyridin-3-ylmethyl)urea | 0.004 | 0.005 |
| 3-(4-{4-[2-(diethylamino)ethyl]piperazine-1-sulfonyl}phenyl)-1-(pyridin-3-ylmethyl)urea | 0.004 | 0.023 |
| 3-(4-{4-[3-chloro-5-(trifluoromethyl)pyridin-2-yl]piperazine-1-sulfonyl}phenyl)-1-(pyridin-3-ylmethyl)urea | 0.005 | 0.128 |
| 3-(4-{4-[bis(4-fluorophenyl)methyl]piperazine-1-sulfonyl}phenyl)-1-(pyridin-3-ylmethyl)urea | 0.005 | 0.007 |
| 3-(4-{8-methyl-2,8-diazaspiro[5.5]undecane-2-sulfonyl}phenyl)-1-(pyridin-3-ylmethyl)urea | 0.001 | 0.001 |
| 3-(4-{methyl[(1S)-1-phenylethyl]sulfamoyl}phenyl)-1-(pyridin-3-ylmethyl)urea | 0.001 | 0.008 |
| 3-(pyridin-3-ylmethyl)-1-(4-{[(1S,2S,3S,5R)-2,6,6-trimethylbicyclo[3.1.1]heptan-3-yl]sulfamoyl}phenyl)urea | 0.012 | 0.096 |
| 3-(pyridin-3-ylmethyl)-1-(4-{[2-(1H-pyrrol-1-yl)phenyl]sulfamoyl}phenyl)urea | 0.003 | 0.076 |
| 3-(pyridin-3-ylmethyl)-1-(4-{[2-(pyrrolidin-1-yl)phenyl]sulfamoyl}phenyl)urea | 0.013 | 0.011 |
| 3-(pyridin-3-ylmethyl)-1-[4-(5,6,7,8-tetrahydro-1,6-naphthyridine-6-sulfonyl)phenyl]urea | 0.016 | 0.111 |

TABLE 3-continued

| Compound | Biochem IC50 uM | A2780 IC50 uM |
|---|---|---|
| 3-(pyridin-3-ylmethyl)-1-[4-(pyrrolidine-1-sulfonyl)phenyl]urea | 0.037 | 1.399 |
| 3-(pyridin-3-ylmethyl)-1-{4-[(3S)-3-[(pyrrolidin-1-yl)carbonyl]piperidine-1-sulfonyl]phenyl}urea | 0.009 | 0.137 |
| 3-(pyridin-3-ylmethyl)-1-{4-[(5,6,7,8-tetrahydronaphthalen-1-yl)sulfamoyl]phenyl}urea | 0.0003 | 0.045 |
| 3-[(2-fluorophenyl)methyl]-1-[4-(piperidine-1-sulfonyl)phenyl]urea | 0.016 | >30 |
| 3-[(3-fluorophenyl)methyl]-1-[4-(piperidine-1-sulfonyl)phenyl]urea | 0.033 | >30 |
| 3-[(5-chloropyridin-3-yl)methyl]-1-[4-(piperidine-1-sulfonyl)phenyl]urea | 0.048 | 18 |
| 3-[(6-chloropyridin-3-yl)methyl]-1-[4-(piperidine-1-sulfonyl)phenyl]urea | 0.008 | >30 |
| 3-[2-fluoro-4-(piperidine-1-sulfonyl)phenyl]-1-(pyridin-3-ylmethyl)urea | 0.023 | 1.005 |
| 3-[4-({[4-(dimethylamino)phenyl]methyl}sulfamoyl)phenyl]-1-(pyridin-3-ylmethyl)urea | 0.003 | 0.148 |
| 3-[4-({2-[(2S)-2-hydroxypropoxy]phenyl}sulfamoyl)phenyl]-1-(pyridin-3-ylmethyl)urea | 0.012 | 0.088 |
| 3-[4-({3-[(1S)-1-hydroxyethyl]phenyl}sulfamoyl)phenyl]-1-(pyridin-3-ylmethyl)urea | 0.007 | 0.164 |
| 3-[4-(2,3-dihydro-1H-indole-1-sulfonyl)phenyl]-1-(pyridin-3-ylmethyl)urea | 0.002 | 0.031 |
| 3-[4-(3,3-difluoroazetidine-1-sulfonyl)phenyl]-1-(pyridin-3-ylmethyl)urea | 0.059 | 7.859 |
| 3-[4-(3-methylpiperidine-1-sulfonyl)phenyl]-1-(pyridin-3-ylmethyl)urea | 0.007 | 0.067 |
| 3-[4-(4-methylpiperidine-1-sulfonyl)phenyl]-1-(pyridin-3-ylmethyl)urea | 0.004 | 0.254 |
| 3-[4-(azepane-1-sulfonyl)phenyl]-1-(pyridin-3-ylmethyl)urea | 0.007 | 0.139 |
| 3-[4-(azetidine-1-sulfonyl)phenyl]-1-(pyridin-3-ylmethyl)urea | 0.041 | 1.622 |
| 3-[4-(diethylsulfamoyl)phenyl]-1-(pyridin-3-ylmethyl)urea | 0.016 | |
| 3-[4-(piperidine-1-sulfonyl)phenyl]-1-(pyrazin-2-ylmethyl)urea | 0.273 | >30 |
| 3-[4-(piperidine-1-sulfonyl)phenyl]-1-(pyrimidin-5-ylmethyl)urea | 1.14 | >30 |
| 3-[4-(piperidine-1-sulfonyl)phenyl]-1-[1-(pyridin-3-yl)ethyl]urea | 22.089 | >30 |
| 3-[4-(piperidine-1-sulfonyl)phenyl]-1-[2-(pyridin-3-yl)ethyl]urea | 0.01 | 0.661 |
| 3-[4-(piperidine-1-sulfonyl)phenyl]-1-{[6-(trifluoromethyl)pyridin-3-yl]methyl}urea | 0.189 | >30 |
| 3-{[4-(piperidine-1-sulfonyl)phenyl]methyl}-1-(pyridin-3-yl)urea | 0.037 | 2.259 |
| 3-{[4-(piperidine-1-sulfonyl)phenyl]methyl}-1-(pyridin-3-ylmethyl)urea | 0.017 | 0.547 |
| 3-{4-[(2,2-dimethylpropyl)sulfamoyl]phenyl}-1-(pyridin-3-ylmethyl)urea | 0.017 | 0.159 |
| 3-{4-[(2,3-dichlorophenyl)sulfamoyl]phenyl}-1-(pyridin-3-ylmethyl)urea | 0.002 | 0.030 |
| 3-{4-[(2,3-dimethylphenyl)sulfamoyl]phenyl}-1-(pyridin-3-ylmethyl)urea | 0.0009 | 0.074 |
| 3-{4-[(2,4-dichlorophenyl)sulfamoyl]phenyl}-1-(pyridin-3-ylmethyl)urea | 0.003 | 0.189 |
| 3-{4-[(2,4-dimethoxyphenyl)sulfamoyl]phenyl}-1-(pyridin-3-ylmethyl)urea | 0.003 | 0.109 |
| 3-{4-[(2,5-dimethoxyphenyl)sulfamoyl]phenyl}-1-(pyridin-3-ylmethyl)urea | 0.0012 | 0.004 |
| 3-{4-[(2,5-dimethylphenyl)sulfamoyl]phenyl}-1-(pyridin-3-ylmethyl)urea | 0.006 | 0.116 |
| 3-{4-[(2-bromophenyl)sulfamoyl]phenyl}-1-(pyridin-3-ylmethyl)urea | 0.002 | 0.024 |
| 3-{4-[(2-chloro-4-fluorophenyl)sulfamoyl]phenyl}-1-(pyridin-3-ylmethyl)urea | 0.0009 | 0.036 |
| 3-{4-[(2-chloro-4-methylphenyl)sulfamoyl]phenyl}-1-(pyridin-3-ylmethyl)urea | 0.001 | 0.032 |
| 3-{4-[(2-chloro-5-methylphenyl)sulfamoyl]phenyl}-1-(pyridin-3-ylmethyl)urea | 0.0003 | 0.009 |
| 3-{4-[(2-chlorophenyl)sulfamoyl]phenyl}-1-(pyridin-3-ylmethyl)urea | 0.003 | 0.041 |
| 3-{4-[(2-ethoxyphenyl)sulfamoyl]phenyl}-1-(pyridin-3-ylmethyl)urea | 0.003 | 0.032 |
| 3-{4-[(2-fluoro-4-methylphenyl)sulfamoyl]phenyl}-1-(pyridin-3-ylmethyl)urea | 0.002 | 0.157 |
| 3-{4-[(2-fluorophenyl)sulfamoyl]phenyl}-1-(pyridin-3-ylmethyl)urea | 0.008 | |
| 3-{4-[(2-iodophenyl)sulfamoyl]phenyl}-1-(pyridin-3-ylmethyl)urea | 0.0008 | 0.039 |
| 3-{4-[(2-methoxy-5-methylphenyl)sulfamoyl]phenyl}-1-(pyridin-3-ylmethyl)urea | 0.002 | 0.002 |
| 3-{4-[(2-methoxypyridin-3-yl)sulfamoyl]phenyl}-1-(pyridin-3-ylmethyl)urea | 0.007 | 0.114 |
| 3-{4-[(2-phenylpropan-2-yl)sulfamoyl]phenyl}-1-(pyridin-3-ylmethyl)urea | 0.005 | 0.039 |
| 3-{4-[(2R,6S)-2,6-dimethylmorpholine-4-sulfonyl]phenyl}-1-(pyridin-3-ylmethyl)urea | 0.01 | 0.009 |
| 3-{4-[(2S)-2-(methoxymethyl)pyrrolidine-1-sulfonyl]phenyl}-1-(pyridin-3-ylmethyl)urea | 0.002 | 0.060 |
| 3-{4-[(2S)-2-ethylpiperidine-1-sulfonyl]phenyl}-1-(pyridin-3-ylmethyl)urea | 0.004 | 0.018 |
| 3-{4-[(3,4-dichlorophenyl)sulfamoyl]phenyl}-1-(pyridin-3-ylmethyl)urea | 0.006 | 0.122 |
| 3-{4-[(3,4-dimethoxyphenyl)sulfamoyl]phenyl}-1-(pyridin-3-ylmethyl)urea | 0.005 | 0.116 |
| 3-{4-[(3,4-dimethylphenyl)sulfamoyl]phenyl}-1-(pyridin-3-ylmethyl)urea | 0.003 | 0.093 |
| 3-{4-[(3,5-dimethoxyphenyl)sulfamoyl]phenyl}-1-(pyridin-3-ylmethyl)urea | 0.005 | 0.096 |
| 3-{4-[(3,5-dimethylphenyl)sulfamoyl]phenyl}-1-(pyridin-3-ylmethyl)urea | 0.001 | 0.041 |
| 3-{4-[(3-aminophenyl)(methanesulfonyl)sulfamoyl]phenyl}-1-(pyridin-3-ylmethyl)urea | 0.003 | 0.110 |
| 3-{4-[(3-bromophenyl)sulfamoyl]phenyl}-1-(pyridin-3-ylmethyl)urea | 0.003 | |
| 3-{4-[(3-chloro-4-methylphenyl)sulfamoyl]phenyl}-1-(pyridin-3-ylmethyl)urea | 0.0014 | 0.026 |
| 3-{4-[(3-chlorophenyl)sulfamoyl]phenyl}-1-(pyridin-3-ylmethyl)urea | 0.001 | |
| 3-{4-[(3-methoxy-2-methylphenyl)sulfamoyl]phenyl}-1-(pyridin-3-ylmethyl)urea | 0.002 | 0.057 |
| 3-{4-[(3-methoxy-4-methylphenyl)sulfamoyl]phenyl}-1-(pyridin-3-ylmethyl)urea | 0.004 | 0.148 |

TABLE 3-continued

| Compound | Biochem IC50 uM | A2780 IC50 uM |
|---|---|---|
| 3-{4-[(3-methylphenyl)sulfamoyl]phenyl}-1-(pyridin-3-ylmethyl)urea | 0.010 | |
| 3-{4-[(3S)-3-methyl-4-(3-methylphenyl)piperazine-1-sulfonyl]phenyl}-1-(pyridin-3-ylmethyl)urea | 0.003 | 0.034 |
| 3-{4-[(3S)-3-methyl-4-(4-methylphenyl)piperazine-1-sulfonyl]phenyl}-1-(pyridin-3-ylmethyl)urea | 0.004 | 0.095 |
| 3-{4-[(3S)-3-methylpiperidine-1-sulfonyl]phenyl}-1-(pyridin-3-ylmethyl)urea | 0.003 | 0.105 |
| 3-{4-[(4-chloro-2-methoxy-5-methylphenyl)sulfamoyl]phenyl}-1-(pyridin-3-ylmethyl)urea | 0.001 | 0.006 |
| 3-{4-[(4-chloronaphthalen-1-yl)sulfamoyl]phenyl}-1-(pyridin-3-ylmethyl)urea | 0.005 | 0.053 |
| 3-{4-[(4-ethoxy-2-fluorophenyl)sulfamoyl]phenyl}-1-(pyridin-3-ylmethyl)urea | 0.004 | 0.157 |
| 3-{4-[(4-ethylphenyl)sulfamoyl]phenyl}-1-(pyridin-3-ylmethyl)urea | 0.007 | |
| 3-{4-[(4-fluoro-2-methoxyphenyl)sulfamoyl]phenyl}-1-(pyridin-3-ylmethyl)urea | 0.007 | 0.116 |
| 3-{4-[(4-tert-butyl-2-chlorophenyl)sulfamoyl]phenyl}-1-(pyridin-3-ylmethyl)urea | 0.0014 | 0.097 |
| 3-{4-[(5-chloro-2-methoxyphenyl)sulfamoyl]phenyl}-1-(pyridin-3-ylmethyl)urea | 0.0009 | 0.003 |
| 3-{4-[(5-chloro-2-methylphenyl)sulfamoyl]phenyl}-1-(pyridin-3-ylmethyl)urea | 0.001 | 0.035 |
| 3-{4-[(5-fluoro-2-methoxyphenyl)sulfamoyl]phenyl}-1-(pyridin-3-ylmethyl)urea | 0.0010 | 0.033 |
| 3-{4-[(5-methoxy-2-methylphenyl)sulfamoyl]phenyl}-1-(pyridin-3-ylmethyl)urea | 0.002 | 0.079 |
| 3-{4-[3-(2-methoxyethyl)piperidine-1-sulfonyl]phenyl}-1-(pyridin-3-ylmethyl)urea | 0.004 | 0.089 |
| 3-{4-[4-(2,5-dimethylphenyl)piperazine-1-sulfonyl]phenyl}-1-(pyridin-3-ylmethyl)urea | 0.005 | 0.101 |
| 3-{4-[4-(2-ethoxyphenyl)piperazine-1-sulfonyl]phenyl}-1-(pyridin-3-ylmethyl)urea | 0.002 | 0.006 |
| 3-{4-[4-(2-methoxyphenyl)piperazine-1-sulfonyl]phenyl}-1-(pyridin-3-ylmethyl)urea | 0.007 | 0.035 |
| 3-{4-[4-(2-methylphenyl)piperazine-1-sulfonyl]phenyl}-1-(pyridin-3-ylmethyl)urea | 0.006 | 0.106 |
| 3-{4-[4-(3,5-dichloropyridin-4-yl)piperazine-1-sulfonyl]phenyl}-1-(pyridin-3-ylmethyl)urea | 0.003 | 0.029 |
| 3-{4-[4-(3-chloropyridin-2-yl)piperazine-1-sulfonyl]phenyl}-1-(pyridin-3-ylmethyl)urea | 0.001 | 0.018 |
| 3-{4-[4-(5-chloro-2-methoxyphenyl)piperazine-1-sulfonyl]phenyl}-1-(pyridin-3-ylmethyl)urea | 0.002 | 0.050 |
| 3-{4-[4-(5-chloro-2-methylphenyl)piperazine-1-sulfonyl]phenyl}-1-(pyridin-3-ylmethyl)urea | 0.002 | 0.162 |
| 3-{4-[4-(diethylamino)piperidine-1-sulfonyl]phenyl}-1-(pyridin-3-ylmethyl)urea | 0.005 | 0.014 |
| 3-{4-[4-(dipropylamino)piperidine-1-sulfonyl]phenyl}-1-(pyridin-3-ylmethyl)urea | 0.004 | 0.003 |
| 3-{4-[4-(methoxymethyl)piperidine-1-sulfonyl]phenyl}-1-(pyridin-3-ylmethyl)urea | 0.022 | 0.130 |
| 3-{4-[benzyl(ethyl)sulfamoyl]phenyl}-1-(pyridin-3-ylmethyl)urea | 0.0009 | 0.007 |
| 3-{4-[benzyl(methyl)sulfamoyl]phenyl}-1-(pyridin-3-ylmethyl)urea | 0.0011 | 0.107 |
| 3-{4-[benzyl(propan-2-yl)sulfamoyl]phenyl}-1-(pyridin-3-ylmethyl)urea | 0.002 | 0.026 |
| 3-{4-[cyclohexyl(ethyl)sulfamoyl]phenyl}-1-(pyridin-3-ylmethyl)urea | 0.005 | 0.123 |
| 3-{4-[methyl({[3-(trifluoromethyl)phenyl]methyl})sulfamoyl]phenyl}-1-(pyridin-3-ylmethyl)urea | 0.007 | |
| 3-{4-[methyl(2-methylpropyl)sulfamoyl]phenyl}-1-(pyridin-3-ylmethyl)urea | 0.007 | |
| 3-{imidazo[1,2-a]pyridin-6-ylmethyl}-1-(4-{8-oxa-3-azabicyclo[3.2.1]octane-3-sulfonyl}phenyl)urea | 0.008 | 0.006 |
| 3-{imidazo[1,2-a]pyridin-6-ylmethyl}-1-{4-[4-(morpholin-4-yl)piperidine-1-sulfonyl]phenyl}urea | 0.004 | 0.005 |
| 3-benzyl-1-[4-(piperidine-1-sulfonyl)phenyl]urea | 0.718 | >30 |
| 5-[({[4-(piperidine-1-sulfonyl)phenyl]carbamoyl}amino)methyl]pyridine-2-carboxamide | >10 | 27.477 |
| N-(propan-2-yl)-2-{4-[(4-{[(pyridin-3-ylmethyl)carbamoyl]amino}benzene)sulfonyl]piperazin-1-yl}acetamide | 0.003 | 0.037 |
| N,N-diethyl-2-[4-({[(pyridin-3-ylmethyl)carbamoyl]amino}benzene)sulfonamido]benzamide | 0.008 | 0.006 |
| N,N-diethyl-2-{4-[(4-{[(pyridin-3-ylmethyl)carbamoyl]amino}benzene)sulfonyl]piperazin-1-yl}acetamide | 0.005 | 0.045 |
| N,N-dimethyl-1-[(4-{[(pyridin-3-ylmethyl)carbamoyl]amino}benzene)sulfonyl]piperidine-4-carboxamide | 0.009 | 0.164 |
| N,N-dimethyl-2-[4-({[(pyridin-3-ylmethyl)carbamoyl]amino}benzene)sulfonamido]benzamide | 0.016 | 0.055 |
| N-ethyl-N-[(3S)-1-[(4-{[(pyridin-3-ylmethyl)carbamoyl]amino}benzene)sulfonyl]pyrrolidin-3-yl]acetamide | 0.006 | 0.079 |

TABLE 3-continued

| Compound | Biochem IC50 uM | A2780 IC50 uM |
|---|---|---|
| N-methyl-2-[(4-{[(pyridin-3-ylmethyl)carbamoyl]amino}benzene)sulfonamido]benzamide | 0.001 | 0.011 |
| N-methyl-N-phenyl-2-{4-[(4-{[(pyridin-3-ylmethyl)carbamoyl]amino}benzene)sulfonyl]piperazin-1-yl}acetamide | 0.008 | 0.030 |
| rel-3-{4-[(4aR,8aS)-decahydroisoquinoline-2-sulfonyl]phenyl}-1-(pyridin-3-ylmethyl)urea | 0.002 | 0.101 |
| tert-butyl N-{5-[({[4-(piperidine-1-sulfonyl)phenyl]carbamoyl}amino)methyl]pyridin-2-yl}carbamate | 3.135 | 9.782 |
| 1-(4-{8-oxatricyclo[7.4.0.0²,⁷]trideca-1(9),2(7),3,5,10,12-hexaene-6-sulfonyl}phenyl)-3-(pyridin-3-ylmethyl)urea | 0.002 | 0.003 |
| 1-(4-benzoylphenyl)-3-(pyridin-3-ylmethyl)urea | 0.017 | 0.735 |
| 1-(pyridin-3-ylmethyl)-3-(4-{[2-(trifluoromethoxy)benzene]sulfonyl}phenyl)urea | 0.001 | 0.003 |
| 1-(pyridin-3-ylmethyl)-3-(4-{[2-(trifluoromethyl)benzene]sulfonyl}phenyl)urea | 0.003 | 0.569 |
| 1-(pyridin-3-ylmethyl)-3-(4-{[3-(trifluoromethoxy)benzene]sulfonyl}phenyl)urea | 0.001 | 0.083 |
| 1-(pyridin-3-ylmethyl)-3-(4-{[3-(trifluoromethyl)benzene]sulfonyl}phenyl)urea | 0.004 | 0.247 |
| 1-(pyridin-3-ylmethyl)-3-(4-{[4-(trifluoromethoxy)benzene]sulfonyl}phenyl)urea | 0.005 | 0.420 |
| 1-(pyridin-3-ylmethyl)-3-(4-{[4-(trifluoromethyl)benzene]sulfonyl}phenyl)urea | 0.009 | 0.604 |
| 1-(pyridin-3-ylmethyl)-3-[4-(trifluoromethane)sulfonylphenyl]urea | 0.226 | 10.0 |
| 1-(pyridin-3-ylmethyl)-3-{4-[(2,4,6-trimethylbenzene)sulfonyl]phenyl}urea | 0.011 | >1 |
| 1-[(6-aminopyridin-3-yl)methyl]-3-[4-(benzenesulfonyl)phenyl]urea | 0.003 | 0.081 |
| 1-[(6-aminopyridin-3-yl)methyl]-3-{4-[(4-fluorobenzene)sulfonyl]phenyl}urea | 0.002 | 0.043 |
| 1-[4-(2H-1,3-benzodioxole-5-sulfonyl)phenyl]-3-(pyridin-3-ylmethyl)urea | 0.001 | 0.322 |
| 1-[4-(benzenesulfonyl)phenyl]-3-(1H-pyrazol-3-ylmethyl)urea | >10 | >20 |
| 1-[4-(benzenesulfonyl)phenyl]-3-{imidazo[1,2-a]pyridin-6-ylmethyl}urea | 0.001 | 0.033 |
| 1-[4-(benzenesulfonyl)phenyl]-3-{thieno[2,3-c]pyridin-2-ylmethyl}urea | 0.46 | >30 |
| 1-[4-(cyclopentanesulfonyl)phenyl]-3-(pyridin-3-ylmethyl)urea | 0.043 | 1.86 |
| 1-[6-(benzenesulfonyl)pyridin-3-yl]-3-(pyridin-3-ylmethyl)urea | 0.015 | 2.356 |
| 1-{[4-(benzenesulfonyl)phenyl]methyl}-3-(quinolin-6-yl)urea | 2.258 | >30 |
| 1-{4-[(2-phenoxybenzene)sulfonyl]phenyl}-3-(pyridin-3-ylmethyl)urea | 0.002 | 0.008 |
| 1-{4-[(4-fluorobenzene)sulfonyl]phenyl}-3-{imidazo[1,2-a]pyridin-6-ylmethyl}urea | 0.003 | 0.029 |
| 3-(4-{[2-(methoxymethyl)benzene]sulfonyl}phenyl)-1-(pyridin-3-ylmethyl)urea | 0.006 | 0.039 |
| 3-(4-{[2-chloro-5-(trifluoromethyl)benzene]sulfonyl}phenyl)-1-(pyridin-3-ylmethyl)urea | 0.005 | 0.339 |
| 3-(4-{[2-fluoro-4-(1H-pyrazol-1-yl)benzene]sulfonyl}phenyl)-1-(pyridin-3-ylmethyl)urea | 0.001 | 0.014 |
| 3-(4-{[2-methoxy-4-(1H-pyrazol-1-yl)benzene]sulfonyl}phenyl)-1-(pyridin-3-ylmethyl)urea | 0.002 | 0.003 |
| 3-(4-{[2-methoxy-5-(propan-2-yl)benzene]sulfonyl}phenyl)-1-(pyridin-3-ylmethyl)urea | 0.003 | 0.031 |
| 3-(4-{[2-methyl-4-(1H-pyrazol-1-yl)benzene]sulfonyl}phenyl)-1-(pyridin-3-ylmethyl)urea | 0.002 | 0.021 |
| 3-(4-{[3-(propan-2-yl)benzene]sulfonyl}phenyl)-1-(pyridin-3-ylmethyl)urea | 0.002 | 0.038 |
| 3-(4-{[3-(propan-2-yloxy)benzene]sulfonyl}phenyl)-1-(pyridin-3-ylmethyl)urea | 0.004 | 0.079 |
| 3-(4-{[3-fluoro-4-(1H-pyrazol-1-yl)benzene]sulfonyl}phenyl)-1-(pyridin-3-ylmethyl)urea | 0.000 | 0.054 |
| 3-(4-{[4-chloro-3-(trifluoromethyl)benzene]sulfonyl}phenyl)-1-(pyridin-3-ylmethyl)urea | 0.005 | 0.167 |
| 3-(pyridin-3-ylmethyl)-1-[4-(pyridine-2-sulfonyl)phenyl]urea |  | 0.869 |
| 3-(pyridin-3-ylmethyl)-1-[4-(pyridine-3-sulfonyl)phenyl]urea | 0.005 | 0.595 |
| 3-(pyridin-3-ylmethyl)-1-[4-(pyridine-4-sulfonyl)phenyl]urea | 0.011 | 0.488 |
| 3-(pyridin-3-ylmethyl)-1-[4-(pyrimidine-5-sulfonyl)phenyl]urea | 0.020 | 0.871 |
| 3-[4-(1-methyl-1H-pyrazole-4-sulfonyl)phenyl]-1-(pyridin-3-ylmethyl)urea | 0.004 | 0.247 |
| 3-[4-(2-methoxynaphthalene-1-sulfonyl)phenyl]-1-(pyridin-3-ylmethyl)urea | 0.002 | 0.012 |
| 3-[4-(3,5-dimethyl-1,2-oxazole-4-sulfonyl)phenyl]-1-(pyridin-3-ylmethyl)urea | 0.020 | 0.850 |
| 3-[4-(5-methylthiophene-2-sulfonyl)phenyl]-1-(pyridin-3-ylmethyl)urea | 0.003 | 0.383 |
| 3-[4-(benzenesulfonyl)phenyl]-1-(pyridin-3-yl)urea | >30 | 27.465 |
| 3-[4-(benzenesulfonyl)phenyl]-1-(quinolin-6-yl)urea | 0.090 | 15.86 |
| 3-[4-(benzenesulfonyl)phenyl]-1-{[6-(1H-imidazol-1-yl)pyridin-3-yl]methyl}urea |  | >10 |
| 3-[4-(benzenesulfonyl)phenyl]-1-{[6-(1H-pyrazol-1-yl)pyridin-3-yl]methyl}urea | 3.791 | >10 |
| 3-[4-(benzenesulfonyl)phenyl]-1-{[6-(2-methoxyethoxy)pyridin-3-yl]methyl}urea | 2.121 | >10 |

TABLE 3-continued

| Compound | Biochem IC50 uM | A2780 IC50 uM |
| --- | --- | --- |
| 3-{[({4-[(4-chlorobenzene)sulfinyl]phenyl}carbamoyl)amino]methyl}pyridin-1-ium-1-olate | 0.444 | 20.611 |
| 3-{[({4-[(4-chlorobenzene)sulfonyl]phenyl}carbamoyl)amino]methyl}pyridin-1-ium-1-olate | 0.728 | >30 |
| 3-{4-[(2,3-dichlorobenzene)sulfonyl]phenyl}-1-(pyridin-3-ylmethyl)urea | 0.001 | 0.446 |
| 3-{4-[(2,3-difluorobenzene)sulfonyl]phenyl}-1-(pyridin-3-ylmethyl)urea | 0.004 | 0.546 |
| 3-{4-[(2,3-dimethylbenzene)sulfonyl]phenyl}-1-(pyridin-3-ylmethyl)urea | 0.005 | 0.298 |
| 3-{4-[(2,4-dichlorobenzene)sulfonyl]phenyl}-1-(pyridin-3-ylmethyl)urea | 0.004 | 0.827 |
| 3-{4-[(2,4-difluorobenzene)sulfonyl]phenyl}-1-(pyridin-3-ylmethyl)urea | 0.001 | 0.344 |
| 3-{4-[(2,4-dimethoxybenzene)sulfonyl]phenyl}-1-(pyridin-3-ylmethyl)urea | 0.005 | 0.047 |
| 3-{4-[(2,4-dimethylbenzene)sulfonyl]phenyl}-1-(pyridin-3-ylmethyl)urea | 0.018 | 0.967 |
| 3-{4-[(2,5-dichlorobenzene)sulfonyl]phenyl}-1-(pyridin-3-ylmethyl)urea | 0.006 | 0.652 |
| 3-{4-[(2,5-difluoro-4-methoxybenzene)sulfonyl]phenyl}-1-(pyridin-3-ylmethyl)urea | 0.004 | 0.105 |
| 3-{4-[(2,5-difluorobenzene)sulfonyl]phenyl}-1-(pyridin-3-ylmethyl)urea | 0.004 | 0.403 |
| 3-{4-[(2,5-dimethoxybenzene)sulfonyl]phenyl}-1-(pyridin-3-ylmethyl)urea | 0.001 | 0.007 |
| 3-{4-[(2,5-dimethylbenzene)sulfonyl]phenyl}-1-(pyridin-3-ylmethyl)urea | 0.014 | 0.473 |
| 3-{4-[(2,6-dimethoxybenzene)sulfonyl]phenyl}-1-(pyridin-3-ylmethyl)urea | 0.007 | 0.026 |
| 3-{4-[(2,6-dimethylbenzene)sulfonyl]phenyl}-1-(pyridin-3-ylmethyl)urea | 0.008 | 0.387 |
| 3-{4-[(2-acetylbenzene)sulfonyl]phenyl}-1-(pyridin-3-ylmethyl)urea | 0.002 | 0.326 |
| 3-{4-[(2-bromobenzene)sulfonyl]phenyl}-1-(pyridin-3-ylmethyl)urea | 0.006 | 0.250 |
| 3-{4-[(2-chloro-4-fluorobenzene)sulfonyl]phenyl}-1-(pyridin-3-ylmethyl)urea | 0.008 | |
| 3-{4-[(2-chloro-6-fluoro-3-methylbenzene)sulfonyl]phenyl}-1-(pyridin-3-ylmethyl)urea | 0.007 | 0.336 |
| 3-{4-[(2-chlorobenzene)sulfonyl]phenyl}-1-(pyridin-3-ylmethyl)urea | 0.005 | 0.475 |
| 3-{4-[(2-ethoxybenzene)sulfonyl]phenyl}-1-(pyridin-3-ylmethyl)urea | 0.002 | 0.0004 |
| 3-{4-[(2-ethylbenzene)sulfonyl]phenyl}-1-(pyridin-3-ylmethyl)urea | 0.002 | 0.169 |
| 3-{4-[(2-fluoro-3-methoxybenzene)sulfonyl]phenyl}-1-(pyridin-3-ylmethyl)urea | 0.001 | 0.387 |
| 3-{4-[(2-fluoro-4-methoxybenzene)sulfonyl]phenyl}-1-(pyridin-3-ylmethyl)urea | 0.003 | 0.311 |
| 3-{4-[(2-fluoro-4-methylbenzene)sulfonyl]phenyl}-1-(pyridin-3-ylmethyl)urea | 0.002 | 0.517 |
| 3-{4-[(2-fluoro-5-methylbenzene)sulfonyl]phenyl}-1-(pyridin-3-ylmethyl)urea | 0.012 | >1 |
| 3-{4-[(2-fluoro-6-methoxybenzene)sulfonyl]phenyl}-1-(pyridin-3-ylmethyl)urea | 0.002 | 0.010 |
| 3-{4-[(2-fluorobenzene)sulfonyl]phenyl}-1-(pyridin-3-ylmethyl)urea | 0.003 | 0.493 |
| 3-{4-[(2-methoxy-5-methylbenzene)sulfonyl]phenyl}-1-(pyridin-3-ylmethyl)urea | 0.004 | 0.007 |
| 3-{4-[(2-methoxybenzene)sulfonyl]phenyl}-1-(pyridin-3-ylmethyl)urea | 0.002 | 0.010 |
| 3-{4-[(2-methylbenzene)sulfonyl]phenyl}-1-(pyridin-3-ylmethyl)urea | 0.002 | 0.450 |
| 3-{4-[(3,4-difluorobenzene)sulfonyl]phenyl}-1-(pyridin-3-ylmethyl)urea | 0.003 | 0.214 |
| 3-{4-[(3,4-dimethoxybenzene)sulfonyl]phenyl}-1-(pyridin-3-ylmethyl)urea | 0.005 | 0.017 |
| 3-{4-[(3,5-difluorobenzene)sulfonyl]phenyl}-1-(pyridin-3-ylmethyl)urea | 0.003 | 0.284 |
| 3-{4-[(3,5-dimethylbenzene)sulfonyl]phenyl}-1-(pyridin-3-ylmethyl)urea | 0.001 | 0.040 |
| 3-{4-[(3-bromobenzene)sulfonyl]phenyl}-1-(pyridin-3-ylmethyl)urea | 0.002 | 0.322 |
| 3-{4-[(3-chlorobenzene)sulfonyl]phenyl}-1-(pyridin-3-ylmethyl)urea | 0.003 | 0.518 |
| 3-{4-[(3-fluoro-4-methoxybenzene)sulfonyl]phenyl}-1-(pyridin-3-ylmethyl)urea | 0.002 | 0.173 |
| 3-{4-[(3-fluoro-4-methylbenzene)sulfonyl]phenyl}-1-(pyridin-3-ylmethyl)urea | 0.001 | 0.206 |
| 3-{4-[(3-fluorobenzene)sulfonyl]phenyl}-1-(pyridin-3-ylmethyl)urea | 0.001 | 0.238 |
| 3-{4-[(3-methylbenzene)sulfonyl]phenyl}-1-(pyridin-3-ylmethyl)urea | 0.002 | 0.157 |
| 3-{4-[(4-chloro-2-fluorobenzene)sulfonyl]phenyl}-1-(pyridin-3-ylmethyl)urea | 0.002 | 0.415 |
| 3-{4-[(4-chloro-2-methylbenzene)sulfonyl]phenyl}-1-(pyridin-3-ylmethyl)urea | 0.006 | 0.755 |
| 3-{4-[(4-chloro-3-fluorobenzene)sulfonyl]phenyl}-1-(pyridin-3-ylmethyl)urea | 0.003 | 0.221 |
| 3-{4-[(4-chlorobenzene)sulfinyl]phenyl}-1-(pyridin-3-ylmethyl)urea | 0.008 | 0.041 |
| 3-{4-[(4-ethylbenzene)sulfonyl]phenyl}-1-(pyridin-3-ylmethyl)urea | 0.003 | 0.533 |
| 3-{4-[(4-fluoro-2-methylbenzene)sulfonyl]phenyl}-1-(pyridin-3-ylmethyl)urea | 0.005 | 0.287 |
| 3-{4-[(4-fluorobenzene)sulfonyl]phenyl}-1-(pyridin-3-ylmethyl)urea | 0.004 | 0.171 |
| 3-{4-[(4-methanesulfonylbenzene)sulfonyl]phenyl}-1-(pyridin-3-ylmethyl)urea | 0.002 | 0.091 |
| 3-{4-[(4-methoxy-2-methylbenzene)sulfonyl]phenyl}-1-(pyridin-3-ylmethyl)urea | 0.008 | 0.352 |
| 3-{4-[(5-chloro-2-methoxybenzene)sulfonyl]phenyl}-1-(pyridin-3-ylmethyl)urea | 0.005 | 0.021 |
| 3-{4-[(5-fluoro-2-methoxybenzene)sulfonyl]phenyl}-1-(pyridin-3-ylmethyl)urea | 0.002 | 0.004 |

TABLE 3-continued

| Compound | Biochem IC50 uM | A2780 IC50 uM |
|---|---|---|
| 3-{4-[(5-fluoro-2-methylbenzene)sulfonyl]phenyl}-1-(pyridin-3-ylmethyl)urea | 0.004 | 0.489 |
| 3-{4-[2-chloro-6-(propan-2-yl)pyridine-3-sulfonyl]phenyl}-1-(pyridin-3-ylmethyl)urea | 0.003 | 0.006 |
| N,N-dimethyl-4-[(4-{[(pyridin-3-ylmethyl)carbamoyl]amino}benzene)sulfonyl]benzamide | 0.005 | 0.053 |
| 1-(4-{[2-(morpholin-4-ylmethyl)benzene]sulfonyl}phenyl)-3-(pyridin-3-ylmethyl)urea | 0.0036 | 0.0079 |
| 1-(4-{[3-(1H-pyrazol-1-yl)benzene]sulfonyl}phenyl)-3-(pyridin-3-ylmethyl)urea | 0.0022 | 0.0980 |
| 1-(4-{[3-(cyclopropylmethoxy)benzene]sulfonyl}phenyl)-3-(pyridin-3-ylmethyl)urea | 0.0086 | 0.1-1 |
| 1-(4-{[4-(1H-pyrazol-1-yl)benzene]sulfonyl}phenyl)-3-(pyridin-3-ylmethyl)urea | 0.0055 | 0.0550 |
| 1-(4-{[4-(morpholin-4-yl)benzene]sulfonyl}phenyl)-3-(pyridin-3-ylmethyl)urea | 0.0018 | 0.0147 |
| 1-(pyridin-3-ylmethyl)-3-[4-(3,3,5-trimethylazepane-1-sulfonyl)phenyl]urea | 0.0020 | 0.0092 |
| 1-(pyridin-3-ylmethyl)-3-{4-[(3-sulfamoylbenzene)sulfonyl]phenyl}urea | 0.0038 | 0.1-1 |
| 1-(pyridin-3-ylmethyl)-3-{4-[6-(trifluoromethyl)pyridine-3-sulfonyl]phenyl}urea | 0.0279 | 1-10 |
| 1-[4-({3-[(morpholin-4-yl)carbonyl]benzene}sulfonyl)phenyl]-3-(pyridin-3-ylmethyl)urea | 0.0050 | 0.1-1 |
| 1-[4-(1H-indole-4-sulfonyl)phenyl]-3-(pyridin-3-ylmethyl)urea | 0.0016 | 0.0134 |
| 1-[4-(1H-indole-7-sulfonyl)phenyl]-3-(pyridin-3-ylmethyl)urea | 0.0005 | 0.0034 |
| 1-[4-(2,3-dihydro-1,4-benzodioxine-6-sulfonyl)phenyl]-3-(pyridin-3-ylmethyl)urea | 0.0011 | 0.1-1 |
| 1-[4-(2,3-dihydro-1-benzofuran-7-sulfonyl)phenyl]-3-(pyridin-3-ylmethyl)urea | 0.0011 | 0.0105 |
| 1-[4-(2H-1,3-benzodioxole-4-sulfonyl)phenyl]-3-(pyridin-3-ylmethyl)urea | 0.0043 | 0.1-1 |
| 1-[4-(isoquinoline-4-sulfonyl)phenyl]-3-(pyridin-3-ylmethyl)urea | 0.0014 | 0.0083 |
| 1-[4-(phenoxathiine-4-sulfonyl)phenyl]-3-(pyridin-3-ylmethyl)urea | 0.0029 | 0.0018 |
| 1-{4-[(3-benzoylphenyl)sulfamoyl]phenyl}-3-(pyridin-3-ylmethyl)urea | 0.0044 | 1-10 |
| 1-{4-[(3-cyanobenzene)sulfonyl]phenyl}-3-(pyridin-3-ylmethyl)urea | 0.0080 | 0.1-1 |
| 1-{4-[(3-phenylbenzene)sulfonyl]phenyl}-3-(pyridin-3-ylmethyl)urea | 0.0068 | 0.1-1 |
| 1-{4-[(4-cyanobenzene)sulfonyl]phenyl}-3-(pyridin-3-ylmethyl)urea | 0.0076 | 0.1-1 |
| 1-{4-[(4-phenylbenzene)sulfonyl]phenyl}-3-(pyridin-3-ylmethyl)urea | 0.0058 | 0.1-1 |
| 1-{4-[(pyridin-2-ylmethyl)sulfamoyl]phenyl}-3-(pyridin-3-ylmethyl)urea | 0.0084 | 1-10 |
| 1-{4-[2-(morpholin-4-yl)pyridine-3-sulfonyl]phenyl}-3-(pyridin-3-ylmethyl)urea | 0.0160 | 0.1-1 |
| 1-{4-[4-(2-phenylacetyl)piperazine-1-sulfonyl]phenyl}-3-(pyridin-3-ylmethyl)urea | 0.0030 | 0.9323 |
| 1-{4-[6-(morpholin-4-yl)pyridine-3-sulfonyl]phenyl}-3-(pyridin-3-ylmethyl)urea | 0.0036 | 0.0304 |
| 2-fluoro-N-(propan-2-yl)-5-[(4-{[(pyridin-3-ylmethyl)carbamoyl]amino}benzene)sulfonyl]benzamide | 0.0209 | 0.1-1 |
| 2-methyl-N-{3-[(4-{[(pyridin-3-ylmethyl)carbamoyl]amino}benzene)sulfonyl]phenyl}propanamide | 0.0012 | 0.0101 |
| 3-(4-{[2-chloro-5-(trifluoromethoxy)benzene]sulfonyl}phenyl)-1-(pyridin-3-ylmethyl)urea | 0.0063 | 0.1-1 |
| 3-(4-{[2-methoxy-5-(trifluoromethyl)benzene]sulfonyl}phenyl)-1-(pyridin-3-ylmethyl)urea | 0.0014 | 0.0033 |
| 3-(4-{[2-methyl-4-(trifluoromethyl)benzene]sulfonyl}phenyl)-1-(pyridin-3-ylmethyl)urea | 0.0118 | 0.1-1 |
| 3-(4-{[3-(2-methylpropoxy)benzene]sulfonyl}phenyl)-1-(pyridin-3-ylmethyl)urea | 0.0033 | 0.1-1 |
| 3-(4-{[3-(3,5-dimethyl-1H-pyrazol-1-yl)benzene]sulfonyl}phenyl)-1-(pyridin-3-ylmethyl)urea | 0.0016 | 0.0159 |
| 3-(4-{[3-(5-methyl-1,3,4-oxadiazol-2-yl)benzene]sulfonyl}phenyl)-1-(pyridin-3-ylmethyl)urea | 0.0073 | 0.1-1 |
| 3-(4-{[3-(dimethylsulfamoyl)benzene]sulfonyl}phenyl)-1-(pyridin-3-ylmethyl)urea | 0.0033 | 0.0793 |
| 3-(4-{[3-(ethanesulfonyl)benzene]sulfonyl}phenyl)-1-(pyridin-3-ylmethyl)urea | 0.0076 | 0.1-1 |
| 3-(4-{[3-(ethylsulfamoyl)benzene]sulfonyl}phenyl)-1-(pyridin-3-ylmethyl)urea | 0.0072 | 0.1-1 |
| 3-(4-{[3-(methoxymethyl)benzene]sulfonyl}phenyl)-1-(pyridin-3-ylmethyl)urea | 0.0033 | 0.0933 |
| 3-(4-{[3-(propane-1-sulfonamido)benzene]sulfonyl}phenyl)-1-(pyridin-3-ylmethyl)urea | 0.0016 | 0.0860 |
| 3-(4-{[3-chloro-4-(trifluoromethyl)benzene]sulfonyl}phenyl)-1-(pyridin-3-ylmethyl)urea | 0.0040 | 0.1-1 |
| 3-(4-{[3-chloro-5-(trifluoromethyl)benzene]sulfonyl}phenyl)-1-(pyridin-3-ylmethyl)urea | 0.0013 | 0.0255 |
| 3-(4-{[3-fluoro-4-(2,2,2-trifluoroethoxy)benzene]sulfonyl}phenyl)-1-(pyridin-3-ylmethyl)urea | 0.0022 | 0.1-1 |

TABLE 3-continued

| Compound | Biochem IC50 uM | A2780 IC50 uM |
|---|---|---|
| 3-(4-{[3-fluoro-4-(trifluoromethoxy)benzene]sulfonyl}phenyl)-1-(pyridin-3-ylmethyl)urea | 0.0055 | 0.1-1 |
| 3-(4-{[3-fluoro-4-(trifluoromethyl)benzene]sulfonyl}phenyl)-1-(pyridin-3-ylmethyl)urea | 0.0041 | 0.1-1 |
| 3-(4-{[3-fluoro-5-(2,2,2-trifluoroethoxy)benzene]sulfonyl}phenyl)-1-(pyridin-3-ylmethyl)urea | 0.0011 | 0.0297 |
| 3-(4-{[3-fluoro-5-(2-methylpropoxy)benzene]sulfonyl}phenyl)-1-(pyridin-3-ylmethyl)urea | 0.0040 | 0.0564 |
| 3-(4-{[3-fluoro-5-(trifluoromethyl)benzene]sulfonyl}phenyl)-1-(pyridin-3-ylmethyl)urea | 0.0007 | 0.0576 |
| 3-(4-{[4-(ethoxymethyl)benzene]sulfonyl}phenyl)-1-(pyridin-3-ylmethyl)urea | 0.0010 | 0.1-1 |
| 3-(4-{[4-(propan-2-yl)benzene]sulfonyl}phenyl)-1-(pyridin-3-ylmethyl)urea | 0.0030 | 0.1-1 |
| 3-(4-{[4-(propan-2-yloxy)benzene]sulfonyl}phenyl)-1-(pyridin-3-ylmethyl)urea | 0.0017 | 0.0291 |
| 3-(4-{[4-fluoro-3-(2,2,2-trifluoroethoxy)benzene]sulfonyl}phenyl)-1-(pyridin-3-ylmethyl)urea | 0.0021 | 0.0234 |
| 3-(4-{[4-fluoro-3-(trifluoromethyl)benzene]sulfonyl}phenyl)-1-(pyridin-3-ylmethyl)urea | 0.0015 | 0.0862 |
| 3-(4-{4-[2-(3,4-dichlorophenyl)acetyl]piperazine-1-sulfonyl}phenyl)-1-(pyridin-3-ylmethyl)urea | 0.0037 | 1-10 |
| 3-(pyridin-3-ylmethyl)-1-[4-({4-[(pyrrolidin-1-yl)carbonyl]benzene}sulfonyl)phenyl]urea | 0.0013 | 0.0076 |
| 3-(pyridin-3-ylmethyl)-1-[4-(quinoline-3-sulfonyl)phenyl]urea | 0.0028 | 0.0280 |
| 3-(pyridin-3-ylmethyl)-1-[4-(quinoline-6-sulfonyl)phenyl]urea | 0.0027 | 0.0441 |
| 3-(pyridin-3-ylmethyl)-1-[4-(quinoline-8-sulfonyl)phenyl]urea | 0.0014 | 0.0022 |
| 3-[(4-{[(pyridin-3-ylmethyl)carbamoyl]amino}benzene)sulfonyl]benzamide | 0.0080 | 1-10 |
| 3-[4-(1-methyl-1H-indazole-4-sulfonyl)phenyl]-1-(pyridin-3-ylmethyl)urea | 0.0010 | 0.0599 |
| 3-[4-(1-methyl-1H-indazole-5-sulfonyl)phenyl]-1-(pyridin-3-ylmethyl)urea | 0.0018 | 0.0925 |
| 3-[4-(1-methyl-1H-indazole-6-sulfonyl)phenyl]-1-(pyridin-3-ylmethyl)urea | 0.0025 | 0.0354 |
| 3-[4-(1-methyl-1H-indazole-7-sulfonyl)phenyl]-1-(pyridin-3-ylmethyl)urea | 0.0144 | 0.1-1 |
| 3-[4-(1-methyl-1H-indole-2-sulfonyl)phenyl]-1-(pyridin-3-ylmethyl)urea | 0.0030 | 0.0635 |
| 3-[4-(1-propyl-1H-pyrazole-4-sulfonyl)phenyl]-1-(pyridin-3-ylmethyl)urea | 0.0063 | 0.0131 |
| 3-[4-(2,4-dimethoxypyrimidine-5-sulfonyl)phenyl]-1-(pyridin-3-ylmethyl)urea | 0.0067 | 0.0210 |
| 3-[4-(2-methoxypyrimidine-5-sulfonyl)phenyl]-1-(pyridin-3-ylmethyl)urea | 0.0087 | 0.1-1 |
| 3-[4-(2-methylpyridine-3-sulfonyl)phenyl]-1-(pyridin-3-ylmethyl)urea | 0.0072 | 0.1-1 |
| 3-[4-(4-{[4-(propan-2-yl)phenyl]methyl}piperazine-1-sulfonyl)phenyl]-1-(pyridin-3-ylmethyl)urea | 0.0358 | 1-10 |
| 3-[4-(5-chloropyridine-3-sulfonyl)phenyl]-1-(pyridin-3-ylmethyl)urea | 0.0026 | 0.0982 |
| 3-[4-(5-fluoropyridine-3-sulfonyl)phenyl]-1-(pyridin-3-ylmethyl)urea | 0.0087 | 0.1-1 |
| 3-[4-(6-methoxynaphthalene-2-sulfonyl)phenyl]-1-(pyridin-3-ylmethyl)urea | 0.0016 | 0.1-1 |
| 3-[4-(6-methoxypyridine-3-sulfonyl)phenyl]-1-(pyridin-3-ylmethyl)urea | 0.0050 | 0.1-1 |
| 3-[4-(6-methylpyridine-3-sulfonyl)phenyl]-1-(pyridin-3-ylmethyl)urea | 0.0049 | 0.1-1 |
| 3-{4-[(3,4-dichlorobenzene)sulfonyl]phenyl}-1-(pyridin-3-ylmethyl)urea | 0.0029 | 0.1-1 |
| 3-{4-[(3,5-dichlorobenzene)sulfonyl]phenyl}-1-(pyridin-3-ylmethyl)urea | 0.0019 | 0.1-1 |
| 3-{4-[(3-acetylbenzene)sulfonyl]phenyl}-1-(pyridin-3-ylmethyl)urea | 0.0021 | 0.1-1 |
| 3-{4-[(3-chloro-4-methoxybenzene)sulfonyl]phenyl}-1-(pyridin-3-ylmethyl)urea | 0.0013 | 0.0929 |
| 3-{4-[(3-chloro-4-methylbenzene)sulfonyl]phenyl}-1-(pyridin-3-ylmethyl)urea | 0.0009 | 0.1-1 |
| 3-{4-[(3-chloro-4-propoxybenzene)sulfonyl]phenyl}-1-(pyridin-3-ylmethyl)urea | 0.0046 | 0.1-1 |
| 3-{4-[(3-chloro-5-methoxybenzene)sulfonyl]phenyl}-1-(pyridin-3-ylmethyl)urea | 0.0013 | 0.0272 |
| 3-{4-[(3-chloro-5-methylbenzene)sulfonyl]phenyl}-1-(pyridin-3-ylmethyl)urea | 0.0018 | 0.0671 |
| 3-{4-[(3-ethanesulfonamidobenzene)sulfonyl]phenyl}-1-(pyridin-3-ylmethyl)urea | 0.0011 | 0.0695 |
| 3-{4-[(3-ethoxy-4-fluorobenzene)sulfonyl]phenyl}-1-(pyridin-3-ylmethyl)urea | 0.0039 | 0.0283 |
| 3-{4-[(3-ethoxybenzene)sulfonyl]phenyl}-1-(pyridin-3-ylmethyl)urea | 0.0017 | 0.0837 |
| 3-{4-[(3-ethylbenzene)sulfonyl]phenyl}-1-(pyridin-3-ylmethyl)urea | 0.0020 | 0.0708 |
| 3-{4-[(3-fluoro-4-propoxybenzene)sulfonyl]phenyl}-1-(pyridin-3-ylmethyl)urea | 0.0013 | 0.0585 |
| 3-{4-[(3-fluoro-5-methoxybenzene)sulfonyl]phenyl}-1-(pyridin-3-ylmethyl)urea | 0.0017 | 0.1-1 |
| 3-{4-[(3-fluoro-5-methylbenzene)sulfonyl]phenyl}-1-(pyridin-3-ylmethyl)urea | 0.0017 | 0.0993 |
| 3-{4-[(3-methanesulfonamidobenzene)sulfonyl]phenyl}-1-(pyridin-3-ylmethyl)urea | 0.0013 | 0.0761 |
| 3-{4-[(3-methanesulfonylbenzene)sulfonyl]phenyl}-1-(pyridin-3-ylmethyl)urea | 0.0066 | 0.1-1 |

TABLE 3-continued

| Compound | Biochem IC50 uM | A2780 IC50 uM |
|---|---|---|
| 3-{4-[(3-methoxy-4-methylbenzene)sulfonyl]phenyl}-1-(pyridin-3-ylmethyl)urea | 0.0027 | 0.0179 |
| 3-{4-[(3-propoxybenzene)sulfonyl]phenyl}-1-(pyridin-3-ylmethyl)urea | 0.0038 | 0.1-1 |
| 3-{4-[(4-acetylbenzene)sulfonyl]phenyl}-1-(pyridin-3-ylmethyl)urea | 0.0020 | 0.1-1 |
| 3-{4-[(4-acetylphenyl)sulfamoyl]phenyl}-1-(pyridin-3-ylmethyl)urea | 0.0144 | 1-10 |
| 3-{4-[(4-chloro-3-methoxybenzene)sulfonyl]phenyl}-1-(pyridin-3-ylmethyl)urea | 0.0044 | 0.0632 |
| 3-{4-[(4-chlorobenzene)sulfonyl]phenyl}-1-(pyridin-3-ylmethyl)urea | 0.0031 | 0.1-1 |
| 3-{4-[(4-ethoxy-3-fluorobenzene)sulfonyl]phenyl}-1-(pyridin-3-ylmethyl)urea | 0.0012 | 0.0217 |
| 3-{4-[(4-ethoxybenzene)sulfonyl]phenyl}-1-(pyridin-3-ylmethyl)urea | 0.0022 | 0.1-1 |
| 3-{4-[(4-fluoro-2-methoxybenzene)sulfonyl]phenyl}-1-(pyridin-3-ylmethyl)urea | 0.0020 | 0.0282 |
| 3-{4-[(4-fluoro-3-methoxybenzene)sulfonyl]phenyl}-1-(pyridin-3-ylmethyl)urea | 0.0037 | 0.0446 |
| 3-{4-[(4-fluoro-3-methylbenzene)sulfonyl]phenyl}-1-(pyridin-3-ylmethyl)urea | 0.0037 | 0.1-1 |
| 3-{4-[(4-methoxy-3,5-dimethylbenzene)sulfonyl]phenyl}-1-(pyridin-3-ylmethyl)urea | 0.0021 | 0.0089 |
| 3-{4-[(4-methoxybenzene)sulfonyl]phenyl}-1-(pyridin-3-ylmethyl)urea | 0.0024 | 0.1-1 |
| 3-{4-[(5-acetyl-2-methoxybenzene)sulfonyl]phenyl}-1-(pyridin-3-ylmethyl)urea | 0.0013 | 0.0017 |
| 3-{4-[2-(dimethylamino)pyrimidine-5-sulfonyl]phenyl}-1-(pyridin-3-ylmethyl)urea | 0.0059 | 0.1-1 |
| 3-{4-[3-chloro-2-(morpholin-4-yl)pyridine-4-sulfonyl]phenyl}-1-(pyridin-3-ylmethyl)urea | 0.0040 | 0.0142 |
| 3-{4-[4-(3-chlorophenyl)-4-hydroxypiperidine-1-sulfonyl]phenyl}-1-(pyridin-3-ylmethyl)urea | 0.0052 | 0.9563 |
| 3-{4-[6-(dimethylamino)pyridine-3-sulfonyl]phenyl}-1-(pyridin-3-ylmethyl)urea | 0.0030 | 0.0749 |
| 3-chloro-N,N-diethyl-5-[(4-{[(pyridin-3-ylmethyl)carbamoyl]amino}benzene)sulfonyl]benzamide | 0.0035 | 0.0017 |
| 3-fluoro-N,N-dimethyl-5-[(4-{[(pyridin-3-ylmethyl)carbamoyl]amino}benzene)sulfonyl]benzamide | 0.0015 | 0.0133 |
| 4-fluoro-N-(propan-2-yl)-3-[(4-{[(pyridin-3-ylmethyl)carbamoyl]amino}benzene)sulfonyl]benzamide | 0.0154 | 0.1-1 |
| N-(2-hydroxyethyl)-3-[(4-{[(pyridin-3-ylmethyl)carbamoyl]amino}benzene)sulfonyl]benzamide | 0.0078 | 0.1-1 |
| N-(2-methylpropyl)-3-[(4-{[(pyridin-3-ylmethyl)carbamoyl]amino}benzene)sulfonyl]benzamide | 0.0097 | 0.1-1 |
| N-(propan-2-yl)-3-[(4-{[(pyridin-3-ylmethyl)carbamoyl]amino}benzene)sulfonyl]benzamide | 0.0100 | 0.1-1 |
| N,N-diethyl-3-fluoro-5-[(4-{[(pyridin-3-ylmethyl)carbamoyl]amino}benzene)sulfonyl]benzamide | 0.0012 | 0.0015 |
| N,N-diethyl-4-fluoro-3-[(4-{[(pyridin-3-ylmethyl)carbamoyl]amino}benzene)sulfonyl]benzamide | 0.0024 | 0.0885 |
| N,N-dimethyl-3-[(4-{[(pyridin-3-ylmethyl)carbamoyl]amino}benzene)sulfonyl]benzamide | 0.0074 | 0.1-1 |
| N-{3-[(4-{[(pyridin-3-ylmethyl)carbamoyl]amino}benzene)sulfonyl]phenyl}acetamide | 0.0015 | 0.0395 |
| N-cyclopentyl-3-[(4-{[(pyridin-3-ylmethyl)carbamoyl]amino}benzene)sulfonyl]benzamide | 0.0096 | 0.1-1 |
| N-cyclopropyl-3-[(4-{[(pyridin-3-ylmethyl)carbamoyl]amino}benzene)sulfonyl]benzamide | 0.0064 | 0.1-1 |
| N-ethyl-3-[(4-{[(pyridin-3-ylmethyl)carbamoyl]amino}benzene)sulfonyl]benzamide | 0.0067 | 0.1-1 |
| N-ethyl-4-[(4-{[(pyridin-3-ylmethyl)carbamoyl]amino}benzene)sulfonyl]benzamide | 0.0013 | 0.0402 |
| N-methyl-5-[(4-{[(pyridin-3-ylmethyl)carbamoyl]amino}benzene)sulfonyl]pyridine-2-carboxamide | 0.0038 | 0.0838 |
| rel-3-{4-[(2R,6S)-2,6-dimethylmorpholine-4-sulfonyl]phenyl}-1-(pyridin-3-ylmethyl)urea | 0.0039 | 0.0135 |
| 4-[(3-chlorophenyl)sulfamoyl]-N-{imidazo[1,2-a]pyridin-6-ylmethyl}benzamide | 0.138 | 0.00712 |
| 4-[(5-chloro-2-methoxyphenyl)sulfamoyl]-N-[2-(pyridin-3-yl)ethyl]benzamide | 4.72 | 0.0312 |
| 4-[(5-chloro-2-methoxyphenyl)sulfamoyl]-N-{imidazo[1,2-a]pyridin-6-ylmethyl}benzamide | 0.00216 | 0.0023 |
| N-[2-(pyridin-3-yl)ethyl]-4-{[3-(trifluoromethoxy)phenyl]sulfamoyl}benzamide | 20.5 | 1.55 |
| N-[4-(pyridin-3-yl)-1,3-thiazol-2-yl]-4-(1,2,3,4-tetrahydroisoquinoline-2-sulfonyl)benzamide | 11.1 | 2.62 |
| N-{imidazo[1,2-a]pyridin-6-ylmethyl}-4-{[3-(trifluoromethoxy)phenyl]sulfamoyl}benzamide | 0.467 | 0.00858 |
| N-{imidazo[1,2-a]pyridin-6-ylmethyl}-4-{8-oxa-3-azabicyclo[3.2.1]octane-3-sulfonyl}benzamide | 0.109 | 0.0271 |

TABLE 3-continued

| Compound | Biochem IC50 uM | A2780 IC50 uM |
|---|---|---|
| 4-(benzenesulfonyl)-N-(pyridin-3-yl)benzamide | 1.89 | 2.73 |
| 4-(benzenesulfonyl)-N-(pyridin-4-yl)benzamide | 0.651 | 1.31 |
| 4-(benzenesulfonyl)-N-(pyridin-3-ylmethyl)benzamide | 0.0805 | 0.216 |
| N-[2-(pyridin-3-yl)ethyl]-4-{[3-(trifluoromethoxy)benzene]sulfonyl}benzamide | 9.37 | 0.374 |
| N-(1,3-benzothiazol-6-ylmethyl)-4-[(3-chlorobenzene)sulfonyl]benzamide | 11.4 | 0.00971 |
| N-{imidazo[1,2-a]pyridin-6-ylmethyl}-4-{[3-(trifluoromethoxy)benzene]sulfonyl}benzamide | 0.139 | 0.0018 |
| N-{imidazo[1,2-a]pyridin-6-ylmethyl}-4-{[3-(trifluoromethyl)benzene]sulfonyl}benzamide | 0.00703 | 0.00433 |
| 4-(benzenesulfonyl)-N-{imidazo[1,2-a]pyridin-7-ylmethyl}benzamide | 0.0308 | 0.0259 |
| N-{imidazo[1,2-a]pyridin-6-ylmethyl}-4-[(3-methoxybenzene)sulfonyl]benzamide | 0.0192 | 0.00354 |
| 4-[(3-chlorobenzene)sulfonyl]-N-{imidazo[1,2-a]pyridin-6-ylmethyl}benzamide | 0.0121 | 0.00639 |
| 4-[(2-chlorobenzene)sulfonyl]-N-{imidazo[1,2-a]pyridin-6-ylmethyl}benzamide | 0.0195 | 0.00392 |
| 4-[(3,5-difluorobenzene)sulfonyl]-N-{imidazo[1,2-a]pyridin-6-ylmethyl}benzamide | 0.0177 | 0.00571 |
| 3-[(5-fluoropyridin-3-yl)methyl]-1-[4-(piperidine-1-sulfonyl)phenyl]urea | 0.024 | 0.752 |
| 3-[(6-aminopyridin-3-yl)methyl]-1-[4-(piperidine-1-sulfonyl)phenyl]urea | 0.0085 | 0.0714 |
| 1-[(3-aminophenyl)methyl]-3-[4-(benzenesulfonyl)phenyl]urea | 0.011 | 2.54 |
| 3-[4-(benzenesulfonyl)phenyl]-1-(pyridin-3-ylmethyl)urea | 0.0035 | 0.16 |
| 3-[4-(benzenesulfonyl)phenyl]-1-{[6-(dimethylamino)pyridin-3-yl]methyl}urea | >30 | 27.6 |
| 3-{4-[(4-bromobenzene)sulfonyl]phenyl}-1-(pyridin-3-ylmethyl)urea | 0.003 | 0.239 |
| 3-{4-[(4-chlorobenzene)sulfonyl]phenyl}-1-(pyridin-3-ylmethyl)urea | 0.00452 | 0.241 |
| 3-{4-[(4-methylbenzene)sulfonyl]phenyl}-1-(pyridin-3-ylmethyl)urea | 0.00433 | 0.141 |
| 1-[4-(piperazine-1-sulfonyl)phenyl]-3-(pyridin-3-ylmethyl)urea | 0.0486 | >2 |

Xenograft Studies:

C.B-17-Igh-1b-Prkdc$^{scid}$ mice (female) were injected s.c. with $5\times10^6$ A2780 cells (NCI) in the left flank. 10-12 days later when tumors reached 100-200 mm3 in size, mice were randomized into treatment groups of 8 mice per group including vehicle control and reference standard groups. The compounds were formulated in 60:30:10 PEG-400:D5W:Ethanol and administered p.o., at the dose volume of 10 ml/kg BID for a duration of 5 or 10 days. The dose used for efficacy was selected from the MTD (Maximum Tolerated Dose) study. Mice were weighed and tumors measured using vernier calipers every alternate day. Tumor volume was calculated according to the formula (length×width$^2$)/2. All animal work was approved by the Institutional Animal Care and Use Committee of Biological Resource Centre, Singapore.

Results:

The following compound produced tumor regression.

1-(4-{8-oxa-3-azabicyclo[3.2.1]octane-3-sulfonyl}phenyl)-3-(pyridin-3-ylmethyl)urea; and 1-(pyridin-3-ylmethyl)-3-(4-{[2-(trifluoromethoxy)benzene]sulfonyl}phenyl)urea.

The following compound produced tumor stasis:

3-{4-[(4-chloro-2-methoxy-5-methylphenyl)sulfamoyl]phenyl}-1-(pyridin-3-ylmethyl)urea;

1-{4-[(4-fluorobenzene)sulfonyl]phenyl}-3-{imidazo[1,2-a]pyridin-6-ylmethyl}urea;

3-[4-(benzenesulfonyl)phenyl]-1-(pyridin-3-ylmethyl)urea; and

1-[(6-aminopyridin-3-yl)methyl]-3-[4-(benzenesulfonyl)phenyl]urea.

The following compounds delayed tumor growth:

1-{4-[4-(morpholin-4-yl)piperidine-1-sulfonyl]phenyl}-3-(pyridin-3-ylmethyl)urea;

3-(4-{[2-methoxy-5-(trifluoromethyl)phenyl]sulfamoyl}phenyl)-1-(pyridin-3-ylmethyl)urea;

1-(4-{[(1S,2S,4R)-bicyclo[2.2.1]heptan-2-yl]sulfamoyl}phenyl)-3-(pyridin-3-ylmethyl)urea;

3-{4-[(2R,6S)-2,6-dimethylmorpholine-4-sulfonyl]phenyl}-1-(pyridin-3-ylmethyl)urea;

3-{imidazo[1,2-a]pyridin-6-ylmethyl}-1-{4-[4-(morpholin-4-yl)piperidine-1-sulfonyl]phenyl}urea;

1-{4-[(2R,6S)-2,6-dimethylmorpholine-4-sulfonyl]phenyl}-3-{imidazo[1,2-a]pyridin-6-ylmethyl}urea;

3-{4-[(2-chloro-5-methylphenyl)sulfamoyl]phenyl}-1-(pyridin-3-ylmethyl)urea;

1-{4-[(naphthalen-1-yl)sulfamoyl]phenyl}-3-(pyridin-3-ylmethyl)urea;

3-{4-[(3-methoxy-2-methylphenyl)sulfamoyl]phenyl}-1-(pyridin-3-ylmethyl)urea;

3-{4-[(5-chloro-2-methoxyphenyl)sulfamoyl]phenyl}-1-(pyridin-3-ylmethyl)urea;

3-{4-[(4-fluorobenzene)sulfonyl]phenyl}-1-(pyridin-3-ylmethyl)urea;

1-[4-(benzenesulfonyl)phenyl]-3-{imidazo[1,2-a]pyridin-6-ylmethyl}urea; and

1-{4-[(4-fluorobenzene)sulfonyl]phenyl}-3-{imidazo[1,2-a]pyridin-6-ylmethyl}urea While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

We claim:
1. A compound of Formula IIA:

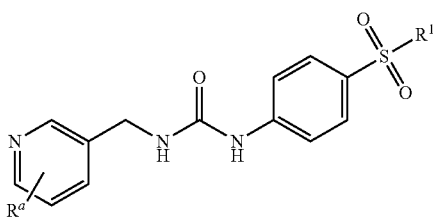

or a pharmaceutically acceptable salt thereof,
wherein:
$R^a$ is present 1, 2, 3 or 4 times, and each $R^a$ is independently selected from the group consisting of hydrogen, amino, oxo, halo, alkoxy, alkyl, haloalkyl, —N(alkyl)$_2$, —NH(CO)O-alkyl, 1H-pyrazole, 1H-imidazole, and —C(O)NH$_2$;
the pyridine to which $R^a$ is attached can comprise a N-oxide formed with its N atom member; and
$R^1$ is haloalkyl, cycloalkyl, aryl, heterocycloalkyl, or heteroaryl;
wherein each of said cycloalkyl, heterocycloalkyl, or heteroaryl of $R^1$ is unsubstituted or substituted by one or more halo, nitro, haloalkyl, haloalkoxy, oxo, cyano, alkyl, or alkoxy;
wherein said aryl of $R^1$ is substituted by one or more halo, nitro, haloalkyl, haloalkoxy, oxo, cyano, alkyl, or alkoxy.

2. The compound of claim 1, wherein $R^1$ is haloalkyl.

3. The compound of claim 1, wherein $R^1$ is cycloalkyl that is optionally substituted by one or more halo, nitro, haloalkyl, haloalkoxy, oxo, cyano, alkyl, or alkoxy.

4. The compound of claim 1, wherein $R^1$ is aryl that is substituted by one or more halo, nitro, haloalkyl, haloalkoxy, oxo, cyano, alkyl, or alkoxy.

5. The compound of claim 1, wherein $R^1$ is heterocycloalkyl that is unsubstituted or substituted by one or more halo, nitro, haloalkyl, haloalkoxy, oxo, cyano, alkyl, or alkoxy.

6. The compound of claim 1, wherein $R^1$ is heteroaryl that is unsubstituted or substituted by one or more halo, nitro, haloalkyl, haloalkoxy, oxo, cyano, alkyl, or alkoxy.

7. The compound of claim 1, wherein each $R^a$ is hydrogen.

8. A compound selected from the group consisting of:
1-(pyridin-3-ylmethyl)-3-(4-{[2-(trifluoromethoxy)benzene]sulfonyl}phenyl)urea;
3-{4-[(4-bromobenzene)sulfonyl]phenyl}-1-(pyridin-3-ylmethyl)urea;
3-{4-[(4-methoxy-2-methylbenzene)sulfonyl]phenyl}-1-(pyridin-3-ylmethyl)urea;
3-{4-[(2,4-dimethoxybenzene)sulfonyl]phenyl}-1-(pyridin-3-ylmethyl)urea;
1-[(6-aminopyridin-3-yl)methyl]-3-{4-[(4-fluorobenzene)sulfonyl]phenyl}urea;
3-{4-[(3,5-dimethylbenzene)sulfonyl]phenyl}-1-(pyridin-3-ylmethyl)urea;
3-{4-[(4-methylbenzene)sulfonyl]phenyl}-1-(pyridin-3-ylmethyl)urea;
3-{4-[(2-bromobenzene)sulfonyl]phenyl}-1-(pyridin-3-ylmethyl)urea;
3-{4-[(2-ethoxybenzene)sulfonyl]phenyl}-1-(pyridin-3-ylmethyl)urea;
3-{4-[(3,4-dimethoxybenzene)sulfonyl]phenyl}-1-(pyridin-3-ylmethyl)urea;
1-(pyridin-3-ylmethyl)-3-(4-{[4-(trifluoromethyl)benzene]sulfonyl}phenyl)urea;
3-{4-[(2,5-dimethylbenzene)sulfonyl]phenyl}-1-(pyridin-3-ylmethyl)urea;
1-(pyridin-3-ylmethyl)-3-(4-{[3-(trifluoromethoxy)benzene]sulfonyl}phenyl)urea;
3-{4-[(3-bromobenzene)sulfonyl]phenyl}-1-(pyridin-3-ylmethyl)urea;
1-(pyridin-3-ylmethyl)-3-(4-{[3-(trifluoromethyl)benzene]sulfonyl}phenyl)urea;
3-{4-[(5-fluoro-2-methylbenzene)sulfonyl]phenyl}-1-(pyridin-3-ylmethyl)urea;
3-{4-[(4-chloro-2-methylbenzene)sulfonyl]phenyl}-1-(pyridin-3-ylmethyl)urea;
3-{4-[(2-fluoro-3-methoxybenzene)sulfonyl]phenyl}-1-(pyridin-3-ylmethyl)urea;
3-{4-[(2,3-difluorobenzene)sulfonyl]phenyl}-1-(pyridin-3-ylmethyl)urea;
3-{4-[(2-chloro-6-fluoro-3-methylbenzene)sulfonyl]phenyl}-1-(pyridin-3-ylmethyl)urea;
3-(pyridin-3-ylmethyl)-1-[4-(pyrimidine-5-sulfonyl)phenyl]urea;
3-{4-[(3,5-difluorobenzene)sulfonyl]phenyl}-1-(pyridin-3-ylmethyl)urea;
3-{4-[(2,4-dichlorobenzene)sulfonyl]phenyl}-1-(pyridin-3-ylmethyl)urea;
3-{4-[(2,5-difluoro-4-methoxybenzene)sulfonyl]phenyl}-1-(pyridin-3-ylmethyl)urea;
3-{4-[(4-ethylbenzene)sulfonyl]phenyl}-1-(pyridin-3-ylmethyl)urea;
3-{4-[(2-chlorobenzene)sulfonyl]phenyl}-1-(pyridin-3-ylmethyl)urea;
3-{4-[(4-chloro-2-fluorobenzene)sulfonyl]phenyl}-1-(pyridin-3-ylmethyl)urea;
3-{4-[(4-chlorobenzene)sulfonyl]phenyl}-1-(pyridin-3-ylmethyl)urea;
3-{4-[(5-fluoro-2-methoxybenzene)sulfonyl]phenyl}-1-(pyridin-3-ylmethyl)urea;
3-{4-[(2-methoxybenzene)sulfonyl]phenyl}-1-(pyridin-3-ylmethyl)urea;
3-{4-[(4-fluorobenzene)sulfonyl]phenyl}-1-(pyridin-3-ylmethyl)urea;
3-[4-(2-methoxynaphthalene-1-sulfonyl)phenyl]-1-(pyridin-3-ylmethyl)urea;
3-{[({4-[(4-chlorobenzene)sulfonyl]phenyl}carbamoyl)amino]methyl}pyridin-1-ium-1-olate;
3-{4-[(3-fluorobenzene)sulfonyl]phenyl}-1-(pyridin-3-ylmethyl)urea;
3-{4-[(3-chlorobenzene)sulfonyl]phenyl}-1-(pyridin-3-ylmethyl)urea;
3-(4-{[2-(methoxymethyl)benzene]sulfonyl}phenyl)-1-(pyridin-3-ylmethyl)urea;
3-{4-[(2,3-dichlorobenzene)sulfonyl]phenyl}-1-(pyridin-3-ylmethyl)urea;
3-{4-[(4-fluoro-2-methylbenzene)sulfonyl]phenyl}-1-(pyridin-3-ylmethyl)urea;
3-(4-{[3-(propan-2-yl)benzene]sulfonyl}phenyl)-1-(pyridin-3-ylmethyl)urea;
3-{4-[(2,3-dimethylbenzene)sulfonyl]phenyl}-1-(pyridin-3-ylmethyl)urea;
1-[4-(cyclopentanesulfonyl)phenyl]-3-(pyridin-3-ylmethyl)urea;

3-{4-[(2-fluoro-6-methoxybenzene)sulfonyl]phenyl}-1-(pyridin-3-ylmethyl)urea;
3-{4-[(2,5-dimethoxybenzene)sulfonyl]phenyl}-1-(pyridin-3-ylmethyl)urea;
1-(pyridin-3-ylmethyl)-3-[4-(trifluoromethane)sulfonylphenyl]urea;
3-{4-[(2-fluoro-4-methoxybenzene)sulfonyl]phenyl}-1-(pyridin-3-ylmethyl)urea;
3-[4-(3,5-dimethyl-1,2-oxazole-4-sulfonyl)phenyl]-1-(pyridin-3-ylmethyl)urea;
3-{4-[(4-chloro-3-fluorobenzene)sulfonyl]phenyl}-1-(pyridin-3-ylmethyl)urea;
3-(4-{[2-chloro-5-(trifluoromethyl)benzene]sulfonyl}phenyl)-1-(pyridin-3-ylmethyl)urea;
3-{4-[(2-fluorobenzene)sulfonyl]phenyl}-1-(pyridin-3-ylmethyl)urea;
1-(pyridin-3-ylmethyl)-3-(4-{[2-(trifluoromethyl)benzene]sulfonyl}phenyl)urea;
3-(4-{[4-chloro-3-(trifluoromethyl)benzene]sulfonyl}phenyl)-1-(pyridin-3-ylmethyl)urea;
3-{4-[(2-fluoro-4-methylbenzene)sulfonyl]phenyl}-1-(pyridin-3-ylmethyl)urea;
3-{4-[2-chloro-6-(propan-2-yl)pyridine-3-sulfonyl]phenyl}-1-(pyridin-3-ylmethyl)urea;
3-{4-[(2-methoxy-5-methylbenzene)sulfonyl]phenyl}-1-(pyridin-3-ylmethyl)urea;
3-(pyridin-3-ylmethyl)-1-[4-(pyridine-4-sulfonyl)phenyl]urea;
3-{4-[(2-chloro-4-fluorobenzene)sulfonyl]phenyl}-1-(pyridin-3-ylmethyl)urea;
3-{4-[(2-ethylbenzene)sulfonyl]phenyl}-1-(pyridin-3-ylmethyl)urea;
3-{4-[(3-fluoro-4-methylbenzene)sulfonyl]phenyl}-1-(pyridin-3-ylmethyl)urea;
3-{4-[(2,5-dichlorobenzene)sulfonyl]phenyl}-1-(pyridin-3-ylmethyl)urea;
3-(pyridin-3-ylmethyl)-1-[4-(pyridine-3-sulfonyl)phenyl]urea;
3-{4-[(3-methylbenzene)sulfonyl]phenyl}-1-(pyridin-3-ylmethyl)urea;
3-{4-[(2,4-difluorobenzene)sulfonyl]phenyl}-1-(pyridin-3-ylmethyl)urea;
3-{4-[(2,6-dimethoxybenzene)sulfonyl]phenyl}-1-(pyridin-3-ylmethyl)urea;
1-(4-{8-oxatricyclo[7.4.0.0²,⁷]trideca-1(9),2(7),3,5,10,12-hexaene-6-sulfonyl}phenyl)-3-(pyridin-3-ylmethyl)urea;
3-(pyridin-3-ylmethyl)-1-[4-(pyridine-2-sulfonyl)phenyl]urea;
3-{4-[(5-chloro-2-methoxybenzene)sulfonyl]phenyl}-1-(pyridin-3-ylmethyl)urea;
3-(4-{[2-methoxy-5-(propan-2-yl)benzene]sulfonyl}phenyl)-1-(pyridin-3-ylmethyl)urea;
3-(4-{[3-(propan-2-yloxy)benzene]sulfonyl}phenyl)-1-(pyridin-3-ylmethyl)urea;
1-(pyridin-3-ylmethyl)-3-{4-[(2,4,6-trimethylbenzene)sulfonyl]phenyl}urea;
3-{4-[(3-fluoro-4-methoxybenzene)sulfonyl]phenyl}-1-(pyridin-3-ylmethyl)urea;
3-{4-[(2-methylbenzene)sulfonyl]phenyl}-1-(pyridin-3-ylmethyl)urea;
3-{4-[(2,4-dimethylbenzene)sulfonyl]phenyl}-1-(pyridin-3-ylmethyl)urea;
3-{4-[(2,5-difluorobenzene)sulfonyl]phenyl}-1-(pyridin-3-ylmethyl)urea;
3-{4-[(2-fluoro-5-methylbenzene)sulfonyl]phenyl}-1-(pyridin-3-ylmethyl)urea;
1-(pyridin-3-ylmethyl)-3-(4-{[4-(trifluoromethoxy)benzene]sulfonyl}phenyl)urea;
3-[4-(1-methyl-1H-pyrazole-4-sulfonyl)phenyl]-1-(pyridin-3-ylmethyl)urea;
3-[4-(5-methylthiophene-2-sulfonyl)phenyl]-1-(pyridin-3-ylmethyl)urea;
3-{4-[(3,4-difluorobenzene)sulfonyl]phenyl}-1-(pyridin-3-ylmethyl)urea;
3-{4-[(2,6-dimethylbenzene)sulfonyl]phenyl}-1-(pyridin-3-ylmethyl)urea;
3-[4-(2-methoxypyrimidine-5-sulfonyl)phenyl]-1-(pyridin-3-ylmethyl)urea;
3-{4-[(2R)-2-(methoxymethyl)pyrrolidine-1-sulfonyl]phenyl}-1-(pyridin-3-ylmethyl)urea;
3-(4-{[3-fluoro-5-(2,2,2-trifluoroethoxy)benzene]sulfonyl}phenyl)-1-(pyridin-3-ylmethyl)urea;
3-{4-[(3-fluoro-4-propoxybenzene)sulfonyl]phenyl}-1-(pyridin-3-ylmethyl)urea;
3-(4-{[4-fluoro-3-(trifluoromethyl)benzene]sulfonyl}phenyl)-1-(pyridin-3-ylmethyl)urea;
1-[4-(3,5-dimethylpiperidine-1-sulfonyl)phenyl]-3-(pyridin-3-ylmethyl)urea;
3-[4-(1-methyl-1H-indole-2-sulfonyl)phenyl]-1-(pyridin-3-ylmethyl)urea;
3-{[4-(piperidine-1-sulfonyl)phenyl]methyl}-1-(pyridin-3-ylmethyl)urea;
3-{4-[(3-ethoxy-4-fluorobenzene)sulfonyl]phenyl}-1-(pyridin-3-ylmethyl)urea;
3-{4-[3-(2-methoxyethyl)piperidine-1-sulfonyl]phenyl}-1-(pyridin-3-ylmethyl)urea;
3-[4-(1-methyl-1H-indazole-7-sulfonyl)phenyl]-1-(pyridin-3-ylmethyl)urea;
3-{4-[(4-methoxybenzene)sulfonyl]phenyl}-1-(pyridin-3-ylmethyl)urea;
3-{4-[(4-methoxy-3,5-dimethylbenzene)sulfonyl]phenyl}-1-(pyridin-3-ylmethyl)urea;
3-(4-{[2-methyl-4-(trifluoromethyl)benzene]sulfonyl}phenyl)-1-(pyridin-3-ylmethyl)urea;
3-(4-{[3-chloro-5-(trifluoromethyl)benzene]sulfonyl}phenyl)-1-(pyridin-3-ylmethyl)urea;
1-[4-(piperidine-1-sulfonyl)phenyl]-3-(pyridin-3-ylmethyl)urea;
1-{4-[(3S)-3-cyanopiperidine-1-sulfonyl]phenyl}-3-(pyridin-3-ylmethyl)urea;
3-{4-[(2S)-2-(methoxymethyl)pyrrolidine-1-sulfonyl]phenyl}-1-(pyridin-3-ylmethyl)urea;
3-[4-(3-methylpiperidine-1-sulfonyl)phenyl]-1-(pyridin-3-ylmethyl)urea;
3-{4-[(3-chloro-5-methylbenzene)sulfonyl]phenyl}-1-(pyridin-3-ylmethyl)urea;
3-(4-{[4-(ethoxymethyl)benzene]sulfonyl}phenyl)-1-(pyridin-3-ylmethyl)urea;
1-(pyridin-3-ylmethyl)-3-{4-[3-(trifluoromethyl)piperidine-1-sulfonyl]phenyl}urea;
3-{4-[(3,4-dichlorobenzene)sulfonyl]phenyl}-1-(pyridin-3-ylmethyl)urea;
3-(pyridin-3-ylmethyl)-1-[4-(quinoline-6-sulfonyl)phenyl]urea;
3-[(5-chloropyridin-3-yl)methyl]-1-[4-(piperidine-1-sulfonyl)phenyl]urea;
1-(pyridin-3-ylmethyl)-3-[4-(1H-pyrrole-1-sulfonyl)phenyl]urea;
3-(pyridin-3-ylmethyl)-1-[4-(thiomorpholine-4-sulfonyl)phenyl]urea;
3-(pyridin-3-ylmethyl)-1-[4-(pyrrolidine-1-sulfonyl)phenyl]urea;

1-[4-(phenoxathiine-4-sulfonyl)phenyl]-3-(pyridin-3-yl-methyl)urea;
3-(pyridin-3-ylmethyl)-1-[4-(quinoline-8-sulfonyl)phenyl]urea;
3-[4-(4-methylpiperidine-1-sulfonyl)phenyl]-1-(pyridin-3-ylmethyl)urea;
3-(pyridin-3-ylmethyl)-1-[4-(quinoline-3-sulfonyl)phenyl]urea;
3-(4-{[3-fluoro-5-(2-methylpropoxy)benzene]sulfonyl}phenyl)-1-(pyridin-3-ylmethyl)urea;
1-{4-[(3-cyanobenzene)sulfonyl]phenyl}-3-(pyridin-3-ylmethyl)urea;
3-[(5-fluoropyridin-3-yl)methyl]-1-[4-(piperidine-1-sulfonyl)phenyl]urea;
1-[4-(isoquinoline-4-sulfonyl)phenyl]-3-(pyridin-3-ylmethyl)urea;
1-(4-{3-azaspiro[5.5]undecane-3-sulfonyl}phenyl)-3-(pyridin-3-ylmethyl)urea;
3-[4-(6-methoxypyridine-3-sulfonyl)phenyl]-1-(pyridin-3-ylmethyl)urea;
3-{4-[(3-propoxybenzene)sulfonyl]phenyl}-1-(pyridin-3-ylmethyl)urea;
1-(pyridin-3-ylmethyl)-3-{4-[4-(trifluoromethyl)piperidine-1-sulfonyl]phenyl}urea;
3-(4-{[4-(propan-2-yloxy)benzene]sulfonyl}phenyl)-1-(pyridin-3-ylmethyl)urea;
3-{4-[(4-ethoxybenzene)sulfonyl]phenyl}-1-(pyridin-3-ylmethyl)urea;
1-[4-(4,4-difluoropiperidine-1-sulfonyl)phenyl]-3-(pyridin-3-ylmethyl)urea;
3-[4-(1-methyl-1H-indazole-4-sulfonyl)phenyl]-1-(pyridin-3-ylmethyl)urea;
1-[4-(piperazine-1-sulfonyl)phenyl]-3-(pyridin-3-ylmethyl)urea;
1-(pyridin-3-ylmethyl)-3-{4-[(3 S)-3-(trifluoromethyl)piperidine-1-sulfonyl]phenyl}urea;
1-[4-(2,3-dihydro-1-benzofuran-7-sulfonyl)phenyl]-3-(pyridin-3-ylmethyl)urea;
3-{4-[4-(2-methoxyethyl)piperazine-1-sulfonyl]phenyl}-1-(pyridin-3-ylmethyl)urea;
1-[4-(2,3-dihydro-1,4-benzodioxine-6-sulfonyl)phenyl]-3-(pyridin-3-ylmethyl)urea;
3-{4-[4-(propan-2-yl)piperazine-1-sulfonyl]phenyl}-1-(pyridin-3-ylmethyl)urea;
3-[4-(2-methyl-3-oxopiperazine-1-sulfonyl)phenyl]-1-(pyridin-3-ylmethyl)urea;
3-{4-[(3-ethoxybenzene)sulfonyl]phenyl}-1-(pyridin-3-ylmethyl)urea;
1-[4-(1H-indole-4-sulfonyl)phenyl]-3-(pyridin-3-ylmethyl)urea;
3-{4-[(4-chlorobenzene)sulfonyl]phenyl}-1-(pyridin-3-ylmethyl)urea;
3-[4-(1-methyl-1H-indazole-6-sulfonyl)phenyl]-1-(pyridin-3-ylmethyl)urea;
3-(4-{[3-fluoro-4-(trifluoromethoxy)benzene]sulfonyl}phenyl)-1-(pyridin-3-ylmethyl)urea;
3-{4-[(3-chloro-4-methoxybenzene)sulfonyl]phenyl}-1-(pyridin-3-ylmethyl)urea;
3-(4-{[4-fluoro-3-(2,2,2-trifluoroethoxy)benzene]sulfonyl}phenyl)-1-(pyridin-3-ylmethyl)urea;
1-[4-(morpholine-4-sulfonyl)phenyl]-3-(pyridin-3-ylmethyl)urea;
1-(4-{3-azatricyclo[7.3.1.0$^{5,13}$]trideca-1(13),5,7,9,11-pentaene-3-sulfonyl}phenyl)-3-(pyridin-3-ylmethyl)urea;
3-[(6-chloropyridin-3-yl)methyl]-1-[4-(piperidine-1-sulfonyl)phenyl]urea;
1-(pyridin-3-ylmethyl)-3-[4-(3,3,5-trimethylazepane-1-sulfonyl)phenyl]urea;
3-[4-(1-propyl-1H-pyrazole-4-sulfonyl)phenyl]-1-(pyridin-3-ylmethyl)urea;
3-(4-{[3-fluoro-5-(trifluoromethyl)benzene]sulfonyl}phenyl)-1-(pyridin-3-ylmethyl)urea;
3-(4-{[3-fluoro-4-(2,2,2-trifluoroethoxy)benzene]sulfonyl}phenyl)-1-(pyridin-3-ylmethyl)urea;
1-[4-(4-cyanopiperidine-1-sulfonyl)phenyl]-3-(pyridin-3-ylmethyl)urea;
1-(4-{3-oxa-8-azabicyclo[3.2.1]octane-8-sulfonyl}phenyl)-3-(pyridin-3-ylmethyl)urea;
tert-butyl N-{5-[({[4-(piperidine-1-sulfonyl)phenyl]carbamoyl}amino)methyl]pyridin-2-yl}carbamate;
3-{4-[(4-chloro-3-methoxybenzene)sulfonyl]phenyl}-1-(pyridin-3-ylmethyl)urea;
rel-3-{4-[(2R,6S)-2,6-dimethylmorpholine-4-sulfonyl]phenyl}-1-(pyridin-3-ylmethyl)urea;
1-[4-(decahydroquinoline-1-sulfonyl)phenyl]-3-(pyridin-3-ylmethyl)urea;
3-{4-[(3-chloro-4-methylbenzene)sulfonyl]phenyl}-1-(pyridin-3-ylmethyl)urea;
3-(4-{[3-fluoro-4-(trifluoromethyl)benzene]sulfonyl}phenyl)-1-(pyridin-3-ylmethyl)urea;
3-{4-[(4-fluoro-3-methylbenzene)sulfonyl]phenyl}-1-(pyridin-3-ylmethyl)urea;
3-[4-(2-methylpyridine-3-sulfonyl)phenyl]-1-(pyridin-3-ylmethyl)urea;
3-{4-[(3-fluoro-5-methoxybenzene)sulfonyl]phenyl}-1-(pyridin-3-ylmethyl)urea;
rel-3-{4-[(4aR,8aS)-decahydroisoquinoline-2-sulfonyl]phenyl}-1-(pyridin-3-ylmethyl)urea;
3-(4-{[3-(2-methylpropoxy)benzene]sulfonyl}phenyl)-1-(pyridin-3-ylmethyl)urea;
3-[4-(1-methyl-1H-indazole-5-sulfonyl)phenyl]-1-(pyridin-3-ylmethyl)urea;
3-{4-[(4-ethoxy-3-fluorobenzene)sulfonyl]phenyl}-1-(pyridin-3-ylmethyl)urea;
3-{4-[(3,5-dichlorobenzene)sulfonyl]phenyl}-1-(pyridin-3-ylmethyl)urea;
3-{4-[(3-methoxy-4-methylbenzene)sulfonyl]phenyl}-1-(pyridin-3-ylmethyl)urea;
3-[4-(6-methylpyridine-3-sulfonyl)phenyl]-1-(pyridin-3-ylmethyl)urea;
3-(pyridin-3-ylmethyl)-1-[4-(5,6,7,8-tetrahydro-1,6-naphthyridine-6-sulfonyl)phenyl]urea;
3-[4-(2,4-dimethoxypyrimidine-5-sulfonyl)phenyl]-1-(pyridin-3-ylmethyl)urea;
3-[(6-aminopyridin-3-yl)methyl]-1-[4-(piperidine-1-sulfonyl)phenyl]urea;
3-{4-[(4-fluoro-3-methoxybenzene)sulfonyl]phenyl}-1-(pyridin-3-ylmethyl)urea;
1-[4-(3,4-dihydro-2H-1,4-benzoxazine-4-sulfonyl)phenyl]-3-(pyridin-3-ylmethyl)urea;
3-{4-[(3 S)-3-methylpiperidine-1-sulfonyl]phenyl}-1-(pyridin-3-ylmethyl)urea;
3-[4-(azepane-1-sulfonyl)phenyl]-1-(pyridin-3-ylmethyl)urea;
3-(4-{[3-chloro-4-(trifluoromethyl)benzene]sulfonyl}phenyl)-1-(pyridin-3-ylmethyl)urea;
3-[4-(piperidine-1-sulfonyl)phenyl]-1-{[6-(trifluoromethyl)pyridin-3-yl]methyl}urea;
3-[4-(5-fluoropyridine-3-sulfonyl)phenyl]-1-(pyridin-3-ylmethyl)urea;
3-{4-[4-(methoxymethyl)piperidine-1-sulfonyl]phenyl}-1-(pyridin-3-ylmethyl)urea;

3-{4-[2-(dimethylamino)pyrimidine-5-sulfonyl]phenyl}-1-(pyridin-3-ylmethyl)urea;
3-{4-[(3-chloro-4-propoxybenzene)sulfonyl]phenyl}-1-(pyridin-3-ylmethyl)urea;
3-(4-{[3-(methoxymethyl)benzene]sulfonyl}phenyl)-1-(pyridin-3-ylmethyl)urea;
3-(4-{[2-methoxy-5-(trifluoromethyl)benzene]sulfonyl}phenyl)-1-(pyridin-3-ylmethyl)urea;
1-[4-(2,6-dimethylpiperidine-1-sulfonyl)phenyl]-3-(pyridin-3-ylmethyl)urea;
1-(pyridin-3-ylmethyl)-3-{4-[6-(trifluoromethyl)pyridine-3-sulfonyl]phenyl}urea;
3-{4-[4-(2-methylpropyl)piperazine-1-sulfonyl]phenyl}-1-(pyridin-3-ylmethyl)urea;
5-[({[4-(piperidine-1-sulfonyl)phenyl]carbamoyl}amino)methyl]pyridine-2-carboxamide;
3-[4-(azetidine-1-sulfonyl)phenyl]-1-(pyridin-3-ylmethyl)urea;
3-{4-[(3-ethylbenzene)sulfonyl]phenyl}-1-(pyridin-3-ylmethyl)urea;
3-[4-(5-chloropyridine-3-sulfonyl)phenyl]-1-(pyridin-3-ylmethyl)urea;
3-{4-[(3-fluoro-5-methylbenzene)sulfonyl]phenyl}-1-(pyridin-3-ylmethyl)urea;
3-[4-(3,3-difluoroazetidine-1-sulfonyl)phenyl]-1-(pyridin-3-ylmethyl)urea;
1-(4-{8-azabicyclo[3.2.1]octane-8-sulfonyl}phenyl)-3-(pyridin-3-ylmethyl)urea;
1-(4-{8-oxa-3-azabicyclo[3.2.1]octane-3-sulfonyl}phenyl)-3-(pyridin-3-ylmethyl)urea;
1-(4-{[3-(cyclopropylmethoxy)benzene]sulfonyl}phenyl)-3-(pyridin-3-ylmethyl)urea;
1-(4-{2-azabicyclo[2.2.1]heptane-2-sulfonyl}phenyl)-3-(pyridin-3-ylmethyl)urea;
3-[4-(2,3-dihydro-1H-indole-1-sulfonyl)phenyl]-1-(pyridin-3-ylmethyl)urea;
3-(4-{[4-(propan-2-yl)benzene]sulfonyl}phenyl)-1-(pyridin-3-ylmethyl)urea;
3-{4-[(2R,6 S)-2,6-dimethylmorpholine-4-sulfonyl]phenyl}-1-(pyridin-3-ylmethyl)urea;
3-{4-[(4-fluoro-2-methoxybenzene)sulfonyl]phenyl}-1-(pyridin-3-ylmethyl)urea;
3-{4-[(2S)-2-ethylpiperidine-1-sulfonyl]phenyl}-1-(pyridin-3-ylmethyl)urea; and
1-{4-[(4-cyanobenzene)sulfonyl]phenyl}-3-(pyridin-3-ylmethyl)urea;
or a pharmaceutically acceptable salt thereof.

9. A pharmaceutical composition comprising a compound of claim 1, or a pharmaceutically acceptable salt thereof, and a pharmaceutically acceptable carrier.

10. A pharmaceutical composition comprising a compound of claim 8, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 10,329,275 B2
APPLICATION NO. : 16/008378
DATED : June 25, 2019
INVENTOR(S) : Kenneth W. Bair et al.

Page 1 of 1

It is certified that error appears in the above-identified patent and that said Letters Patent is hereby corrected as shown below:

In the Claims

In Claim 1, Column 383, Line 1, please delete:
"A compound of Formula IIA:"
And insert:
-- A compound of Formula IIIA --

In Claim 8, Column 387, beginning at Line 63 and ending at Line 65, please delete:
"1-(4-{3-azatricyclo[7.3.1.0$^5$,1$^3$]trideca-1(13),5,7,9,11-pentaene-3-sulfonyl}phenyl)-3-(pyridin-3-ylmethyl)urea;"
And insert:
-- 1-(4-{3-azatricyclo[7.3.1.0$^{5,13}$]trideca-1(13),5,7,9,11-pentaene-3-sulfonyl}phenyl)-3-(pyridin-3-ylmethyl)urea; --

Signed and Sealed this
Seventh Day of April, 2020

Andrei Iancu
*Director of the United States Patent and Trademark Office*